US009217158B2

(12) United States Patent
Pugachev et al.

(10) Patent No.: US 9,217,158 B2
(45) Date of Patent: Dec. 22, 2015

(54) REPLICATION-DEFECTIVE FLAVIVIRUS VACCINES AND VACCINE VECTORS

(71) Applicants: Konstantin V. Pugachev, Natick, MA (US); Maryann Giel-Moloney, Brighton, MA (US); Harold Kleanthous, Westford, MA (US); Mark Parrington, Bradford (CA); Linong Zhang, Maple (CA)

(72) Inventors: Konstantin V. Pugachev, Natick, MA (US); Maryann Giel-Moloney, Brighton, MA (US); Harold Kleanthous, Westford, MA (US); Mark Parrington, Bradford (CA); Linong Zhang, Maple (CA)

(73) Assignee: Sanofi Pasteur Biologics, LLC, Cambridge, MA (US)

(*) Notice: Subject to any disclaimer, the term of this patent is extended or adjusted under 35 U.S.C. 154(b) by 139 days.

(21) Appl. No.: 13/633,436

(22) Filed: Oct. 2, 2012

(65) Prior Publication Data

US 2013/0243812 A1 Sep. 19, 2013

Related U.S. Application Data

(63) Continuation of application No. 13/364,187, filed on Feb. 1, 2012, now abandoned, which is a continuation-in-part of application No. 12/922,513, filed as application No. PCT/US2009/001666 on Mar. 16, 2009, now Pat. No. 8,815,564.

(60) Provisional application No. 61/092,814, filed on Aug. 29, 2008, provisional application No. 61/069,451, filed on Mar. 14, 2008.

(51) Int. Cl.

| | |
|---|---|
| *A61K 39/12* | (2006.01) |
| *C12N 15/86* | (2006.01) |
| *A61K 39/295* | (2006.01) |

(52) U.S. Cl.
CPC .............. *C12N 15/86* (2013.01); *A61K 39/295* (2013.01); *C12N 2770/24121* (2013.01); *C12N 2770/24134* (2013.01)

(58) Field of Classification Search
None
See application file for complete search history.

(56) References Cited

U.S. PATENT DOCUMENTS

| | | | |
|---|---|---|---|
| 4,393,201 | A | 7/1983 | Curtis et al. |
| 5,830,477 | A | 11/1998 | Lathe et al. |
| 6,486,135 | B1 | 11/2002 | Li et al. |
| 6,696,281 | B1 | 2/2004 | Monath et al. |
| 2001/0046499 | A1 | 11/2001 | Kantor et al. |
| 2004/0005542 | A1 | 1/2004 | Krempl et al. |
| 2004/0223979 | A1 | 11/2004 | Chambers et al. |
| 2006/0159704 | A1 | 7/2006 | Bonaldo et al. |
| 2006/0204523 | A1 | 9/2006 | Khromykh et al. |
| 2007/0207166 | A1* | 9/2007 | Nabel et al. ................ 424/199.1 |
| 2007/0218078 | A1 | 9/2007 | Clarke et al. |
| 2007/0249032 | A1 | 10/2007 | Pang et al. |
| 2008/0175862 | A1 | 7/2008 | Pugachev et al. |
| 2011/0135686 | A1 | 6/2011 | Pugachev et al. |

FOREIGN PATENT DOCUMENTS

| | | | |
|---|---|---|---|
| EP | 0117657 | A1 | 9/1984 |
| WO | WO-98/37911 | A1 | 9/1998 |
| WO | WO-99/28487 | A1 | 6/1999 |
| WO | WO-02/102828 | A2 | 12/2002 |
| WO | WO-03/046189 | A1 | 6/2003 |
| WO | WO-2006/086838 | A1 | 8/2006 |
| WO | WO-2007/098267 | A2 | 8/2007 |
| WO | WO-2008/137163 | A1 | 11/2008 |
| WO | WO 2009/114207 | A2 * | 9/2009 |
| WO | WO-2010/107847 | A1 | 9/2010 |

OTHER PUBLICATIONS

Jamieson et al., Lancet, 2009, 374:451-458.*
Shustov et al., Journal of Virology, available online Aug. 22, 2007, 81(21):11737-11748.*
International Search Report and Written Opinion from PCT/US2013/024495, mailed Apr. 11, 2013 (11 pages).
International Preliminary Report on Patentability for PCT/US2013/024495, dated Aug. 5, 2014 (8 pages).
Bonaldo et al., "The yellow fever 17D vaccine virus as a vector for the expression of foreign proteins: development of new live flavivirus vaccines," Mem Inst Oswaldo Cruz. Suppl 1:215-23 (2000).
Bredenbeek et al., "A recombinant Yellow Fever 17D vaccine expressing Lassa virus glycoproteins," Virology. 345(2):299-304 (2006).
Hsu et al., "Efficacy of adenovirus-vectored respiratory syncytial virus vaccines in a new ferret model," Vaccine. 12(7):607-12 (1994).
Li et al., "Chimeric influenza virus induces neutralizing antibodies and cytotoxic T cells against human immunodeficiency virus type 1," J Virol. 67(11):6659-66 (1993).
Martinez-Sobrido et al., "Protection against respiratory syncytial virus by a recombinant Newcastle disease virus vector," J Virol. 80(3):1130-9 (2006).
McAllister et al., "Recombinant yellow fever viruses are effective therapeutic vaccines for treatment of murine experimental solid tumors and pulmonary metastases," J Virol. 74(19):9197-205 (2000).
Pang et al., "Development of dengue virus replicons expressing HIV-1 gp120 and other heterologous genes: a potential future tool for dual vaccination against dengue virus and HIV," BMC Microbiol. 1(28):1-9 (2001).
Shustov et al., "Production of pseudoinfectious yellow fever virus with a two-component genome," J Virol. 81(21):11737-48 (2007).
Extended European Search Report for European Patent Application No. 097020269.1, dated Mar. 26, 2012 (9 pages).

(Continued)

*Primary Examiner* — Stacy B Chen

(74) *Attorney, Agent, or Firm* — Clark & Elbing LLP; Susan M. Michaud

(57) ABSTRACT

This invention provides replication-defective flavivirus vaccines and vaccine vectors, and corresponding compositions and methods.

8 Claims, 37 Drawing Sheets

(56) References Cited

OTHER PUBLICATIONS

International Preliminary Report on Patentability for International Application No. PCT/US09/01666, dated Apr. 25, 2011 (date of completion of report) and Jun. 20, 2011 (date of mailing of report). 10 pages.
International Search Report for International Patent Application No. PCT/US2009/001666, dated Aug. 12, 2009 (date of completion of search) and Sep. 1, 2009 (date of mailing of report). 3 pages.
International Search Report for International Patent Application No. PCT/US2010/027552, dated May 20, 2010 (date of completion of search) and Jun. 15, 2010 (date of mailing of report). 4 pages.
Search Report and Written Opinion issued by the Hungarian Intellectual Property Office for Singapore Patent Application No. 201006578-7, dated Jul. 19, 2012 (19 pages).
Written Opinion for International Patent Application No. PCT/US2009/001666, dated Aug. 12, 2009 (date of completion of opinion and Sep. 1, 2009 (date of mailing of opinion). 9 pages.
Written Opinion for International Patent Application No. PCT/US2010/027552, dated May 20, 2010 (date of completion of opinion) and Jun. 15, 2010 (date of mailing of opinion). 5 pages.
Scherret et al., "The relationships between West Nile and Kunjin viruses," Emerg Infect Dis. 7(4):697-705 (2001).
Weyer et al., "Generation and evaluation of a recombinant modified vaccinia virus Ankara vaccine for rabies," Vaccine. 25(21):4213-22 (2007).
Search Report and Written Opinion for Singapore Patent Application No. 2013018320, dated May 6, 2015 (22 pages).

* cited by examiner

Fig. 1. Principle of single-component PIV (s-PIV; single-round replication in vivo)

For recombinant vaccines: foreign immunogen inserted in place of the ΔC deletion, or elsewhere, e.g. intergenically etc.

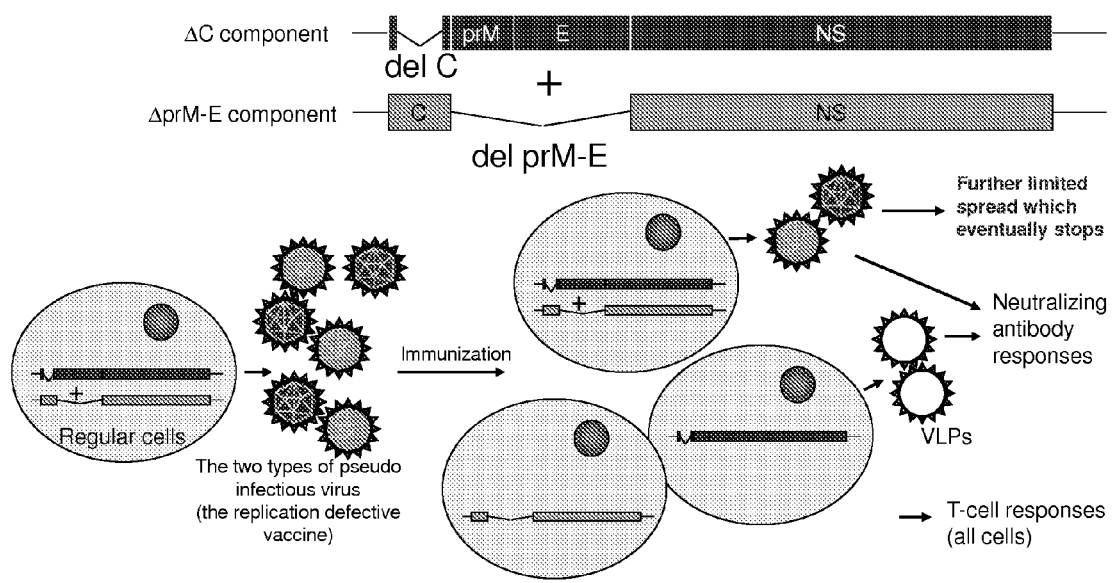
Fig. 2. Principle of two-component PIV (d-PIV; limited spread in vivo)
For recombinant vaccines: foreign immunogen inserted in place of ΔC and/or ΔprM-E, or elsewhere.

Fig. 3. Immunogenicity/efficacy: general experiment design (mice)
Experiment design in mice
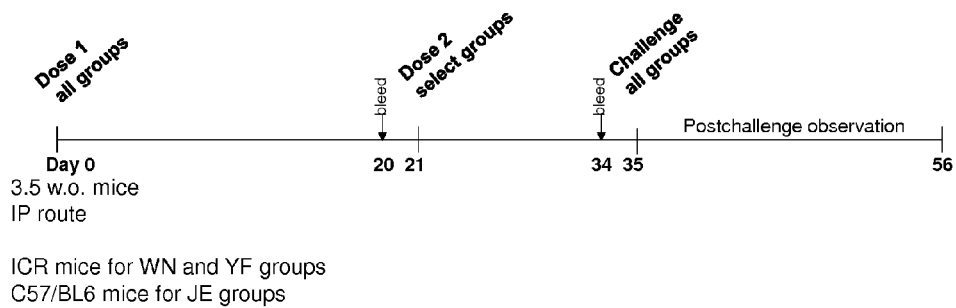
3.5 w.o. mice
IP route
ICR mice for WN and YF groups
C57/BL6 mice for JE groups Fig. 4. PIV-WN induces uniform humoral immunity in mice ICR mice, IP inoculation Fig. 5. PIV-YF and PIV-WN protect hamsters against post-challenge viremia and morbidity Fig. 6. YF/TBE viruses

| prM-E genes | | P0 virus titer $\log_{10}$ PFU/ml | P1 virus titer $\log_{10}$ PFU/ml | Immuno-staining αRSSE mHIAF | |
|---|---|---|---|---|---|
| Hypr | TBEV prM-SP (p42) | 7.6 | 7.9 | | <p42 |
| | WNV prM-SP (p45) | 7.1 | 7.4 | | p45> |
| Hypr + dC2 "CΔ3aa" (p59) | | 5.6 | 6.5 | | p59> |
| LGT/E5 (p43) | | 7.8 | 8.1 | | <p43 |

NOTES:
- p42, p45, p59, and p43 are designations of plasmids
- plaque morphology for p59-derived chimera was determined in a separate titration experiment (not shown; result of immunofluorescence assay shown)

Fig. 7. PIV-WNV/TBE constructs

| prM-E genes | P0 titer log₁₀ FFU/ml | | P1 titer log₁₀ FFU/ml | | Immuno-staining αRSSE mHIAF |
|---|---|---|---|---|---|
| | C helper cells | CprME helper cells | C helper cells | CprME helper cells | |
| Hypr (TBEV signal) (p39) | 7.2 | 6.7 | 6.9 | 7.1 | |
| Hypr (WNV signal) (p40) | 6.7 | 6.0 | 5.9 | 6.9 | |

Fig. 8. Replication kinetics of live YF/TBE and replication defective PIV-WNV/TBE variants in cell substrates

Growth on Vero at 0.001MOI

- CV-Hypr p42
- CV-Hypr p45
- CV-LGT E5 p43
- CV-Hypr dC2 p59

Growth on helper BHK at 0.01MOI

- RV-WN/TBEV p39
- RV-WN/TBEV p40
- RV-WN/TBEV p39
- RV-WN/TBEV p40

Solid line - BHK helper expressing WNV C protein
Discontinues line - BHK cells expressing WNV CprME proteins Fig. 9. Survival of mice inoculated IC with PIV-TBE and YF/TBE constructs in the neurovirulence test (3.5 week-old ICR mice)

Fig. 10. Survival of mice inoculated IP with PIV-TBE and YF/TBE constructs in a neuroinvasiveness test (3.5 week-old ICR mice)

Survival after $5\log_{10}$ IP inoculation with

- RV-WN/Hypr p39
- RV-WN/Hypr p40
- CV-Hypr p42
- CV-Hypr p45
- CV-LGT E5 p43
- CV-Hypr dC2 p59
- YF17D Fig. 11. Post-TBE-challenge morbidity (weight loss); day 9 post-challenge Fig. 12. Examples of PIV constructs expressing foreign antigens (rabies G)

WN parent virus — [C|prM|E|NS]

ΔC-RabG sPIV — [prM|E|NS]

+

ΔprME-RabG d-PIV helper — [C|NS]

ΔCprME-RabG — [NS]

+

ΔNS1-helper — [C|prM|E|NS]

C or CprME proteins supplied in trans by VEE replicon or stable helper cells; d-PIVs produced in regular cells Packaging cells → Pseudo infectious virus (the replication defective vaccine) → Immunization NOTE: possible d-PIV formulations are shown (+).

Fig. 13. Schematic representation of insertion designs resulting in viable/expressing constructs (exemplified by rabies G)

Fig. 14. PIV-WN/Rabies G PIVs: immunofluorescence of transfected cells and growth curves after transfection Fig. 15. Efficient expression of RabG on the plasma membrane of Vero cells
MOI 0.1, day 2 post infection, 4% PFA Fixed non-permeabilized

| ΔC-Rabies G | ΔPrM-E-Rabies G | ΔC-PrM-E-Rabies G |

1Ab (Abcam) Anti Rabies 1:500 2-3hrs RT, 2Ab Anti-Mouse IgG 1:1000 1hr RT
Images are 40X and exposure time is 40ms Fig. 16. PIV - Rabies G spread in helper cells, no spread in naïve cells PIV WN ΔC - RabG Packaging Cell Lines BHK-CprME | BHK-C | BHK α rabies-G Mab MOI 0.001 D 4 p.i.

PIVs spread in helper cells and not naïve cells.
No infectious material in supernatants from BHK cells.

Similarly, VSV G was expressed, and no spread in regular cells (Vero, BHK) was observed and no infectious material detected in the supernatants Fig. 17. Stability of rabies G protein gene in PIV-WN vectors
Passages in BHK-C-prM-E helper cells, MOI 0.1; titration in Vero by immunostaining Fig. 18. Comparison of spread in Vero cells of single-component vs. two-component PIV-Rabies variants RV-WN (ΔprME)/RabG alone RV-WN (ΔprME)/RabG + RV-WN (ΔC)

Vero cells: αRabies G-Mab

Vero cells: αRabies G-Mab

Titer on helper BHK cells: 2.0x10$^8$ FFU/ml

Titer on naïve Vero cells after transfection (P0): 2.0x10$^8$ FFU/ml

Fig. 19. Example of expression of full-length RSV F protein (strain A2): immunostaining of helper cells after transfection Control BHK helper cells (WN C-prM-E)   PIV-WNΔprME-RSV F, 3 days post-transfection Cells stained with anti-RSVF Mab, DAPI

Fig. 20. PIV (WN) SIV Constructs

Synthesized genes: sequences optimized for repeats

RV WN Vectors: ΔC-prM-E, ΔprM-E, and ΔC
Construct Designs:

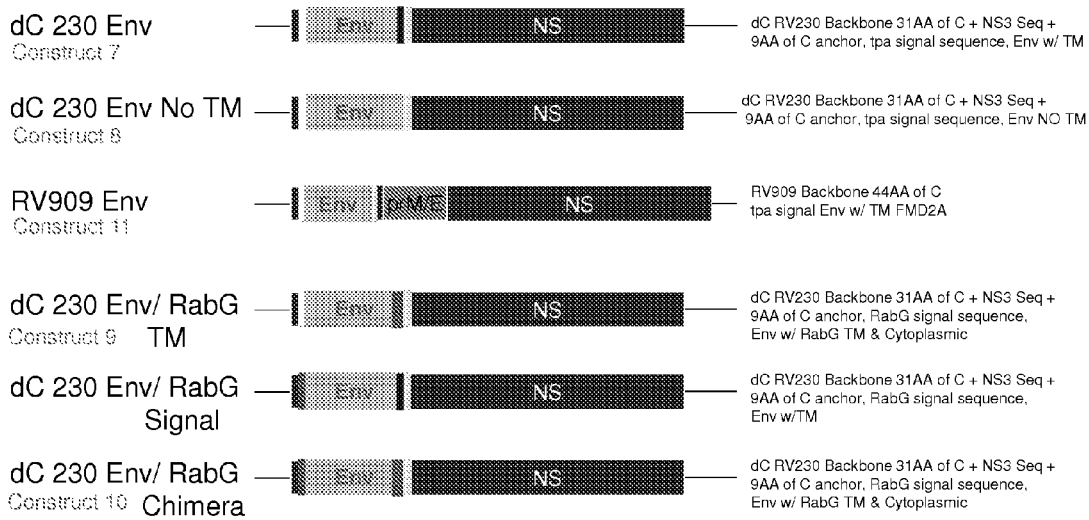
Fig. 21. Env Construct Designs

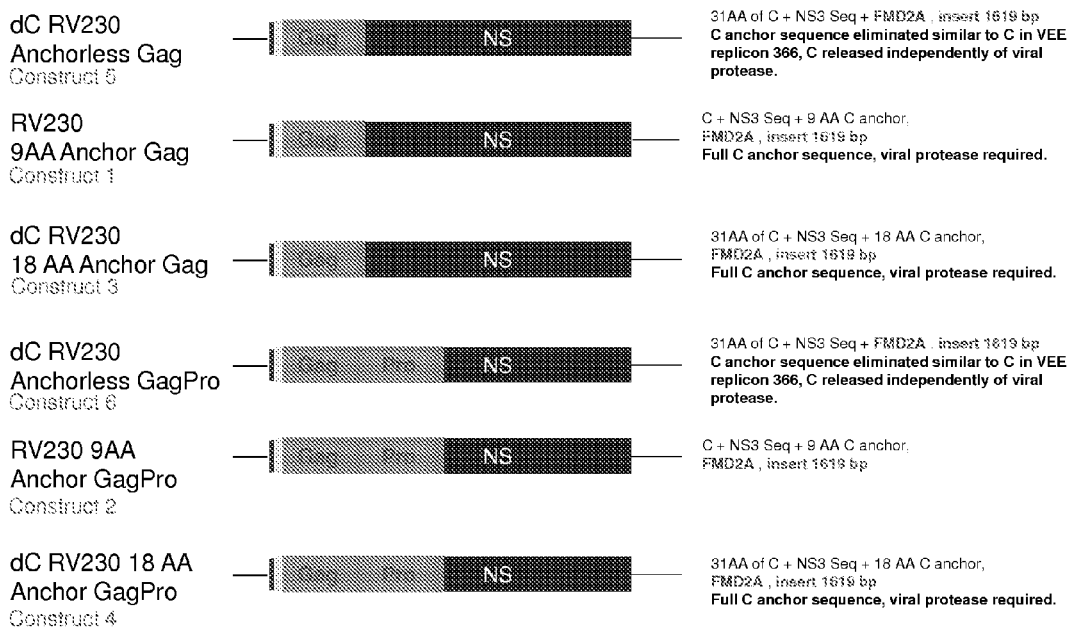
Fig. 22. Gag Construct Designs

Fig. 23. Gag Western demonstrating correct polyprotein processing
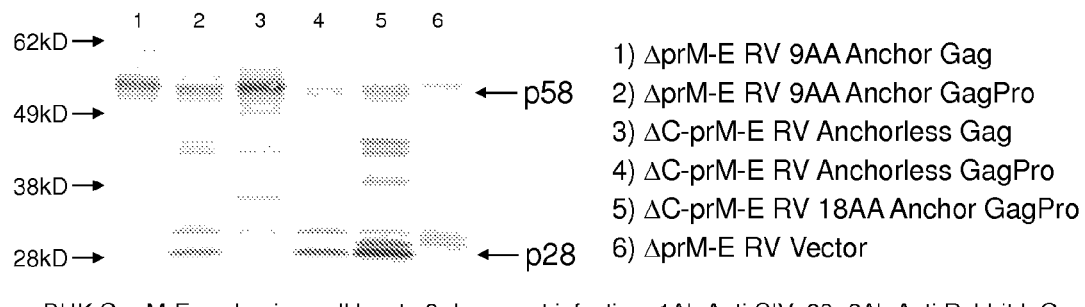
1) ΔprM-E RV 9AA Anchor Gag
2) ΔprM-E RV 9AA Anchor GagPro
3) ΔC-prM-E RV Anchorless Gag
4) ΔC-prM-E RV Anchorless GagPro
5) ΔC-prM-E RV 18AA Anchor GagPro
6) ΔprM-E RV Vector
BHK C-prM-E packaging cell lysate 3 days post infection. 1Ab Anti-SIVp28, 2Ab Anti Rabbit IgG Fig. 24. Immunostaining of RV-SIV Gag infected naïve Vero cells.

A — Lipo Control (20X)
B — RV230 9AA-FMD-Gag (20X)
C — RV230 FMD-Gag (20X)

D

RV230 9AA-FMD-Gag

105AA of C + NS3 Seq + 9AA Anchor FMD2A, insert 1619 bp

RV230 FMD-Gag

105AA of C + NS3 Seq + FMD2A, insert 1619 bp
C anchor sequence eliminated similar to C in VEE replicon 366, C released independently of viral protease.

Titration on vero cells.
Primary Lifespan Bio anti-SIV gag 1:500
Secondary: Pierce anti-rabbit IgG (Fc) 1:1000

Fig. 25. RV-SIV Gag & GagPro Growth Curves. PIVs recovered in BHK-C-prM-E helper cells; titration in Vero by immunostaining.

A. Anchorless Gag in ΔC-prM-E RepliVax
B. 9AA Anchor Gag in ΔprM-E RepliVax
C. 18AA Anchor Gag in ΔC-prM-E RepliVax
D. Anchorless GagPro in ΔC-prM-E RepliVax
E. 9AA Anchor GagPro in ΔprM-E RepliVax
F. 18AA Anchor GagPro in ΔC-prM-E RepliVax

- Similar high titers achieved for WN and SIV antigens post transfection

Fig. 26. d-PIV Gag Growth Curves in naïve Vero.
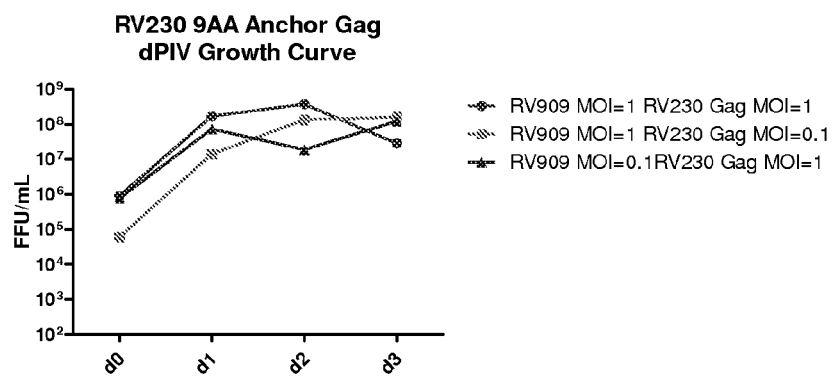
Vero cells coinfected with RV230 9AA Anchor Gag and RV230 at various MOIs. Gag specific titers are shown.

Fig. 27. Stability of the large Gag insert of RV-SIV Gag after 10 serial passages in helper cells, as demonstrated by titration using anti-WN and anti-Gag antibodies.

Serial passages of gag constructs on BHK363 cells (P10-P20) @ MOI=0.1 relative to gag titers Fig. 28. Expression of SIV Env, and better surface presentation using RabG TM.

dC230 Env RabG Chimera #7 4

Fig. 29. SIV Env on the surface of PIV-SIV Env/RabG TM infected Vero cells dC RV230 Env RabG TM 20X Magnification of Vero cells infected at a MOI of ~0.3 and fixed with 4% PFA
Primary: Genway Bio Anti-SIV Env rabbit poly 1:500.
Secondary: Anti rabbit IgG Alexa 488 1:1000

Fig. 30. PIV-flu HA Construct Designs

RV230 — [C] —ΔprME— [NS Genes]

RV230 HA Construct 1 — [C][Flu HA][NS Genes]

dC RV230 HA Construct 2 — [Flu HA][NS Genes]

Blue blocks denote WNV backbone
Green blocks denote inserted HA gene

Construct #s indicate sequences in Appendix 3

Fig. 31. RV230 HA New Caledonia P0 Growth Curves.

A
RV230 HA New Caledonia #6
— HA
— WNV

B
RV230 HA New Caledonia #10
— HA
— WNV

Day Post Transfection

Day Post Transfection

BHK 363 cells transfected at P14 with RNA from RV230 HA New Caledonia clones 6 and 10

Fig. 32. RV230 & ΔC RV230 HA New Caledonia Growth Curves.

Fig. 33. RV230 HA New Caledonia IF
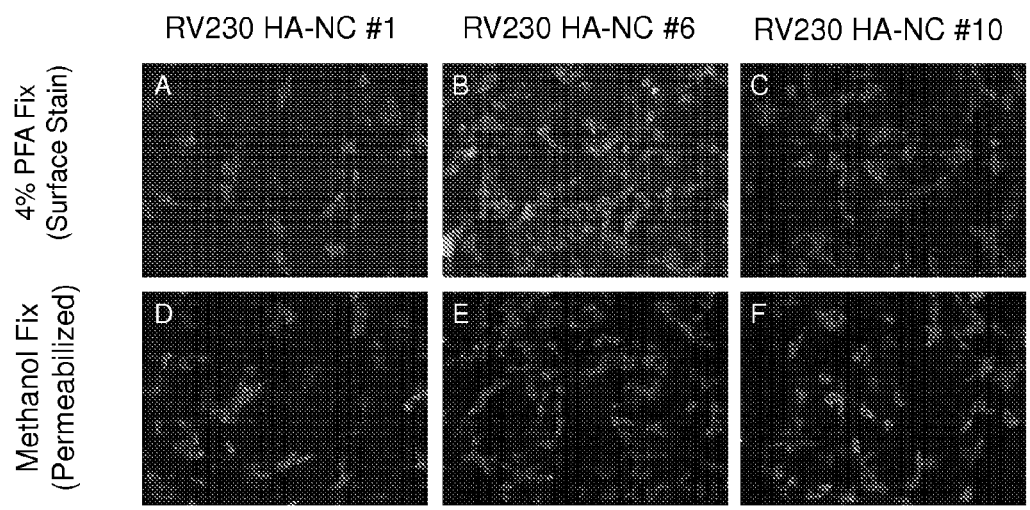
C179 & IT-003-001M2 antibodies pooled and used at final dilution of 1:1000
Pictures taken at 20X Magnification
Exposure Times: PFA Fix- HA 500 ms, DAPI 200 ms
       Methanol Fix: HA 200 ms, DAPI 100 ms

Fig. 34. dC RV230 HA New Caledonia IF
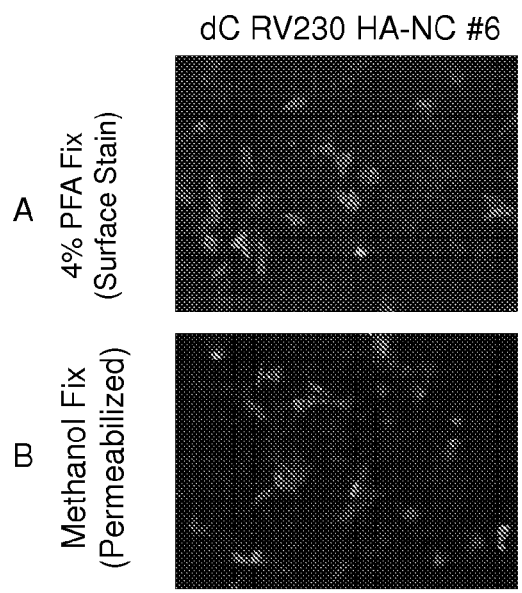
C179 & IT-003-001M2 antibodies pooled and used at final dilution of 1:1000
Pictures taken at 20X Magnification
Exposure Times:  PFA Fix- HA 500 ms, DAPI 200 ms
           Methanol Fix: HA 200 ms, DAPI 100 ms

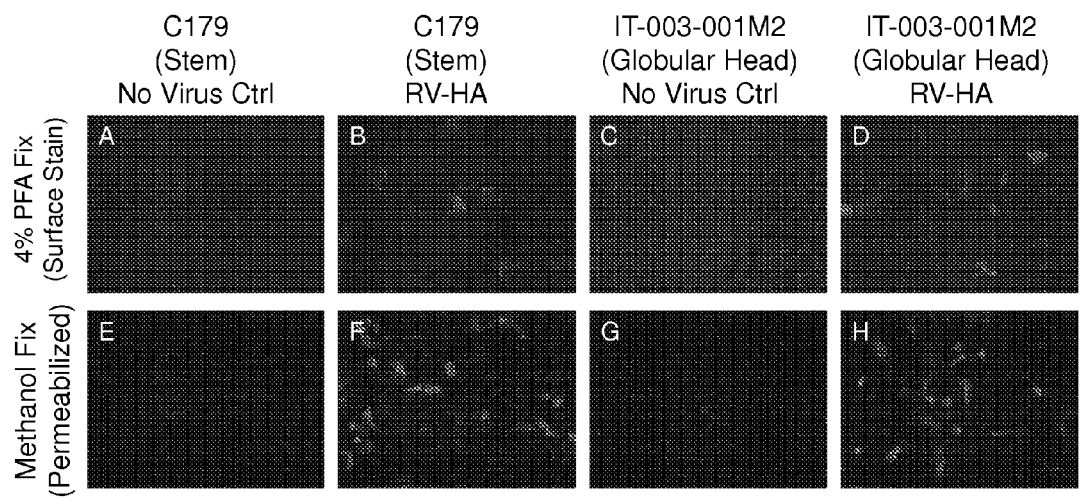
Fig. 35. Control IF of uninfected cells (see no virus controls).
C179 & IT-003-001M2 antibodies used at 1:500
Pictures taken at 20X Magnification
Exposure Times: PFA Fix- HA 500 ms, DAPI 200 ms
　　　　　　　　Methanol Fix: HA 200 ms, DAPI 100 ms Fig. 36. RV-HA New Caledonia IF Staining

|  | RV230 HA<br>New Caledonia #6 | RV230 HA<br>New Caledonia #10 |
|---|---|---|
| 4% PFA Fix<br>(Surface Stain) | A | B |
| Methanol Fix<br>(Intracellular Stain) | C | D |

Vero cell staining 48 hr post infection, 20X magnification
4% PFA fix 800 ms exposure, methanol fix 300 ms exposure, 20X Magnification
HA stained with 1:500 final pool of C179 (stem specific) and ITM-003-001M2 (globular head specific) mAbs Fig. 37. Efficient staining of RV230-HA infected Vero cells separately by anti-HA stem and anti-HA globular head antibodies.

C179 1:500
Stem Specific

ITM-003-001M2 1:500
Globular Head Specific

A

B

Vero cells 48 hr pi with RV230 HA New Caledonia,
4% PFA fixation, 800 ms exposure

REPLICATION-DEFECTIVE FLAVIVIRUS VACCINES AND VACCINE VECTORS

CROSS-REFERENCE TO RELATED APPLICATIONS

This application is a continuation of U.S. Ser. No. 13/364,187, filed Feb. 1, 2012 (abandoned), which is a continuation in part of U.S. Ser. No. 12/922,513, filed Sep. 14, 2010 (U.S. Pat. No. 8,815,564), which is the U.S. national stage filing under 35 U.S.C. §371 of international application PCT/US2009/001666, filed Mar. 16, 2009, which claims benefit of Provisional Application Nos. 61/069,451, filed Mar. 14, 2008 and 61/092,814, filed Aug. 29, 2008. The prior applications are incorporated herein by reference.

Sequence Listing

The instant application contains a Sequence Listing which has been filed electronically in ASCII format and is hereby incorporated by reference in its entirety. Said ASCII copy, created on Sept. 18, 2015, is named 06132-152003_SL.txt and is 477,191 bytes in size.

FIELD OF THE INVENTION

This invention relates to replication-defective flavivirus vaccines and vaccine vectors, and corresponding compositions and methods.

BACKGROUND OF THE INVENTION

Flaviviruses are distributed worldwide and represent a global public health problem. Flaviviruses also have a significant impact as veterinary pathogens. Flavivirus pathogens include yellow fever (YF), dengue types 1-4 (DEN 1-4), Japanese encephalitis (JE), West Nile (WN), tick-borne encephalitis (TBE), and other viruses from the TBE serocomplex, such as Kyasanur Forest disease (KFD) and Omsk hemorrhagic fever (OHF) viruses. Vaccines against YF [live attenuated vaccine (LAV) strain 17D], JE [inactivated vaccines (INV) and LAV], and TBE (INV) are available. No licensed human vaccines are currently available against DEN and WN. Veterinary vaccines have been in use including, for example, vaccines against WN in horses (INV, recombinant and live chimeric vaccines), JE (INV and LAV) to prevent encephalitis in horses and stillbirth in pigs in Asia, louping ill flavivirus (INV) to prevent neurologic disease in sheep in the UK, and TBE (INV) used in farm animals in Czech Republic (INV) (Monath and Heinz, Flaviviruses, in Fields et al. Eds., Fields Virology, 3rd Edition, Philadelphia, New York, Lippincott-Raven Publishers, 1996, pp. 961-1034).

Tick-borne encephalitis (TBE) is the most important tick-borne viral disease of humans. It is endemic in parts of Europe and Northern Asia, causing more than 10,000 hospitalizations annually, with a case-fatality rate 0.5-1.5% in Europe and 6-40% in Siberia and the Far East. A significant proportion of patients suffer from long-lasting neuropsychiatric sequelae. Inactivated vaccines produced in chick embryo cell cultures have proven effective in preventing the disease. For example, an 86% vaccination coverage of the Austrian population (the highest among European countries) has resulted in an approximately 90% reduction of hospitalized cases (Heinz and Kunz, Arch. Virol. Suppl. 18:201-205, 2004). The inactivated vaccines are expensive and require three inoculations for primary immunization. Periodic boosters (every 2-5 years) are required to maintain immunity. Therefore, a less costly TBE vaccine, which is effective after one-two doses and provides durable, such as life-long immunity (similar to that achieved by YF 17D immunization) is needed, and indeed has been identified by the WHO as a major priority. Development of TBE LAV candidates in the past several decades by means of empirical or rational attenuation of TBE virus parent per se or chimerization of TBE or Langat (LGT, a naturally attenuated flavivirus that is closely related (serologically) to TBE) viruses with dengue 4 virus has faced difficulties due to problems with residual virulence of candidates and/or low immunogenicity/overattenuation (Wright et al., Vaccine 26:882-890, 2008; Maximova et al., J. Virol. 82:5255-5268, 2008; Rumyantsev et al., Vaccine 24:133-143, 2006; Kofler et al., Arch. Virol. Suppl. 18:191-200, 2004; and references therein).

Flaviviruses are small, enveloped, plus-strand RNA viruses transmitted primarily by arthropod vectors (mosquitoes or ticks) to natural hosts, which are primarily vertebrate animals, such as various mammals, including humans, and birds. The flavivirus genomic RNA molecule is about 11,000 nucleotides (nt) in length and encompasses a long open reading frame (ORF) flanked by 5' and 3' untranslated terminal regions (UTRs) of about 120 and 500 nucleotides in length, respectively. The ORF encodes a polyprotein precursor that is cleaved co- and post-translationally to generate individual viral proteins. The proteins are encoded in the order: C-prM/M-E-NS1-NS2A/2B-NS3-NS4A/4B-NS5, where C (core/capsid), prM/M (pre-membrane/membrane), and E (envelope) are the structural proteins, i.e., the components of viral particles, and the NS proteins are non-structural proteins, which are involved in intracellular virus replication. Flavivirus replication occurs in the cytoplasm. Upon infection of cells and translation of genomic RNA, processing of the polyprotein starts with translocation of the prM portion of the polyprotein into the lumen of endoplasmic reticulum (ER) of infected cells, followed by translocation of E and NS1 portions, as directed by the hydrophobic signals for the prM, E, and NS1 proteins. Amino-termini of prM, E, and NS1 proteins are generated by cleavage with cellular signalase, which is located on the luminal side of the ER membrane, and the resulting individual proteins remain carboxy-terminally anchored in the membrane. Most of the remaining cleavages, in the nonstructural region, are carried out by the viral NS2B/NS3 serine protease. The viral protease is also responsible for generating the C-terminus of the mature C protein found in progeny virions. Newly synthesized genomic RNA molecules and the C protein form a dense spherical nucleocapsid, which becomes surrounded by cellular membrane in which the E and prM proteins are embedded. The mature M protein is produced by cleavage of prM shortly prior to virus release by cellular furin or a similar protease. E, the major protein of the envelope, is the principal target for neutralizing antibodies, the main correlate of immunity against flavivirus infection. Virus-specific cytotoxic T-lymphocyte (CTL) response is the other key attribute of immunity. Multiple CD8+ and CD4+ CTL epitopes have been characterized in various flavivirus structural and non-structural proteins. In addition, innate immune responses contribute to both virus clearance and regulating the development of adaptive immune responses and immunologic memory.

In addition to the inactivated (INV) and live-attenuated (LAV) vaccines against flaviviruses discussed above, other vaccine platforms have been developed. One example is based on chimeric flaviviruses that include yellow fever virus capsid and non-structural sequences and prM-E proteins from other flaviviruses, to which immunity is sought. This technology has been used to develop vaccine candidates against dengue (DEN), Japanese encephalitis (JE), West Nile (WN), and St. Louis encephalitis (SLE) viruses (see, e.g., U.S. Pat. Nos. 6,962,708 and 6,696,281). Yellow fever virus-based chimeric flaviviruses have yielded highly promising results in clinical trials.

Another flavivirus vaccine platform is based on the use of pseudoinfectious virus (PIV) technology (Mason et al., Virology 351:432-443, 2006; Shustov et al., J. Virol. 21:11737-11748, 2007; Widman et al., Adv. Virus. Res. 72:77-126, 2008; Suzuki et al., J. Virol. 82:6942-6951, 2008; Suzuki et al., J. Virol. 83:1870-1880, 2009; Ishikawa et al., Vaccine 26:2772-2781, 2008; Widman et al., Vaccine 26:2762-2771, 2008). PIVs are replication-defective viruses attenuated by a deletion(s). Unlike live flavivirus vaccines, they undergo a single round replication in vivo (or optionally limited rounds, for two-component constructs; see below), which may provide benefits with respect to safety. PIVs also do not induce viremia and systemic infection. Further, unlike inactivated vaccines, PIVs mimic whole virus infection, which can result in increased efficacy due to the induction of robust B- and T-cell responses, higher durability of immunity, and decreased dose requirements. Similar to whole viruses, PIV vaccines target antigen-presenting cells, such as dendritic cells, stimulate toll-like receptors (TLRs), and induce balanced Th1/Th2 immunity. In addition, PIV constructs have been shown to grow to high titers in substrate cells, with little or no cytopathic effect (CPE), allowing for high-yield manufacture, optionally employing multiple harvests and/or expansion of infected substrate cells.

The principles of the PIV technology are illustrated in FIGS. 1 and 2. There are two variations of the technology. In the first variation, a single-component pseudoinfectious virus (s-PIV) is constructed with a large deletion in the capsid protein (C), rendering mutant virus unable to form infectious viral particles in normal cells (FIG. 1). The deletion does not remove the first ~20 codons of the C protein, which contain an RNA cyclization sequence, and a similar number of codons at the end of C, which encode a viral protease cleavage site and the signal peptide for prM. The s-PIV can be propagated, e.g., during manufacture, in substrate (helper) cell cultures in which the C protein is supplied in trans, e.g., in stably transfected cells producing the C protein (or a larger helper cassette including C protein), or in cells containing an alphavirus replicon [e.g., a Venezuelan equine encephalitis virus (VEE) replicon] expressing the C protein or another intracellular expression vector expressing the C protein. Following inoculation in vivo, e.g., after immunization, the PIV undergoes a single round of replication in infected cells in the absence of trans-complementation of the deletion, without spread to surrounding cells. The infected cells produce empty virus-like particles (VLPs), which are the product of the prM-E genes in the PIV, resulting in the induction of neutralizing antibody response. A T-cell response should also be induced via MHCI presentation of viral epitopes. This approach has been applied to YF 17D virus and WN viruses and WN/JE and WN/DEN2 chimeric viruses (Mason et al., Virology 351:432-443, 2006; Suzuki et al., J. Virol. 83:1870-1880, 2009; Ishikawa et al., Vaccine 26:2772-2781, 2008; Widman et al., Vaccine 26:2762-2771, 2008; WO 2007/098267; WO 2008/137163).

In the second variation, a two-component PIV (d-PIV) is constructed (FIG. 2). Substrate cells are transfected with two defective viral RNAs, one with a deletion in the C gene and another lacking the prM-E envelope protein genes. The two defective genomes complement each other, resulting in accumulation of two types of PIVs in the cell culture medium (Shustov et al., J. Virol. 21:11737-11748, 2007; Suzuki et al., J. Virol. 82:6942-6951, 2008). Optionally, the two PIVs can be manufactured separately in appropriate helper cell lines and then mixed in a two-component formulation. The latter may offer an advantage of adjusting relative concentrations of the two components, increasing immunogenicity and efficacy. This type of PIV vaccine should be able to undergo a limited spread in vivo due to coinfection of some cells at the site of inoculation with both components. The spread is expected to be self-limiting as there are more cells in tissues than viral particles produced by initially coinfected cells. In addition, a relatively high MOI is necessary for efficient co-infection, and cells outside of the inoculation site are not expected to be efficiently coinfected (e.g., in draining lymph nodes). Cells infected with the AC PIV alone produce the highly immunogenic VLPs. Coinfected cells produce the two types of packaged defective viral particles, which also stimulate neutralizing antibodies. The limited infection is expected to result in a stronger neutralizing antibody response and T-cell response compared to s-PIVs. To decrease chances of recombination during manufacture or in vivo, including with circulating flaviviruses, viral sequences can be modified in both s-PIVs and d-PIVs using, e.g., synonymous codon replacements, to reduce nucleotide sequence homologies, and mutating the complementary cyclization 5' and 3' elements.

SUMMARY OF THE INVENTION

The invention provides replication-deficient or defective pseudoinfectious flaviviruses including a flavivirus genome that includes (i) one or more deletions or mutations in nucleotide sequences encoding one or more proteins selected from the group consisting of capsid (C), pre-membrane (prM), envelope (E), non-structural protein 1 (NS1), non-structural protein 3 (NS3), and non-structural protein 5 (NS5), and (ii) sequences encoding one or more heterologous pathogen, cancer, or allergy-related immunogens. For example, the deletion/mutation can be within capsid (C) sequences; pre-membrane (prM) and/or envelope (E) sequences; capsid (C), pre-membrane (prM), and envelope (E) sequences; or non-structural protein 1 (NS1) sequences.

The heterologous immunogen can be, for example, from a pathogen selected from the group consisting of a rabies virus (e.g., a rabies virus G protein epitope), *Borrelia burgdorferi* (e.g., OspA immunogen or an immunogenic fragment thereof), a tick (e.g., a tick saliva protein selected from the group consisting of 64TRP, Isac, and Salp20, or an immunogenic fragment thereof), an influenza virus (e.g., an influenza virus M2, hemaglutinnin (HA), or neuraminidase (NA) epitope, or an immunogenic fragment thereof), a human immunodeficiency virus (e.g., a codon-optimized HIV gag, pol, tat/nef, pro, or variants of Env protein, such as gp160, gp145, gp140, gp120, gp41, etc., or immunogenic fragments thereof), a simian immunodeficiency virus (e.g., a codon-optimized SIV gag, pol, tat/nef, pro, or variants of Env, or immunogenic fragments thereof), a human papilloma virus (e.g., an HPV16 or HPV18 capsid protein L1 or L2, or an immunogenic fragment thereof), a respiratory syncytial virus (e.g., a respiratory syncytial virus F or G glycoprotein), malaria parasite, and *Mycobacterium tuberculosis* (also see below).

The replication-deficient pseudoinfectious flaviviruses can include sequences encoding a pre-membrane (prM) and/or envelope (E) protein. Further, the replication-deficient pseudoinfectious flavivirus genomes can be selected from those of yellow fever virus, West Nile virus, tick-borne encephalitis virus, Langat virus, Japanese encephalitis virus, dengue virus, and St. Louis encephalitis virus, attenuated strains thereof, and chimeras thereof (also see below). In various examples, the chimeras include pre-membrane (prM) and envelope (E) sequences of a first flavivirus (e.g., a tick-borne encephalitis virus or a Langat virus), and capsid (C) and non-structural sequences of a second, different flavivirus (e.g., a yellow fever, a West Nile, or Langat virus).

The replication-deficient pseudoinfectious flavivirus genomes can be packaged in particles including pre-membrane (prM) and envelope (E) sequences from a flavivirus that is the same or different from that of the genomes. Further, the sequences encoding the heterologous immunogens can be inserted in the place of, or in combination with, the deletion(s) or mutation(s) of the one or more proteins.

The sequences encoding the heterologous immunogens can be inserted in the flavivirus genomes within sequences encoding the envelope (E) protein, within sequences encoding the non-structural 1 (NS1) protein, within sequences encoding the pre-membrane (prM) protein, intergenically between sequences encoding the envelope (E) protein and non-structural protein 1 (NS1), intergenically between non-structural protein 2B (NS2B) and non-structural protein 3 (NS3), and/or as a bicistronic insertion in the 3' untranslated region of the flavivirus genome.

In several embodiments, the replication-deficient pseudoinfectious flavivirus genomes include heterologous immunogen sequences from HIV, SIV, or influenza virus, such as any one or more of those described in Appendices 6-8. In particular embodiments, the replication-deficient pseudoinfectious virus is selected from any one of the SIV constructs 1-11 of Appendix 6, a construct having at least 50% sequence identity (e.g., 50%, 60%, 70%, 85%, 90%, 95%, or 99% or more sequence identity) to the nucleic acid or amino acid sequences described therein, or a construct that includes homologs and/or other naturally occurring variants of the SIV protein(s). In other embodiments, the replication-deficient pseudoinfectious virus is selected from the HIV Gag construct (PIV-WN (ΔprME)-HIV Gag) of Appendix 7, a construct having at least 50% sequence identity (e.g., 50%, 60%, 70%, 85%, 90%, 95%, or 99% or more sequence identity) to the nucleic acid or amino acid sequences described therein, or a construct that includes homologs and/or other naturally occurring variants of the HIV Gag protein. In still other embodiments, the replication-deficient pseudoinfectious virus is selected from the HIV Env construct (PIV-WN (ΔprME)-HIV Env Gp140) of Appendix 7, a construct having at least 50% sequence identity (e.g., 50%, 60%, 70%, 85%, 90%, 95%, or 99% or more sequence identity) to the nucleic acid or amino acid sequences described therein, or a construct that includes homologs and/or other naturally occurring variants of the HIV Env protein. In yet other embodiments, the replication-deficient pseudoinfectious virus is selected from construct 1 or 2 of Appendix 8, a construct having at least 50% sequence identity (e.g., 50%, 60%, 70%, 85%, 90%, 95%, or 99% or more sequence identity) to the nucleic acid or amino acid sequences described therein, or a construct that includes homologs and/or other naturally occurring variants of the HA protein.

The invention also includes compositions including a first replication-deficient pseudoinfectious flavivirus, as described above, and a second (or further), different replication-deficient pseudoinfectious flavivirus including a genome that includes one or more deletions or mutations in nucleotide sequences encoding one or more proteins selected from the group consisting of capsid (C), pre-membrane (prM), envelope (E), non-structural protein 1 (NS1), non-structural protein 3 (NS3), and non-structural protein 5 (NS5). In these compositions, the one or more proteins encoded by the sequences in which the deletion(s) or mutation(s) occur in the second, different replication-deficient pseudoinfectious flavivirus are different from the one or more proteins encoded by the sequences in which the deletion(s) occur in the first replication-deficient pseudoinfectious flavivirus.

The invention further includes methods of inducing immune responses to an immunogen in a subject, which involves administering to the subject one or more replication-deficient pseudoinfectious flavivirus and/or composition as described herein to the subject. In particular embodiments, the replication-deficient pseudoinfectious flavivirus and/or composition includes any one or more of those described in Appendices 6-8, constructs having at least 50% sequence identity (e.g., 50%, 60%, 70%, 85%, 90%, 95%, or 99% or more sequence identity) to the nucleic acid or amino acid sequences described therein, or constructs that include homologs and/or other naturally occurring variants of the immunogenic SIV, HIV, and/or HA proteins. In various examples, the subject is at risk of but does not have an infection by the pathogen or a disease or condition associated with the cancer or allergy-related immunogen. In other examples, the subject has an infection by the pathogen or a disease or condition associated with the cancer or allergy-related immunogen. The invention thus includes prophylactic and therapeutic methods. In these methods, the immunogen can be from, for example, a pathogen selected from the group consisting of a rabies virus, *Borrelia burgdorferi*, a tick, an influenza virus, a human immunodeficiency virus, a simian immunodeficiency virus, a human papilloma virus, a respiratory syncytial virus, malaria parasite, and *Mycobacterium tuberculosis* (also see below). Further, the methods can be for inducing an immune response against a protein encoded by the flavivirus genome, in addition to the source of the immunogen. In various examples, the subject is at risk of but does not have an infection by the flavivirus corresponding to the genome of the pseudoinfectious flavivirus, which includes sequences encoding a flavivirus pre-membrane and/or envelope protein. In other examples, the subject has an infection by the flavivirus corresponding to the genome of the pseudoinfectious flavivirus, which includes sequences encoding a flavivirus pre-membrane and/or envelope protein.

The invention also includes live, attenuated chimeric flaviviruses including a yellow fever virus in which sequences encoding pre-membrane and envelope proteins are replaced with sequences encoding pre-membrane and envelope proteins of a tick-borne encephalitis virus or a Langat virus, and the signal sequence between the capsid and pre-membrane proteins of the chimeric flavivirus includes a hybrid of yellow fever virus and tick-borne encephalitis or Langat virus capsid/pre-membrane signal sequences, or a variant thereof. In various examples, the capsid/pre-membrane signal sequence of the chimeric flavivirus includes yellow fever virus sequences in the amino terminal region and tick-borne encephalitis or Langat virus sequences in the carboxy terminal region (see below).

Further, the invention includes live, attenuated chimeric flaviviruses including a West Nile virus in which sequences encoding pre-membrane and envelope proteins are replaced with sequences encoding pre-membrane and envelope proteins of a tick-borne encephalitis or a Langat virus, and the signal sequence between the capsid and pre-membrane proteins of the chimeric flavivirus includes a tick-borne encephalitis or a Langat virus capsid/pre-membrane signal sequence, or a variant thereof.

The invention also includes pharmaceutical compositions including one or more pseudoinfectious flavivirus, composition, or live, attenuated flavivirus as described herein, and a pharmaceutically acceptable carrier or diluent. Further, the compositions can include an adjuvant.

Also included in the invention are replication-deficient pseudoinfectious flaviviruses including a flavivirus genome including one or more deletion(s) or mutation(s) in nucleotide sequences encoding non-structural protein 1 (NS1), non-structural protein 3 (NS3), or non-structural protein 5 (NS5).

Further, the invention includes nucleic acid molecules corresponding to the genome of a pseudoinfectious flavivirus, or the genome of the live, attenuated flavivirus, as described herein, and complements thereof.

The invention also provides methods of making replication-deficient pseudoinfectious flaviviruses as described herein, involving introducing one or more nucleic acid molecules, as described above, into a cell that expresses the protein(s) corresponding to any sequences deleted from the flavivirus genome of the replication-deficient pseudoinfectious flaviviruses. In these methods, the protein can be expressed in the cell from the genome of a second (or further), different, replication-deficient pseudoinfectious flavivirus. In other examples, the protein is expressed from a replicon (e.g., an alphavirus replicon, such as a Venezuelan Equine Encephalitis virus replicon; see below).

The invention also includes compositions containing two or more replication-deficient pseudoinfectious flaviviruses, in which two of the replication-deficient pseudoinfectious flaviviruses are selected from the groups consisting of: (a) a replication-deficient pseudoinfectious flavivirus including a genome containing Japanese encephalitis virus sequences, and a replication-deficient pseudoinfectious flavivirus including a genome containing dengue virus sequences; (b) a replication-deficient pseudoinfectious flavivirus including a genome containing yellow fever virus sequences, and a replication-deficient pseudoinfectious flavivirus including a genome containing dengue virus sequences; and (c) a replication-deficient pseudoinfectious flavivirus including a genome containing tick-borne encephalitis or Langat virus sequences and an inserted sequence encoding a *Borrelia burgdorferi* immunogen, and a replication-deficient pseudoinfectious flavivirus including a genome containing tick-borne encephalitis or Langat virus sequences and an inserted sequence encoding a tick saliva protein immunogen, or a replication-deficient pseudoinfectious flavivirus including a genome containing tick-borne encephalitis or Langat virus sequences and inserted sequences encoding a *Borrelia burgdorferi* immunogen and a tick saliva protein immunogen.

Pharmaceutical compositions including the live, attenuated chimeric flaviviruses described herein are also included in the invention. Further, the invention includes methods of inducing an immune response to tick-borne encephalitis virus or Langat virus in a subject, involving administering to the subject such a pharmaceutical composition. In various examples, the subject does not have but is at risk of developing infection by tick-borne encephalitis virus or Langat virus. In other examples, the subject is infected with tick-borne encephalitis virus or Langat virus.

The invention further includes replication-deficient pseudoinfectious flaviviruses including a flavivirus genome including one or more deletions or mutations in nucleotide sequences encoding one or more proteins selected from the group consisting of capsid (C), pre-membrane (prM), envelope (E), non-structural protein 1 (NS1), non-structural protein 3 (NS3), and non-structural protein 5 (NS5), wherein the flavivirus genome includes yellow fever virus sequences in which sequences encoding pre-membrane and envelope proteins are replaced with sequences encoding pre-membrane and envelope proteins of a tick-borne encephalitis virus or a Langat virus, and sequences encoding the signal sequence between the capsid and pre-membrane proteins of the flavivirus genome include a hybrid of sequences encoding yellow fever virus and tick-borne encephalitis or Langat virus capsid/pre-membrane signal sequences, or a variant thereof. In various examples, the sequences encoding the capsid/pre-membrane signal sequence of the flavivirus genome include yellow fever virus sequences in the 5' region and tick-borne encephalitis or Langat virus sequences in the 3' region.

Further, the invention includes replication-deficient pseudoinfectious flaviviruses including a flavivirus genome including one or more deletions or mutations in nucleotide sequences encoding one or more proteins selected from the group consisting of capsid (C), pre-membrane (prM), envelope (E), non-structural protein 1 (NS1), non-structural protein 3 (NS3), and non-structural protein 5 (NS5), wherein the flavivirus genome includes West Nile virus sequences in which sequences encoding pre-membrane and envelope proteins are replaced with sequences encoding pre-membrane and envelope proteins of a tick-borne encephalitis or a Langat virus, and the sequences encoding the signal sequence between the capsid and pre-membrane proteins of the flavivirus genome include sequences encoding a tick-borne encephalitis or a Langat virus capsid/pre-membrane signal sequence, or a variant thereof.

In addition, the invention includes replication-deficient pseudoinfectious flaviviruses including a flavivirus genome including one or more deletions or mutations in nucleotide sequences encoding one or more proteins selected from the group consisting of capsid (C), pre-membrane (prM), envelope (E), non-structural protein 1 (NS1), non-structural protein 3 (NS3), and non-structural protein 5 (NS5), wherein any capsid (C) and non-structural (NS) proteins in the flavivirus genome are from Langat virus and any pre-membrane (prM) and envelope (E) proteins are from a tick-borne encephalitis virus.

By "replication-deficient pseudoinfectious flavivirus" or "PIV" is meant a flavivirus that is replication-deficient due to a deletion or mutation in the flavivirus genome. The deletion or mutation can be, for example, a deletion of a large sequence, such as most of the capsid protein, as described herein (with the cyclization sequence remaining; see below). In other examples, sequences encoding different proteins (e.g., prM, E, NS1, NS3, and/or NS5; see below) or combinations of proteins (e.g., prM-E or C-prM-E) are deleted. This type of deletion may be advantageous if the PIV is to be used a vector to deliver a heterologous immunogen, as the deletion can permit insertion of sequences that may be, for example, at least up to the size of the deleted sequence. In other examples, the mutation can be, for example, a point mutation, provided that it results in replication deficiency, as discussed above. Because of the deletion or mutation, the genome does not encode all proteins necessary to produce a full flavivirus particle. The missing sequences can be provided in trans by a complementing cell line that is engineered to express the missing sequence (e.g., by use of a replicon; s-PIV; see below), or by co-expression of two replication-deficient genomes in the same cell, where the two replication-deficient genomes, when considered together, encode all proteins necessary for production (d-PIV system; see below).

Upon introduction into cells that do not express complementing proteins, the genomes replicate and, in some instances, generate "virus-like particles," which are released from the cells and are able to leave the cells and be immunogenic, but cannot infect other cells and lead to the generation of further particles. For example, in the case of a PIV including a deletion in capsid protein encoding sequences, after infection of cells that do not express capsid, VLPs including prM-E proteins are released from the cells. Because of the lack of capsid protein, the VLPs lack capsid and a nucleic acid genome. In the case of the d-PIV approach, production of further PIVs is possible in cells that are infected with two PIVs that complement each other with respect to the production of all required proteins (see below).

Also included in the invention are replication-defective pseudoinfectious flaviviruses including multiple heterologous immunogens from, e.g., a human immunodeficiency virus or a simian immunodeficiency virus. In various examples, the multiple immunogens can include heterologous transmembrane and/or signal sequences (from, e.g., a rabies virus G protein).

The invention provides several advantages. For example, the PIV vectors and PIVs of the invention are highly attenuated and highly efficacious after one-to-two doses, providing durable immunity. Further, unlike inactivated vaccines, PIVs mimic whole virus infection, which can result in increased efficacy due to the induction of robust B- and T-cell responses, higher durability of immunity, and decreased dose requirements. In addition, similar to whole viruses, PIV vaccines target antigen-presenting cells, such as dendritic cells, stimulate toll-like receptors (TLRs), and induce balanced Th1/Th2 immunity. PIV constructs have also been shown to grow to high titers in substrate cells, with little or no CPE, allowing for high-yield manufacture, optionally employing multiple harvests and/or expansion of infected substrate cells. Further, the PIV vectors of the invention provide an option for developing vaccines against non-flavivirus pathogens for which no vaccines are currently available.

Other features and advantages of the invention will be apparent from the following detailed description, the drawings, and the claims.

BRIEF DESCRIPTION OF THE DRAWINGS

FIG. 1 is a schematic illustration of single component PIV (s-PIV) technology.

FIG. 2 is a schematic illustration of two-component PIV (d-PIV) technology.

FIG. 3 is a schematic illustration of a general experimental design for testing immunogenicity and efficacy of PIVs in mice.

FIG. 4 is a graph comparing the humoral immune response induced by PIV-WN (RV-WN) with that of YF/WN LAV (CV-WN) in mice.

FIG. 5 is a series of graphs showing the results of challenging hamsters immunized with PIV-YF (RV-YF), YF17D, PIV-WN(RV-WN), and YF/WN LAV (CVWN) with hamster-adapted Asibi (PIV-YF and YF 17D vaccinees) and wild type WN-NY99 (PIV-WN and YF/WN LAV vaccinees).

FIG. 6 is a table showing YF/TBE and YF/LGT virus titers and plaque morphology obtained with the indicated chimeric flaviviruses.

FIG. 7 is a table showing WN/TBE PIV titers and examples of immunofluorescence of cells containing the indicated PIVs.

FIG. 8 is a set of graphs showing the replication kinetics of YF/TBE LAV and PIV-WN/TBE in Vero and BHK cell lines (CV-Hypr=YF/Hypr LAV; CV-LGT=YF/LGT LAV; RV-WN/TBEV=PIV-WN/TBEV).

FIG. 9 is a series of graphs showing survival of mice inoculated IC with PIV-TBE and YF/TBE LAV constructs in a neurovirulence test (3.5 week old ICR mice; RV-WN/Hypr=PIV-WN/TBE(Hypr); CV-Hypr=YF/TBE(Hypr) LAV; CV-LGT=YF/LGT LAV).

FIG. 10 is a graph showing survival of mice inoculated IP with PIV-WN/TBE(Hypr) (RV-WN/Hypr), YF/TBE(Hypr) LAV (CV-Hypr), and YF/LGT LAV (CV-LGT) constructs and YF17D in a neuroinvasiveness test (3.5 week old ICR mice).

FIG. 11 is a series of graphs illustrating morbidity in mice measured by dynamics of body weight loss after TBE virus challenge, for groups immunized with S-PIV-TBE candidates (upper left panel), YF/TBE and YF/LGT chimeric viruses (upper right panel), and controls (YF 17D, human killed TBE vaccine, and mock; bottom panel).

FIG. 12 is a schematic representation of PIV constructs expressing rabies virus G protein, as well as illustration of packaging of the constructs to make pseudoinfectious virus and immunization.

FIG. 13 is a schematic representation of insertion designs resulting in viable/expressing constructs (exemplified by rabies G).

FIG. 14 is series of images showing immunofluorescence analysis and graphs showing growth curves of cells transfected with the indicated PIV-WN constructs (ΔC-Rabies G, ΔPrM-E-Rabies G, and ΔC-PrM-E-Rabies G).

FIG. 15 is a series of images showing immunofluorescence analysis of RabG expressed on the plasma membranes of Vero cells transfected with the indicated PIV constructs (ΔC-Rabies G, ΔPrM-E-Rabies G, and AC-PrM-E-Rabies G).

FIG. 16 is a schematic illustration of a PIV-WN-rabies G construct and a series of images showing that this construct spreads in helper cells, but not in naïve cells.

FIG. 17 is a series of graphs showing stability of the rabies G protein gene in PIV-WN vectors.

FIG. 18 is a set of images showing a comparison of spread of single-component vs. two-component PIV-WN-rabies G variants in Vero cells.

FIG. 19 is a set of immunofluorescence images showing expression of full-length RSV F protein (strain A2) by the AprM-E component of d-PIV-WN in helper cells after transfection.

FIG. 20 is a schematic representation of an artificial cassette containing SIV (GenBank accession number ADM52218.1) gp120 (the native signal sequence in the gene was replaced with the tPA signal and gp41 was truncated to contain only the TM domain), Gag, and Pro (protease) genes.

FIG. 21 is a schematic representation of inserts of the first three constructs in FIG. 20 (the three top constructs shown in FIG. 21), starting with the Env glycoprotein that were designed similarly to the PIV WN-rabies G vectors described herein (see, e.g., FIGS. 12-14 and hereinbelow), in which the gp120 signal is fused with a portion of the signal sequence for prM (e.g., at the end of the C gene or downstream from ΔC deletion depending on vector). In addition, schematic representations of alternate dC RV230 Env PIV constructs are shown (the three bottom constructs shown in FIG. 21).

FIG. 22 is a schematic representation of Gag and Gag-Pro PIV construct designs, in which Gag and Gag-Pro were cloned in place of the ΔprM-E or ΔC-prM-E deletions.

FIG. 23 is a photograph of a Western blot using anti-Gag antibodies, which shows correct processing of the polyprotein in recovered SIV Gag and SIV Gag/Pro PIVs grown in helper cells.

FIGS. 24A-24C are photomicrographs showing that immunostaining of naïve Vero cells infected with the Gag PIVs, showed individual stained cells as expected from sPIV. FIG. 24A is a negative control, FIG. 24B shows immunostaining of naïve Vero cells infected with RV230 9AA-FMD-Gag PIV, and FIG. 24C shows immunostaining of naïve Vero cells infected with RV230 FMD-Gag PIV. The two constructs are illustrated schematically in FIG. 24D.

FIGS. 25A-F are graphs showing growth curves of SIV Gag PIV variants after transfection of helper cells with in vitro synthesized PIV RNA (P0 passage) indicating efficient replication in vivo. Immunofluorescence images of Vero cells infected with the variants are shown inset.

FIG. 26 is a graph showing growth curves in naïve Vero cells of SIV Gag PIV as a two-component formulation (d-PIV, sometimes also designated as tc-PIV) together with PIV-WN helper with ΔC deletion (RV909).

FIG. 27 is a graph showing high insert stability for one of the SIV Gag PIV variants (RV230-Gag variant, containing Gag gene in place of large ΔprM-E deletion, in helper BHK-CprME(WN) cells at MOI 0.1 FFU/cell) when examined by ten serial passages.

FIGS. 28A-D are immunofluorescence images showing efficient expression of SIV Env (gp120) in Vero cells using PIV-(WN)-SIV Env variants. Efficient intracellular expression of the original gp120 was observed in Vero cells infected with packaged dC230Env PIV variant as determined by immunostaining using anti-SIV Env antibody after methanol fixation (FIG. 28D), although transport of gp120 to the surface of infected Vero cells was inefficient, as determined following formalin fixation (FIG. 28B). In contrast, the dC230Env/RabG anchor PIV construct (see FIG. 21), in which the SIV Env TM domain was replaced with the TM anchor sequence from rabies virus G protein, showed efficient intracellular (FIG. 28C) and extracellular expression (FIG. 28A).

FIG. 29 is an immunofluorescence image showing expression of SIV Env on the surface of PIV-SIV Env/RabG TM infected Vero cells.

FIG. 30 is a schematic representation of PIV-flu HA construct designs, in which the full-length HA gene of Flu strain New Calcdonia was cloned in place of ΔprM-E and ΔC-prM-E deletions of PIV-WN vectors in the same fashion as described for Rabies G, RSV F and SIV Env (as is described herein).

FIGS. 31A-B are graphs showing growth curves in BHK 363 helper cells transfected at P14 with RNA from RV230 HA New Calcdonia PIV clones 6 (FIG. 31A) and 10 (FIG. 31B), as determined by immunostaining with anti-WN and anti-HA antibodies.

FIGS. 32A-D are graphs showing growth curves in BHK 363 helper cells transfected at P14 with RNA from RV230 HA New Calcdonia PIV clones 1, 6, and 10 (FIGS. 32A-C, respectively) and from dC RV230 HA New Calcdonia PIV clone 6 (FIG. 32D), as determined by immunostaining with anti-WN and anti-HA antibodies.

FIGS. 33A-F are immunofluorescence images showing surface expression (FIGS. 33A-C) and intracellular expression (FIGS. 33D-F) of HA in Vero cells infected with RV230 HA New Calcdonia PIV clones 1, 6, and 10, respectively.

FIGS. 34A-B are immunofluorescence images showing surface expression (FIG. 34A) and intracellular expression (FIG. 34B) of HA in Vero cells infected with dC RV230 HA New Calcdonia PIV clone 6.

FIG. 35 shows immunofluorescence images confirming surface expression (FIGS. 35B and D) and intracellular expression (FIGS. 35F and H) of HA in Vero cells infected with RV230 HA New Calcdonia PIV. FIGS. 35A, C, E, and G are negative controls showing the lack surface expression (FIGS. 35A and C) and intracellular expression (FIGS. 35E and G) of HA in uninfected Vero cells. The immunofluorescence images in FIGS. 35B and F were produced using antibodies against the stem of HA, while the immunofluorescence images in FIGS. 35D and H were produced using antibodies against the HA globular head. FIGS. 35B, D, F, and H confirm the correct, native protein confirmation of HA.

FIGS. 36A-D are immunofluorescence images showing surface expression (FIGS. 36A and B) and intracellular expression (FIGS. 36C and D) of HA in Vero cells infected with RV230 HA New Calcdonia PIV clones 6 and 10, respectively, 48 hours post infection. Staining was performed with a mix of HA stem and globular head antibodies.

FIG. 37A is an immunofluorescence image showing staining of RV230-HA PIV infected Vero cells by HA stem-specific antibodies. FIG. 37B is an immunofluorescence image showing staining of RV230-HA PIV infected Vero cells by HA globular head-specific antibodies.

DETAILED DESCRIPTION OF THE INVENTION

The invention provides replication-defective or deficient pseudoinfectious virus (PIV) vectors including flavivirus sequences, which can be used in methods for inducing immunity against heterologous pathogen, cancer, and allergy-related immunogens inserted into the vectors as well as, optionally, the vectors themselves. The invention also includes compositions including combinations of PIVs and/or PIV vectors, as described herein, and methods of using such compositions to induce immune responses against inserted immunogen sequences and/or sequences of the PIVs themselves. Further, the invention includes particular PIVs and live, attenuated chimeric flaviviruses including tick-borne encephalitis virus sequences, and related vectors, compositions, and methods of use. The PIV vectors, PIVs, live attenuated chimeric flaviviruses, compositions, and methods of the invention are described further below.

PIV Vectors and PIVs

The PIV vectors and PIVs of the invention can be based on the single- or two-component PIVs described above (also see WO 2007/098267 and WO 2008/137163). Thus, for example, in the case of single component PIVs, the PIV vectors and PIVs can include a genome including a large deletion in capsid protein encoding sequences and be produced in a complementing cell line that produces capsid protein in trans (single component; FIG. 1 and FIG. 12). According to this approach, most of the capsid-encoding region is deleted, which prevents the PIV genome from producing infectious progeny in normal cell lines (i.e., cell lines not expressing capsid sequences) and vaccinated subjects. The capsid deletion typically does not disrupt RNA sequences required for genome cyclization (i.e., the sequence encoding amino acids in the region of positions 1-26), and/or the prM sequence required for maturation of prM to M. In specific examples, the deleted sequences correspond to those encoding amino acids 26-100, 26-93, 31-100, or 31-93 of the C protein.

Single component PIV vectors and PIVs can be propagated in cell lines that express either C or a C-prM-E cassette, where they replicate to high levels. Exemplary cell lines that can be used for expression of single component PIV vectors and PIVs include BHK-21 (e.g., ATCC CCL-10), Vero (e.g., ATCC CCL-81), C7/10, and other cells of vertebrate or mosquito origin. The C or C-prM-E cassette can be expressed in such cells by use of a viral vector-derived replicon, such as an alphavirus replicon (e.g., a replicon based on Venezuelan Equine Encephalitis virus (VEEV), Sindbis virus, Semliki Forest virus (SFV), Eastern Equine Encephalitis virus (EEEV), Western Equine Encephalitis virus (WEEV), or Ross River virus). To decrease the possibility of productive recombination between the PIV vectors/PIVs and complementing sequences, the sequences in the replicons (encoding C, prM, and/or E) can include nucleotide mutations. For example, sequences encoding a complementing C protein can include an unnatural cyclization sequence. The mutations can result from codon optimization, which can provide an additional benefit with respect to PIV yield. Further, in the case of complementing cells expressing C protein sequences (and not a C-prM-E cassette), it may be beneficial to include an anchoring sequence at the carboxy terminus of the C protein including, for example, about 20 amino acids of prM (see, e.g., WO 2007/098267).

The PIV vectors and PIVs of the invention can also be based on the two-component genome technology described above. This technology employs two partial genome constructs, each of which is deficient in expression of at least one protein required for productive replication (capsid or prM/E) but, when present in the same cell, result in the production of all components necessary to make a PIV. Thus, in one example of the two-component genome technology, the first component includes a large deletion of C, as described above in reference to single component PIVs, and the second component includes a deletion of prM and E (FIG. 2 and FIG. 12). In another example, the first component includes a deletion of C, prM, and E, and the second component includes a deletion of NS1 (FIG. 12). Both components can include cis-acting promoter elements required for RNA replication and a complete set of non-structural proteins, which form the replicative enzyme complex. Thus, both defective genomes can include a 5'-untranslated region and at least about 60 nucleotides (Element 1) of the following, natural protein-coding sequence, which comprises an amino-terminal fragment of the capsid protein. This sequence can be followed by a protease cleavage sequence such as, for example, a ubiquitine or foot-and-mouth disease virus (FAMDV)-specific 2A protease sequence, which can be fused with either capsid or envelope (prM-E) coding sequences. Further, artificial, codon optimized sequences can be used to exclude the possibility of recombination between the two defective viral genomes, which could lead to formation of replication-competent viruses (see, e.g., WO 2008/137163). Use of the two-component genome approach does not require the development of cell lines expressing complementing genomes, such as the cells transformed with replicons, as discussed above in reference to the single component PIV approach. Exemplary cell lines that can be used in the two-component genome approach include Vero (e.g., ATCC CCL-81), BHK-21 (e.g., ATCC CCL-10), C7/10, and other cells of vertebrate or mosquito origin.

Additional examples of d-PIV approaches that can be used in the invention are based on use of complementing genomes including deletions in NS3 or NS5 sequences. A deletion in, e.g., NS1, NS3, or NS5 proteins can be used as long as several hundred amino acids in the ORF, removing the entire chosen protein sequence, or as short as 1 amino acid inactivating protein enzymatic activity (e.g., NS5 RNA polymerase activity, NS3 helicase activity, etc.). Alternatively, point amino acid changes (as few as 1 amino acid mutation, or optionally more mutations) can be introduced into any NS protein, inactivating enzymatic activity. In addition, several ΔNS deletions can be combined in one helper molecule. The same heterologous gene, i.e., expressed by the first d-PIV component, can be expressed in place or in combination with the NS deletion(s) in the second component, increasing the amount of expressed immunogen. Notably, the insertion capacity of the helper will increase proportionally to the size of NS deletion(s). Alternatively, a different foreign immunogen(s) can be inserted in place of deletion(s) of the helper to produce multivalent vaccines.

Further, additional approaches that can be used in making PIV vectors and PIVs for use in the present invention are described, for example, in WO 99/28487, WO 03/046189, WO 2004/108936, US 2004/0265338, US 2007/0249032, and U.S. Pat. No. 7,332,322.

The PIV vectors and PIVs of the invention can be comprised of sequences from a single flavivirus type (e.g., tick-borne encephalitis (TBE, e.g., strain Hypr), Langat (LGT), yellow fever (e.g., YF17D), West Nile, Japanese encephalitis, dengue (serotype 1-4), St. Louis encephalitis, Kunjin, Rocio encephalitis, Ilheus, Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, and Apoi viruses), or can comprise sequences from two or more different flaviviruses. Sequences of some strains of these viruses are readily available from generally accessible sequence databases; sequences of other strains can be easily determined by methods well known in the art. In the case of PIV vectors and PIVs including sequences of more than one flavivirus, the sequences can be those of a chimeric flavivirus, as described above (also see, e.g., U.S. Pat. Nos. 6,962,708; 6,696,281; and 6,184,024). In certain examples, the chimeras include pre-membrane and envelope sequences from one flavivirus (such as a flavivirus to which immunity may be desired), and capsid and non-structural sequences from a second, different flavivirus. In one specific example, the second flavivirus is a yellow fever virus, such as the vaccine strain YF17D. Other examples include the YF/TBE, YF/LGT, WN/TBE, and WN/LGT chimeras described below. Another example is an LGT/TBE chimera based on LGT virus backbone containing TBE virus prM-E proteins. A PIV vaccine based on this genetic background would have an advantage, because LGT replicates very efficiently in vitro and is highly attenuated and immunogenic for humans. Thus, a chimeric LGT/TBE PIV vaccine is expected to provide a robust specific immune response in humans against TBE, particularly due to inclusion of TBE prM-E genes. Vectors of the invention can be based on PIV constructs or live, attenuated chimeric flaviviruses as described herein (in particular, YF/TBE, YF/LGT, WN/TBE, and WN/LGT; see below). Use of PIV constructs as vectors provides particular advantages in certain circumstances, because these constructs by necessity include large deletions, which render the constructs more amenable to accommodation of insertions that are at least up to the size of the deleted sequences, without there being a loss in replication efficiency. Thus, PIV vectors in general can comprise very small insertions (e.g., in the range 6-10, 11-20, 21-100, 101-500, or more amino acid residues combined with the ΔC deletion or other deletions), as well as relatively large insertions or insertions of intermediate size (e.g., in the range 501-1000, 1001-1700, 1701-3000, or 3001-4000 or more residues). In contrast, in certain examples, it may be advantageous to express relatively short sequences in live attenuated viruses, particularly if the insertions are made in the absence of a corresponding deletion. Additional information concerning insertion sites that can be used in the invention is provided below. In addition, as discussed further below, expression of non-flavivirus immunogens in PIVs and chimeric flaviviruses of the invention can result in dual vaccines that elicit protective immunity against both a flavivirus vector virus pathogen and a target heterologous immunogen (e.g., a pathogen (such as a bacterial, viral, parasite, or fungal pathogen), cancer, or allergy-related immunogen).

As discussed above, the PIV vectors and PIVs of the invention can comprise sequences of chimeric flaviviruses, for example, chimeric flaviviruses including pre-membrane and envelope sequences of a first flavivirus (e.g., a flavivirus to which immunity is sought), and capsid and non-structural sequences of a second, different flavivirus, such as a yellow fever virus (e.g., YF17D; see above and also U.S. Pat. No. 6,962,708; 6,696,281; and 6,184,024). Further, chimeric flaviviruses of the invention, used as a source for constructing PIVs, or as vaccines/vaccine vectors per se, can optionally include one or more specific attenuating mutations (e.g., E protein mutations, prM protein mutations, deletions in the C protein, and/or deletions in the 3'UTR), such as any of those described in WO 2006/116182. For example, the C protein or 3'UTR deletions can be directly applied to YF/TBE or YF/LGT chimeras. Similar deletions can be designed and introduced in other chimeric LAV candidates such as based on LGT/TBE, WN/TBE, and WN/LGT genomes. With respect to E protein mutations, attenuating mutations similar to those described for YF/WN chimera in WO 2006/116182 can be designed, e.g., based on the knowledge of crystal structure of the E protein (Rey et al., Nature 375(6529):291-298, 1995), and employed. Further, additional examples of attenuating E protein mutations described for TBE virus and other flaviviruses are provided in Table 9. These can be similarly introduced into chimeric vaccine candidates.

The invention also provides new, particular chimeric flaviviruses, which can be used as a basis for the design of PIV vectors and PIVs, as live attenuated chimeric flavivirus vectors, and as vaccines against the source(s) of the pre-membrane and envelope components of the chimeras. These chimeras include tick-borne encephalitis (TBE) virus or related prM-E sequences. Thus, the chimeras can include prM-E sequences from, for example, the Hypr strain of TBE or Langat (LGT) virus. Capsid and non-structural proteins of the chimeras can include those from yellow fever virus (e.g., YF17D) or West Nile virus (e.g., NY99).

A central feature of these exemplary YF/TBE, YF/LGT, WN/TBE, and WN/LGT chimeras is the signal sequence between the capsid and prM proteins. As is shown in the Examples, below, we have found that, in the case of YF-based PIV chimeras, it is advantageous to use a signal sequence comprising yellow fever and TBE sequences (see below). In one example, the signal sequence includes yellow fever sequences in the amino terminal region (e.g., SHDVLTVQ-FLIL) and TBE sequences in the carboxy terminal region (e.g., GMLGMTIA), resulting in the sequence SHDVLTVQ-FLILGMLGMTIA. We have also found that, in the case of WN-based PIV chimeras, it is advantageous to use a signal sequence comprising TBE sequences (e.g., GGTDWM-SWLLVIGMLGMTIA). The invention thus includes YF/TBE, YF/LGT, WN/TBE, and WN/LGT chimeras, both PIVs and LAVs, which include the above-noted signal sequences, or variants thereof having, e.g., 1-8,2-7, 3-6, or 4-5 amino acid substitutions, deletions, or insertions, which do not substantially interfere with processing at the signal sequence. In various examples, the substitutions are "conservative substitutions," which are characterized by replacement of one amino acid residue with another, biologically similar residue. Examples of conservative substitutions include the substitution of one hydrophobic residue such as isoleucine, valine, leucine, or methionine for another, or the substitution of one polar residue for another, such as between arginine and lysine, between glutamic and aspartic acids, or between glutamine and asparagine and the like. Examples of exemplary PIVs of the present invention include those described in Appendices 6-8, constructs having at least 50% sequence identity (e.g., 50%, 60%, 70%, 85%, 90%, 95%, or 99% or more sequence identity) to the nucleic acid or amino acid sequences described therein, or constructs that include homologs and/or other naturally occurring variants of the SIV, HIV, and/or HA proteins. Additional information concerning these and other chimeras is provided below, in the Examples.

Insertion Sites

Sequences encoding immunogens can be inserted at one or more different sites within the vectors of the invention. Relatively short peptides can be delivered on the surface of PIV or LAV glycoproteins (e.g., prM, E, and/or NS1 proteins) and/or in the context of other proteins (to induce predominantly B-cell and T-cell responses, respectively). Other inserts, including larger portions of foreign proteins, as well as complete proteins, can be expressed intergenically, at the N- and C-termini of the polyprotein, or bicistronically (e.g., within the ORF under an IRES or in the 3'UTR under an IRES; see, e.g., WO 02/102828, WO 2008/036146, WO 2008/094674, WO 2008/100464, WO 2008/115314, and below for further details). In PIV constructs, there is an additional option of inserting a foreign amino acid sequence directly in place of introduced deletion(s). Insertions can be made in, for example, ΔC, ΔprM-E, ΔC-prM-E, ΔNS1, ΔNS3, and ΔNS5. Thus, in one example, in the case of s-PIVs and the ΔC component of d-PIVs, immunogen-encoding sequences can be inserted in place of deleted capsid sequences. Immunogen-encoding sequences can also, optionally, be inserted in place of deleted prM-E sequences in the ΔprM-E component of d-PIVs. In another example, the sequences are inserted in place of or combined with deleted sequences in ΔC-prM-E constructs. Examples of such insertions are provided in the Examples section, below.

In the case of making insertions into PIV deletions, the insertions can be made with a few (e.g., 1, 2, 3, 4, or 5) additional vector-specific residues at the N- and/or C-termini of the foreign immunogen, if the sequence is simply fused in-frame (e.g., ~20 first a.a. and a few last residues of the C protein if the sequence replaces the ΔC deletion), or without, if the foreign immunogen is flanked by appropriate elements well known in the field (e.g., viral protease cleavage sites; cellular protease cleavage sites, such as signalase, furin, etc.; autoprotease; termination codon; and/or IRES elements).

If a protein is expressed outside of the continuous viral open reading frame (ORF), e.g., if vector and non-vector sequences are separated by an internal ribosome entry site (IRES), cytoplasmic expression of the product can be achieved or the product can be directed towards the secretory pathway by using appropriate signal/anchor segments, as desired. If the protein is expressed within the vector ORF, important considerations include cleavage of the foreign protein from the nascent polyprotein sequence, and maintaining correct topology of the foreign protein and all viral proteins (to ensure vector viability) relative to the ER membrane, e.g., translocation of secreted proteins into the ER lumen, or keeping cytoplasmic proteins or membrane-associated proteins in the cytoplasm/in association with the ER membrane.

In more detail, the above-described approaches to making insertions can employ the use of, for instance, appropriate vector-derived, insert-derived, or unrelated signal and anchor sequences included at the N and C termini of glycoprotein inserts. For example, all or a portion of the rabies G-derived signal and/or anchor sequences can be used in place of all or a portion of the signal and/or anchor sequences for glycoprotein inserts (e.g., one or more of the SIV, HIV, or influenza virus proteins described herein) to produce a heterologous polypeptide sequence. Standard autoproteases, such as FMDV 2A autoprotease (~20 amino acids) or ubiquitin (gene ~500 nt), or flanking viral NS2B/NS3 protease cleavage sites can be used to direct cleavage of an expressed product from a growing polypeptide chain, to release a foreign protein from a vector polyprotein, and to ensure viability of the construct. Optionally, growth of the polyprotein chain can be terminated by using a termination codon, e.g., following a foreign gene insert, and synthesis of the remaining proteins in the constructs can be re-initiated by incorporation of an IRES element, e.g., the encephalomyocarditis virus (EMCV) IRES commonly used in the field of RNA virus vectors. Viable recombinants can be recovered from helper cells (or regular cells for d-PIV versions). Optionally, backbone PIV sequences can be rearranged, e.g., if the latter results in more efficient expression of a foreign gene. For example, a gene rearrangement has been applied to TBE virus, in which the prM-E genes were moved to the 3' end of the genome under the control of an IRES (Orlinger et al., J. Virol. 80:12197-12208, 2006). Translocation of prM-E or any other genes can be applied to PIV flavivirus vaccine candidates and expression vectors, according to the invention.

Additional details concerning different insertion sites that can be used in the invention are as follows (also see WO 02/102828, WO 2008/036146, WO 2008/094674, WO 2008/100464, WO 2008/115314, as noted above). Peptide sequences can be inserted within the envelope protein, which is the principle target for neutralizing antibodies. The sequences can be inserted into the envelope in, for example, positions corresponding to amino acid positions 59, 207, 231, 277, 287, 340, and/or 436 of the Japanese encephalitis virus envelope protein (see, e.g., WO 2008/115314 and WO 02/102828). To identify the corresponding loci in different flaviviruses, the flavivirus sequences are aligned with that of Japanese encephalitis virus. As there may not be an exact match, it should be understood that, in non-JE viruses, the site of insertion may vary by, for example, 1, 2, 3, 4, or 5 amino acids, in either direction. Further, given the identification of such sites as being permissive in JE, they can also vary in JE by, for example, 1, 2, 3, 4, or 5 amino acids, in either direction. Additional permissive sites can be identified using methods such as transposon mutagenesis (see, e.g., WO 02/102828 and WO 2008/036146). The insertions can be made at the indicated amino acids by insertion just C-terminal to the indicated amino acids (i.e., between amino acids 51-52, 207-208, 231-232, 277-278, 287-288, 340-341, and 436-437), or in place of short deletions (e.g., deletions of 1, 2, 3, 4, 5, 6, 7, or 8 amino acids) beginning at the indicated amino acids (or within 1-5 positions thereof, in either direction).

In addition to the envelope protein, insertions can be made into other virus proteins including, for example, the membrane/pre-membrane protein and NS1 (see, e.g., WO 2008/036146). For example, insertions can be made into a sequence preceding the capsid/pre-membrane cleavage site (at, e.g., −4, −2, or −1) or within the first 50 amino acids of the pre-membrane protein (e.g., at position 26), and/or between amino acids 236 and 237 of NS1 (or in regions surrounding the indicated sequences, as described above). In other examples, insertions can be made intergenically. For example, an insertion can be made between E and NS1 proteins and/or between NS2B and NS3 proteins (see, e.g., WO 2008/100464). In one example of an intergenic insertion, the inserted sequence can be fused with the C-terminus of the E protein of the vector, after the C-terminal signal/anchor sequence of the E protein, and the insertion can include a C-terminal anchor/signal sequence, which is fused with vector NS1 sequences. In another example of an intergenic insertion, the inserted sequences, with flanking protease cleavage sites (e.g., YF 17D cleavage sites), can be inserted into a unique restriction site introduced at the NS2B/NS3 junction (WO 2008/100464).

In other examples, a sequence can be inserted in the context of an internal ribosome entry site (IRES, e.g., an IRES derived from encephalomyocarditis virus; EMCV), as noted above, such as inserted in the 3'-untranslated region (WO 2008/094674). In one example of such a vector, employing, for example, yellow fever virus sequences, an IRES-immunogen cassette can be inserted into a multiple cloning site engineered into the 3'-untranslated region of the vector, e.g., in a deletion (e.g., a 136 nucleotide deletion in the case of a yellow fever virus-based example) after the polyprotein stop codon (WO 2008/094674).

Details concerning the insertion of rabies virus G protein and full-length respiratory syncytial virus (RSV) F protein into s-PIV and d-PIV vectors of the invention are provided below in Example 3. The information provided in Example 3 can be applied in the context of other vectors and immunogens described herein.

Immunogens

PIVs (s-PIVs and d-PIVs) based on flavivirus sequences and live, attenuated chimeric flaviviruses (e.g., YF/TBE, YF/LGT, WN/TBE, and WN/LGT), as described above, can be used in the invention to deliver foreign (e.g., non-flavivirus) pathogen (e.g., viral, bacterial, fungal, and parasitic pathogens), cancer, and allergy-related immunogens. As discussed further below, in certain examples, it may be advantageous to target several pathogens occupying the same ecological niche, in a particular geographical region. Specific, non-limiting examples of such immunogens are provided as follows.

In addition to TBE virus, ticks are known to transmit another major disease, Lyme disease. Thus, in a first example, PIVs of the invention, such as PIVs including TBE/LGT sequences, as well as chimeric flaviviruses including TBE sequences (e.g., YF/TBE, YF/LGT, WN/TBE, LGT/TBE, and WN/LGT; in all instances where "TBE" is indicated, this includes the option of using the Hypr strain), can be used as vectors to deliver protective immunogens of the causative agent of Lyme disease (tick-borne spirochete *Borrelia burgdorferi*). This combination, targeting both infectious agents (TBE and *B. burgdorferi*) is advantageous, because TBE and Lyme disease are both tick-borne diseases. The PIV approaches can be applied to chimeras (e.g., YF/TBE, YF/LGT, WN/TBE, or WN/LGT), according to the invention, as well as to non-chimeric TBE and LGT viruses. An exemplary immunogen from *B. burgdorferi* that can be used in the invention is OspA (Gipson et al., Vaccine 21:3875-3884, 2003). Optionally, to increase safety and/or immunogenicity, OspA can be mutated to reduce chances of autoimmune responses and/or to eliminate sites for unwanted post-translational modification in vertebrate animal cells, such as N-linked glycosylation, which may affect immunogenicity of the expression product. Mutations that decrease autoimmunity can include, e.g., those described by Willett et al., Proc. Natl. Acad. Sci. U.S.A. 101:1303-1308, 2004. In one example, FTK-OspA, a putative cross-reactive T cell epitope, Bb OspA$_{165-173}$ (YVLEGTLTA) is altered to resemble the corresponding peptide sequence of *Borrelia afzelli* (FTLEGKVAN). In FTK-OspA, the corresponding sequence is FTLEGKLTA.

The sequence of OspA is as follows:

```
  1 mkkyllgigl ilaliackgn vssldeknsv svdlpgemkv lvskeknkdg
kydliatvdk 61 lelkgtsdkn ngsgvlegvk adkskvklti sddlgqttle vfkedgktlv
skkvtskdks 121 steekfnekg evsekiitra dgtrleyttgi ksdgsgkake vlkgyvlegt
ltaekttlvv 181 kegtvtlskn isksgevsve lndtdssaat kktaawnsgt stltitvnsk
ktkdlvftke 241 ntitvqqyds ngtklegsav eitkldeikn alk
```

The full-length sequence and/or immunogenic fragments of the full-length sequence can be used in the present invention. Exemplary fragments can include one or more of domains 1 (amino acids 34-41), 2 (amino acids 65-75), 3 (amino acids 190-220), and 4 (amino acids 250-270) (Jiang et al., Clin. Diag. Lab. Immun. 1(4):406-412, 1994). Thus, for example, a peptide comprising any one (or more) of the following sequences (which include sequence variations that can be included in the sequence listed above, in any combination) can be delivered: LPGE/GM/IK/T/GVL; GTSDKN/S/DNGSGV/T; N/H/EIS/P/L/A/SK/NSGEV/IS/TV/AE/ALN/DDT/SD/NS/TS/TA/Q/RATKKTA/GA/K/TWN/DS/AG/N/KT; SN/AGTK/NLEGS/N/K/TAVEIT/KK/TLD/KEI/LKN.

In addition to *B. burgdorferi* immunogens, tick saliva proteins, such as 64TRP, Isac, and Salp20, can be expressed, e.g., to generate a vaccine candidate of trivalent-specificity (TBE+Lyme disease+ticks). Alternatively, tick saliva proteins can be expressed instead of *B. burgdorferi* immunogens in TBE sequence-containing vectors. In addition, there are many other candidate tick saliva proteins that can be used for tick vector vaccine development according to the invention (Francischetti et al., Insect Biochem. Mol. Biol. 35:1142-1161, 2005). One or more of these immunogens can be expressed in s-PIV-TBE. However, d-PIV-TBE may also be selected, because of its large insertion capacity. In addition to PIV-TBE, other PIV vaccines can be used as vectors, e.g., to protect from Lyme disease and another flavivirus disease, such as West Nile virus. Expression of these immunogens can be evaluated in cell culture, and immunogenicity/protection examined in available animal models (e.g., as described in Gipson et al., Vaccine 21:3875-3884, 2003; Labuda et al., Pathog. 2(e27):0251-0259, 2006). Immunogens of other pathogens can be similarly expressed, in addition to Lyme disease and tick immunogens, with the purpose of making multivalent vaccine candidates. Exemplary tick saliva immunogens that can be used in the invention include the following:

```
64TRP (AF469170)
MKAFFVLSLL STAALTNAAR AGRLGSDLDT FGRVHGNLYA GIERAGPRGY PGLTASIGGE

VGARLGGRAG VGVSSYGYGY PSWGYPYGGY GGYGGYGGYG GYDQGFGSAY GGYPGYYGYY

YPSGYGGGYG GSYGGSYGGS YTYPNVRASA GAAA

Isac (AF270496)
MRTAFTCALL AISFLGSPCS SSEDGLEQDT IVETTTQNLY ERHYRNHSGL CGAQYRNSSH

AEAVYNCTLN HLPPVVNATW EGIRHRINKT IPQFVKLICN FTVAMPQEFY LVYMGSDGNS

DFEEDKESTG TDEDSNTGSS AAAKVTEALI IEAEENCTAH ITGWTTETPT TLEPTTESQF EAIP

Sal20 (EU008559)
MRTALTCALL AISFLGSPCS SSEGGLEKDS RVETTTQNLY ERYYRKHPGL CGAQYRNSSH

AEAVYNCTLS LLPLSVNTTW EGIRHRINKT IPEFVNLICN FTVAMPDQFY LVYMGSNGNS

YSEEDEDGKT GSSAAVQVTE QLIIQAEENC TAHITGWTTE APTTLEPTTE TQFEAIS
```

Additional details concerning the TBE-related PIVs and LAVs are provided in Example 2, below.

The invention further provides PIV and LAV-vectored vaccines against other non-flavivirus pathogens, including vaccines having dual action, eliciting protective immunity against both flavivirus (as specified by the vector envelope proteins) and non-flavivirus pathogens (as specified by expressed immunologic determinant(s)). These are similar to the example of PIV-TBE-Lyme disease-tick vector vaccines described above. As mentioned above, such dual-action vaccines can be developed against a broad range of pathogens by expression of immunogens from, for example, viral, bacterial, fungal, and parasitic pathogens, and immunogens associated with cancer and allergy. As specific non-limiting examples, we describe herein the design and biological properties of PIV vectored-rabies and -respiratory syncytial virus (RSV) vaccine candidates constructed by expression of rabies virus G protein or full-length RSV F protein in place of or in combination with various deletions in one- and two-component PIV vectors (see Example 3, below). Also described in Example 4 are SIV/HIV-based PIV vectors. Example 5 provides influenza virus HA-based PIV vectors.

As is demonstrated in the Examples, below, s-PIV constructs may be advantageously used to stably deliver relatively short foreign immunogens (similar to Lyme disease agent OspA protein and tick saliva proteins), because insertions are combined with a relatively short ΔC deletion. Two-component PIV vectors may be advantageously used to stably express relatively large immunogens, such as rabies G protein and RSV F, as the insertions in such vectors are combined with, for example, large ΔprM-E, ΔC-prM-E, and/or ΔNS1 deletions. Some of the d-PIV components can be manufactured and used as vaccines individually, for instance, the PIV-RSV F construct described below containing a ΔC-prM-E deletion. In this case, the vaccine induces an immune response (e.g., neutralizing antibodies) predominantly against the expressed protein, but not against the flavivirus vector virus pathogen. In other examples of the invention, dual immunity is obtained by having immunity induced both to vector and insert components. Additionally, because of the large insertion capacity of PIV vectors, and the option of using two-component genomes, PIV vectors offer the opportunity to target several non-flavivirus pathogens simultaneously, e.g., by expressing foreign immunogens from two different non-flavivirus pathogens in the two components of a d-PIV.

In addition to the RSV F protein, rabies G protein, Lyme disease protective immunogens, and tick saliva proteins, as examples of foreign immunogens described above, other foreign immunogens can be expressed to target respective diseases including, for example, influenza virus type A and B immunogens. In these examples, a few short epitopes and/or whole genes of viral particle proteins can be used, such as the M2, HA, and NA genes of influenza A, and/or the NB or BM2 genes of influenza B (see, e.g., the PIV constructs of Example 5 below). Shorter fragments of M2, NB, and BM2, corresponding for instance to M2e, the extracellular fragment of M2, can also be used. In addition, fragments of the HA gene, including epitopes identified as HA0 (23 amino acids in length, corresponding to the cleavage site in HA) can be used. Specific examples of influenza-related sequences that can be used in the invention include PAKLLKERGFFGAIAGFLE (HA0), PAKLLKERGFFGAIAGFLEGSGC (HA0), NNATFNYTNVNPISHIRGS (NBe), MSLLTEVETPIRNEWGCRCNDSSD (M2e), MSLLTEVETPTRNEWECRCSDSSD (M2e), MSLLTEVETLTRNGWGCRCSDSSD (M2e), EVETPTRN (M2e), SLLTEVETPIRNEWGCRCNDSSD (M2e), and SLLTEVETPIRNEWGCR (M2e). Additional M2e sequences that can be used in the invention include sequences from the extracellular domain of BM2 protein of influenza B (consensus MLEPFQ, e.g., LEPFQILSISGC), and the M2e peptide from the H5N1 avian flu (MSLLTEVETLTRNGWGCRCSDSSD).

Other examples of pathogen immunogens that can be delivered in the vectors of the invention include codon-optimized SIV or HIV gag (55 kDa), gp120, gp140, gp145, gp41, gp160, SIV mac239 pol/−rev/tat/nef/pro genes or analogs or homologs and/or other naturally occurring variants from SIV and/or HIV, and other SIV and/or HIV immunogens (see, e.g., the PIV vectors described in Example 4 below); immunogens from HPV viruses, such as HPV16, HPV18, etc., e.g., the capsid protein L1 which self-assembles into HPV-like particles, the capsid protein L2 or its immunodominant portions (e.g., amino acids 1-200, 1-88, or 17-36), the E6 and E7 proteins which are involved in transforming and immortalizing mammalian cells fused together and appropriately mutated (fusion of the two genes creates a fusion protein, referred to as E6E7Rb⁻, that is about 10-fold less capable of transforming fibroblasts, and mutations of the E7 component at 2 residues renders the resulting fusion protein mutant incapable of inducing transformation (Boursnell et al., Vaccine 14:1485-1494, 1996). Other immunogens include protective immunogens from HCV, CMV, HSV2, viruses, malaria parasite, *Mycobacterium tuberculosis* causing tuberculosis, *C. difficile*, and other nosocomial infections, that are known in the art, as well as fungal pathogens, cancer immunogens, and proteins associated with allergy that can be used as vaccine targets.

Foreign immunogen inserts of the invention can be modified in various ways. For instance, codon optimization is used to increase the level of expression and eliminate long repeats in nucleotide sequences to increase insert stability in the RNA genome of PIV vectors. Immunogenicity can be increased by chimerization of proteins with immunostimulatory moieties well known in the art, such as TLR agonists, stimulatory cytokines, components of complement, heat-shock proteins, etc. (e.g., reviewed in "Immunopotentiators in Modern Vaccines," Schijns and O'Hagan Eds., 2006, Elsevier Academic Press: Amsterdam, Boston).

With respect to construction of dual vaccines against rabies and other flavivirus diseases, other combinations, such as TBE+rabies, YF+rabies, etc., can be of interest both for human and veterinary use in corresponding geographical regions, and thus can be similarly generated. Possible designs of expression constructs are not limited to those described herein. For example deletions and insertions can be modified, genetic elements can be rearranged, or other genetic elements (e.g. non-flavivirus, non-rabies signals for secretion, intracellular transport determinants, inclusion of or fusion with immunostimulatory moieties such as cytokines, TLR agonists such as flagellin, multimerization components such as leucine zipper, and peptides that increase the period of protein circulation in the blood) can be used to facilitate antigen presentation and increase immunogenicity. Further, such designs can be applied to s-PIV and d-PIV vaccine candidates based on vector genomes of other flaviviruses, and expressing immunogens of other pathogens, e.g., including but not limited to pathogens described in elsewhere herein.

Other examples of PIV and LAV vectors of the invention including combination vaccines such as DEN+Chikungunya virus (CHIKV) and YF+CHIKV. CHIKV, an alphavirus, is endemic in Africa, South East Asia, Indian subcontinent and the Islands, and the Pacific Islands and shares ecological/geographical niches with YF and DEN1-4. It causes serious disease primarily associated with severe pain (arthritis, other symptoms similar to DEN) and long-lasting sequelae in the majority of patients (Simon et al., Med. Clin. North Am. 92:1323-1343, 2008; Seneviratne et al., J. Travel Med. 14:320-325, 2007). Other examples of PIV and LAV vectors of the invention include YF+Ebola or DEN+Ebola, which co-circulate in Africa.

Immunogens for the above-noted non-flavivirus pathogens, sequences of which are well known in the art, may include glycoprotein B or a pp65/IE1 fusion protein of CMV (Reap et al., Vaccine 25(42):7441-7449, 2007; and references therein), several TB proteins (reviewed in Skeiky et al., Nat. Rev. Microbiol. 4(6):469-476, 2006), malaria parasite antigens such as RTS,S (a pre-erythrocytic circumsporozoite protein, CSP) and others (e.g., reviewed in Li et al., Vaccine 25(14):2567-2574, 2007), CHIKV envelope proteins E1 and E2 (or the C-E2-E1, E2-E1 cassettes), HCV structural proteins C-E1-E2 forming VLPs (Ezelle et al., J. Virol. 76(23): 12325-12334, 2002) or other proteins to induce T-cell responses, Ebola virus glycoprotein GP (Yang et al., Virology 377(2):255-264, 2008).

In addition to the immunogens described above, the vectors described herein may include one or more immunogen(s) derived from or that direct an immune response against one or more viruses (e.g., viral target antigen(s)) including, for example, a dsDNA virus (e.g., adenovirus, herpesvirus, epstein-barr virus, herpes simplex type 1, herpes simplex type 2, human herpes virus simplex type 8, human cytomegalovirus, varicella-zoster virus, poxvirus); ssDNA virus (e.g., parvovirus, papillomavirus (e.g., E1, E2, E3, E4, E5, E6, E7, E8, BPV1, BPV2, BPV3, BPV4, BPV5, and BPV6 (In Papillomavirus and Human Cancer, edited by H. Pfister (CRC Press, Inc. 1990)); Lancaster et al., Cancer Metast. Rev. pp. 6653-6664, 1987; Pfister et al., Adv. Cancer Res. 48:113-147, 1987)); dsRNA viruses (e.g., reovirus); (+)ssRNA viruses (e.g., picornavirus, coxsackie virus, hepatitis A virus, poliovirus, togavirus, rubella virus, flavivirus, hepatitis C virus, yellow fever virus, dengue virus, west Nile virus); (−)ssRNA viruses (e.g., orthomyxovirus, influenza virus, rhabdovirus, paramyxovirus, measles virus, mumps virus, parainfluenza virus, rhabdovirus, rabies virus); ssRNA-RT viruses (e.g., retrovirus, human immunodeficiency virus (HIV)); and dsDNA-RT viruses (e.g. hepadnavirus, hepatitis B). Immunogens may also be derived from other viruses not listed above but available to those of skill in the art.

With respect to HIV, immunogens may be selected from any HIV isolate. As is well-known in the art, HIV isolates are now classified into discrete genetic subtypes. HIV-1 is known to comprise at least ten subtypes (A, B, C, D, E, F, G, H, J, and K). HIV-2 is known to include at least five subtypes (A, B, C, D, and E). Subtype B has been associated with the HIV epidemic in homosexual men and intravenous drug users worldwide. Most HIV-1 immunogens, laboratory adapted isolates, reagents and mapped epitopes belong to subtype B. In sub-Saharan Africa, India, and China, areas where the incidence of new HIV infections is high, HIV-1 subtype B accounts for only a small minority of infections, and subtype HIV-1 C appears to be the most common infecting subtype. Thus, in certain embodiments, it may be desirable to select immunogens from HIV-1 subtypes B and/or C. It may be desirable to include immunogens from multiple HIV subtypes (e.g., HIV-1 subtypes B and C, HIV-2 subtypes A and B, or a combination of HIV-1 and HIV-2 subtypes) in a single immunological composition. Suitable HIV immunogens include ENV, GAG, PRO, POL, NEF, as well as variants, derivatives, and fusion proteins thereof, for example.

Further, as described in Example 4 in reference to particular constructs, the invention includes constructs including multiple different proteins in a single precursor, wherein the open reading frames may be, optionally, separated by protease cleavage sites, such as FMDV 2A cleavage sites, as described herein. Thus, in one example, a cassette may include gp120 (e.g., modified as described in Example 4), gag, and pro genes from SIV or HIV. Further, the invention includes the hybrid sequences including, e.g., heterologous transmembrane and.or signal sequences, as described in detail in Example 4. Thus, for example, the invention includes the use of rabies virus G protein-specific signale and/or anchor sequences in the contect of gp120-containing PIV constructs, as described herein.

Immunogens may also be derived from or direct an immune response against one or more bacterial species (spp.) (e.g., bacterial target antigen(s)) including, for example, *Bacillus* spp. (e.g., *Bacillus anthracis*), *Bordetella* spp. (e.g., *Bordetella pertussis*), *Borrelia* spp. (e.g., *Borrelia burgdorferi*), *Brucella* spp. (e.g., *Brucella abortus, Brucella canis, Brucella melitensis, Brucella suis*), *Campylobacter* spp. (e.g., *Campylobacter jejuni*), *Chlamydia* spp. (e.g., *Chlamydia pneumoniae, Chlamydia psittaci, Chlamydia trachomatis*), *Clostridium* spp. (e.g., *Clostridium botulinum, Clostridium difficile, Clostridium perfringens, Clostridium tetani*), *Corynebacterium* spp. (e.g., *Corynebacterium diptheriae*), *Enterococcus* spp. (e.g., *Enterococcus faecalis, enterococcus faecum*), *Escherichia* spp. (e.g., *Escherichia coli*), *Francisella* spp. (e.g., *Francisella tularensis*), *Haemophilus* spp. (e.g., *Haemophilus influenza*), *Helicobacter* spp. (e.g., *Helicobacter pylori*), *Legionella* spp. (e.g., *Legionella pneumophila*), *Leptospira* spp. (e.g., *Leptospira interrogans*), *Listeria* spp. (e.g., *Listeria monocytogenes*), *Mycobacterium* spp. (e.g., *Mycobacterium leprae, Mycobacterium tuberculosis*), *Mycoplasma* spp. (e.g., *Mycoplasma pneumoniae*), *Neisseria* spp. (e.g., *Neisseria gonorrhea, Neisseria meningitidis*), *Pseudomonas* spp. (e.g., *Pseudomonas aeruginosa*), *Rickettsia* spp. (e.g., *Rickettsia rickettsii*), *Salmonella* spp. (e.g., *Salmonella typhi, Salmonella typhinurium*), *Shigella* spp. (e.g., *Shigella sonnei*), *Staphylococcus* spp. (e.g., *Staphylococcus aureus, Staphylococcus epidermidis, Staphylococcus saprophyticus*, coagulase negative *staphylococcus* (e.g., U.S. Pat. No. 7,473,762)), *Streptococcus* spp. (e.g., *Streptococcus agalactiae, Streptococcus pneumoniae, Streptococcus pyrogenes*), *Treponema* spp. (e.g., *Treponema pallidum*), *Vibrio* spp. (e.g., *Vibrio cholerae*), and *Yersinia* spp. (*Yersinia pestis*). Immunogens may also be derived from or direct the immune response against other bacterial species not listed above but available to those of skill in the art.

Immunogens may also be derived from or direct an immune response against one or more parasitic organisms (spp.) (e.g., parasite target antigen(s)) including, for example, *Ancylostoma* spp. (e.g., *A. duodenale*), *Anisakis* spp., *Ascaris lumbricoides, Balantidium coli, Cestoda* spp., *Cimicidae* spp., *Clonorchis sinensis, Dicrocoelium dendriticum, Dicrocoelium hospes, Diphyllobothrium latum, Dracunculus* spp., *Echinococcus* spp. (e.g., *E. granulosus, E. multilocularis*), *Entamoeba histolytica, Enterobius vermicularis, Fasciola* spp. (e.g., *F. hepatica, F. magna, F. gigantica, F. jacksoni*), *Fasciolopsis buski, Giardia* spp. (*Giardia lamblia*), *Gnathostoma* spp., *Hymenolepis* spp. (e.g., *H. nana, H. diminuta*), *Leishmania* spp., *Loa loa, Metorchis* spp. (*M. conjunctus, M. albidus*), *Necator americanus, Oestroidea* spp. (e.g., botfly), *Onchocercidae* spp., *Opisthorchis* spp. (e.g., *O. viverrini, O. felineus, O. guayaquilensis*, and *O. noverca*), *Plasmodium* spp. (e.g., *P. falciparum*), *Protofasciola robusta, Parafasciolopsis fasciomorphae, Paragonimus westermani, Schistosoma* spp. (e.g., *S. mansoni, S. japonicum, S. mekongi, S. haematobium*), *Spirometra erinaceieuropaei, Strongyloides stercoralis, Taenia* spp. (e.g., *T. saginata, T. solium*), *Toxocara* spp. (e.g., *T. canis, T. cati*), *Toxoplasma* spp. (e.g., *T. gondii*), *Trichobilharzia regenti, Trichinella spiralis, Trichuris trichiura, Trombiculidae* spp., *Trypanosoma* spp., *Tunga penetrans*, and/or *Wuchereria bancrofti*. Immunogens may also be derived from or direct the immune response against other parasitic organisms not listed above but available to those of skill in the art.

Immunogens may be derived from or direct the immune response against tumor target antigens (e.g., tumor target antigens). The term tumor target antigen (TA) may include both tumor-associated antigens (TAAs) and tumor-specific antigens (TSAs), where a cancerous cell is the source of the antigen. A TA may be an antigen that is expressed on the surface of a tumor cell in higher amounts than is observed on normal cells or an antigen that is expressed on normal cells during fetal development. A TSA is typically an antigen that is unique to tumor cells and is not expressed on normal cells. TAs are typically classified into five categories according to their expression pattern, function, or genetic origin: cancer-testis (CT) antigens (i.e., MAGE, NY-ESO-1); melanocyte differentiation antigens (e.g., Melan A/MART-1, tyrosinase, gp100); mutational antigens (e.g., MUM-1, p53, CDK-4);

overexpressed 'self' antigens (e.g., HER-2/neu, p53); and viral antigens (e.g., HPV, EBV). Suitable TAs include, for example, gp100 (Cox et al., Science 264:716-719, 1994), MART-1/Melan A (Kawakami et al., J. Exp. Med., 180:347-352, 1994), gp75 (TRP-1) (Wang et al., J. Exp. Med., 186: 1131-1140, 1996), tyrosinase (Wolfel et al., Eur. J. Immunol., 24:759-764, 1994), NY-ESO-1 (WO 98/14464; WO 99/18206), melanoma proteoglycan (Hellstrom et al., J. Immunol., 130:1467-1472, 1983), MAGE family antigens (e.g., MAGE-1, 2, 3, 4, 6, and 12; Van der Bruggen et al., Science 254:1643-1647, 1991; U.S. Pat. No. 6,235,525), BAGE family antigens (Boel et al., Immunity 2:167-175, 1995), GAGE family antigens (e.g., GAGE-1,2; Van den Eynde et al., J. Exp. Med. 182:689-698, 1995; U.S. Pat. No. 6,013,765), RAGE family antigens (e.g., RAGE-1; Gaugler et al., Immunogenetics 44:323-330, 1996; U.S. Pat. No. 5,939,526), N-acetylglucosaminyltransferase-V (Guilloux et al., J. Exp. Med. 183:1173-1183, 1996), p15 (Robbins et al., J. Immunol. 154:5944-5950, 1995), β-catenin (Robbins et al., J. Exp. Med., 183:1185-1192, 1996), MUM-1 (Coulie et al., Proc. Natl. Acad. Sci. U.S.A. 92:7976-7980, 1995), cyclin dependent kinase-4 (CDK4) (Wolfel et al., Science 269: 1281-1284, 1995), p21-ras (Fossum et al., Int. J. Cancer 56:40-45, 1994), BCR-abl (Bocchia et al., Blood 85:2680-2684, 1995), p53 (Theobald et al., Proc. Natl. Acad. Sci. U.S.A. 92:11993-11997, 1995), p185 HER2/neu (erb-B1; Fisk et al., J. Exp. Med., 181:2109-2117, 1995), epidermal growth factor receptor (EGFR) (Harris et al., Breast Cancer Res. Treat, 29:1-2, 1994), carcinoembryonic antigens (CEA) (Kwong et al., J. Natl. Cancer Inst., 85:982-990, 1995) U.S. Pat. Nos. 5,756,103; 5,274,087; 5,571,710; 6,071,716; 5,698, 530; 6,045,802; EP 263933; EP 346710; and EP 784483; carcinoma-associated mutated mucins (e.g., MUC-1 gene products; Jerome et al., J. Immunol., 151:1654-1662, 1993); EBNA gene products of EBV (e.g., EBNA-1; Rickinson et al., Cancer Surveys 13:53-80, 1992); E7, E6 proteins of human papillomavirus (Ressing et al., J. Immunol. 154:5934-5943, 1995); prostate specific antigen (PSA; Xue et al., The Prostate 30:73-78, 1997); prostate specific membrane antigen (PSMA; Israeli et al., Cancer Res. 54:1807-1811, 1994); idiotypic epitopes or antigens, for example, immunoglobulin idiotypes or T cell receptor idiotypes (Chen et al., J. Immunol. 153:4775-4787, 1994); KSA (U.S. Pat. No. 5,348,887), kinesin 2 (Dietz, et al., Biochem. Biophys. Res. Commun. 275(3): 731-738, 2000), HIP-55, TGFβ-1 anti-apoptotic factor (Toomey et al., Br. J. Biomed. Sci. 58(3):177-183, 2001), tumor protein D52 (Bryne et al., Genomics 35:523-532, 1996), H1FT, NY-BR-1 (WO 01/47959), NY-BR-62, NY-BR-75, NY-BR-85, NY-BR-87, and NY-BR-96 (Scanlan, M. Serologic and Bioinformatic Approaches to the Identification of Human Tumor Antigens, in *Cancer Vaccines* 2000, Cancer Research Institute, New York, N.Y.), and/or pancreatic cancer antigens (e.g., SEQ ID NOs: 1-288 of U.S. Pat. No. 7,473, 531). Immunogens may also be derived from or direct the immune response against include TAs not listed above but available to one of skill in the art.

In addition to the specific immunogen sequences listed above, the invention also includes the use of analogs of the sequences. Such analogs include sequences that are, for example, at least 80%, 90%, 95%, or 99% identical to the reference sequences, or fragments thereof. The analogs also include fragments of the reference sequences that include, for example, one or more immunogenic epitopes of the sequences. Further, the analogs include truncations or expansions of the sequences (e.g., insertion of additional/repeat immunodominant/helper epitopes) by, e.g., 1, 2, 3, 4, 5, 6, 7, 8, 9, 10, 11-20, etc., amino acids on either or both ends. Truncation may remove immunologically unimportant or interfering sequences, e.g., within known structural/immunologic domains, or between domains; or whole undesired domains can be deleted; such modifications can be in the ranges 21-30, 31-50, 51-100, 101-400, etc. amino acids. The ranges also include, e.g., 20-400, 30-100, and 50-100 amino acids.

Cocktails

The invention also includes compositions including mixtures of two or more PIVs and/or PIV vectors, as described herein. As discussed above, use of such mixtures or cocktails may be particularly advantageous when induction of immunity to more than one immunogen and/or pathogen is desired. This may be useful, for example, in vaccination against different flaviviruses that may be endemic to the region in which the vaccine recipient resides. This may also be useful in the context of administration of multiple immunogens against the same target.

Non-limiting examples of PIV cocktails included in the invention are those including PIV-JE+PIV-DEN, and PIV-YF+PIV-DEN. In both of these examples, the PIVs for either or both components can be single or dual component PIVs, as described above. In addition, in the case of the PIV-DEN, the PIV can include sequences of just one dengue serotype selected from the group consisting of dengue serotypes 1-4, or the cocktail can include PIVs expressing sequences from two, three, or all four of the serotypes. Further, the TBE/*Borrelia burgdorferi*/tick saliva protein (e.g., 64TRP, Isac, Salp20) vaccines described herein can be based on including the different immunogens within a single PIV or live attenuated flavivirus, or can be based on mixtures of PIVs (or LAVs), which each include one or more of the immunogens. The cocktails of the invention can be formulated as such or can be mixed just prior to administration.

Use, Formulation, and Administration

The invention includes the PIV vectors, PIVs, LAV vectors, and LAVs, as well as corresponding nucleic acid molecules, pharmaceutical or vaccine compositions, and methods of their use and preparation. The PIV vectors, PIVs, LAV vectors, and LAVs of the invention can be used, for example, in vaccination methods to induce an immune response to TBE or other flavivirus, and/or another expressed immunogen, as described herein. These methods can be prophylactic, in which case they are carried out on subjects (e.g., human subjects or other mammalian subjects) not having, but at risk of developing infection or disease caused by TBE or another flavivirus and/or a pathogen from which the other expressed immunogen is derived. The methods can also be therapeutic, in which they are carried out on subjects already having an infection by one or more of the relevant pathogens. Further, the viruses and vectors can be used individually or in combination with one another or other vaccines. The subjects treated according to the methods of the invention include humans, as well as non-human mammals (e.g., livestock, such as, cattle, pigs, horses, sheep, and goats, and domestic animals, including dogs and cats).

Formulation of the PIV vectors, PIVs, LAV vectors, and LAVs of the invention can be carried out using methods that are standard in the art. Numerous pharmaceutically acceptable solutions for use in vaccine preparation are well known and can readily be adapted for use in the present invention by those of skill in this art (see, e.g., *Remington's Pharmaceutical Sciences* (18$^{th}$ edition), ed. A. Gennaro, 1990, Mack Publishing Co., Easton, Pa.). In two specific examples, the PIV vectors, PIVs, LAV vectors, and LAVs are formulated in Minimum Essential Medium Earle's Salt (MEME) containing 7.5% lactose and 2.5% human serum albumin or MEME containing 10% sorbitol. However, the PIV vectors, PIVs, LAV vectors, and LAVs can simply be diluted in a physiologically acceptable solution, such as sterile saline or sterile buffered saline.

The PIV vectors, PIVs, LAV vectors, and LAVs of the invention can be administered using methods that are well known in the art, and appropriate amounts of the viruses and vectors to be administered can readily be determined by those of skill in the art. What is determined to be an appropriate amount of virus to administer can be determined by consideration of factors such as, e.g., the size and general health of the subject to whom the virus is to be administered. For example, in the case of live, attenuated viruses of the invention, the viruses can be formulated as sterile aqueous solutions containing between $10^2$ and $10^8$, e.g., $10^3$ to $10^7$, infectious units (e.g., plaque-forming units or tissue culture infectious doses) in a dose volume of 0.1 to 1.0 ml. PIVs can be administered at similar doses and in similar volumes; PIV titers however are usually measured in, e.g., focus-forming units determined by immunostaining of foci, as these defective constructs tend not to form virus-like plaques. Doses can range between $10^2$ and $10^8$ FFU and administered in volumes of 0.1 to 1.0 ml.

All viruses and vectors of the invention can be administered by, for example, intradermal, subcutaneous, intramuscular, intraperitoneal, or oral routes. In specific examples, dendritic cells are targeted by intradermal or transcutaneous administration, by use of, for example, microneedles or microabrasion devices. Further, the vaccines of the invention can be administered in a single dose or, optionally, administration can involve the use of a priming dose followed by a booster dose that is administered, e.g., 2-6 months later, as determined to be appropriate by those of skill in the art. Optionally, PIV vaccines can be administered via DNA or RNA immunization using methods known to those skilled in the art (Chang et al., Nat. Biotechnol. 26:571-577, 2008; Kofler et al., Proc. Natl. Acad. Sci. U.S.A. 101:1951-1956, 2004).

Optionally, adjuvants that are known to those skilled in the art can be used in the administration of the viruses and vectors of the invention. Adjuvants that can be used to enhance the immunogenicity of the viruses include, for example, liposomal formulations, synthetic adjuvants, such as (e.g., QS21), muramyl dipeptide, monophosphoryl lipid A, polyphosphazine, CpG oligonucleotides, or other molecules that appear to work by activating Toll-like Receptor (TLR) molecules on the surface of cells or on nuclear membranes within cells. Although these adjuvants are typically used to enhance immune responses to inactivated vaccines, they can also be used with live or replication-defective vaccines. Both agonists of TLRs or antagonists may be useful in the case of live or replication-defective vaccines. The vaccine candidates can be designed to express TLR agonists. In the case of a virus delivered via a mucosal route, for example, orally, mucosal adjuvants such as the heat-labile toxin of E. coli (LT) or mutant derivations of LT can be used as adjuvants. In addition, genes encoding cytokines that have adjuvant activities can be inserted into the vaccine candidates. Thus, genes encoding desired cytokines, such as GM-CSF, IL-2, IL-12, IL-13, IL-5, etc., can be inserted together with foreign immunogen genes to produce a vaccine that results in enhanced immune responses, or to modulate immunity directed more specifically towards cellular, humoral, or mucosal responses (e.g., reviewed in "Immunopotentiators in Modern Vaccines", Schijns and O'Hagan Eds., 2006, Elsevier Academic Press: Amsterdam, Boston, etc.). Optionally, a patch containing a layer of an appropriate toxin-derived adjuvant, can be applied over the injection site. Toxin promotes local inflammation attracting lymphocytes, which leads to a more robust immune response.

EXAMPLES

Additional details concerning the invention are provided in the Examples, below. In the Examples, experiments are described in which PIVs based on WN, JE, and YF viruses (see, e.g., WO 2007/098267 and WO 2008/137163) were tested. Firstly, we demonstrated that the constructs are significantly more attenuated in a sensitive suckling mouse neurovirulence model (zero mortality at all tested doses) as compared to available LAV controls (YF 17D, YF/JE LAV, and YF/WN LAV). We demonstrated for the first time that d-PIV constructs were avirulent in this model and thus that two-component PIVs do not undergo uncontrolled (unlimited) spread in vivo and cannot cause clinical signs. Secondly, we performed comparisons of the immunogenicity and efficacy of the PIVs and the LAVs, and demonstrated that PIV vaccines can induce immune response comparable to LAVs and be equally efficacious (e.g., as observed for PIV-WN and YF/WN LAV pair of vaccines). In one pair examined, YF 17D LAV was significantly more immunogenic than PIV-YF. Thus, production of VLPs can vary between different, similarly designed PIV constructs. Specifically, we propose that PIV-YF does not generate a large amount of YF VLPs compared to PIV-WN (WN VLPs), and that increased production of VLPs can be achieved by genetic modifications at the C/prM junction in suboptimal PIV constructs. Specifically, the C/prM junction is an important location in the flavivirus polyprotein orchestrating the formation of viral envelope and synthesis of viral proteins (Yamshchikov and Compans, Virology 192:38-51, 1993; Amberg and Rice, J. Virol. 73:8083-8094, 1999; Stocks and Lobigs, J. Virol. 72:2141-2149, 1998). We propose that secretion of VLPs in PIV infected cells (in contrast to production of viral particles in whole viruses) can be increased by uncoupling of the viral protease and signalase cleavages at the junction, or use of a strong heterologous signal peptide (tPA, etc.) in place of the signal for prM, or by mutagenesis of the signal for prM. The efficiency of signalase cleavage at the C/prM junction of flaviviruses is low (Stocks and Lobigs, J. Virol. 72:2141-2149, 1998), e.g., as predicted by SignalP 3.0 on-line program. It is expected that more efficient cleavage efficiency can be achieved by analysis of specific amino acid substitutions near the cleavage site with SignalP 3.0 (e.g., as described in application WO 2008/100464), followed by incorporation of chosen mutation(s) into PIV genomes, recovery of PIV progeny and measuring VLP secretion. Non-flavivirus signals are inserted by methods standard in the art. Uncoupling between the viral protease and signalase cleavages can be achieved by ablating the viral cleavage site by any non-conservative mutation (e.g., RRS in YF17D C to RRA or GRS or RSS, etc.), or deletion of the entire site or some of its 3 residues. If necessary, formation of free N-terminus of the signal of foreign protein can be achieved by using such elements as autoprotease, or termination codon followed by an IRES. Alternatively, the native AUG initiation codon of C can be ablated (in constructs where C protein sequence is unnecessary, e.g., ΔC PIV) and AUG placed in front of foreign gene. Optimization of vector signal can be performed by random mutagenesis, e.g., by insertion of synthetic randomized sequence followed by identification of viable PIV variants with increased VLP secretion.

We also discovered that PIV constructs were substantially more immunogenic in hamsters when administered by the IP route, as compared to the subcutaneous route. We concluded that this was most likely due to better targeting of antigen presenting cells in lymphoid tissues, which are abundant in the abdomen, but not abundant in tissues underlying the skin. Based on these observations, we concluded that efficient targeting of PIVs to dendritic cells, abundant in the skin, can be achieved by cutaneous inoculation, e.g., via skin microabrasion or intradermal injection using microneedles (Dean et al., Hum Vaccin. 1:106-111, 2005).

Further, we have carried out experiments to show the feasibility of administering mixtures, or cocktails, of different PIVs, such as those described herein (e.g., JE+DEN and YF+DEN). In order to administer cocktails, it is important to verify that there is no interference between co-administered components, and that a balanced immune response is induced. Several PIV mixtures were used to immunize rodents and immune responses were compared to PIV constructs administered individually. No interference was observed in mixtures, and thus cocktail PIV vaccines are feasible. Such formulations may be of particular significance in geographical regions where different flaviviruses co-circulate. This could be also used to simultaneously administer several PIV-based vaccines against non-flavivirus pathogens.

Further, we have demonstrated that no neutralizing antibody response is induced against packaging envelope after at least two doses of PIV (and thus antibodies are elicited against VLPs secreted from infected cells). This was demonstrated using the helper (ΔprM-E) component of a d-PIV (see in FIG. 2) packaged individually, or by measuring neutralizing antibodies to heterologous packaging envelopes (e.g., to the WN envelope used to package PIV-JE in helper cells providing WN-specific C-prM-E proteins in trans). The latter observations support sequential use of different PIV vaccines manufactured in a universal helper packaging cells line, and sequential use of different recombinant PIV-vectored vaccines in the same individual, as discussed above. In addition, we confirmed previous observations that PIV constructs can be stably propagated to high yields in vitro, and that no recombination restoring whole virus occurs after prolonged passaging in substrate cells (Mason et al., Virology 351:432-443, 2006; Shustov et al., J. Virol. 21:11737-11748, 2007).

These and other aspects of the invention are further described in the Examples, below.

Example 1

Pseudoinfectious Virus Platform Development Studies

Attenuation in Suckling Mouse Neurovirulence (NV) Model

Materials used in the studies described below are described in Table 1 and the references cited therein. These include s-PIV-WN (based on wt WN virus strain NY99 sequences), s-PIV-JE, s-PIV-WN/JE (based on wt WN virus backbone and prM-E genes from wt JE virus Nakayama strain), s-PIV-YF/WN (YF 17D backbone and prM-E genes from WN virus), and s-PIV-YF (based on YF 17D sequences). Additional materials include d-PIV-YF (YF d-PIV, grown in regular BHK cells (Shustov et al., J. Virol. 21:11737-11748, 2007), and two-component d-PIV-WN (grown in regular Vero cells; Suzuki et al., J. Virol. 82:6942-6951, 2008).

Attenuation of these PIV prototypes was compared to LAVs YF 17D, a chimeric YF/JE virus, and a chimeric YF/WN virus in suckling mouse NV test (IC inoculation) using highly susceptible 5-day old ICR mice (the chimeric viruses include yellow fever capsid and non-structural sequences, and JE or WN prM-E sequences). None of the animals that received PIV constructs showed clinical signs or died, while mortality was observed in animals inoculated with LAVs (Table 2). The YF 17D virus is neurovirulent for mice of all ages, while the chimeric vaccines are not neurovirulent for adult mice, but can cause dose-dependent mortality in more sensitive suckling mice (Guirakhoo et al., Virology 257:363-372, 1999; Arroyo et al., J. Virol. 78:12497-12507, 2004). Accordingly, 90%400% of suckling mice that received doses as low as 1 PFU of YF 17D died. YF/JE and YF/WN LAVs caused partial mortality at much higher doses (>2 $\log_{10}$ PFU and 3 $\log_{10}$ PFU, respectively), with longer average survival time (AST) of animals that died, as expected. Thus, PIV constructs are completely avirulent in this sensitive model (at least 20,000-200,000 times less neurovirulent than the licensed YF 17D vaccine).

The YF d-PIV and WN d-PIV caused no mortality or clinical signs. Thus, the two-component PIV variants that theoretically could spread within brain tissue from cells co-infected by both of their components did not cause disease. Moreover, we tried to detect the d-PIVs in the brains of additional animals in this experiment, sacrificed on day 6 post-inoculation by titration, and detected none (brain tissues from 10 and 11 mice that received 4 $\log_{10}$ FFU of YF d-PIV and WN d-PIV, respectively, were homogenized and used for titration). Thus, the d-PIVs did not cause spreading infection characteristic of whole virus. YF/JE LAV has been shown to replicate in the brain of adult ICR mice inoculated by the IC route with a peak titer of ~6 $\log_{10}$ PFU/g on day 6, albeit without clinical signs (Guirakhoo et al., Virology 257:363-372, 1999). Co-infection of cells with components of a d-PIV is clearly a less efficient process than infection with whole virus. The data show that d-PIV replication in vivo is quickly brought under control by innate immune responses (and adaptive responses in older animals).

Immunogenicity/Efficacy in Mice and Hamsters

Immunogenicity/efficacy of the PIV prototypes described above was compared to that of chimeric LAV counterparts and YF 17D in mice and Syrian hamsters. The general experiment design is illustrated in FIG. 3 (mice, IP immunization). Experiments in hamsters were performed similarly (plus-minus a few days, SC or IP inoculation with doses indicated below). 3.5-week old ICR mice (for s-PIV-WN and -YF, YF/WN LAV, and YF 17D groups) or C57/BL6 mice (for s-PIV-JE and YF/JE LAV groups) were immunized IP with graded doses of PIV constructs (4-6 $\log_{10}$ FFU/dose) or chimeric LAV and YF 17D LAV controls (4 $\log_{10}$ PFU). Select PIV-WN, -JE and -YF groups were boosted on day 21 with 5 $\log_{10}$ FFU of corresponding constructs (Table 3). Neutralizing antibody responses were determined in animal sera by standard $PRNT_{50}$ against YF/WN or /JE LAVs, or YF 17D viruses. PIV-WN induced very high WN-specific neutralizing antibody responses in all groups, with or without boost, as evidenced by $PRNT_{50}$ titers determined in pools of sera from immunized animals on days 20 and 34, which was comparable to that in the YF/WN LAV control group. Accordingly, animals immunized with both PIV-WN and YF/WN LAV were protected from lethal challenge on day 35 with wt WN virus (IP, 270 $LD_{50}$), but not mock-immunized animals (Table 3). When WN neutralizing antibodies were measured in sera from individual mice, high uniformity of immune responses was observed (FIG. 4). Thus, single-round PIV vaccines can be as immunogenic and efficacious as corresponding LAVs. PIV-JE was also highly immunogenic (black mice), while immunogenicity of PIV-YF was significantly lower compared to the YF 17D control (ICR mice). Yet, dose-dependent protection of PIV-YF immunized animals (but not mock-immunized animals) was observed following a severe lethal IC challenge with wt YF strain Asibi virus (500 LD$_{50}$) (Table 3), which is in agreement with the knowledge that neutralizing antibody titers as low 1:10 are protective against flavivirus infections.

The YF 17D control virus was highly immunogenic (e.g., PRNT$_{50}$ titer 1:1,280 on day 34), and thus it is able to infect cells and replicate efficiently in vivo, and its envelope is a strong immunogen. Therefore, it is unlikely that low immunogenicity of PIV-YF was due to its inability to infect cells or replicate efficiently in infected cells in vivo. We believe that the low immunogenicity of PIV-YF (e.g., compared to PIV-WN) was most likely due to a low-level production of YF-specific VLPs in PIV-YF infected cells (while VLP secretion is high in PIV-WN infected cells). As discussed above, we propose that immunogenicity of PIV-YF can be significantly increased, e.g., by appropriate modifications at the C/prM junction, e.g., by uncoupling the two protease cleavages that occur at this junction (viral protease and signalase cleavages), and/or by using a strong heterologous signal [e.g., rabies virus G protein signal, or eukaryotic tissue plasminogen activator (tPA) signal (Malin et al., Microbes and Infection, 2:1677-1685, 2000), etc.] in place of the YF signal for prM.

A similar experiment was performed in ~4.5-week old Syrian hamsters, to compare immunogenicity of PIV constructs to LAV controls in this model. Animals were immunized SC with graded doses of the test articles (Table 4). PIV-WN was highly immunogenic, e.g., WN-specific PRNT$_{50}$ titers on day 38 (pre-challenge) were 1:320, 1:640, and 1:1280 in groups that received 5, 6, and 6 (prime)+5 (boost) log$_{10}$ FFU doses, respectively. This was somewhat lower compared to YF/WN LAV 4 log$_{10}$ PFU control (≥1:2560). PIV-JE and -YF induced detectable specific neutralizing antibody responses, albeit with lower titers compared to YF/JE LAV and YF 17D controls. All animals immunized with PIV-WN and YF/WN were solidly protected from lethal challenge with wt WN virus as evidenced by the absence of mortality and morbidity (e.g., loss of body weight after challenge), as well as absence or a significant reduction of postchallenge WN virus viremia. Mock-immunized animals were not protected (Table 4). PIV-JE and -WN protected animals from respective challenge in dose-dependent fashion. Protective efficacy in this experiment is additionally illustrated in FIG. 5. For example, high post-challenge YF virus (hamster adapted Asibi strain) viremia was observed in mock immunized animals, peaking on day 3 at a titer of >8 log$_{10}$ PFU/ml (upper left panel); all of the animals lost weight, and 1 out of 4 died (upper right panel). In contrast, viremia was significantly reduced or absent in hamsters immunized with PIV-YF (two doses; despite relatively low neutralizing titers) or YF 17D; none of these animals lost weight. Similarly, animals immunized with PIV-WN or YF/WN LAV were significantly or completely protected in terms of post-challenge WN virus viremia and body weigh loss/mortality, in contrast to mock controls (compare in bottom panels). Thus, high immunogenicity/efficacy of PIV was demonstrated in a second animal model.

In another hamster experiment, animals were immunized with PIV constructs by the IP route, with two doses. Table 5 compares neutralizing immune responses (specific for each vaccine) determined in pooled sera of hamsters in the above-described experiment (SC inoculation) to those after IP immunization, for PIV-WN, -YF/WN, -WN/JE, and -YF after the first dose (days 20-21) and second dose (days 34-38). A clear effect of the immunization route was observed both after the 1$^{st}$ and 2$^{nd}$ doses. For instance, for PIV-WN after 1$^{st}$ dose, SC immunization resulted in WN-specific PRNT50 titer of 1:40, while IP inoculation resulted in much higher titer 1:320 (and after the 2$^{nd}$ dose, titers were similar). A more pronounced effect was observed for other constructs after both the 1$^{st}$ and 2$^{nd}$ doses. Interestingly, PIV-YF/WN was very highly immunogenic by IP route (titer 1:320 after 1$^{st}$ IP dose vs. 1:20 by SC, and 1:1,280 after 2$^{nd}$ dose vs. 1:160 by SC). Similarly, immunogenicity of PIV-JE was significantly increased (e.g., JE-specific titer of 1:640 after two IP poses). Thus, better targeting of lymphoid cells, specifically antigen-presenting cells (which are more abundant in the abdomen as opposed to tissues under the skin), is an important consideration for use of PIV vaccines. In humans, efficient targeting of dendritic cells of the skin, increasing the magnitude of immune response, can be achieved by intradermal delivery, which we thus propose for a route for PIV immunization of humans.

In the above-described experiments, we also determined whether a neutralizing antibody response was induced against packaging envelopes (as opposed to response to VLPs encoded by PIV constructs and secreted by infected cells). No WN-specific neutralizing antibodies were detected by PRNT$_{50}$ in animals immunized with 5 log$_{10}$ FFU of the second component of WN d-PIV, containing the AC-prM-E deletion and thus not encoding VLPs, but packaged into the WN envelope in BHK-CprME(WN) helper cells, and no YF-specific neutralizing activity was found in sera from animals immunized with 4 log$_{10}$ FFU of the second component of YF d-PIV packaged in YF envelope. No YF-specific neutralizing response was induced by two doses of PIV-YF/WN packaged into YF envelope, and similarly, no WN-specific response was induced by two doses of PIV-JE packaged into WN envelope. The absence of neutralizing response against packaging envelopes permits manufacturing different PIV vaccines in one (universal) manufacturing helper cell line, or immunization of one individual with different recombinant vaccines based on the same vector, according to the present invention.

PIV Cocktails

Because PIVs undergo a single (optionally several, but limited) round(s) of replication in vivo, we considered that mixtures of different PIV vaccines can be administered without interference between individual constructs in the mixture (cocktail). To elucidate whether PIV vaccines can be used in cocktail formulations, immune responses in mice and hamsters to several PIV constructs given as mixtures were compared to the same constructs given individually. Similar results were obtained in both animal models. Results of mouse experiments are shown in Table 6. Similar anti-JE neutralizing antibody titers were observed in pools of sera from animals that were given one or two doses of either PIV-JE+PIV-WN mixture or PIV-JE alone (1:20 vs. 1:80 and 1:640 vs. 1:160, for one and two doses, respectively). Similarly, WN-specific titers against PIV-JE+PIV-WN mixture and PIV-WN alone were similar (1:320 vs. 1:640 and 1:5,120 vs. 1:5,120 for one and 2 doses, respectively). No or little cross-specific response was induced by either PIV-JE or -WN. The result was also confirmed by measuring PRNT$_{50}$ titers in sera from individual animals. Thus, it is clear that PIV vaccines can be efficiently administered as cocktails, inducing immunity against two or more flavivirus pathogens. In addition, as discussed above, various cocktails can be made between non-flavivirus PIV vaccines, or between any of flavivirus and non-flavivirus PIV vaccines.

In Vitro Studies

Different PIV prototypes were serially passaged up to 10 times in helper BHK cells, for s-PIVs, or in regular Vero cells, for d-PIVs. Samples harvested after each passage were titrated in Vero cells by immunostaining. Constructs grew to high titers, and no recombination restoring whole virus was observed. For instance, PIV-WN consistently grew to titers 7-8 $\log_{10}$ FFU/ml in BHK-CprME(WN) helper cells (containing a VEE replicon expressing the WN virus C-prM-E proteins), and WN d-PIV grew to titers exceeding 8 $\log_{10}$ FFU/ml in Vero cells, without recombination.

Example 2

PIV-TBE

PIV-TBE vaccine candidates can be assembled based entirely on sequences from wt TBE virus or the closely serologically related Langat (LGT) virus (naturally attenuated virus, e.g., wt strain TP-21 or its empirically attenuated variant, strain E5), or based on chimeric sequences containing the backbone (capsid and non-structural sequences) from YF 17D or other flaviviruses, such as WN virus, and the prM-E envelope protein genes from TBE, LGT, or other serologically related flaviviruses from the TBE serocomplex. YF/TBE LAV candidates are constructed based on the backbone from YF 17D and the prM-E genes from TBE or related viruses (e.g., the E5 strain of LGT), similar to other chimeric LAV vaccines.

Construction of PIV-TBE and YF/TBE LAV vaccine prototypes was performed by cloning of appropriate genetic elements into plasmids for PIV-WN (Mason et al., Virology 351:432-443, 2006; Suzuki et al., J. Virol. 82:6942-6951, 2008), or plasmids for chimeric LAVs (e.g., pBSA-AR1, a single-plasmid version of infectious clone of YF/JE LAV; WO 2008/036146), respectively, using standard methods in the art of reverse genetics. The prM-E sequences of TBE virus strain Hypr (GenBank accession number U39292) and LGT strain E5 (GenBank accession number AF253420) were first computer codon-optimized to conform to the preferential codon usage in the human genome, and to eliminate nucleotide sequence repeats longer than 8 nt to ensure high genetic stability of inserts (if determined to be necessary, further shortening of nt sequence repeats can be performed). The genes were chemically synthesized and cloned into plasmids for PIV-WN and YF/JE LAV, in place of corresponding prM-E genes. Resulting plasmids were in vitro transcribed and appropriate cells (Vero for chimeric viruses, and helper BHK cells for PIV) were transfected with RNA transcripts to generate virus/PIV samples.

YF/TBE LAV Constructs

In YF/TBE constructs containing either the TBE Hypr (plasmids p42, p45, and p59) or LGT E5 (plasmid P43) prM-E genes, two different types of the C/prM junction were first examined (see in FIG. 6; C/prM junctions only are shown in Sequence Appendix 1, and complete 5'-terminal sequences covering the 5'UTR-C-prM-E-beginning of NS1 region are shown in Sequence Appendix 2). The p42-derived YF17D/Hypr chimera contained a hybrid YF17D/Hypr signal peptide for the prM protein, while the p45-derived YF17D/Hypr chimera contained a hybrid YF17D/WN signal peptide for prM (Sequence Appendix 1). The former chimeric virus produced very high titers at both P0 (immediately after transfection) and P1 (the next passage in Vero cells), up to 7.9 $\log_{10}$ PFU/ml, which were 0.5 $\log_{10}$ times higher, compared to the latter virus; in addition it formed significantly larger plaques in Vero cells (FIG. 6). Thus, use of TBE-specific residues in the signal peptide for prM conferred a significant growth advantage over the signal containing WN-specific residues. The p43-derived YF17D/LGT chimera had the same prM signal as the p42-derived virus; it also produced very high titers at P0 and P1 passages (up to 8.1 $\log_{10}$ PFU/ml) and formed large plaques. A derivative of the p42-derived virus was also produced from plasmid p59, which contained a strong attenuating mutation characterized previously in the context of a YF/WN LAV vaccine virus, specifically, a 3-a.a. deletion in the YF17D-specific C protein (PSR, residues 40-42 in the beginning of α-Helix I; WO 2006/116182). As expected, the p59 virus grew to lower titers (5.6 and 6.5 $\log_{10}$ PFU/ml at P0 and P1, respectively), and formed small plaques (determined in a separate titration experiment and thus not shown in FIG. 6), compared to the parent p42-derived chimera. These initial observations of growth properties of YF/TBE LAV prototypes, and correlation of replication in vitro with plaque morphologies, have been confirmed in growth curve experiments (FIG. 8).

PIV-TBE Constructs

PIV-WN/TBE variants were constructed, and packaged PIV samples were derived from plasmids p39 and p40 (FIG. 7; Sequence Appendix 1 for C/prM junction sequences, and Sequence Appendix 3 for complete 5'UTR-ΔC-prM-E-beginning of NS1 sequences). These contained complete Hypr or WN prM signals, respectively. Both PIVs were successfully recovered and propagated in BHK-CprME(WN) or BHK-C(WN) helper cells (Mason et al., Virology 351:432-443, 2006; Widman et al., Vaccine 26:2762-2771, 2008). The P0 and P1 sample titers of the p39 variant were 0.2-1.0 $\log_{10}$ times, higher than p40 variant. In addition, Vero cells infected with p39 variant were stained brighter in immunofluorescence assay using a polyclonal TBE-specific antibody, compared to p40, indicative of more efficient replication (FIG. 7). The higher rate of replication of the p39 candidate than p40 candidate was confirmed in a growth curve experiment (FIG. 8). In the latter experiment, both candidates appeared to grow better in the BHK-C(WN) helper cells compared to BHK-CprME(WN), with the p39 variant reaching titer of ~7 $\log_{10}$ PFU/ml on day 5 (note that peak titers have not been reached). The discovery of the effect of prM signal on replication rates of both PIV and chimeric LAV vaccine candidates, and head-to-head comparison of different signals to generate the most efficiently replicating and immunogenic (see above) construct, are a distinguishing feature of our approach. As discussed above, the invention also includes the use of other flavivirus signals, including with appropriate mutations, the uncoupling the viral protease and signalase cleavages at the C/prM junction, e.g., by mutating or deleting the viral protease cleavage site at the C-terminus of C preceding the prM signal, the use of strong non-flavivirus signals (e.g., tPA signal, etc.) in place of prM signal, as well as optimization of sequences downstream from the signalase cleavage site.

Other PIV-TBE variants based entirely on wt TBE (Hypr strain) and LGT virus (TP21 wild type strain or attenuated E5 strain), and chimeric YF 17D backbone/prM-E (TBE or LGT) sequences are also included in the invention. Helper cells providing appropriate C, C-prM-E, etc., proteins (e.g., TBE-specific) for trans-complementation can be constructed by means of stable DNA transfection or through the use of an appropriate vector, e.g., an alphavirus replicon, such as based on VEE strain TC-83, with antibiotic selection of replicon-containing cells. Vero and BHK21 cells can be used in practice of the invention. The former are an approved substrate for human vaccine manufacture; any other cell line acceptable for human and/or veterinary vaccine manufacturing can be also used. In addition to s-PIV constructs, d-PIV constructs can also be assembled. To additionally ascertain safety for vaccinees and the environment, appropriate modifications can be employed, including the use of degenerate codons and complementary mutations in the 5' and 3' CS elements, to minimize chances of recombination that theoretically could result in viable virus. Following construction, all vaccine candidates can be evaluated in vitro for manufacturability/stability, and in vivo for attenuation and immunogenicity/efficacy, in available pre-clinical animal models, such as those used in development and quality control of TBE and YF vaccines.

Neurovirulence and Neuroinvasiveness in Mice of PIV-TBE and YF/TBE LAV Constructs Young adult ICR mice (~3.5 week-old), were inoculated with graded doses of PIV-TBE and YF/TBE LAV candidates by the IC route to measure neurovirulence, or IP route to measure neuroinvasiveness (and later immunogenicity/efficacy). Animals that received 5 $\log_{10}$ FFU of PIV-Hypr (p39 and p40) variants by both routes survived and showed no signs of sickness, similar to mock-inoculated animals (Table 7), and thus PIV-TBE vaccines are completely avirulent. Mice inoculated IC with YF 17D control (1-3 $\log_{10}$ PFU) showed dose-dependent mortality, while all animals inoculated IP (5 $\log_{10}$ PFU) survived, in accord with the knowledge that YF 17D virus is not neuroinvasive. All animals that received graded IC doses (2-4 $\log_{10}$ PFU) of YF/TBE LAV prototypes p42, p45, p43, and p59 died (moribund animals were humanely euthanized). These variants appear to be less attenuated than YF 17D, e.g., as evidenced by complete mortality and shorter AST at the 2 $\log_{10}$ PFU dose, the lowest dose tested for YF/TBE LAV candidates. The non-neurovirulent phenotype of PIV-TBE, virulent phenotype of YF/TBE LAV and intermediate-virulence phenotype of YF 17D are also illustrated in FIG. 9, showing survival curves of mice after IC inoculation. It should be noted that the p43 (LGT prM-E genes) and p59 (the dC2 deletion variant of YF/Hypr LAV) were less neurovirulent than p42 and p45 YF/Hypr LAV constructs as evidenced by larger AST values for corresponding doses (Table 7). In addition, p43 and p59 candidates were non-neuroinvasive, while p42 and p45 caused partial mortality after IP inoculation (5 $\log_{10}$ PFU/dose) (Table 7; FIG. 10). It should be noted however that all the YF/TBE LAV constructs were significantly attenuated as compared to wt TBE viruses, e.g., compared to wt TBE Hypr virus, which is uniformly highly virulent for mice, both at very low IC ($LD_{50}$~0.1 PFU) and IP ($LD_{50}$≤10 PFU) doses (Wallner et al., J. Gen. Virol. 77:1035-1042, 1996; Mandl et al., J. Virol. 72:2132-2140, 1998; Mandl et al., J. Gen. Virol. 78:1049-1057, 1997

Immunogenicity/Efficacy of PIV-TBE and YF/TBE LAV Constructs in Mice

TBE-specific neutralizing antibody responses in mice immunized IP with one or two doses of the PIV-TBE or YF/TBE LAV variants described above, or a human formalin-inactivated TBE vaccine control (1:30 of human dose) are being measured. Animals have been challenged with a high IP dose (500 PFU) of wt Hypr TBE virus; morbidity (e.g., weight loss), and mortality after challenge are monitored.

Immunogenicity/Efficacy of PIV-TBE and YF/TBE LAV Constructs in Mice

TBE-specific neutralizing antibody responses in mice immunized IP with one or two doses of the PIV-TBE or YF/TBE LAV variants described above (from experiment in Table 7), or a human formalin-inactivated TBE vaccine control (1:20 of human dose; one or two doses), or YF 17D and mock controls, were measured on day 20 by $PRNT_{50}$ against wt TBE Hypr virus (Table 8; second dose of indicated test articles was given on day 14). [Titers were determined in individual sera, or pooled sera from two animals in most cases, or pooled sera from 4 animals for the YF17D and Mock negative controls]. Titers in individual test samples as well as GMTs for each group are provided in Table 8. Titers in test samples were similar within each group, e.g., in groups immunized with PIVs, indicating high uniformity of immune response in animals. As expected, no TBE-specific neutralizing antibodies were detected in negative control groups (YF 17D and Mock; GMTs<1:10); accordingly, animals in these groups were not protected from challenge on day 21 post-immunization with a high IP dose (500 PFU) of wt Hypr TBE virus. Mortalities from partial observation (on day 9 post-challenge; observation being continued) are provided in Table 8, and dynamics of average post-challenge body weights indicative of morbidity are shown in FIG. 11. Neutralizing antibodies were detected in killed vaccine controls, which were particularly high after two doses (GMT 1:1,496); animals in the 2-dose group were completely protected in that there was no mortality or body weight loss (but not animals in the 1-dose group). Animals that received both one and two doses of PIV-Hypr p39 had very high antibody titers (GMTs 1:665 and 1:10,584) and were solidly protected, demonstrating that robust protective immunity can be induced by s-PIV-TBE defective vaccine. The two animals that survived immunization with YF/Hypr p42 chimera (see in Table 7) also had high antibody titers (GMT 1:6,085) and were protected (Table 8; FIG. 11). Interestingly, PIV-Hypr p40 and YF/Hypr p45 were poorly immunogenic (GMTs 1:15 and 1:153 for one and two doses, and 1:68, respectively). As discussed above, these contained WN-specific sequences in the signal for prM, while the highly immunogenic PIV-Hypr p39 and YF/Hypr p42 constructs contained TBE-specific signal sequences. In agreement with discussion above, this result demonstrates the importance of choosing the right prM signal, e.g., the TBE-specific signal, to achieve high-level replication/VLP secretion, which in this experiment in vivo resulted in drastically different immune responses. Immunogenicity of YF/LGT p43 and YF/Hypr dC2 p59 chimeras was relatively low which could be expected, because of the use of a heterologous envelope (LGT, different from challenge TBE virus) and high attenuating effect of the dC2 deletion, respectively.

Example 3

Foreign Gene Expression

In the examples of recombinant PIV constructs described below, genes of interest were codon optimized (e.g., for efficient expression in a target vaccination host) and to eliminate long nt sequence repeats to increase insert stability (≥8 nt long; additional shortening of repeats can be performed if necessary), and then chemically synthesized. The genes were cloned into PIV-WN vector plasmids using standard methods of molecular biology well known in the art, and packaged PIVs were recovered following in vitro transcription and transfection of appropriate helper (for s-PIVs) or regular (for d-PIVs) cells.

Expression of Rabies Virus G Protein in WN s-PIV and d-PIV

Rabies virus, Rhabdoviridae family, is a significant human and veterinary pathogen. Despite the availability of several (killed) vaccines, improved vaccines are still needed for both veterinary and human use (e.g. as an inexpensive pre-exposure prophylactic vaccines). Rabies virus glycoprotein G mediates entry of the virus into cells and is the main immunogen. It has been expressed in other vectors with the purpose of developing veterinary vaccines (e.g., Pastoret and Brochier, Epidemio. Infect. 116:235-240, 1996; Li et al., Virology 356:147-154, 2006).

Full length rabies virus G protein (original Pasteur virus isolate, GenBank accession number NC_001542) was codon-optimized, chemically synthesized, and inserted adjacent to the ΔC, ΔprM-E and ΔC-prM-E deletions in PIV-WN vectors (FIG. 12). The sequences of constructs are provided in Sequence Appendix 4. General designs of the constructs are illustrated in FIG. 13. The entire G protein containing its own signal peptide was inserted in-frame downstream from the WN C protein either with the ΔC deletion (ΔC and ΔC-prM-E constricts) or without (ΔprM-E) and a few residues from the prM signal. Foot and mouth disease virus (FMDV) 2A autoprotease was placed downstream from the transmembrane C-terminal anchor of G to provide cleavage of C-terminus of G from the viral polyprotein during translation. The FMDV 2A element is followed by WN-specific signal for prM and prM-E-NS1-5 genes in the ΔC construct, or signal for NS1 and NS1-5 genes in ΔprM-E and ΔC-prM-E constructs.

Packaged WN(ΔC)-rabiesG, WN(ΔprME)-rabiesG, and WN(ΔCprME)-rabiesG PIVs were produced by transfection of helper BHK cells complementing the PIV vector deletion [containing a Venezuelan equine encephalitis virus (strain TC-83) replicon expressing WN virus structural proteins for trans-complementation]. Efficient replication and expression of rabies G protein was demonstrated for the three constructs by transfection/infection of BHK-C(WN) and/or BHK-C-prM-E(WN) helper cells, as well as regular BHK cells, by immunostaining and immunofluorescence assay (IFA) using anti-Rabies G monoclonal antibody (RabG-Mab) (FIG. 14). Titers were determined in Vero cells by immunostaining with the Mab or an anti-WN virus polyclonal antibody. Growth curves of the constructs in BHK-CprME(WN) cells after transfection with in vitro RNA transcripts are shown in FIG. 14, bottom panels. The PIVs grew efficiently to titers ~6 to >7 $\log_{10}$ FFU/ml. Importantly, nearly identical titers were detected by both RabG-Mab and WN-antibody staining, which was the first evidence of genetic stability of the insert. In PIV-infected Vero cells, which were fixed but not permeabilized, strong membrane staining was observed by RabG-Mab staining, demonstrating that the product was efficiently delivered to the cell surface (FIG. 15). The latter is known to be the main prerequisite for high immunogenicity of expressed G. Individual packaged PIVs can spread following infection of helper BHK cells, but cannot spread in regular cells as illustrated for WN(ΔC)-rabiesG PIV in FIG. 16. The fact that there is no spread in naïve BHK cells demonstrates that the recombinant RNA genomes cannot be non-specifically packaged into membrane vesicles containing the G protein, if produced by PIV infected cells. An identical result was obtained with the G protein of another rhabdovirus, Vesicular stomatitis virus (VSV), contrary to previous observations of non-specific packaging of Semliki Forest virus (SFV) replicon expressing VSV G protein (Rolls et al., Cell 79:497-506, 1994). The latter is a desired safety feature. [Alternatively, some non-specific packaging could result in a limited spread of PIV in vivo, potentially enhancing anti-rabies immune response. The latter could be also a beneficial feature, given that such PIV is demonstrated to be safe]. The stability of the rabies G insert in the three PIVs was demonstrated by serial passages in helper BHK-CprME(WN) cells at high or low MOI (0.1 or 0.001 FFU/cell). At each passage, cell supernatants were harvested and titrated in regular cells (e.g., Vero cells) using immunostaining with an anti-WN polyclonal antibody to determine total PIV titer, or anti-rabies G monoclonal antibody to determine titer of particles containing the G gene (illustrated for MOI 0.1 in FIG. 17; similar results were obtained at MOI 0.001). The WN(ΔC)-rabiesG PIV was stable for 5 passages, while the titer of insert-containing PIV started declining at passage 6, indicative of insert instability. This could be expected, because in this construct, large G gene insert (~1500 nt) is combined with a small ΔC deletion (~200 nt), significantly increasing the overall size of the recombinant RNA genome. In contrast, in WN(ΔprME)-rabiesG, and WN(ΔCprME)-rabiesG PIVs, the insert is combined with a much larger deletion (~2000 nt). Therefore, these constructs stably maintained the insert for all 10 passages examined (FIG. 17). Further, it can be seen in FIG. 17 that at some passages, titers as high as 8 $\log_{10}$ FFU/ml, or higher, were attained for all three PIVs, additionally demonstrating that PIVs can be easily propagated to high yields.

Following inoculation in vivo individually, the WN(ΔC)-rabiesG s-PIV is expected to induce strong neutralizing antibody immune responses against both rabies and WN viruses, as well as T-cell responses. The WN(ΔprME)-rabiesG and WN(ΔCprME)-rabiesG PIVs will induce humoral immune response only against rabies because they do not encode the WN prM-E genes. WN(ΔC)-rabiesG s-PIV construct can be also co-inoculated with WN(ΔprME)-rabiesG construct in a d-PIV formulation (see in FIG. 12), increasing the dose of expressed G protein, and with enhanced immunity against both pathogens due to limited spread. As an example of spread, titration results in Vero cells of a s-PIV sample, WN(ΔprME)-rabiesG, and a d-PIV sample, WN(ΔprME)-rabiesG+WN(ΔC) PIV (the latter did not encode rabies G protein), are shown in FIG. 18. Infection of naïve Vero cells with s-PIV gave only individual cells stainable with RabG-Mab (or small clusters formed due to division of cells). In contrast, large foci were observed following infection with the d-PIV sample (FIG. 18, right panel) that were products of coinfection with the two PIV types.

The WN(ΔCprME)-rabiesG construct can be also used in a d-PIV formulation, if it is co-inoculated with a helper genome providing C-prM-E in trans (see in FIG. 12). For example it can be a WN virus genome containing a deletion of one of the NS proteins, e.g., NS1, NS3, or NS5, which are known to be trans-complementable (Khromykh et al., J. Virol. 73:10272-10280, 1999; Khromykh et al., J. Virol. 74:3253-3263, 2000). We have constructed a WN-ΔNS1 genome (sequence provided in Sequence Appendix 4) and obtained evidence of co-infection with WN(ΔprME)-rabiesG or WN(ΔCprME)-rabiesG constructs, and spread in vitro, by immunostaining. In the case of such d-PIVs, rabies G protein can be also inserted and expressed in helper genome, e.g., WN-ΔNS1 genome, to increase the amount of expressed rabies G protein resulting in an increased anti-rabies immune response. As with any d-PIV versions, one immunogen can be from one pathogen (e.g., rabies G) and the other from a second pathogen, resulting in three antigenic specificities of vaccine. As discussed above, ΔNS1 deletions can be replaced with or used in combination with ΔNS3 and/or ΔNS5 deletions/mutations, in other examples.

Expression of RSV F Protein in WN s-PIV and d-PIV

Respiratory syncytial virus (RSV), member of Paramyxoviridae family, is the leading cause of severe respiratory tract disease in young children worldwide (Collins and Crowe, Respiratory Syncytial Virus and Metapneumovirus, In: Knipe et al. Eds., Fields Virology, 5$^{th}$ ed., Philadelphia: Wolters Kluwer/Lippincott Williams and Wilkins, 2007:1601-1646). Fusion protein F of the virus is a lead viral antigen for developing a safe and effective vaccine. To avoid post-vaccination exacerbation of RSV infection observed previously with a formalin-inactivated vaccine candidate, a balanced Th1/Th2 response to F is required which can be achieved by better TLR stimulation, a prerequisite for induction of high-affinity antibodies (Delgado et al., Nat. Med. 15:34-41, 2009), which should be achievable through delivering F in a robust virus-based vector. We have previously demonstrated the capacity of yellow fever virus-based chimeric LAV vectors to induce a strong, balanced Th1/Th2 response in vivo against an influenza antigen (WO 2008/036146). In the present invention, both yellow fever virus-based chimeric LAVs and PIV vectors are used for delivering RSV F to induce optimal immune response profile. Other LAVs and PIV vectors described herein can also be used for this purpose.

Full-length RSV F protein of A2 strain of the virus (GenBank accession number P03420) was codon optimized as described above, synthesized, and cloned into plasmids for PIV-WN s-PIV and d-PIV, using the insertion schemes shown in FIGS. 12 and 13 for rabies G protein, by applying standard methods of molecular biology. Exact sequences of the insertions and surrounding genetic elements are provided in Sequence Appendix 5. In vitro RNA transcripts of resulting WN(ΔC)—RSV F, WN(ΔprME)-RSV F, and WN(ΔCprME)-RSV F PIV constructs were used to transfect helper BHK-CprME(WN) cells. Efficient replication and expression of RSV F protein was first demonstrated by immunostaining of transfected cells with an anti-RSV F Mab, as illustrated for the WN(ΔprME)-RSV F construct in FIG. 19. The presence of packaged PIVs in the supernatants from transfected cells (titer as high as 7 log10 FFU/ml) was determined by titration in Vero cells with immunostaining. Additionally, similar constructs can be used that contain a modified full length F protein gene. Specifically, the N-terminal native signal peptide of F is replaced in modified F protein with the one from rabies virus G protein. The modification is intended to elucidate whether the use of a heterologous signal can increase the rate of F protein synthesis and/or replication of PIVs.

TABLE 1

PIV prototype constructs used in platform development studies

| Construct | Genetic composition | Packaged in |
|---|---|---|
| PIV-WN | wt NY99 WN virus | WN envelope; BHK-CprME(WN) or BHK-C(WN) helper cells (Mason et al., Virology 2006, 351: 432-43; Widman et al., Vaccine 2008, 26: 2762-71) |
| PIV-YF/WN | Envelope (VLP): wt WN NY99 Backbone: YF 17D | YF 17D envelope; BHK-CprME(YF) helper cells (Widman et al., Adv Virus Res. 2008, 72: 77-126) |
| PIV-WN/JE | Envelope (VLP): wt JE Nakayama Backbone: wt WN NY99 | JE or WN envelope; BHK-C(WN) or BI-IK-CprME(WN) helper cells (Ishikawa et al., Vaccine 2008, 26: 2772-8) |
| PIV-YF | YF 17D | YF 17D envelope; BHK-CprME(YF) or BHK-C(YF) helper cells (Mason et al., Virology 2006, 351: 432-43) |

TABLE 2

Safety: Suckling mouse neurovirulence[1]

| Construct | Doses (log$_{10}$) | Mortality (%) | AST (days)[2] |
|---|---|---|---|
| PIV-YF | 1-4 | 0/10 (0%) | na |
| PIV-WN | 2-5 | 0/10 (0%) | na |
| PIV-WN/JE | 1-4 | 0/11 (0%) | na |
| PIV-YF/WN | 1-4 | 0/10-11 (0%) | na |
| WN d-PIV | 1-4 | 0/10-11 (0%) | na |
| YF d-PIV | 1-4 | 0/10 (0%) | na |
| YF17D | 2 | 10/10 (100%) | 7.6 |
|  | 1 | 10/10 (100%) | 9.3 |
|  | 0 | 9/10 (90%) | 9.9 |
|  | −1 | 3/10 (30%) | 9.6 |
| YF/JE | 4 | 9/11 (82%) | 9.7 |
|  | 3 | 7/10 (70%) | 12.3 |
|  | 2 | 3/11 (27%) | 12 |
|  | 1 | 0/11 (0%) | na |
| YF/WN | 3 | 2/11 (18%) | 12.5 |
|  | 0-2 | 0/10-11 (0%) | na |

[1]Single dose, IC inoculation, ICR 5-day old mice, graded log doses administered.
[2]AST for mice that died; na, not applicable.

TABLE 3

PIV highly immunogenic and efficacious in mice[1]

| Group | Dose | PRNT Day 20 | PRNT Day 34 | Post-challenge mortality (%) |
|---|---|---|---|---|
| PIV-WN | 10$^5$ | 640 | 1280 | 0/8 (0%) |
|  | 10$^6$ | 1280 | 2560 | 1/8 (12.5%) |
|  | 10$^6$ + 10$^5$ | 2560 | 2560 | 0/6 (0%) |
| YF/WN control | 10$^4$ | 1280 | 2560 | 1/8 (12.5%) |
| PIV-WN/JE | 10$^4$ | 10 | 20 | N/D |
|  | 10$^5$ | 20 | 20 | N/D |
|  | 10$^5$ + 10$^5$ | 20 | 160 | N/D |
| YF/JE control | 10$^4$ | 160 | 320 | N/D |
| PIV-YF | 10$^4$ | <10 | <10 | 8/8 (100%) |
|  | 10$^5$ | <10 | <10 | 5/7 (71%) |
|  | 10$^5$ + 10$^5$ | 10 | 10 | 2/5 (40%) |
| YF17D control | 10$^4$ | 640 | 1280 | 0/7 (0%) |
| Mock control | - WN challenge | Diluent | N/D | 0 | 7/7 (100%) |
| | - YF challenge | Diluent | N/D | 0 | 8/8 (100%) |

[1]IP immunization (d0 prime, and d21 boost in select groups); challenge on d35: wt WN NY99, 3 log$_{10}$ PFU IP, 270 LD50; wt YF Asibi, 3 log$_{10}$ PFU IC, 500 LD50; N/D, not determined.

TABLE 4

PIV are immunogenic in hamsters and protect against challenge[1]

| Group | Dose(s) | PRNT Day 38 | Mortality POST-CHALLENGE | Morbidity | Peak viremia (log) |
|---|---|---|---|---|---|
| PIV-WN | $10^5$ | 320 | 0/5 (0%) | 0/5 (0%) | 2.3 |
|  | $10^6$ | 640 | 0/5 (0%) | 0/5 (0%) | 1.8 |
|  | $10^6 + 10^5$ | 1280 | 0/5 (0%) | 0/5 (0%) | <1.3 |
| YF/WN control | $10^4$ | ≥2560 | 0/5 (0%) | 0/5 (0%) | <1.3 |
| PIV-WN/JE | $10^4$ | 20 | 2/5 (40%) | 2/5 (40%) | 2.2 |
|  | $10^5 + 10^5$ | 40 | 0/5 (0%) | 0/5 (0%) | <1.3 |
| YF/JE control | $10^4$ | 2560 | 0/5 (0%) | 0/5 (0%) | 1.3 |
| PIV-YF | $10^4$ | <10 | 1/3 (33%) | 3/3 (100%) | 8.3 |
|  | $10^5$ | <10 | 1/5 (20%) | 4/5 (80%) | 8.3 |
|  | $10^5 + 10^5$ | 20 | 0/4 (0%) | 0/4 (0%) | 2.5 |
| YF17D control | $10^4$ | ≥2560 | 0/4 (0%) | 0/4 (0%) | <1.3 |
| Mock control - WN challenge | Diluent | <10 | 3/4 (75%) | 4/4 (100%) | 4.0 |
| - YF challenge | Diluent | <10 | 1/4 (25%) | 4/4 (100%) | 8.4 |
| - JE challenge | Diluent | <10 | 2/5 (40%) | 2/5 (40%) | 3.0 |

[1]Syrian hamsters, SC inoculation (d0, and d21 in select groups); challenge (d39): wt WN NY385/99 6 $\log_{10}$ PFU IP, wt JE Nakayama 5.8 $\log_{10}$ PFU IC, or hamster-adapted YF Asibi 7 $\log_{10}$ PFU IP (McArthur et al., J. Virol. 77:1462-1468, 2003; McArthur et al., Virus Res. 110:65-71, 2005).

TABLE 5

Immunization of hamsters with PIV: comparison of SC and IP routes

| Inoculums | PRNT Day 20-21 SC | PRNT Day 20-21 IP | Boost ($\log_{10}$) | PRNT Day 34-38 SC | PRNT Day 34-38 IP |
|---|---|---|---|---|---|
| PIV-WN | 40 | 320 | 5 | 1280 | 1280 |
| PIV-YF/WN | 10 | 320 | 5 | 160 | 1280 |
| PIV-WN/JE | 10 | 80 | 5 | 40 | 640 |
| PIV-YF | <10 | 10 | 5 | 20 | 80 |

TABLE 6

Immune responses to PIV cocktails (mice)[1]

| Group | Dose | PRNT Day 20 Anti-JE | PRNT Day 20 Anti-WN | PRNT Day 34 Anti-JE | PRNT Day 34 Anti-WN |
|---|---|---|---|---|---|
| PIV-WN/JE + RV-WN | $10^5 + 10^5$ | 20 | 320 | 640 | 5120 |
| PIV-WN/JE alone | $10^5$ | 80 | <10 | 160 | 20 |
| PIV-WN alone | $10^5$ | <10 | 640 | <10 | 5120 |
| Mock | — | <10 | <10 | <10 | <10 |

[1]C57/BL6 mice, IP inoculations on days 0 and 21; pooled serum PRNT titers.

TABLE 7

Neurovirulence (IC inoculation) and neuroinvasiveness (IP inoculation) of PIV-TBE and YF/TBE vaccine constructs in adult ICR mice

| Construct | Neurovirulence (IC route) Dose(s) ($\log_{10}$) | Mortality (%) | AST, days[1] | Neuroinvasiveness (IP route) Dose(s) ($\log_{10}$) | Mortality (%) | AST, days[1] |
|---|---|---|---|---|---|---|
| PIV-Hypr p39 | 5 | 0/7 (0%) | na | 5 | 0/16 (0%) | na |
| PIV-Hypr p40 | 5 | 0/6 (0%) | na | 5 | 0/16 (0%) | na |
| YF/Hypr p42 | 4 | 8/8 (100%) | 6.3 | 5 | 6/8 (75%) | 13.3 |
|  | 3 | 8/8 (100%) | 6.4 |  |  |  |
|  | 2 | 8/8 (100%) | 7.4 |  |  |  |
| YF/LGT p43 | 4 | 8/8 (100%) | 7.9 | 5 | 0/8 (0%) | na |
|  | 3 | 8/8 (100%) | 7.6 |  |  |  |
|  | 2 | 8/8 (100%) | 8.4 |  |  |  |
| YF/Hypr p45 | 4 | 8/8 (100%) | 6.1 | 5 | 5/8 (62.5%) | 112 |
|  | 3 | 8/8 (100%) | 6.6 |  |  |  |
|  | 2 | 8/8 (100%) | 6.8 |  |  |  |
| YF/Hypr dC2 p59 | 4 | 8/8 (100%) | 6.6 | 5 | 0/8 (0%) | na |
|  | 3 | 8/8 (100%) | 7.4 |  |  |  |
|  | 2 | 8/8 (100%) | 8.1 |  |  |  |
| YF 17D | 3 | 8/8 (100%) | 9 | 5 | 0/8 (0%) | na |
|  | 2 | 7/8 (87.5%) | 9.6 |  |  |  |
|  | 1 | 4/8 (50%) | 10 |  |  |  |
| Mock (diluent) | none | 0/8 (0%) | na | none | 0/8 (0%) | na |

[1]AST for mice that died.

TABLE 8

Neutralizing antibody titers ($PRNT_{50}$) in mice immunized IP (determined against wt TBE virus Hypr), and protection from challenge (postchallenge observation, day 9)

| Immunogen | Dose(s), $\log_{10}$ | $PRNT_{50}$ titer, individ. samples[1] | $PRNT_{50}$ GMT | Postchallenge mortality (%) on day 9[2] |
|---|---|---|---|---|
| PIV-Hypr p39, 1 dose | 5 | 1746 (2) | 665 | 0/8 (0%) |
|  |  | 1187 (2) |  |  |
|  |  | 164 (2) |  |  |
|  |  | 574 (2) |  |  |

TABLE 8-continued

Neutralizing antibody titers (PRNT$_{50}$) in mice immunized IP (determined against wt TBE virus Hypr), and protection from challenge (postchallenge observation, day 9)

| Immunogen | Dose(s), log$_{10}$ | PRNT$_{50}$ titer, individ. samples[1] | PRNT$_{50}$ GMT | Postchallenge mortality (%) on day 9[2] |
|---|---|---|---|---|
| PIV-Hypr p39, 2 doses | 5 + 5 | 16229 (2) | 10,584 | 0/8 (0%) |
|  |  | 12928 (2) |  |  |
|  |  | 12927 (2) |  |  |
|  |  | 4627 (2) |  |  |
| PIV-Hypr p40, 1 dose | 5 | <10 (2) | 15 | 6/8 (75%) |
|  |  | <10 (2) |  |  |
|  |  | 18 (2) |  |  |
|  |  | 33 (2) |  |  |
| PIV-Hypr p40, 2 doses | 5 + 5 | 169 (2) | 153 | 1/8 (12.5%) |
|  |  | 638 (2) |  |  |
|  |  | 26 (2) |  |  |
|  |  | 192 (2) |  |  |
| YF/Hypr p42 | 5 | 9210 (1) | 6,085 | 0/2 (0%) |
|  |  | 4020 (1) |  |  |
| YF/LGT p43 | 5 | 123 (2) | 64 | 1/8 (12.5%) |
|  |  | 32 (2) |  |  |
|  |  | 96 (2) |  |  |
|  |  | 45 (2) |  |  |
| YF/Hypr p45 | 5 | 292 (2) | 68 | 0/3 (0%) |
|  |  | 16 (1) |  |  |
| YF/Hypr dC2 p59 | 5 | 194 (2) | 68 | 0/8 (0%) |
|  |  | 93 (2) |  |  |
|  |  | 45 (2) |  |  |
|  |  | 26 (2) |  |  |
| Killed human TBE vaccine, 1 dose (at 1/20 of human dose) | 1/20 | 19 (2) | 12 | 1/8 (12.5%) |
|  |  | <10 (2) |  |  |
|  |  | 13 (2) |  |  |
|  |  | <10 (2) |  |  |
| Killed human TBE vaccine, 2 doses (each at 1/20 of human dose) | 1/20 + 1/20 | 3435 (2) | 1,496 | 0/6 (0%) |
|  |  | 1267 (2) |  |  |
|  |  | 770 (2) |  |  |
| YF 17D control | 5 | <10 (4) | <10 | 5/8 (62.5%) |
|  |  | 11 (4) |  |  |
| Mock | none | <10 (4) | <10 | 4/8 (50%) |
|  |  | <10 (4) |  |  |

[1]Numbers in parenthesis correspond to number of mice in each pooled serum sample tested.
[2]Mortalities on day 9 are shown.

TABLE 9

Examples of published attenuating E protein mutations that can be used for attenuation of chimeric TBE LAV candidates

| Residue | Domain | Comments | Attenuation in | Reference |
|---|---|---|---|---|
| N52R | II | DI-DII hinge, possibly involved in hinge motion required for fusion activation | JE, YF | Hasegawa et al, 1992, Schlesinger et al, 1996 |
| E84K | II | conserved, E in TBE, K/R in others, attenuated by passage in *Ixodes ricinus* ticks, DII contains flavivirus cross reactive epitopes | TBE | Labuda et al, 1994 |
| E85K | II | conserved, E in TBE, K/R in others, attenuation obtained as plaque variants in Vero cells, DII contains flavivirus cross reactive epitopes | JE | Wu et al, 1997 |
| H104K | II | within highly conserved fusion peptide (aa 98-113), H in TBE, G in others | TBE | Rey et al, 1995 |
| L107F | II | within highly conserved fusion peptide (aa 98-113), L in all flaviviruses, F in attenuated JE | TBE, JE, WN | Rey et al, 1995, Arroyo et al, 1999, 2004 |
| T123K | II | DI-DII hinge, T in TBE, A in KFD | TBE | Holzmann et al, 1997 |
| K126E | II | DI-DII hinge, K in TBE, E in D-2 | DEN2 | Bray, 98 |
| K136E | II | DI-DII hinge, K in TBE and JE, E in D-2 | JE |  |
| N154L(Y) | I | glycosylation site, packed with conserved H 104, involved in fusion. | DEN2, DEN4, YF | Guirakhoo et al, 1993, Pletnev et al, 1993, Kawano et al, 1993, Jennings et al, 1994 |
| K171E | I | external edge of DI, involved in fusion | TBE | Mandl, 1989, Holzmann, 1997 |
| I173T |  | external edge of DI, involved in fusion | YF | Chambers and Nickells 2001 |
| D181Y |  | DI- DII hinge | TBE | Holzmann et al, 1997 |

TABLE 9-continued

Examples of published attenuating E protein mutations that can be used for attenuation of chimeric TBE LAV candidates

| Residue | Domain | Comments | Attenuation in | Reference |
|---------|--------|----------|----------------|-----------|
| K204R | | Lining Hydrophobic pocket, involve in fusion | DEN1, DEN3 | Guirakhoo et al, 2004 |
| P272S | II | highly conserved, junction of one the of 2 alpha helices | JE | Cecilia et al, 1991 |
| G308N | III | cell attachment, DKT in TBE, EGS in KFD, T-X in others, change to N produced glycosylation site in LI and reduced virulence, N-X-T/S glycosylation motif | LI | Jiang et al, 1993, Gao et al, 1994 |
| S310K | III | putative cell attachment, change from E to G in JE reduced virulence | JE | Jiang et al, 1993, Gao et al, 1994, Wu et al, 1997 |
| K311E | III | highly conserved, putative cell attachment | TBE, YF | Rey et al, 1995, Jennings, 1994 |
| T333L | III | putative cell attachment | YF, LGT | Raynman et al, 1998 |
| G334K | III | putative cell attachment | YF | Chambers and Nickells, 2001 |
| S335K | III | putative cell attachment | JE | Wu et al, 1997 |
| K336D | III | putative cell attachment | JE | Cecilia and Gould, 1991 |
| P337D | III | putative cell attachment | JE | Cecilia and Gould, 1991 |
| G368R | III | putative cell attachment | TBE, JE | Holzman et at 1997, Hasegawa et al 1992 |
| Y384H | III | change to H attenuated TBE, putative cell attachment, −3 position to deleted RGD in TBE | TBE | Holzmann et al, 1990 |
| V385R | III | conserved, −2 position to deleted RGD in TBE, putative cell attachment | D2 | Hiramatsu et al, 1996, Lobigs, 1990 |
| G386R | III | highly conserved, −1 position to deleted RGD in TBE, putative cell attachment | D2, MVE | Hiramatsu, 1996, Lobigs et al, 1990 |
| E387R | III | conserved, +2 position to deleted RGD in TBE, putative cell attachment | D2, MVE | Hiramatsu, 1996, Lobigs et al, 1990 |
| F403K | none | highly conserved, C-terminal region not included in crystal structure sE | D-2, D-4 | Kawano et al, 1993, Bray et al, 1998 |
| H438Y | None | highly conserved, C-terminal region not included in crystal structure sE | LGT | Campbell and Pletnev 2000 |
| H496R | none | highly conserved, C-terminal region not included in crystal structure sE | TBE | Gritsun et al, 2001 |

References: Hasegawa et al., Virology 191(1): 158-165; Schlesinger et al., J. Gen. Virol. 1996, 77 (Pt 6): 1277-1285, 1996; Labuda et al., Virus Res. 31(3): 305-315, 1994; Wu et al., Virus Res. 51(2): 173-181, 1997; Holzmann et al., J. Gen. Virol. 78 (Pt 1): 31-37, 1997; Bray et al., J. Virol. 72(2): 1647-1651, 1998; Guirakhoo et al., Virology 194(1): 219-223, 1993; Pletnev et al., J. Virol. 67(8): 4956-4963, 1993; Kawano et al., J. Virol. 67(11): 6567-6575, 1993; Jennings et al., J. Infect. Dis. 169(3): 512-518, 1994; Mandl et al., J. Virol. 63(2): 564-571, 1989; Chambers et al., J. Virol. 75(22): 10912-10922, 2001; Cecilia et al., Virology 181(1): 70-77, 1991; Jiang et al., J. Gen. Virol. 74 (Pt 5): 931-935, 1993; Gao et al., J. Gen. Virol. 75 (Pt 3): 609-614, 1994; Holzmann et al., J. Virol. 64(10): 5156-5159, 1990; Hiramatsu et al., Virology 224(2): 437-445, 1996; Lobigs et al., Virology 176(2): 587-595, 1990; Campbell et al., Virology 269(1): 225-237, 2000; Gritsun et al., J. Gen. Virol. 82 (Pt 7): 1667-1675, 2001.

Example 4

Delivery of SIV Gag and Env Proteins (HIV Prototypes) in WN s-PIV and d-PIV

An artificial cassette containing SIV (GenBank accession number ADM52218.1) gp120 (a modified gene where the native signal sequence was replaced with the tPA signal and gp41 was truncated to contain only the TM domain), Gag, and Pro (protease) genes is shown in FIG. 20. The cassette was designed in a way that would allow its expression in the recombinant PIV ORF as a single precursor (different from SIV or HIV gene organization). To allow for cleavage into individual SIV proteins, the genes are separated by FMDV 2A autoprotease sequences (see above). The nucleotide sequence of the entire cassette (~4 kb in length) was optimized by silent nucleotide changes to eliminate direct sequence repeats (e.g., all repeats longer than 8 nt were eliminated) to increase insert stability (using optimization algorithms at DNA 2.0) and by incorporating monkey codon preference to enable efficient protein translation in primate cells.

The codon-optimized cassette was chemically synthesized, followed by in-frame insertion of the genes, alone or in different combinations, in PIV-WN vectors in place of the ΔC (RV909 vector), ΔprM-E (RV230 vector) or ΔC-prM-E (dC RV230 vector) deletions. Examples of sequences of the constructs are provided in Sequence Appendix 6. Inserts of the first three constructs in FIG. 20, starting with the Env glycoprotein, were designed similarly to the PIV WV-rabies G described hereinabove (gp120 signal fused with a portion of the signal sequence for prM at the end of the C gene or downstream from ΔC deletion depending on vector), as is also additionally illustrated for individual Env constructs in FIG. 21. In addition, alternate dC RV230 Env constructs were generated, in which the tPA signal and/or the SIV Env TM region of the gp120 gene were replaced with rabies virus G protein-specific signal and/or anchor sequences (three bottom constructs in FIG. 21), to determine whether these heterologous rabies G-derived sequences will have a beneficial effect on gp120 presentation or recombinant PIV replication. Gag and Gag-Pro insertions were designed to start with and end with FMDV 2A autoprotease sequences, to free the N- and C-termini of the cytoplasmically synthesized Gag protein. They were cloned in place of the ΔprM-E or ΔC-prM-E deletions (FIGS. 20 and 22). The N-terminal FMDV 2A was positioned either downstream from the viral cleavage site in C, or downstream from additional 9 or 18 amino acids following the cleavage site (from the prM signal) in the RV230 and dC RV230 vectors (FIG. 22) in order to determine which fusion type is preferable for efficient cleavage of FMDV 2A preceding Gag, which theoretically can be important in terms of both transgene expression and PIV replication.

Correct processing of the polyprotein in recovered SIV Gag and SIV Gag/Pro PIVs grown in helper cells was confirmed by Western blot using anti-Gag antibodies (FIG. 23).

Constructs expressing Gag alone showed the correct individual p58 Gag band of ~58 kDa, and constructs that also included Pro also showed an additional band of p28 which is a product of Gag cleavage by Pro. Immunostaining of naïve Vero cells infected with the Gag PIVs (constructs shown in FIG. 24D), showed individual stained cells as expected from sPIV (FIGS. 24A-C).

Efficient replication in vivo is illustrated by growth curves of SIV Gag PIV variants after transfection of helper cells with in vitro synthesized PIV RNA (P0 passage) (FIGS. 25A-F). Some of the PIV variants grew efficiently to titers in excess of 7 $\log_{10}$ FFU/ml, and nearly identical titers were detected by both anti-Gag and anti-WN antibody staining, which was the first evidence of genetic stability of the Gag insert. When SIV Gag PIV was propagated in naïve Vero cells as a two-component formulation (d-PIV, sometimes also designated as tc-PIV), together with PIV-WN helper with ΔC deletion (RV909), titers in the excess of 8 $\log_{10}$ FFU/ml were observed (FIG. 26). These results confirm that this formulation does not require helper cells for production (the principle of dPIV is described above).

High insert stability is illustrated for one of the SW Gag PIV variants in FIG. 27. The stability of Gag was examined by ten serial passages of a RV230-Gag variant, containing Gag gene in place of large ΔprM-E deletion, in helper BHK-CprME(WN) cells at MOI 0.1 FFU/cell. At each passage, cell supernatants were harvested and titrated in regular Vero cells using immunostaining with an anti-WN antibody to determine total PIV titer, or an anti-SW Gag antibody to determine titer of particles containing the Gag gene. Similar WN and Gag titers were observed after all 10 passages and no significant progressive decline in Gag positive titers was observed, e.g., as compared to the WN(ΔC)-rabies G PIV expressing the G insert in place of the very short AC deletion (see above).

Viable PIV-(WN)-SIV Env variants (FIGS. 20 and 21) were also recovered in helper BHK cells transfected with in vitro RNA transcripts and efficient expression of gp120 was demonstrated by immunofluorescence (FIGS. 28A-D and FIG. 29). Interestingly, efficient intracellular expression of the original gp120 was observed in Vero cells infected with packaged dC230Env variant as determined by immunostaining using anti-SIV Env antibody after methanol fixation (FIG. 28D), but little gp120 was detected on the surface of the infected cells fixed by formalin (FIG. 28B), indicating inefficient transport of the translation product through the secretory pathway or cleavage of the TM domain away from the gp120 molecule. The dC230Env/RabG anchor construct (FIG. 21), in which the SIV Env TM domain was replaced with the TM anchor sequence from rabies virus G protein, not only provided efficient intracellular expression of gp120 (FIG. 28C), but also enabled its efficient cell surface delivery (FIG. 28A and FIG. 29). Better surface expression/secretion of Env variants should result in higher immunogenicity of vaccine candidates. Therefore, the results presented with these constructs confirm the beneficial effect of using heterologous TM and/or signal sequences to increase immunogenicity of HIV Env glycoproteins.

Examples of sequences of similar PIV-HIV vaccine designs, using HIV-1 Clade C gene sequences, are provided in Appendix 7.

These examples demonstrate the feasibility of robust delivery of SIV (HIV) glycoproteins (e.g., variants of Env) as well as cytoplasmic antigens (Gag, Pol, Nef and any other desired intracellular antigens), some of which can be secreted as SIV/HIV VLPs (e.g., Gag with or without Env), by PIV vaccine vectors.

In addition to gp120, other variants of the HIV Env immunogen, such as the full-length gp160, gp140, gp145, gp41, etc., with or without desired mutations, truncations, deletions, or insertions (e.g., of dominant CD4 T cell epitopes, etc., including of non-HIV origin) in expressed molecules increasing immunogenicity and/or breadth of immune response against the variable HIV genotypes/strains, can be expressed without changing the meaning of this invention. Examples of possible modifications of Env are discussed below.

The Envelope (Env) protein is one of the primary targets of the humoral immune response upon infection with HIV. However, the Env protein has a number of defenses which prevent an effective antibody response from being mounted. These defenses include high degree of sequence variability, protection of functionally important domains through the use of variable loops and quaternary interactions, and high levels of glycosylation to shield the underlying protein backbone. In order to overcome this researchers have attempted a number of methods to increase the potency and breadth of antibody responses to Env. These modifications begin with an alteration of the underlying protein backbone itself. Attempts to minimize the genetic distance between immunizing isolates and those seen in the wild have led to the use of centralized sequences (consensus and ancestral) as immunogens (Kothe et al., Virology 2007, 360:218-234; Liao et al., Virology 2006, 353: 268-282). Modifying specific glycosylations has also been attempted. In some instances, hyperglycosylation of Env to mask unwanted epitopes in order to focus the humoral response on neutralizing domains has been utilized (Selvarajah et al., J. Virol. 2005, 79-12148-12163). Others have attempted to eliminate specific glycans to increase the availability of critical domains and hence increase Env immunogenicity (Li et al., J. Virol. 2008, 82:638-651). Altering the total glycosylation of the Env protein with expression in different systems has also been investigated (Kong et al., J. Mol. Biol. 2010, 403:131-147). Outside of post translational modifications other groups have focused on manipulating Env variable loops as a means to increase immunogenicity. These modifications include shortening or deletion of variable loops (Ching and Stamatatos, J. Virol. 2010, 84:9932-9946; Yang et al., J. Virol. 2004, 78:4029-4036) as means to expose underlying domains. On the surface of virions, functional Env spikes exist as non-covalently linked trimers. However, these trimers are highly unstable making them difficult to use as immunogens. To overcome this hurdle attempts have been made to stabilize these trimers through mutagenesis (Beddows et al., J. Virol. 2005, 79:8812-8827) and introduction of heterologous trimerization domains (Yang et al., J. Virol. 2002, 76:4634-4642). Attempts have also been made to graft known epitopes recognized by mAbs to heterologous scaffolds (Phogat et al., Virology 2008, 373: 72-84; Zolla-Pazner et al., J. Virol. 2011, 85:9887-9898). Others have attempted to overcome the low immunogenicity of HIV Env by combining Env with immunostimulatory molecules in an effort to nonspecifically raise the immunogenicity of immunization (Melchers et al., J. Virol. 2011, published ahead of print, doi:101128/JVI.06259-11).

If necessary, these and/or any other modifications of Env or other expressed HIV immunogens leading to increased immunogenicity and/or breadth of humoral or cellular responses can be incorporated in the HIV antigenic moieties of PIV-HIV without changing the meaning of this invention.

Example 5

Delivery of HA Protein of Influenza H1N1 Virus (Strain New Calcdonia) in WN s-PIV (which Optionally can be Used in d-PIV)

Figure 32:
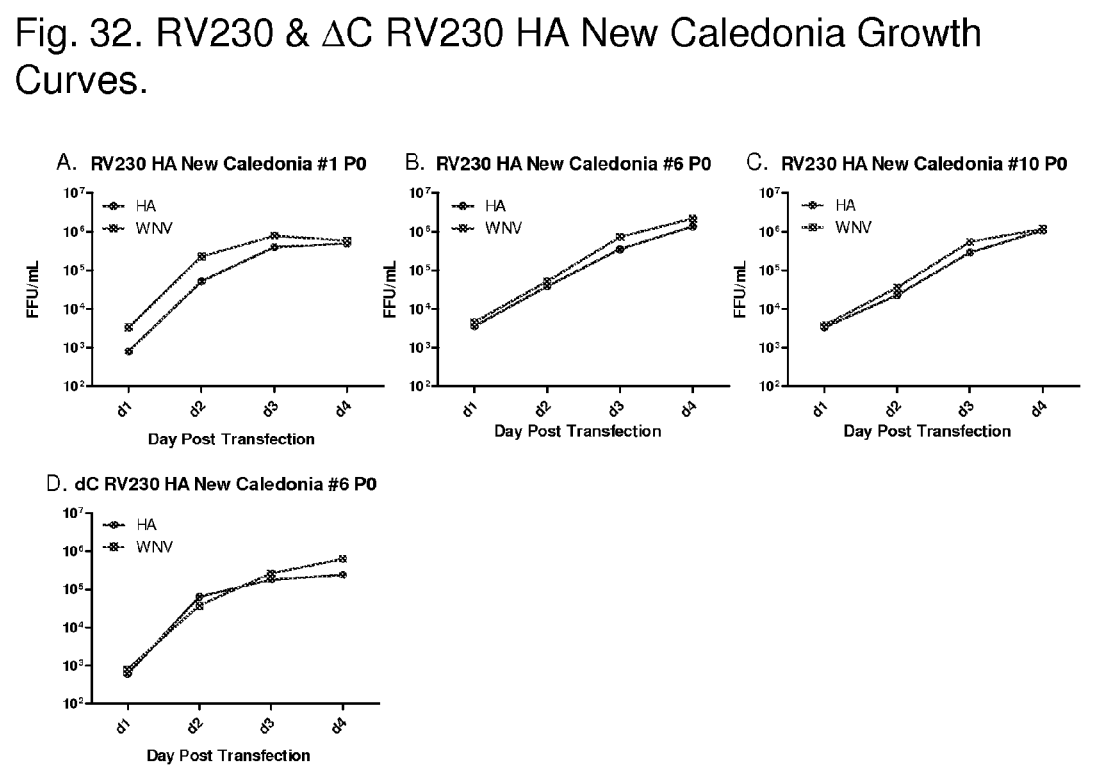

The full-length HA gene of Flu strain New Calcdonia was cloned in place of ΔprM-E and ΔC-prM-E deletions of PIV-WN vectors in the same fashion as described for Rabies G, RSV F, and SIV Env (as described above; FIG. 30). Examples of sequences are provided in Sequence Appendix 8. The variants were viable, and grew to high titers immediately after RNA transfections of helper cells (FIGS. 31A-B and FIGS. 32A-D). Identical titers in the growth curves using immunostaining with anti-WN and anti-HA antibodies provided evidence of insert stability.

All variants efficiently expressed the HA protein both intracellularly (methanol fixation) and on the cell surface (formalin fixation) of infected Vero cells as shown by immuno-fluorescence (FIGS. 33A-F, 34A-B, 35A-H, 36A-D, and 37A-B). The latter is a known prerequisite for high HA immunogenicity. Importantly, the expressed HA was efficiently recognized by both antibodies against the HA stem and HA globular head, confirming correct, native protein conformation (FIGS. 37A-B).

Other flu antigens can be similarly delivered, such as NA, M2 (e.g., M2e), etc., or fragments thereof. With respect to HA, various modifications can be introduced, and modified antigens then expressed in PIV vaccine vectors, without changing the meaning of this invention.

The PIV-SIV and PIV-Flu vaccine candidates described in Examples 4 and 5 can be tested for immunogenicity and efficacy in animal models. Earlier in vivo data have demonstrated that PIV vaccines expressing transgenes are highly immunogenic in animals, as has been shown for PIV-RSV F (see, e.g., WO 2010/107847, incorporated herein by reference), and more recent experiments for PIV-Rabies G.

The following Sequence Appendices include the following sequences:

Appendix 1

Construct 1: Sequence of RepliVax-WN (ΔCprME)-SIV 9AA FMD Gag (partial). DNA disclosed as SEQ ID NO: 79 and protein disclosed as SEQ ID NO: 80.

Construct 2: Sequence of RepliVax-WN (ΔCprME)-SIV 9AA FMD Gag & Pr (partial). DNA disclosed as SEQ ID NO: 81 and protein disclosed as SEQ ID NO: 82.

Construct 3: Sequence of RepliVax-WN (ΔCprME)-SIV Anch Gag (partial). DNA disclosed as SEQ ID NO: 83 and protein disclosed as SEQ ID NO: 84.

Construct 4: Sequence of RepliVax-WN (ΔCprME)-SIV Anch Gag & Pro (partial). DNA disclosed as SEQ ID NO: 85 and protein disclosed as SEQ ID NO: 86.

Construct 5: Sequence of RepliVax-WN (ΔCprME)-SIV FMD2a Gag. DNA disclosed as SEQ ID NO: 87 and protein disclosed as SEQ ID NO: 88.

Construct 6: Sequence of RepliVax-WN (ΔCprME)-SIV fmd2A Gag & Pr (partial). DNA disclosed as SEQ ID NO: 89 and protein disclosed as SEQ ID NO: 90.

Construct 7: Sequence of RepliVax-WN (ΔCprME)-SIV Env (partial). DNA disclosed as SEQ ID NO: 91 and protein disclosed as SEQ ID NO: 92.

Construct 8: Sequence of RepliVax-WN (ΔCprME)-SIV Env No Transmembrane (partial). DNA disclosed as SEQ ID NO: 93 and protein disclosed as SEQ ID NO: 94.

Construct 9: Sequence of RepliVax-WN (ΔCprME)- SIV ENV Rab G Transmembrane (TM) (partial). DNA disclosed as SEQ ID NO: 95 and protein disclosed as SEQ ID NO: 96.

Construct 10: Sequence of RepliVax-WN (ΔCprME)-SIV Env RabG Chimera, Signal Seqeunce and Transmembrane (TM). DNA disclosed as SEQ ID NO: 97 and protein disclosed as SEQ ID NO: 98.

Construct 11: Sequence of RepliVax-WN (ΔC)-SIV Env (partial). DNA disclosed as SEQ ID NO: 99 and proteins disclosed as SEQ ID NOS 100-102, respectively, in order of appearance.

Appendix 2

Sequence of RepliVax-WN (ΔprME)-HIV Gag (partial). DNA disclosed as SEQ ID NO: 103 and protein disclosed as SEQ ID NO: 104.

Sequence of RepliVax-WN (ΔprME)-HIV Env Gp140 (partial). DNA disclosed as SEQ ID NO: 105 and protein disclosed as SEQ ID NO: 106.

Appendix 3

Construct 1: Sequence of RepliVax-WN (ΔprME)-HA New Caledonia (partial). DNA disclosed as SEQ ID NO: 107 and protein disclosed as SEQ ID NO: 108.

Construct 2: Sequence of RepliVax-WN (ΔprME)-HA New Caledonia (partial). DNA disclosed as SEQ ID NO: 109 and protein disclosed as SEQ ID NO: 110.

Sequence Appendix 1

CV-TBEV Hypr or CV-LGT E5 with YFV/TBEV chimeric signal (p42, p59, and p43 constructs)

```
                              YF17D partial signal
                        ~~~~~~~~~~~~~~~~~~~~~~~~~~~~~~~~~~
                                                  TBEV partial signal
                                          ~~~~~~~~~~~~~~~~~~~~~~~~~~~~~
        C protein YF17D
        ~~~~~~~~~~~~~~~                                         Hypr or LGT E5 prM protein
                                                                ~~~~~~~~~~~~~~~~
        R   K R R   S H D   V L T V   Q F L   I L G   M L G M   T I A   A T V   R
401   A GGAAACGCCG TTCCCATGAT GTTCTGACTG TGCAATTCCT AATTTTGGGC ATGCTGGGCA TGACAATCGC AGCTACGGTT CGC
      T CCTTTGCGGC AAGGGTACTA CAAGACTGAC ACGTTAAGGA TTAAAACCCG TACGACCCGT ACTGTTAGCG TCGATGCCAA GCG
```

CV-TBEV Hypr with YFV/WNV chimeric signal (p45)

```
        C protein YF17D                               WNV partial signal
        ~~~~~~~~~~~~~~~                           ~~~~~~~~~~~~~~~~~~~~~~~~~~~
                            YF 17D partial signal
                        ~~~~~~~~~~~~~~~~~~~~~~~~~                    Hypr prM protein
                                                                     ~~~~~~~~~~~~~~~~
        R   K R R   S H D   V L T V   Q F L   I L G   M L A C   V G A   A T V   R
401   A GGAAACGCCG TTCCCATGAT GTTCTGACTG TGCAATTCCT AATTTTGGGC ATGCTGGCTT GTGTCGGAGC AGCTACCGTG CGA
      T CCTTTGCGGC AAGGGTACTA CAAGACTGAC ACGTTAAGGA TTAAAACCCG TACGACCGAA CACAGCCTCG TCGATGGCAC GCT
```

RV-WNV/TBEV Hypr with TBEV signal (p39)

```
                                  TBEV signal
                        ~~~~~~~~~~~~~~~~~~~~~~~~~~~~~~~~~~~~~~~~~~~~~~~~~~~~~~~
        WNV C protein                                                Hypr prM protein
        ~~~~~~~~~~~~~                                                ~~~~~~~~~~~~~~~~
        Q   K K   R G G T   D W M   S W L   L V I G   M L G   M T I   A A T V   R
201   CAAAAGAAA CGGGGGGGAA CAGACTGGAT GAGCTGGCTG CTCGTAATCG GCATGCTGGG CATGACAATC GCAGCTACGG TTCGC
      GTTTTCTTT GCCCCCCCTT GTCTGACCTA CTCGACCGAC GAGCATTAGC CGTACGACCC GTACTGTTAG CGTCGATGCC AAGCG
```

RV-WNV/TBEV Hypr with WNV signal (p40)

```
                           WNV signal
                        ~~~~~~~~~~~~~~~~~~~~~~~~~~~~~~~~~~~~~~~~~~~~~
        WNV C protein                                           Hypr prM protein
        ~~~~~~~~~~~~~                                           ~~~~~~~~~~~~~~~~
        Q   K K   R G G K   T G I   A V M   I G M L   A C V   G A A   T V R
201   CAAAAGAAA CGCGGGGGAA AGACAGGCAT AGCTGTGATG ATAGGCATGC TGGCTTGTGT CGGAGCAGCT ACCGTGCGA
      GTTTTCTTT GCGCCCCCTT TCTGTCCGTA TCGACACTAC TATCCGTACG ACCGAACACA GCCTCGTCGA TGGCACGCT
```

Sequence Appendix 2

CV-TBEV Hypr with YFV/TBEV chimeric signal (p42)

```
                                                  5' UTR
          ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
  1  AGTAAATCCT GTGTGCTAAT TGAGGTGCAT TGGTCTGCAA ATCGAGTTGC TAGGCAATAA ACACATTTGG ATTAAATTTA ATCGTTCGTT GAGCGATTAG
     TCATTTAGGA CACACGATTA ACTCCACGTA ACCAGACGTT TAGCTCAACG ATCCGTTATT TGTGTAAACC TAATTAAAAT TAGCAAGCAA CTCGCTAATC
     5' UTR
     ~~~~~~~~~~~~~~~~~~~~
                                                                                    C protein
                                                       ~~~~~~~~~~~~~~~~~~~~~~~~~~~~~~~~~~~~~~~~~~~~~~~~~~~~~~~~~~~~
                   M   S   G   R   K   A   Q   G   K   T   L   G   V   N   M   V   R   R   G   V   R   S   L   S   N   K   I   K ·
101  CAGAGAACTG ACCAGAACAT GTCTGGTCGT AAAGCTCAGG GAAAAACCCT GGGCGTCAAT ATGGTACGAC GAGGAGTTCG CTCCTTGTCA AACAAAATAA
     GTCTCTTGAC TGGTCTTGTA CAGACCAGCA TTTCGAGTCC CTTTTTGGGA CCCGCAGTTA TACCATGCTG CTCCTCAAGC GAGGAACAGT TTGTTTTATT
                                                             C protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
     · Q   K   T   K   Q   I   G   N   R   P   G   P   S   R   G   V   Q   G   F   I   F   F   F   L   F   N   I   L   T   G   K   K   I ·
201  AACAAAAAAC AAAACAAATT GGAAACAGAC CTGGACCTTC AAGAGGTGTT CAAGGATTTA TCTTTTTCTT TTTGTTCAAC ATTTTGACTG GAAAAAAGAT
     TTGTTTTTTG TTTTGTTTAA CCTTTGTCTG GACCTGGAAG TTCTCCACAA GTTCCTAAAT AGAAAAAGAA AAACAAGTTG TAAAACTGAC CTTTTTTCTA
                                                            C protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
     · T   A   H   L   K   R   L   W   K   M   L   D   P   R   Q   G   L   A   V   L   R   K   V   K   R   V   V   A   S   L   M   R   G
301  CACAGCCCAC CTAAAGAGGT TGTGAAAAAT GCTGGACCCA AGACAAGGCT TGGCTGTTCT AAGGAAAGTC AAGAGAGTGG TGGCCAGTTT GATGAGAGGA
     GTGTCGGGTG GATTTCTCCA ACACTTTTTA CGACCTGGGT TCTGTTCCGA ACCGACAAGA TTCCTTTCAG TTCTCTCACC ACCGGTCAAA CTACTCTCCT
                                                   YF17D partial signal
                                                ~~~~~~~~~~~~~~~~~~~~~~~~~~~~~~~~~~~~~~~~~~~~~~~~
                                                                            TBEV partial signal
                                                                         ~~~~~~~~~~~~~~~~~~~~~~~~~~~~~~~~~~~~~~~~~~
                C protein                                                                                    prM protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~    ~~~~~~~~~~~~~~~~
     L   S   S   R   K   R   R   S   H   D   V   L   T   V   Q   F   L   I   L   G   M   L   G   M   T   I   A   A   T   V   R   K   E   R ·
401  TTGTCCTCAA GGAAACGCCG TTCCCATGAT GTTCTGACTG TGCAATTCCT AATTTTGGGC ATGCTGGGCA TGACAATCGC AGCTACGGTT CGCAAGGAAA
     AACAGGAGTT CCTTTGCGGC AAGGGTACTA CAAGACTGAC ACGTTAAGGA TTAAAACCCG TACGACCCGT ACTGTTAGCG TCGATGCCAA GCGTTCCTTT
                                                          prM protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
     · D   G   S   T   V   I   R   A   E   G   K   D   A   A   T   Q   V   R   V   E   N   G   T   C   V   I   L   A   T   D   M   G   S ·
501  GAGACGGCAG TACGGTCATA CGCGCGGAAG GTAAGGATGC CGCTACCCAA GTGAGAGTGG AAAATGGTAC CTGCGTCATT CTGGCCACCG ACATGGGCTC
     CTCTGCCGTC ATGCCAGTAT GCGCGCCTTC CATTCCTACG GCGATGGGTT CACTCTCACC TTTTACCATG GACGCAGTAA GACCGGTGGC TGTACCCGAG
                                                              prM protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
     · W   C   D   D   S   L   S   Y   E   C   V   T   I   D   Q   G   E   E   P   V   D   V   D   C   F   C   R   N   V   D   G   V   Y
601  TTGGTGTGAT GATAGCCTTT CTTATGAGTG CGTAACCATA GATCAAGGTG AGGAACCTGT TGACGTTGAT TGCTTCTGCC GAAACGTGGA TGGGGTGTAT
     AACCACACTA CTATCGGAAA GAATACTCAC GCATTGGTAT CTAGTTCCAC TCCTTGGACA ACTGCAACTA ACGAAGACGG CTTTGCACCT ACCCCACATA
                                                                                                                   prM protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
     L   E   Y   G   R   C   G   K   Q   E   G   S   R   T   R   R   S   V   L   I   P   S   H   A   Q   G   E   L   T   G   R   G   H   K ·
701  CTCGAATATG GACGGTGTGG TAAACAAGAA GGAAGCAGAA CCAGACGCTC AGTGCTTATA CCCTCCCACG CTCAAGGAGA GCTGACCGGA CGGGGACATA
     GAGCTTATAC CTGCCACACC ATTTGTTCTT CCTTCGTCTT GGTCTGCGAG TCACGAATAT GGGAGGGTGC GAGTTCCTCT CGACTGGCCT GCCCCTGTAT
```

```
                                                          prM protein
       ·W  L  E    G  D  S    L  R  T  H    L  T  R    V  E  G    W  V  W  K    N  R  L    L  A  L    A  M  V  T    V  V  W·
   801 AATGGTTGGA GGGCGACTCA CTCCGAACAC ATTTGACCCG CGTCGAGGGC TGGGTCTGGA AAAATCGGCT GTTGGCCCTC GCTATGGTGA CAGTCGTTTG
       TTACCAACCT CCCGCTGAGT GAGGCTTGTG TAAACTGGGC GCAGCTCCCG ACCCAGACCT TTTTAGCCGA CAACCGGGAG CGATACCACT GTCAGCAAAC
                                                                                                     Hypr E protein
                 prM protein
       ·L  T  L    E  S  V  V    T  R  V    A  V  L    V  V  L  L    C  L  A    P  V  Y    A  S  R  C    T  H  L    E  N  R
   901 GCTCACGCTG GAGTCTGTGG TTACTCGCGT GGCAGTGCTG GTGGTGCTCC TCTGTCTTGC CCCTGTCTAC GCGTCCAGGT GTACTCATTT GGAAAACAGA
       CGAGTGCGAC CTCAGACACC AATGAGCGCA CCGTCACGAC CACCACGAGG AGACAGAACG GGGACAGATG CGCAGGTCCA CATGAGTAAA CCTTTTGTCT
                                                                                         Hypr E protein
             D  F  V  T    G  T  Q    G  T  T    R  V  T  L    V  L  E    L  G  G    C  V  T  I    T  A  E    G ·K  P    S  M  D  V·
  1001 GATTTTGTCA CCGGCACCCA GGGGACGACT CGGGTAACCC TGGTGCTTGA ACTGGGTGGT TGCGTTACTA TTACCGCTGA GGGCAAACCC TCTATGGATG
       CTAAAACAGT GGCCGTGGGT CCCCTGCTGA GCCCATTGGG ACCACGAACT TGACCCACCA ACGCAATGAT AATGCGACT CCCGTTTGGG AGATACCTAC
                                                                                Hypr E protein
       ·W  L  D    A  I  Y    Q  E  N  P    A  Q  T    R  E  Y    C  L  H  A    K  L  S    D  T  K    V  A  A  R    C  P  T·
  1101 TGTGGCTGGA TGCAATCTAT CAGGAGAATC CCGCACAAAC CAGGGAATAT TGCCTTCACG CAAAGCTGTC CGATACAAAG GTCGCGGCTA GGTGCCCAAC
       ACACCGACCT ACGTTAGATA GTCCTCTTAG GGCGTGTTTG GTCCCTTATA ACGGAAGTGC GTTTCGACAG GCTATGTTTC CAGCGCCGAT CCACGGGTTG
                                                                                Hypr E protein
       ·M  G  P    A  T  L  A    E  E  H    Q  G  G    T  V  C  K    R  D  Q    S  D  R    G  W  G  N    H  C  G    L  F  G
  1201 AATGGGACCG GCCACCCTGG CGGAGGAACA TCAGGGAGGT ACAGTGTGCA AACGGGACCA GAGTGATAGA GGCTCGGGTA ATCACTGGG CCTGTTCGGC
       TTACCCTGGC CGGTGGGACC GCCTCCTTGT AGTCCCTCCA TGTCACACGT TTGCCCTGGT CTCACTATCT CCGACCCCAT TAGTGACGCC GGACAAGCCG
                                                                                Hypr E protein
             K  G  S    I  V  A  C    V  K  A    A  C  E  A    K  K  K    A  T  G    H  V  Y  D    A  N  K    I  V  Y    T  V  K  V·
  1301 AAAAGGAAGTA TTGTCGCTGC CGTCAAGGCA GCCTGTGAGG CCAAAAAGAA GGCTACTGGG CACGTCTATG ACGCCAACAA GATCGTTTAT ACAGTGAAAG
       TTTTCCTTCAT AACAGCGAAC GCAGTTCCGT CGGACACTCC GGTTTTTCTT CCGATGACCC GTGCAGATAC TGCGGTTGTT CTAGCAAATA TGTCACTTTC
                                                                                Hypr E protein
       ·E  P  H    T  G  D    Y  V  A  A    N  E  T    H  S  G    R  K  T  A    S  F  T    V  S  S    E  K  T  I    L  T  M·
  1401 TGGAACCACA CACAGGGGAT TACGTGGCGG CCAACGAGAC TCATTCCGGT CGCAAAACCG CCAGCTTCAC CGTGTCATCC GAAAAGACCA TCCTCACTAT
       ACCTTGGTGT GTGTCCCCTA ATGCACCGCC GGTTGCTCTG AGTAAGGCCA GCGTTTTGGC GGTCGAAGTG GCACAGTAGG CTTTTCTGGT AGGAGTGATA
                                                                                Hypr E protein
       ·G  E  Y    G  D  V  S    L  L  C    R  V  A    S  G  V  D    L  A  Q    T  V  I    L  E  L  D    K  T  V    E  H  L
  1501 GGGGGAGTAT GGCGACGTTT CTCTGCTCTG CCGGGTGGCT AGCGGAGTCG ACCTGGCCCA GACAGTCATC CTGGAACTGG ATAAAACAGT TGAGCATCTG
       CCCCCTCATA CCGCTGCAAA GAGACGAGAC GGCCCACCGA TCGCCTCAGC TGGACCGGGT CTGTCAGTAG GACCTTGACC TATTTTGTCA ACTCGTAGAC
                                                                                Hypr E protein
             P  T  A  W    Q  V  H    R  D  W    F  N  D  L    A  L  P    W  K  H    E  G  A  R    N  W  N    N  A  E    R  L  V  E·
  1601 CCTACCGCTT GGCAGGTGCA CAGGGATTGG TTTAACGACC TTGCCCTGCC ATGGAAACAT GAAGGAGCGA GAAACTGGAA TAATGCAGAG CGACTCGTAG
       GGATGGCGAA CCGTCCACGT GTCCCTAACC AAATTGCTGG AACGGGACGG TACCTTTGTA CTTCCTCGCT CTTTGACCTT ATTACGTCTC GCTGAGCATC
                                                                                Hypr E protein
       ·F  G  A    P  H  A    V  K  M  D    V  Y  N    L  G  D    Q  T  G  V    L  L  K    A  L  A    G  V  P  V    A  H  I·
  1701 AATTCGGTGC CCCTCATGCC GTGAAGATGG ACGTCTACAA TCTGGGTGAT CAGACCGGCG TTCTCCTTAA AGCTCTCGCT GGCGTACCAG TTGCCCACAT
       TTAAGCCACG GGGAGTACGG CACTTCTACC TGCAGATGTT AGACCCACTA GTCTGGCCGC AAGAGGAATT TCGAGAGCGA CCGCATGGTC AACGGGTGTA
                                                                                Hypr E protein
```

```
              · E  G  T     K  Y  H  L    K  S  G     H  V  T     C  E  V  G     L  E  K     L  K  M    K  G  L  T     Y  T  M     C  D  K ·
         1801 CGAAGGAACG AAGTACCACC TGAAGTCAGG CCATGTAACT TGCGAGGTGG GCCTGGAGAA GTTGAAAATG AAAGGTCTTA CGTACACAAT GTGTGACAAG
              GCTTCCTTGC TTCATGGTGG ACTTCAGTCC GGTACATTGA ACGCTCCACC CGGACCTCTT CAACTTTTAC TTTCCAGAAT GCATGTGTTA CACACTGTTC
              ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                Hypr E protein T  K  F  T    W  K  R     A  P  T     D  S  G  H    D  T  V     V  M  E     V  T  F  S    G  T  K     P  C  R     I  P  V  R ·
         1901 ACCAAGTTCA TGGAAGCGGG CCCCCCACA GATAGCGGCC ACGATACTGT GGTGATGGAG GTGACCTTTT CTGGAACAAA ACCCTGCAGA ATACCCGTGC
              TGGTTCAAGT GTACCTTCGC CGGGGGGTGT CTATCGCCGG TGCTATGACA CCACTACCTC CACTGGAAAA GACCTTGTTT GGGACGTCTT ATGGGCACG
              ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                Eypr E protein · A  V  A     H  G  S     P  D  V  N    V  A  M     L  I  T     P  N  P  T    I  E  N    N  G  G     G  F  I  E     M  Q  L ·
         2001 GGGCTGTAGC TCACGGATCT CCCGATGTCA ATGTTGCTAT GCTGATTACA CCTAACCCTA CCATCGAGAA TAACGGTGGT GGTTTTATTG AGATGCAGCT
              CCCGACATCG AGTGCCTAGA GGGCTACAGT TACAACGATA CGACTAATGT GGATTGGGAT GGTAGCTCTT ATTGCCACCA CCAAAATAAC TCTACGTCGA
              ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                Hypr E protein · P  P  G    D  N  I  I    Y  V  G    E  L  S     Y  Q  W  F    Q  K  G     S  S  I     G  R  V  F    Q  K  T     K  K  G ·
         2101 TCCGCCAGGC GATAACATCA TCTACGTGGG CGAACTCTCT TACCAGTGGT TCAGAAAGG GAGTTCAATT GGGCGGCTCT TCCAAAAAAC GAAGAAGGGA
              AGGCGGTCCG CTATTGTAGT AGATGCACCC GCTTGAGAGA ATGGTCACCA AAGTCTTTCC CTCAAGTTAA CCCGCCAGA AGGTTTTTTG CTTCTTCCCT
              ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                Hypr E protein I  E  R  L   T  V  I     G  E  H    A  W  D  F   G  S  A     G  G  F     L  S  S  I   G  K  A     L  H  T     V  L  G  G ·
         2201 ATCGAACCAT TGACGGTTAT CGGCGAGCAC AGGGGGATTT CGGTTCCGC CCTAACCCAA GGCCAAGGCG TCTCCCCTAAG GACAGAAGAT AACCATTCCG TGACGTATGC CACGACCCCC
              TAGCTTGCTA ACTGCCAATA GCCGCTCGTG TCCCCCTAA GCCAAGGCG TGGATTGGGTT CCGGTTCCGC GGATTGGGTT CCTGTCTTCTA TTGGTAAGGC ACTGCATACC GTGCTGGGGG
              ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                Hypr E protein · A  F  N   S  I  F     G  G  V  G   F  L  P     K  L  L     L  G  V  A   L  A  W     L  G  L     N  M  R  N    P  T  M ·
         2301 GCGCATTCAA TTCTATTTTC GGGGGCGTGG CCCCCCGCACC CCAAGGACGG TAAACTCCTG CTGGAGTAG CCCTGGCCTG GTTGGGACTG AATATGCGGA ATCCGACGAT
              CGCGTAAGTT AAGATAAAAG CCCCCGCACC CCAAGGACGG ATTTCAGGAC GACCCTCATC GGGACCGGAC CAACCCTGAC TTATACGCCT TAGGCTGCTA
              ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                Hypr E protein                                          NS1 gene of YF17D
                                                                                                          ~~~~~~~~~~~~~~~~~~~~~~~~~~~~~~~~
              · S  M  S    F  L  L  A    G  V  L    V  L  A     M  T  L  G    V  G  A    D  Q  G    C  A  I  N    F  G  K     R  E  L ·
         2401 GTCCATGTCA TTCCTCTTGG CCGGCGTGCT TGTACTGGCC ATGACACTGG GCGTTGGCGC CGATCAAGGA TGCGCCATCA ACTTTGGCAA GAGAGAGCTC
              CAGGTACAGT AAGGAGAACC GGCCCACGA ACATGACCGG TACTGTGACC CGCAACCGCG GCTAGTTCCT ACGCGGTAGT TGAAACCGTT CTCTCTCGAG
```

CV-TBEV Hypr with YFV/WNV chimeric signal (p45)

```
                                                                5' UTR
              ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
            1 AGTAAATCCT GTGTGCTAAT TGAGGTGCAT TGGTCTGCAA ATCGAGTTGC TAGGCAATAA ACACATTTGG ATTAATTTTA ATCGTTCGTT GAGCGATTAG
              TCATTTAGGA CACACGATTA ACTCCACGTA ACCAGACGTT TAGCTCAACG ATCCGTTATT TGTGTAAACC TAATTAAAAT TAGCAAGCAA CTCGCTAATC
              ~~~~~~~~~~~~~~~~~~~~
                       5' UTR
                                                                                                              C protein YF17D
                                                                                       ~~~~~~~~~~~~~~~~~~~~~~~~~~~~~~~~~~~
                                                                                       M    S  G  R    K  A  Q  G     K  T  L    G  V  N     M  V  R  R    G  V  R     S  L  S    N  K  I  K ·
          101 CAGAGAACTG ACCAGAACAT GTCTGGTCGT AAAGCTCAGG GAAAAACCCT GGGCGTCAAT ATGGTACGAC GAGGAGTTCG CTCCTTGTCA AACAAAATAA
              GTCTCTTGAC TGGTCTTGTA CAGACCAGCA TTTCGAGTCC CTTTTTGGGA CCCGCAGTTA TACCATGCTG CTCCTCAAGC GAGGAACAGT TTGTTTTATT
                                                                                       ~~~~~~~~~~~~~~~~~~~~~~~~~~~~~~~~~~~
                                                                                                              C protein YF17D · Q  K  T   K  Q  I     G  N  R  P   G  P  S     R  G  V     Q  G  F  I   F  F  F     L  F  N    I  L  T    G  K  K  I ·
```

```
201 AACAAAAAAC AAAACAAATT GGAAACAGAC CTGGACCTTC AAGAGGTGTT CAAGGATTTA TCTTTTTCTT TTTGTTCAAC ATTTTGACTG GAAAAAAGAT
    TTGTTTTTTG TTTTGTTTAA CCTTTGTCTG GACCTGGAAG TTCTCCACAA GTTCCTAAAT AGAAAAAGAA AAACAAGTTG TAAAACTGAC CTTTTTTCTA
                                   C protein YF17D
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      · T  A  H   L  K  R  L   W  K  M   L  D  P   R  Q  G  L   A  V  L   R  K  V   K  R  V  V   A  S  L   M  R  G
301 CACAGCCCAC CTAAAGAGGT TGTGAAAAT GCTGGACCCA AGACAAGGCT TGGCTGTTCT AAGGAAAGTC AAGAGAGTGG TGGCCAGTTT GATGAGAGGA
    GTGTCGGGTG GATTTCTCCA ACACTTTTA CGACCTGGGT TCTGTTCCGA ACCGACAAGA TTCCTTTCAG TTCTCTCACC ACCGGTCAAA CTACTCTCCT
        C protein YF17D                                                     WNV partial signal
    ~~~~~~~~~~~~~~~~~~~~~~~~~~~~~~              ~~~~~~~~~~~~~~~~~~~~~~~~~~~~~~~~~~~~~~~~~~~
                         YF 17D partial signal                                 ~~~~~~~~~~~~~~~~~~~~~~~~~~~~~~~~~~
                                                                                                 Hypr prM protein
     L  S  S  R   K  R  R   S  H  D   V  L  T  V   Q  F  L   I  L  G   M  L  A  C   V  G  A   A  T  V   R  K  E  R·
401 TTGTCCTCAA GGAAACGCCG TTCCCATGAT GTTCTGACTG TGCAATTCCT AATTTTGGGC ATGCTGGCTT GTGTCGGAGC AGCTACCGTG CGAAAGAAC
    AACAGGAGTT CCTTTGCGGC AAGGGTACTA CAAGACTGAC ACGTTAAGGA TTAAAACCCG TACGACCGAA CACAGCCTCG TCGATGGCAC GCTTTTCTTG
                                                           Hypr prM protein
                                                      ~~~~~~~~~~~~~~~~~~~~~~~~~~~~~~~~~~~~~~~~~~~~~~~~~~~~~~~~~
     · D  G  S   T  V  I   R  A  E  G   K  D  A   A  T  Q   V  R  V  E   N  G  T   C  V  I   L  A  T  D   M  G  S·
501 GCGACGGAAG CACCGTGATA AGGGCTGAGG GTAAGGATGC AGCTACGCAG GTGAGAGTAG AGAATGGCAC TTGCGTAATA CTCGCGACTG ATATGGGATC
    CGCTGCCTTC GTGGCACTAT TCCCGACTCC CATTCCTACG TCGATGCGTC CACTCTCATC TCTTACCGTG AACGCATTAT GAGCGCTGAC TATACCCTAG
                                                    Hypr prM protein
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
     · W  C  D   D  S  L  S   Y  E  C   V  T  I   D  Q  G  E   E  P  V   D  V  D   C  F  C  R   N  V  D   G  V  Y
601 CTGGTGTGAC GATAGCCTCA GTTATGAATG CGTAACAATA GACCAGGGCG AGGAACCTGT TGATGTTGAC TGTTTCTGTA GAAATGTGGA TGGCGTTTAT
    GACCACACTG CTATCGGAGT CAATACTTAC GCATTGTTAT CTGGTCCCGC TTCTTGGACA ACTACAACTG ACAAAGACAT CTTTACACCT ACCGCAAATA
                                                    Hypr prM protein
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      L  E  Y  G   R  C  G   K  Q  E   G  S  R  T   R  R  S   V  L  I   P  S  H  A   Q  G  E   L  T  G   R  G  H  K·
701 CTGGAAGTACG GCCGCTGTGG AAAACAGGAG GGCTCACGAA CTCGGACTAG TGTGCTGATT CCAAGTCACG CGCAAGGAGA GTTGACCGGT AGAGGCCACA
    GACCTCATGC CGGCGACACC TTTTGTCCTC CCGAGTGCTT GAGCTTCTAG ACACGACTAA GGTTCAGTGC GCGTTCCTCT CAACTGGCCA TCTCCGGTGT
                                                   Hypr prM protein
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
     · W  L  E   G  D  S   L  R  T  H   L  T  R   V  E  G   W  V  W  X   N  R  L   L  A  L   A  M  V  T   V  V  W·
801 AGTGGCTTGA AGGGGACTCA TTGAGGACTAG GGTGGAGGGT TGGGTTTGGA AGAATCGCTT GCTCGCGCTC GCTATGGTCA CCGTCGTGTG
    TCACCGAACT TCCCCTGAGT AACTCCTGATC CCACCTCCCA ACCCAAACCT TCTTAGCCAA CGAGCGCGAG CGATACCAGT GGCAGCACAC
                                                   Hypr prM protein                                 Hypr E protein
    ~~~~~~~~~~~~~~~~~~~~~~~~~~~~~~~~~~~~~~~~~~~~~~~~~~~~~~~~~~~~~~~~~~~~~~~~~~~~~~                 ~~~~~~~~~~~~~~
     · L  T  L   E  S  V  V   T  R  V   A  V  L   V  V  L  L   C  L  A   P  V  Y   A  S  R  C   T  H  L   E  N  R
901 GCTGACACTG GAGAGTGTCG TGACTCGGGT TGCTGTGTTG GTTGTCCTCC TCTGTTTGGC CCCAGTGTAC GCGTCCAGGT GTACTCATTT GGAAAACAGA
    CGACTGTGAC CTCTCACAGC ACTGAGCCCA ACGACACAAC CAACAGGAGG AGACAAACCG GGGTCACATG CGCAGGTCCA CATGAGTAAA CCTTTTGTCT
                                                   Hypr E protein
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
       D  F  V  T   G  T  Q   G  T  T   R  V  T  L   V  L  E   L  G  G   C  V  T  I   T  A  E   G  K  P   S  M  D  V·
1001 GATTTTGTCA CCGGCACCCA GGGGACGACT CGGGTAACCC TGGTGCTTGA ACTGGGTGGT TGCGTTACTA TTACCGCTGA GGGCAAACCC TCTATGGATG
     CTAAAACAGT GGCCGTGGGT CCCCTGCTGA GCCCATTGGG ACCACGAACT TGACCCACCA ACGCAATGAT AATGGCGACT CCCGTTTGGG AGATACCTAC
                                                   Hypr E protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
     · W  L  D   A  I  Y   Q  E  N  F   A  Q  T   R  E  Y   C  L  H  A   K  L  S   D  T  K   V  A  A  R   C  P  T·
1101 TGTGGCTGGA TGCAATCTAT CAGGAGAATC CCCACAAAAC CAGGGAATAT TGCCTTCACG CAAAGCTGTC CGATACAAAG GTCGCGGCTA GGTGCCCAAC
     ACACCGACCT ACGTTAGATA GTCCTCTTAG GGCGTGTTTG GTCCCTTATA ACGGAAGTGC GTTTCGACAG GCTATGTTTC CAGCGCCGAT CCACGGGTTG
                                                    Hypr E protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      · M  G  P   A  T  L  A   E  E  H   Q  G  G   T  V  C  K   R  D  Q   S  D  R   G  W  G  N   H  C  G   L  F  G
```

```
                                                                                                          Hypr E protein
1201 AATGGGACCG GCCACCCTGG CGGAGGAACA TCAGGGAGGT ACAGTGTGCA AACGGGACCA GAGTGATAGA GGCTGGGGTA ATCACTGCGG CCTGTTCGGC
     TTACCCTGGC CGGTGGGACC GCCTCCTTGT AGTCCCTCCA TGTCACACGT TTGCCCTGGT CTCACTATCT CCGACCCCAT TAGTGACGCC GGACAAGCCG
                                                                                                          Hypr E protein
        K G S I V A C   V K A   A C E A K K K   A T G   H V Y D A N K   I V Y   T V K V ·
1301 AAAGGAAGTA TTGTCGCTTG CGTCAAGGCA GCCTGTGAGG CCAAAAAGAA GGCTACTGGG CACGTCTATG ACGCCAACAA GATCGTTTAT ACAGTGAAAG
     TTTCCTTCAT AACAGCGAAC GCAGTTCCGT CGGACACTCC GGTTTTTCTT CCGATGACCC GTGCAGATAC TGCGGTTGTT CTAGCAAATA TGTCACTTTC
                                                                                                          Hypr E protein
     · E P H   T G D   Y V A A N E T   H S G   R K T A   S F T   V S S   E K T I L T M ·
1401 TGGAACCACA CACAGGGGAT TACGTGGCGG CCAACGAGAC TCATTCCGGT CGCAAAACGG CCAGCTTCAC CGTGTCATCC GAAAAGACCA TCCTCACTAT
     ACCTTGGTGT GTGTCCCCTA ATGCACCGCC GGTTGCTCTG AGTAAGGCCA GCGTTTTGCC GGTCGAAGTG GCACAGTAGG CTTTTCTGGT AGGAGTGATA
                                                                                                          Hypr E protein
     · G E Y   G D V S L L C   R V A   S G V D   L A Q   T V I   L E L D   K T V   E H L ·
1501 GGGGGAGTAT GGCGACGTTT CTCTGCTCTG CCGGGTGGCT AGCGGAGTCG ACCTGGCCCA GACAGTCATC CTGGAACTGG ATAAAACAGT TGAGCATCTG
     CCCCCTCATA CCGCTGCAAA GAGACGAGAC GGCCCACCGA TCGCCTCAGC TGGACCGGGT CTGTCAGTAG GACCTTGACC TATTTTGTCA ACTCGTAGAC
                                                                                                          Hypr E protein
     · P T A W   Q V H   R D W   F N D L A L P   W K H   E G A R   N W N N A E   R L V E ·
1601 CCTACCGCTT GGCAGGTGCA CAGGGATTGG TTTAACGACC TTGCCCTGCC ATGGAAACAT GAAGGAGCGA GAAACTGGAA TAATGCAGAG CGACTCGTAG
     GGATGGCGAA CCGTCCACGT GTCCCTAACC AAATTGCTGG AACGGGACGG TACCTTTGTA CTTCCTCGCT CTTTGACCTT ATTACGTCTC GCTGAGCATC
                                                                                                          Hypr E protein
     · F G A   P H A   V K M D V Y N   L G D   Q T G V   L L K   A L A   G V P V   A H I ·
1701 AATTCGGTGC CCCTCATGCC GTGAAGATGG ACGTCTACAA TCTGGGTGAT CAGACCGGCG TTCTCCTTAA AGCTCTCGCT GGCGTACCAG TTGCCCACAT
     TTAAGCCACG GGGAGTACGG CACTTCTACC TGCAGATGTT AGACCCACTA GTCTGGCCGC AAGAGGAATT TCGAGAGCGA CCGCATGGTC AACGGGTGTA
                                                                                                          Hypr E protein
     · E G T   K

```
                  · A  F  N  S  I  F     G  G  V  G     F  L  P     K  L  L     L  G  V  A     L  A  W     L  G  L     N  M  R  N     P  T  M ·
2301 GCGCATTCAA TTCTATTTTC GGGGGCGTGG GGTTCCTGCC TAAACTCCTG CTGGGAGTAG CCCTGGCCTG GTTGGGACTG AATATGCGGA ATCCGACGAT
     CGCGTAAGTT AAGATAAAAG CCCCCGCACC CCAAGGACGG ATTTGAGGAC GACCCTCATC GGGACCGGAC CAACCCTGAC TTATACGCCT TAGGCTGCTA
                                                 Hypr E protein
     ~~~~~~~~~~~~~~~~~~~~~~~~~~~~~~~~~~~~~~~~~~~~~~~~~~~~~~~~~~~~~~~~~~~~~~~~   NS1 gene of YF17D
                                                                              ~~~~~~~~~~~~~~~~~~~~~~~~~~~~~~~~~~~~
                  · S  M  S     F  L  L  A     G  V  L     V  L  A     M  T  L  G     V  G  A     D  Q  G     C  A  I  N     F  G  K     R  E  L
2401 GTCCATGTCA TTCCTCTTGG CCGGCGTGCT TGTACTGGCC ATGACACTGG GCGTTGGCGC CGATCAAGGA TGCGCCATCA ACTTTGGCAA GAGAGAGCTC
     CAGGTACAGT AAGGAGAACC GGCCGCACGA ACATGACCGG TACTGTGACC CGCAACCGCG GCTAGTTCCT ACGCGGTAGT TGAAACCGTT CTCTCTCGAG

CV-LGTV E5 with YFV/TBEV chimeric signal (p43)

5' UTR
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
   1 AGTAAATCCT GTGTGCTAAT TGAGGTGCAT TGCTCTGCAA ATCGAGTTGC TAGGCAATAA ACACATTTGG ATTAATTTTA ATCGTTCGTT GAGCGATTAG
     TCATTTAGGA CACACGATTA ACTCCACGTA ACCAGACGTT TAGCTCAACG ATCCGTTATT TGTGTAAACC TAATTAAAAT TAGCAAGCAA CTCGCTAATC
       5' UTR
     ~~~~~~~~~~~~~~~~~~~                                                    C protein YF17D
                                                                 ~~~~~~~~~~~~~~~~~~~~~~~~~~~~~~~~~~~~~~~~~~~~~~~~~
                                                      M  S  G  R  K  A  Q  G     K  T  L     G  V  N     M  V  R  R     G  V  R     S  L  S  N  K  I  K ·
 101 CAGAGAACTG ACCAGAACTG TCTGGTCGT AAAGCTCAGG GAAAAACCCT GGGCGTCAAT ATGGTACGAC GAGGAGTTCG CTCCTTGTCA AACAAAATAA
     GTCTCTTGAC TGGTCTTGTA CAGACCAGCA TTTCGAGTCC CTTTTTGGGA CCCGCAGTTA TACCATGCTG CTCCTCAAGC GAGGAACAGT TTGTTTTATT
                                                      C protein YF17D
                                                 ~~~~~~~~~~~~~~~~~~~~~~~~~~~~~~~~~~~~~~~~~~~~~~~~~~~~~~~~~~~~~~~~~~
     · Q  K  T  K  Q  I     G  N  R  P     G  P  S     R  G  V     Q  G  F  I     F  F  F     L  F  N     I  L  T  G     K  K  I ·
 201 AACAAAAAAC AAAACAAATT GGAAACAGAC CTGGACCTTC AAGAGGTGTT CAAGGATTTA TCTTTTTCTT TTTGTTCAAC ATTTTGACTG GAAAAAAGAT
     TTGTTTTTTG TTTTGTTTAA CCTTTGTCTG GACCTGGAAG TTCTCCACAA GTTCCTAAAT AGAAAAAGAA AAACAAGTTG TAAAACTGAC CTTTTTTCTA
                                                 C protein YF17D
     ~~~~~~~~~~~~~~~~~~~~~~~~~~~~~~~~~~~~~~~~~~~~~~~~~~~~~~~~~~~
     · T  A  H     L  K  R  L     W  K  M     L  D  P     R  Q  G  L     A  V  L     R  K  V     K  R  V  V     A  S  L     M  R  G
 301 CACAGCCCAC CTAAAGAGGT TGTGCAAAAT GCTGCACCCA AGACAAGGCT TGGCTGTTCT AAGGAAAGTC AAGAGAGTGG TGGCCAGTTT GATGAGAGGA
     GTGTCGGGTG GATTTCTCCA ACACGTTTTA CGACCTGGGT TCTGTTCCGA ACCGACAAGA TTCCTTTCAG TTCTCTCACC ACCGGTCAAA CTACTCTCCT
       C protein YF17D                                                                          TBEV partial signal
     ~~~~~~~~~~~~~~~~~~~~                                                                      ~~~~~~~~~~~~~~~~~~~~
                       YF 17D partial signal                                                                          prM protein Langat E5
                  ~~~~~~~~~~~~~~~~~~~~~~~~~~~~~~~~~~~~~~~~~~~~~~~~~~~~~~~~~~~~~~~~~~~~~~~~~~~~~~~~~   ~~~~~~~~~~~~~~~~~~~~~~~~~~~~~~~~~~~~~
        L  S  S  R  K  R  R     S  H  D     V  L  T  V     Q  F  L     I  L  G     M  L  G  M     T  I  A     A  T  V     R  R  E  R ·
 401 TTGTCCTCAA GGAAACGCCG TTCCCATGGT GTTCTGACTG TGCAATTCCT AATTTTGGGC ATGCTGGGGA TGACGATCGC AGCTACTGTG CGAAGGGAGA
     AACAGGAGTT CCTTTGCGGC AAGGGTACCA CAAGACTGAC ACGTTAAGGA TTAAAACCCG TACGACCCCT ACTGCTAGCG TCGATGACAC GCTTCCCTCT
                                                                                                prM protein Langat E5
                                                                                             ~~~~~~~~~~~~~~~~~~~~~~~~~~~~~~~~~~~~~~~~~~~~
     · D  G  S     M  V  I     R  A  E  G     K  V  G  D     C  D  T  Q     V  R  S     K  M  H     C  V  I     L  G  D     R  M  G  S ·
 501 GAGACGGCTC TATGGTGATC AGAGCCGAAG GTAGGGACGC TGCCACCCAG GTGAGGGTCG AAAATGGCAC CTGTGTTATT CTGGCCGACG ACATGGGCTC
     CTCTGCCGAG ATACCACTGA TCTCGGCTTC CATCCCTGCG ACGGTGGGTC CACTCCCAGC TTTTACCGTG GACACAATAA GACCGGCTGC TGTACCCGAG
                                                                       prM protein Langat E5
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
     · W  C  D     D  S  L  A     Y  E  C     V  T  I     I  D  Q  G     E     E  P  V     D  V  D     C  F  C  R     G  V  E     K  V  T
 601 CTGGTGTGAT GATTCTCTGG CTTATGAATG TGTTACTATT GATCAGGGTG AAGAGCCTGT GGACGTGGAC TGTTTCTGTA GAGGCGTCGA GAAAGTGACC
     GACCACACTA CTAAGAGACC GAATACTTAC ACAATGATAA CTAGTCCCAC TTCTCGGACA CCTGCACCTG ACAAAGACAT CTCCGCAGCT CTTTCACTGG
```

```
                                       prM protein Langat E5
       L  E  Y  G  R  C  G  R  R  E  G  S  R  S  R  R  S  V  L  I  P  S  H  A  Q  R  D  L  T  G  R  G  H  Q
  701  CTGGAATATG ACGATGTGG  CCGGCGAGAA GGCTCCAGGA GTCGGAGATC CGTGTTGATC CCTTCACATG CGCAGCGCGA TCTGACAGGG AGGGGTCACC
       GACCTTATAC CTGCTACACC GGCCGCTCTT CCGAGGTCCT CAGCCTCTAG GCACAACTAG GGAAGTGTAC GCGTCGCGCT AGACTGTCCC TCCCCAGTGG
                                                  prM protein Langat E5
       ·  W  L  E  G  E  A  V  K  A  H  L  T  R  V  E  G  W  V  W  K  N  K  L  F  T  L  S  L  V  M  V  A  W  ·
  801  AGTGGCTCGA AGGCGAAGCA GTCAAGGCCC ATCTGACTCG CGTTGAAGGC TGGGTGTGGA AAAACAAACT CTTTACCCTT AGCCTGGTGA TGGTCGCGTG
       TCACCGAGCT TCCGCTTCGT CAGTTCCGGG TAGACTGAGC GCAACTTCCG ACCCACACCT TTTTGTTTGA GAAATGGGAA TCGGACCACT ACCAGCGCAC
                                                  prM protein Langat E5
                                                                                                E protein Langat E5
       ·  L  M  V  D  G  L  L  P  R  I  L  I  V  V  V  A  L  A  P  A  Y  A  S  R  C  T  H  L  E  N  R
  901  GCTGATGGTA GACGGACTCC TTCCCCGCAT TCTCATTGTT GTGGTGGCTC TCGCGCTCGC CCCTGCATAC GCGTCCAGGT GTACCCACCT CGAAAATCGA
       CGACTACCAT CTGCCTGAGG AAGGGGCGTA AGAGTAACAA CACCACCGAG AGCGCGAGCG GGGACGTATG CGCAGGTCCA CATGGGTGGA GCTTTTAGCT
                                                  E protein Langat E5
       D  F  V  T  G  V  Q  G  T  T  R  L  T  L  V  L  E  L  G  G  C  V  T  V  T  A  D  G  K  P  S  L  D  V  ·
 1001  GATTTCGTCA CAGGCGTCCA AGGTACTACC CGGCTCACCC TCGTGCTGGA GCTGGGAGGC TGTGTCACTG TTACAGCCGA CGGAAAACCT AGTCTGGATG
       CTAAAGCAGT GTCCGCAGGT TCCATGATGG GCCGAGTGGG AGCACGACCT CGACCCTCCG ACACAGTGAC AATGTCGGCT GCCTTTTGGA TCAGACCTAC
                                                  E protein Langat E5
       ·  W  L  D  S  I  Y  Q  E  S  P  A  Q  T  R  E  Y  C  L  H  A  K  L  T  G  T  K  V  A  A  R  C  P  T  ·
 1101  TGTGGCTGGA CTCCATCTAT CAGGAGAGCC CGGCACAGAC CAGGGAGTAC TGCCTCCACG CTAAGCTGAC TGGGACAAAG GTAGCCGCAA GATGTCCCAC
       ACACCGACCT GAGGTAGATA GTCCTCTCGG GCCGTGTCTG GTCCCTCATG ACGGAGGTGC GATTCGACTG ACCCTGTTTC CATCGGCGTT CTACAGGGTG
                                                  E protein Langat E5
       ·  M  G  P  A  T  L  P  E  E  H  Q  S  G  T  V  C  K  R  D  Q  S  D  R  G  W  G  N  H  C  G  L  F  G
 1201  AATGGGGCCT GCCACCTTGC CCGAGGAACA CCAATCCGGT ACGGTATGCA AGCGAGATCA GTCTGATCGG GGATGGGGGA ATCATTGCGG CCTCTTCGGT
       TTACCCCGGA CGGTGGAACG GGCTCCTTGT GGTTAGGCCA TGCCATACGT TCGCTCTAGT CAGACTAGCC CCTACCCCCT TAGTAACGCC GGAGAAGCCA
                                                  E protein Langat E5
       K  G  S  I  V  T  C  V  K  V  T  C  E  D  K  K  K  A  T  G  H  V  Y  D  V  N  K  I  T  Y  T  I  K  V  ·
 1301  AAAGGCAGCA TTGTCACTTG CGTGAAGGTG ACATGCGAGG ACAAGAAGAA GGCCACAGGT CATGTATATG ATGTGAACAA AATCACATAT ACCATTAAGG
       TTTCCGTCGT AACAGTGAAC GCACTTCCAC TGTACGCTCC TGTTCTTCTT CCGGTGTCCA GTACATATAC TACACTTGTT TTAGTGTATA TGGTAATTCC
                                                  E protein Langat E5
       ·  E  P  H  T  G  E  F  V  A  A  N  E  T  H  S  G  R  K  S  A  S  F  T  V  S  S  E  K  T  I  L  T  L  ·
 1401  TAGAACCACA TACAGGGGAA TTCGTGCCAG CAAACGAGAC TCATAGCGGA CGAAAGTCCG CCTCCTTCAC CGTGTCCTCC GAGAAACAAA TCCTGACCCT
       ATCTTGGTGT ATGTCCCCTT AAGCACCGTC GTTTGCTCTG AGTATCGCCT GCTTTCAGGC GGAGGAAGTG GCAGAGGAGG CTCTTTGTTT AGGACTGGGA
                                                  E protein Langat E5
       ·  G  D  Y  G  D  V  S  L  L  C  R  V  A  S  G  V  D  L  A  Q  T  V  V  L  A  L  D  K  T  H  E  H  L
 1501  CGGAGACTAC GGCGACGTAT CTTTGCTGTG CAGGGTGGCC AGCGGCGTGG ACCTTGCTCA GACAGTCGTG TTGGCCCTGG ACAAGACACA TGAGCACTTG
       GCCTCTGATG CCGCTGCATA GAAACGACAC GTCCCACCGG TCGCCGCACC TGGAACGAGT CTGTCAGCAC AACCGGGACC TGTTCTGTGT ACTCGTGAAC
                                                  E protein Langat E5
       P  T  A  W  Q  V  E  R  D  W  F  N  D  L  A  L  P  W  K  H  D  G  A  E  A  W  N  E  A  G  R  L  V  E  ·
 1601  CCAACAGCCT GGCAGGTGCA CAGGGACTGG TTTAACGACC TGGCGCTCCC GTGGAAACAT GACGGCGCTG AAGCATGGAA TGAGGCAGGG AGACTGGTGG
       GGTTGTCGGA CCGTCCACGT GTCCCTGACC AAATTGCTGG ACCGCGAGGG CACCTTTGTA CTGCCGCGAC TTCGTACCTT ACTCCGTCCC TCTGACCACC
                                                  E protein Langat E5
```

```
      · F  G  T    P  H  A    V  K  M  D    V  F  N    L  G  D    Q  T  G  V    L  L  K    S  L  A    G  V  P  V  A  S  I ·
1701  AATTTGGAAC CCCACACGCC GTAAAGATGG ACGTTTTCAA TCTTGGTGAC CAGACAGGGG TGCTCCTGAA ATCACTGGCG GGCGTGCCTG TAGCCAGCAT
      TTAAACCTTG GGGTGTGCGG CATTTCTACC TGCAAAAGTT AGAACCACTG GTCTGTCCCC ACGAGGACTT TAGTGACCGC CCGCACGGAC ATCGGTCGTA
                                                            E protein Langat E5
      · E  G  T    K  Y  H  L    K  S  G    H  V  T    C  E  V  G    L  E  K    L  K  M    K  G  L  T    Y  T  V    C  D  K
1801  CGAGGGCACA AAGTATCACC TGAAGTCTGG CATGTGAACC TGCGAAGTGG GCCTGGAAAA GCTGAAGATG AAAGGACTTA CGTACACTGT TTGTGATAAG
      GCTCCCGTGT TTCATAGTGG ACTTCAGACC CGTACATTGG ACGCTTCACC CGGACCTTTT CGACTTCTAC TTTCCTGAAT GCATGTGACA AACACTATTC
                                                            E protein Langat E5
      · T  K  F  T    W  K  R    A  P  T    D  S  G  H    D  T  V    V  M  E    V  G  F  S    G  T  R    P  C  R    I  P  V  R ·
1901  ACCAAGTTTA CATGGAAGCG AGCCCCAACC GATTCCGGCC ATGATACCGT CGTGATGGAG GTTGGTTTCT CCGGCACCAG ACCATGTAGA ATACCAGTGA
      TGGTTCAAAT GTACCTTCGC TCGGGGTTGG CTAAGGCCGG TACTATGGCA GCACTACCTC CAACCAAAGA GGCCGTGGTC TGGTACATCT TATGGTCACT
                                                            E protein Langat E5
      · A  V  A    H  G  V    P  E  V  N    V  A  M    L  I  T    P  N  P  T    M  E  N    N  G  G    F  I  E    M  Q  L ·
2001  GAGCTGTCGC CCACGGTGTA CCCGGAGGTA ACGTGGCCAT GCTGATTACA CCGAATCCCA CTATGGAGAA CAATGGCGGA GGGTTCATCG AAATGCAGCT
      CTCGACAGCG GGTGCCACAT GGGCCTCCAT TGCACCGGTA CGACTAATGT GGCTTAGGGT GATACCTCTT GTTACCGCCT CCCAAGTAGC TTTACGTCGA
                                                            E protein Langat E5
      · P  P  G    D  N  I  I    Y  V  G    D  L  D    H  Q  W  F    Q  K  G    S  S  I    G  R  V  L    Q  K  T    R  K  G
2101  GCCGCCTGGA GACAACATCA TTTATGTCGG CGACCTCGAT CATCAATGGT TCCAGAAAGG GTCTTCCATC GGCCGCGTCC TTCAGAAGAC ACGAAAAGGC
      CGGCGGACCT CTGTTGTAGT AAATACAGCC GCTGGAGCTA GTAGTTACCA AGGTCTTTCC CAGAAGGTAG CCGGCGCAGG AAGTCTTCTG TGCTTTTCCG
                                                            E protein Langat E5
      I  E  R  L    T  V  L    G  E  H    A  W  D  F    G  S  V    G  G  V    M  T  S  I    G  R  A    M  H  T    V  L  G  G ·
2201  ATTGAAAGAC TTACAGTCCT GGGCGAACAT GCCTGGGACT TCGGGTCAGT GGCGGGGTA ATGACAAGCA TAGGCAGAGC TATGCACACC GTTCTCGGTG
      TAACTTTCTG AATGTCAGGA CCCGCTTGTA CGGACCCTGA AGCCCAGTCA CCGCCCCAT TACTGTTCGT ATCCGTCTCG ATACGTGTGG CAAGAGCCAC
                                                            E protein Langat E5
      · A  F  N    T  L  L    G  G  V  G    F  L  P    K  I  L    L  G  V  A    M  A  W    L  G  L    N  M  R  N    P  T  L ·
2301  GGGCATTTAA TACTCTGTTG GGTGGCGTGG GTTTTCTTCC GAAAATCCTG CTCGGTGTCG CAATGGCCTG GCTTGGACTA AATATGCGCA ATCCTACACT
      CCCGTAAATT ATGAGACAAC CCACCGCACC CAAAAGAAGG CTTTTAGGAC GAGCCACAGC GTTACCGGAC CGAACCTGAC TTATACGCGT TAGGATGTGA
                                                            E protein Langat E5
                                                                                                NS1 gene of YF17D
      · S  M  G    F  L  L  S    G  G  L    V  L  A    M  T  L  G    V  G  A    D  Q  G    C  A  I  N    F  G  K    R  E  L
2401  GAGTATGGGG TTTCTTCTGT CAGGAGGCCT GGTCCTGGCA ATGACTCTGG GAGTGGGCGC CGATCAAGGA TGCGCCATCA ACTTTGGCAA GAGAGAGCTC
      CTCATACCCC AAAGAAGACA GTCCTCCGGA CCAGGACCGT TACTGAGACC CTCACCCGCG GCTAGTTCCT ACGCGGTAGT TGAAACCGTT CTCTCTCGAG
```

CV-TBEV Hypr with YFV/TBEV chimeric signal and dC2 deletion in C protein (p59)

```
                                                            5' UTR
   1  AGTAAATCCT GTGTGCTAAT TGAGGTGCAT TGCTCTGCAA ATCGAGTTGC TAGGCAATAA ACACATTTGG ATTAATTTTA ATCGTTCGTT GAGCGATTAG
      TCATTTAGGA CACACGATTA ACTCCACGTA ACCAGACGTT AGCTCAACG ATCCGTTATT TGTGTAAACC TAATTAAAAT TAGCAAGCAA CTCGCTAATC
         5' UTR
                                                            C protein
```

```
                   M   S   G   R   K   A   Q   G   K   T   L   G   V   N   M   V   R   R   G   V   R   S   L   S   N   K   I   K
101 CAGAGAACTG ACCAGAACAT GTCTGGTCGT AAAGCTCAGG GAAAAACCCT GGGCGTCAAT ATGGTACGAC GAGGAGTTCG CTCCTTGTCA AACAAAATAA
    GTCTCTTGAC TGGTCTTGTA CAGACCAGCA TTTCGAGTCC CTTTTTGGGA CCCGCAGTTA TACCATGCTG CTCCTCAAGC GAGGAACAGT TTGTTTTATT
                     dC2 deletion (PSR)
                      ~
                                C protein
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

Q   K   T   K   Q   I   G   N   R   P   G   G   V   Q   G   F   I   F   F   F   L   F   N   I   L   T   G   K   K   I   T   A   H
201 AACAAAAAAC AAAACAAATT GGAAACAGAC CTGGAGGTGT TCAAGGATTT ATCTTTTTCT TTTTGTTCAA CATTTTGACT GGAAAAAAGA TCACAGCCCA
    TTGTTTTTTG TTTTGTTTAA CCTTTGTCTG GACCTCCACA AGTTCCTAAA TAGAAAAAGA AAAACAAGTT GTAAAACTGA CCTTTTTTCT AGTGTCGGGT
                                C protein
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

L   K   R   L   W   K   M   L   D   P   R   Q   G   L   A   V   L   R   K   V   K   R   V   V   A   S   L   M   R   G   L   S   S
301 CCTAAAGAGG TTGTGAAAAA TGCTGGACCC AAGACAAGGC TTGGCTGTTC TAAGGAAAGT CAAGAGAGTG GTGGCCAGTT TGATGAGAGG ATTGTCCTCA
    GGATTTCTCC AACACCTTTT ACGACCTGGG TTCTGTTCCG AACCGACAAG ATTCCTTTCA GTTCTCTCAC CACCGGTCAA ACTACTCTCC TAACAGGAGT
                          YF17D partial signal
                         ~~~~~~~~~~~~~~~~~~~~~~~~~~~~~~~~~~~
                                     TBEV partial signal
                                    ~~~~~~~~~~~~~~~~~~~~~~~~~~~~~~~~~~~~~~~~~~~~~~~~~~~~~~~~~~~~~~~~~~~~~~~~~~~~
            C protein
    ~~~~~~~~~~~~~~~~~~~~                                                                    Hypr prM protein
                                                                                           ~~~~~~~~~~~~~~~~~~~~~
     R   K   R   R   S   H   D   V   L   T   V   Q   F   L   I   L   G   M   L   G   M   T   I   A   A   T   V   R   K   E   R   D   G   S
401 AGGAAACGCC GTTCCCATGA TGTTCTGACT GTGCAATTCC TAATTTTGGG CATGCTGGGC ATGACAATCG CAGCTACGGT TCGCAAGGAA AGAGACGGCA
    TCCTTTGCGG CAAGGGTACT ACAAGACTGA CACGTTAAGG ATTAAAACCC GTACGACCCG TACTGTTAGC GTCGATGCCA AGCGTTCCTT TCTCTGCCGT
                                                                                        Hypr prM protein
                                                                                  ~~~~~~~~~~~~~~~~~~~~~~~~~~~~~~

T   V   I   R   A   E   G   K   D   A   A   T   Q   V   R   V   E   N   G   T   C   V   I   L   A   T   D   M   G   S   W   C   D
501 GTACGGTCAT ACGCGCGGAA GGTAAGGATG CCGCTACCCA AGTGAGAGTG GAAAATGGTA CCTGCGTCAT TCTGGCCACC GACATGGGCT CTTGGTGTGA
    CATGCCAGTA TGCGCGCCTT CCATTCCTAC GGCGATGGGT TCACTCTCAC CTTTTACCAT GGACGCAGTA AGACCGGTGG CTGTACCCGA GAACCACACT
                                                      Hypr prM protein
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

D   S   L   S   Y   E   C   V   T   I   D   Q   G   E   E   P   V   D   V   D   C   F   C   R   N   V   D   G   V   Y   L   E   Y
601 TGATAGCCTT TCTTATGAGT GCGTAACCAT AGATCAAGGT GAGGAACCTG TTGACGTTGA TTGCTTCTGC CGAAACGTGG ATGGGGTGTA TCTCGAATAT
    ACTATCGGAA AGAATACTCA CGCATTGGTA TCTAGTTCCA CTCCTTGGAC AACTGCAACT AACGAAGACG GCTTTGCACC TACCCCACAT AGAGCTTATA
                                                  Hypr prM protein
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

G   R   C   G   K   Q   E   G   S   R   T   R   R   S   V   L   I   P   S   H   A   Q   G   E   L   T   G   R   G   H   K   W   L   E
701 GGACGGTGTG GTAAACAAGA AGGAAGCAGA ACCAGACGCT CAGTGCTTAT ACCCTCCCAC GCTCAAGGAG AGCTGACCGG ACGGGACATA AATGGTTGG
    CCTGCCACAC CATTTGTTCT TCCTTCGTCT TGGTCTGCGA GTCACGAATA TGGGAGGGTG CGAGTTCCTC TCGACTGGCC TGCCCCTGTA TTTACCAACC
                                                      Hypr prM protein
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

G   D   S   L   R   T   H   L   T   R   V   E   G   W   V   W   K   N   R   L   L   A   L   A   M   V   T   V   V   W   L   T   L
801 AGGGCGACTC ACTCCGAACA CATTTGACCC GCGTCGAGGG CTGGGTCTGG AAAAATCGGC TGTTGGCCCT CGCTATGGTG ACAGTCGTTT GGCTCACGCT
    TCCCGCTGAG TGAGGCTTGT GTAAACTGGG CGCAGCTCCC GACCCAGACC TTTTTAGCCG ACAACCGGGA GCGATACCAC TGTCAGCAAA CCGAGTGCGA
                                                                                                 Hypr E protein
                                                                                             ~~~~~~~~~~~~~~~~~~~
                  Hypr prM protein
    ~~~~~~~~~~~~~~~~~~~~~~~~~~~~~~~~~~~~~~~~~~~~~~~~~~~~~~~~~~~~~~~~~~~~~
     E   S   V   V   T   R   V   A   V   L   V   V   L   L   C   L   A   P   V   Y   A   S   R   C   T   H   L   E   N   R   D   F   V
901 GGAGTCTGTG GTTACTCGCG TGGCAGTGCT GGTGGTGCTC CTCTGTCTTG CCCCTGTCTA CGCGTCCAGG TGTACTCATT TGGAAAACAG AGATTTTGTC
    CCTCAGACAC CAATGAGCGC ACCGTCACGA CCACCACGAG GAGACAGAAC GGGGACAGAT GCGCAGGTCC ACATGAGTAA ACCTTTTGTC TCTAAAACAG
                                                   Hypr E protein
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

T   G   T   Q   G   T   T   R   V   T   L   V   L   E   L   G   G   C   V   T   I   T   A   E   G   K   P   S   M   D   V   W   L   D
```

```
                  · A  I  Y  Q  E  N    P  A  Q  T     R  E  Y    C  L  H     A  K  L  S    D  T  K    V  A  A     R  C  P  T    M  G  P ·
1001 ACCGGCACCC AGGGGACGAC TCGGGTAACC CTGGTGCTTG AACTGGGTGG TTGCGTTACT ATTACCGCTG AGGGCAAACC CTCTATGGAT GTGTGGCTGG
     TGGCCGTGGG TCCCCTGCTG AGCCCATTGG GACCACGAAC TTGACCCACC AACGCAATGA TAATGGCGAC TCCCGTTTGG GAGATACCTA CACACCGACC
                                                                Hypr E protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

· A  I  Y  Q  E  N    P  A  Q  T     R  E  Y    C  L  H     A  K  L  S    D  T  K    V  A  A     R  C  P  T    M  G  P ·
1101 ATGCAATCTA TCAGGAGAAT CCCGCACAAA CCAGGGAATA TTGCCTCAC GCAAAGCTGT CCGATACAAA GGTCGCGGCT AGGTGCCCAA CAATGGGACC
     TACGTTAGAT AGTCCTCTTA GGGCGTGTTT GGTCCCTTAT AACGGAAGTG CGTTTCGACA GGCTATGTTT CCAGCGCCGA TCCACGGGTT GTTACCCTGG
                                                                Hypr E protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

· A  T  L    A  E  E  H    Q  G  G    T  V  C    K  R  D  Q    S  D  R    G  W  G     N  H  C  G    L  F  G    K  G  S
1201 GGGCACCCTG GCGGAGGAAC ATCAGGGAGG TACAGTGTGC AAACGGGACC AGAGTGATAG AGGCTGGGGT AATCACTGCG GCCTGTTCGG CAAAGGAAGT
     CCCGTGGGAC CGCCTCCTTG TAGTCCCTCC ATGTCACACG TTTGCCCTGG TCTCACTATC TCCGACCCCA TTAGTGACGC CGGACAAGCC GTTTCCTTCA
                                                                Hypr E protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

I  V  A  C    V  K  A    A  C  E     A  K  K  K    A  T  G    H  V  Y    D  A  N  K    I  V  Y    T  V  K    V  E  P  H ·
1301 ATTGTCGCTT GCGTCAAGGC AGCCTGTGAG GCCAAAAAGA AGGCTACTGG GCACGTCTAT GACGCCAACA AGATCGTTTA TACAGTGAAA GTGGAACCAC
     TAACAGCGAA CGCAGTTCCG TCGGACACTC CGGTTTTTCT TCCGATGACC CGTGCAGATA CTGCGGTTGT TCTAGCAAAT ATGTCACTTT CACCTTGGTG
                                                                Hypr E protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

· T  G  D    Y  V  A     A  N  E  T    H  S  G    R  K  T     A  S  F  T    V  S  S    E  K  T    I  L  T  M    G  E  Y ·
1401 ACACAGGGGA TTACGTGGCG GCCAACGAGA CTCATTCCGG TCGCAAAACG GCCAGCTTCA CCGTGTCATC CGAAAAGACC ATCCTCACTA TGGGGGAGTA
     TGTGTCCCCT AATGCACCGC CGGTTGCTCT GAGTAAGGCC AGCGTTTTGC CGGTCGAAGT GGCACAGTAG GCTTTTCTGG TAGGAGTGAT ACCCCCTCAT
                                                                Hypr E protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

· G  D  V    S  L  L  C    R  V  A    S  G  V     D  L  A  Q    T  V  I    L  E  L    D  K  T    V  E  H  L    P  T  A
1501 TGGCGACGTT TCTCTGCTCT GCCGGGTGGC TAGCGGAGTC AGACAGTCAT CCTGGAACTG GATAAACAG TTGAGCATCT GCCTACCGCT
     ACCGCTGCAA AGAGACGAGA CGGCCCACCG ATCGCCTCAG TCTGTCAGTA GGACCTTGAC CTATTTGTC AACTCGTAGA CGGATGGCGA
                                                                Hypr E protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

W  Q  V  H  R  D  W    F  N  D    L  A  L  P    W  K  H    E  G  A    R  N  W  N    N  A  E    R  L  V    E  F  G  A ·
1601 TGGCAGGTGC ACAGGGATTG GTTTAACGAC CTTGCCCTGC CATGGAAACA TGAAGGAGCG AGAAACTGGA ATAATGCAGA GCGACTCGTA GAATTCGGTG
     ACCGTCCACG TGTCCCTAAC CAAATTGCTG GAACGGGACG GTACCTTTGT ACTTCCTCGC TCTTTGACCT TATTACGTCT CGCTGAGCAT CTTAAGCCAC
                                                                Eypr E protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

· P  H  A    V  K  M    D  V  Y  N    L  G  D    Q  T  G     V  L  L  K    A  L  A    G  V  P    V  A  H  I    E  G  T ·
1701 CCCCTCATGC CGTGAAGATG GACGTCTACA ATCTGGGTGA TCAGACCGGC GTTCTCCTTA AAGCTCTCGC TGGCGTACCA GTTGCCCACA TCGAAGGAAC
     GGGGAGTACG GCACTTCTAC CTGCAGATGT TAGACCCACT AGTCTGGCCG CAAGAGGAAT TTCGAGAGCG ACCGCATGGT CAACGGGTGT AGCTTCCTTG
                                                                Hypr E protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

· K  Y  H    L  K  S  G    H  V  T    C  E  V    G  L  E  K    L  K  M    K  G  L    T  Y  T  M    C  D  K    T  K  F
1801 GAAGTACCAC CTGAAGTCAG GCCATGTAAC TTGCGAGGTG GGCCTGGAGA AGTTGAAAAT GAAGGGTCTT ACGTACACAA TGTGTGACAA GACCAAGTTC
     CTTCATGGTG GACTTCAGTC CGGTACATTG AACGCTCCAC CCGGACCTCT TCAACTTTTA CTTCCCAGAA TGCATGTGTT ACACACTGTT CTGGTTCAAG
                                                                Hypr E protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

T  W  K  R    A  P  T    D  S  G    H  D  T  V    V  M  E    V  T  F    S  G  T  K    P  C  R    I  P  V    R  A  V  A ·
1901 ACATGGAAGA GGGCCCCCAC AGATAGCGGC CACGATACTG TGGTGATGGA GGTCACCTTT TCTGGAACAA AACCCTGCAG AATACCCGTC GGGGCTGTAG
     TGTACCTTCT CCCGGGGGTG TCTATCGCCG GTGCTATGAC CACCACTACCT CCAGTGGAAA AGACCTTGTT TTGGGACGTC TTATGGGCAC GCCCGACATC
                                                                Hypr E protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

· H  G  S    P  D  V    N  V  A  M    L  I  T    P  N  P    T  I  E  N    N  G  G    G  F  I    E  M  Q  L    P  P  G ·
2001 CTCACGGATC TCCCGATGTC AATGTTGCTA TGCTGATTAC ACCTAACCCT ACCATCGAGA ATAACGGTGG TGGTTTTATT GAGATGCAGC TTCCGCCAGG
     GAGTGCCTAG AGGGCTACAG TTACAACGAT ACGACTAATG TGGATTGGGA TGGTAGCTCT TATTGCCACC ACCAAAATAA CTCTACGTCG AAGGCGGTCC
                                                                Hypr E protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
```

```
                  · D  N  I   I  Y  V  G   E  L  S   Y  Q  W    F  Q  K  G   S  S  I   G  R  V    F  Q  K  T   K  K  G   I  E  R
        2101  CGATAACATC ATCTACGTGG GCGAACTCTC TTACCAGTGG TTTCAGAAAG GGAGTTCAAT TGGGCGGGTC TTCCAAAAAA CCAAGAAGGG AATCGAACGA
              GCTATTGTAG TAGATGCACC CGCTTGAGAG AATGGTCACC AAAGTCTTTC CCTCAAGTTA ACCCGCCCAG AAGGTTTTTT GGTTCTTCCC TTAGCTTGCT
                                                                                Hypr E protein L  T  V  I   G  E  H   A  W  D   F  G  S  A   G  G  F   L  S  S    I  G  K  A   L  H  T   V  L  G   G  A  F  N ·
        2201  TTGACGGTTA TCGGCGAGCA CGCATGGGAT TTTGGTTCCG CAGGGGGATT CCTGTCTTCT ATTGGTAAGC CACTGCATAC CGTGCTGGGG GGCGCATTCA
              AACTGCCAAT AGCCGCTCGT GCGTACCCTA AAACCAAGGC GTCCCCCTAA GGACAGAAGA TAACCATTCC GTGACGTATG GCACGACCCC CCGCGTAAGT
                                                                                Hypr E protein · S  I  F   G  G  V   G  F  L  P   K  L  L   L  G  V   A  L  A  W   L  G  L   N  M  R   N  P  T  M   S  M  S ·
        2301  ATTCTATTTT CGGGGGCGTG GGGTTCCTGC CTAAACTCCT GCTGGGAGTA GCCCTGGCCT GGTTGGGACT GAATATGCGG AATCCGACGA TGTCCATGTC
              TAAGATAAAA GCCCCCGCAC CCCAAGGACG GATTTGAGGA CGACCCTCAT CGGGACCGGA CCAACCCTGA CTTATACGCC TTAGGCTGCT ACAGGTACAG
                                                                                Hypr E protein                                      NS1 gene of YF17D · F  L  L   A  G  V   L  V  L  A   M  T  L   G  V  G  A    D  Q  G   C  A  I   N  F  G  K   R  E  L
        2401  ATTCCTCTTG GCCGGCGTGC TTGTACTGGC CATGACACTG GGCGTTGGCG CCGATCAAGG ATGCGCCATC AACTTTGGCA AGAGAGAGCT C
              TAAGGAGAAC CGGCCGCACG AACATGACCG GTACTGTGAC CCGCAACCGC GGCTAGTTCC TACGCGGTAG TTGAAACCGT TCTCTCTCGA G
```

Sequence Appendix 3

PIV-WN/TBEV Hypr with TBEV signal (p39)

```
                                                                                                                                        deleted C
                                                      5' UTR
                                                                                                                                 M   S ·
           1  AGTAGTTCGC CTGTGTGAGC TGACAAACTT AGTAGTGTTT GTGAGGATTA ACAACAATTA ACACAGTGCG AGCTGTTTCT TAGCACGAAG ATCTCGATGT
              TCATCAAGCG GACACACTCG ACTGTTTGAA TCATCACAAA CACTCCTAAT TGTTGTTAAT TGTGTCACGC TCGACAAAGA ATCGTGCTTC TAGAGCTACA
                                                                                WNV deleted C protein · K  K  P   G  G  P   G  K  S  R   A  V  Y   L  L  K   R  G  M  P   R  V  L    S  L  I   G  L  K  R   S  S  K ·
         101  CTAAGAAACC AGGAGGGCCC GGCAAGAGCC GGGCTGTCTA TTTGCTAAAA CGCGGAATGC CCCGCGTGTT GTCCTTGATT GGACTTAAGC GGAGCTCCAA
              GATTCTTTGG TCCTCCCGGG CCGTTCTCGG CCCGACAGAT AAACGATTTT GCGCCTTACG GGGCGCACAA CAGGAACTAA CCTGAATTCG CCTCGAGGTT
                  deleted C                                                                                        prM Hypr · Q  K  K   R  G  G   T  D  W  M   S  W  L   L  V  I  G   M  L  G   M  T   I   A  A  T  V   R  K  E   R  D  G
         201  ACAAAAGAAA CGGGGGGGAA CAGACTGGAT GAGCTGGCTG CTCGTAATCG GCATGCTGGG CATGACAATC GCAGCTACGG TTCGCAAGGA AAGAGACGGC
              TGTTTTCTTT GCCCCCCCTT GTCTGACCTA CTCGACCGAC GAGCATTAGC CGTACGACCC GTACTGTTAG CGTCGATGCC AAGCGTTCCT TTCTCTGCCG
                                                                                prM Hypr S  T  V  I   R  A  E   G  K  D   A  A  T  Q   V  R  V   E  N  G   T  C  V  I   L  A  T   D  M  G   S  W  C  D ·
         301  AGTACGGTCA TACGCGCGGA AGGTAAGGAT GCCGCTACCC AAGTGAGAGT GGAAAATGGT ACCTGCGTCA TTCTGGCCAC CGACATGGGC TCTTGGTGTG
```

```
              TCATGCCAGT ATGCGCGCCT TCCATTCCTA CGGCGATGGG TTCACTCTCA CCTTTTACCA TGGACGCAGT AAGACCGGTG GCTGTACCCG AGAACCACAC
                                                                 prM Hypr
                 D  S  L  S  Y  E  C  V  T  I  D  Q  G  E  E  P  V  D  V  D  C  F  C  R  N  V  D  G  V  Y  L  E  Y
         401  ATGATAGCCT TTCTTATGAG TGCGTAACCA TAGATCAAGG TGAGGAACCT GTTGACGTTG ATTGCTTCTG CCGAAACGTG GATGGGGTGT ATCTCGAATA
              TACTATCGGA AAGAATACTC ACGCATTGGT ATCTAGTTCC ACTCCTTGGA CAACTGCAAC TAACGAAGAC GGCTTTGCAC CTACCCCACA TAGAGCTTAT
                                                                 prM Hypr
                 G  R  C  G  K  Q  E  G  S  R  T  R  R  S  V  L  I  P  S  H  A  Q  G  E  L  T  G  R  G  H  K  W  L
         501  TGGACGGTGT GGTAAACAAG AAGGAAGCAG AACCAGACGC TCAGTGCTTA TACCCTCCCA CGCTCAAGGA GAGCTGACCG GACGGGGACA TAAATGGTTG
              ACCTGCCACA CCATTTGTTC TTCCTTCGTC TTGGTCTGCG AGTCACGAAT ATGGGAGGGT GCGAGTTCCT CTCGACTGGC CTGCCCCTGT ATTTACCAAC
                                                                 prM Hypr
                 E  G  D  S  L  R  T  H  L  T  R  V  E  G  W  V  W  K  N  R  L  L  A  L  A  M  V  T  V  V  W  L  T  L
         601  GAGGGCGACT CACTCCGAAC ACATTTGACC CGCGTCGAGG GCTGGGTCTG GAAAAATCGG CTGTTGGCCC TCGCTATGGT GACAGTCGTT GGCTCACGC
              CTCCCGCTGA GTGAGGCTTG TGTAAACTGG GCGCAGCTCC CGACCCAGAC CTTTTTAGCC GACAACCGGG AGCGATACCA CTGTCAGCAA ACCGAGTGCG
                                                                                                            E Hypr
                                   prM Hypr
                 E  S  V  V  T  R  V  A  V  L  V  V  L  L  C  L  A  P  V  Y  A  S  R  C  T  H  L  E  N  R  D  F  V
         701  TGGAGTCTGT GGTTACTCGC GTGGCAGTGC TGGTGGTGCT CCTCTGTCTT GCCCCTGTCT ACGCGTCCAG GTGTACTCAT TTGGAAAACA GAGATTTTGT
              ACCTCAGACA CCAATGAGCG CACCGTCACG ACCACCACGA GGAGACAGAA CGGGGACAGA TGCGCAGGTC CACATGAGTA AACCTTTTGT CTCTAAAACA
                                                                    E Hypr
                 T  G  T  Q  G  T  T  R  V  T  L  V  L  E  L  G  G  C  V  T  I  T  A  E  G  K  P  S  M  D  V  W  L
         801  CACCGGCACC CAGGGGACGA CTCGGGTAAC CCTGGTGCTT GAACTGGGTG GTTGCGTTAC TATTACCGCT GAGGGCAAAC CCTCTATGGA TGTGTGGCTG
              GTGGCCGTGG GTCCCCTGCT GAGCCCATTG GGACCACGAA CTTGACCCAC CAACGCAATG ATAATGGCGA CTCCCGTTTG GGAGATACCT ACACACCGAC
                                                                    E Hypr
                 D  A  I  Y  Q  E  N  P  A  Q  T  R  E  Y  C  L  H  A  K  L  S  D  T  K  V  A  A  R  C  P  T  M  G  P
         901  GATGCAATCT ATCAGGAGAA TCCCGCACAA ACCAGGGAAT ATTGCCTTCA CGCCAAAGCTG TCCGATACAA AGGTCGCGGC TAGGTGCCCA ACAATGGGAC
              CTACGTTAGA TAGTCCTCTT AGGGCGTGTT TGGTCCCTTA TAACGGAAGT GCGTTTCGAC AGGCTATGTT TCCAGCGCCG ATCCACGGGT TGTTACCCTG
                                                                    E Hypr
                 A  T  L  A  E  E  H  Q  G  G  T  V  C  K  R  D  Q  S  D  R  G  W  G  N  H  C  G  L  F  G  K  G  S
        1001  CGGCCACCCT GGCGGAGGAA CATCAGGGAG GTACAGTGTG CAAACGGGAC CAGAGTGATA GAGGCTGGGG TAATCACTGC GGCCTGTTCG GCAAAGGAAG
              GCCGGTGGGA CCGCCTCCTT GTAGTCCCTC CATGTCACAC GTTTGCCCTG GTCTCACTAT CTCCGACCCC ATTAGTGACG CCGGACAAGC CGTTTCCTTC
                                                                    E Hypr
                 I  V  A  C  V  K  A  A  C  E  A  K  K  K  A  T  G  H  V  Y  D  A  N  K  I  V  Y  T  V  K  V  E  P
        1101  TATTGTCGCT TGCGTCAAGG CAGCCTGTGA GGCCAAAAAG AAGGCCACTG GGCACGTCTA TGACGCCAAC AAGATCGTTT ATACAGTGAA AGTGGAACCA
              ATAACAGCGA ACGCAGTTCC GTCGGACACT CCGGTTTTTC TTCCGGTGAC CCGTGCAGAT ACTGCGGTTG TTCTAGCAAA TATGTCACTT TCACCTTGGT
                                                                    E Hypr
                 H  T  G  D  Y  V  A  A  N  E  T  H  S  G  R  K  T  A  S  F  T  V  S  S  E  K  T  I  L  T  M  G  E  Y
        1201  CACACAGGGG ATTACGTGGC GGCCAACGAG ACTCATTCCG GTCGGAAAAC GGCCAGCTTC ACCGTGTCAT CCGAAAAGAC CATCCTCACT ATGGGGGAGT
              GTGTGTCCCC TAATGCACCG CCGGTTGCTC TGAGTAAGGC CAGCCTTTTG CCGGTCGAAG TGGCACAGTA GGCTTTTCTG TAGGAGTGA TACCCCCTCA
                                                                    E Hypr
                 G  D  V  S  L  L  C  R  V  A  S  G  V  D  L  A  Q  T  V  I  L  E  L  D  K  T  V  E  H  L  P  T  A
        1301  ATGGCGACGT TTCTCTGCTC TGCCGGGTGG CTAGCGGAGT CGACCTGGCC CAGACAGTAC TCGAACTGGA CAAAACA GTTGAGCATC TGCCTACCGC
              TACCGCTGCA AAGAGACGAG ACGGCCCACC GATCGCCTCA GCTGGACCGG GTCTGTCATG AGGACCTTGA CCTATTTTGT CAACTCGTAG ACGGATGGCG
                                                                    E Hypr
```

```
            · W  Q  V    H R D W    F N D    L A L    P W K H    E G A    R N W    N N A E    R L V    E F G
      1401  TTGGCAGGTG CACAGGGATT GGTTTAACGA CCTTGCCCTG CCATGGAAAC ATGAAGGAGC GAGAAACTGG AATAATGCAG AGCCGACTCG AGAATTCGGT
            AACCGTCCAC GTGTCCCTAA CCAAATTGCT GGAACGGGAC GGTACCTTTG TACTTCCTCG CTCTTTGACC TTATTACGTC TCGCTGAGCA TCTTAAGCCA
                                                                   E Hypr A  P H A    V K M    D V Y    N L G D    Q T G    V L L    K A L A    G V P    V A H    I E G T ·
      1501  GCCCCTCATG CCGTGAAGAT GGACGTCTAC AATCTGGGTG ATCAGACCGG CGTTCTCCTT AAAGCTCTCG CTGGCGTACC AGTTGCCCAC ATCGAAGGAA
            CGGGGAGTAC GGCACTTCTA CCTGCAGATG TTAGACCCAC TAGTCTGGCC GCAAGAGGAA TTTCGAGAGC GACCGCATGG TCAACGGGTG TAGCTTCCTT
                                                                   E Hypr · K  Y H    L K S    G H V T    C E V    G L E    K L K M    K G L    T Y T    M C D K    T K F ·
      1601  CGAAGTACCA CCTGAAGTCA GGCCATGTAA CTTGCGAGGT GGGCCTGGAG AAGTTGAAAA TGAAAGGTCT TACGTACACA ATGTGTGACA AGACCAAGTT
            GCTTCATGGT GGACTTCAGT CCGGTACATT GAACGCTCCA CCCGGACCTC TTCAACTTTT ACTTTCCAGA ATGCATGTGT TACACACTGT TCTGGTTCAA
                                                                   E Hypr · T W K    R A P T    D S G    H D T    V V M E    V T F    S G T    K P C R    I P V    R A V
      1701  CACATGGAAG AGGGCCCCCA CAGATAGCGG CCACGATACT GTGGTGATGG AGGTGACCTT TTCTGGAACA AAACCCTGCA GAATACCCGT GCGGGCTGTA
            GTGTACCTTC TCCCGGGGGT GTCTATCGCC GGTGCTATGA CACCACTACC TCCACTGGAA AAGACCTTGT TTTGGGACGT CTTATGGGCA CGCCCGACAT
                                                                   E Hypr A H G    S P D V    N V A    M L I T    P N P    T I E    N N G G    G F I    E M Q    L P P G ·
      1801  GCTCACGGAT CTCCCGATGT CAATGTTGCT ATGCTGATTA CACCTAACCC TACCATCGAG AATAACGGTG GTGGTTTTAT TGAGATGCAG CTTCCGCCAG
            CGAGTGCCTA GAGGGCTACA GTTACAACGA TACGACTAAT GTGGATTGGG ATGGTAGCTC TTATTGCCAC CACCAAAATA ACTCTACGTC GAAGGCGGTC
                                                                   E Hypr · D N I    I Y V    G E L S    Y Q W    F Q K    G S S I    G R V    F Q K    T K K G    I E R ·
      1901  GCGATAACAT CATCTACGTG GGCGAACTCT CTTACCAGTG GTTTCAGAAG GGAGTTCAA TTGGGCGGGT CTTCCAAAAA ACGAAGAAGG GAATCGAACG
            CGCTATTGTA GTAGATGCAC CCGCTTGAGA GAATGGTCAC CAAAGTCTTT CCCTCAAGTT AACCCGCCCA GAAGGTTTTT TGCTTCTTCC CTTAGCTTGC
                                                                   E Hypr · L T V    I G E H    A W D    F G S    A G G F    L S S    I G K    A L H T    V L G    G A F
      2001  ATTGACGGTT ATCGGCGAGC ACGCATGGGA TTTTGGTTCC GCAGGGGGAT TCCTGTCTTC TATTGGTAAG GCACTGCATA CCGTGCTGGG GGGCGCATTC
            TAACTGCCAA TAGCCGCTCG TGCGTACCCT AAAACCAAGG CGTCCCCCTA AGGACAGAAG ATAACCATTC CGTGACGTAT GGCACGACCC CCCGCGTAAG
                                                                   E Hypr N S I F    G G V    G F L    P K L L    L G V    A L A    W L G L    N M R    N P T    M S M S ·
      2101  AATTCTATTT TCGGGGGCGT GGGGTTCCTG CCTAAACTCC TGCTGGGAGT AGCCCTGGCC TGGTTGGGAC TGAATATGCG GAATCCGACG ATGTCCATGT
            TTAAGATAAA AGCCCCCGCA CCCCAAGGAC GGATTTGAGG ACGACCCTCA TCGGGACCGG ACCAACCCTG ACTTATACGC CTTAGGCTGC TACAGGTACA
                                                                   E Hypr
                                                                                                WNV NS1 protein · F L L    A G V    L V L A    M T L    G V G    A D T G    C A I    D I S    R Q
      2201  CATTCCTCTT GGCCGGCGTG CTTGTACTGG CCATGACACT GGGCGTTGGC GCCGACACTG GTGTGGCCAT AGACATCAGC CGGCAA
            GTAAGGAGAA CCGGCCGCAC GAACATGACC GGTACTGTGA CCCGCAACCG CGGCTGTGAC CCACACCGGTA TCTGTAGTCG GCCGTT
```

PIV-WN/TBEV Hypr with WNV signal (p40)

```
                                                                                                deleted C
                            5' UTR
                                                                                                   M  S·
  1 AGTAGTTCGC CTGTGTGAGC TGACAAACTT AGTAGTGTTT GTGAGGATTA ACAACAATTA ACACAGTGCG AGCTGTTTCT TAGCACGAAG ATCTCGATGT
    TCATCAAGCG GACACACTCG ACTGTTTGAA TCATCACAAA CACTCCTAAT TGTTGTTAAT TGTGTCACGC TCGACAAAGA ATCGTGCTTC TAGAGCTACA
                                                  WNV deleted C
    · K  K  P     G  G  P     G  K  S  R     A  V  Y     L  L  K     R  G  M     P  R  V  L     S  L  I     G  L  K     R  S  S  K·
101 CTAAGAAACC AGGAGGGCCC GGCAAGAGCC GGGCTGTCTA TTTGCTAAAA CGCGGAATGC CCCGCGTGTT GTCCTTGATT GGACTTAAGC GGAGCTCCAA
    GATTCTTTGG TCCTCCCGGG CCGTTCTCGG CCCGACAGAT AAACGATTTT GCGCCTTACG GGGCGCACAA CAGGAACTAA CCTGAATTCG CCTCGAGGTT
                              WNV signal
       WNV deleted C                                                                                    prM Hypr
    ·Q  K  K     R  G  G  K     T  G  I     A  V  M     I  G  M  L     A  C  V     G  A  A     T  V  R  K     E  R  D     G  S  T
201 GCAAAAGAAA CGCGGGGGAA AGACAGGCAT ACCTGTGATG ATAGGCATGC TGGCTTGTGT CGGAGCAGCT ACCGTGCGAA AGAACGCGA CGGAAGCACC
    CGTTTTCTTT GCGCCCCCTT TCTGTCCGTA TGGACACTAC TATCCGTACG ACCGAACACA GCCTCGTCGA TGGCACGCTT TCTTGCGCT GCCTTCGTGG
                                                  prM Hypr
      V  I  R  A     E  G  K     D  A  A     T  Q  V  R     V  E  N     G  T  C     V  I  L  A     T  D  M     G  S  W     C  D  D  S·
301 GTGATAAGGG CTGAGGGTAA GGATGCGGCT ACGCAGGTGA GAGTAGAGAA TGGCACTTGC GTAATACTCG CGACTGATAT GGGATCCTGG TGTGACGATA
    CACTATTCCC GACTCCCATT CCTACGCCGA TGCGTCCACT CTCATCTCTT ACCGTGAACG CATTATGAGC GCTGACTATA CCCTAGGACC ACACTGCTAT
                                                                       prM Hypr
    · L  S  Y     E  C  V     T  I  D  Q     G  E  E     P  V  D     V  D  C  F     C  R  N     V  D  G     V  Y  L  E     Y  G  R·
401 GCCTCAGTTA TGAATGCGTA ACAATAGACC AGGGCGAAGA TGTTATCTGG TCCCGCTTCT TGGACACCTG CAACTGACAA AGACATCTTT ACACCTACCG CAAATAGACC TCATGCCGGC
    CGGAGTCAAT ACTTACGCAT TGTTATCTGG TCCCGCTTCT TGGACACCTG CAACTGACAA AGACATCTTT ACACCTACCG CAAATAGACC TCATGCCGGC
                                                  prM Hypr
    ·C  G  K     Q  E  G  S     R  T  R     R  S  V     L  I  P  S     H  A  Q     G  E  L     T  G  R  G     H  K  W     L  E  G
501 CTGTGGAAAA CAGGAGGGCT CACGAACTCG AAGATCGTG CTGATTCCAA GTCACGCGCA ACCAGAGTTG ACCGGTAGAG GCCACAAGTG GCTTGAAGGG
    GACACCTTTT GTCCTCCCGA GTGCTTGAGC TTCTAGACAC GACTAAGGTT CAGTGCGCGT TCCTCTCAAC TGGCCATCTC CGGTGTTCAC CGAACTTCCC
                                                                       prM Hypr
       D  S  L  R     T  E  L     T  R  V     E  G  W  V     W  K  N     R  L  L     A  L  A  M     V  T  V     V  W  L     T  L  E  S·
601 GACTCATTGA GGACCCACCT GACTAGGGTG GAGGGTTGGG TTTGGAAGAA TCGGTTGCTC GCGCTCGCTA TGGTCACCGT CGTGTGGCTG ACACTGGAGA
    CTGAGTAACT CCTGGGTGGA CTGATCCCAC CTCCCAACCC AAACCTTCTT AGCCAACGAG CGCGAGCGAT ACCAGTGGCA GCACACCGAC TGTGACCTCT
                                                                                                   E Hypr
                 prM Hypr
    · V  V  T     R  V  A     V  L  V  V     L  L  C     L  A  P     V  Y  A  S     R  C  T     H  L  E     N  R  D  F     V  T  G·
701 GTGTCGTGAC TCGGGTTGCT GTGTTGGTTG TCCTCCTCTG TTTGGCCCCA GTGTACGCGT CCAGGTGTAC TCATTTGGAA AACAGAGATT TTGTCACCGG
    CACAGCACTG AGCCCAACGA CACAACCAAC AGGAGGAGAC AAACCGGGGT CACATGCGCA GGTCCACATG AGTAAACCTT TTGTCTCTAA AACAGTGGCC
                                                                                                   E Hypr
```

```
              ·T  Q   G   T   T   R   V   T   L   V   L   E   L   G   G   C   V   T   I   T   A   E   G   K   P   S   M   D   V   W   L   D   A
 801 CACCCAGGGG ACGACTCGGG TAACCCTGGT GCTTGAACTG GGTGGTTGTG TTACTATTAC CGCTGAGGGC AAACCCTCTA TGGATGTGTG GCTGGATGCA
     GTGGGTCCCC TGCTGAGCCC ATTGGGACCA CGAACTTGAC CCACCAACGC AATGATAATG GCGACTCCCG TTTGGGAGAT ACCTACACAC CGACCTACGT
                                                                   E Hypr
              I   Y   Q   E   N   P   A   Q   T   R   E   Y   C   L   H   A   K   L   S   D   T   K   V   A   A   R   C   P   T   M   G   P   A   T·
 901 ATCTATCAGG AGAATCCCGC ACAAACCAGG GAATATTGCC TTCACGCAAA GCTGTCCGAT ACAAAGGTCG CGGCTAGGTG CCCAACAATG GGACCGGCCA
     TAGATAGTCC TCTTAGGGCG TGTTTGGTCC CTTATAACGG AAGTGCGTTT CGACAGGCTA TGTTTCCAGC GCCGATCCAC GGGTTGTTAC CCTGGCCGGT
                                                                   E Hypr
              ·L  A   E   E   H   Q   G   G   T   V   C   K   R   D   Q   S   D   R   G   W   G   N   H   C   G   L   F   G   K   G   S   I   V·
1001 CCCTGGCGGA GGAACATCAG GGAGGTACAG TGTGCAAACG GGACCAGAGT GATAGAGGCT GGGGTAATCA CTGCCGGCCTG TTCGGCAAAG GAAGTATTGT
     GGGACCGCCT CCTTGTAGTC CCTCCATGTC ACACGTTTGC CCTGGTCTCA CTATCTCCGA CCCCATTAGT GACGCCGGAC AAGCCGTTTC CTTCATAACA
                                                                   E Hypr
              ·A  C   V   K   A   A   C   E   A   K   K   K   A   T   G   H   V   Y   D   A   N   K   I   V   Y   T   V   K   V   E   P   H   T
1101 CGCTTGCGTC AAGGCAGCCT GTGAGGCCAA AAAGAAGGCT ACTGGGCACG TCTATGACGC AACAAGATCG TTTATACAG TGAAAGTGGA ACCACACACA
     GCGAACGCAG TTCCGTCGGA CACTCCGGTT TTTCTTCCGA TGACCCGTGC AGATACTGCG TTGTTCTAG CAAATATGTC ACTTTCACCT TGGTGTGTGT
                                                                   E Hypr
              G   D   Y   V   A   A   N   E   T   H   S   G   R   K   T   A   S   F   T   V   S   S   E   K   T   I   L   T   M   G   E   Y   G   D·
1201 GGGGATTACG TGGCGGCCAA CGAGACTCAT TCCGGTCGCA AAACGGCCAG CTTCACCGTG TCATCCGAAA AGACCATCCT CACTATGGGG GAGTATGGCG
     CCCCTAATGC ACCGCCGGTT GCTCTGAGTA AGGCCAGCGT TTTGCCGGTC GAAGTGGCAC AGTAGGCTTT TCTGGTAGGA GTGATACCCC CTCATACCGC
                                                                   E Hypr
              ·V  S   L   L   C   R   V   A   S   G   V   D   L   A   Q   T   V   I   L   E   L   D   K   T   V   E   H   L   P   T   A   W   Q·
1301 ACGTTTCTCT GCTCTGCCGG GTGGCTAGCG GAGTCGACCT GGCCCAGACA GTCATCCTGG AACTGGATAA AACAGTTGAG CATCTGCCTA CCGCTTGGCA
     TGCAAAGAGA CGAGACGGCC CACCGATCGC CTCAGCTGGA CCGGGTCTGT CAGTAGGACC TTGACCTATT TTGTCAACTC GTAGACGGAT GGCGAACCGT
                                                                   E Hypr
              ·V  H   R   D   W   F   N   D   L   A   L   P   W   K   H   E   G   A   R   N   W   N   N   A   E   R   L   V   E   F   G   A   P
1401 GGTGCACAGG GATTGGTTTA ACGACCTTGC CCTGCCATGG AAACATGAAG GAGCGAGAAA CTGGAATAAT GCAGAGCGAC TCGTAGAATT CGGTGCCCCT
     CCACGTGTCC CTAACCAAAT TGCTGGAACG GGACGGTACC TTTGTACTTC CTCGCTCTTT GACCTTATTA CGTCTCGCTG AGCATCTTAA GCCACGGGGA
                                                                   E Hypr
              H   A   V   K   M   D   V   Y   N   L   G   D   Q   T   G   V   L   L   K   A   L   A   G   V   P   V   A   H   I   E   G   T   K   Y·
1501 CATGCCGTGA AGATGGACGT CTACAATCTG GGTGATCAGA CCGGCGTTCT CCTTAAAGCT CTCGCTGGCG TACCAGTTGC CCACATCGAA GGAACGAAGT
     GTACGGCACT TCTACCTGCA GATGTTAGAC CCACTAGTCT GGCCGCAAGA GGAATTTCGA GAGCGACCGC ATGGTCAACG GGTGTAGCTT CCTTGCTTCA
                                                                   E Hypr
              ·H  L   K   S   G   H   V   T   C   E   V   G   L   E   K   L   K   M   K   G   L   T   Y   T   M   C   D   K   T   K   F   T   W·
1601 ACCACCTGAA GTCAGGCCAT GTAACTTGCG AGGTCGGGCT GGAGAAGTTG AAAATGAAAG GTCTTACGTA CACAATGTGT GACAAGACCA AGTTCACATG
     TGGTGGACTT CAGTCCGGTA CATTGAACGC TCCAGCCCGA CCTCTTCAAC TTTTACTTTC CAGAATGCAT GTGTTACACA CTGTTCTGGT TCAAGTGTAC
                                                                   E Hypr
              ·K  R   A   P   T   D   S   G   H   D   T   V   V   M   E   V   T   F   S   G   T   K   P   C   R   I   P   V   R   A   V   A   H
1701 GAAGAGGGCC CCCACAGATA GCGGCCACGA TACTGTGGTG ATGGAGGTGA CCTTTTCTGG AACAAAACCC TGCAGAATAC CCGTGCGGGC TGTAGCTCAC
     CTTCTCCCGG GGGTGTCTAT CGCCGGTGCT ATGACACCAC TACCTCCACT TGGAAAAGACC TTGTTTTGGG ACGTCTTATG GGCACGCCCG ACATCGAGTG
                                                                   E Hypr
              G   S   P   D   V   N   V   A   M   L   I   T   P   N   P   T   I   E   N   N   G   G   F   I   E   M   Q   L   P   P   G   D   N·
1801 GGATCTCCCG ATGTCAATGT TGCTATGCTG ATTACACCTA ACCCTACCAT CGAGAATAAC GGTGGTGTT TTATTGAGAT GCAGCTTCCG CCAGGCGATA
     CCTAGAGGGC TACAGTTACA ACGATACGAC TAATGTGGAT TGGGATGGTA GCTCTTATTG CCACCACCAA AATAACTCTA CGTCGAAGGC GGTCCGCTAT
                                                                   E Hypr
```

```
              . I  I  Y     V  G  E     L  S  Y  Q     W  F  Q     K  G  S     S  I  G  R     V  F  Q     K  T  K     K  G  I  E     R  L  T .
       1901   ACATCATCTA CGTGGGCGAA CTCTCTTACC AGTGGTTTCA GAAAGGGAGT TCAATTGGGC GGGTCTTCCA AAAAACGAAG AAGGGAATCG AACGATTGAC
              TGTAGTAGAT GCACCCGCTT CAGAGAATGG TCACCAAAGT CTTTCCCTCA GTTAACCCG CCCAGAAGGT TTTTTGCTTC TTCCCTTAGC TTGCTAACTG
                                                     E Hypr . V  I  G     E  H  A  W     D  F  G     S  A  G     G  F  L  S     S  I  G     K  A  L     H  T  V  L     G  G  A     F  N  S
       2001   GGTTATCGGC GAGCACGCAT GGGATTTTGG TTCCGCAGGG GGATTCCTGT CTTCTATTGG TAAGGCACTG CATACCGTGC TGGGGGGCGC ATTCAATTCT
              CCAATAGCCG CTCGTGCGTA CCCTAAAACC AAGGCGTCCC CCTAAGGACA GAAGATAACC ATTCCGTGAC GTATGGCACG ACCCCCCGCG TAAGTTAAGA
                                                     E Hypr I  F  G  G     V  G  F     L  P  K     L  L  L  G     V  A  L     A  W  L     G  L  N  M     R  N  P     T  M  S     M  S  F  L .
       2101   ATTTTCGGGG GCGTGGGGTT CCTGCCTAAA CTCCTGCTGG GAGTAGCCCT GGCCTGGTTG GGACTGAATA TGCGGAATCC GACGATGTCC ATGTCATTCC
              TAAAAGCCCC CGCACCCCAA GGACGGATTT GAGGACGACC CTCATCGGGA CCGGACCAAC CCTGACTTAT ACGCCTTAGG CTGCTACAGG TACAGTAAGG
                                                     E Hypr                                          WNV  NS1 protein . L  A  G     V  L  V     L  A  M  T     L  G  V     G  A  D     T  G  C  A     I  D  I     S  R  Q
       2201   TCTTGGCCGG CGTGCTTGTA CTGGCCATGA CACTGGGCGT GGCGCCGAC ACTGGGTGTG CCATAGACAT CAGCCGGCAA
              AGAACCGGCC GCACGAACAT GACCGGTACT GTGACCCGCA ACCGCGGCTG TGACCCACAC GGTATCTGTA GTCGGCCGTT
```

Sequence Appendix 4. WN PIV constructs expressing rabies virus G protein.

WN (ΔCprME)-Rabies PIV sequence (partial)

```
                                                                                            N-terminus of C
                         5' UTR                                                             ~~~~~~~~~~~~~~
~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                                           M  S ·
  1  AGTAGTTCGC CTGTGTGAGC TGACAAACTT AGTAGTGTTT GTGAGGATTA ACAACAATTA ACACAGTGCG AGCTGTTTCT TAGCACGAAG ATCTCGATGT
     TCATCAAGCG GACACACTCG ACTGTTTGAA TCATCACAAA CACTCCTAAT TGTTGTTAAT TGTGTCACGC TCGACAAAGA ATCGTGCTTC TAGAGCTACA
                                     N-terminus of C · K  K  P  G  G  P  G  K  S  R  A  V  Y  L  L  K  R  G  M  P  R  V  L  S  L  I  G  L  K  Q  K  K  R ·
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 101 CTAAGAAACC AGGAGGGCCC GGCAAGAGCC GGGCTGTCTA TTTGCTAAGA CGCGGAATGC CCCGCGTGTT GTCCTTGATT GGACTTAAGC AAAAGAAGCG
     GATTCTTTGG TCCTCCCGGG CCGTTCTCGG CCCGACAGAT AAACGATTTT GCGCCTTACG GGGCGCACAA CAGGAACTAA CCTGAATTCG TTTTCTTCGC
     N-terminus of C                                                Rabies-G signal
     ~~                                                             ~~~~~~~~~~~~~~~~~~~~~~~~~~~~~~~~~~~~~~~~~~
        partial C signal                                                                  Rabies-G protein
                                                                                          ~~~~~~~~~~~~~~~~
     · G  G  K  T  G  I  A  V  I  V  P  Q  A  L  L  F  V  P  L  L  V  F  P  L  C  F  G  K  F  P  I  Y  T
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 201 AGGGGGCAAG ACTGGTATAC CTCTGATCGT TCCTCAGGCT CTTTTGTTTG TACCCTTGCT GGTATTTCCC CTTTGCTTTG GTAAATTTCC TATCTATACC
     TCCCCCGTTC TGACCATATC GACACTAGCA AGGAGTCCGA GAAACAAAC ATGGGAACGA CCATAAAGGG GAAACCAAAC CATTTAAAGG ATAGATATGG
                                                      Rabies-G protein · I  P  D  K  L  G  P  W  S  P  I  D  I  H  H  L  S  C  P  N  L  V  V  E  D  E  G  C  T  N  L  S  G ·
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 301 ATCCCTGATA AGCTCGGGCC TTGGAGTCCC ATTGATATTC ACCATTTGAG CTGCCCAAAC AACCTCGTCG TTGAGGATGA AGGGTGCACT AATCTTTCTG
     TAGGGACTAT TCGAGCCCGG AACCTCAGGG TAACTATAAG TGGTAAACTC GACGGGTTTG TTGGAGCAGC AACTCCTACT TCCCACGTGA TTAGAAAGAC
                                                        Rabies-G protein · F  S  Y  M  E  L  K  V  G  Y  I  S  A  I  K  M  N  G  F  T  C  T  G  V  V  T  E  A  E  T  Y  T  N ·
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 401 GATTTTCCTA CATGGAGTTG AAAGTGGGCT ATATTTCAGC CATTAAGATG AACGGCTTTA CTTGTACAGG AGTCGTGACC GAAGCCGAGA CATATACAAA
     CTAAAAGGAT GTACCTCAAC TTTCACCCGA TATAAAGTCG GTAATTCTAC TTGCCGAAAT GAACATGTCC TCAGCACTGG CTTCGGCTCT GTATATGTTT
                                                      Rabies-G protein · F  V  G  Y  V  T  T  T  F  K  R  K  H  F  R  P  T  P  D  A  C  R  A  A  Y  N  W  K  M  A  G  D  P ·
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 501 TTTCGTGGGA TACGTCACCA CCACCTTCAA GAGAAAACAC TTCCGCCCAA CGCCTGACGC TTGTCGGGCC GCTTACAACT GGAAGATGGC AGGAGATCCT
     AAAGCACCCT ATGCAGTGGT GGTGGAAGTT CTCTTTTGTG AAGGCGGGTC GCGGACTGCG AACAGCCCGG CGAATGTTGA CCTTCTACCG TCCTCTAGGA
                                                      Rabies-G protein · R  Y  E  E  S  L  H  N  P  Y  P  D  Y  H  W  L  R  T  V  K  T  T  K  E  S  L  V  I  I  S  P  S  V  A ·
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 601 CGATATGAAG AATCTCTGCA CAACCCGTAT CCTGATTACC ATTGGCTGCG GACAGTCAAG ACTACCAAGG AGAGTCTGGT CATTATATCA CCAAGCGTGG
     GCTATACTTC TTAGAGACGT GTTGGGCATA GGACTAATGG TAACCGACGC CTGTCAGTTC TGATGGTTCC TCTCAGACCA GTAATATAGT GGTTCGCACC
                                                      Rabies-G protein · D  L  D  P  Y  D  R  S  L  H  S  R  V  F  P  G  G  N  C  S  G  V  A  V  S  S  T  Y  C  S  T  N  H ·
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 701 CCGATCTTCA TCCTTATGAT AGATCCCTGC ACAGTAGGGT TTTCCTGGC GGGAATTGTA GCGGTGTTGC AGTATCAAGT ACCTACTGCT CCACTAACCA
     GGCTAGAACT AGGAATACTA TCTAGGGACG TGTCATCCCA AAAAGGACCC CCCTTAACAT CGCCACAACG TCATAGTTCA TGGATGACGA GGTGATTGGT
                                                      Rabies-G protein · D  Y  T  I  W  M  P  E  N  P  R  L  G  M  S  C  D  I  F  T  N  S  R  G  K  R  A  S  K  G  S  E  T
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 801 CGACTACACT ATATGGATGC CTGAGAACCC TCGACTCGGT ATGAGTTGCG ACATTTTTAC GAACTCACGG GGCAAGCGGG CATCTAAGGG GTCTGAAACA
     GCTGATGTGA TATACCTACG GACTCTTGGG AGCTGAGCCA TACTCAACGC TGTAAAAATG CTTGAGTGCC CCGTTCGCCC GTAGATTCCC CAGACTTTGT
                                                      Rabies-G protein · C  G  F  V  D  E  R  G  L  Y  K  S  L  K  G  A  C  K  L  K  L  C  G  V  L  G  L  R  L  M  D  G  T  W ·
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 901 TGCGGGTTTG TTGATGAGCG GGGGTTGTAT AAATCTCTTA AAGGCGCCTG TAAGCTGAAA CTCTGTGGCG TACTGGGGCT GCGCCTGATG GACGGCACAT
     ACGCCCAAAC AACTACTCGC CCCCAACATA TTTAGAGAAT TTCCGCGGAC ATTCGACTTT GAGACACCGC ATGACCCCGA CGCGGACTAC CTGCCGTGTA
                                                      Rabies-G protein · V  A  M  Q  T  S  N  E  T  K  W  C  P  P  G  Q  L  V  N  L  H  D  F  R  S  D  E  I  E  H  L  V  V ·
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
1001 GGGTGGCTAT GCAGACAAGC AATGAAACAA AGTGGTGTCC CCCTGGTCAG CTGGTTAATC TGCACGACTT TAGGTCTGAC GAAATCGAGC ACCTTGTGGT
     CCCACCGATA CGTCTGTTCG TTACTTTGTT TCACCACAGG GGGACCAGTC GACCAATTAG ACGTGCTGAA ATCCAGACTG CTTTAGCTCG TGGAACACCA
                                                      Rabies-G protein
```

```
         · E  E  L  V  K  K  R    E  E  C  L  D  A    L  E  S  I  M    I  T  T  K  S  V    S  F  R  R  L  S  H    L  R  K
1101 GGAGGAACTG GTGAAGAAAC GCGAAGAGTG CCTGGACGCA CTTGAGAGTA TTATGACCAC CAAATCCGTT TCCTTCAGAA GACTGAGCCA CCTGCGAAAG
     CCTCCTTGAC CACTTCTTTG CGCTTCTCAC GGACCTGCGT GAACTCTCAT AATACTGGTG GTTTAGGCAA AGGAAGTCTT CTGACTCGGT GGACGCTTTC
                                                                                Rabies-G protein L  V  P  G  F  G  K    A  Y  T    I  F  N  K  T  L  M    E  A  D  A  H  Y  K    S  V  R    T  W  N  E  I  I  P  ·
1201 CTGGTGCCAG GGTTCGGGAA GGCTTATACT ATTTTCAACA AGACTCTTAT GGAGGCGGAT GCCCATTATA AGTCAGTTAG ACTTGGAAT GAGATAATTC
     GACCACGGTC CCAAGCCCTT CCGAATATGA TAAAAGTTGT TCTGAGAATA CCTCCGCCTA CGGGTAATAT TCAGTCAATC CTGAACCTTA CTCTATTAAG
                                                                                Rabies-G protein · S  K  G    C  L  R    V  G  G  R    C  H  P    H  V  N    G  V  F  F    N  G  I    I  L  S    P  D  G  N    V  L  I  ·
1301 CCTCCAAAGG ATGTCTGAGA GTCGGTGGGA GATGCCACCC CCATGTCAAT GGGGTGTTCT TAACGGAAT CATCCTGGGA CCTGACGGGA ACGTGCTGAT
     GGAGGTTTCC TACAGACTCT CAGCCACCCT CTACGGTGGG GGTACAGTTA CCCCACAAGA ATTGCCTTA GTAGGACCCT GGACTGCCCT TGCACGACTA
                                                                                Rabies-G protein · P  E  M    Q  S  S  L    L  Q  Q    H  M  E    L  L  V  S    S  V  I    P  L  M    H  P  L  A    D  P  S    T  V  F
1401 TCCCGAGATG CAATCTTCCC TTCTGCAGCA ACACATGGAA CTCCTGGTGT CTTCAGTGAT ACCCCTGATG CACCCACTGG CCGACCCCAG CACTGTGTTC
     AGGGCTCTAC GTTAGAAGGG AAGACGTCGT TGTGTACCTT GAGGACCACA GAAGTCACTA TGGGGACTAC GTGGGTGACC GGCTGGGGTC GTGACACAAG
                                                                                Rabies-G protein K  N  G  D    E  A  E    D  F  V    E  V  H  L    P  D  V    H  E  R    I  S  G  V    D  L  G    L  P  N    W  G  K  Y  ·
1501 AAAAATGGCG ATGAGGCCGA AGACTTTGTG GAAGTTCACC TGCCCGATGT ACACGAAAGG ATATCTGGAG TAGACCTGGG CCTTCCTAAT TGGGGTAAGT
     TTTTTACCGC TACTCCGGCT TCTGAAACAC CTTCAAGTGG ACGGGCTACA TGTGCTTTCC TATAGACCTC ATCTGGACCC GGAAGGATTA ACCCCATTCA
                                                                                Rabies-G protein · V  L  L    S  A  G    A  L  T  A    L  M  L    I  I  F    L  M  T  C    W  R  R    V  N  R    S  E  P  T    Q  H  N  ·
1601 ACGTGCTCCT GAGTGCCGGG GCCTTGACCG CTTTGATGCT GATCATTTTT CTGATGACCT GCTGGCGGAG GGTGAATCGC TCCGAGCCGA CACAGCACAA
     TGCACGAGGA CTCACGGCCC CGGAACTGGC GAAACTACGA CTAGTAAAAA GACTACTGGA CGACCGCCTC CCACTTAGCG AGGCTCGGCT GTGTCGTGTT
                                                                                Rabies-G protein
                                                                                                                    FMDV 2A
         · L  R  G    T  G  R  E    V  S  V    T  P  G    S  G  K  I    I  S  S    W  E  S    Y  K  S  G    E  T    G  L  N
1701 TCTCAGAGGG ACAGGCCGGG AAGTAAGTGT GACTCCGCAA TCTGCAAGA TTATTAGTAG TTGGGAGAGT TACAAGTCTG GAGGAGAGAC TGGCTTGAAT
     AGAGTCTCCC TGTCCGGCCC TTCATTCACA CTGAGGCGTT AGACCGTTCT AATAATCATC AACCCTCTCA ATGTTCAGAC CTCCTCTCTG ACCCAACTTA
                                                                   preNS1 signal FMDV 2A                                                          NS1 signal
         F  D  L  L    K  L  A    G  D  V    E  S  N  P    G  P  A    R  D  R    S  I  A  L    T  F  L    A  V  G    G  V  L  L  ·
1801 TTTGACCTGC TCAAACTTGC AGGCGATGTA GAATCAAATC CTGGACCCGC CCGGGACAGG TCCATAGCTC TCACGTTTCT CGCAGTTGGA GGAGTTCTGC
     AAACTAGACG AGTTTGAACG TCCGCTACAT CTTAGTTTAG GACCTGGGCG GGCCCTGTCC AGGTATCGAG AGTGCAAAGA GCGTCAACCT CCTCAAGACG
            NS1 signal
                                                NS1
         · F  L  S    V  N  V    H  A  D  T    G  C  A    I  D  I    S  R  Q  E    I  R  C    G  S  G    V  F  I  H    N  D  V ·
1901 TCTTCCTCTC CGTGAACGTG CACGCTGACA CTGGCTGTGC CATAGACATC AGCCGGCAAG AGCTGAGAT TGGAAGTGGA GTGTTCATAC ACAATGATGT
     AGAAGGAGAG GCACTTGCAC GTGCGACTGT GACCGACACG GTATCTGTAG TCGGCCGTTC TCGACTCTAC ACCTTCACCT CACAAGTATG TGTTACTACA
```

WN (ΔC)-Rabies G PIV sequence (partial).

```
                                                  5'UTR
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                                                      N-terminus
    of C
                                                                                                       -----
                                                                                                       M  S  ·
  1 AGTAGTTCGC CTGTGTGAGC TCACAAACTT AGTAGTGTTT GTGAGGATTA ACAACAATTA ACACAGTGCG AGCTGTTTCT TAGCACGAAG ATCTCGATGT
    TCATCAAGCG GACACACTCG ACTGTTTGAA TCATCACAAA CACTCCTAAT TGTTGTTAAT TGTGTCACGC TCGACAAAGA ATCGTGCTTC TAGAGCTACA
                                          N-terminus of C
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
    · K  K  P   G  G  P   G  K  S  R   A  V  N   M  L  K   R  G  M   P  R  V  L   S  L  I   G  L  K  Q   K  K  R ·
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
101 CTAAGAAACC AGGAGGGCCC GGCAAGAGCC GGGCTGTCAA TATGCTAAAA CGCGGAATGC CCCGCGTGTT GTCCTTGATT GGACTTAAGC AAAAGAAGCG
    GATTCTTTGG TCCTCCCGGG CCGTTCTCGG CCCGACAGTT ATACGATTTT GCGCCTTACG GGGCGCACAA CAGGAACTAA CCTGAATTCG TTTTCTTCGC
    N-terminus of C                                                                                 Rabies-G protein
     ~~       partial C signal          ~~~~~~~~~~~  RAbies-G signal  ~~~~~~~~~~~~~~~~~~~~~~~~~~~~  ~~~~~~~~~~~~~~
    · G  G  K   T  G  I  A   V  I  V   P  Q  A   L  L  F  V   P  L  L   V  F  P   L  C  F  S   K  F  P   I  Y  T
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
201 AGGGGGCAAG ACTGGTATAG CTGTGATCGT TCCTCAGGCT CTTTTGTTTG TACCCTTGCT GGTATTTCCC CTTTGCTTTG GTAAATTTCC TATCTATACC
    TCCCCCGTTC TGACCATATC GACACTAGCA AGGAGTCCGA GAAAACAAAC ATGGGAACGA CCATAAAGGG GAAACGAAAC CATTTAAAGG ATAGATATGG
                                                                  Rabies-G protein
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      I  P  D  K   L  G  P   W  S  P   I  D  I  H   H  L  S   C  P  N   L  V  V   E  D  E   G  C  T   N  L  S  C ·
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
301 ATCCCTGATA AGCTCGGGCC TTGGAGTCCC ATTGATATTC ACCATTTGAG CTGCCCAAAC AACCTCGTCG TTGAGGATGA AGGGTGCACT AATCTTTCTG
    TAGGGACTAT TCGAGCCCGG AACCTCAGGG TAACTATAAG TGGTAAACTC GACGGGTTTG TTGGAGCAGC AACTCCTACT TCCCACGTGA TTAGAAAGAC
                                                                Rabies-G protein
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
    · F  S  Y   M  E  L   K  V  G  Y   I  S  A   I  K  M   N  G  F  T   C  T  G   V  V  T   E  A  E  T   Y  T  N ·
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
401 GATTTTCCTA CATGGAGTTG AAAGTGGGCT ATATTTCAGC CATTAAGATG AACGGCTTTA CTTGTACAGG AGTCGTGACC GAAGCCGAGA CATATACAAA
    CTAAAAGGAT GTACCTCAAC TTTCACCCGA TATAAAGTCG GTAATTCTAC TTGCCGAAAT GAACATGTCC TCAGCACTGG CTTCGGCTCT GTATATGTTT
                                                                Rabies-G protein
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
    · F  V  G   Y  V  T  T   T  F  K   R  K  H   F  R  P  T   P  D  A   C  R  A   A  Y  N  W   K  M  A   G  D  P
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
501 TTTCGTGGGA TACGTCACCA CCACCTTCAA GACAAAACAC TTCCGCCCAA CGCCTGACGC TTGTCGGGCC GCTTACAACT GGAAGATGGC AGGAGATCCT
    AAAGCACCCT ATGCAGTGGT GGTGGAAGTT CTGTTTTGTG AAGGCGGGTT GCGGACTGCG AACAGCCCGG CGAATGTTGA CCTTCTACCG TCCTCTAGGA
                                                                Rabies-G protein
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      R  Y  E   E  S  L  H   N  P  Y   P  D  Y   H  W  L  R   T  V  K   T  T  K  E   S  L  V   I  I  S   P  S  V  A ·
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
601 CGATATGAAG AATCTCTGCA CAACCCGTAT CCTGATTACC ATTGGCTGCG GACAGTCAAG ACTACCAAGG AGAGTCTGGT CATTATATCA CCAAGCGTGG
    GCTATACTTC TTAGAGACGT GTTGGGCATA GGACTAATGG TAACCGACGC CTGTCAGTTC TGATGGTTCC TCTCAGACCA GTAATATAGT GGTTCGCACC
                                                                Rabies-G protein
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
    · D  L  D   P  Y  D   R  S  L  H   S  R  V   F  P  G   G  N  C  S   G  V  A   V  S  S   T  Y  C  S   T  N  H ·
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
701 CCGATCTTGA TCCTTATGAT AGATCCCTGC ACACTAGGGT TTTTCCTGGC GGGAATTGTA GCGGTGTTGC AGTATCAAGT ACCTACTGCT CCACTAACCA
    GGCTAGAACT AGGAATACTA TCTAGGGACG TGTGATCCCA AAAAGGACCG CCCTTAACAT CGCCACAACG TCATAGTTCA TGGATGACGA GGTGATTGGT
                                                                Rabies-G protein
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
    · D  Y  T   I  W  M  P   E  N  P   R  L  G   M  S  C  D   I  F  T   N  S  R   G  K  R  A   S  K  G   S  E  T
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
801 CGACTACACT ATATGGATGC CTGAGAACCC TCGACTCGGT ATCAGTTGCG ACATTTTTAC GAACTCACGG GGCAAGCGGG CATCTAAGGG GTCTGAAACA
    GCTGATGTGA TATACCTACG GACTCTTGGG AGCTGAGCCA TAGTCAACGC TGTAAAAATG CTTGAGTGCC CCGTTCGCCC GTAGATTCCC CAGACTTTGT
                                                                Rabies-G protein
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      C  G  F  V   D  E  R   G  L  Y   K  S  L  K   G  A  C   K  L  K   L  C  G  V   L  G  L   R  L  M   D  C  T  W ·
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
901 TGCGGGTTTG TTGATGAGCG GGGGTTGTAT AAATCTCTTA AAGGGGCCTG TAAGCTGAAA CTCTGTGGCG TACTGGGGCT CGCCTGATG GACGGCACAT
    ACGCCCAAAC AACTACTCGC CCCCAACATA TTTAGAGAAT TTCCCGGGAC ATTCGACTTT GAGACACCGC ATGACCCCGA GCGGACTAC CTGCCGTGTA
                                                                Rabies-G protein
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
    · V  A  M   Q  T  S   N  E  T  K   W  C  P   P  G  Q   L  V  N  L   H  D  F   R  S  D   E  I  E  H   L  V  V ·
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
1001 GGGTGGCTAT GCAGACAAGC AATGAAACAA AGTGGTGTCC CCCTGGTCAG CTGGTTAATC TGCACGACTT TAGGTCTGAC GAAATCGAGC ACCTTGTCGT
     CCCACCGATA CGTCTGTTCG TTACTTTGTT TCACCACAGG GGGACCAGTC GACCAATTAG ACGTGCTGAA ATCCAGACTG CTTTAGCTCG TGGAACACCA
                                                                Rabies-G protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
     · E  E  L   V  K  K  R   E  E  C   L  D  A   L  E  S  I   M  T  T   K  S  V   S  F  R  R   L  S  H   L  R  K
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
1101 GGAGGAACTG GTGAAGAAAC GCGAAGAGTG CCTGGACGCA CTTGAGAGTA TTATGACCAC CAAATCCGTT TCCTTCAGAA GACTGAGCCA CCTGCGAAAG
     CCTCCTTGAC CACTTCTTTG CGCTTCTCAC GGACCTGCGT GAACTCTCAT AATACTGGTG GTTTAGGCAA AGGAAGTCTT CTGACTCGGT GGACGCTTTC
                                                                Rabies-G protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
```

```
          L  V  P  G  F  G  K  A  Y  T  I  F  N  K  T  L  M  E  A  D  A  H  Y  K  S  V  R  T  W  N  E  I  I  P·
1201 CTGGTGCCAG GGTTCGGGAA GGCTTATACT ATTTTCAACA AGACTCTTAT GGAGGCGGAT GCCCATTATA AGTCAGTTAG GACTTGGAAT GAGATAATTC
     GACCACGGTC CCAAGCCCTT CCGAATATGA TAAAAGTTGT TCTGAGAATA CCTCCGCCTA CGGGTAATAT TCAGTCAATC CTGAACCTTA CTCTATTAAG
                                                                                 Rabies-G protein ·  S  K  G  C  L  R  V  G  G  R  C  H  P  H  V  N  G  V  F  F  N  G  I  I  L  G  P  D  G  N  V  L  I·
1301 CCTCCAAAGG ATGTCTGAGA GTCGGTGGGA GATGCCACCC CCATGTCAAT GGGGTGTTCT TTAACGGAAT CATCCTGGGA CCTGACGGGA ACGTGCTGAT
     GGAGGTTTCC TACAGACTCT CAGCCACCCT CTACGGTGGG GGTACAGTTA CCCCACAAGA AATTGCCTTA GTAGGACCCT GGACTGCCCT TGCACGACTA
                                                                Rabies-G protein ·  P  E  M  Q  S  S  L  L  Q  Q  H  M  E  L  L  V  S  S  V  I  P  L  M  H  P  L  A  D  P  S  T  V  F
1401 TCCCGAGATG CAATCCTCCC TTCTGCAGCA ACACATGGAA CTCCTGGTGT CTTCAGTGAT ACCCCTGATG CACCCACTGG CCGACCCCAG CACTGTGTTC
     AGGGCTCTAC GTTAGGAGGG AAGACGTCGT TGTGTACCTT GAGGACCACA GAAGTCACTA TGGGGACTAC GTGGGTGACC GGCTGGGGTC GTGACACAAG
                                                                Rabies-G protein K  N  G  D  E  A  E  D  F  V  E  V  H  L  P  D  V  H  E  R  I  S  G  V  D  L  G  L  P  N  W  G  K  Y·
1501 AAAAATGGCG ATGAGGCCGA AGACTTTGTG GAAGTTCACC TGCCCGATGT ACACGAAAGG ATATCTGGAG TAGACCTGGG CCTTCCTAAT TGGGGTAAGT
     TTTTTACCGC TACTCCGGCT TCTGAAACAC CTTCAAGTGG ACGGGCTACA TGTGCTTTCC TATAGACCTC ATCTGGACCC GGAAGGATTA ACCCCATTCA
                                                                Rabies-G protein ·  V  L  L  S  A  G  A  L  T  A  L  M  L  I  I  F  L  M  T  C  W  R  R  V  N  R  S  E  P  T  Q  H  N·
1601 ACGTGCTCCT GAGTGCGGGT GCCTTGACCG CTTTGATGCT GATCATTTTT CTGATGACCT GCTGGCGGAG GGTGAATCGC TCCGAGCCGA CACAGCACAA
     TGCACGAGGA CTCACGCCCA CGGAACTGGC GAAACTACGA CTAGTAAAAA GACTACTGGA CGACCGCCTC CCACTTAGCG AGGCTCGGCT GTGTCGTGTT
                                                                                                        FMDV 2A
                                    Rabies-G protein ·  L  R  G  T  G  R  E  V  S  V  T  P  Q  S  G  K  I  I  S  S  W  E  S  Y  K  S  G  E  T  G  L  N
1701 TCTCAGAGGG ACAGGCCGGG AAGTAAGTGT GACTCCGCAA TCTGGCAAGA TTATTACTAG TTGGGAGAGT TACAAGTCTG GAGGAGAGAC TGGGTTGAAT
     AGAGTCTCCC TGTCCGGCCC TTCATTCACA CTGAGGCGTT AGACCGTTCT AATAATGATC AACCCTCTCA ATGTTCAGAC CTCCTCTCTG ACCCAACTTA
                                                                                          C/prM signal
              FMDV 2A F  D  L  L  K  L  A  G  D  V  E  S  N  P  G  P  G  K  T  G  I  A  V  M  I  G  L  I  A  C  V  G  A·
1801 TTTGATCTGC TCAAACTTGC AGGCGATGTA GAATCAAATC CTGGACCCGG AGGAAAGACC GGTATTGCAG TCATGATTGG CCTGATCGCC TGCGTAGGAG
     AAACTAGACG AGTTTGAACG TCCGCTACAT CTTAGTTTAG GACCTGGGCC TCCTTTCTGG CCATAACGTC AGTACTAACC GGACTAGCGG ACGCATCCTC
     C/prM signal
                                              prM ·  V  T  L  S  N  F  Q  G  K  V  M  M  T  V  N  A  T  D  V  T  D  V  I  T  I  P  T  A  A  G  K  N  L·
1901 CAGTTACCCT CTCTAACTTC CAAGGGAAGG TGATGATGAC GGTAAATGCT ACTGACGTCA CAGATGTCAT CACCATTCCA ACAGCTGCTG AAAGAAACCT
     GTCAATGGGA GAGATTGAAG GTTCCCTTCC ACTACTACTG CCATTTACGA TGACTGCAGT GTCTACAGTA GTGGTAAGGT TGTCGACGAC CTTTCTTGGA
                                                                prM ·  C  I  V  R  A  M  D  V  G  Y  M  C  D  D  T  I  T  Y  E  C  P  V  L  S  A  G  N  D  P  E  D  I  D
2001 ATGCATTGTC AGAGCAATGG ATGTGGGATA CATGTGCGAT GATACATCA CTTATGAATG CCCAGTGCTG TCGGCTGGTA ATGACCCAGA AGACATCGAC
     TACGTAACAG TCTCGTTACC TACACCCTAT GTACACGCTA CTATGTAGT GAATACTTAC GGGTCACGAC AGCCGACCAT TACTGGGTCT TCTGTAGCTG
                                                                prM C  W  C  T  K  S  A  V  Y  V  R  Y  G  R  C  T  K  T  R  H  S  R  R  S  R  R  S  L  T  V  Q  T  H  G·
2101 TGTTGGTGCA CAAAGTCAGC AGTCTACGTC AGGTATGGAA GATGCACCAA GACACGCCAC TCAAGACGCA GTCGGAGGTC ACTGACAGTG CAGACACACG
     ACAACCACGT GTTTCAGTCG TCAGATGCAG TCCATACCTT CTACGTGGTT CTGTGCGGTG AGTTCTGCGT CAGCCTCCAG TGACTGTCAC GTCTGTGTGC
                                                                prM ·  E  S  T  L  A  N  K  K  G  A  W  M  D  S  T  K  A  T  R  Y  L  V  K  T  E  S  W  I  L  R  N  P  G·
2201 GAGAAAGCAC TCTAGCGAAC AAGAAGGGGG CTTGGATGGA CAGCACCAAG GCCACAAGGT ATTTGGTAAA AACAGAATCA TGGATCTTGA GGAACCCTGG
     CTCTTTCGTG AGATCGCTTG TTCTTCCCCG GAACCTACCT GTCGTGGTTC CGGTGTTCCA TAAACCATTT TTGTCTTAGT ACCTAGAACT CCTTGGGACC
                                                                prM ·  Y  A  L  V  A  A  V  I  G  W  M  L  G  S  N  T  M  Q  R  V  V  F  V  V  L  L  L  L  V  A  P  A  Y
2301 ATATGCCCTG GTGGCAGCCG TCATTGGTTG GATGCTTGGG AGCAACACCA TGCAGAGAGT TGTGTTTGTC GTGCTATTGC TTTTGGTGGC CCCAGCTTAC
     TATACGGGAC CACCGTCGGC AGTAACCAAC CTACGAACCC TCGTTGTGGT ACGTCTCTCA ACACAAACAG CACGATAACG AAAACCACCG GGGTCGAATG
                                                                                                            E
     prM S  F  N  C  L  G  M  S  N  R  D  F  L  E  G  V  S  G  A  T  W  V  D  L  V  L  E  G  D  S  C  V  T  I·
2401 AGCTTTAACT GCCTTGGAAT GAGCAACAGA GACTTCTTGG AAGGAGTGTC TGGAGCAACA TGGGTGGATT TGGTTCTCGA AGGCGACAGC TGCGTGACTA
     TCGAAATTGA CGGAACCTTA CTCGTTGTCT CTGAAGAACC TTCCTCACAG ACCTCGTTGT ACCCACCTAA ACCAAGAGCT TCCGCTGTCG ACGCACTGAT
                                                                E
```

```
       · M  S  K   D  K  P   T  I  D  V   K  M  M   N  M  E   A  A  N   L  A  E  V   R  S  Y   C  Y  L  A   T  V  S ·
2501   TCATGTCTAA GGACAAGCCT ACCATCGATG TGAAGATGAT GAATATGGAG GCGGCCAACC TGGCAGAGGT CCGCAGTTAT TGCTATTTGG CTACCGTCAG
       AGTACAGATT CCTGTTCGGA TGGTAGCTAC ACTTCTACTA CTTATACCTC CGCCGGTTGG ACCGTCTCCA GGCGTCAATA ACGATAAACC GATGGCAGTC
                                                                                                            E

· D  L  S   T  K  A  A   C  P  A   M  G  E   A  H  N  D   K  R  A   D  P  A   F  V  C  R   Q  G  V   V  D  R
2601   CGATCTCTCC ACCAAAGCTG CGTGCCCGGC CATGGGAGAA GCTCACAATG ACAAACGTGC TGACCCAGCT TTTGTGTGCA GACAAGGAGT GGTGGACAGG
       GCTAGAGAGG TGGTTTCGAC GCACGGGCCG GTACCCTCTT CGAGTGTTAC TGTTTGCACG ACTGGGTCGA AAACACACGT CTGTTCCTCA CCACCTGTCC
                                                                                                            E

G  W  G  N   G  C  G   L  F  G   K  G  S  I   D  T  C   A  K  F   A  C  S  T   K  A  I   G  R  T   I  L  K  E ·
2701   GGCTGGGGCA ACGGCTGCGG ACTATTTGGC AAAGGAAGCA TTGACACATG CGCCAAATTT GCCTGCTCTA CCAAGGCAAT AGGAACAACC ATTTTGAAAG
       CCGACCCCGT TGCCGACGCC TGATAAACCG TTTCCTTCGT AACTGTGTAC GCGGTTTAAA CGGACGAGAT GGTTCCGTTA TCCTTCTTGG TAAAACTTTC
                                                                                                            E

· N  I  K   Y  E  V   A  I  F  V   H  G  P   T  T  V   E  S  H  G   N  Y  S   T  Q  V   G  A  T  Q   A  G  R ·
2801   AGAATATCAA GTACGAAGTG GCCATTTTTG TCCATGGACC AACTACTGTG GAGTCGCACG GAAACTACTC CACACAGGTT GGAGCCACTC AGGCAGGAG
       TCTTATAGTT CATGCTTCAC CGGTAAAAAC AGGTACCTGG TTGATGACAC CTCAGCGTGC CTTTGATGAG GTGTGTCCAA CCTCGGTGAG TCCGTCCCTC
                                                                                                            E

· F  S  I   T  P  A  A   P  S  Y   T  L  K   L  G  E  Y   G  E  V   T  V  D   C  E  P  R   S  G  I   D  T  N
2901   ATTCAGCATC ACTCCTGCGG CGCCTTCATA CACACTAAAG CTTGAGAAT ATGGAGAGGT GACAGTGGAC TGTGAACCAC GGTCAGGAT TGACACCAAT
       TAAGTCGTAG TGAGGACGCC GCGGAAGTAT GTGTGATTTC GAACCTCTTA TACCTCTCCA CTGTCACCTG ACACTTGGTG CCAGTCCCTA ACTGTGGTTA
                                                                                                            E

A  Y  Y  V   M  T  V   G  T  K   T  F  L  V   H  R  E   W  F  M   D  L  N  L   P  W  S   S  A  G   S  T  V  W ·
3001   GCATACTACG TGATGACTGT TGGAACAAAG ACGTTCTTGG TCCATCGTGA GTGGTTCATG GACCTCAACC TCCCTTGGAG CAGTGCTGGA AGTACTGTGT
       CGTATGATGC ACTACTGACA ACCTTGTTTC TGCAAGAACC AGGTAGCACT CACCAAGTAC CTGGAGTTGG AGGGAACCTC GTCACGACCT TCATGACACA
                                                                                                            E

· R  N  R   E  T  L   M  E  F  E   E  P  H   A  T  K   Q  S  V  I   A  L  G   S  Q  E   G  A  L  H   Q  A  L ·
3101   GGAGGAACAG AGAGACGTTA ATGGAGTTTG AGGAACCACA CGCCACGAAG CAGTCTGTGA TAGCATTGGG CTCACAAGAG GGAGCTCTGC ATCAAGCTTT
       CCTCCTTGTC TCTCTGCAAT TACCTCAAAC TCCTTGGTGT GCGGTGCTTC GTCAGACACT ATCGTAACCC GAGTGTTCTC CCTCGAGACG TAGTTCGAAA
                                                                                                            E

· A  G  A   I  P  V  E   F  S  S   N  T  V   K  L  T  S   G  H  L   K  C  R   V  K  M  E   K  L  Q   L  K  G
3201   GGCTGGAGCC ATTCCTGTGG AATTTTCAAG CAACACTGTC AAGTTGACGT CGGGTCATTT GAAGTGTAGA GTGAAGATGG AAAAATTGCA GTTGAAGGGA
       CCGACCTCGG TAAGGACACC TTAAAAGTTC GTTGTGACAG TTCAACTGCA GCCCAGTAAA CTTCACATCT CACTTCTACC TTTTTAACGT CAACTTCCCT
                                                                                                            E

T  T  Y  G   V  C  S   K  A  F   K  F  L  G   T  P  A   D  T  G   H  G  T  V   V  L  E   L  Q  Y   T  G  T  D ·
3301   ACAACCTATG GCGTCTGTTC AAACGCTTTC AAGTTTCTTG GACTCCCGC AGACACAGGT CACGGCACTG TGGTGTTGGA ATTGCAGTAC ACTGGCACGG
       TGTTGGATAC CGCAGACAAG TTTGCGAAAG TTCAAAGAAC CTGAGGGCG TCTGTGTCCA GTGCCGTGAC ACCACAACCT TAACGTCATG TGACCGTGCC
                                                                                                            E

· G  P  C   K  V  P   I  S  S  V   A  S  L   N  D  L   T  P  V  G   R  L  V   T  V  N   P  F  V  S   V  A  T ·
3401   ATGGACCTTG CAAAGTTCCT ATCTCGTCAG TGGCTTCATT GAACGACCTA ACGCCAGTGG GCAGATTGT CACTGTCAAC CCTTTTGTT CAGTGGCCAC
       TACCTGGAAC GTTTCAAGGA TAGAGCAGTC ACCGAAGTAA CTTGCTGGAT TGCGGTCACC CGTCTAACCA GTGACAGTTG GGAAAACAAA GTCACCGGTG
                                                                                                            E

· A  N  A   K  V  L  I   E  L  E   P  P  F   G  D  S  Y   I  V  V   G  R  G   E  Q  Q  I   N  H  H   W  H  K
3501   GGCCAACGCT AAGGTCCTGA TTGAATTGGA ACCACCCTTT GGAGACTCAT ACATAGTGGT GGGCAGAGGA GAACAACAGA TCAATCACCA CTGGCACAAG
       CCGGTTGCGA TTCCAGGACT AACTTAACCT TGGTGGGAAA CCTCTGAGTA TGTATCACCA CCCGTCTCCT CTTGTTGTCT AGTTAGTGGT GACCGTGTTC
                                                                                                            E

S  G  S  S   I  G  K   A  F  T   T  L  K   G  A  Q   R  L  A   A  L  G  D   T  A  W   D  F  G   S  V  G  G ·
3601   TCTGGAAGCA GCATTGGCAA AGCCTTTACA ACCACCCTCA AAGGAGCGCA GAGACTAGCC GCTCTAGGAG ACACAGCTTG GGACTTTGGA TCAGTTGGAG
       AGACCTTCGT CGTAACCGTT TCGGAAATGT TGGTGGGAGT TTCCTCGCGT CTCTGATCGG CGAGATCCTC TGTGTCGAAC CCTGAAACCT AGTCAACCTC
                                                                                                            E

· V  F  T   S  V  G   K  A  V  H   Q  V  F   G  G  A   F  R  S  L   F  G  G   M  S  W   I  T  Q  G   L  L  G ·
3701   GGGTGTTCAC CTCAGTTGGG AAGGCTGTCC ATCAAGTGTT CGGAGGAGCA TTCCGCTCAC TGTTCGGAGG CATGTCCTGG ATAACGCAAG GATTGCTGGG
       CCCACAAGTG GAGTCAACCC TTCCGACAGG TAGTTCACAA GCCTCCTCGT AAGGCGAGTG ACAAGCCTCC GTACAGGACC TATTGCGTTC CTAACGACCC
                                                                                                            E

· A  L  L   L  W  M  G   I  N  A   R  D  R   S  I  A  L   T  F  L   A  V  G   G  V  L  L   F  L  S   V  N  V
3801   GGCTCTCCTG TTGTGGATGG GCATCAATGC TCGTGACAGG TCCATAGCTC TCACGTTTCT CGCAGTTGGA GGAGTTCTCC TCTTCCTCTC CGTGAACGTG
       CCGAGAGGAC AACACCTACC CGTAGTTACG AGCACTGTCC AGGTATCGAG AGTGCAAAGA GCGTCAACCT CCTCAAGAGG AGAAGGAGAG GCACTTGCAC
                                                                                                            E
                                                         NS1
```

```
            H  A  D  T   G  C  A  I  D  I   S  R  Q  E   L  R  C   G  S  C   V  F  I  H   N  D  V   E  A  W   M  D  R  Y ·
3901  CACGCTGACA CTGGGTGTGC CATAGACATC AGCCGGCAAG AGCTGAGATG TGGAAGTGGA GTGTTCATAC ACAATGATGT GCAGCCTTGG ATGGACCGGT
      GTGCGACTGT GACCCACACG GTATCTGTAG TCGGCCGTTC TCGACTCTAC ACCTTCACCT CACAAGTATG TGTTACTACA CCTCCGAACC TACCTGGCCA
```

WN (ΔprME)-Rabies G PIV sequence (partial)

```
                                                                                                              C protein
                                             5' UTR
                                                                                                              M S ·
  1   AGTAGTTCGC CTGTGTGAGC TGACAAACTT AGTAGTGTTT GTGAGGATTA ACAACAATTA ACACAGTGCG AGCTGTTTCT TAGCACGAAG ATCTCGATGT
      TCATCAAGCG GACACACTCG ACTGTTTGAA TCATCACAAA CACTCCTAAT TGTTGTTAAT TGTGTCACGC TCGACAAAGA ATCGTGCTTC TAGAGCTACA
                                                                           C protein
      · K  K  P   G  G  P   G  K  S  R   A  V  Y   L  L  K   R  G  M  P   R  V  L   S  L  I   G  L  K  R   A  M  L  ·
101   CTAAGAAACC AGGAGGGCCC GGCAAGAGCC GGGCTGTCTA TTTGCTAAAA CGCGGAATGC CCCGCGTGTT GGACTTAAGA GGGCTATGTT
      GATTCTTTGG TCCTCCCGGG CCGTTCTCGG CCCGACAGAT AAACGATTTT GCGCCTTACG GGGCGCACAA CACGAACTAA CCTGAATTCT CCCGATACAA
                                                            C protein
      · S  L  I   D  G  K   G  P  I  R   F  V  L   A  L  L  A   F  F  R   F  T  A   I  A  P  T   R  A  V   L  D  R
201   GAGCCTGATC GACGGCAAGG GGCCAATACG ATTTGTGTTG GCTCTCTTGG CGTTCTTCAG GTTCACAGCA ATTGCTCCGA CCCGAGCAGT GCTGGATCGA
      CTCGGACTAG CTGCCGTTCC CCGGTTATGC TAAACACAAC CGAGAAGAAG AAGTCCAAGT CAAGTGTCGT TAACGAGGCT GGGCTCGTCA CGACCTAGCT
                                                            C protein
      W  R  G  V   N  K  Q   T  A  M   K  H  L  L   S  F  K   K  E  L   G  T  L  T   S  A  I   N  R  R   S  S  K  Q ·
301   TCGACAGGTG TGAACAAACA AACAGCGATG AAAACACCTTC TGAGTTTCAA GAAGGAACTA GGGACCTTGA CCAGTGCTAT CAATCGGCGG AGCTCAAAGC
      ACCTGTCCAC ACTTGTTTGT TTGTCGCTAC TTTGTGGAAG ACTCAAAGTT CTTCCTTGAT CCCTGGAACT GGTCACGATA GTTAGCCGCC TCGAGTTTCG
                                                                                  Rabies-G signal
      C protein        partial C signal                                                                       Rabies-G
      protein
      · K  K  R   G  G  K   T  G  I  A   V  I  V   P  Q  A   L  L  F  V   P  L  L   V  F  P   L  C  F  G   K  F  P ·
401   AAAAGAAGCG AGGGGGCAAC ACTGGTATAG CTGTGATCGT TCCTCAGGCT CTTTTGTTTG TACCCTTGCT GGTATTTCCC CTTTGCTTTG GTAAATTTCC
      TTTTCTTCGC TCCCCCGTTG TGACCATATC GACACTAGCA AGGAGTCCGA GAAAACAAAC ATGGGAACGA CCATAAAGGG GAAACGAAAC CATTTAAAGG
                                                            Rabies-G protein
      · I  Y  T   I  P  D  K   L  G  P   W  S  P   I  D  I  H   H  L  S   C  P  N   N  L  V  V   E  D  E   G  C  T
501   TATCTATACC ATCCCTGATA AGCTCGGGCC TTGGAGTCCC ATTGATATTC ACCATTTGAG CTGCCCAAAC AACCTCGTCG TTGAGGATGA AGGGTGCACT
      ATAGATATGG TAGGGACTAT TCGAGCCCGG AACCTCAGGG TAACTATAAG TGGTAAACTC GACGGGTTTG TTGGAGCAGC AACTCCTACT TCCCACGTGA
                                                            Rabies-G protein
      N  L  S  G   F  S  Y   M  E  L   K  V  G  Y   I  S  A   I  K  M   N  G  F  T   C  T  G   V  V  T   E  A  E  T ·
601   AATCTTTCTG GATTTTCCTA CATGGAGTTG AAAGTGGGCT ATATTTCAGC CATTAAGATG AACGGCTTTA CTTGTACAGG AGTCGTGACC GAAGCCGAGA
      TTAGAAAGAC CTAAAAGGAT GTACCTCAAC TTTCACCCGA TATAAAGTCG GTAATTCTAC TTGCCGAAAT GAACATGTCC TCAGCACTGG CTTCGGCTCT
                                                            Rabies-G protein
      · Y  T  N   F  V  G   Y  V  T  T   T  F  K   R  K  H   F  R  P  T   P  D  A   C  R  A   A  Y  N  W   K  M  A ·
701   CATATACAAA TTTCGTGGGA TACGTCACCA CCACCTTCAA GAGAAAACAC TTCCGCCCAA CGCCTGACGC TTGTCGGGCC GCTTACAACT GGAAGATGGC
      GTATATGTTT AAAGCACCCT ATGCAGTGGT GGTGGAAGTT CTCTTTTGTG AAGGCGGGTT GCGGACTGCG AACAGCCCGG CGAATGTTGA CCTTCTACCG
                                                            Rabies-G protein
      · G  D  P   R  Y  E  E   S  L  H   N  P  Y   P  D  Y  H   W  L  R   T  V  K   T  T  K  E   S  L  V   I  I  S
801   AGGAGATCCT CGATATGAAG AATCTCTGCA CAACCCGTAT CCTGATTACC ATTGGCTGCG GACAGTCAAG ACTACCAAGG AGAGTCTGGT CATTATATCA
      TCCTCTAGGA GCTATACTTC TTAGAGACGT GTTGGGCATA GGACTAATGG TAACCGACGC CTGTCAGTTC TGATGGTTCC TCTCAGACCA GTAATATAGT
                                                            Rabies-G protein
      P  S  V  A   D  L  D   P  Y  D   R  S  L  H   S  R  V   F  P  G   G  N  C  S   G  V  A   V  S  S   T  Y  C  S ·
901   CCAAGCGTGG CCGATCTTGA TCCTTATGAT AGATCCCTGC ACAGTAGGGT TTTTCCTGGC GGGAATTGTA GCCGTGTTGC AGTATCAAGT ACCTACTGCT
      GGTTCGCACC GGCTAGAACT AGGAATACTA TCTAGGGACG TGTCATCCCA AAAAGGACCG CCCTTAACAT CGCCACAACG TCATAGTTCA TGGATGACGA
                                                            Rabies-G protein
      · T  N  H   D  Y  T   I  W  M  P   E  N  P   R  L  G   M  S  C  D   I  F  T   N  S  R   G  K  R  A   S  K  G ·
```

1001 CCACTAACCA CGACTACACT ATATGGATGC CTGAGAACCC TCGACTCGGT ATGAGTTGCG ACATTTTTAC GAACTCACGG GGCAAGCGGG CATCTAAGGG
GGTGATTGGT GCTGATGTGA TATACCTACG GACTCTTGGG AGCTGAGCCA TACTCAACGC TGTAAAAATG CTTGAGTGCC CCGTTCGCCC GTAGATTCCC
RAbies-G protein
· S E T C G F V D E R G L Y K S L K G A C K L K L C G V L G L R L M 1101 GTCTGAAACA TGCGGGTTTG TTGATGAGCG GGGGTTGTAT AAATCTCTTA AAGGCGCCTG TAAGCTGAAA CTCTGTGGCG TACTGGGGCT GCGCCTGATG
CAGACTTTGT ACGCCCAAAC AACTACTCGC CCCCAACATA TTTAGAGAAT TTCCGCGGAC ATTCGACTTT GAGACACCGC ATGACCCCGA CGCGGACTAC
RAbies-G protein
D G T W V A M Q T S N E T K W C P P G Q L V N L H D F R S D E I E H ·

1201 GACGCCACAT GGGTGGCTAT GCAGACAAGC AATGAAACAA AGTGGTGTCC CCCTGGTCAG CTCGTTAATC TGCACGACTT TAGGTCTGAC GAAATCGAGC
CTGCCGTGTA CCCACCGATA CGTCTGTTCG TTACTTTGTT TCACCACAGG GGGACCAGTC GACCAATTAG ACGTGCTGAA ATCCAGACTG CTTTAGCTCG
RAbies-G protein
· L V V E E L V K K R E E C L D A L E S I M T T K S V S F R R L S H ·

1301 ACCTTGTGGT GGAGGAACTG GTGAAGAAAC GCGAAGAGTG CCTGGACGCA CTTGAGAGTA TTATGACCAC CAAATCCGTT TCCTTCAGAA GACTGAGCCA
TGGAACACCA CCTCCTTGAC CACTTCTTTG CGCTTCTCAC GGACCTGCGT GAACTCTCAT AATACTGGTG GTTTAGGCAA AGGAAGTCTT CTGACTCGGT
RAbies-G protein
· L R K L V P G F G K A Y T I F N K T L M E A D A H Y K S V R T W N 1401 CCTGCGAAAG CTGGTGCCAG GGTTCCCCAA GGCTTATACT ATTTTCAACA AGACTCTTAT GGAGGCGGAT GCCCATTATA AGTCAGTTAG GACTTGGAAT
GGACGCTTTC GACCACGGTC CCAAGCCCTT CCGAATATGA TAAAAGTTGT TCTGAGAATA CCTCCGCCTA CGGGTAATAT TCAGTCAATC CTGAACCTTA
RAbies-G protein
E I I P S K G C L R V G G R C H P H V N G V F F N G I I L G P D G N ·

1501 GAGATAATTC CCTCCAAAGG ATGTCTGAGA GTCGGTGGGA GATGCCACCC CCATGTCAAT GGGGTGTTCT TTAACGGAAT CATCCTGGGA CCTGACGGGA
CTCTATTAAG GGAGGTTTCC TACAGACTCT CAGCCACCCT CTACGGTGGG GGTACAGTTA CCCCACAAGA AATTGCCTTA GTAGGACCCT GGACTGCCCT
RAbies-G protein
· V L I P E M Q S S L L Q Q H M E L L V S S V I P L M H P L A D P S ·

1601 ACGTGCTGAT TCCCGAGATG CAATCTTCCC TTCTGCAGCA ACACATGGAA CTCCTGGTGT CTTCAGTGAT ACCCCTGATG CACCCACTGG CCGACCCCAG
TGCACGACTA AGGGCTCTAC GTTAGAAGGG AAGACGTCGT TGTGTACCTT GAGGACCACA GAAGTCACTA TGGGGACTAC GTGGGTGACC GGCTGGGGTC
RAbies-G protein
· T V F K N G D E A E D F V E V H L P D V H E R I S G V D L G L P N 1701 CACTGTGTTC AAAAATGGCG ATGAGGCCGA AGACTTTGTG GAAGTTCACC TGCCCGATGT ACACGAAAGG ATATCTGGAG TAGACCTGGG CCTTCCTAAT
GTGACACAAG TTTTTACCGC TACTCCGGCT TCTGAAACAC CTTCAAGTGG ACGGGCTACA TGTGCTTTCC TATAGACCTC ATCTGGACCC GGAAGGATTA
RAbies-G protein
W G K Y V L L S A G A L T A L M L I I F L M T C W R R V N R S E P T ·

1801 TGGGGTAAGT ACGTGCTCCT GAGTGCCGGT GCCTTGACCG CTTTGATGCT GATCATTTTT CTGATGACCT GCTGGCGGAG GGTGAATCGC TCCGAGCCGA
ACCCCATTCA TGCACGAGGA CTCACGGCCA CGGAACTGGC GAAACTACGA CTAGTAAAAA GACTACTGGA CGACCGCCTC CCACTTAGCG AGGCTCGGCT
RAbies-G protein
· Q H N L R G T G R E V S V T P Q S G K I I S S W E S Y K S G G E T ·

1901 CACAGCACAA TCTCAGAGGG ACAGGCCGGG AAGTAAGTGT GACTCCGCAA TCTGGCAAGA TTATTAGTAG TTGGGAGAGT TACAAGTCTG GAGGAGAGAC
GTGTCGTGTT AGAGTCTCCC TGTCCGGCCC TTCATTCACA CTGAGGCGTT AGACCGTTCT AATAATCATC AACCCTCTCA ATGTTCAGAC CTCCTCTCTG
FMDV 2A NS1 signal
RAbies-G protein preNS1 signal
· G L N F D L L K L A G D V E S N P G P A R D R S I A L T F L A V G 2001 TGGGTTCAAT TTTGATCTGC TCAAACTTGC AGGCGATGTA GAATCAAATC CTGGACCCGC CCGGGACAGG TCCATAGCTC TCACGTTTCT CGCAGTTGGA
ACCCAACTTA AAACTAGACG AGTTTGAACG TCCGCTACAT CTTAGTTTAG GACCTGGGCG GGCCCTGTCC AGGTATCGAG AGTGCAAAGA GCGTCAACCT
NS1
NS1 signal
G V L L F L S V N V H A D T G C A I D I S R Q E L R C G S G V F I H ·

2101 GGAGTTCTGC TCTTCCTCTC CGTCAACGTG CACGCTGACA CTGGGTGTGC CATAGACATC AGCCGGCAAG AGCTGAGATG TGCAAGTGGA GTGTTCATAC
CCTCAAGACG AGAAGGAGAG GCACTTGCAC GTGCGACTGT GACCCACACG GTATCTGTAG TCGGCCGTTC TCGACTCTAC ACCTTCACCT CACAAGTATG

Sequence Appendix 4 (continued)

PIV-WNV helper ΔNS1

```
                                                                                                                      C
                                                                                                                     ~~~~
                        5' UTR
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                                                           M   S  ·
  1 AGTAGTTCGC CTGTGTGAGC TGACAAACTT AGTAGTGTTT GTGAGGATTA ACAACAATTA ACACAGTGCG AGCTGTTTCT TAGCACGAAG ATCTCGATGT
    TCATCAAGCG GACACACTCG ACTGTTTGAA TCATCACAAA CACTCCTAAT TGTTGTTAAT TGTGTCACGC TCGACAAAGA TCGTGCTTC  TAGAGCTACA
                                                                 C
     ·  K   K   P   G   G   P   G   K   S   R   A   V   N   M   L   K   R   G   M   P   R   V   L   S   L   I   G   L   K   R   A   M   L  ·
101 CTAAGAAACC AGGAGGGCCC GGCAAGAGCC GGGCTGTCAA TATGCTAAAA CGCGGAATGC CCCGCGTGTT GTCCTTGATT GGACTTAAGA GGGCTATGTT
    GATTCTTTGG TCCTCCCGGG CCGTTCTCGG CCCGACAGTT ATACGATTTT GCGCCTTACG GGGCGCACAA CAGGAACTAA CCTGAATTCT CCCGATACAA
                                                                 C
     ·  S   L   I   D   G   K   G   P   I   R   F   V   L   A   L   L   A   F   F   R   F   T   A   I   A   P   T   R   A   V   L   D   R
201 GAGCCTGATC GACGGCAAGG GGCCAATACG ATTTGTGTTG GCTCTCTTGG CGTTCTTCAG GTTCACAGCA ATTGCTCCGA CCCGAGCAGT GCTGGATCGA
    CTCGGACTAG CTGCCGTTCC CCGGTTATGC TAAACACAAC CGAGAGAACC GCAAGAAGTC CAAGTGTCGT TAACGAGGCT GGGCTCGTCA CGACCTAGCT
     W   R   G   V   N   K   Q   T   A   M   K   H   L   L   S   F   K   K   E   L   G   T   L   T   S   A   I   N   R   R   S   S   K   Q  ·
301 TGGAGAGGTG TGAACAAACA AACAGCGATG AAACACCTTC TGAGTTTCAA GAAGGAACTA GGGACCTTGA CCAGTGCTAT CAATCGGCGG AGCTCAAAAC
    ACCTCTCCAC ACTTGTTTGT TTGTCGCTAC TTTGTGGAAG ACTCAAAGTT CTTCCTTGAT CCCTGGAACT GGTCACGATA GTTAGCCGCC TCGAGTTTTG
                                                                      Signal peptide
               C                                                                                    prM
          ~~~~~~~~~~~                                                                         ~~~~~~~~~~~~~~~~~~~~~~~
     ·  K   K   R   G   G   K   T   G   I   A   V   M   I   G   L   I   A   S   V   G   A   V   T   L   S   N   F   Q   G   K   V   M   M  ·
401 AAAAGAAAAG AGGAGGAAAG ACCGGAATTG CAGTCATGAT TGGCCTGATC GCCAGCGTAG GAGCAGTTAC CCTCTCTAAC TTCCAAGGGA AGGTGATGAT
    TTTTCTTTTC TCCTCCTTTC TGGCCTTAAC GTCAGTACTA ACCGGACTAG CGGTCGCATC CTCGTCAATG GGAGAGATTG AAGGTTCCCT TCCACTACTA
                                                                                        prM
     ·  T   V   N   A   T   D   V   T   D   V   I   T   I   P   T   A   A   G   K   N   L   C   I   V   R   A   M   D   V   G   Y   M   C  ·
501 GACGGTAAAT GCTACTGACG TCACAGATGT CATCACGATT CCAACAGCTG CTGGAAAGAA CCTATGCATT GTCAGAGCAA TGGATGTGGG ATACATGTGC
    CTGCCATTTA CGATGACTGC AGTGTCTACA GTAGTGCTAA GGTTGTCGAC GACCTTTCTT GGATACGTAA CAGTCTCGTT ACCTACACCC TATGTACACG
                                                                                        prM
     D   D   T   I   T   Y   E   C   P   V   L   S   A   G   N   D   P   E   D   I   D   C   W   C   T   K   S   A   V   Y   V   R   Y   G  ·
601 GATGATACTA TCACTTATGA ATGCCCAGTG CTGTCGGCTG GTAATGATCC AGAAGACATC GACTGTTGGT GCACAAAGTC AGCAGTCTAC GTCAGGTATG
    CTACTATGAT AGTGAATACT TACGGGTCAC GACAGCCGAC CATTACTAGG TCTTCTGTAG CTGACAACCA CGTGTTTCAG TCGTCAGATG CAGTCCATAC
                                                                                        prM
     ·  R   C   T   K   T   R   H   S   R   R   S   R   R   S   L   T   V   Q   T   H   G   E   S   T   L   A   N   K   K   G   A   W   M  ·
701 GAAGATGCAC CAAGACACGC CACTCAAGAC GCAGTCGGAG GTCACTGACA GTGCAGACAC ACGGAGAAAG CACTCTAGCG AACAAGAAGG GGGCTTGGAT
    CTTCTACGTG GTTCTGTGCG GTGAGTTCTG CGTCAGCCTC CAGTGACTGT CACGTCTGTG TGCCTCTTTC GTGAGATCGC TTGTTCTTCC CCCGAACCTA
```

```
                                          prM
         · D   S   T   K  A  T  R   Y  L  V  K  T   E   S  W  I  L   R  N  P   G  Y  A   L  V  A  A   V  I  G   W  M  L
     801 GGACAGCACC AAGGCCACAA GGTATTTGGT AAAAACAGAA TCATGGATCT TGAGGAACCC TGGATATGCC CTGGTGGCAG CCGTCATTGG TTGGATGCTT
         CCTGTCGTGG TTCCGGTGTT CCATAAACCA TTTTTGTCTT AGTACCTAGA ACTCCTTGGG ACCTATACGG GACCACCGTC GGCAGTAACC AACCTACGAA
                                                                                                         E
                  prM
          G  S  N   T  M  Q  R   V  V  F   V  V  L   L  L  L  V   A  P  A   Y  S  F   N  C  L  G   M  S  N   R  D  F  L  ·
     901 GGGAGCAACA CCATGCAGAG AGTTGTCTTT GTCGTGCTAT TGCTTTTGGT GGCCCCAGCT TACAGCTTTA ACTGCCTTGG AATGAGCAAC AGAGACTTCT
         CCCTCGTTGT GGTACGTCTC TCAACACAAA CAGCACGATA ACGAAAACCA CCGGGGTCGA ATGTCGAAAT TGACGGAACC TTACTCGTTG TCTCTGAAGA
                                                                                      E
         · E  G  V   S  G  A   T  W  V  D   L  V  L   E  G  D   S  C  V  T   I  M  S   K  D  K   P  T  I  D   V  K  M  ·
    1001 TGGAAGGAGT GTCTGGAGCA ACATGGGTGG ATTTGGTTCT CGAAGGCGAC AGCTGCGTGA CTATCATGTC TAAGGACAAG CCTACCATCG ATGTGAAGAT
         ACCTTCCTCA CAGACCTCGT TGTACCCACC TAAACCAAGA GCTTCCGCTG TCGACGCACT GATAGTACAG ATTCCTGTTC GGATGGTAGC TACACTTCTA
                                                                                 E
         · M  N  M   E  A  A  N   L  A  E   V  R  S   Y  C  Y  L   A  T  V   S  D  L   S  T  K  A   A  C  P   A  M  G
    1101 GATGAATATG GAGGCGGCCA ACCTGGCAGA GGTCCGCAGT TATTGCTATT TGGCTACCGT CAGCGATCTC TCCACCAAAG CTGCCGTGCCC GGCCATGGGA
         CTACTTATAC CTCCGCCGGT TGGACCGTCT CCAGGCGTCA ATAACGATAA ACCGATGGCA GTCGCTAGAG AGGTGGTTTC GACGCACGGG CCGGTACCCT
                                                                                      E
          E  A  H  N   D  K  R   A  D  P   A  F  V  C   R  Q  G   V  V  D   R  S  W  G   N  G  C   G  L  F   G  K  G  S  ·
    1201 GAAGCTCACA ATGACAAACG TGCTGACCCA GCTTTTGTGT GCAGACAAGG AGTGGTGGAC AGGGGCTGGG GCAACGGCTG CGGACTATTT GGCAAAGGAA
         CTTCGAGTGT TACTGTTTGC ACGACTGGGT CGAAAACACA CGTCTGTTCC TCACCACCTG TCCCCGACCC CGTTGCCGAC GCCTGATAAA CCGTTTCCTT
         · I   D  T   C  A  K   F  A  C  S   T  K  A   I  G  R   T  I  L  K   E  N  I   K  Y  E   V  A  I  F   V  H  G ·
    1301 GCATTGACAC ATGCGCCAAA TTTGCCTGCT CTACCAAGGC AATAGGAAGA ACCATTTTGA AAGAGAATAT CAAGTACGAA GTGGCCATTT TTGTCCATGG
         CGTAACTGTG TACGCGGTTT AAACGGACGA GATGGTTCCG TTATCCTTCT TGGTAAAACT TTCTCTTATA GTTCATGCTT CACCGGTAAA AACAGGTACC
          P  T  T   V  E  S  H   G  N  Y   S  T  Q   V  G  A  T   Q  A  G   R  F  S   I  T  P  A   A  P  S   Y  T  L
    1401 ACCAACTACT GTGGAGTCGC ACGGAAACTA CTCCACACAG GTTGGAGCCA CTCAGGCAGG GAGATTCAGC ATCACTCCTG CGGCGCCTTC ATACACACTA
         TGGTTGATGA CACCTCAGCG TGCCTTTGAT GAGGTGTGTC CAACCTCGGT GAGTCCGTCC CTCTAAGTCG TAGTGAGGAC GCCGCGGAAG TATGTGTGAT
          K  L  G  E   Y  G  E   V  T  V   D  C  E  P   R  S  G   I  D  T   N  A  Y  Y   V  M  T   V  G  T   K  T  F  L ·
    1501 AAGCTTGGAG AATATGGAGA GGTGACAGTG GACTGTGAAC CACGGTCAGG GATTGACACC AATGCATACT ACGTGATGAC TGTTGGAACA AAGACGTTCT
         TTCGAACCTC TTATACCTCT CCACTGTCAC CTGACACTTG GTGCCAGTCC CTAACTGTGG TTACGTATGA TGCACTACTG ACAACCTTGT TTCTGCAAGA
                                                                                                                      E
         · V  H  R   E  W  F   M  D  L  N   L  P  W   S  S  A   G  S  T  V   W  R  N   R  E  T   L  M  E  F   E  E  P ·
    1601 TGGTCCATCG TGAGTGGTTC ATGGACCTCA ACCTCCCTTG GAGCACTGCT GGAAGTACTG TGTGGAGGAA CAGAGAGACG TTAATGGAGT TTGAGGAACC
         ACCAGGTAGC ACTCACCAAG TACCTGGAGT TGGAGGGAAC CTCGTCACGA CCTTCATGAC ACACCTCCTT GTCTCTCTGC AATTACCTCA AACTCCTTGG
                                                                                                               E
         · H  A  T   K  Q  S  V   I  A  L   G  S  Q   E  G  A  L   H  Q  A   L  A  G   A  I  P  V   E  F  S   S  N  T
    1701 ACACGCCACG AAGCAGTCTG TGATAGCATT GGGCTCACAA GAGGGAGCTC TGCATCAAGC TTTGGCTGGA GCCATTCCTG TGGAATTTTC AAGCAACACT
         TGTGCGGTGC TTCGTCAGAC ACTATCGTAA CCCGAGTGTT CTCCCTCGAG ACGTAGTTCG AAACCGACCT CGGTAAGGAC ACCTTAAAAG TTCGTTGTGA
                                                                                                               E
```

```
      V  K  L  T   S  G  H   L  K  C   R  V  K  M   E  K  L   Q  L  K   G  T  T  Y   G  V  C   S  K  A   F  K  F  L ·
1801  GTCAAGTTGA CGTCGGGTCA TTTGAAGTGT AGAGTGAAGA TGGAAAAATT GCAGTTGAAG GGAACAACCT ATGGCGTCTG TTCAAAGGCT TTCAAGTTTC
      CAGTTCAACT GCAGCCCAGT AAACTTCACA TCTCACTTCT ACCTTTTTAA CGTCAACTTC CCTTGTTGGA TACCGCAGAC AAGTTTCCGA AAGTTCAAAG
                                                  E
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      · G  T  P   A  D  T   G  H  G  T   V  V  L   E  L  Q   Y  T  G  T   D  G  P   C  K  V   P  I  S  S   V  A  S ·
1901  TTGGGACTCC CGCAGACACA GGTCACGGCA CTGTGGTGTT GGAATTGCAG TACACTGGCA CGGATGGACC TTGCAAAGTT CCTATCTCGT CAGTGGCTTC
      AACCCTGAGG GCGTCTGTGT CCAGTGCCGT GACACCACAA CCTTAACGTC ATGTGACCGT GCCTACCTGG AACGTTTCAA GGATAGAGCA GTCACCGAAG
                                                  E
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      ·L  N  D   L  T  P  V   G  R  L   V  T  V   N  P  F  V   S  V  A   T  A  N   A  K  V  L   I  E  L   E  P  P
2001  ATTGAACGAC CTAACGCCAG TGGGCAGATT GGTCACTGTC AACCCTTTTG TTTCAGTGGC CACGGCCAAC GCTAAGGTCC TGATTGAATT GGAACCACCC
      TAACTTGCTG GATTGCGGTC ACCCGTCTAA CCAGTGACAG TTGGGAAAAC AAAGTCACCG GTGCCGGTTG CGATTCCAGG ACTAACTTAA CCTTGGTGGG
                                                  E
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      F  G  D  S   Y  I  V   V  G  R   G  E  Q  Q   I  N  H   H  W  H   K  S  G  S   S  I  G   K  A  F   T  T  T  L ·
2101  TTTGGAGACT CATACATAGT GGTGGGCAGA GGAGAACAAC AGATCAATCA CCACTGGCAC AAGTCTGGAA GCAGCATTGG CAAAGCCTTT ACAACCACCC
      AAACCTCTGA GTATGTATCA CCACCCGTCT CCTCTTGTTG TCTAGTTAGT GGTGACCGTG TTCAGACCTT CGTCGTAACC GTTTCGGAAA TGTTGGTGGG
                                                  E
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      · K  G  A   Q  R  L   A  A  L  G   D  T  A   W  D  F   G  S  V  G   G  V  F   T  S  V   G  K  A  V   H  Q  V ·
2201  TCAAAGGAGC GCAGAGACTA GCCGCTCTAG GAGACACAGC TTGGGACTTT GGATCAGTTG GAGGGGTGTT CACCTCAGTT GGGAAGGCTG TCCATCAAGT
      AGTTTCCTCG CGTCTCTGAT CGGCGAGATC CTCTGTGTCG AACCCTGAAA CCTAGTCAAC CTCCCCACAA GTGGAGTCAA CCCTTCCGAC AGGTAGTTCA
                                                  E
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      ·F  G  G   A  F  R  S   L  F  G   G  M  S   W  I  T  Q   G  L  L   G  A  L   L  L  W  M   G  I  N   A  R  D
2301  GTTCGGAGGA GCATTCCGCT CACTGTTCGG AGGCATGTCC TGGATAACGC AAGGATTGCT GGGGGCTCTC CTGTTGTGGA TGGCATCAA TGCTCGTGAC
      CAAGCCTCCT CGTAAGGCGA GTGACAAGCC TCCGTACAGG ACCTATTGCG TTCCTAACGA CCCCCGAGAG GACAACACCT ACCCGTAGTT ACGAGCACTG
                                                                                                deleted NS1
                                                                                         ~~~~~~~~~~~~~~~~~~~~~~~~~~~
                                       E
      ~~~~~~~~~~~~~~~~~~~~~~~~~~~~~~~~~~~~~~~~~~~~~~~~~~~~~~~~~~~~~~~~~~~~~~
      R  S  I  A   L  T  F   L  A  V   G  G  V  L   L  F  L   S  V  N   V  H  A  D   T  G  I   H  R  G   P  A  T  R ·
2401  AGGTCCATAG CTCTCACGTT TCTCGCAGTT GGAGGAGTTC TGCTCTTCCT CTCCGTGAAC GTGCACGCTG ACACTGGGAT CCACCGTGGA CCTGCCACTC
      TCCAGGTATC GAGAGTGCAA AGAGCGTCAA CCTCCTCAAG ACGACAAGGA GAGGCACTTG CACGTGCGAC TGTGACCCTA GGTGGCACCT GGACGGTGAG
                                                  deleted NS1
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      · T  T  T   E  S  G   K  L  I  T   D  W  C   C  R  S   C  T  L  P   P  L  R   Y  Q  T   D  S  G  C   W  Y  G ·
2501  GCACCACCAC AGAGAGCGGA AAGTTGATAA CAGATTGGTG CTGCAGGAGC TGCACCTTAC CACCACTGCG CTACCAAACT GACAGCGGCT GTTGGTATGG
      CGTGGTGGTG TCTCTCGCCT TTCAACTATT GTCTAACCAC GACGTCCTCG ACGTGGAATG GTGGTGACGC GATGGTTTGA CTGTCGCCGA CAACCATACC
                                  deleted NS1
      ~~~~~~~~~~~~~~~~~~~~~~~~~~~~~~~~~~~~~~~~~~~~~~~~~~~~~~~~~~~~~~~~~~~~~~~~~~~~~~

NS2A
                                                                               ~~~~~~~~~~~~~~~~~~~~~~~~~~~~~~~~~~~
      ·M  E  I   R  P  Q  R   H  D  E   K  T  L   V  Q  S  Q   V  N  A   Y  N  A   D  M  I  D   P  F  Q   L  G  L
2601  TATGGAGATC AGACCACAGA GACATGATGA AAAGACCCTC GTGCAGTCAC AAGTGAATGC TTATAATGCT GATATGATTG ACCCTTTTCA GTTGGGCCTT
      ATACCTCTAG TCTGGTGTCT CTGTACTACT TTTCTGGGAG CACGTCAGTG TTCACTTACG AATATTACGA CTATACTAAC TGGGAAAAGT CAACCCGGAA
```

Sequence Appendix 5

PIV-WNV(ΔprME)/RSV-F

```
                                                                                                   C protein
                                                                                                   ~~~~
                                        5' UTR
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                                                M  S ·
  1   AGTAGTTCGC CTGTGTGAGC TGACAAAACTT AGTAGTGTTT GTGAGGATTA ACAACAATTA ACACAGTGCG AGCTGTTTCT TAGCACGAAG ATCTCGATGT
      TCATCAAGCG GACACACTCG ACTGTTTGAA TCATCACAAA CACTCCTAAT TGTTGTTAAT TGTGTCACGC TCGACAAAGA ATCGTGCTTC TAGAGCTACA
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                          C protein
       ·  K  K  P    G  G  P    G  K  S  R    A  V  Y    L  L  K  R  G  M  P  R  V  L    S  L  I    G  L  K  R  A  M  L ·
101   CTAAGAAACC AGGAGGGCCC GGCAAGAGCC GGGCTGTCTA TTTGCTAAAA CGCGGAATGC CCCGCGTGTT GTCCTTGATT GGACTTAAGA GGGCTATGTT
      GATTCTTTGG TCCTCCCGGG CCGTTCTCGG CCCGACAGAT AAACGATTTT GCGCCTTACG GGGCGCACAA CAGGAACTAA CCTGAATTCT CCCGATACAA
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                          C protein
       ·  S  L  I    D  G  K  G    P  I  R    F  V  L    A  L  L  A    F  F  R    F  T  A    I  A  P  T    R  A  V    L  D  R
201   GAGCCTGATC GACGGCAAGG GGCCAATACG AATTTGTGTTG GCTCTCTTGG CGTTCTTCAG GTTCACAGCA ATTGCTCCGA CCCGAGCAGT GCTGGATCGA
      CTCGGACTAG CTGCCGTTCC CCGGTTATGC TAAACACAAC CGAGAGAACC GCAAGAAGTC CAAGTGTCGT TAACGAGGCT GGGCTCGTCA CGACCTAGCT
                                                                                                          NS3 cleavage
                                                                                                          ~~~~
                       C protein
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
       W  R  G  V    N  K  Q    T  A  M    K  H  L  L    S  F  K    K  E  L    G  T  L  T    S  A  I    N  R  R    S  S  K  Q ·
301   TGGAGAGGTG TGAACAAACA AACAGCGATG AAACACCTTC TGAGTTTCAA GAAGGAACTA GGGACCTTGA CCAGTGCTAT CAATCGGCGG AGCTCAAAGC
      ACCTCTCCAC ACTTGTTTGT TTGTCGCTAC TTTGTGGAAG ACTCAAAGTT CTTCCTTGAT CCCTGGAACT GGTCACGATA GTTAGCCGCC TCGAGTTTCG
                                                                          F signal
       NS3 cleavage                                                                                  F1
       ~~~~~~~~~~~                                                                                   ~~~~~~~~~~
       ·  K  K  R    G  G  E    L  L  I  L    K  A  N    A  I  T    T  I  L  T    A  V  T    F  C  F    A  S  G  Q    N  I  T ·
401   AAAAGAAGCG AGGGGGCGAG TTGCTAATCC TCAAAGCAAA TGCAATTACC ACAATCCTCA CTGCAGTCAC ATTTTGTTTT GCTTCTGGTC AAAACATCAC
      TTTTCTTCGC TCCCCCGCTC AACGATTAGG AGTTTCGTTT ACGTTAATGG TGTTAGGAGT GACGTCAGTG TAAAACAAAA CGAAGACCAG TTTTGTAGTG
                                                                          F1
       ·  E  E  F    Y  Q  S  T    C  S  A    V  S  K    G  Y  L  S    A  L  R    T  G  W    Y  T  S  V    I  T  I    E  L  S
501   TGAAGAATTT TATCAATCAA CATGCAGTGC AGTTAGCAAA GGCTATCTTA GTGCTCTGAG AACTGGTTGG TATACCAGTG TTATAACTAT AGAATTAAGT
      ACTTCTTAAA ATAGTTAGTT GTACGTCACG TCAATCGTTT CCGATAGAAT CACGAGACTC TTGACCAACC ATATGGTCAC AATATTGATA TCTTAATTCA
                                                                          F1
       N  I  K  E    N  K  C    N  G  T    D  A  K  V    K  L  I    K  Q  E    L  D  K  Y    K  N  A    V  T  E    L  Q  L  L ·
601   AATATCAAGG AAAATAAGTG TAATGGAACA GATGCTAAGG TAAAATTGAT AAAACAAGAA TTAGATAAAT ATAAAAATGC TGTAACAGAA TTGCAGTTGC
      TTATAGTTCC TTTTATTCAC ATTACCTTGT CTACGATTCC ATTTTAACTA TTTTGTTCTT AATCTATTTA TATTTTTACG ACATTGTCTT AACGTCAACG
                                                                          F1
       ·  M  Q  S    T  P  P    T  N  N  R    A  R  R    E  L  P    R  F  M  N    Y  T  L    N  N  A    K  K  T  N    V  T  L ·
701   TCATGCAAAG CACACCACCA ACAAACAATC GAGCCAGAAG AGAACTACCA AGGTTTATGA ATTATACACT CAACAATGCC AAAAAAACCA ATGTAACATT
      AGTACGTTTC GTGTGGTGGT TGTTTGTTAG CTCGGTCTTC TCTTGATGGT TCCAAATACT TAATATGTGA GTTGTTACGG TTTTTTTGGT TACATTGTAA
       F1
      ~~~~~~~~~~~~~~~~~~~~~~~
                                      F2
```

```
            · S  K  K   R  K  R  R    F  L  G   F  L  L    G  V  G   S  A  I  A   S  G  V   A  V  S  K   V  L  H   L  E  G
 801  AAGCAAGAAA AGGAAAAGAA GATTTCTTGG TTTTTTGTTA GGTGTTGGAT CTGCAATCGC CAGTGGCGTT GCTGTATCTA AGGTCCTGCA CCTAGAAGGG
      TTCGTTCTTT TCCTTTTCTT CTAAAGAACC AAAAAACAAT CCACAACCTA GACGTTAGCG GTCACCGCAA CGACATAGAT TCCAGGACGT GGATCTTCCC
                                                                F2
             E  V  N  K   I  K  S   A  L  L   S  T  N  K   A  V  V   S  L  S   N  G  V   S  V  L  T   S  K  V   L  D  L  K ·
 901  GAAGTGAACA AGATCAAAAG TGCTCTACTA TCCACAAACA AGGCTGTAGT CAGCTTATCA AATGGAGTTA GTGTCTTAAC CAGCAAAGTG TTAGACCTCA
      CTTCACTTGT TCTAGTTTTC ACGAGATGAT AGGTGTTTGT TCCGACATCA GTCGAATAGT TTACCTCAAT CACAGAATTG GTCGTTTCAC AATCTGGAGT
                                                                F2
            · N  Y  I   D  K  Q    L  L  P   I  V  N   K  Q  S    C     S  I  S  N   I  E  T   V  I  E   F  Q  Q  K   N  N  R ·
1001  AAAACTATAT AGATAAACAA TTGTTACCTA TTGTGAACAA GCAAAGCTGC AGCATATCAA ATATAGAAAC TGTGATAGAG TTCCAACAAA AGAACAACAG
      TTTTGATATA TCTATTTGTT AACAATGGAT AACACTTGTT CGTTTCGACG TCGTATAGTT TATATCTTTG ACACTATCTC AAGGTTGTTT TCTTGTTGTC
                                                                F2
            · L  L  E   I  T  R  E   F  S  V   N  A  G   V  T  T  P   V  S  T   Y  M  L   T  N  S  E   L  L  S   L  I  N
1101  ACTACTAGAG ATTACCAGGG AATTTAGTGT TAATGCAGGT GTAACTACAC CTGTAAGCAC TTACATGTTA ACTAATAGTG AATTATTGTC ATTAATCAAT
      TGATGATCTC TAATGGTCCC TTAAATCACA ATTACGTCCA CATTGATGTG GACATTCGTG AATGTACAAT TGATTATCAC TTAATAACAG TAATTAGTTA
                                                                F2
             D  M  P   I  T  N   D  Q  K  K   L  M  S   N  N  V   Q   I  V  R    Q  Q  S  Y   S  I  M   S  I  I   K  E  E  V ·
1201  GATATGCCTA TAACAAATGA TCAGAAAAAG TTAATGTCCA ACAATGTTCA AATAGTTAGA CAGCAAAGTT ACTCTATCAT GTCCATAATA AAAGAGGAAG
      CTATACGGAT ATTGTTTACT AGTCTTTTTC AATTACAGGT TGTTACAAGT TTATCAATCT GTCGTTTCAA TGAGATAGTA CAGGTATTAT TTTCTCCTTC
                                                                F2
            · L  A  Y   V  V  Q   L  P  L  Y   G  V  I   D  T  P   C  W  K  L   H  T  S   P  L  C   T  T  N  T   K  E  G
1301  TCTTAGCATA TGTAGTACAA TTACCACTAT ATGGTGTTAT AGATACACCC TGTTGGAAAC TACACACATC CCCTCTATGT ACAACCAACA CAAAAGAAGG
      AGAATCGTAT ACATCATGTT AATGGTGATA TACCACAATA TCTATGTGGG ACAACCTTTG ATGTGTGTAG GGGAGATACA TGTTGGTTGT GTTTTCTTCC
                                                                F2
            · S  N  I    C  L  T  R   T  D  R   G  W  Y   C  D  N   A   G  S  V    S  F  F   P  Q  A   E  T  C  K   V  Q  S
1401  GTCCAACATC TGTTTAACAA GAACTGACAG AGGATGGTAC TGTGACAATG CAGGATCAGT ATCTTCTTCC CCACAAGCTG AAACATGTAA AGTTCAATCA
      CAGGTTGTAG ACAAATTGTT CTTGACTGTC TCCTACCATG ACACTGTTAC GTCCTAGTCA TAGAAGAAGG GGTGTTCGAC TTTGTACATT TCAAGTTAGT
                                                                F2
             N  R  V   F  C  D  T   M  N  S   L  T  L  P   S  E  I   N  L  C   N  V  D  I   F  N  P   K  Y  D   C  K  I  M ·
1501  AATCGAGTAT TTTGTGACAC AATGAACAGT TTAACATTAC CAAGTGAAAT AAATCTCTGC AATGTTGACA TATTCAACCC CAAATATGAT TGTAAAATTA
      TTAGCTCATA AAACACTGTG TTACTTGTCA AATTGTAATG GTTCACTTTA TTTAGAGACG TTACAACTGT ATAAGTTGGG GTTTATACTA ACATTTTAAT
                                                                F2
            · T  S  K   T  D  V   S  S  S  V   I  T  S   L  G  A   I  V  S  C   Y  G  K   T  K  C   T  A  S  N   V  K  N  R ·
1601  TGACTTCAAA ACAGATGTA AGCAGCTCCG TTATCACATC TCTAGGAGCC ATTGTGTCAT GCTATGGCAA AACTAAATGT ACAGCATCCA ATAAAAATCG
      ACTGAAGTTT TGTCTACAT TCGTCGAGGC AATAGTGTAG AGATCCTCGG TAACACAGTA CGATACCGTT TTGATTTACA TGTCGTAGGT TATTTTTAGC
                                                                F2
            · G  I  I   K  T  F  S   N  G  C   D  Y  V   S  N  K  G   M  D  T   V  S  V   G  N  T  L   Y  Y  V   N  K  Q
1701  TGGAATCATA AAGACATTTT CTAACGGGTG CGATTATGTA TCAAATAAAG GGATGGACAC TGTGTCTGTA GGTAACACAT TATATTATGT AAATAAGCAA
      ACCTTAGTAT TTCTGTAAAA GATTGCCCAC GCTAATACAT AGTTTATTTC CCTACCTGTG ACACAGACAT CCATTGTGTA ATATAATACA TTTATTCGTT
                                                                F2
             E  G  K   S  L  Y  V   K  G  E   P  I  I   N  F  Y  D   P  L  V   F  P  S  D   E  F  D   A  S  I   S  Q  V  N ·
1801  GAAGGTAAAA GTCTCTATGT AAAAGGTGAA CCAATAATAA ATTTCTATGA CCCATTAGTA TTCCCCTCTG ATGAATTTGA TGCATCAATA TCTCAAGTCA
```

```
     CTTCCATTTT CAGAGATACA TTTTCCACTT GGTTATTATT TAAAGATACT GGGTAATCAT AAGGGGAGAC TACTTAAACT ACGTAGTTAT AGAGTTCAGT
                                  F2
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                                                      TM Domain
                                                                                                     ~~~~~~~~~~~~~~~
       · E  K  I  N  Q  S  L  A  F  I  R  K  S  D  E  L  H  N  V  N  A  G  K  S  T  N  I  M  I  T  T ·
1901   ACGAGAAGAT TAACCAGAGC CTAGCATTTA TTCGTAAATC CGATGAATTA TTACATAATG TAAATGCTGG TAAATCCACC ACAAATATCA TGATAACTAC
       TGCTCTTCTA ATTGGTCTCG GATCGTAAAT AAGCATTTAG GCTACTTAAT AATGTATTAC ATTTACGACC ATTTAGGTGG TGTTTATAGT ACTATTGATG
                     TM Domain
       ~~~~~~~~~~~~~~~~~~~~~~~~~~~~~~~~~~~~~~~~~~~~~~~~~~~~~
                                                                                             Cytoplasmic Tail
                                                                                             ~~~~~~~~~~~~~~~~~~~~~~~
       · I  T  I  V  I  I  V  I  L  L  S  L  I  A  V  G  L  L  L  Y  C  K  A  R  S  T  P  V  T  L  S  K  D
2001   TATAATTATA GTGATTATAG TAATATTGTT ATCATTAATT GCTGTTGGAC TGCTCTTATA CTGTAAGGCC AGAAGCACAC CAGTCACACT AAGCAAAGAT
       ATATTAATAT CACTAATATC ATTATAACAA TTATAACAA CGACAACCTG ACGAGAATAT GACATTCCGG TCTTCGTGTG GTCAGTGTGA TTCGTTTCTA
                                                                                             FMDV 2A
                                                                                             ~~~~~~~~~~~~~~~~~~~~~~~~~~~~~~~~~~~~~~~~~~
                                                                                                           Transmembrane
     domain of WNV E (split)                                                                                    ~~~~
       ~~~~~~~~~~~~~~~~~~~~~~~~~~~~~~~~
            Cytoplasmic Tail                                                                    pre E/NS1 signal
       ~~~~~~~~~~~~~~~~~~~~~~~~~~~~~~~~~                                                        ~~~~~~~~~~~~~~~~
       · Q  L  S  G  I  N  N  I  A  F  S  N  N  F  D  L  L  K  L  A  G  D  V  E  S  N  P  G  P  A  R  D  R  S ·
2101   CAACTGAGTG GTATAAATAA TATTGCATTT AGTAACAATT TTGATCTCT CAAACTTGCA GGCGATGTAG AATCAAATCC TGGACCCGCC CGGGACAGGT
       GTTGACTCAC CATATTTATT ATAACGTAAA TCATTGTTAA AACTAGACGA GTTTGAACGT CCGCTACATC TTAGTTTAGG ACCTGGGCGG GCCCTGTCCA
                                                                                                         NS1
                                                                                                         ~~~~~~~~~~~~~~~~~~~~~~~
       Transmembrane domain of WNV E (split)
       ~~~~~~~~~~~~~~~~~~~~~~~~~~~~~~~~~~~~~~~~
       · I  A  L  T  F  L  A  V  G  G  V  L  L  F  L  S  V  N  V  H  A  D  T  G  C  A  I  D  I  S  R  Q
2201   CCATAGCTCT CACGTTTCTC GCAGTTGGAG GAGTTCTGCT CTTCCTCTCC GTGAACGTGC ACGCTGACAC TGGGTGTGCC ATAGACATCA GCCGGCAA
       GGTATCGAGA GTGCAAAGAG CGTCAACCTC CTCAAGACGA GAAGGAGAGG CACTTGCACG TGCGACTGTG ACCCACACGG TATCTGTAGT CGGCCGTT
```

PIV-WNV(ΔCprME)/RSV-F

```
                                                                                                   deleted C protein
                                                                                                   ~~~~~~~~~~~~~~~~
                                            5' UTR
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                                                        M  S ·
1    AGTAGTTCGC CTGTGTGAGC TGACAAACTT AGTAGTGTTT GTGAGGATTA ACAACAATTA ACACAGTGCG AGCTGTTTCT TAGCACGAAG ATCTCGATGT
     TCATCAAGCG GACACACTCG ACTGTTTGAA TCATCACAAA CACTCCTAAT TGTTGTTAAT TGTGTCACGC TCGACAAAGA ATCGTGCTTC TAGAGCTACA
                    deleted C protein
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                                                 NS3 cleavage
                                                                                                 ~~~~~~~~~~~~~~~~
       · K  K  P  G  G  P  G  K  S  R  A  V  N  M  L  K  R  G  M  P  R  V  L  S  L  I  G  L  K  Q  K  K  R ·
```

```
                                                                          NS3 cleavage
101 CTAAGAAACC AGGAGGGCCC GGCAAGAGCC GGGCTGTCAA TATGCTAAAA CGCGGAATGC CCCGCGTGTT GTCCTTGATT GGACTTAAGC AAAAGAAGCG
    GATTCTTTGG TCCTCCCGGG CCGTTCTCGG CCCGACAGTT ATACGATTTT GCGCCTTACG GGGCGCACAA CAGGAACTAA CCTGAATTCG TTTTCTTCGC
                                            F signal                                                        F1

· G  G  E    L  L  I  L  K  A  N   A  I  T   T  I  L  T   A  V  T   F  C  F   A  S  G  Q   N  I  T    E  E  F
201 AGGGGGCGAG TTGCTAATCC TCAAAGCAAA TGCAATTACC ACAATCCTCA CTGCAGTCAC ATTTTGTTTT GCTTCTGGTC AAAACATCAC TGAAGAATTT
    TCCCCCGCTC AACGATTAGG AGTTTCGTTT ACGTTAATGG TGTTAGGAGT GACGTCAGTG TAAAACAAAA CGAAGACCAG TTTTGTAGTG ACTTCTTAAA
                                                                     F1

Y  Q  S  T   C  S  A  V   S  K    G  Y  L  S   A  L  R   T  G  W   Y  T  S  V   I  T  I    E  L  S   N  I  K  E·
301 TATCAATCAA CATGCAGTGC AGTTAGCAAA GGCTATCTTA GTGCTCTGAG AACTGGTTGG TATACCAGTG TTATAACTAT AGAATTAAGT AATATCAAGG
    ATAGTTAGTT GTACGTCACG TCAATCGTTT CCGATAGAAT CACGAGACTC TTGACCAACC ATATGGTCAC AATATTGATA TCTTAATTCA TTATAGTTCC
                                                                     F1

· N  K  C    N  G  T    D  A  K  V   K  L  I   K  Q  E   L  D  K  Y   K  N  A   V  T  E   L  Q  L  L   M  Q  S·
401 AAAATAAGTG TAATGCAACA GATGCTAAGG TAAAATTGAT AAAACAAGAA TTAGATAAAT ATAAAAATGC TGTAACAGAA TTGCAGTTGC TCATGCAAAG
    TTTTATTCAC ATTACCTTGT CTACGATTCC ATTTTAACTA TTTTGTTCTT AATCTATTTA TATTTTTACG ACATTGTCTT AACGTCAACG AGTACGTTTC
                                                                     F1

· T  P  P    T  N  N  R   A  R  R   E  L  P   R  F  M  N   Y  T  L   N  N  A   K  K  T  N   V  T  L   S  K  K
501 CACACCACCA ACAAACAATC GAGCCAGAAG AGAACTACCA AGGTTTATGA ATTATATACT CAACAATGCC AAAAAAACCA ATGTAACATT AAGCAAGAAA
    GTGTGGTGGT TGTTTGTTAG CTCGGTCTTC TCTTGATGGT TCCAAATACT TAATATGTGA GTTGTTACGG TTTTTTTGGT TACATTGTAA TTCGTTCTTT
                     F1                                                      F2

R  K  R  R   F  L  G    F  L  L    G  V  G  S   A  I  A   S  G  V   A  V  S  K   V  L  H   L  E  G   E  V  N  K·
601 AGGAAAAGAA GATTTCTTGG TTTTTTGTTA GGTGTTGGAT CTGCAATCGC CAGTGGCGTT GCTGTATCTA AGGTCCTGCA CCTAGAAGGG GAAGTGAACA
    TCCTTTTCTT CTAAAGAACC AAAAAACAAT CCACAACCTA GACGTTAGCG GTCACCGCAA CGACATAGAT TCCAGGACGT GGATCTTCCC CTTCACTTGT
                                                                     F2

· I  K  S    A  L  L    S  T  N  K   A  V  V   S  L  S   N  G  V  S   V  L  T   S  K  V   L  D  L  K   N  Y  I·
701 AGATCAAAAG TGCTCTACTA TCCACAAACA AGGCTGTAGT CAGCTTATCA AATGGAGTTA GTGTCTTAAC CAGCAAAGTG TTAGACCTCA AAAACTATAT
    TCTAGTTTTC ACGAGATGAT AGGTGTTTGT TCCGACATCA GTCGAATAGT TTACCTCAAT CACAGAATTG GTCGTTTCAC AATCTGGAGT TTTTGATATA
                                                                     F2

· D  K  Q    L  L  P  I   V  N  K   Q  S  C   S  I  S  N   I  E  T   V  I  E   F  Q  Q  K   N  N  R   L  L  E
801 AGATAAACAA TTGTTACCTA TTGTGAACAA GCAAAGCTGC AGCATATCAA ATATAGAAAC TGTGATAGAG TTCCAACAAA AGAACAACAG ACTACTAGAG
    TCTATTTGTT AACAATGGAT AACACTTGTT CGTTTCGACG TCGTATAGTT TATATCTTTG ACACTATCTC AAGGTTGTTT TCTTGTTGTC TGATGATCTC
                                                                     F2

I  T  R  E   F  S  V    N  A  G   V  T  T  P   V  S  T   Y  M  L   T  N  S  E   L  L  S   L  I  N   D  M  P  I·
901 ATTACCAGGG AATTTAGTGT TAATGCAGGT GTAACTACAC CTGTAAGCAC TTACATGTTA ACTAATAGTG AATTATTGTC ATTAATCAAT GATATGCCTA
    TAATGGTCCC TTAAATCACA ATTACGTCCA CATTGATGTG GACATTCGTG AATGTACAAT TGATTATCAC TTAATAACAG TAATTAGTTA CTATACGGAT
                                                                     F2

· T  N  D    Q  K  K    L  M  S  N   N  V  Q   I  V  R   Q  Q  S  Y   S  I  M   S  I  I   K  E  E  V   L  A  Y·
1001 TAACAAATGA TCAGAAAAAG TTAATGTCCA ACAATGTTCA AATAGTTAGA CAGCAAAGTT ACTCTATCAT GTCCATAATA AAAGAGGAAG TCTTAGCATA
     ATTGTTTACT AGTCTTTTTC AATTACAGGT TGTTACAAGT TTATCAATCT GTCGTTTCAA TGAGATAGTA CAGGTATTAT TTTCTCCTTC AGAATCGTAT
                                                                     F2

· V  V  Q   L  P  L  Y   G  V  I   D  T  P   C  W  K  L   H  T  S   P  L  C   T  T  N  T   K  E  G   S  N  I
```

```
1101 TGTAGTACAA TTACCACTAT ATGGTGTTAT AGATACACCC TGTTGGAAAC TACACACATC CCCTCTATGT ACAACCAACA CAAAAGAAGG GTCCAACATC
     ACATCATGTT AATGGTGATA TACCACAATA TCTATGTGGG ACAACCTTTG ATGTGTGTAG GGGAGATACA TGTTGGTTGT GTTTTCTTCC CAGGTTGTAG
                                                                                            F2
            C  L  T  R  T  D  R  G  W  Y     C  D  N  A  G  S  V     S  F  F     P  Q  A  E  T  C  K  V  Q  S     N  R  V  F ·
1201 TGTTTAACAA GAACTGACAG AGGATGGTTA CTGTGACAAT CAGGATCAGT ATCTTTCTTC CCACAAGCTG AAACATGTAA AGTTCAATCA AATCGAGTAT
     ACAAATTGTT CTTGACTGTC TCCTACCATG ACACTGTTAC GTCCTAGTCA TAGAAAGAAG GGTGTTCGAC TTTGTACATT TCAAGTTAGT TTAGCTCATA
                                                                                            F2
          ·  C  D  T     M  N  S  L  T  L  P  S  E  I     N  L  C  N  V  D  I     F  N  P  K  Y  D  C  K  I  M  T  S  K ·
1301 TTTGTGACAC AATGAACAGT TTAACATTAC CAAGTGAAAT AAATCTCTGC AATGTTGACA TATTCAACCC CAAATATGAT TGTAAAATTA TGACTTCAAA
     AAACACTGTG TTACTTGTCA AATTGTAATG GTTCACTTTA TTTAGAGACG TTACAACTGT ATAAGTTGGG GTTTATACTA ACATTTTAAT ACTGAAGTTT
                                                                                            F2
          ·  T  D  V     S  S  S  V     I  T  S     L  G  A     I  V  S  C     Y  G  K     T  K  C     T  A  S  N     K  N  R     G  I  I
1401 AACAGATGTA AGCAGCTCCG TTATCACATC TCTAGGAGCC ATTGTGTCAT GCTATGGCAA AACTAAATGT ACAGCATCCA ATAAAAATCG TGGAATCATA
     TTGTCTACAT TCGTCGAGGC AATAGTGTAG AGATCCTCGG TAACACAGTA CGATACCGTT TTGATTTACA TGTCGTAGGT TATTTTTAGC ACCTTAGTAT
                                                                                            F2
          K  T  F  S     N  G  C     D  Y  V     S  N  K  G     M  D  T     V  S  V     G  N  T  L     Y  Y  V     N  K  Q     E  G  K  S ·
1501 AAGACATTTT CTAACGGGTG CGATTATGTA TCAAATAAAG GGATGGACAC TGTGTCTGTA GGTAACACAT TATATTATGT AAATAAGCAA GAAGGTAAAA
     TTCTGTAAAA GATTGCCCAC GCTAATACAT AGTTTATTTC CCTACCTGTG ACACAGACAT CCATTGTGTA ATATAATACA TTTATTCGTT CTTCCATTTT
                                                                                            F2
          ·  L  Y  V     K  G  E     P  I  I  N     F  Y  D     P  L  V     F  P  S  D     E  F  D     A  S  I     S  Q  V  N     E  K  I ·
1601 GTCTCTATGT AAAAGGTGAA CCAATAATAA ATTTCTATGA CCCATTAGTA TTCCCCTCTG ATGAATTTGA TGCATCAATA TCTCAAGTCA ACGAGAAGAT
     CAGAGATACA TTTTCCACTT GGTTATTATT TAAAGATACT GGGTAATCAT AAGGGGAGAC TACTTAAACT ACGTAGTTAT AGAGTTCAGT TGCTCTTCTA
                                                                                            F2
                                                                                                      TM Domain
          ·  N  Q  S     L  A  F  I  R  K  S     D  E  L     L  H  N  V     N  A  G     K  S  T     T  N  I  M     I  T  T     I  I  I
1701 TAACCAGAGC CTAGCATTTA TTCGTAAATC CGATGAATTA TTACATAATG TAAATGCTGG TAAATCCACC ACAAATATCA TGATAACTAC TATAATTATA
     ATTGGTCTCG GATCGTAAAT AAGCATTTAG GCTACTTAAT AATGTATTAC ATTTACGACC ATTTAGGTGG TGTTTATAGT ACTATTGATG ATATTAATAT
         TM Domain
                                                                           Cytoplasmic Tail
          V  I  I  V     I  L  L     S  L  I     A  V  C  L     L  L  Y     C  K  A     R  S  T  P     V  T  L     S  K  D     Q  L  S  G ·
1801 GTGATTATAG TAATATTGTT ATCATTAATT GCTGTTGGAC TGCTCTTATA CTGTAAGGCC AGAAGCACAC CAGTCACACT AAGCAAAGAT CAACTGAGTG
     CACTAATATC ATTATAACAA TAGTAATTAA CGACAACCTG ACGAGAATAT GACATTCCGG TCTTCGTGTG GTCAGTGTGA TTCGTTTCTA GTTGACTCAC
                                                                                 FMDV 2A
                                                                                                      membrane domain of WNV E (split)
             Cytoplasmic Tail                                                                   pre E/NS1 signal
          ·  I  N  N     I  A  F     S  N  N  F     D  L  L     K  L  A     G  D  V  E     S  N  P     G  P  A     R  D  R  S     I  A  L ·
1901 GTATAAATAA TATTGCATTT AGTAACAATT TTGATCTGCT CAAACTTGCA GGCGATGTAG AATCAAATCC TGGACCCGCC CGGGACAGGT CCATAGCTCT
     CATATTTATT ATAACGTAAA TCATTGTTAA AACTAGACGA GTTTGAACGT CCGCTACATC TTAGTTTAGG ACCTGGGCGG GCCCTGTCCA GGTATCGAGA
           Transmembrane domain of WNV E (split)
                                                                                   NS1
```

```
              · T F L   A V G G   V L L   F L S   V N V H   A D T   G C A   I D I S   R Q E   L R
     2001  CACGTTTCTC GCAGTTGGAG GAGTTCTGCT CTTCCTCTCC GTGAACGTGC ACCCTGACAT GGGTGTGCC ATAGACATCA GCCGGCAAGA GCTGAGA
           GTGCAAAGAG CGTCAACCTC CTCAAGACGA GAAGGAGAGG CACTTGCACG TGCGACTGTG ACCCACACGG TATCTGTAGT CGGCCGTTCT CGACTCT
```

PIV-WNV(ΔC)/RSV-F

```
        1  GATCCTAATA CGACTCACTA TAGAGTAGTT CGCCTGTGTG AGCTGACAAA CTTAGTAGTG TTTGTGAGGA TTAACAACAA TTAACACAGT GCGAGCTGTT
           CTAGGATTAT GCTGAGTGAT ATCTCATCAA GCGGACACAC TCGACTGTTT GAATCATCAC AAACACTCCT AATTGTTGTT AATTGTGTCA CGCTCGACAA
                                                                                                   N-terminus of C M   S K K   P G G   P G K S   R A V   N M L   K R G M   P R V   L S L
      101  TCTTAGCACG AAGATCTCGA TGTCTAAGAA ACCAGGAGGG CCCGGCAAGA GCCGGGCTGT CAATATGCTA AAACGCGGAA TGCCCCGCGT GTTGTCCTTG
           AGAATCGTGC TTCTAGAGCT ACAGATTCTT TGGTCCTCCC GGGCCGTTCT CGGCCCGACA GTTATACGAT TTTGCGCCTT ACGGGGCGCA CAACAGGAAC
           N-terminus of C                                                    F signal
                       NS3 cleavage                                                                              F1

I G L K   Q K K   R G G   E L L I   L K A   N A I   T T I L   T A V   T F C   F A S G ·
      201  ATTGGACTTA AGCAAAAGAA GCGAGGGGGC GAGTTGCTAA TCCTCAAAGC AAATGCAATT ACCACAATCC TCACTGCAGT CACATTTTGT TTTGCTTCTG
           TAACCTGAAT TCGTTTTCTT CGCTCCCCCG CTCAACGATT AGGAGTTTCG TTTACGTTAA TGGTGTTAGG AGTGACGTCA GTGTAAAACA AAACGAAGAC
                                                                                                                  F1

· Q N I   T E E   F Y Q S   T C S   A V S   K G Y L   S A L   R T G   W Y T S   V I T ·
      301  GTCAAAACAT CACTGAAGAA TTTTATCAAT CAACATGCAG TGCAGTTAGC AAAGGCTATC TTAGTCTCCT GAGAACTGGT TGGTATACCA GTGTTATAAC
           CAGTTTTGTA GTGACTTCTT AAAATAGTTA GTTGTACGTC ACGTCAATCG TTTCCGATAG AATCAGAGGA CTCTTGACCA ACCATATGGT CACAATATTG
                                                                                                                  F1

· I E L   S N I K   E N K   C N G   T D A K   V K L   I K Q   E L D K   Y K N   A V T
      401  TATAGAATTA AGTAATATCA AGGAAAATAA GTGTAATGGA ACAGATGCTA AGGTAAAATT GATAAAACAA GAATTAGATA AATATAAAAA TGCTGTAACA
           ATATCTTAAT TCATTATAGT TCCTTTTATT CACATTACCT TGTCTACGAT TCCATTTTAA CTATTTGTT CTTAATCTAT TTATATTTTT ACGACATTGT
                                                                                                                  F1

E L Q L   L M Q   S T P   P T N N   R A R   R E L   P R F M   N Y T   L N N   A K K T ·
      501  GAATTGCAGT TGCTCATGCA AAGCACACCA CCAACAAACA ATCGAGCCAG AAGAGAACTA CCAAGGTTTA TGAATTATAC ACTCAACAAT GCCAAAAAAA
           CTTAACGTCA ACGAGTACGT TTCGTGTGGT GGTTGTTTGT TAGCTCGGTC TTCTCTTGAT GGTTCCAAAT ACTTAATATG TGAGTTGTTA CGGTTTTTTT
                                                                                                   F2
                        F1

· N V T   L S K   K R K R   R F L   G F L   L G V G   S A I   A S G   V A V S   K V L ·
      601  CCAATGTAAC ATTAAGCAAG AAAAGGAAAA GAAGATTTCT TGGTTTTTTG TTAGGTGTTG GATCTGCAAT CGCCAGTGGC GTTGCTGTAT CTAAGGTCCT
           GGTTACATTG TAATTCGTTC TTTTCCTTTT CTTCTAAAGA ACCAAAAAAC AATTCACAAC CTAGACGTTA GCGGTCACCG CAACGACATA GATTCCAGGA
                                                                                                                   F2

· H L E   G E V N   K I K   S A L   L S T N   K A V   V S L   S N G V   S V L   T S K
      701  GCACCTAGAA GGGGAAGTGA ACAAGATCAA AAGTGCTCTA CTATCCACAA ACAAGGCTGT AGTCAGCTTA TCAAATGGAG TTAGTGTCTT AACCAGCAAA
           CGTGGATCTT CCCCTTCACT TGTTCTAGTT TTCACGAGAT GATAGGTGTT TGTTCCGACA TCAGTCGAAT AGTTTACCTC AATCACAGAA TTGGTCGTTT
                                                                                                                    F2

V L D L   K N Y   I D K   Q L L P   I V N   K Q S   C S I S   N I E   T V I   E F Q Q ·
```

```
 801 GTGTTAGACC TCAAAAACTA TATAGATAAA CAATTGTTAC CTATTGTGAA CAAGCAAAGC TGCAGCATAT CAAATATAGA AACTGTGATA GAGTTCCAAC
     CACAATCTGG AGTTTTTGAT ATATCTATTT GTTAACAATG GATAACACTT GTTCGTTTCG ACGTCGTATA GTTTATATCT TTGACACTAT CTCAAGGTTG
                                                                F2
     · K  N  N    R  L  L    E  I  T  R    E  F  S    V  N  A    G  V  T  T    P  V  S    T  Y  M    L  T  N  S    E  L  L ·
 901 AAAAGAACAA CAGACTACTA GAGATTACCA GGGAATTTAG TGTTAATGCA GGTGTAACTA CACCTGTAAG CACTTACATG TTAACTAATA GTGAATTATT
     TTTTCTTGTT GTCTGATGAT CTCTAATGGT CCCTTAAATC ACAATTACGT CCACATTGAT GTGGACATTC GTGAATGTAC AATTGATTAT CACTTAATAA
                                                                F2
     · S  L  I    N  D  M  P    I  T  N    D  Q  K    K  L  M  S    N  N  V    Q  I  V    R  Q  Q  S    Y  S  I    M  S  I
1001 GTCATTAATC AATGATATGC CTATAACAAA TGATCAGAAA AAGTTAATGT CCAACAATGT TCAAATAGTT AGACAGCAAA GTTACTCTAT CATGTCCATA
     CAGTAATTAG TTACTATACG GATATTGTTT ACTAGTCTTT TTCAATTACA GGTTGTTACA AGTTTATCAA TCTGTCGTTT CAATGAGATA GTACAGGTAT
                                                                F2
       I  K  E  E    V  L  A    Y  V  V    Q  L  P  L    Y  G  V    I  D  T    P  C  W  K    L  H  T    S  P  L    C  T  T  T  N ·
1101 ATAAAAGAGG AAGTCCTAGC ATATGTAGTA CAATTACCAC TATATGGTGT TATAGATACA CCCTGTTGGA AACTACACAC ATCCCCTCTA TGTACAACCA
     TATTTTCTCC TTCAGAATCG TATACATCAT GTTAATGGTG ATATACCACA ATATCTATGT GGGACAACCT TTGATGTGTG TAGGGGAGAT ACATGTTGGT
                                                                F2
     · T  K  E    G  S  N    I  C  L  T    R  T  D    R  G  W    Y  C  D  N    A  G  S    V  S  F    F  P  Q  A    E  T  C ·
1201 ACACAAAAGA AGGGTCCAAC ATCTGTTTAA CAAGAACTGA CAGAGGATGG TACTGTGACA ATGCAGGATC AGTATCTTTC TTCCCACAAG CTGAAACATG
     TGTGTTTTCT TCCCAGGTTG TAGACAAATT GTTCTTGACT GTCTCCTACC ATGACACTGT TACGTCCTAG TCATAGAAAG AAGGGTGTTC GACTTTGTAC
                                                                F2
     · K  V  Q    S  N  R  V    F  C  D    T  M  N    S  L  T  L    P  S  E    I  N  L    C  N  V  D    I  F  N    P  K  Y
1301 TAAAGTTCAA TCAATCGAG TATTTTGTGA CACAATGAAC AGTTTAACAT TACCAAGTGA AATAAATCTC TGCAATGTTG ACATATTCAA CCCCAAATAT
     ATTTCAAGTT AGTTTAGCTC ATAAAACACT GTGTTACTTG TCAAATTGTA ATGGTTCACT TTATTTAGAG ACGTTACAAC TGTATAAGTT GGGGTTTATA
     · D  C  K  I    M  T  S    K  T  D    V  S  S  S    V  I  T    S  L  G    A  I  V  S    C  Y  G    K  T  K    C  T  A  S ·
1401 GATTGTAAAA TTATGACTTC AAAAACAGAT GTAAGCAGCT CCGTTATCAC ATCTCTAGGA GCCATTGTGT CATGCTATGG CAAAACTAAA TGTACAGCAT
     CTAACATTTT AATACTGAAG TTTTTGTCTA CATTCGTCGA GGCAATAGTG TAGAGATCCT CGGTAACACA GTACGATACC GTTTTGATTT ACATGTCGTA
     · N  K  N    R  G  I    I  K  T  F    S  N  G    C  D  Y    V  S  N  K    G  M  D    T  V  S    V  G  N  T    L  Y  Y ·
1501 CCAATAAAAA TCGTGGAATC ATAAAGACAT TTTCTAACGG GTGCGATTAT CTATCAAATA AAGGGATGGA CACTGTGTCT GTAGGTAACA CATTATATTA
     GGTTATTTTT AGCACCTTAG TATTTCTGTA AAAGATTGCC CACGCTAATA GATAGTTTAT TTCCCTACCT GTGACACAGA CATCCATTGT GTAATATAAT
     · V  N  K    Q  E  G  K    S  L  Y    V  K  G    E  P  I  I    N  F  Y    D  P  L    V  F  P  S    D  E  F    D  A  S
1601 TGTAAATAAG CAAGAAGGTA AAAGTCTCTA TGTAAAAGGT GAACCAATAA TAAATTCTA TGACCCATTA GTATTCCCCT CTGATGAATT TGATGCATCA
     ACATTTATTC GTTCTTCCAT TTTCAGAGAT ACATTTTCCA CTTGGTTATT ATTTAAAGAT ACTGGGTAAT CATAAGGGGA GACTACTTAA ACTACGTAGT
                                                                                                                    TM Domain
       I  S  Q  V    N  E  K    I  N  Q    S  L  A  F    I  R  K    S  D  E    L  L  H  N    V  N  A    G  K  S    T  T  N  I ·
1701 ATATCTCAAG TCAACGAGAA GATTAACCAG AGCCTAGCAT TTATTCGTAA ATCCGATGAA TTATTACATA ATGTAAATGC TGGTAAATCC ACCACAAATA
     TATAGAGTTC AGTTGCTCTT CTAATTGGTC TCGGATCGTA AATAAGCATT TAGGCTACTT AATAATGTAT TACATTTACG ACCATTTAGG TGGTGTTTAT
                                                                TM Domain
                                                                                         Cytoplasmic Tail
     · M  I  T    T  I  I    I  V  I  I    V  I  L    L  S  L    I  A  V  G    L  L  L    Y  C  K    A  R  S  T    P  V  T ·
```

```
1801  TCATGATAAC TACTATAATT ATAGTGATTA TAGTAATATT GTTATCATTA ATTGCTGTTG GACTGCTCTT ATACTGTAAG GCCAGAAGCA CACCAGTCAC
      AGTACTATTG ATGATATTAA TATCACTAAT ATCATTATAA CAATAGTAAT TAACGACAAC CTGACGAGAA TATGACATTC CGGTCTTCGT GTGGTCAGTG
                                                                                FMDV 2A

Cytoplasmic Tail

·L S K  D Q L S  G I N  N I A  F S N N  F D L  L K L  A G D V  E S N  P G P
1901  ACTAAGCAAA GATCAACTGA GTGGTATAAA TAATATTGCA TTTAGTAACA ATTTTGATCT GCTCAAACTT GCAGGCGATG TAGAATCAAA TCCTGGACCC
      TGATTCGTTT CTAGTTGACT CACCATATTT ATTATAACGT AAATCATTGT TAAAACTAGA CGAGTTTGAA CGTCCGCTAC ATCTTAGTTT AGGACCTGGG
                                                                                prM

C/prM signal

G G K T  G I A  V M I  G L I A  C V G  A V T  L S N F  Q G K  V M M  T V N A·
2001  GGAGGAAAGA CCGGTATTGC AGTCATGATT GGCCTGATCG CCTGCGTAGG AGCAGTTACC CTCTCTAACT TCCAAGGGAA GGTGATGATG ACGGTAAATG
      CCTCCTTTCT GGCCATAACG TCAGTACTAA CCGGACTAGC GGACGCATCC TCGTCAATGG GAGAGATTGA AGGTTCCCTT CCACTACTAC TGCCATTTAC
                                                      prM

· T D V  T D V  I T I P  T A A  G K N  L C I V  R A M  D V G  Y M C D  D T I·
2101  CTACTGACGT CACAGATGTC ATCACGATTC CAACAGCTGC TGGAAAGAAC CTATGCATTG TCAGAGCAAT GGATGTGGGA TACATGTGCG ATGATACTAT
      GATGACTGCA GTGTCTACAG TAGTGCTAAG GTTGTCGACG ACCTTTCTTG GATACGTAAC AGTCTCGTTA CCTACACCCT ATGTACACGC TACTATGATA
                                                      prM

·T Y E  C P V L  S A G  N D P  E D I D  C W C  T K S  A V Y V  R Y G  R C T
2201  CACTTATGAA TGCCCAGTGC TGTCGGCTGG TAATGATCCA GAAGACATCG ACTGTTGGTG CACAAAGTCA GCAGTCTACG TCAGGTATGG AAGATGCACC
      GTGAATACTT ACGGGTCACG ACAGCCGACC ATTACTAGGT CTTCTGTAGC TGACAACCAC GTGTTTCAGT CGTCAGATGC AGTCCATACC TTCTACGTGG
                                                      prM

K T R H  S R R  S R R  S L T V  Q T H  G E S  T L A N  K K G  A W M  D S T K·
2301  AAGACACGCC ACTCAAGACG CAGTCGGAGG TCACTGACAG TGCAGACACA CGGAGAAAGC ACTCTAGCGA ACAAGAAGGG GGCTTGGATG GACAGCACCA
      TTCTGTGCGG TGAGTTCTGC GTCAGCCTCC AGTGACTGTC ACGTCTGTGT GCCTCTTTCG TGAGATCGCT TGTTCTTCCC CCGAACCTAC CTGTCGTGGT
                                                      prM

· A T R  Y L V  K T E S  W I L  R N P  G Y A L  V A A  V I G  W M L G  S N T·
2401  AGGCCACAAG GTATTTGGTA AAAACAGAAT CATGGATCTT GAGGAACCCT GGATATGCCC TGGTGGCAGC CGTCATTGGT TGGATGCTTG GGAGCAACAC
      TCCGGTGTTC CATAAACCAT TTTTGTCTTA GTACCTAGAA CTCCTTGGGA CCTATACGGG ACCACCGTCG GCAGTAACCA ACCTACGAAC CCTCGTTGTG
                                                      prM

·M Q R  V V F V  V L L  L L V  A P A Y  S F N  C L G  M S N R  D F L  E G V
2501  CATGCAGAGA GTTGTGTTTG TCGTGCTATT GCTTTTGGTG GCCCCAGCTT ACAGCTTTAA CTGCCTTGGA ATGAGCAACA GAGACTTCTT GGAAGGAGTG
      GTACGTCTCT CAACACAAAC AGCACGATAA CGAAAACCAC CGGGGTCGAA TGTCGAAATT GACGGAACCT TACTCGTTGT CTCTGAAGAA CCTTCCTCAC
                                           prM

E

S G A T  W V D  L V L  E G D S  C V T  I M S  K D K P  T I D  V K M  M N M E·
2601  TCTGGAGCAA CATGGGTGGA TTTGGTTCTC GAAGGCGACA GCTGCGTGAC TATCATGTCT AAGGACAAGC CTACCATCGA TGTGAAGATG ATGAATATGG
      AGACCTCGTT GTACCCACCT AAACCAAGAG CTTCCGCTGT CGACGCACTG ATAGTACAGA TTCCTGTTCG GATGGTAGCT ACACTTCTAC TACTTATACC
                                                      E

· A A N  L A E  V R S Y  C Y L  A T V  S D L S  T K A  A C P  A M G E  A H N·
2701  AGGCGGCCAA CCTGGCAGAG GTCCGCAGTT ATTGCTATTT GGCTACCGTC AGCGATCTCT CCACCAAAGC TGCGTGCCCG GCCATGGGAG AAGCTCACAA
      TCCGCCGGTT GGACCGTCTC CAGGCGTCAA TAACGATAAA CCGATGGCAG TCGCTAGAGA GGTGGTTTCG ACGCACGGGC CGGTACCCTC TTCGAGTGTT
                                                      E
```

```
          · D K R   A D P A   F V C   R Q G   V V D R   G W G   N G C   G L F G   K G S   I D T
2801 TGACAAACGT GCTGACCCAG CTTTTGTGTG CAGACAAGGA GTGGTGGACA GGGGCTGGGG CAACGGCTGC GGACTATTTG GCAAAGGAAG CATTGACACA
     ACTGTTTGCA CGACTGGGTC GAAAACACAC GTCTGTTCCT CACCACCTGT CCCCGACCCC GTTGCCGACG CCTGATAAAC CGTTTCCTTC GTAACTGTGT
                                                                                                         E
      C A K F   A C S   T K A   I G R T   I L K   E N I   K Y E V   A I F   V H G   P T T V ·
2901 TGCGCCAAAT TTGCCTGCTC TACCAAGGCA ATAGGAAGAA CCATTTTGAA AGAGAATATC AAGTACGAAG TGGCCATTTT TGTCCATGGA CCAACTACTG
     ACGCGGTTTA AACGGACGAG ATGGTTCCGT TATCCTTCTT GGTAAAACTT TCTCTTATAG TTCATGCTTC ACCGGTAAAA ACAGGTACCT GGTTGATGAC
                                                                                                E
     · E S H   G N Y   S T Q V   G A T   Q A G   R F S   I T P A   A P S   Y T L K   L G E ·
3001 TGGAGTCGCA CGGAAACTAC TCCACACAGG TTGGAGCCAC TCAGGCAGGG AGATTCAGCA TCACTCCTGC GGCGCCTTCA TACACACTAA AGCTTGGACA
     ACCTCAGCGT GCCTTTGATG AGGTGTGTCC AACCTCGGTG AGTCCGTCCC TCTAAGTCGT AGTGAGGACG CCGCGGAAGT ATGTGTGATT TCGAACCTCT
                                                                                                       E
     · Y G E   V T V D   C E P   R S G   I D T N   A Y Y   V M T   V G T K   T F L   V H R
3101 ATATGGAGAG GTGACAGTGG ACTGTGAACC ACGGTCAGGG ATTGACACCA ATGCATACTA CGTGATGACT GTTGGAACAA AGACGTTCTT GGTCCATCGT
     TATACCTCTC CACTGTCACC TGACACTTGG TGCCAGTCCC TAACTGTGGT TACGTATGAT GCACTACTGA CAACCTTGTT TCTGCAAGAA CCAGGTAGCA
                                                                                                       E
      E W F M   D L N   L P W   S S A G   S T V   W R N   R E T L   M E F   E E P   H A T K ·
3201 GAGTGGTTCA TGGACCTCAA CCTGCCTTGG AGCAGTCACG GAAGTACTGT GTGGAGGAAC AGAGAGACGT TAATGGAGTT TGAGGAACCA CACGCCACGA
     CTCACCAAGT ACCTGGAGTT GGACGGAACC TCGTCAGTGC CTTCATGACA CACCTCCTTG TCTCTCTGCA ATTACCTCAA ACTCCTTGGT GTGCGGTGCT
     · Q S V   I A L   G S Q E   G A L   H Q A   L A G A   = P V   E F S   S N T V   K L T ·
3301 AGCAGTCTGT GATAGCATTG GGCTCACAAG AGGGAGCTCT GCATCAAGCT TTGGCTGGAG CCATTCCTGT GGAATTTTCA AGCAACACTG TCAAGTTGAC
     TCGTCAGACA CTATCGTAAC CCGAGTGTTC TCCCTCGAGA CGTAGTTCGA AACCGACCTC GGTAAGGACA CCTTAAAAGT TCGTTGTGAC AGTTCAACTG
                                                                                                      E
      S G H   L K C R   V K M   E K L   Q L K G   T T Y   G V C   S K A F   K F L   G T P
3401 GTCGGGTCAT TTGAAGTGTA GAGTGAAGAT GGAAAAATTG CAGTTGAAGG GAACAACCTA TGGCGTCTGT TCAAAGGCTT TCAAGTTTCT TGGGACTCCC
     CAGCCCAGTA AACTTCACAT CTCACTTCTA CCTTTTTAAC GTCAACTTCC CTTGTTGGAT ACCGCAGACA AGTTTCCGAA AGTTCAAAGA ACCCTGAGGG
                                                                                                     E
      A D T G   H G T   V V L   E L Q Y   T G T   D G P   C K V P   I S S   V A S   L N D L ·
3501 GCAGACACAG GTCACGGCAC TGTGGTGTTG GAATTGCAGT ACACTGGCAC GGATGGACCT TGCAAAGTTC CTATCTCGTC AGTGGCTTCA TTGAACGACC
     CGTCTGTGTC CAGTGCCGTG ACACCACAAC CTTAACGTCA TGTGACCGTG CCTACCTGGA ACGTTTCAAG GATAGAGCAG TCACCGAAGT AACTTGCTGG
                                                                                                       E
     · T P V   G R L   V T V N   P F V   S V A   T A N A   K V L   I E L   E P P F   G D S ·
3601 TAACGCCAGT GGGCAGATTG GTCACTGTCA ACCCTTTTGT TTCAGTGGCC ACGGCCAACG CTAAGGTCCT GATTGAATTG GAACCACCCT TTGGAGACTC
     ATTGCGGTCA CCCGTCTAAC CAGTGACAGT TGGGAAAACA AAGTCACCGG TGCCGGTTGC GATTCCAGGA CTAACTTAAC CTTGGTGGGA AACCTCTGAG
                                                                                                      E
     · Y I V   V G R G   E Q Q   I N H   H W H K   S G S   S I G   K A F T   T T L   K G A
3701 ATACATAGTG GTGGGCAGAG GAGAACAACA GATCAATCAC CACTGGCACA AGTCTGGAAG CAGCATTGGC AAAGCCTTTA CAACCACCCT CAAAGGAGCG
     TATGTATCAC CACCCGTCTC CTCTTGTTGT CTAGTTAGTG GTGACCGTGT TCAGACCTTC GTCGTAACCG TTTCGGAAAT GTTGGTGGGA GTTTCCTCGC
                                                                                                      E
      Q R L A   A L G   D T A   W D F G   S V G   G V F   T S V G   K A V   H Q V   F G G A ·
3801 CAGAGACTAC CCGCTCTAGG AGACACAGCT TGGGACTTTG GATCAGTTGG AGGGGTGTTC ACCTCAGTTG GAAGGCTGT CCATCAAGTG TTCGGAGGAG
     GTCTCTGATC GGCGAGATCC TCTGTGTCGA ACCCTGAAAC CTAGTCAACC TCCCCACAGA TGGAGTCAAC CCTTCCGACA GGTAGTTCAC AAGCCTCCTC
```

```
                                               E
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
       · F  R  S    L  F  G    G  M  S  W    I  T  Q    G  L  L    G  A  L  L    L  W  M    G  I  N    A  R  D  R    S  I  A ·
3901   CATTCCGCTC ACTGTTCGGA GGCATGTCCT GGATAACGCA AGGATTGCTG GGGGCTCTCC TGTTGTGGAT GGGCATCAAT GCTCGTGACA GGTCCATAGC
       GTAAGGCGAG TGACAAGCCT CCGTACAGGA CCTATTGCGT TCCTAACGAC CCCCGAGAGG ACAACACCTA CCCGTAGTTA CGAGCACTGT CCAGGTATCG
                                                                                                  NS1
                        E                                                 ~~~~~~~~~~~~~~~~~~~~~~~~~~~~~~~~~~~~~~~~~~~~~
      ~~~~~~~~~~~~~~~~~~~~~~~~~~~~~~~~~~~~~~~~~~~~~~~~~~~~~~~~~~~~~~~~~~
       · L  T  F    L  A  V  G    G  V  L    L  F  L    S  V  N  V    H  A  D    T  G  C    A  I  D  I    S  R  Q    E  L  R
4001   TCTCACGTTT CTCGCAGTTG GAGGAGTTCT GCTCTTCCTC TCCGTGAACG TGCACGCTGA CACTGGGTGT GCCATAGACA TCAGCCGGCA AGAGCTGAGA
       AGAGTGCAAA GAGCGTCAAC CTCCTCAAGA CGAGAAGGAG AGGCACTTGC ACGTGCGACT GTGACCCACA CGGTATCTGT AGTCGGCCGT TCTCGACTCT
```

Sequence Appendix 6

Construct 1
1. PIV-WN (ΔCprME)-SIV 9AA FMD Gag

RV230 9AA-FMD-Gag
13266 bp

2. Sequence of PIV-WN (ΔCprME)-SIV 9AA FMD Gag (partial).

```
                                                                                        C
                                    5' UTR
     ~~~~~~~~~~~~~~~~~~~~~~~~~~~~~~~~~~~~~~~~~~~~~~~~~~~~~~~~~~~~~~~~~~~~~~~~~~~~~~~~~~
                                                                                  M  S  ·
  1  AGTAGTTCGC CTGTGTGAGC TGACAAACTT AGTAGTGTTT GTGAGGATTA ACAACAATTA ACACAGTGCG AGCTGTTTCT TAGCACGAAG ATCTCGATGT
     TCATCAAGCG GACACACTCG ACTGTTTGAA TCATCACAAA CACTCCTAAT TGTTGTTAAT TGTGTCACGC TCGACAAAGA ATCGTGCTTC TAGAGCTACA
                                            C
     · K   K   P   G   G   P   G   K   S   R   A   V   Y   L   L   K   R   G   M   P   R   V   L   S   L   I   G   L   K   R   A   M   L  ·
 101 CTAAGAAACC AGGAGGGCCC GGCAAGAGCC GGGCTGTCTA TTTGCTAAAA CGCGGAATGC CCCGCGTGTT GTCCTTGATT GGACTTAAGA GGGCTATGTT
     GATTCTTTGG TCCTCCCGGG CCGTTCTCGG CCCGACAGAT AAACGATTTT GCGCCTTACG GGGCGCACAA CAGGAACTAA CCTGAATTCT CCCGATACAA
                                                                                C
     · S   L   I   D   G   K   G   P   I   R   F   V   L   A   L   L   A   F   F   R   F   T   A   I   A   P   T   R   A   V   L   D   R
 201 GAGCCTGATC GACGGCAAGG GGCCAATACG ATTTGTGTTG GCTCTCTTGG CGTTCTTCAG GTTCACAGCA ATTGCTCCGA CCCGAGCAGT GCTGGATCGA
     CTCGGACTAG CTGCCGTTCC CCGGTTATGC TAAACACAAC CGAGAGAACC GCAAGAAGTC CAAGTGTCGT TAACGAGGCT GGGCTCGTCA CGACCTAGCT
                                            C
                                                                                                                 NS3 Cleavage
                                                                                                                 ~~~~~~
       W   R   G   V   N   K   Q   T   A   M   K   H   L   L   S   F   K   K   E   L   G   T   L   T   S   A   I   N   R   R   S   S   K   Q ·
 301 TGGAGAGGTG TGAACAAACA AACAGCGATG AAACACCTTC TGAGTTTCAA GAAGGAACTA GGGACCTTGA CCAGTGCTAT CAATCGGCGG AGCTCAAAGC
     ACCTCTCCAC ACTTGTTTGT TTGTCGCTAC TTTGTGGAAG ACTCAAAGTT CTTCCTTGAT CCCTGGAACT GGTCACGATA GTTAGCCGCC TCGAGTTTCG
                                                                             FMDV2A
```

```
                                        9AA C Signal
            NS3 Cleavage                                                                Gag
            ~~~~~~~~~~~~                                                                ~~~~~~~~~~
           · K  K  R   G  G  K   T  G  I   A  V  I   N  F  D   L  L  K   L  A  G   D  V  E   S  N   P  G  P   M  G  A  R ·
       401 AGAAAAAGCG GGGCGGAAAG ACAGGTATTG CTGTGATCAA TTTTGACCTG TTAAAACTGG CCGGGGACGT CGAAAGCAAC CCCGGTCCGA TGGGCGCTAG
           TCTTTTTCGC CCCGCCTTTC TGTCCATAAC GACACTAGTT AAAACTGGAC AATTTTGACC GGCCCCTGCA GCTTTCGTTG GGGCCAGGCT ACCCGCGATC
                                                                                           Gag
           · N  S  V   L  S  G  K   K  A  D   E  L  E   K  I  R   L  R  P  G   G  K  K   K  Y  M   L  K  H   V  V  W  A
       501 GAATAGCGTG CTTAGTGGCA AAAAGGCTGA TGAACTTGAG AAGATCCGGC TCCGTCCGGG CGGGAAGAAG AAGTATATGT TGAAACATGT CGTGTGGGCC
           CTTATCGCAC GAATCACCGT TTTTCCGACT ACTTGAACTC TTCTAGGCCG AGGCAGGCCC GCCCTTCTTC TTCATATACA ACTTTGTACA GCACACCCGG
                                                                                           Gag
           · A  N  E   L  D  R  F   G  L  A   E  S  L   L  E  N   K  E  G  C   Q  K  I   L  S  V   L  A  P   L  V  P  T  G ·
       601 GCCAACGAGT TAGATAGGTT TGGGCTAGCA GAGTCATTGC TCGAAAACAA GGAAGGATGT CAGAAGATAC TAAGTGTCCT GGCACCTTTG GTACCCACGG
           CGGTTGCTCA ATCTATCCAA ACCCGATCGT CTCAGTAACG AGCTTTTGTT CCTTCCTACA GTCTTCTATG ATTCACAGGA CCGTGGAAAC CATGGGTGCC
                                                                                           Gag
           · S  E  N   L  K  S   L  Y  N  T   V  C  V   I  W  C   T  H  A  E   E  K  V   K  H  T   E  E  A  K   Q  I  V ·
       701 GGTCTGAGAA CTTAAAGAGT CTGTATAACA CTGTGTGCGT GATCTGGTGC ATTCACCCCG AAGAGAAAGT GAAGCACACC GAAGAAGCTA AGCAAATAGT
           CCAGACTCTT GAATTTCTCA GACATATTGT GACACACGCA CTAGACCACG TAAGTGGCGC TTCTCTTTCA CTTCGTGTGG CTTCTTCGAT TCGTTTATCA
                                                                                           Gag
           · Q  R  H   L  V  V  E   T  G  T   A  E  T   M  P  K  T   S  R  P   T  A  P   S  S  G  R   G  G  N   Y  P  V
       801 GCAGAGACAT TTGGTCGTGG AAACCGGGAC CGCCGAGACT ATGCCCAAAA CATCCCGTCC AACCGCTCCA AGTAGTGGAA GAGGAGGTAA CTACCCCGTT
           CGTCTCTGTA AACCAGCACC TTTGGCCCTG GCGGCTCTGA TACGGGTTTT GTAGGGCAGG TTGGCGAGGT TCATCACCTT CTCCTCCATT GATGGGGCAA
                                                                                           Gag
           · Q  Q  I  G   C  N  Y   V  H  L   P  L  S  P   R  T  L   N  A  W   V  K  L  I   E  E  K   K  F  G   A  E  V  V ·
       901 CAGCAAATCG GGGGAATTA CGTGCATCTC CCTTTGTCAC CAAGGACCCT CAATGCATGG GTCAAACTCA TCGAGGAAAA GAAGTTCGGA GCGGAAGTGG
           GTCGTTTAGC CCCCCTTAAT GCACGTAGAG GGAAACAGTG GTTCCTGGGA GTTACGTACC CAGTTTGAGT AGCTCCTTTT CTTCAAGCCT CGCCTTCACC
                                                                                           Gag
           · P  G  F   Q  A  L   S  E  G  C   T  P  Y   D  I  N   Q  M  L  N   C  V  G   D  H  Q   A  A  M  Q   I  I  R ·
      1001 TCCCAGGGTT CCAGGCACTG AGTGAAGGGT GCACTCCCTA TGACATCAAC CAGATGCTTA ACTGCGTCGG CGACCATCAG GCCGCGATGC AGATTATTCG
           AGGGTCCCAA GGTCCGTGAC TCACTTCCCA CGTGAGGGAT ACTGTAGTTG GTCTACGAAT TGACGCAGCC GCTGGTAGTC CGGCGCTACG TCTAATAAGC
                                                                                           Gag
           · D  I  I   N  E  E  A   A  D  W   D  L  Q   H  P  Q  P   A  P  Q   Q  G  Q   L  R  E  P   S  G  S   D  I  A
      1101 GGACATAATC AACGAGGAGG CTGCAGACTG GGATTTGCAG CACCCCCAAC CCGCCCCTCA GCAAGGGCAG CTAAGGGAGC CTTCCGGCAG CGACATAGCT
           CCTGTATTAG TTGCTCCTCC GACGTCTGAC CCTAAACGTC GTGGGGGTTG GGCGGGGAGT CGTTCCCGTC GATTCCCTCG GAAGGCCGTC GCTGTATCGA
                                                                                           Gag
           G  T  T  S   S  V  D   E  Q  I   Q  W  M  Y   R  Q  Q   N  P  I   P  V  G  N   I  Y  R   R  W  I   Q  L  G  L ·
      1201 GGGACTACTA GCTCCGTGGA TGAACAGATT CAATGGATGT ACAGACAAGA GAATCCGATC CCCGTTGGCA ACATCTACCG GCGCTGGATT CAACTCGGAC
           CCCTGATGAT CGAGGCACCT ACTTGTCTAA GTTACCTACA TGTCTGTTCT CTTAGGCTAG GGCAACCGT TGTAGATGGC CGCGACCTAA GTTGAGCCTG
                                                                                           Gag
           · Q  K  C   V  R  M   Y  N  P  T   N  I  L   D  V  K   Q  G  P  K   E  P  F   Q  S  Y   V  D  R  F   Y  K  S ·
      1301 TTCAGAAGTG CGTCAGAATG TACAACCCCA CCAATATTCT GGATGTGAAA CAGGGGCCGA AAGAGCCCTT CAATCCTAC GTCGACCGTT CTACAAAAG
           AAGTCTTCAC GCAGTCTTAC ATGTTGGGGT GGTTATAAGA CCTACACTTT GTCCCCGGCT TTCTCGGGAA GTTAGGATG CAGCTGGCAA GATGTTTTC
```

```
                                                      Gag
              ·L  R   A   E   Q   T   D   A   A   V   K   N   W   M   T   Q   T   L   L   I   Q   N   A   N   P   D   C   K   L   V   L   K   G
      1401   TCTACGCGCC GAGCAGACCG ATGCCGGAGT GAAGAACTGG ATGACACAGA CGCTCCTGAT ACAGAATGCT AACCCTGATT GTAAACTCGT GCTGAAGGGC
             AGATGCGCGG CTCGTCTGGC TACGGCCGTCA CTTCTTGACC TACTGTGTCT GCGAGGACTA TGTCTTACGA TTGGGACTAA CATTTGAGCA CGACTTCCCG
                                                                                     Gag
               L   G   V   N   P   T   L   E   E   M   L   T   A   C   Q   G   S   V   G   G   P   G   Q   K   A   R   L   M   A   E   A   L   K   E   A·
      1501   TTAGGGGTAA ACCCAACGCT GGAAGAAATG TTAACCGCCT GCCAGGGAGT TGGTGGACCC GGACAGAAGG CCCGGCTAAT GGCCGAGGCG CTGAAAGAAG
             AATCCCCATT TGGGTTGCGA CCTTCTTTAC AATTGGCGGA CGGTCCCTCA ACCACCTGGG CCTGTCTTCC GGGCCGATTA CCGGCTCCGC GACTTTCTTC
                                                                    Gag
              ·L   A   P   V   P   I   P   F   A   A   A   Q   Q   R   G   P   R   K   P   I   K   C   W   N   C   G   K   E   G   H   S   A   K·
      1601   CATTGGCTCC AGTACCCATT CCTTTTGCTG CCGCACAACA GAGAGGTCCC CGTAAACCGA TCAAATGCTG GAACTGTGGG AAGGAGGGGC ACTCCGCTAA
             GTAACCGAGG TCATGGGTAA GGAAAACGAC GGCGTGTTGT CTCTCCAGGG GCATTTGGCT AGTTTACGAC CTTGACACCC TTCCTCCCCG TGAGGCGATT
                                                                                    Gag
              ·Q   C   R   A   P   R   R   Q   G   C   G   W   K   C   G   K   M   D   H   V   M   A   K   C   P   D   R   Q   A   G   F   L   G   L
      1701   ACAATGTCGA GCGCCTAGAC GTCAGGGGTG TTGGAAGTGT GGTAAAATGG ACCACGTTAA GGCCAAATGC CCCGACAGAC AAGCCGGGTT CCTCGGGTTA
             TGTTACAGCT CGCGGATCTG CAGTCCCCAC AACCTTCACA CCATTTTACC TGGTGCAATA CCGGTTTACG GGGCTGTCTG TTCGGCCCAA GGAGCCCAAT
                                                                        Gag
               G   P   W   G   K   K   P   R   N   F   P   M   A   Q   V   H   Q   G   L   T   P   T   A   P   P   E   D   P   A   V   D   L   L   K·
      1801   GGGCCTTGGG GAAAAAAGCC CAGAAACTTC CCAATGGCGC AAGTACACCA GGGCCTGACC CCGACCGCCC CCCAGAGGA CCCAGCCGTA GACCTCTTGA
             CCCGGAACCC CTTTTTTCGG GTCTTTGAAG GGTTACCGCG TTCATGTGGT CCCGGACTGG GGCTGGCGGG GGGGTCTCCT GGGTCGGCAT CTGGAGAACT
                                                                               Gag
              ·N   Y   M   Q   L   G   K   Q   Q   R   E   S   R   E   K   P   Y   K   E   V   T   E   D   L   L   H   L   N   S   L   F   G   G·
      1901   AAAACTATAT GCAGCTGGGG AAGCAGCAGC GCGAGAGTAG AGAGAAGCCC TACAAGGAGG TTACGGAAGA TCTGTTACAC CTTAATTCGT TATTTGGTGG
             TTTTGATATA CGTCGACCCC TTCGTCGTCG CGCTCTCATC TCTCTTCGGG ATGTTCCTCC AATGCCTTCT AGACAATGTG GAATTAAGCA ATAAACCACC
                                                                   FMDV2A                                          TM Domain WN E (split)
                                        Gag

```
GCCAGATGCT AGTCAAAGGT CTGACCTCGT AGTTTACACC CTTCGTCACT TCCTGCTCGA CTTGTGAGAA AACTTC
```

Construct 2

1. PIV-WN (ΔCprME)-SIV 9AA FMD Gag & Pr

RV230 9AA-FMD-GagPro
13059bp

2. Sequence of PIV-WN (ΔCprME)-SIV 9AA FMD Gag & Pr (partial).

```
                                                                                                          C
                                                                                                         ~~~~
                                  5' UTR
                                                                                                       M  S ·
  1 AGTAGTTCGC CTGTGTGAGC TGACAAACTT AGTAGTGTTT GTGAGGATTA ACAACAATTA ACACAGTGCG AGCTGTTTCT TAGCACGAAG ATCTCGATGT
    TCATCAAGCG GACACACTCG ACTGTTTGAA TCATCACAAA CACTCCTAAT TGTTGTTAAT TGTGTCACGC TCGACAAAGA TCGTGCTTC  TAGAGCTACA
                                                                  C
    · K   K   P   G   G   P   G   K   S   R   A   V   Y   L   L   K   R   G   M   P   R   V   L   S   L   I   G   L   K   R   A   M   L ·
101 CTAAGAAACC AGGAGGGCCC GGCAAGAGCC GGGCTGTCTA TTTGCTAAAA CGCGGAATGC CCCGCGTGTT GTCCTTGATT GGACTTAAGA GGGCTATGTT
    GATTCTTTGG TCCTCCCGGG CCGTTCTCGG CCCGACAGAT AAACGATTTT GCGCCTTACG GGGCGCACAA CAGGAACTAA CCTGAATTCT CCCGATACAA
                                                                  C
    · S   L   I   D   G   K   G   P   I   R   F   V   L   A   L   L   A   F   F   R   F   T   A   I   A   P   T   R   A   V   L   D   R
201 GAGCCTGATC GACGGCAAGG GGCCAATACG ATTTGTGTTG GCTCTCTTGG CGTTCTTCAG GTTCACAGCA ATTGCTCCGA CCCGAGCAGT GCTGGATCGA
    CTCGGACTAG CTGCCGTTCC CCGGTTATGC TAAACACAAC CGAGAGAACC GCAAGAAGTC CAAGTGTCGT TAACGAGGCT GGGCTCGTCA CGACCTAGCT
                                                                  C
                                                                                                       NS3 Cleavage
```

```
                W  R  G  V    N  K  Q  T  A  M    K  H  L  L    S  F  K    K  E  L    G  T  L  T    S  A  I    N  R  R    S  S  K  Q  ·
301  TGGAGAGGTG TGAACAAACA AACAGCGATG AAACACCTTC TGAGTTTCAA GAAGGAACTA GGGACCTTGA CCAGTGCTAT CAATCGGCGG AGCTCAAAGC
     ACCTCTCCAC ACTTGTTTGT TTGTCGCTAC TTTGTGGAAG ACTCAAAGTT CTTCCTTGAT CCCTGGAACT GGTCACGATA GTTAGCCGCC TCGAGTTTCG
                                                                                                      FMDV2A
            9AA C Signal
     ~~~~~~~~~~~~~~~~~~~~~~~~~~~~~~~
     NS3 Cleavage                                                                                                      Gag
     ~~~~~~~~~~~~                                                                                              ~~~~~~~~~~~~
     ·  K  K  R    G  G  K    T  G  I  A    V  I  N    F  D  L    L  K  L  A    G  D  V    E  S  N    P  G  P  M    G  A  R  ·
401  AGAAAAAGCG GGGCGGAAAG ACAGGTATTG CTGTGATCAA TTTTGACCTG TTAAAACTGG CCGGGGACGT CGAAAGCAAC CCCGGTCCGA TGGGCGCTAG
     TCTTTTTCGC CCCGCCTTTC TGTCCATAAC GACACTAGTT AAAACTGGAC AATTTTGACC GGCCCCTGCA GCTTTCGTTG GGGCCAGGCT ACCCGCGATC
                                                                Gag
     ·  N  S  V    L  S  G  K    K  A  D    E  L  E    K  I  R  L    R  P  G    G  K  K    K  Y  M  L    K  H  V    V  W  A  ·
501  GAATAGCGTG CTTAGTGGCA AAAAGGCTGA TGAACTTGAG AAGATCCGGC TCCGTCCGGC CGGGAAGAAG AAGTATATGT TGAAACATGT CGTGTGGGCC
     CTTATCGCAC GAATCACCGT TTTTCCGACT ACTTGAACTC TTCTAGGCCG AGGCAGGCCG CCCTTCTTC TTCATATACA ACTTTGTACA GCACACCCGG
                                                                Gag
     ·  A  N  E  L    D  R  F    G  L  A    E  S  L  L    E  N  K    E  G  C    Q  K  I  L    S  V  L    A  P  L    V  P  T  G  ·
601  GCCAACGAGT TAGATAGGTT TGGGCTAGCA GAGTCATTGC TCGAAAACAA GGAAGGATGT CAGAAGATAC TAAGTGTCCT GGCACCTTTG GTACCCACGG
     CGGTTGCTCA ATCTATCCAA ACCCGATCGT CTCAGTAACG AGCTTTTGTT CCTTCCTACA GTCTTCTATG ATTCACAGGA CCGTGGAAAC CATGGGTGCC
                                                                Gag
     ·  S  E  N    L  K  S    L  Y  N  T    V  C  V    I  H  A  E    E  K  V    K  H  T    E  E  A  K    Q  I  V  ·
701  GGTCTGAGAA CTTAAAGAGT CTGTATAACA CTGTGTGCGT GATCTGGTGC ATTCACGCCG AAGAGAAAGT GAAGCACACC GAAGAAGCTA AGCAAATAGT
     CCAGACTCTT GAATTTCTCA GACATATTGT GACACACGCA CTAGACCACG TAAGTGCGGC TTCTCTTTCA CTTCGTGTGG CTTCTTCGAT TCGTTTATCA
                                                                Gag
     ·  Q  R  H    L  V  V  E    T  G  T    A  E  T    M  P  K  T    S  R  P    T  A  P    S  S  G  R    G  G  N    Y  P  V
801  GCAGAGACAT TTGGTCGTGG AAACCGGGAC CGCCGAGACT ATGCCCAAAA CATCCCGTCC AACCGCTCCA AGTAGTGGAA GAGGAGGTAA CTACCCCGTT
     CGTCTCTGTA AACCAGCACC TTTGGCCCTG GCGGCTCTGA TACGGGTTTT GTAGGGCAGG TTGGCGAGGT TCATCACCTT CTCCTCCATT GATGGGGCAA
                                                                Gag
     Q  Q  I  G    G  N  Y    V  H  L    P  L  S  P    R  T  L    N  A  W    V  K  L  I    E  E  K    K  F  G    A  E  V  V  ·
901  CAGCAAATCG GGGGAATTA CGTGCATCTC CCTTTGTCAC CAAGGACCCT CAATGCATGG GTCAAACTGA TCGAGGAAAA GAAGTTCGGA GCGGAAGTGG
     GTCGTTTAGC CCCCCTTAAT GCACGTAGAG GGAAACAGTG GTTCCTGGGA GTTACGTACC CAGTTTGAGT AGCTCCTTTT CTTCAAGCCT CGCCTTCACC
                                                                Gag
     ·  P  G  F    Q  A  L    S  E  G  C    T  P  Y    D  I  N    Q  M  L  N    C  V  G    D  H  Q    A  A  M  Q    I  I  R  ·
1001 TCCCAGGGTT CCAGGCACTG AGTGAAGGGT GCACTCCCTA TGACATCAAC CAGATGCTTA ACTGCGTCGG CGACCATCAG GCCGCGATGC AGATTATTCG
     AGGGTCCCAA GGTCCGTGAC TCACTTCCCA CGTGAGGGAT ACTGTAGTTG GTCTACGAAT TGACGCAGCC GCTGGTAGTC CGGCGCTACG TCTAATAAGC
                                                                Gag
     ·  D  I  I    N  E  E  A    A  D  W    D  L  Q    H  P  Q  P    A  P  Q    Q  G  Q    L  R  E  P    S  G  S    D  I  A
1101 GGACATAATC AACGAGGAGG CTGCAGACTG GGATTTGCAG CACCCCCAAC CCGCCCCTCA GCAAGGGCAG CTAAGGGAGC CTTCGGCAG CGACATAGCT
     CCTGTATTAG TTGCTCCTCC GACGTCTGAC CCTAAACGTC GTGGGGGTTG GGCGGGGAGT CGTTCCCGTC GATTCCCTCG GAAGGCCGTC GCTGTATCGA
                                                                Gag
     G  T  T  S    S  V  D    E  Q  I    Q  W  M  Y    R  Q  Q    N  P  I    P  V  G  N    I  Y  R    R  W  I    Q  L  G  L  ·
1201 GGGACTACTA GCTCCGTGGA TGAACAGATT CAATGGATGT ACAGACAGCA GAATCCGATC CCCGTTGGCA ACATCTACCG GCGCTGGATT CAACTCGGAC
     CCCTGATGAT CGAGGCACCT ACTTGTCTAA GTTACCTACA TGTCTGTCGT CTTAGGCTAG GGGCAACCGT TGTAGATGGC CGCGACCTAA GTTGAGCCTG
```

```
                                                   Gag
              · Q  K  C    V  R  M   Y  N  P  T   N  I  L   D  V  K    Q  G  P   K  E  P  F   Q  S  Y    V  D  R  F   Y  K  S ·
       1301   TTCAGAAGTG CGTCAGAATG TACAACCCCA CCAATATTCT GGATGTGAAA CAGGGGCCGA AAGAGCCCTT TCAATCCTAC GTCGACCGTT TCTACAAAAG
              AAGTCTTCAC GCAGTCTTAC ATGTTGGGGT GGTTATAAGA CCTACACTTT GTCCCCGGCT TTCTCGGGAA AGTTAGGATG CAGCTGGCAA AGATGTTTTC
                                                                               Gag
              · L  R  A    E  Q  T  D   A  A  V    K  N  W    M  T  Q  T   L  L  I   Q  N  A   N  P  D   C   K  L  V   L  K  G
       1401   TCTACCGCGCC GAGCGACCG ATGCCGCAGT GAAGAACTGG ATGACACACA CGCTCCTGAT ACAGAATGCT AACCCTGATT GTAAACTCGT GCTGAAGGGC
              AGATGCGCGG CTCGTCTGGC TACGGCGTCA CTTCTTGACC TACTGTGTCT GCGAGGACTA TGTCTTACGA TTGGGACTAA CATTTGAGCA CGACTTCCCG
                                                                  Gag
                L  G  V  N    P  T  L    E  E  M    L  T  A  C    Q  G  V   G  G  P   G  Q  K  A   R  L  M   A  E  A    L  K  E  A ·
       1501   TTAGGGGTAA ACCCAACGCT GGAAGAAATG TTAACCGCCT GCCAGGGAGT TGGTGGACCC GGACAGAAGG CCCGGCTAAT GGCCGAGGCG CTGAAAGAAG
              AATCCCCATT TGGGTTGCGA CCTTCTTTAC AATTGGCGGA CGGTCCCTCA ACCACCTGGG CCTGTCTTCC GGGCCGATTA CCGGCTCCGC GACTTTCTTC
                                                          Gag
              · L  A  P    V  P  I    P  F  A  A   A  Q  Q   R  G  P    R  K  P  I   C  W    N  C  G   K  E  G  H   S  A  K ·
       1601   CATTGGCTCC AGTACCCATT CCTTTTGCTG CCGCACAACA GAGAGGTCCC CGTAAACCCA TCAAATGCTG AACTGTGGG AAGGAGGGGC ACTCCGCTAA
              GTAACCGAGG TCATGGGTAA GGAAAACGAC GGCGTGTTGT CTCTCCAGGG GCATTTGGCT AGTTTACGAC CTTGACACCC TTCCTCCCCG TGAGGCGATT
                                                                 Gag
                Q  C  R    A  P  R  R    Q  G  C    W  K  C    G  K  M  D   H  V  M    A  K  C    P  D  R  Q    A  G  F    L  G  L
       1701   ACAATGTCGA GCGCCTAGAC GTCAGGGGTG TTGGAAGTGT GGTAAAATGG ACCACGTTAA GGCCAAATGC CCCGACAGAC AAGCGGGGTT CCTCGGGTTA
              TGTTACAGCT CGCGGATCTG CAGTCCCCAC AACCTTCACA CCATTTTACC TGGTGCAATT CCGGTTTACG GGGCTGTCTG TTCGCCCCAA GGAGCCCAAT
                                                                      Gag
                G  P  W    G  K  K  F    R  N  F    P  M  A  Q    V  H  Q   G  L  T    P  T  A  P    P  E  D    P  A  V    D  L  L  K ·
       1801   GGGCCTTGGG GAAAAAAGCC CAGAAACTTC CCAATGGCGC AAGTACACCA GGGCCTGACC CCGACCGCCC CCCAGAGGA CCCAGCCGTA GACCTCTTGA
              CCCGGAACCC CTTTTTTCGG GTCTTTGAAG GGTTACCGCG TTCATGTGGT CCCGGACTGG GGCTGGCGGG GGGGTCTCCT GGGTCGGCAT CTGGAGAACT
                                                     Gag
              · N  Y  M    Q  L  G    K  Q  Q  R    E  S  R    E  K  P    Y  K  E  V   T  E  D    L  L  H   L  N  S  L   F  G  G ·
       1901   AAAACTATAT GCAGCTGGGG AAGCAGCAGC GCGAGAGTAG AGAGAAGCCC TACAAGGAGG TTACGGAAGA TCTGTTACAC CTTAATTCGT TATTTGGTGG
              TTTTGATATA CGTCGACCCC TTCGTCGTCG CGCTCTCATC TCTCTTCGGG ATGTTCCTCC AATGCCTTCT AGACAATGTG GAATTAAGCA ATAAACCACC
                                                                                                           FMDV2A
                        Gag                                                                          Pro
              · D  Q  N    F  D  L  L    K  L  A    G  D  V    E  S  N  P    G  P  V   L  E  L    R  Q  R  G    P  Q  R    Q  A  V
       2001   TGATCAGAAT TTCGACCTGC TTAAACTTGC TGGCGACGTT GAGTCAAATC CGGGCCCTGT GCTGGAGTTG AGACAGCGCG GGCCCCAGCG GCAGGCTGTT
              ACTAGTCTTA AAGCTGGACG AATTTGAACG ACCGCTGCAA CTCAGTTTAG GCCCGGGACA CGACCTCAAC TCTGTCGCGC CCGGGGTCGC CGTCCGACAA
                                                                          Pro
                Q  S  P  S    E  T  G    L  L  E    V  W  Q  D    G  P  R    D  G  Q    M  P  R  Q    T  G  G    F  F  R    P  W  S  M ·
       2101   CAGAGCCCAT CAGAGACGGG TCTACTTGAG GTGTGGCAGG ATGGCCCCGG TGATGGACAG ATGCCTCGCC AGACGGGAGG GTTCTTCCGA CCCTGGAGTA
              GTCTCGGGTA GTCTCTGCCC AGATGAACTC CACACCGTCC TACCGGGGCC ACTACCTGTC TACGGAGCGG TCTGCCCTCC CAAGAAGGCT GGGACCTCAT
                                                                                           Pro
              · G  K  E    A  P  Q    F  P  H  G    S  S  A    S  G  A    D  A  N  C    S  P  R    G  P  S    C  G  S  A    K  E  L ·
       2201   TGGGAAAGGA GGCCCCGCAG TTCCCTCATG GCTCTTCTCC CTCTGGCGCG GATGCCAATT GTAGCCCCCG AGGCCCTTCT TGCGGCTCAG CCAAGGAGCT
              ACCCTTTCCT CCGGGGCGTC AAGGGAGTAC CGAGAAGACG GAGACCGCGC CTACGGTTAA CATCGGGGGC TCCGGGAAGA ACGCCGAGTC GGTTCCTCGA
                                                                                           Pro
```

```
              ·  H  A  V    G  Q  A  A    E  R  K    Q  R  E    A  L  Q  G    G  D  R    G  F  A    A  P  Q  F    S  L  W    R  R  P
2301  GCACGCAGTG GGCCAGGCAG CAGAGCGAAA ACAGCGAGAA GCACTGCAGG GCGGTGACCG TGGTTTTGCC GCCCCACAAT TCAGTCTGTG GCGCCGACCT
      CGTGCGTCAC CCGGTCCGTC GTCTCGCGTT TGTCGCTCTT CGTGACGTCC CGCCACTGGC ACCAAAACGG CGGGGTGTTA AGTCAGACAC CGCGGCTGGA
                                                                                  Pro

V  V  T  A    H  I  E    G  Q  P    V  E  V  L    L  D  T    G  A  D    D  S  I  V    T  G  I    E  L  G    P  H  Y  T  ·
2401  GTCGTGACTG CTCATATCGA GGGTCAGCCC GTGGAGGTTT TACTGGACAC TGGCGCAGAC GATTCTATTG TGACTGGCAT TGAACTAGGC CCCCATTACA
      CAGCACTGAC GAGTATAGCT CCCAGTCGGG CACCTCCAAA ATGACCTGTG ACCGCGTCTG CTAAGATAAC ACTGACCGTA ACTTGATCCG GGGGTAATGT
                                                       Pro

·  P  K  I    V  G  G    I  G  G  F    I  N  T    K  E  Y    K  N  V  E    I  E  V    L  G  K    R  I  K  G    T  I  M  ·
2501  CTCCAAAAAT CGTAGGGGGG ATAGGAGGAT TTATCAACAC GAAGGAGTAT AAGAATGTGG AGATCGAGGT TCTCGGAAAA CGCATTAAGG GAACGATTAT
      GAGGTTTTTA GCATCCCCCC TATCCTCCTA AATAGTTGTG CTTCCTCATA TTCTTACACC TCTAGCTCCA AGAGCCTTTT GCGTAATTCC CTTGCTAATA
                                                                                                                       FMDV2A
                                                                Pro

·  T  G  D    T  P  I  N    I  F  G    R  N  L    L  T  A  L    G  M  S    L  N  L    N  F  D  L    I  K  L    A  G  D
2601  GACAGGCGAT ACACCCATTA ACATCTTTGG ACGCAATCTA CTTACGGCCC TCGGAATGAG CCTTAACCTC AACTTCGACT TACTCAAGCT CGCCGGAGAC
      CTGTCCGCTA TGTGGGTAAT TGTAGAAACC TGCGTTAGAT GAATGCCGGG AGCCTTACTC GGAATTGGAG TTGAAGCTGA ATGAGTTCGA GCGGCCTCTG
                                                                                                          TM domain WN E (split)
                                                                 preE/NS1 Sig
                          FMDV2A                                                                                                       NS1
         V  E  S  N    P  G  P    A  R  D    R  S  I  A    L  T  F    L  A  V    G  G  V  L    L  F  L    S  V  N    V  H  A  D  ·
2701  GTGGAGTCCA ATCCCGGCCC AGCCCGGGAC AGGTCCATAG CTCTCACGTT TCTCGCAGTT GGAGGAGTTC TGCTCTTCCT CTCCGTGAAC GTGCACGCTG
      CACCTCAGGT TAGGGCCGGG TCGGGCCCTG TCCAGGTATC GAGAGTGCAA AGAGCGTCAA CCTCCTCAAG ACGAGAAGGA GAGGCACTTG CACGTGCGAC
                                                                       NS1

·  T  G  C    A  I  D    I  S  R  Q    E  L  R    C  G  S    G  V  F  I    H  N  D    V  E  A    W  M  D  R    Y  K  Y  ·
2801  ACACTGGGTG TGCCATAGAC ATCAGCCGGC AAGAGCTGAG ATGTGGAAGT GGAGTGTTCA TACACAATGA TGTGGAGGCT TGGATGGACC GGTACAAGTA
      TGTGACCCAC ACGGTATCTG TAGTCGGCCG TTCTCGACTC TACACCTTCA CCTCACAAGT ATGTGTTACT ACACCTCCGA ACCTACCTGG CCATGTTCAT
                                                                        NS1

·  Y  P  E    T  P  Q  G    L  A  K    I  I  Q    K  A  H  K    E  G  V    C  G  L    R  S  V  S    R  L  E    H  Q  M
2901  TTACCCTGAA ACGCCACAAG GCCTAGCCAA GATCATTCAG AAAGCTCATA AGGAAGGAGT GTGCGGTCTA CGATCAGTTT CCAGACTGGA GCATCAAATG
      AATGGGACTT TGCGGTGTTC CGGATCGGTT CTAGTAAGTC TTTCGAGTAT TCCTTCCTCA CACGCCAGAT GCTAGTCAAA GGTCTGACCT CGTAGTTTAC
                                                                                                                     NS1

W  E  A  V    K  D  E    L  N  T    L  L  K
3001  TGGGAAGCAG TGAAGGACGA GCTGAACACT CTTTTGAAG
      ACCCTTCGTC ACTTCCTGCT CGACTTGTGA GAAAACTTC
```

Construct 3
1. PIV-WN (ΔCprME)-SIV Anch Gag

2. Sequence of PIV-WN (ΔCprME)-SIV Anch Gag (partial).

```
                                                                                                        C
                                                                                                        ~~~~
                                        5' UTR
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                                                     M  S ·
  1   AGTAGTTCGC CTGTGTGAGC TGACAAACTT AGTAGTGTTT GTGAGGATTA ACAACAATTA ACACAGTGCG AGCTGTTTCT TAGCACGAAG ATCTCGATGT
      TCATCAAGCG GACACACTCG ACTGTTTGAA TCATCACAAA CACTCCTAAT TGTTGTTAAT TGTGTCACGC TCGACAAAGA ATCGTGCTTC TAGAGCTACA
                                                                                C
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                                               NS3 cleavage
                                                                                               ~~~~~~~~~~~~~~
      ·  K  K  P  G  G  P  G  K  S  R  A  V  Y  L  L  K  R  G  M  P  R  V  L  S  L  I  G  L  K  Q  K  K  R ·
  101 CTAAGAAACC AGGAGGCCCC GGCAAGAGCC GGGCTGTCTA TTTGCTAAAA CGCGGAATGC CCCGCGTGTT GTCCTTGATT GGACTTAAGC AAAAGAAGCG
      GATTCTTTGG TCCTCCGGGG CCGTTCTCGG CCCGACAGAT AAACGATTTT GCGCCTTACG GGGCGCACAA CAGGAACTAA CCTGAATTCG TTTTCTTCGC
                        C Anchor
      ~~~~~~~~~~~~~~~~~~~~~~~~~~~~~~~~~~~~~~~~~~~~~~~~~~~~~~~~~~~
      NS3 cleavage                                                                       FMDV2A
      ~                                                                                  ~~~~~~~~~~~~~~~~~~~~
      ·  G  G  K  T  G  I  A  V  M  I  G  L  I  A  S  V  G  A  N  F  D  L  L  K  L  A  G  D  V  E  S  N  P
  201 AGGCGGAAAG ACAGGTATTG CTGTGATGAT TGGCCTGATC GCCAGCGTAG GAGCAAATTT TGACCTGTTA AAACTGGCCG GGGACGTCGA AAGCAACCCC
      TCCGCCTTTC TGTCCATAAC GACACTACTA ACCGGACTAG CGGTCGCATC CTCGTTTAAA ACTGGACAAT TTTGACCGGC CCCTGCAGCT TTCGTTGGGG
      FMDV2A
      ~~~~~~
                                                                          Gag
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
         G  P  M  G  A  R  N  S  V  L  S  G  K  K  A  D  E  L  E  K  I  R  L  R  P  G  G  K  K  K  Y  M  L  K ·
  301 GGTCCGATGG GCGCTAGGAA TAGCGTGCTT AGTGGCAAAA AGGCTGATGA ACTTGAGAAG ATCCGGCTCC GTCCGGGCGG GAAGAAGAAG TATATGTTGA
```

```
     CCAGGCTACC CGCGATCCTT ATCGCACGAA TCACCGTTTT TCCGACTACT TGAACTCTTC TAGGCCGAGG CAGGCCCGCC CTTCTTCTTC ATATACAACT
                                                                     Gag
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
        · H  V  V   W  A  A   N  E  L  D   R  F  G   L  A  E   S  L  L  E  N   K  E  G  C   Q   K  I  L  S   V  L  A ·
 401  AACATGTCGT GTGGGCCGCC AACGAGTTAG ATAGGTTTGG GCTAGCAGAG TCATTGCTCG AAAACAAGGA AGGATGTCAG AAGATACTAA GTGTCCTGGC
      TTGTACAGCA CACCCGGCGG TTGCTCAATC TATCCAAACC CGATCGTCTC AGTAACGAGC TTTTGTTCCT TCCTACAGTC TTCTATGATT CACAGGACCG
                                                                     Gag
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
        · P  L  V    P  T  G  S   E  K  L   K  S  L   Y  N  T  V   C  V  I   W  C  I   H  A  E  E   K  V  K   H  T  E
 501  ACCTTTGGTA CCCACGGGGT CTGAGAACTT AAAGAGTCTG TATAACACTG TGTGCGTGAT CTGGTGCATT CACGCCGAAG AGAAAGTGAA GCACACCGAA
      TGGAAACCAT GGGTGCCCCA GACTCTTGAA TTTCTCAGAC ATATTGTGAC ACACGCACTA GACCACGTAA GTGCGGCTTC TCTTTCACTT CGTGTGGCTT
                                                                     Gag
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
         E  A  K  Q   I  V  Q   R  E  L   V  V  E  T   G  T  A   E  T  M   P  K  T  S   R  P  T    A  P  S   S  G  R  G ·
 601  GAAGCTAAGC AAATAGTGCA GAGACATTTG GTCGTGGAAA CCGGGACCGC CGAGACTATG CCCAAAACAT CCCGTCCAAC CGCTCCAAGT AGTGGAAGAG
      CTTCGATTCG TTTATCACGT CTCTGTAAAC CAGCACCTTT GGCCCTGGCG GCTCTGATAC GGGTTTTGTA GGGCAGGTTG GCGAGGTTCA TCACCTTCTC
                                                                     Gag
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
        · G  N  Y   P  V  Q   Q  I  G  G   N  Y  V   H  L  P   L  S  P  R   T  L  N   A  W  V   K  L  I  E   E  K  K  ·
 701  GAGGTAACTA CCCCGTTCAG CAAATCGGGG GAATTACGT GCATCTCCCT TTGTCACCAA GGACCCTCAA TGCATGGGTC AAACTCATCG AGGAAAAGAA
      CTCCATTGAT GGGGCAAGTC GTTTAGCCCC CCTTAATGCA CGTAGAGGGA AACAGTGGTT CCTGGGAGTT ACGTACCCAG TTTGAGTAGC TCCTTTTCTT
                                                                     Gag
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
        · F  G  A   E  V  V  P   G  F  Q   A  L  S   E  G  C  T   P  Y  D   I  N  Q   M  L  N  C   V  G  D   H  Q  A
 801  GTTCGGAGCG GAAGTGGTCC CAGGGGTTCCA GGCACTGAGT GAAGGGGTGCA CTCCCTATGA CATCAACCAG ATGCTTAACT GCGTCGGCGA CCATCAGGCC
      CAAGCCTCGC CTTCACCAGG GTCCCAAGGT CCGTGACTCA CTTCCCCACGT GAGGGATACT GTAGTTGGTC TACGAATTGA CGCAGCCGCT GGTAGTCCGG
                                                                     Gag
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
         A  M  Q  I   I  R  D   I  I  N   E  E  A  A   D  W  D   L  Q  H    P  Q  P  A   P  Q  Q    G  Q  L   R  E  P  S ·
 901  GCGATGCAGA TTATTCGGGA CATAATCAAC GAGGAGGCTG CAGACTGGGA TTTGCAGCAC CCCCAACCCG CCCCTCAGCA AGGGCAGCTA AGGGAGCCTT
      CGCTACGTCT AATAAGCCCT GTATTAGTTG CTCCTCCGAC GTCTGACCCT AAACGTCGTG GGGGTTGGGC GGGGAGTCGT TCCCGTCGAT TCCCTCGGAA
                                                                     Gag
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
        · G  S  D    I  A  G   T  T  S  S   V  D  E   Q  I  Q   W  M  Y  R   Q  Q  N    P  I  P   V  G  N  I   Y  R  R ·
1001  CCGGCAGCGA CATAGCTGGG ACTACTAGCT CCGTGGATGA ACAGATTCAA TGGATGTACA GACAGCAGAA TCCGATCCCC GTTGGCAACA TCTACCGGCG
      GGCCGTCGCT GTATCGACCC TGATGATCGA GGCACCTACT TGTCTAAGTT ACCTACATGT CTGTCGTCTT AGGCTAGGGG CAACCGTTGT AGATGGCCGC
                                                                     Gag
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
        · W  I  Q    L  G  L  Q   K  C  V   R  M  Y   N  P  T  N   I  L  D   V  K  Q    G  P  K  E    P  F  Q    S  Y  V
1101  CTGGATTCAA CTCGGACTTC AGAAGTGCGT CAGAATGTAC AACCCCACCA ATATTCTGGA TGTGAAACAG GGGCCGAAAG AGCCCTTTCA ATCCTACGTC
      GACCTAAGTT GAGCCTGAAG TCTTCACGCA GTCTTACATG TTGGGGTGGT TATAAGACCT ACACTTTGTC CCCGGCTTTC TCGGGAAAGT TAGGATGCAG
                                                                     Gag
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
         D  R  F  Y   K  S  L   R  A  E    Q  T  D  A    A  V  K    N  W  M    T  Q  T  L    L  I  Q    N  A  N    P  D  C  K ·
1201  GACCGTTTCT ACAAAAGTCT ACGCGCCGAG CAGACCGATG CCGCAGTGAA GAACTGGATG ACACAGACGC TCCTGATACA GAATGCTAAC CCTGATTGTA
      CTGGCAAAGA TGTTTTCAGA TGCGCGGCTC GTCTGGCTAC GGCGTCACTT CTTGACCTAC TGTGTCTGCG AGGACTATGT CTTACGATTG GGACTAACAT
                                                                     Gag
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
        · L  V  L    K  G  L    G  V  N  P    T  L  E    E  M  L    T  A  C  Q    G  V  G    G  P  G    Q  K  A  R    L  M  A ·
1301  AACTCGTGCT GAAGGGCTTA GGGGTAAACC CAACGCTGGA AGAAATGTTA ACCGCCTGCC AGGGAGTTGG TGGACCCGGA CAGAAGGCCC GGCTAATGGC
      TTGAGCACGA CTTCCCGAAT CCCCATTTGG GTTGCGACCT TCTTTACAAT TGGCGGACGG TCCCTCAACC ACCTGGGCCT GTCTTCCGGG CCGATTACCG
                                                                     Gag
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
```

```
            · E  A  L  K  E  A  L  A  ?  V   P  I  P  F  A  A  A   Q  Q  R   G  P  R   K  P  I  K   C  W  N   C  G  K
      1401  CGAGGCGCTG AAAGAAGCAT TGGCTCCAGT ACCCATTCCT TTTGCTGCCG CACAACAGAG AGGTCCCCGT AAACCGATCA AATGCTGGAA CTGTGGGAAG
            GCTCCGCGAC TTTCTTCGTA ACCGAGGTCA TGGGTAAGGA AAACGACGGC GTGTTGTCTC TCCAGGGGCA TTTGGCTAGT TTACGACCTT GACACCCTTC
                                                            Gag
            ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
              E  G  H  S   A  K  Q   C  R  A   P  R  R  Q   G  C  W   K  C  G   K  M  D  H   V  M  A  K  C  P   D  R  Q  A  ·
      1501  GAGGGGCACT CCGCTAAACA ATGTCGAGCG CCTAGACGTC AGGGGTGTTG GAAGTGTGGT AAAATGGACC ACGTTATGGC CAAATGCCCC GACAGACAAG
            CTCCCCGTGA GGCGATTTGT TACAGCTCGC GGATCTGCAG TCCCCACAAC CTTCACACCA TTTTACCTGG TGCAATACCG GTTTACGGGG CTGTCTGTTC
                                                            Gag
            ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
            · G  F  L   G  L  G   P  W  G  K   K  P  R   N  F  P   M  A  Q  V   H  Q  G   L  T  P   T  A  P  P   E  D  P  ·
      1601  CCCGGGTTCCT CGGGTTAGGG CCTTGGGGAA AAAGCCCAAG AAACTTCCCA ATGGCGCAAG TACACCAGGG CCTGACCCCG ACCGCCCCCC CAGAGGACCC
            GGCCCAAGGA GCCCAATCCC GGAACCCCTT TTTCGGGTTC TTTGAAGGGT TACCGCGTTC ATGTGGTCCC GGACTGGGGC TGGCGGGGGG GTCTCCTGGG
                                                            Gag
            ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
            · A  V  D   L  L  K  N   Y  M  Q   L  G  K   Q  Q  R  E   S  R  E   K  P  Y   K  E  V  T   E  D  L    L  H  L
      1701  AGCCGTAGAC CTCTTGAAAA ACTATATGCA GCTGGGGAAG CAGCAGCGCG AGAGTAGAGA GAAGCCCTAC AAGGAGGTTA CGGAAGATCT GTTACACCTT
            TCGGCATCTG GAGAACTTTT TGATATACGT CGACCCCTTC GTCGTCGCGC TCTCATCTCT CTTCGGGATG TTCCTCCAAT GCCTTCTAGA CAATGTGGAA
                                                     FMDV2A                                        pre E/NS1 signal
                                                                                                  ~~~~~~~~~~~~~~~~
                  Gag                                                                                Transmembrane domain of WNV E
              (split)                                                                               ~~~~~~~~~~~~~~~~~~~~~~~~~~~~~~
            ~~~~~~~~~~~~~~~~~~~~~~~~~~~~~~~~~~~~~~~~~~~~~~
              N  S  L  F  G  G  D  Q  N  F   D  L  L  K  L  A  G   D  V  E   S  N  P  G   P  A  R   D  R  S   I  A  L  T  ·
      1801  AATTCGTTAT TGGTGGTGA TCAGAATTTC GACCTGCTTA AACTTGCTGG CGACGTTGAG TCAAATCCGG GCCCTGCCCG GGACAGGTCC ATAGCTCTCA
            TTAAGCAATA AACCACCACT AGTCTTAAAG CTGGACGAAT TTGAACGACC GCTGCAACTC AGTTTAGGCC CGGGACGGGC CCTGTCCAGG TATCGAGAGT
                Transmembrane domain of WNV E (split)
            ~~~~~~~~~~~~~~~~~~~~~~~~~~~~~~~~~~~~~~~~~~~~~~~~~~                ~~~~~~~~~~~~~~~~~~~~~~~~~~~~~~~~~~~~~~~~~~~~~~
                                                                                                NS1
            · F  L  A   V  G  G   V  L  L  F   L  S  V   N  V  H   A  D  T  G   C  A  I   D  I  S   R  Q  E  L   R  C  G  ·
      1901  CGTTTCTCGC AGTTGGAGGA GTTCTGCTCT TCCTCTCCGT GAACGTGCAC GCTGACACTG GGTGTGCCAT AGACATCAGC CGGCAAGAGC TGAGATGTGG
            GCAAAGAGCG TCAACCTCCT CAAGACGAGA AGGAGAGGCA CTTGCACGTG CGACTGTGAC CCACACGGTA TCTGTAGTCG GCCGTTCTCG ACTCTACACC
                                                                       NS1
            ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
            · S  G  V   F  I  H  N   D  V  E   A  W  M   D  R  Y  K   Y  Y  P   E  T  P   Q  G  L  A   K  I  I   Q  K  A
      2001  AAGTGGAGTG TTCATACACA ATGATGTGGA GGCCTGGATG GACCGGTACA AGTATTACCC TGAAACGCCA CAAGGCCTAG CCAAGATCAT TCAGAAAGCT
            TTCACCTCAC AAGTATGTGT TACTACACCT CCGGACCTAC CTGGCCATGT TCATAATGGG ACTTTGCGGT GTTCCGGATC GGTTCTAGTA AGTCTTTCGA
                                                                               NS1
            ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
               H  K  E  G   V  C  G   L  R  S   V  S  R  L   E  H  Q   M  W  E   A  V  K  D   E  L  N   T  L  L   K
      2101  CATAAGGAAG GACTGTGCGG TCTACGATCA GTTCCAGAC TGGAGCATCA AATGTGGGAA GCAGTGAAGG ACGAGCTGAA CACTCTTTTG AAG
            GTATTCCTTC CTGACACGCC AGATGCTAGT CAAGGTCTG ACCTCGTAGT TTACACCCTT CGTCACTTCC TGCTCGACTT GTGAGAAAAC TTC
```

Construct 4
1. PIV-WN (ΔCprME)-SIV Anch Gag &Pro

2. Sequence of PIV-WN (ΔCprME)-SIV Anch Gag & Pro (partial).

```
                                              C
                     5' UTR
    ~~~~~~~~~~~~~~~~~~~~~~~~~~~~~~~~~~~~~~~~~~~~~~~~~~~~~~~~~~~~~~~~~~~~~~~~~~~~~~
                                                                               M  S ·
  1 AGTAGTTCGC CTGTGTGAGC TGACAAACTT AGTAGTGTTT GTGAGGATTA ACAACAATTA ACACAGTGCG AGCTGTTTCT TAGCACGAAG ATCTCGATGT
    TCATCAAGCG GACACACTCG ACTGTTTGAA TCATCACAAA CACTCCTAAT TGTTGTTAAT TGTGTCACGC TCGACAAAGA ATCGTGCTTC TAGAGCTACA
                                                                                          NS3 cleavage
                                                                                          ~~~~~~~~~~~~~~~
                    C
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
    · K   K   P    G   G   P    G   K   S   R    A   V   Y    L   L   K   R   G   M   P    R   V   I    S   L   I    G   L   K   Q    K   K   R ·
101 CTAAGAAACC AGGAGGGCCC GGCAAGAGCC GGGCTGTCTA TTTGCTAAAA CGCGGAATGC CCCGCGTGTT GTCCTTGATT GGACTTAAGC AAAAGAAGCG
    GATTCTTTGG TCCTCCCGGG CCGTTCTCGG CCCGACAGAT AAACGATTTT GCGCCTTACG GGGCGCACAA CAGGAACTAA CCTGAATTCG TTTTCTTCGC
                         C Anchor
    NS3 cleavage                                                                 FMDV2A
    ~                                                                            ~~~~~~~~~~~~~~~~~~~~~~~~~~~~~~~
    · G  G   K    T   G   I   A    V   M   I    G   L   I    A   S   V   G    A   N   F    D   L   L    K   L   A   G    D   V   E    S   N   P
201 AGGCGGAAAG ACAGGTATTG CTGTGATGAT TGGCCTGATC GCCAGCGTAG GAGCAAATTT TGACCTGTTA AAACTGGCCG GGGACGTCGA AAGCAACCCC
    TCCGCCTTTC TGTCCATAAC GACACTACTA ACCGGACTAG CGGTCGCATC CTCGTTTAAA ACTGGACAAT TTTGACCGGC CCCTGCAGCT TTCGTTGGGG
    FMDV2A
```

```
                                                           Gag
         G   P   M   G   A   R   N   S   V   L   S   G   K   K   A   D   E   L   E   K   I   R   L   R   P   G   G   K   K   K   Y   M   L   K  ·
   301   GGTCCGATGG GCGCTAGGAA TAGCGTGCTT AGTGGCAAAA AGGCTGATGA ACTTGAGAAG ATCCGGCTCC GTCCGGGCGG GAAGAAGAAG TATATGTTGA
         CCAGGCTACC CGCGATCCTT ATCGCACGAA TCACCGTTTT TCCGACTACT TGAACTCTTC TAGGCCGAGG CAGGCCCGCC CTTCTTCTTC ATATACAACT
                                                           Gag
       ·  H   V   V   W   A   A   N   E   L   D   R   F   G   L   A   E   S   L   L   E   N   K   E   G   C   Q   K   I   L   S   V   L   A  ·
   401   AACATGTCGT GTGGGCCGCC AACGAGTTAG ATAGGTTTGG GCTAGCAGAG TCATTGCTCG AAAACAAGGA AGGATGTCAG AAGATACTAA GTGTCCTGGC
         TTGTACAGCA CACCCGGCGG TTGCTCAATC TATCCAAACC CGATCGTCTC AGTAACGAGC TTTTGTTCCT TCCTACAGTC TTCTATGATT CACAGGACCG
                                                           Gag
       ·  P   L   V   P   T   G   S   E   N   L   K   S   L   Y   N   T   V   C   V   I   W   C   I   H   A   E   E   K   V   K   H   T   E  ·
   501   ACCCTTGGTA CCCACGGGGT CTGAGAACTT AAAGAGTCTG TATAACACTG TGTGCGTGAT CTGGTGCATT CACGCCGAAG AGAAAGTGAA GCACACCGAA
         TGGGAAACCAT GGGTGCCCCA GACTCTTGAA TTTCTCAGAC ATATTGTGAC ACACGCACTA GACCACGTAA GTGCGGCTTC TCTTTCACTT CGTGTGGCTT
                                                           Gag
       ·  E   A   K   Q   I   V   Q   R   H   L   V   V   E   T   G   T   A   E   T   M   P   K   T   S   R   P   T   A   P   S   S   G   R   G  ·
   601   GAAGCTAAGC AAATAGTGCA GAGACATTTG GTCGTGGAAA CCGGGACCGC CGAGACTATG CCCAAAACAT CCCGTCCAAC CGCTCCAAGT AGTGGAAGAG
         CTTCGATTCG TTTATCACGT CTCTGTAAAC CAGCACCTTT GGCCCTGGCG GCTCTGATAC GGGTTTTGTA GGGCAGGTTG GCGAGGTTCA TCACCTTCTC
                                                           Gag
       ·  G   N   Y   P   V   Q   Q   I   G   G   N   Y   V   H   L   P   L   S   P   R   T   L   N   A   W   V   K   L   I   E   E   K   K  ·
   701   GAGGTAACTA CCCCGTTCAG CAAATCGGGG GGAATTACGT GCATCTCCCT TTGTCACCAA GGACCCTCAA TGCATGGGTC AAACTCATCG AGGAAAAGAA
         CTCCATTGAT GGGGCAAGTC GTTTAGCCCC CCTTAATGCA CGTAGAGGGA AACAGTGGTT CCTGGGAGTT ACGTACCCAG TTTGAGTAGC TCCTTTTCTT
                                                           Gag
       ·  F   G   A   E   V   V   P   G   F   Q   A   L   S   E   G   C   T   P   Y   D   I   N   Q   M   L   N   C   V   G   D   H   Q   A  ·
   801   GTTCGGAGCG GAAGTGGTCC CAGGGTTCCA GGCACTGAGT GAAGGGTGCA CTCCCTATGA CATCAACCAG ATGCTTAACT GCGTCGGCGA CCATCAGGCC
         CAAGCCTCGC CTTCACCAGG GTCCCAAGGT CCGTGACTCA CTTCCCACGT GAGGGATACT GTAGTTGGTC TACGAATTGA CGCAGCCGCT GGTAGTCCGG
                                                           Gag
       ·  A   M   Q   I   I   R   D   I   I   N   E   E   A   A   D   W   D   L   Q   H   P   Q   P   A   P   Q   Q   G   Q   L   R   E   P   S  ·
   901   GCGATGCAGA TTATTCGGGA CATAATCAAC GAGGAGGCTG CAGACTGGGA TTTGCAGCAC CCCCAACCCG CCCCTCAGCA AGGGCAGCTA AGGGAGCCTT
         CGCTACGTCT AATAAGCCCT GTATTAGTTG CTCCTCCGAC GTCTGACCCT AAACGTCGTG GGGGTTGGGC GGGGAGTCGT TCCCGTCGAT TCCCTCGGAA
                                                           Gag
       ·  G   S   D   I   A   G   T   T   S   S   V   D   E   Q   I   Q   W   M   Y   R   Q   Q   N   P   I   P   V   G   N   I   Y   R   R  ·
  1001   CCGGCAGCGA CATAGCTGGG ACTACTAGCT CCGTCGATGA ACAGATTCAA TGGATGTACA GACAGCAGAA TCCGATCCCC GTTGGCAACA TCTACCGGCG
         GGCCGTCGCT GTATCGACCC TGATGATCGA GGCACCTACT TGTCTAAGTT ACCTACATGT CTGTCGTCTT AGGCTAGGGG CAACCGTTGT AGATGGCCGC
                                                           Gag
       ·  W   I   Q   L   G   L   Q   K   C   V   R   M   Y   N   P   T   N   I   L   D   V   K   Q   G   P   K   E   P   F   Q   S   Y   V  ·
  1101   CTGGATTCAA CTCGGACTTC AGAAGTGCGT CAGAATGTAC AACCCCACCA ATATTCTGGA TCTGAAACAG GGGCCGAAAG AGCCCTTTCA ATCCTACGTC
         GACCTAAGTT GAGCCTGAAG TCTTCACGCA GTCTTACATG TTGGGGTGGT TATAAGACCT AGACTTTGTC CCCGGCTTTC TCGGGAAAGT TAGGATGCAG
                                                           Gag
       ·  D   R   F   Y   K   S   L   R   A   E   Q   T   D   A   A   V   K   N   W   M   T   Q   T   L   L   I   Q   N   A   N   P   D   C   K  ·
  1201   GACCGTTTCT ACAAAAGTCT ACGCGCCGAG CAGACCGATG CCGCAGTGAA GAACTGGATG ACACAGACGC TCCTGATACA GAATGTCAAC CCTGATTGTA
         CTGGCAAAGA TGTTTTCAGA TGCGCGGCTC GTCTGGCTAC GGCGTCACTT CTTGACCTAC TGTGTCTGCG AGGACTATGT CTTACGATTG GGACTAACAT
                                                           Gag
```

```
                  · L  V  L    K  G  L    G  V  N  P    T  L  E    E  M  L    T  A  C  Q    G  V  G    G  P  G    Q  K  A  R    L  M  A·
      1301 AACTCGTGCT GAAGGGCTTA GGGGTAAACC CAACGCTGGA AGAAATGTTA ACCGCCTGCC AGGGAGTTGG TGGACCCGGA CAGAAGGCCC GGCTAATGGC
           TTGAGCACGA CTTCCCGAAT CCCCATTTGG GTTGCGACCT TCTTTACAAT TGGCGGACGG TCCCTCAACC ACCTGGGCCT GTCTTCCGGG CCGATTACCG
                                                                               Gag

· E  A  L    K  E  A  L    A  P  V    P  I  P    F  A  A  A    Q  Q  R    G  P  R    K  P  I  K    C  W  N    C  G  K
      1401 CCAGGCGCTG AAAGAAGCAT TGGCTCCAGT ACCCATTCCT TTTGCTGCCG CACAACAGAG AGGTCCCCGT AAACCGATCA AATGCTGGAA CTGTGGGAAG
           GGTCCGCGAC TTTCTTCGTA ACCGAGGTCA TGGGTAAGGA AAACGACGGC GTGTTGTCTC TCCAGGGGCA TTTGGCTAGT TTACGACCTT GACACCCTTC
                                                                               Gag

E  G  H  S    A  K  Q    C  R  A    P  R  R  Q    G  C  W    K  C  G    K  M  D  H    V  M  A    K  C  P    D  R  Q  A·
      1501 GAGGGGCACT CCCTAAACA ATGTCGAGCG CCTAGACGTC AGGGGTGTTG GAAGTGTGGT AAAATGGACC ACGTTATGGC CAAATGCCCC GACAGACAAG
           CTCCCCGTGA GGGCGATTTGT TACAGCTCGC GGATCTGCAG TCCCCACAAC CTTCACACCA TTTTACCTGG TGCAATACCG GTTTACGGGG CTGTCTGTTC
                                                                               Gag

· G  F  L    G  L  G    P  W  G  K    K  P  R    N  F  P    M  A  Q  V    H  Q  G    L  T  P    T  A  P  P    E  D  P·
      1601 CCGGGTCCT CGGGTTAGGG CCTTGGGGAA AAAAGCCCAG AAACTTCCCA ATGGCGCAAG TACACCAGGG CCTGACCCCG ACCGCCCCCC CAGAGGACCC
           GGCCCAAGGA GCCCAATCCC GGAACCCCTT TTTTCGGGTC TTTGAAGGGT TACCGCGTTC ATGTGGTCCC GGACTGGGGC TGGCGGGGGG GTCTCCTGGG
                                                                               Gag

· A  V  D    L  L  K  N    Y  M  Q    L  G  K    Q  Q  R  E    S  R  E    K  P  Y    K  E  V  T    E  D  L    L  H  L
      1701 AGCCGTAGAC CTCTTGAAAA ACTATATGCA GCTGGGGAAG CAGCAGCGCG AGAGTAGAGA GAAGCCCTAC AAGGAGGTTA CGGAAGATCT GTTACACCTT
           TCGGCATCTG GAGAACTTTT TGATATACGT CGACCCCTTC GTCGTCGCGC TCTCATCTCT CTTCGGGATG TTCCTCCAAT GCCTTCTAGA CAATGTGGAA
                                                                                                                    FMDV2A
                                                                              Gag                                                                                              Pro

N  S  L  F    G  G  D    Q  N  F    D  L  L  K    L  A  G    D  V  E    S  N  P  G    P  V  L    E  L  R    Q  R  G  P·
      1801 AATTCGTTAT TTGGTGGTGA TCAGAATTTC GACCTGCTTA AACTTGCTGG CGACGTTGAG TCAAATCCGG GCCCTGTGCT GGAGTTGAGA CAGCGCGGGC
           TTAAGCAATA AACCACCACT AGTCTTAAAG CTGGACGAAT TTGAACGACC GCTGCAACTC AGTTTAGGCC CGGGACACGA CCTCAACTCT GTCGCGCCCG
                                                                               Pro

· Q  R  Q    A  V  Q    S  P  S  E    T  G  L    L  E  V    W  Q  D  G    P  R  D    G  Q  M    P  R  Q  T    G  G  F·
      1901 CCCAGCGGCA GGCTGTTCAG AGCCCATCAG ACAGGGTCT ACTTGAGGTG TGGCAGGATG GCCCCCGTGA TCGACAGATG CCTCGCCAGA CGGGAGGGTT
           GGGTCGCCGT CCGACAAGTC TCGGGTAGTC TGTCCCAGA TGAACTCCAC ACCGTCCTAC CGGGGGCACT ACCTGTCTAC GGAGCGGTCT GCCCTCCCAA
                                                                               Pro

· F  R  P    W  S  M  G    K  E  A    P  Q  F    P  H  G  S    S  A  S    G  A  D    A  N  C  S    P  R  G    P  S  C
      2001 CTTCCGACCC TGGAGTATGG GAAAGGAGGC CCCGCAGTTC CCTCATGGCT CTTCTGCCTC TGGCGCGGAT GCCAATTGTA GCCCCCGAGG CCCTTCTTGC
           GAAGGCTGGG ACCTCATACC CTTTCCTCCG GGGCGTCAAG GGAGTACCGA GAAGACGGAG ACCGCGCCTA CGGTTAACAT CGGGGGCTCC GGGAAGAACG
                                                                               Pro

G  S  A  K    E  L  H    A  V  G    Q  A  A  E    R  K  Q    R  E  A    L  Q  G  G    D  R  G    F  A  A    P  Q  F  S·
      2101 GGCTCAGCCA AGGAGCTGCA CGCAGTGGGC CAGGCAGCAG AGCGCAAACA GCGAGAAGCA CTGCAGGGCG GTGACCGTGG TTTTGCCGCC CCACAATTCA
           CCGAGTCGGT TCCTCGACGT GCGTCACCCG GTCCGTCGTC TCGCGTTTGT CGCTCTTCGT GACGTCCCGC CACTGGCACC AAAACGGCGG GGTGTTAAGT
                                                                               Pro

· L  W  R    R  P  V    V  T  A  H    I  E  G    Q  P  V    E  V  L  L    D  T  G    A  D  D    S  I  V  T    G  I  E·
      2201 GTCTGTGGCG CCGACCTGTC GTGACTGCTC ATATCGAGGG TCAGCCCGTG GAGGTTTTAC TGGACACTGG CGCAGACGAT TCTATTGTGA CTGGCATTGA
           CAGACACCGC GGCTGGACAG CACTGACGAG TATAGCTCCC AGTCGGGCAC CTCCAAAATG ACCTGTGACC GCGTCTGCTA AGATAACACT GACCGTAACT
                                                                               Pro

· L  G  P    H  Y  T  P    K  I  V    G  G  I    G  G  F  I    N  T  K    E  Y  K    N  V  E  I    E  V  L    G  K  R
```

```
2301 ACTAGGCCCC CATTACACTC CAAAAATCGT AGGGGGGATA GGAGGATTTA TCAACACGAA GGAGTATAAG AATGTGGAGA TCGAGGTTCT CGGAAAACGC
     TGATCCGGGG GTAATGTGAG GTTTTTAGCA TCCCCCCTAT CCTCCTAAAT AGTTGTGCTT CCTCATATTC TTACACCTCT AGCTCCAAGA GCCTTTTGCG
                                                                                                     FMDV2A
                                                    Pro
             I  K  G  T  I  M  T  G  D  T   P  I  N  I  F  G  R   N  L  L   T  A  L  G  M  S  L  N  L  N   F  D  L  L  ·
2401 ATTAAGGGAA CGATTATGAC AGGCGATACA CCCATTAACA TCTTTGGACG CAATCTACTT ACGGCCCTCG GAATGAGCCT AACCTCAAC TTCGACTTAC
     TAATTCCCTT GCTAATACTG TCCGCTATGT GGGTAATTGT AGAAACCTGC GTTAGATGAA TGCCGGGAGC CTTACTCGGA ATTGGAGTTG AAGCTGAATG
                                            pre E/NS1 signal
                    FMDV2A                                              Transmembrane domain of WNV E (split)
     · K  L  A   G  D  V   E  S  N  P  G  P  A   R  D  R   S  I  A  L   T  F  L   A  V  G   G  V  L  L   F  L  S  ·
2501 TCAAGCTCGC CGGAGACGTG GAGTCCAATC CCGGCCCAGC CCGGGACAGG TCCATAGCTC TCACGTTTCT CGCAGTTGGA GGAGTTCTGC TCTTCCTCTC
     AGTTCGAGCG GCCTCTGCAC CTCAGGTTAG GGCCGGGTCG GGCCCTGTCC AGGTATCGAG AGTGCAAAGA GCGTCAACCT CCTCAAGACG AGAAGGAGAG
     Transmembrane domain of WNV E (split)
                                                                              NS1
     · V  N  V   E  A  D  T   G  C  A   I  D  I   S  R  Q  E   L  R  C   G  S  G   V  F  I  H   N  D  V   E  A  W  ·
2601 CGTGAACGTG CACGCTGACA CTGGGTGTGC CATAGACATC AGCCGGCAAG AGCTGAGATG TGGAAGTGGA GTGTTCATAC ACAATGATGT GGAGGCTTGG
     GCACTTGCAC GTGCGACTGT GACCCACACG GTATCTGTAG TCGGCCGTTC TCGACTCTAC ACCTTCACCT CACAAGTATG TGTTACTACA CCTCCGAACC
                                                              NS1
     M  D  R  Y  K  Y  Y   P  E  T   P  Q  G  L   A  K  I   I  Q  K   A  H  K  E   G  V  C   G  L  R   S  V  S  R  ·
2701 ATGGACCGGT ACAAGTATTA CCCTGAAACG CCACAAGGCC TAGCCAAGAT CATTCAGAAA GCTCATAAGG AAGGAGTGTG CGGTCTACGA TCAGTTTCCA
     TACCTGGCCA TGTTCATAAT GGGACTTTGC GGTGTTCCGG ATCGGTTCTA GTAAGTCTTT CGAGTATTCC TTCCTCACAC GCCAGATGCT AGTCAAAGGT
                                                              NS1
     · L  E  H   Q  M  W   E  A  V  K   D  E  L   N  T  L   L  K
2801 GACTGGAGCA TCAAATGTGG GAAGCAGTGA AGGACGAGCT GAACACTCTT TTGAAG
     CTGACCTCGT AGTTTACACC CTTCGTCACT TCCTGCTCGA CTTGTGAGAA AACTTC
```

Construct 5
1. PIV-WN (ΔCprME)-SIV FMD2a Gag

2. Sequence of PIV-WN (ΔCprME)-SIV FMD2a Gag

```
                                                                                                                   C
                                           5' UTR
                                                                                                       M   S  ·
  1 AGTAGTTCGC CTGTGTGAGC TGACAAACTT AGTAGTGTTT GTGAGGATTA ACAACAATTA ACACAGTGCG AGCTGTTTCT TAGCACGAAG ATCTCGATGT
    TCATCAAGCG GACACACTCG ACTGTTTGAA TCATCACAAA CACTCCTAAT TGTTGTTAAT TGTGTCACGC TCGACAAAGA ATCGTGCTTC TAGAGCTACA
                                                                                                     C
                                                                                      NS3 cleavage
    ·  K   K   P   G   G   P   G   K   S   R   A   V   Y   L   L   K   R   G   M   P   R   V   L   S   L   I   G   L   K   Q   K   K   R ·
101 CTAAGAAACC AGGAGGGCCC GGCAAGAGCC GGGCTGTCTA TTTGCTAAAA CGCGGAATGC CCCGCGTGTT GTCCTTGATT GGACTTAAGC AAAAGAAGCG
    GATTCTTTGG TCCTCCCGGG CCGTTCTCGG CCCGACAGAT AAACGATTTT GCGCCTTACG GGGCGCACAA CAGGAACTAA CCTGAATTCG TTTTCTTCGC
                            FMDV2A
    NS3 cleavage                                                            Gag
    · N   F   D   L   L   K   L   A   G   D   V   E   S   N   P   G   P   M   G   A   R   N   S   V   L   S   G   K   K   A   D   E   L
201 AAATTTTGAC CTGTTAAAAC TGGCCGGGGA CGTCGAAAGC AACCCCGGTC CGATGGGCGC TAGGAATAGC GTGCTTAGTG GCAAAAAGGC TGATGAACTT
    TTTAAAACTG GACAATTTTG ACCGGCCCCT GCAGCTTTCG TTGGGGCCAG GCTACCCGCG ATCCTTATCG CACGAATCAC CGTTTTTCCG ACTACTTGAA
                                                                    Gag
    E   K   I   R   L   R   P   G   G   K   K   K   Y   M   L   K   H   V   V   W   A   A   N   E   L   D   R   F   G   L   A   E   S   L ·
301 GAGAAGATCC GGCTCCGTCC GGGCGGGAAG AAGAAGTATA TGTTGAAACA TGTCGTGTGG GCCGCCAACG AGTTAGATAG GTTTGGGCTA GCAGAGTCAT
    CTCTTCTAGG CCGAGGCAGG CCCGCCCTTC TTCTTCATAT ACAACTTTGT ACAGCACACC CGGCGGTTGC TCAATCTATC CAAACCCGAT CGTCTCAGTA
                                                                    Gag
```

```
      · L  E  N   K  E  G   C  Q  K   I  L  S   V  L  A  P   L  V  P   T  G  S   E  N  L   K  S  L   Y  N   T  V  C·
 401  TGCTCGAAAA CAAGGAAGGA TGTCAGAAGA TACTAAGTGT CCTGGCACCT TTGGTACCCA CGGGGTCTGA GAACTTAAAG AGTCTGTATA ACACTGTGTG
      ACGAGCTTTT GTTCCTTCCT ACAGTCTTCT ATGATTCACA GGACCGTGGA AACCATGGGT GCCCCAGACT CTTGAATTTC TCAGACATAT TGTGACACAC
                                                          Gag
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

· V  I  W   C  I  H   A  E  E   K  V  K   H  T  E  E   A  K  Q   I  V  Q   R  H  L   V  V   E  T  G   T  A  E
 501  CGTGATCTGG TGCATTCACG CCGAAGAGAA AGTGAAGCAC ACCGAAGAAG CTAAGCAAAT AGTCCAGAGA CATTTGGTCG TGGAAACCGG GACCGCCGAG
      GCACTAGACC ACGTAAGTGC GGCTTCTCTT TCACTTCGTG TGGCTTCTTC GATTCGTTTA TCAGGTCTCT GTAAACCAGC ACCTTTGGCC CTGGCGGCTC
                                                          Gag
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

T  M  P   K  T  S   R  P  T  A   P  S  S   G  R  G   G  N  Y  P   V  Q  Q   I  G  G   N   Y  V  H   L  P  L  S·
 601  ACTATGCCCA AAACATCCCG TCCAACCGCT CCAAGTAGTG GAAGAGGAGG TAACTACCCC GTTCAGCAAA TCGGGGGGAA TTACGTGCAT CTCCCTTTGT
      TGATACGGGT TTTGTAGGGC AGGTTGGCGA GGTTCATCAC CTTCTCCTCC ATTGATGGGG CAAGTCGTTT AGCCCCCCTT AATGCACGTA GAGGGAAACA
                                                          Gag
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

· P  R  T   L  N  A   W  V  K  L   I  E  E   K  K  F   G  A  E   V  V  P  G   F  Q  A   L  S  E   G  C  T  P·
 701  CACCAAGGAC CCTCAATGCA TGGGTCAAAC TCATCGAGGA AAAGAAGTTC GGAGCGGAAG TGGTCCCAGG GTTCCAGGCA CTGAGTGAAG GGTGCACTCC
      GTGGTTCCTG GGAGTTACGT ACCCAGTTTG AGTAGCTCCT TTTCTTCAAG CCTCGCCTTC ACCAGGGTCC CAAGGTCCGT GACTCACTTC CCACGTGAGG
                                                          Gag
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

· Y  D  I   N  Q  M   L  N  C   V  G  D   H  Q  A  A  M   Q  I  I   R  D  I   I  N  E  E   A  A  D   W  D  L
 801  CTATGACATC AACCAGATGC TTAACTGCGT CGGCGACCAT CAGGCCGCGA TGCAGATTAT TCGGGACATA ATCAACGAGG AGGCTGCAGA CTGGGATTTG
      GATACTGTAG TTGGTCTACG AATTGACGCA GCCGCTGGTA GTCCGGCGCT ACGTCTAATA AGCCCTGTAT TAGTTGCTCC TCCGACGTCT GACCCTAAAC
                                                          Gag
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

Q  H  P  Q   P  A  P   Q  Q  G   Q  L  R  E   P  S  G   S  D  I   A  G  T  T   S  S  V   D  E  Q   I  Q  W  M·
 901  CAGCACCCCC AACCCGCCCC TCAGCAAGGG CAGCTAAGGG AGCCTCCGG  CAGCGGACATA GCTGACGGACTA CTAGCTCCGT GGATGAACAG ATTCAATGGA
      GTCGTGGGGG TTGGGCGGGG AGTCGTTCCC GTCGATTCCC TCGGAAGGCC GTCGCTGTAT CGACCCTGAT GATCGAGGCA CCTACTTGTC TAAGTTACCT
                                                          Gag
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

· Y  R  Q   Q  N  P   I  P  V   G  N  I   Y  R  R  W   I  Q  L   G  L  Q   K  C  V   R  M  Y   N  P  T   N  I·
1001  TGTACAGACA GCAGAATCCG ATCCCCGTTG GCAACATCTA CCGGCGCCAC GAATTCAACTCG GACTTCAGAA GTGCGTCAGA ATGTACAACC CCACCAATAT
      ACATGTCTGT CGTCTTAGGC TAGGGGCAAC CGTTGTAGAT GGCCGCGGTG CTTAAGTTGAGC CTGAAGTCTT CACGCAGTCT TACATGTTGG GGTGGTTATA
                                                          Gag
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

· L  D  V   K  Q  G   P  K  E  P   F  Q  S   Y  V  D  R   F  Y  K   S  L  R   A  E  Q  T   D  A  A   V  K  N
1101  TCTGGATGTG AAACAGGGGC CGAAAGAGCC CTTTCAATCC TACGTCGACC GTTTCTACAA AAGTCTACGC GCCGAGCAGA CCGATGCCGC AGTGAAGAAC
      AGACCTACAC TTTGTCCCCG GCTTTCTCGG GAAAGTTAGG ATGCAGCTGG CAAAGATGTT TTCAGATGCG CGGCTCGTCT GGCTACGGCG TCACTTCTTG
                                                          Gag
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

W  M  T  Q   T  L  L   I  Q  N   A  N  P  D   C  K  L   V  L  K   G  L  G   V  N  P  T   L  E  E   M  L  T  A·
1201  TGGATGACAC AGACGCTCCT GATACAGAAT GCTAACCCTG ATTGTAAACT CGTGCTGAAG GGCTTAGGGG TAAACCCAAC GCTGGAAGAA ATGTTAACCG
      ACCTACTGTG TCTGCGAGGA CTATGTCTTA CGATTGGGAC TAACATTTGA GCACGACTTC CCGAATCCCC ATTTGGGTTG CGACCTTCTT TACAATTGGC
                                                          Gag
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

· C  Q  G   V  G  G   P  G  Q  K   A  R  L   M  A  E   A  L  K  E   A  L  A   P  V  P   I  P  F   A  A  A  Q·
1301  CCTGCCAGGG AGTGGTGGA  CCCGGACAGA AGGCCCGGCT AATGGCCGAG GCGCTGAAAG AAGCATTGGC TCCAGTACCC ATTCCTTTTG CTGCCGCACA
      GGACGGTCCC TCAACCACCT GGGCCTGTCT TCCGGGCCGA TTACCGGCTC CGCGACTTTC TTCGTAACCG AGGTCATGGG TAAGGAAAAC GACGGCGTGT
                                                          Gag
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~

· Q  R  G   P  R  K  P   I  K  C   W  N  C   G  K  E  G   H  S  A   K  Q  C   R  A  P  R   R  Q  G   C  W  K
1401  ACAGAGAGGT CCCCGTAAAC CGATCAAATG CTGGAACTGT GGGAAGGAGG GGCACTCCGC TAAACAATGT CGAGCGCCTA GACGTCAGGG GTGTTGGAAG
      TGTCTCTCCA GGGGCATTTG GCTAGTTTAC GACCTTGACA CCCTTCCTCC CCGTGAGGCG ATTTGTTACA GCTCGCGGAT CTGCAGTCCC CACAACCTTC
```

```
                                       Gag
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~
       C  G  K  M  D  H  V  M  A  K   C  P  D  R   Q  A  G   F  L  G   L  G  P  W   G  K  K    P  R  N   F  P  M  A ·
1501  TGTGGTAAAA TGGACCACGT TATGGCCAAA TGCCCCGACA GACAAGCCGG GTTCCTCGGG TTAGGGCCTT GGGGAAAAAA GCCCAGAAAC TTCCCAATGG
      ACACCATTTT ACCTGGTGCA ATACCGGTTT ACGGGGCTGT CTGTTCGGCC CAAGGAGCCC AATCCCGGAA CCCCTTTTTT CGGGTCTTTG AAGGGTTACC
                                          Gag
      ~~~~~~~~~~~~~~~~~~~~~~~~~~~~~~~~~~~~~~~~~~~~~~~~~~~~~~~~~~~~~~~~~~~~~~~~~~~~~~~~~~~~~~
      · Q  V  H   Q  G  L   T  P  T  A    P  P  E   D  P  A   V  D  L  L   K  N  Y   M  Q  L    G  K  Q  Q   R  E  S ·
1601  CGCAAGTACA CCAGGGCCTG ACCCCGACCG CCCCCCCAGA GGACCCAGCC GTAGACCTCT TGAAAAACTA TATGCAGCTG GGGAAGCAGC AGCGCGAGAG
      GCGTTCATGT GGTCCCGGAC TGGGGCTGGC GGGGGGGTCT CCTGGGTCGG CATCTGGAGA ACTTTTTGAT ATACGTCGAC CCCTTCGTCG TCGCGCTCTC
                                                                                                           FMDV2A
                              Gag
      ~~~~~~~~~~~~~~~~~~~~~~~~~~~~~~~~~~~~~~~~~~~~~~~~~~~~~~~~~~~~~~~                                ~~~~~~~~~~~~~~~~~~~~~~~~~~~~
      · R  E  K    P  Y  K  E   V  T  E   D  L  L   H  L  N  S   L  F  G   G  D  Q   N  F  D  L   L  K  L   A  G  D
1701  TAGAGAGAAG CCCTACAAGG AGGTTACGGA AGATCTGTTA CACCTTAATT CGTTATTTGG TGGTGATCAG AATTTCGACC TGCTTAAACT TGCTGGCGAC
      ATCTCTCTTC GGGATGTTCC TCCAATGCCT TCTAGACAAT GTGGAATTAA GCAATAAACC ACCACTAGTC TTAAAGCTGG ACGAATTTGA ACGACCGCTG
                                                                        Transmembrane domain of WNV E (split)
                            pre E/NS1 signal                            ~~~~~~~~~~~~~~~~~~~~~~~~~~~~~~~~~~~~~~~~~~~~~~~
                            ~~~~~~~~~~~
        FMDV2A                                                                                              NS1
      ~~~~~~~~~~~~~~~~~~~                                                                                   ~~
        V  E  S  N   P  G  P   A  R  D   R  S  I  A   L  T  F   L  A  V   G  G  V  L   L  F  L   S  V  N   V  H  A  D ·
1801  GTTGAGTCAA ATCCGGGCCC TGCCCGGGAC AGGTCCCATAG CTCTCACGTT TCTCGCAGTT GGAGGAGTTC TGCTCTTCCT CTCCGTGAAC GTGCACGCTG
      CAACTCAGTT TAGGCCCGGG ACGGGCCCTG TCCAGGGTATC GAGAGTGCAA AGAGCGTCAA CCTCCTCAAG ACGAGAAGGA GAGGCACTTG CACGTGCGAC
                                                                          NS1
      · T  G  C   A  I  D   I  S  R  Q   E  L  R   C  G  S   G  V  F  I   H  N  D   V  E  A   W  M  D  R   Y  K  Y ·
1901  ACACTGGGTG TGCCATAGAC ATCAGCCGGC AAGAGCTGAG ATGTGGAAGT GGAGTGTTCA TACACAATGA TGTGGAGGCT TGGATGGACC GGTACAAGTA
      TGTGACCCAC ACGGTATCTG TAGTCGGCCG TTCTCGACTC TACACCTTCA CCTCACAAGT ATGTGTTACT ACACCTCCGA ACCTACCTGG CCATGTTCAT
                                                                       NS1
      · Y  P  E   T  P  Q  G   L  A  K   I  I  Q   K  A  H  K   E  G  V   C  G  L   R  S  V  S   R  L  E   H  Q  M
2001  TTACCCTGAA ACGGCACAAG GCCTAGCCAA GATCATTCAG AAAGCTCATA AGGAAGGAGT GTGCGGTCTA CGATCAGTTT CCAGACTGGA GCATCAAATG
      AATGGGACTT TGCCGTGTTC CGGATCGGTT CTAGTAAGTC TTTCGAGTAT TCCTTCCTCA CACGCCAGAT GCTAGTCAAA GGTCTGACCT CGTAGTTTAC
                                                              NS1
         W  E  A  V   K  D  E   L  N  T   L  L  K
2101  TGGGAAGCAG TGAAGGACGA GCTGAACACT CTTTTGAAG
      ACCCTTCGTC ACTTCCTGCT CGACTTGTGA GAAAACTTC
```

Construct 6
1. PIV-WN (ΔCprME)-SIV FMD2a Gag & Pr

DeleteC230FMD2AGag&Pr
13722 bp

2. Sequence of PIV-WN (ΔCprME)-SIV fmd2A Gag & Pr (partial).

```
                                                                                              C
                                                                                            ~~~~
                               5' UTR
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                                         M   S  ·
  1  AGTAGTTCGC CTGTGTGAGC TGACAAACTT AGTAGTGTTT GTGAGGATTA ACAACAATTA ACACAGTGCG AGCTGTTTCT TAGCACGAAG ATCTCGATGT
     TCATCAAGCG GACACACTCG ACTGTTTGAA TCATCACAAA CACTCCTAAT TGTTGTTAAT TGTGTCACGC TCGACAAAGA ATCGTGCTTC TAGAGCTACA
                                                                                           NS3 cleavage
                            C                                                             ~~~~~~~~~~~~~~~
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      ·  K   K   P    G   G   P    G   K   S    R   A   V    Y   L   L    K   R   G    M   P    R   V   L    S   L   I    G   L   K   Q    K   K   R ·
 101  CTAAGAAACC AGGAGGGCCC GGCAAGAGCC GGGCTGTCTA TTTGCTAAAA CGCGGAATGC CCCGCGTGTT GTCCTTGATT GGACTTAAGC AAAAGAAGCG
      GATTCTTTGG TCCTCCCGGG CCGTTCTCGG CCCGACAGAT AAACGATTTT GCGCCTTACG GGGCGCACAA CAGGAACTAA CCTGAATTCG TTTTCTTCGC
                                   FMDV2A
        NS3 cleavage                                                                       Gag
     ~~                                                                         ~~~~~~~~~~~~~~~~~~~~~~~~~~~~~~~~~~~~~~~
      ·  N   F   D    L   L   K   L    A   G   D    V   E   S    N   P   G   P    M   G   A    R   N   S    V   L   S   G    K   K   A    D   E   L
 201  AAATTTTGAC CTGTTAAAAC TGGCCGGGGA CGTCGAAAGC AACCCCGGTC CGATGGGCGC TAGGAATAGC GTGCTTAGTG GCAAAAAGGC TGATGAACTT
      TTTAAAACTG GACAATTTTG ACCGGCCCCT GCAGCTTTCG TTGGGGCCAG GCTACCCGCG ATCCTTATCG CACGAATCAC CGTTTTTCCG ACTACTTGAA
                                                                                  Gag
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
         E   K   I    R   L   R    P   G   G    K   K   K   Y    M   L   K   H    V   V   W    A   A   N   E    L   D   R    F   G   L    A   E   S   L  ·
```

```
                                                                                                              L  E  N  K  E  G  C  Q  K  I    L  S  V  L  A  P   L  V  P  T  G  S  E  N     L  K  S  L  Y  N  T  V  C
301 GAGAAGATCC GGCTCCGTCC GGGCGGGAAG AAGAAGTATA TGTTGAAACA TGTCGTGTGG GCCGCCAACG AGTTAGATAG GTTTGGGCTA GCAGAGTCAT
    CTCTTCTAGG CCGAGGCAGG CCCGCCCTTC TTCTTCATAT ACAACTTTGT ACAGCACACC CGGCGGTTGC TCAATCTATC CAAACCCGAT CGTCTCAGTA
                                                                                                         Gag

V  I  W   C  I  H  A  E  E  K   V  K  H    T  E  E  A  K  Q  I    V  Q  R   H  L  V  V   E  T  G    T  A  E
401 TGCTCGAAAA CAAGGAAGGA TGTCAGAAGA TACTAAGTGT CCTGGCACCT TTGGTACCCA CCGGGTCTGA GAACTTAAAG AGTCTGTATA ACACTGTGTG
    ACGAGCTTTT GTTCCTTCCT ACAGTCTTCT ATGATTCACA GGACCGTGGA AACCATGGGT GCCCCAGACT CTTGAATTTC TCAGACATAT TGTGACACAC
                                                                                                         Gag

V  I  W   C  I  H  A  E  E  K   V  K  H    T  E  E  A  K  Q  I    V  Q  R   H  L  V  V   E  T  G    T  A  E
501 CGTGATCTGG TGCATTCACG CCGAAGAGAA AGTGAAGCAC ACCGAAGAAG CTAAGCAAAT AGTGCAGAGA CATTTGGTCG TGCAAACCGG GACCGCCGAG
    GCACTAGACC ACGTAAGTGC GGCTTCTCTT TCACTTCGTG TGGCTTCTTC GATTCGTTTA TCACGTCTCT GTAAACCAGC ACCTTTGGCC CTGGCGGCTC
                                                                                                         Gag

T  M  P  K   T  S  R   P  T  A   P  S  S  G   R  G  G   N  Y  P   V  Q  Q  I  G  G  N    Y  V  H   L  P  L  S
601 ACTATGCCCA AAACATCCCG TCCAACCGCT CCAAGTAGTG GAAGAGGAGG TAACTACCCC GTTCAGCAAA TCGGGGGGAA TTACGTGCAT CTCCCTTTGT
    TGATACGGGT TTTGTAGGGC AGGTTGGCGA GGTTCATCAC CTTCTCCTCC ATTGATGGGG CAAGTCGTTT AGCCCCCCTT AATGCACGTA GAGGGAAACA
                                                                                                         Gag

P  R  T   L  N  A   W  V  K  L   I  E  E  K  K  F    G  A  E  V    V  P  G   F  Q  A   L  S  E  G   C  T  P
701 CACCAAGGAC CCTCAATGCA TGGGTCAAAC TCATCGAGGA AAAGAAGTTC GGAGCGGAAG TGGTCCCAGG GTTCCAGGCA CTGAGTGAAG GGTGCACTCC
    GTGGTTCCTG GGAGTTACGT ACCCAGTTTG AGTAGCTCCT TTTCTTCAAG CCTCGCCTTC ACCAGGGTCC CAAGGTCCGT GACTCACTTC CCACGTGAGG
                                                                                                         Gag

Y  D  I   N  Q  M  L   N  C  V   G  D  H   Q  A  A  M   Q  I  I    R  D  I   I  N  E  E   A  A  D   W  D  L
801 CTATGACATC AACCAGATGC TTAACTGCGT CGGCGACCAT CAGGCCGCGA TGCAGATTAT TCGGGACATA ATCAACGAGG AGGCTGCAGA CTGGGATTTG
    GATACTGTAG TTGGTCTACG AATTGACGCA GCCGCTGGTA GTCCGGCGCT ACGTCTAATA AGCCCTGTAT TAGTTGCTCC TCCGACGTCT GACCCTAAAC
                                                                                                         Gag

Q  H  P  Q   P  A  P   Q  Q  G   Q  L  R  E   P  S  G   S  D  I   A  G  T  T   S  S  V   D  E  Q   I  Q  W  M
901 CAGCACCCCC AACCCGCCCC TCAGCAAGGG CAGCTAAGGG AGCCTTCCGG CAGCGACATA GCTGGGACTA CTAGCTCCGT GGATGAACAG ATTCAATGGA
    GTCGTGGGGG TTGGGCGGGG AGTCGTTCCC GTCGATTCCC TCGGAAGGCC GTCGCTGTAT CGACCCTGAT GATCGAGGCA CCTACTTGTC TAAGTTACCT
                                                                                                         Gag

Y  R  Q   Q  N  P   I  P  V  G   N  I  Y   R  R  W   I  Q  L  G   L  Q  K   C  V  R   M  Y  N  P   T  N  I
1001 TGTACAGACA GCAGAATCCG ATCCCCGTTG GCAACATCTA CCGGCGCTGG ATTCAACTCG GACTTGCAAA GTGCGTCAGA ATGTACAACC CCACCAATAT
     ACATGTCTGT CGTCTTAGGC TAGGGGCAAC CGTTGTAGAT GGCCGCGACC TAAGTTGAGC CTGAAGTCTT CACGCAGTCT TACATGTTGG GGTGGTTATA
                                                                                                         Gag

L  D  V  K  Q  G  P   K  E  P    F  Q  S   Y  V  D  R   F  Y  K    S  L  R   A  E  Q  T   D  A  A   V  K  N
1101 TCTGGATGTG AAACAGGGGC CGAAAGAGCC CTTTCAATCC TACGTCGACC GTTTCTACAA AAGTCTACGC GCCAGCAGGA CCGATGCCGC AGTGAAGAAC
     AGACCTACAC TTTGTCCCCG GCTTTCTCGG GAAAGTTAGG ATGCAGCTGG CAAAGATGTT TTCAGATGCG CGGTCGTCCT GGCTACGGCG TCACTTCTTG
                                                                                                         Gag

W  M  T  Q   T  L  L   I  Q  N   A  N  P  D   C  K  L   V  L  K    G  L  G   V  N  P  T   L  E  E   M  L  T  A
1201 TGGATGACAC AGACGCTCCT GATACAGAAT GCTAACCCTG ATTGTAAACT CGTGCTGAAG GGCTTAGGGG TAAACCCAAC GCTGGAAGAA ATGTTAACCG
     ACCTACTGTG TCTGCGAGGA CTATGTCTTA CGATTGGGAC TAACATTTGA GCACGACTTC CCGAATCCCC ATTTGGGTTG CGACCTTCTT TACAATTGGC
                                                                                                         Gag

C  Q  G   V  G  G   P  G  Q  K   A  R  L   M  A  E   A  L  K  E   A  L  A   P  V  P   I  P  F  A   A  A  Q
1301 CCTGCCAGGG AGTTGGTGGA CCCGGACAGA AGGCCCGGCT AATGGCCGAG GCGCTGAAAG AAGCATTGGC TCCAGTACCC ATTCCTTTTG CTGCCGCACA
     GGACGGTCCC TCAACCACCT GGGCCTGTCT TCCGGGCCGA TTACCGGCTC CGCGACTTTC TTCGTAACCG AGGTCATGGG TAAGGAAAAC GACGGCGTGT
                                                                                                         Gag
```

```
                    Q  R  G   P  R  K  P   I  K  C   W  N  C   G  K  E  G   H  S  A   K  Q  C   R  A  P  R   R  Q  G   C  W  K
1401  ACAGAGAGGT CCCCGTAAAC CGATCAAATG CTGGAACTGT GGGAAGGAGG GGCACTCCGC TAAACAATGT CGAGCGCCTA GACGTCAGGG GTGTTGGAAG
      TGTCTCTCCA GGGGCATTTG GCTAGTTTAC GACCTTGACA CCCTTCCTCC CCGTGAGGCG ATTTGTTACA GCTCGCGGAT CTGCAGTCCC CACAACCTTC
                                                                                       Gag
        C  G  K  M   D  H  V   M  A  K   C  P  D  R   Q  A  G   F  L  G   L  G  P  W   G  K  K   P  R  N   F  P  M  A
1501  TGTGGTAAAA TGGACCACGT TATGGCCAAA TGCCCCGACA GACAAGCCGG GTTCCTCGGG TTAGGGCCTT GGGGAAAAAA GCCCAGAAAC TTCCCAATGG
      ACACCATTTT ACCTGGTGCA ATACCGGTTT ACGGGGCTGT CTGTTCGGCC CAAGGAGCCC AATCCCGGAA CCCCTTTTTT CGGGTCTTTG AAGGGTTACC
                                                                                       Gag
        Q  V  H   Q  G  L   T  P  T  A   P  P  E   D  P  A   V  D  L  L   L  K  N  Y   M  Q  L   G  K  Q  Q   R  E  S
1601  CGCAAGTACA CCAGGGCCTG ACCCCGACCG CCCCCCCAGA GGACCCAGCC GTAGACCTCT TGAAAAACTA TATGCAGCTG GGGAAGCAGC AGCGCGAGAG
      GCGTTCATGT GGTCCCGGAC TGGGGCTGGC GGGGGGGTCT CCTGGGTCGG CATCTGGAGA ACTTTTTGAT ATACGTCGAC CCCTTCGTCG TCGCGCTCTC
                                                                                                              FMDV2A

```
                                                                               pre E/NS1 signal
                                      FMDV2A                                   ~~~~~~~~~~
              Pro                ~~~~~~~~~~~~~~~~~~~~~~~~~~~~~~~~~~~~~~~~~~~~~
          of WNV E (split)                                                     Transmembrane domain
         L  L  T  A  L  G  M   S  L  N   L  N  F  D   L  L  K   L  A  G   D  V  E  S   N  P  G   P  A  R   D  R  S  I ·
    2401 CTACTTACGG CCCTCGGAAT GAGCCTTAAC CTCAACTTCG ACTTACTCAA GCTCGCCGGA GACGTGGAGT CCAATCCCGG CCCAGCCCGG GACAGGTCCA
         GATGAATGCC GGGAGCCTTA CTCGGAATTG GAGTTGAAGC TGAATGAGTT CGAGCGGCCT CTGCACCTCA GGTTAGGGCC GGGTCGGGCC CTGTCCAGGT Transmembrane domain of WNV E (split)
         ~~~~~~~~~~~~~~~~~~~~~~~~~~~~~~~~~~~~~~~~~~~~~~~~~~~~~~~
                                                                                    NS1
                                                                       ~~~~~~~~~~~~~~~~~~~~~~~~~~~~~~~~~~~~~~~~~~~
         · A  L  T   F  L  A   V  G  G  V   L  L  F   L  S  V   N  V  H  A   D  T  G   C  A  I   D  I  S  R   Q  E  L ·
    2501 TAGCTCTCAC GTTTCTCGCA GTTGGAGGAG TTCTGCTCTT CCTCTCCGTG AACGTGCACG CTGACACTGG GTGTGCCATA GACATCAGCC GGCAAGAGCT
         ATCGAGAGTG CAAAGAGCGT CAACCTCCTC AAGACGAGAA GGAGAGGCAC TTGCACGTGC GACTGTGACC CACACGGTAT CTGTAGTCGG CCGTTCTCGA
                                                                                              NS1
         ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
         · R  C  G   S  G  V  F   I  H  N   D  V  E   A  W  M  D   R  Y  K   Y  Y  P   E  T  P  Q   G  L  A   K  I  I
    2601 GAGATGTGGA AGTGGAGTGT TCATACACAA TGATGTGGAG GCTTGGATGG ACCGGTACAA GTATTACCCT GAAACGCCAC AAGGCCTAGC CAAGATCATT
         CTCTACACCT TCACCTCACA AGTATGTGTT ACTACACCTC CGAACCTACC TGGCCATGTT CATAATGGGA CTTTGCGGTG TTCCGGATCG GTTCTAGTAA
                                                                                              NS1
         ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
             Q  K  A  H   K  E  G   V  C  G   L  R  S  V   S  R  L   E  H  Q   M  W  E  A   V  K  D   E  L  N   T  L  L  K ·
    2701 CAGAAAGCTC ATAAGGAAGG AGTGTGCGGT CTACGATCAG TTTCCAGACT GGAGCATCAA ATGTGGGAAG CAGTGAAGGA CGAGCTGAAC ACTCTTTTGA
         GTCTTTCGAG TATTCCTTCC TCACACGCCA GATGCTAGTC AAAGGTCTGA CCTCGTAGTT TACACCCTTC GTCACTTCCT GCTCGACTTG TGAGAAAACT
                                                                                              NS1
         ~~
         · K
    2801 AG
         TC
```

Construct 7
1. PIV-WN (ΔCprME)-SIV Env

2. Sequence of PIV-WN (ΔCprME)-SIV Env (partial).

```
                                                              C
                       5' UTR                                ~~~
  ~~~~~~~~~~~~~~~~~~~~~~~~~~~~~~~~~~~~~~~~~~~~~~~~~~~~~~~~~~~~~~~~~~~~~~~
                                                                     M  S ·
  1 AGTAGTTCGC CTGTGTGAGC TGACAAACTT AGTAGTGTTT GTGAGGATTA ACAACAATTA ACACAGTGCG AGCTGTTTCT TAGCACGAAG ATCTCGATGT
    TCATCAAGCG GACACACTCG ACTGTTTGAA TCATCACAAA CACTCCTAAT TGTTGTTAAT TGTGTCACGC TCGACAAAGA ATCGTGCTTC TAGAGCTACA
                                        C
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~ NS3 cleavage
    ·  K  K  P  G  G  P  G  K  S  R  A  V  Y  L  L  K  R  G  M  P  R  V  L  S  L  I  G  L  K  Q  K  K  R ·
101 CTAAGAAACC AGGAGGGCCC GGCAAGAGCC GGGCTGTCTA TTTGCTAAAA CGCGGAATGC CCCGCGTGTT GTCCTTGATT GGACTTAAGC AAAAGAAGCG
    GATTCTTTGG TCCTCCCGGG CCGTTCTCGG CCCGACAGAT AAACGATTTT GCGCCTTACG GGGCGCACAA CAGGAACTAA CCTGAATTCG TTTTCTTCGC
    NS3 cleavage                                                            tpa
    ~                                                                ~~~~~~~~~~~~~~~~~~~~~~~~~~~~~~~~~~~~~~~~~
        partial C signal
    ~~~~~~~~~~~~~~~~~~~~~~~~~~~~~~~
    ·  G  G  K  T  G  I  A  V  I  M  D  A  M  K  R  G  L  C  C  V  L  L  L  C  G  A  V  F  V  T  T  T  E
201 AGGGGGCAAG ACTGGTATAG CTGTGATCAT GGACGCCATG AAGAGGGGAC TTTGTTGTGT GCTCCTGCTG TGCGGAGCTG TGTTCGTTAC AACAACGGAG
    TCCCCCGTTC TGACCATATC GACACTAGTA CCTGCGGTAC TTCTCCCCTG AAACAACACA CGAGGACGAC ACGCCTCGAC ACAAGCAATG TTGTTGCCTC
                                                                       Env
```

```
               tpa
      A  I  Y  C  T  Q  Y     V  T  V     F  Y  G  V     P  A  W     R  N  A     T  I  P  L     F  C  A     T  K  N     R  D  T  W  ·
 301  GCGATTTACT GCACCCAGTA TGTCACCGTG TTTTACGGTG TCCCCGCCTG GCGGAACGCC ACCATCCCTC TGTTTTGTGC CACCAAGAAT AGAGATACGT
      CGCTAAATGA CGTGGGTCAT ACAGTGGCAC AAAATGCCAC AGGGGCGGAC CGCCTTGCGG TGGTAGGGAG ACAAAACACG GTGGTTCTTA TCTCTATGCA
                                                                                            Env · G  T  T     Q  C  L     P  D  N  G     D  Y  S     E  L  A     L  N  V  T     E  S  F     D  A  W     E  N  T  V     T  E  Q ·
 401  GGGGCACCAC ACAATGCCTT CCCGATAATG GCGATTACTC TGAATTAGCC CTGAACGTCA CGGAAAGTTT TGATGCTTGG GAAAATACGG TTACCGAACA
      CCCCGTGGTG TGTTACGGAA GGGCTATTAC CGCTAATGAG ACTTAATCGG GACTTGCAGT GCCTTTCAAA ACTACGAACC CTTTTATGCC AATGGCTTGT
                                                                                            Env · A  I  E     D  V  W  Q     L  F  E     T  S  I     K  P  C  V     K  L  S     P  L  C     I  T  M  R     C  N  K     S  E  T
 501  GGCCATCGAA GATGTCTGGC AGTTATTCGA AACTAGTATC AAACCTTGCG TTAAGCTGAG TCCTTTGTGC ATAACGATGC GGTGCAACAA GAGCGAAACG
      CCGGTAGCTT CTACAGACCG TCAATAAGCT TTGATCATAG TTTGGAACGC AATTCGACTC AGGAAACACG TATTGCTACG CCACGTTGTT CTCGCTTTGC
                                                                                            Env D  K  W  G     L  T  K     S  S  T     T  T  A  S     T  T  T     T  T  A     P  A  K  I     D  M  V     N  E  T     S  S  C  I  ·
 601  GACAAATGGG GCTTAACCAA ATCTTCAACC ACCACCGCCT CCACCACTAC GACAACGCCA CCTGCCAAGA TCGACATGGT TAACGAAACC TCTAGTTGCA
      CTGTTTACCC CGAATTGGTT TAGAAGTTGG TGGTGGCGGA GGTGGTGATG CTGTTGCGGT GGACGGTTCT AGCTGTACCA ATTGCTTTGG AGATCAACGT
                                                                                            Env · T  H  D     N  C  T     G  L  E  Q     E  Q  M     I  G  C     K  F  N  M     T  G  L     K  R  D     K  T  K  E     Y  N  E ·
 701  TTACCCATGA CAACTGCACA GGCCTCGAAC AAGAACAAAT GATCGGCTGT AAATTCAATA TGACCGGACT GAAGAGAGAC AAGACAAAAG AGTACAACGA
      AATGGGTACT GTTGACGTGT CCGGAGCTTG TTCTTGTTTA CTAGCCGACA TTTAAGTTAT ACTGGCCTGA CTTCTCTCTG TTCTGTTTTC TCATGTTGCT
                                                                                            Env · T  W  Y     S  T  D  L     V  C  E     Q  G  N     S  T  D  N     E  S  R     C  Y  M     N  H  C  N     T  S  I     I  Q  E
 801  GACTTGGTAC AGCACCGACT TAGTGTGTGA GCAGGGGAAC TCAACCGATA ACGAGTCCCG CTGTTATATG AACCACTGCA ATACGAGCAT CATCCAAGAG
      CTGAACCATG TCGTGGCTGA ATCACACACT CGTCCCCTTG AGTTGGCTAT TGCTCAGGGC GACAATATAC TTGGTGACGT TATGCTCGTA GTAGGTTCTC
                                                                                            Env S  C  D  K     H  Y  W     D  T  I     R  F  R  Y     C  A  P     P  G  Y     A  L  L  R     C  N  D     T  N  Y     S  G  F  M ·
 901  TCGTGCGACA AACACTATTG GGACACTATC CGATTTAGGT ACTGTGCCCC GCCGGGCTAT GCGCTTCTGC GTTGTAATGA TACCAATTAC AGTGGGTTCA
      AGCACGCTGT TTGTGATAAC CCTGTGATAG GCTAAATCCA TGACACGGGG CGGCCCGATA CGCGAAGACG CAACATTACT ATGGTTAATG TCACCCAAGT
                                                                                            Env · P  K  C     S  K  V     V  V  S  S     C  T  R     M  M  E     T  Q  T  S     T  W  F     G  F  N     G  T  R  A     E  N  R ·
1001  TGCCGAAGTG TAGCAAAGTC GTGGTGTCCT CTTGTACCCG CATGATGGAG ACGCAGACTT CCACCTGGTT TGGCTTTAAC GGAACTCGAG CTGAAAACCG
      ACGGCTTCAC ATCGTTTCAG CACCACAGGA GAACATGGGC TGCGTCTGAA GGTGGACCAA ACCGAAATTG CCTTGAGCTC GACTTTTGGC
                                                                                            Env T  Y  I     Y  W  H  G     R  D  N     R  T  I     I  S  L  N     K  Y  Y     N  L  T     M  K  C  R     R  P  G     N  K  T
1101  GACGTATATC TACTGGCACG GACGAGATAA CCGAACGATC ATCTCACTGA ACAAGTACTA CAATCTGACC ATGAAATGCC GGCGCCCAGG CAATAAGACG
      CTGCATATAG ATGACCGTGC CTGCTCTATT GGCTTGCTAG TAGAGTGACT TGTTCATGAT GTTAGACTGG TACTTACGG CCGCGGGTCC GTTATTCTGC
                                                                                            Env · V  L  P  V     T  I  M     S  G  L     V  F  H  S     Q  P  V     N  E  R     P  N  Q  A     W  C  W     F  G  G     N  W  K  D ·
1201  GTACTTCCTG TCACTATTAT GAGCGGACTT GTATTTCACT CGCAGCCGGT CAATGAGCGC CCGAACCAAG CCTGGTGCTG GTTTGGAGGC AACTGGAAAG
      CATGAAGGAC AGTGATAATA CTCGCCTGAA CATAAAGTGA GCGTCGGCCA GTTACTCGCG GGCTTGGTTC GGACCACGAC CAAACCTCCG TTGACCTTTC
                                                                                            Env
```

```
                  A  I  K  E  V  K     Q  T  I  V     K  H  P     R  Y  T     G  T  N  N     T  D  K     I  N  L     T  A  P  R     G  G  D·
1301  ATGCGATTAA GGAAGTTAAA CAAACCATCG TAAAGCATCC CCGCTACACC GGCACCAACA ATACGGATAA GATCAACCTC ACAGCCCCTC GTGGCGGCGA
      TACGCTAATT CCTTCAATTT GTTTGGTAGC ATTTCGTAGG GGCGATGTGG CCGTGGTTGT TATGCCTATT CTAGTTGGAG TGTCGGGGAG CACCGCCGCT
                                                                   Env

·P  E  V     T  F  M  W     T  N  C     R  G  E     F  L  Y  C     K  M  N     W  F  L     N  W  V  E     D  R  D     L  T  T
1401  TCCAGAGGTG ACCTTCATGT GGACTAACTG TCGCGGTGAA TTTCTGTACT GTAAGATGAA TTGGTTTCTG AACTGGGTCG AGGATAGGGA TCTGACAACA
      AGGTCTCCAC TGGAAGTACA CCTGATTGAC AGCGCCACTT AAAGACATGA CATTCTACTT AACCAAAGAC TTGACCCAGC TCCTATCCCT AGACTGTTGT
                                                                   Env

Q  R  P  K     E  R  H     R  R  N     Y  V  P  C     H  I  R     Q  I  I     N  T  W  H     K  V  G     K  N  V     Y  L  P  P·
1501  CAACGGCCTA AGGAGAGGCA CCGCCGTAAC TATGTGCCTT GTCATATCAG ACAGATCATC AATACATGGC ATAAGGTGGG TAAAAACGTA TACCTCCCTC
      GTTGCCGGAT TCCTCTCCGT GGCGGCATTG ATACACGGAA CAGTATAGTC TGTCTAGTAG TTATGTACCG TATTCCACCC ATTTTGCAT ATGGAGGGAG
                                                                   Env

·R  E  G     D  L  T     C  N  S  T     V  T  S     L  I  A     N  I  D  W     T  D  G     N  Q  T     N  I  T  M     S  A  E·
1601  CCCGCGAGGG CGACCTGACA TGTAATAGTA CAGTAACCAG CCTCATCGCT AACATAGACT GGACTGATGG AAATCAGACC AACATCACTA TGTCAGCCGA
      GGGCGCTCCC GCTGGACTGT ACATTATCAT GTCATTGGTC GGAGTAGCGA TTGTATCTGA CCTGACTACC TTTAGTCTGG TTGTAGTGAT ACAGTCGGCT
                                                                   Env

·V  A  E     L  Y  R  L     E  L  G     D  Y  K     L  V  E  I     T  P  I     G  L  A     P  T  D  V     K  R  Y     T  T  G
1701  GGTAGCCGAA CTGTATAGGC TAGAACTCGG TGACTATAAG CTCGTCGAGA TCACCCCGAT AGGGCTCGCC CCTACAGACG TGAAACGTTA TACCACCGGC
      CCATCGGCTT GACATATCCG ATCTTGAGCC ACTGATATTC GAGCAGCTCT AGTGGGGCTA TCCCGAGCGG GGATGTCTGC ACTTTGCAAT ATGGTGGCCG
                                                                   Env
                                                                                                               TM
       G  T  S  R     N  K  R     Y  G  I     Y  I  V  V     G  V  I     L  L  R     I  V  I  Y     I  V  Q     M  L  N     R  V  R  Q·
1801  GGTACATCAA GGAACAAACG CTACGGCATC TACATCGTGG TAGGGGTCAT CCTCTTACGG ATTGTCATCT ATATCGTTCA GATGCTGAAT AGGGTGAGGC
      CCATGTAGTT CCTTGTTTGC GATGCCGTAG ATGTAGCACC ATCCCCAGTA GGAGAATGCC TAACAGTAGA TATATGCAAGT CTACGACTTA TCCCACTCCG
      TM                                                                                                  pre E/NS1 signal
      Env
                    FMDV2A                                    Transmembrane domain of WNV E (split)
      ·G  N  F     D  L  L     K  L  A  G     D  V  E     S  N  P     G  P  A  R     D  R  S     I  A  L     T  F  L  A     V  G  G·
1901  AGGGCAATTT TGACCTGTTA AAACTGGCCG GGGACGTCGA AAGCAACCCC GGTCCGGCCC GGGACAGGTC CATAGCTCTC ACGTTTCTCG CAGTTGGAGG
      TCCCGTTAAA ACTGGACAAT TTTGACCGGC CCCTGCAGCT TTCGTTGGGG CCAGGCCGGG CCCTGTCCAG GTATCGAGAG TGCAAAGAGC GTCAACCTCC
      Transmembrane domain of WNV E (split)
                                                                           NS1
      ·V  L  L     F  L  S  V     N  V  H     A  D  T     G  C  A  I     D  I  S     R  Q  E     L  R  C  G     S  G  V     F  I  H
2001  AGTTCTGCTC TTCCTCTCCG TGAACGTGCA CGCTGACACT GGGTGTGCCA TAGACATCAG CCGGCAAGAG CTGAGATGTG GAAGTGGAGT GTTCATACAC
      TCAAGACGAG AAGGAGAGGC ACTTGCACGT GCGACTGTGA CCCACACGGT ATCTGTAGTC GGCCGTTCTC GACTCTACAC CTTCACCTCA CAAGTATGTG
                                                   NS1
       N  D  V  E     A  W  M     D  R  Y     K  Y  Y  P     E  T  P     Q  G  L     A  K  I  I     Q  K  A     H  K  E     G  V  C  G·
2101  AATGATGTGG AGGCTTGGAT GGACCGGTAC AAGTATTACC CTGAAACGCC ACAAGGCCTA GCCAAGATCA TTCAGAAAGC TCATAAGGAA GGAGTGTGCG
      TTACTACACC TCCGAACCTA CCTGGCCATG TTCATAATGG GACTTTGCGG TGTTCCGGAT CGGTTCTAGT AAGTCTTTCG AGTATTCCTT CCTCACACGC
                                                                   NS1
```

```
                  · L   R   S     V   S   R     L   E   H   Q     M   W   E     A   V   K     D   E   L   N     T   L   L     K
2201   GTCTACGATC AGTTTCCAGA CTGGAGCATC AAATGTGGGA AGCAGTGAAG GACGAGCTGA ACACTCTTTT GAAG
       CAGATGCTAG TCAAAGGTCT GACCTCGTAG TTTACACCCT TCGTCACTTC CTGCTCGACT TGTGAGAAAA CTTC
```

Construct 8

1. PIV-WN (ΔCprME)-SIV Env No Transmembrane (TM)

dC RVC230 ENV No TM
13110 bp

2. Sequence of PIV-WN (ΔCprME)-SIV Env No Transmembrane (partial).

```
                                                                                                                                        C
                                           5' UTR
                                                                                                                                  M   S ·
  1   AGTAGTTCGC CTGTGTGAGC TGACAAACTT AGTAGTGTTT GTGAGGATTA CAACAATTA ACACAGTGCG AGCTGTTTCT TAGCACGAAG ATCTCGATGT
      TCATCAAGCG GACACACTCG ACTGTTTGAA TCATCACAAA CACTCCTAAT TGTTGTTAAT TGTGTCACGC TCGACAAAGA ATCGTGCTTC TAGAGCTACA
                                                                                                     NS3 cleavage
                  C
      · K   K   P     G   G   P     G   K   S   R     A   V   Y     L   L   K     R   G   M     P   R   V   L     S   L   I     G   L   K   Q     K   K   R ·
101   CTAAGAAACC AGGAGGGCCC GGCAAGAGCC GGGCTGTCTA TTTGCTAAAA CGCGGAATGC CCCGCGTGTT GTCCTTGATT GGACTTAAGC AAAAGAAGCG
      GATTCTTTGG TCCTCCCGGG CCGTTCTCGG CCCGACAGAT AAACGATTTT GCGCCTTACG GGGCGCACAA CAGGAACTAA CCTGAATTCG TTTTCTTCGC
      NS3 cleavage                                                                          tpa
```

```
                                    partial C signal
             ·  G  G  K    T  G  I  A    V  I  M    D  A  M    K  R  G  L    C  C  V    L  L  L    C  G  A  V    F  V  T    T  T  E
     201 AGGGGGCAAG ACTGGTATAG CTGTGATCAT GGACGCCATG AAGAGGGGAC TTTGTTGTGT GCTCCTGCTG TGCGGAGCTG TGTTCGTTAC AACAACGGAG
         TCCCCCGTTC TGACCATATC GACACTAGTA CCTGCGGTAC TTCTCCCCTG AAACAACACA CGAGGACGAC ACGCCTCGAC ACAAGCAATG TTGTTGCCTC
             tpa
         ~~~~~~~~~~                                                                              Env
             ·  A  I  Y  C    T  Q  Y    V  T  V    F  Y  G  V    P  A  W    R  N  A    T  I  P  L    F  C  A    T  K  N    R  D  T  W·
     301 GCGATTTACT GCACCCAGTA TGTCACCGTG TTTTACGGTG TCCCCGCCTG GCGGAACGCC ACCATCCCTC TGTTTTGTGC CACCAAGAAT AGAGATACGT
         CGCTAAATGA CGTGGGTCAT ACAGTGGCAC AAAATGCCAC AGGGGCGGAC CGCCTTGCGG TGGTAGGGAG ACAAAACACG GTGGTTCTTA TCTCTATGCA
                                                                                           Env
             ·  G  T  T    Q  C  L    P  D  N  G    D  Y  S    E  L  A    L  N  V  T    E  S  F    D  A  W    E  N  T  V    T  E  Q·
     401 GGGGCACCAC ACAATGCCTT CCCGATAATG GCGATTACTC TGAATTAGCC CTGAACGTCA CGGAAAGTTT TGATGCTTGG GAAAATACGG TTACCGAACA
         CCCCGTGGTG TGTTACGGAA GGGCTATTAC CGCTAATGAG ACTTAATCGG GACTTGCAGT GCCTTTCAAA ACTACGAACC CTTTTATGCC AATGGCTTGT
                                                                                           Env
             ·  A  I  E    D  V  W  Q    L  F  E    T  S  I    K  P  C  V    K  L  S    P  L  C    I  T  M  R    C  N  K    S  E  T
     501 GGCCATCGAA GATGTCTGGC AGTTATTCGA AACTAGTATC AAACCTTGCG TTAAGCTGAG TCCTTTGTGT ATAACGATGC GGTGCAACAA GAGCGAAACG
         CCGGTAGCTT CTACAGACCG TCAATAAGCT TTGATCATAG TTTGGAACGC AATTCGACTC AGGAAACACG TATTGCTACG CCACGTTGTT CTCGCTTTGC
                                                                                           Env
             D  K  W  G    L  T  K    S  S  T    T  T  A  S    T  T  T    T  T  A    P  A  K  I    D  M  V    N  E  T    S  S  C  I
     601 GACAAATGGG GCTTAACCAA ATCTTCAACC ACCACCGCCT CCACCACTAC GACAACCGCA CCTGCCAAGA TCGACATGGT TAACGAAACC TCTAGTTGCA
         CTGTTTACCC CGAATTGGTT TAGAAGTTGG TGGTGGCGGA GGTGGTGATG CTGTTGGCGT GGACGGTTCT AGCTGTACCA ATTGCTTTGG AGATCAACGT
                                                                                           Env
             ·  T  H  D    N  C  T    G  L  E  Q    E  Q  M    I  G  C    K  F  N  M    T  G  L    K  R  D    K  T  K  E    Y  N  E·
     701 TTACCCATGA CAACTGCACA GGCCTCGAAC AAGAACAAAT GATCGGCTGT AAATTCAATA TGACCGGACT GAAGAGAGAC AAGACAAAAG AGTACAACGA
         AATGGGTACT GTTGACGTGT CCGGAGCTTG TTCTTGTTTA CTAGCCGACA TTTAAGTTAT ACTGGCCTGA CTTCTCTCTG TTCTGTTTTC TCATGTTGCT
                                                                                           Env
             ·  T  W  Y    S  T  D  L    V  C  E    Q  G  N    S  T  D  N    E  S  R    C  Y  M    N  H  C  N    T  S  I    I  Q  E
     801 GACTTGGTAC AGCACCGACT TAGTGTGTGA GCAGGGGAAC TCAACCGATA ACGAGTCCCG CTGTTATATG AACCACTGCA ATACGAGCAT CATCCAAGAG
         CTGAACCATG TCGTGGCTGA ATCACACACT CGTCCCCTTG AGTTGGCTAT TGCTCAGGGC GACAATATAC TTGGTGACGT TATGCTCGTA GTAGGTTCTC
                                                                                           Env
             S  C  D  K    H  Y  W    D  T  I    R  F  R  Y    C  A  P    P  G  Y    A  L  L  R    C  N  D    T  N  Y    S  G  F  M·
     901 TCGTGCGACA AACACTATTG GGACACTATC CGATTTAGGT ACTGTGCCCC GCCGGGCTAT GCGCTTCTGC GTTTGTAATG ATACCAATTAC AGTGGGTTCA
         AGCACGCTGT TTGTGATAAC CCTGTGATAG GCTAAATCCA TGACACGGGG CGGCCCGATA CGCGAAGACG CAAACATTACT ATGGTTAATG TCACCCAAGT
                                                                                           Env
             ·  P  K  C    S  K  V    V  V  S  S    C  T  R    M  M  E    T  Q  T  S    T  W  F    G  F  N    G  T  R  A    E  N  R·
    1001 TGCCGAAGTG TAGCAAAGTC GTGGTGTCCT CTTGTACCCG CATGATGGAG ACGCAAACTT CCACCTGGTT TGGCTTTAAC GGAACTCGAG CTGAAAACCG
         ACGGCTTCAC ATCGTTTCAG CACCACAGGA GAACATGGGC GTACTACCTC TGCGTTTGAA GGTGGACCAA ACCGAAATTG CCTTGAGCTC GACTTTTGGC
                                                                                           Env
             ·  T  Y  I    Y  W  H  G    R  D  N    R  T  I    I  S  L  N    K  Y  Y    N  L  T    M  K  C  R    R  P  G    N  K  T
    1101 GACGTATATC TACTGGCACG GACGAGATAA CCGAACGATC ATCTCACTGA ACAAGTACTA CAATCTGACC ATGAAATGCC GGCGCCCAGG CAATAAGACG
         CTGCATATAG ATGACCGTGC CTGCTCTATT GGCTTGCTAG TAGAGTGACT TGTTCATGAT GTTAGACTGG TACTTTACGG CCGCGGGTCC GTTATTCTGC
```

```
                                                Env
          ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
       V  L  P  V    T  I  M    S  G  L    V  F  H  S    Q  P  V    N  E  R    P  N  Q  A    W  C  W    F  G  G    N  W  K  D  ·
1201  GTACTTCCTG TCACTATTAT GAGCGGACTT GTATTTCACT CGCAGCCGGT CAATGAGCGC CCGAACCAAG CCTGGTGCTG GTTTGGAGGC AACTGGAAAG
      CATGAAGGAC AGTGATAATA CTCGCCTGAA CATAAAGTGA GCGTCGGCCA GTTACTCGCG GGCTTGGTTC GGACCACGAC CAAACCTCCG TTGACCTTTC
                                                Env
          ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
       ·  A  I  K    E  V  K    Q  T  I  V    K  H  P    R  Y  T    G  T  N  N    T  D  K    I  N  L    T  A  P  R    G  G  D ·
1301  ATGCGATTAA GGAAGTTAAA CAAACCATCG TAAAGCATCC CCGCTACACC GGCACCAACA ATACGGATAA GATCAACCTC ACAGCCCCTC GTGGCGGCGA
      TACGCTAATT CCTTCAATTT GTTTGGTAGC ATTTCGTAGG GGCGATGTGG CCGTGGTTGT TATGCCTATT CTAGTTGGAG TGTCGGGGAG CACCGCCGCT
                                                Env
          ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
       ·  P  E  V    T  F  M  W    T  N  C    R  G  E    F  L  Y  C    K  M  N    W  F  L    N  W  V  E    D  R  D    L  T  T
1401  TCCAGAGGTG ACCTTCATGT GGACTAACTG TCGCGGTGAA TTTCTGTACT GTAAGATGAA TTGGTTTCTG AACTGGGTCG AGGATAGGGA TCTGACAACA
      AGGTCTCCAC TGGAAGTACA CCTGATTGAC AGCGCCACTT AAAGACATGA CATTCTACTT AACCAAAGAC TTGACCCAGC TCCTATCCCT AGACTGTTGT
                                                Env
          ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
       Q  R  P  K    E  R  H    R  R  N    Y  V  P  C    L  V  E    H  I  R    Q  I  I    N  T  W  H    K  V  G    K  N  V    Y  L  P  P  ·
1501  CAACGGCCTA AGGAGAGGCA CCGCCGTAAC TATGTGCCTT GTCATATCAG ACAGATCATC AATACATGGC ATAAGGTGGG TAAAAACGTA TACCTCCCTC
      GTTGCCGGAT TCCTCTCCGT GGCGGCATTG ATACACGGAA CAGTATAGTC TGTCTAGTAG TTATGTACCG TATTCCACCC ATTTTTGCAT ATGGAGGGAG
                                                Env
          ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
       ·  R  E  G    D  L  T    C  N  S  T    V  T  S    L  I  A    N  I  D  W    T  D  G    N  Q  T    N  I  T  M    S  A  E ·
1601  CCCGCGAGGG CGACCTGACA TGTAATAGTA CAGTAACCAG CCTCATCGCT AACATAGACT GGACTGATGG AAATCAGACC AACATCACTA TGTCAGCCGA
      GGGCGCTCCC GCTGGACTGT ACATTATCAT GTCATTGGTC GGAGTAGCGA TTGTATCTGA CCTGACTACC TTTAGTCTGG TTGTAGTGAT ACAGTCGGCT
                                                Env
          ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
       ·  V  A  E    L  Y  R  L    E  L  G    D  Y  K    L  V  E    I  T  P  I    G  L  A    P  T  D  V    K  R  Y    T  T  G
1701  GGTAGCCGAA CTGTATAGGC TAGAACTCGG TGACTATAAG CTCGTCGAGA TCACCCCGAT AGGGCTCGCC CCTACAGACG TGAAACGTTA TACCACCGGC
      CCATCGGCTT GACATATCCG ATCTTGAGCC ACTGATATTC GAGCAGCTCT AGTGGGGCTA TCCCGAGCGG GGATGTCTGC ACTTTGCAAT ATGGTGGCCG
                                                                                                            pre E/NS1 signal
                                                                                                            ~~~~~~~~~~~~~~~~~
                                                FMDV2A
          Env                                   ~~~~~~~~~~~~~~~~~~~~~~~~~~~~~~~~~~~~~~~~~~~~~~~~~~~~~~~
          (split)                                                                                         Transmembrane domain of WNV E
          ~~~~~~~                                                                                         ~~~~~~~~~~~~~~~~~~~~~~~~~~~~~
       G  T  S  R    N  K  R    N  F  D    L  L  K  L    A  G  D    V  E  S    N  P  G  P    A  R  D    R  S  I    A  L  T  F  ·
1801  GGTACATCAA GGAACAAACG CAATTTTGAC CTGTTAAAAC TGGCCGGGGA CGTCGAAAGC AACCCCGGTC CGGCCCGGGA CAGGTCCATA GCTCTCACGT
      CCATGTAGTT CCTTGTTTGC GTTAAAACTG GACAATTTTG ACCGGCCCCT GCAGCTTTCG TTGGGGCCAG GCCGGGCCCT GTCCAGGTAT CGAGAGTGCA
          Transmembrane domain of WNV E (split)
          ~~~~~~~~~~~~~~~~~~~~~~~~~~~~~~~~~~~~~
                                                                                                          NS1
                                                                                                          ~~~~~~~~~~~~~~~~~~~~~~~~~~~~~
       ·  L  A  V    G  G  V    L  L  F  L    S  V  N    V  H  A    D  T  G  C    A  I  D    I  S  R    Q  E  L  R    C  G  S ·
1901  TTCTCGCAGT GGAGGAGTT CTGCTCTTCC TCTCCGTGAA CGTGCACGCT GACACTGGGT GTGCCATAGA CATCAGCCGG CAAGAGCTGA GATGTGGAAG
      AAGAGCGTCA CCTCCTCAA GACGAGAAGG AGAGGCACTT GCACGTGCGA CTGTGACCCA CACGGTATCT GTAGTCGGCC GTTCTCGACT CTACACCTTC
                                                NS1
          ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
       ·  G  V  F    I  H  N  D    V  E  A    W  M  D    R  Y  K  Y    Y  P  E    T  P  Q    G  L  A  K    I  I  Q    K  A  H
2001  TGGAGTGTTC ATACACAATG ATGTGGAGGC TTGGATGGAC CGGTACAAGT ATTACCCTGA AACGCCACAA GGCCTAGCCA AGATCATTCA GAAAGCTCAT
      ACCTCACAAG TATGTGTTAC TACACCTCCG AACCTACCTG GCCATGTTCA TAATGGGACT TTGCGGTGTT CCGGATCGGT TCTAGTAAGT CTTTCGAGTA
                                                NS1
```

```
           K  E  G     V  C  G  L     R  S  V     S  R  L  E     H  Q  M     W  E  A     V  K  D  E     L  N  T     L  L  K
2101  AAGGAAGGAG TGTGCGGTCT ACGATCAGTT TCCAGACTGG AGCATCAAAT GTGGGAAGCA GTGAAGGACG AGCTGAACAC TCTTTTGAAG
      TTCCTTCCTC ACACGCCAGA TGCTAGTCAA AGGTCTGACC TCGTAGTTTA CACCCTTCGT CACTTCCTGC TCGACTTGTG AGAAAACTTC
```

Construct 9
1. PIV-WN (ΔCprME)-SIV ENV Rab G Transmembrane (TM)

[Diagram of RV230 dC Env Rab TM construct, 13308 bp, showing features: TM Domain WNV E (split), pre E/NS1 Signal, FMDV2A, RabG TM & Cytoplasmic, tpa, Partial C Signal, NS3 Cleavage, AA in 909 are N & M, 5' UTR, C, Env, NS1, NS2A, NS2B, NS3, NS4A, NS4B, NS5, 3' UTR, HDV ribozyme, T7 Term, Ap T7 & 1G]

2. Sequence of PIV-WN (ΔCprME)- SIV ENV Rab G Transmembrane (TM) (partial).

```
                                                                                                         C
                                    5' UTR
                                                                                                       M  S  ·
1  AGTAGTTCGC CTGTGTGAGC TGACAAACTT AGTAGTGTTT GTGAGGATTA ACAACAATTA ACACAGTGCG AGCTGTTTCT TAGCACGAAG ATCTCGATGT
   TCATCAAGCG GACACACTCG ACTGTTTGAA TCATCACAAA CACTCCTAAT TGTTGTTAAT TGTGTCACGC TCGACAAAGA ATCGTGCTTC TAGAGCTACA
                                                                                                       NS3 Cleavage
```

```
                                                        C
                · K K P   G G P   G K S R   A V Y   L L K   R G M P   R V L   S L I   G L K Q   K K R ·
            101 CTAAGAAACC AGGAGGGCCC GGCAAGAGCC GGGCTGTCTA TTTGCTAAAA CGCGGAATGC CCCGCGTGTT GTCCTTGATT GGACTTAAGC AGAAAAAGCG
                GATTCTTTGG TCCTCCCGGG CCGTTCTCGG CCCGACAGAT AAACGATTTT GCGCCTTACG GGGCGCACAA CAGGAACTAA CCTGAATTCG TCTTTTTCGC
                NS3 Cleavage                                                                tpa
                    Partial C Signal · G G K   T G I A   V I M   D A M   K R G L   C C V   L L L   C G A V   F V T   T T E
            201 GGGCGGAAAG ACAGGTATTG CTGTGATCAT GGACGCCATG AAGAGGGGAC TTTGTTGTGT GCTCCTGCTG TGCGGAGCTG TGTTCGTTAC AACAACGGAG
                CCCGCCTTTC TGTCCATAAC GACACTAGTA CCTGCGGTAC TTCTCCCCTG AAACAACACA CGAGGACGAC ACGCCTCGAC ACAAGCAATG TTGTTGCCTC
                                                                                            Env
                tpa A I Y C   T Q Y   V T V   F Y G V   P A W   R N A   T I P L   F C A   T K N   R D T W ·
            301 GCGATTTACT GCACCCAGTA TGTCACCGTG TTTTACGGTG TCCCCGCCTG GCGGAACGCC ACCATCCCTC TGTTTTGTGC CACCAAGAAT AGAGATACGT
                CGCTAAATGA CGTGGGTCAT ACAGTGGCAC AAAATGCCAC AGGGCGGACG CGCCTTGCGG TGGTAGGGAG ACAAAACACG GTGGTTCTTA TCTCTATGCA
                                                                                     Env · G T T   Q C L   P D N G   D Y S   E L A   L N V T   E S F   D A W   E N T V   T E Q ·
            401 GGGGCACCAC ACAATGCCTT CCCGATAATG GCGATTACTC TGAATTAGCC CTGAACGTCA CGGAAAGTTT TGATGCTTGG GAAAATACGG TTACCGAACA
                CCCCGTGGTG TGTTACGGAA GGGCTATTAC CGCTAATGAG ACTTAATCGG GACTTGCAGT GCCTTTCAAA ACTACGAACC CTTTTATGCC AATGGCTTGT
                                                                                     Env · A I E   D V W   Q L F E   T S I   K P C V   K L S   P L C   I T M R   C N K   S E T
            501 GGCCATCGAA GATGTCTGGC AGTTATTCGA AACTAGTATC AAACCTTGCG TTAAGCTGAG TCCTTTGTGC ATAACGATGC GGTGCAACAA GAGCGAAACG
                CCGGTAGCTT CTACAGACCG TCAATAAGCT TTGATCATAG TTTGGAACGC AATTCGACTC AGGAAACACG TATTGCTACG CCACGTTGTT CTCGCTTTGC
                                                                                     Env · D K W   G L T K   S S T   T T A S   T T T   T T A   P A K I   D M V   N E T   S S C I ·
            601 GACAAATGGG GCTTAACCAA ATCTTCAACC ACCACCGCCT CCACCACTAC GACAACCGCA CCTGCCAAGA TCGACATGGT TAACGAAACC TCTAGTTGCA
                CTGTTTACCC CGAATTGGTT TAGAAGTTGG TGGTGGCGGA GGTGGTGATG CTGTTGGCGT GGACGGTTCT AGCTGTACCA ATTGCTTTGG AGATCAACGT
                                                                                     Env · T H D   N C T   G L E Q   E Q M   I G C   K F N M   T G L   K R D   K T K E   Y N E ·
            701 TTACCCATGA CAACTGCACA GGCCTCGAAC AAGAACAAAT GATCGGCTGT AAATTCAATA TGACCGGACT GAAGAGAGAC AAGACAAAAG AGTACAACGA
                AATGGGTACT GTTGACGTGT CCGGAGCTTG TTCTTGTTTA CTAGCCGACA TTTAAGTTAT ACTGGCCTGA CTTCTCTCTG TTCTGTTTTC TCATGTTGCT
                                                                                     Env · T W Y   S T D L   V C E   Q G N   S T D N   E S R   C Y M   N H C N   T S I   I Q E
            801 GACTTGGTAC AGCACCGACT TAGTGTGTGA GCAGGGGAAC TCAACCGATA ACGAGTCCCG CTGTTATATG AACCACTGCA ATACGAGCAT CATCCAAGAG
                CTGAACCATG TCGTGGCTGA ATCACACACT CGTCCCCTTG AGTTGGCTAT TGCTCAGGGC GACAATATAC TTGGTGACGT TATGCTCGTA GTAGGTTCTC
                                                                                     Env S C D   K H Y W   D T I   R F R Y   C A P   P G Y   A L L R   C N D   T N Y   S G F M ·
            901 TCGTGCGACA AACACTATTG GGACACTATC CGATTTAGGT ACTGTGCCCC GCCGGGCTAT GCGCTTCTGC GTTGTAATGA TACCAATTAC AGTGGGTTCA
                AGCACGCTGT TTGTGATAAC CCTGTGATAG GCTAAATCCA TGACACGGGG CGGCCCGATA CGCGAAGACG CAACATTACT ATGGTTAATG TCACCCAAGT
                                                                                     Env · P K C   S K V   V V S S   C T R   M M E   T Q T S   T W F   G F N   G T R A   E N R ·
```

```
1001 TGCCGAAGTG TAGCAAAGTC GTGGTGTCCT CTTGTACCCG CATGATGGAG ACGCAGACTT CCACCTGGTT TGGCTTTAAC GGAACTCGAG CTGAAAACCG
     ACGGCTTCAC ATCGTTTCAG CACCACAGGA GAACATGGGC GTACTACCTC TGCGTCTGAA GGTGGACCAA ACCGAAATTG CCTTGAGCTC GACTTTTGGC
                                                                       Env

· T  Y  I  Y  W  H  G  R  D  N   R  T  I  I  S  L  N  K  Y  Y   N  L  T  M  K  C  R  R  P  G   N  K  T
1101 GACGTATATC TACTGGCACG GACGAGATAA CCGAACGATC ATCTCACTGA ACAAGTACTA CAATCTGACC ATGAAATGCC GGCGCCCAGG CAATAAGACG
     CTGCATATAG ATGACCGTGC CTGCTCTATT GGCTTGCTAG TAGAGTGACT TGTTCATGAT GTTAGACTGG TACTTTACGG CCGCGGGTCC GTTATTCTGC
                                                                       Env

V  L  P  V  T  I  M  S  G  L   V  F  H  S  Q  P  V  N  E  R   P  N  Q  A  W  C  W  F  G  G   N  W  K  D·
1201 GTACTTCCTG TCACTATTAT GAGCGGACTT GTATTTCACT CGCAGCCGGT CAATGAGCGC CCGAACCAAG CCTGGTGCTG GTTTGGAGGC AACTGGAAAG
     CATGAAGGAC AGTGATAATA CTCGCCTGAA CATAAAGTGA GCGTCGGCCA GTTACTCGCG GGCTTGGTTC GGACCACGAC CAAACCTCCG TTGACCTTTC
                                                                       Env

· A  I  K  E  V  K  Q  T  I  V   K  H  P  R  Y  T  G  T  N  N   N  T  D  K  I  N  L  T  A  P   R  G  G  D·
1301 ATGCGATTAA GGAAGTTAAA CAAACCATCG TAAAGCATCC CCGCTACACC GGCACCAACA ATACGGATAA GATCAACCTC ACAGCCCCTC GTGGCGGCGA
     TACGCTAATT CCTTCAATTT GTTTGGTAGC ATTTCGTAGG GGCGATGTGG CCGTGGTTGT TATGCCTATT CTAGTTGGAG TGTCGGGGAG CACCGCCGCT
                                                                       Env

· P  E  V  T  F  M  W  T  N  C   R  G  E  F  L  Y  C  K  M  N   W  F  L  N  W  V  E  D  R  D   L  T  T
1401 TCCAGAGGTG ACCTTCATGT GGACTAACTG TCGCGGTGAA TTTCTGTACT GTAAGATGAA TTGGTTTCTG AACTGGGTCG AGGATAGGGA TCTGACAACA
     AGGTCTCCAC TGGAAGTACA CCTGATTGAC AGCGCCACTT AAAGACATGA CATTCTACTT AACCAAAGAC TTGACCCAGC TCCTATCCCT AGACTGTTGT
                                                                       Env

Q  R  P  K  E  R  H  R  R  N   Y  V  P  C  H  I  R  Q  I  I   N  T  W  H  K  V  G  K  N  V   Y  L  P  P ·
1501 CAACGGCCTA AGGAGAGGCA CCGCCGTAAC TATGTGCCTT GTCATATCAG ACAGATCATC AATACATGGC ATAAGGTGGG TAAAAACGTA TACCTCCCTC
     GTTGCCGGAT TCCTCTCCGT GGCGGCATTG ATACACGGAA CAGTATAGTC TGTCTAGTAG TTATGTACCG TATTCCACCC ATTTTGCAT ATGGAGGGAG
                                                                       Env

· R  E  G  D  L  T  C  N  S  T   V  T  S  L  I  A  N  I  D  W   T  D  G  N  Q  T  N  I  T  M   S  A  E ·
1601 CCCGCGAGGG CGACCTGACA TGTAATAGTA CAGTAACCAG CCTCATCGCT AACATAGACT GGACTGATGG AAATCAGACC AACATCACTA TGTCAGCCGA
     GGGCGCTCCC GCTGGACTGT ACATTATCAT GTCATTGGTC GGAGTAGCGA TTGTATCTGA CCTGACTACC TTTAGTCTGG TTGTAGTGAT ACAGTCGGCT
                                                                       Env

· V  A  E  L  Y  R  L  E  L  G   D  Y  K  L  V  E  I  T  P  I   G  L  A  P  T  D  V  K  R  Y   T  T  G
1701 GGTAGCCGAA CTGTATAGGC TAGAACTCGG TGACTATAAG CTCGTCGAGA TCACCCCGAT AGGGCTCGCC CCTACAGACG TGAAACGTTA CACCACGGGC
     CCATCGGCTT GACATATCCG ATCTTGAGCC ACTGATATTC GAGCAGCTCT AGTGGGGCTA TCCCGAGCGG GGATGTCTGC ACTTTGCAAT GTGGTGCCCG
                                                  Env
                                                                                            RabG TM & Cytoplasmic G  T  S  R  N  K  R   Y  V  L   L  S  A  G  A  L  T  A  L  M   L  I  I  F  L  M  T  C  W  R   R  V  N  R ·
1801 GGTACATCAA GGAACAAACG CTACGTCCTC CTGAGTGCGG GTGCCTTGAC CGCTTTGATG CTGATCATTT TTCTGATGAC CTGCTGGCGG AGGGTGAATC
     CCATGTAGTT CCTTGTTTGC GATGCAGGAG GACTCACGCC CACGGAACTG GCGAAACTAC GACTAGTAAA AAGACTACTG GACGACCGCC TCCCACTTAG
                                                         RabG TM & Cytoplasmic · S  E  P  T  Q  H  N  L  R  G   T  G  R  E  V  S  V  T  P  Q   S  G  K  I  I  S  S  W  E  S   Y  K  S ·
1901 GCTCCGAGCC GACACAGCAC AATCTCAGAG GGACAGGCCG GGAAGTAAGT GTGACTCCGC AATCTGGCAA GATTATTAGT AGTTGGGAGA GTTACAAGTC
     CGAGGCTCGG CTGTGTCGTG TTAGAGTCTC CCTGTCCGGC CCTTCATTCA CACTGAGGCG TTAGACCGTT CTAATAATCA TCAACCCTCT CAATGTTCAG
                                                         FMDV2A                                           TM Domain WNV E (split)
      RabG TM & Cytoplasmic                                                                                pre E/NS1 Signal
```

```
                 · G  G  E    T  G  L  N    F  D  L    L  K  L    A  G  D  V    E  S  N    P  G  P    A  R  D  R    S  I  A    L  T  F
2001  TGGAGGAGAG ACTGGGTTGA ATTTTGATCT GCTCAAACTT GCAGGCGATG TAGAATCAAA TCCTGGACCC GCCCGGGACA GGTCCATAGC TCTCACGTTT
      ACCTCCTCTC TGACCCAACT TAAAACTAGA CGAGTTTGAA CGTCCGCTAC ATCTTAGTTT AGGACCTGGG CGGGCCCTGT CCAGGTATCG AGAGTGCAAA
                                                                                                        NS1
                 ~~~~~~~~~~~~~~~~~~~~~~~~~~~~~~~~~~~~~~~~~~~~~~
          TM Domain WNV E (split)
        L  A  V  G    G  V  L    L  F  L    S  V  N  V    H  A  D    T  G  C    A  I  D  I    S  R  Q    E  L  R    C  G  S  G ·
2101  CTCGCAGTTG GAGGAGTTCT GCTCTTCCTC TCCGTGAACG TGCACGCTGA CACTGGGTGT GCCATAGACA TCAGCCGGCA AGAGCTGAGA TGTGGAAGTG
      GAGCGTCAAC CTCCTCAAGA CGAGAAGGAG AGGCACTTGC ACGTGCGACT GTGACCCACA CGGTATCTGT AGTCGGCCGT TCTCGACTCT ACACCTTCAC
                                                                  NS1
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      · V  F  I    H  N  D    V  E  A  W    M  D  R    Y  K  Y    Y  P  E  T    P  Q  G    L  A  K    I  I  Q  K    A  H  K ·
2201  GAGTGTTCAT ACACAATGAT GTGGAGGCTT GGATGGACCG GTACAAGTAT TACCCTGAAA CGCCACAAGG CCTAGCCAAG ATCATTCAGA AAGCTCATAA
      CTCACAAGTA TGTGTTACTA CACCTCCGAA CCTACCTGGC CATGTTCATA ATGGGACTTT GCGGTGTTCC GGATCGGTTC TAGTAAGTCT TTCGAGTATT
                                                                NS1
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      · E  G  V    C  G  L  R    S  V  S    R  L  E    H  Q  M  W    E  A  V    K  D  E    L  N  T  L    L  K
2301  GGAAGGAGTG TGCGGTCTAC GATCAGTTTC CAGACTGGAG CATCAAATGT GGGAAGCAGT GAAGGACGAG CTGAACACTC TTTTGAAG
      CCTTCCTCAC ACGCCAGATG CTAGTCAAAG GTCTGACCTC GTAGTTTACA CCCTTCGTCA CTTCCTGCTC GACTTGTGAG AAAACTTC
```

Construct 10
1. PIV-WN (ΔCprME)-SIV Env RabG Chimera, Signal Sequence and Transmembrane (TM)

2. Sequence of PIV-WN (ΔCprME)-SIV Env RabG Chimera, Signal Seqeunce and Transmembrane (TM)

```
                                                                                                            C
                                                    5' UTR                                                  ~~~~
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                                                        M   S ·
  1 AGTAGTTCGC CTGTGTGAGC TGACAAACTT AGTAGTGTTT GTGAGGATTA ACAACAATTA ACACAGTGCG AGCTGTTTCT TAGCACGAAG ATCTCGATGT
    TCATCAAGCG GACACACTCG ACTGTTTGAA TCATCACAAA CACTCCTAAT TGTTGTTAAT TGTGTCACGC TCGACAAAGA ATCGTGCTTC TAGAGCTACA
                                                                                                 NS3 cleavage
                    C                                                                            ~~~~~~~~~~~~~~
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
    ·  K   K   P   G   G   P   G   K   S   R   A   V   Y   L   L   K   R   G   M   P   R   V   L   S   L   I   G   L   K   Q   K   K   R ·
101 CTAAGAAACC AGGAGGGCCC GGCAAGAGCC GGGCTGTCTA TTTGCTAAAA CGCGGAATGC CCCGCGTGTT GTCCTTGATT GGACTTAAGC AAAAGAAGCG
    GATTCTTTGG TCCTCCCGGG CCGTTCTCGG CCCGACAGAT AAACGATTTT GCGCCTTACG GGGCGCACAA CAGGAACTAA CCTGAATTCG TTTTCTTCGC
    NS3 cleavage                                                     Rab G Signal
    ~                                                                ~~~~~~~~~~~~~~~~~~~~~~~~~~~~~~~~~~~~~~~~
        partial C signal                                                                                 Env
    ~~~~~~~~~~~~~~~~~~~~                                                                                 ~~~~~~~~~~~~~~~~~~~~
    ·  G   G   K   T   G   I   A   V   I   V   P   Q   A   L   L   F   V   P   L   L   V   F   P   L   C   F   G   C   T   Q   Y   V   T
201 AGGGGGCAAG ACTGGTATAG CTGTGATCGT TCCTCAGGCT CTTTTGTTTG TACCCTTGCT GGTATTTCCC CTTTGCTTTG GTTGCACCCA GTATGTCACC
    TCCCCCGTTC TGACCATATC GACACTAGCA AGGAGTCCGA GAAAACAAAC ATGGGAACGA CCATAAAGGG GAAACGAAAC CAACGTGGGT CATACAGTGG
                                                        Env
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
       V   F   Y   G   V   P   A   W   R   N   A   T   I   P   L   F   C   A   T   K   N   R   D   T   W   G   T   T   Q   C   L   P   D   N ·
```

```
                                                                                              Env
301  GTGTTTTACG GTGTCCCCGC CTGGCGGAAC GCCACCATCC CTCTGTTTTG TGCCACCAAG AATAGAGATA CGTGGGGCAC CACACAATGC CTTCCCGATA
     CACAAAATGC CACAGGGGCG GACCGCCTTG CGGTGGTAGG GAGACAAAAC ACGGTGGTTC TTATCTCTAT GCACCCCGTG GTGTGTTACG GAAGGGCTAT
                                                                  Env

· G  D  Y  S  E  L  A  L  N  V  T  E  S  F  D  A  W  E  N  T  V  T  E  Q  A  I  E  D  V  W  Q  L  F ·
401  ATGGCGATTA CTCTGAATTA GCCCTGAACG TCACGGAAAG TTTTGATGCT TGGGAAAATA CGGTTACCGA ACAGGCCATC GAAGATGTCT GGCAGTTATT
     TACCGCTAAT GAGACTTAAT CGGGACTTGC AGTGCCTTTC AAAACTACGA ACCCTTTTAT GCCAATGGCT TGTCCGGTAG CTTCTACAGA CCGTCAATAA
                                                                  Env

· E  T  S  I  K  P  C  V  K  L  S  P  L  C  I  T  M  R  C  N  K  S  E  T  D  K  W  G  L  T  K  S  S
501  CGAAACTAGT ATCAAACCTT GCGTTAAGCT GAGTCCTTTG TGCATAACGA TGCGGTGCAA CAAGAGCGAA ACGGACAAAT GGGGCTTAAC CAAATCTTCA
     GCTTTGATCA TAGTTTGGAA CGCAATTCGA CTCAGGAAAC ACGTATTGCT ACGCCACGTT GTTCTCGCTT TGCCTGTTTA CCCCGAATTG GTTAGAAGT
                                                                  Env

T  T  T  A  S  T  T  T  T  T  A  P  A  K  I  D  M  V  N  E  T  S  S  C  I  T  H  D  N  C  T  G  L  E ·
601  ACCACCACCG CCTCCACCAC TACGACAACC GCACCTGCCA AGATCGACAT GGTTAACGAA ACCTCTAGTT GCATTACCCA TGACAACTGC ACAGGCCTCG
     TGGTGGTGGC GGAGGTGGTG ATGCTGTTGG CGTGGACGGT TCTAGCTGTA CCAATTGCTT TGGAGATCAA CGTAATGGGT ACTGTTGACG TGTCCGGAGC
                                                                  Env

· Q  E  Q  M  I  G  C  K  F  N  M  T  G  L  K  R  D  K  I  K  E  Y  N  E  T  W  Y  S  T  D  L  V  C ·
701  AACAAGAACA AATGATCGGC TGTAAATTCA ATATGACCGG ACTGAAGAGA GACAAGATAA AAGAGTACAA CGAGACTTGG TACAGCACCG ACTTAGTGTG
     TTGTTCTTGT TTACTAGCCG ACATTTAAGT TATACTGGCC TGACTTCTCT CTGTTCTGTT TTCTCATGTT GCTCTGAACC ATGTCGTGGC TGAATCACAC
                                                                  Env

· E  Q  G  N  S  T  D  N  E  S  R  C  Y  M  N  H  C  N  T  S  I  I  Q  E  S  C  D  K  H  Y  W  D  T
801  TGAGCAGGGG AACTCAACCG ATAACGAGTC CCGCTGTTAT ATGAACCACT GCAATACGAG CATCATCCAA GAGTCGTGCG ACAAACACTA TTGGGACACT
     ACTCGTCCCC TTGAGTTGGC TATTGCTCAG GGCGACAATA TACTTGGTGA CGTTATGCTC GTAGTAGGTT CTCAGCACGC TGTTTGTGAT AACCCTGTGA
                                                                  Env

I  R  F  R  Y  C  A  P  P  G  Y  A  L  L  R  C  N  D  T  N  Y  S  G  F  M  P  K  C  S  K  V  V  V  S ·
901  ATCCGATTTA GGTACTGTGC CCCGCCGGGC TATGCCCTTC TGCGTTGTAA TGATACCAAT TACAGTGGGT TCATGCCGAA GTGTAGCAAA GTCGTGGTGT
     TAGGCTAAAT CCATGACACG GGGCGGCCCG ATACGCGAAG ACGCAACATT ACTATGGTTA ATGTCACCCA AGTACGGCTT CACATCGTTT CAGCACCACA
                                                                  Env

· S  C  T  R  M  M  E  T  Q  T  S  T  W  F  G  F  N  G  T  R  A  E  N  R  T  Y  I  Y  W  H  G  R  D ·
1001 CCTCTTGTAC CCGCATGATG GAGACGCAGA CTTCCACCTG GTTTGGCTTT AACGGAACTC GAGCTGAAAA CCGGACGTAT ATCTACTGGC ACGGACGAGA
     GGAGAACATG GGCGTACTAC CTCTGCGTCT GAAGGTGGAC CAAACCGAAA TTGCCTTGAG CTCGACTTTT GGCCTGCATA TAGATGACCG TGCCTGCTCT
                                                                  Env

· N  R  T  I  I  S  L  N  K  Y  Y  N  L  T  M  K  C  R  R  P  G  N  K  T  V  L  P  V  T  I  M  S  G
1101 TAACCGAACG ATCATCTCAC TGAACAAGTA CTACAATCTG ACCATGAAAT GCCGGCGCCC AGGCAATAAG ACGGTACTTC CTGTCACTAT TATGAGCGGA
     ATTGGCTTGC TAGTAGAGTG ACTTGTTCAT GATGTTAGAC TGGTACTTTA CGGCCGCGGG TCCGTTATTC TGCCATGAAG GACAGTGATA ATACTCGCCT
                                                                  Env

L  V  F  H  S  Q  P  V  N  E  R  P  N  Q  A  W  C  W  F  G  G  N  W  K  D  A  I  K  E  V  K  Q  T  I ·
1201 CTTGTATTTC ACTCGCAGCC GGTCAATGAG CCCCCGAACC AAGCCTGGTG CTGGTTTGGA GGCAACTGGA AAGATGCGAT TAAGGAAGTT AAACAAACCA
     GAACATAAAG TGAGCGTCGG CCAGTTACTC GCGGGCTTGG TTCGGACCAC GACCAAACCT CCGTTGACCT TTCTACGCTA ATTCCTTCAA TTTGTTTGGT
                                                                  Env

· V  K  H  P  R  Y  T  G  T  N  N  T  D  K  I  N  L  T  A  P  R  G  G  D  P  E  V  T  F  M  W  T  N ·
1301 TCGTAAAGCA TCCCCGCTAC ACCGGCACCA ACAATACGGA TAAGATCAAC CTCACAGCCC CTCGTGGCGG CGATCCAGAG GTGACCTTCA TGTGGACTAA
     AGCATTTCGT AGGGGCGATG TGGCCGTGGT TGTTATGCCT ATTCTAGTTG GAGTGTCGGG GAGCACCGCC GCTAGGTCTC CACTGGAAGT ACACCTGATT
                                                                  Env
```

```
                 · C   R   G   E   F   L   Y   C   K   M   N   W   F   L   N   W   V   E   D   R   D   L   T   T   Q   R   P   K   E   R   H   R   R
     1401  CTGTCGCGGT GAATTTCTGT ACTGTAAGAT GAATTGGTTT CTGAACTGGG TCGAGGATAG GGATCTGACA ACACAACGGC TAAGGAGAG GCACCGCCGT
           GACAGCGCCA CTTAAAGACA TGACATTCTA CTTAACCAAA GACTTGACCC AGCTCCTATC CCTAGACTGT TGTGTTGCCG ATTCCTCTC CGTGGCGGCA
                                                                                                    Env
                 N   Y   V   P   C   H   I   R   Q   I   I   N   T   W   H   K   V   G   K   N   V   Y   L   P   P   R   E   G   D   L   T   C   N   S ·
     1501  AACTATGTGC CTTGTCATAT CAGACAGATC ATCAATACAT GGCATAAGGT GGGTAAAAAC GTATACCTCC CTCCCCGCGA GGGCGACCTG ACATGTAATA
           TTGATACACG GAACAGTATA GTCTGTCTAG TAGTTATGTA CCGTATTCCA CCCATTTTTG CATATGGAGG GAGGGGCGCT CCCGCTGGAC TGTACATTAT
                                                                                                    Env
                · T   V   T   S   L   I   A   N   I   D   W   T   D   G   N   Q   T   N   I   T   M   S   A   E   V   A   E   L   Y   R   L   E   L ·
     1601  GTACAGTAAC CAGCCTCATC GCTAACATAG ACTGGACTGA TGGAAATCAG ACCAACATCA CTATGTCAGC CGAGGTAGCC GAACTGTATA GGCTAGAACT
           CATGTCATTG GTCGGAGTAG CGATTGTATC TGACCTGACT ACCTTTAGTC TGGTTGTAGT GATACAGTCG GCTCCATCGG CTTGACATAT CCGATCTTGA
                                                                                                              RabG TM & Cytoplasmic
                                                                  Env
               · G   D   Y   K   L   V   E   I   T   P   I   G   L   A   P   T   D   V   K   R   Y   T   T   G   G   T   S   R   N   K   R   Y   V
     1701  CGGTGACTAT AAGCTCGTCG AGATCACCCC GATAGGGCTC GCCCCTACAG ACGTGAAACG TTATACCACC GGCGGTACAT CAAGGAACAA ACGCTACGTG
           GCCACTGATA TTCGAGCAGC TCTAGTGGGG CTATCCCGAG CGGGGATGTC TGCACTTTGC AATATGGTGG CCGCCATGTA GTTCCTTGTT TGCGATGCAC
                                                                    RabG TM & Cytoplasmic
                 L   L   S   A   G   A   L   T   A   L   M   L   I   I   F   L   M   T   C   W   R   R   V   N   R   S   E   P   T   Q   H   N   L   R ·
     1801  CTCCTGAGTG CGGGTGCCTT GACCGCTTTG ATGCTGATCA TTTTTCTGAT GACCTGCTGG CGGAGGGTGA ATCGCTCCGA GCCGACACAG CACAATCTCA
           GAGGACTCAC GCCCACGGAA CTGGCGAAAC TACGACTAGT AAAAAGACTA CTGGACGACC GCCTCCCACT TAGCGAGGCT CGGCTGTGTC GTGTTAGAGT
                                                                                                                       FMDV2A
                              RabG TM & Cytoplasmic
               · G   T   G   R   E   V   S   V   T   P   Q   S   G   K   I   I   S   S   W   E   S   Y   K   S   G   G   E   T   G   L   N   F   D ·
     1901  GAGGGACAGG CCGGGAAGTA AGTGTGACTC CGCAATCTGG CAAGATTATT AGTAGTTGGG AGAGTTACAA GTCTGGAGGA GAGACTGGGT TGAATTTTGA
           CTCCCTGTCC GGCCCTTCAT TCACACTGAG GCGTTAGACC GTTCTAATAA TCATCAACCC TCTCAATGTT CAGACCTCCT CTCTGACCCA ACTTAAAACT
                                                                                        Pre E/NS1 Signal
                                                                                               TM Domain of WNV E (split)
                          FMDV2A
               · L   L   K   L   A   G   D   V   E   S   N   P   G   P   A   R   D   R   S   I   A   L   T   F   L   A   V   G   G   V   L   L   F
     2001  TCTGCTCAAA CTTGCAGGCG ATGTAGAATC AAATCCTGGA CCCGCCCGGG ACAGGTCCAT AGCTCTCACG TTTCTCGCAG TTGGAGGAGT TCTGCTCTTC
           AGACGAGTTT GAACGTCCGC TACATCTTAG TTTAGGACCT GGGCGGGCCC TGTCCAGGTA TCGAGAGTGC AAAGAGCGTC AACCTCCTCA AGACGAGAAG
                                                                                                    NS1
           TM Domain of WNV E (split)
                 L   S   V   N   V   H   A   D   T   G   C   A   I   D   I   S   R   Q   E   L   R   C   G   S   V   F   I   H   N   D   V   E   A ·
     2101  CTCTCCGTGA ACGTGCACGC TGACACTGGG TGTGCCATAG ACATCAGCCG GCAAGAGCTG AGATGTGCAA GTGGAGTGTT CATACACAAT GATGTGGAGG
           GAGAGGCACT TGCACGTGCG ACTGTGACCC ACACGGTATC TGTAGTCGGC CGTTCTCGAC TCTACACCTT CACCTCACAA GTATGTGTTA CTACACCTCC
                                                                                                    NS1
                · W   M   D   R   Y   K   Y   Y   P   E   T   P   Q   G   L   A   K   I   I   Q   K   A   H   K   E   G   V   C   G   L   R   S   V ·
     2201  CTTGGATGGA CCGGTACAAG TATTACCCTG AAACGCCACA AGGCCTAGCC AAGATCATTC AGAAAGCTCA TAAGGAAGGA GTGTGCGGTC TACGATCAGT
           GAACCTACCT GGCCATGTTC ATAATGGGAC TTTGCGGTGT TCCGGATCGG TTCTAGTAAG TCTTTCGAGT ATTCCTTCCT CACACGCCAG ATGCTAGTCA
                                                                                                    NS1
```

```
       S  R  L     E  H  Q  M     W  E  A     V  K  D     E  L  N  T     L  L  K     E  N  G     V  D  L  S     V  V  V     E  K  Q
2301  TTCCAGACTG GAGCATCAAA TGTGGGAAGC AGTGAAGGAC GAGCTGAACA CTCTTTTGAA GGAGAATGGT GTGGACCTTA GTGTCGTGGT TGAGAAACAA
      AAGGTCTGAC CTCGTAGTTT ACACCCTTCG TCACTTCCTG CTCGACTTGT GAGAAAACTT CCTCTTACCA CACCTGGAAT CACAGCACCA ACTCTTTGTT
```

Construct 11
1. PIV-WN (ΔC)-SIV Env

RV909 Env
19734 bp

2. Sequence of PIV-WN (ΔC)-SIV Env (partial).

```
                                                                                                                      dC
                                                                                                                      ~~~~
                                5' UTR
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      S   S   S   P   V   *   A   D   K   L   S   S   V   C   E   D   *   Q   Q   L   T   Q   C   E   L   F   L   S   T   K   I   S   M   S  ·
  1 AGTAGTTCGC CTGTGTGAGC TGACAAACTT AGTAGTGTTT GTGAGGATTA ACAACAATTA ACACAGTGCG AGCTGTTTCT TAGCACGAAG ATCTCGATGT
    TCATCAAGCG GACACACTCG ACTGTTTGAA TCATCACAAA CACTCCTAAT TGTTGTTAAT TGTGTCACGC TCGACAAAGA TCGTGCTTC  TAGAGCTACA
                                                                                                         NS3 Signal
                  dC                                                                                    ~~~~~~~~~~~~~~~
    ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
    ·  K   K   P   G   G   P   G   K   S   R   A   V   N   M   L   K   R   G   M   P   R   V   L   S   L   I   G   L   K   Q   K   K   R  ·
101 CTAAGAAACC AGGAGGGCCC GGCAAGAGCC GGGCTGTCAA TATGCTAAAA CGCGGAATGC CCCGCGTGTT GTCCTTGATT GGACTTAAGC AAAAGAAGCG
    GATTCTTTGG TCCTCCCGGG CCGTTCTCGG CCCGACAGTT ATACGATTTT GCGCCTTACG GGGCGCACAA CAGGAACTAA CCTGAATTCG TTTTCTTCGC
           partial C signal
    ~~~~~~~~~~~~~~~~~~~~~~~~~~~~~
    NS3 Signal                                                  Env
    ~                      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
    ·  G   G   K   T   G   I   A   V   I   M   D   A   M   K   R   G   L   C   C   V   L   L   L   C   G   A   V   F   V   T   T   T   E
201 AGGGGGCAAG ACTGGTATAG CTGTGATCAT GGACGCCATG AAGAGGGGAC TTTGTTGTGT GCTCCTGCTG TGCGGAGCTG TGTTCGTTAC AACAACGGAG
    TCCCCCGTTC TGACCATATC GACACTAGTA CCTGCGGTAC TTCTCCCCTG AAACAACACA CGAGGACGAC ACGCCTCGAC ACAAGCAATG TTGTTGCCTC
                                                                  Env
```

```
         A  I  Y  C  T  Q  Y  V  T  V  F  Y  G  V  P  A  W  R  N  A  T  I  P  L  F  C  A  T  K  N  R  D  T  W
 301  GCGATTTACT GCACCCAGTA TGTCACCGTG TTTTACGGTG TCCCCGCCTG GCGGAACGCC ACCATCCCTC TGTTTTGTGC CACCAAGAAT AGAGATACGT
      CGCTAAATGA CGTGGGTCAT ACAGTGGCAC AAAATGCCAC AGGGGCGGAC CGCCTTGCGG TGGTAGGGAG ACAAAACACG GTGGTTCTTA TCTCTATGCA
                                                                                                      Env
         G  T  T  Q  C  L  P  D  N  G  D  Y  S  E  L  A  L  N  V  T  E  S  F  D  A  W  E  N  T  V  T  E  Q
 401  GGGGCACCAC ACAATGCCTT CCCGATAATG GCGATTACTC TGAATTAGCC CTGAACGTCA CGGAAAGTTT TGATGCTTGG GAAAATACGG TTACCGAACA
      CCCCGTGGTG TGTTACGGAA GGGCTATTAC CGCTAATGAG ACTTAATCGG GACTTGCAGT GCCTTTCAAA ACTACGAACC CTTTTATGCC AATGGCTTGT
                                                                                                      Env
         A  I  E  D  V  W  Q  L  F  E  T  S  I  K  P  C  V  K  L  S  P  L  C  I  T  M  R  C  N  K  S  E  T
 501  GGCCATCGAA GATGTCTGGC AGTTATTCGA AACTAGTATC AAACCTTGCG TTAAGCTGAG TCCTTTGTGC ATAACGATGC GGTGCAACAA GAGCGAAACG
      CCGGTAGCTT CTACAGACCG TCAATAAGCT TTGATCATAG TTTGGAACGC AATTCGACTC AGGAAACACG TATTGCTACG CCACGTTGTT CTCGCTTTGC
                                                                                                      Env
         D  K  W  G  L  T  K  S  S  T  T  T  A  S  T  T  T  T  T  A  P  A  K  I  D  M  V  N  E  T  S  S  C  I
 601  GACAAATGGG GCTTAACCAA ATCTTCAACC ACCACCGCCT CCACCACTAC GACAACCGCA CCTGCCAAGA TCGACATGGT TAACGAAACC TCTAGTTGCA
      CTGTTTACCC CGAATTGGTT TAGAAGTTGG TGGTGGCGGA GGTGGTGATG CTGTTGGCGT GGACGGTTCT AGCTGTACCA ATTGCTTTGG AGATCAACGT
                                                                                                      Env
         T  H  D  N  C  T  G  L  E  Q  E  Q  M  I  G  C  K  F  N  M  T  G  L  K  R  D  K  T  K  E  Y  N  E
 701  TTACCCATGA CAACTGCACA GGCCTCGAAC AAGAACAAAT GATCGGCTGT AAATTCAATA TGACCGGACT GAAGAGAGAC AAGACAAAAG AGTACAACGA
      AATGGGTACT GTTGACGTGT CCGGAGCTTG TTCTTGTTTA CTAGCCGACA TTTAAGTTAT ACTGGCCTGA CTTCTCTCTG TTCTGTTTTC TCATGTTGCT
                                                                                                      Env
         T  W  Y  S  T  D  L  V  C  E  Q  G  N  S  T  D  N  E  S  R  C  Y  M  N  H  C  N  T  S  I  I  Q  E
 801  GACTTGGTAC AGCACCGACT TAGTGTGTGA GCAGGGGAAC TCAACCGATA ACGAGTCCCG CTGTTATATG AACCACTGCA ATACGAGCAT CATCCAAGAG
      CTGAACCATG TCGTGGCTGA ATCACACACT CGTCCCCTTG AGTTGGCTAT TGCTCAGGGC GACAATATAC TTGGTGACGT TATGCTCGTA GTAGGTTCTC
                                                                                                      Env
         S  C  D  K  H  Y  W  D  T  I  R  F  R  Y  C  A  P  P  G  Y  A  L  L  R  C  N  D  T  N  Y  S  G  F  M
 901  TCGTGCGACA AACACTATTG GGACACTATC CGATTTAGGT ACTGTGCCCC GCCGGGCTAT GCGCTTCTGC GTTGTAATGA TACCAATTAC AGTGGGTTCA
      AGCACGCTGT TTGTGATAAC CCTGTGATAG GCTAAATCCA TGACACGGGG CGGCCCGATA CGCGAAGACG CAACATTACT ATGGTTAATG TCACCCAAGT
                                                                                                      Env
         P  K  C  S  K  V  V  V  S  S  C  T  R  M  M  E  T  Q  T  S  T  W  F  G  F  N  G  T  R  A  E  N  R
1001  TGCCGAAGTG TAGCAAAGTC GTGGTGTCCT CTTGTACCCG CATGATGGAG ACGCAGACTT CCACCTGGTT TGGCTTTAAC GGAACTCGAG CTGAAAACCG
      ACGGCTTCAC ATCGTTTCAG CACCACAGGA GAACATGGGC GTACTACCTC TGCGTCTGAA GGTGGACCAA ACCGAAATTG CCTTGAGCTC GACTTTTGGC
                                                                                                      Env
         T  Y  I  Y  W  H  G  R  D  N  R  T  I  I  S  L  N  K  Y  Y  N  L  T  M  K  C  R  R  P  G  N  K  T
1101  GACGTATATC TACTGGCACG GACGAGATAA CCGAACGATC ATCTCACTGA ACAAGTACTA CAATCTGACC ATGAAATGCC GGCGCCCAGG CAATAAGACG
      CTGCATATAG ATGACCGTGC CTGCTCTATT GGCTTGCTAG TAGAGTGACT TGTTCATGAT GTTAGACTGG TACTTTACGG CCGCGGGTCC GTTATTCTGC
                                                                                                      Env
         V  L  P  V  T  I  M  S  G  L  V  F  H  S  Q  P  V  N  E  R  P  N  Q  A  W  C  W  F  G  G  N  W  K  D
1201  GTACTTCCTG TCACTATTAT GAGCGGACTT GTATTTCACT CGCAGCCGGT CAATGAGCGC CCGAACCAAG CCTGGTGCTG GTTTGGAGGC AACTGGAAAG
      CATGAAGGAC AGTGATAATA CTCGCCTGAA CATAAAGTGA GCGTCGGCCA GTTACTCGCG GGCTTGGTTC GGACCACGAC CAAACCTCCG TTGACCTTTC
                                                                                                      Env
         A  I  K  E  V  K  Q  T  I  V  K  H  P  R  Y  T  G  T  N  N  T  D  K  I  N  L  T  A  P  R  G  G  D
1301  ATGCGATTAA GGAAGTTAAA CAAACCATCG TAAAGCATCC CCGCTACACC GGCACCAACA ATACGGATAA GATCAACCTC ACAGCCCCTC GTGGCGGCGA
```

```
     TACGCTAATT CCTTCAATTT GTTTGGTAGC ATTTCGTAGG GGCGATGTGG CCGTGGTTGT TATGCCTATT CTAGTTGGAG TGTCGGGGAG CACCGCCGCT
                                                     Env
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
     ·P  E  V   T  F  M  W   T  N  C   R  G  E   F  L  Y  C   K  M  N   W  F  L   N  W  V  E   D  R  D   L  T  T
1401 TCCAGAGGTG ACCTTCATGT GGACTAACTG TCGCGGTGAA TTTCTGTACT GTAAGATGAA TTGGTTTCTG AACTGGGTCG AGGATAGGGA TCTGACAACA
     AGGTCTCCAC TGGAAGTACA CCTGATTGAC AGCGCCACTT AAAGACATGA CATTCTACTT AACCAAAGAC TTGACCCAGC TCCTATCCCT AGACTGTTGT
                                                     Env
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      Q  R  P  K   E  R  H   R  R  N   Y  V  P  C   H  I  R   Q  I  I   N  T  W  H   K  V  G   K  N  V   Y  L  P  P·
1501 CAACGGCCTA AGGAGAGGCA CCGCCGTAAC TATGTGCCTT GTCATATCAG ACAGATCATC AATACATGGC ATAAGGTGGG TAAAAACGTA TACCTCCCTC
     GTTGCCGGAT TCCTCTCCGT GGCGGCATTG ATACACGGAA CAGTATAGTC TGTCTAGTAG TTATGTACCG TATTCCACCC ATTTTTGCAT ATGGAGGGAG
                                                     Env
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
     · R  E  G   D  L  T   C  N  S  T   V  T  S   L  I  A   N  I  D  W   T  D  G   N  Q  T   N  I  T  M   S  A  E·
1601 CCCGCGAGGG CGACCTGACA TGTAATAGTA CAGTAACCAG CCTCATCGCT AACATAGACT GGACTGATGG AAATCAGACC AACATCACTA TGTCAGCCGA
     GGGCGCTCCC GCTGGACTGT ACATTATCAT GTCATTGGTC GGAGTAGCGA TTGTATCTGA CCTGACTACC TTTAGTCTGG TTGTAGTGAT ACAGTCGGCT
                                                     Env
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
     ·V  A  E   L  Y  R  L   E  L  G   D  Y  K   L  V  E  I   T  P  I   G  L  A   P  T  D  V   K  R  Y   T  T  G
1701 GGTAGCCGAA CTGTATAGGC TAGAACTCGG TGACTATAAG CTCGTCGAGA TCACCCCGAT AGGGCTCGCC CCTACAGACG TGAAACGTTA TACCACCGGC
     CCATCGGCTT GACATATCCG ATCTTGAGCC ACTGATATTC GAGCAGCTCT AGTGGGGCTA TCCCGAGCGG GGATGTCTGC ACTTTGCAAT ATGGTGGCCG
                                                     Env
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      G  T  S  R   N  K  R   Y  G  I   Y  I  V  V   G  V  I   L  L  R   I  V  I  Y   I  V  Q   M  L  N   R  V  R  Q·
1801 GGTACATCAA GGAACAAACG CTACGGCATC TACATCGTGG TAGGGGTCAT CCTCTTACGG ATTGTCATCT ATATCGTTCA GATGCTGAAT AGGGTGAGGC
     CCATGTAGTT CCTTGTTTGC GATGCCGTAG ATGTAGCACC ATCCCCAGTA GGAGAATGCC TAACAGTAGA TATAGCAAGT CTACGACTTA TCCCACTCCG
                                FMD2a
         ~~~~~~~~~~~~~~~~~~~~~~~~~~~~~~~~~~~~~~~~~~~~~~~~~~~~~~~~
      Env                                                                                  C Anchor
     ~~~~~                                                          ~~~~~~~~~~~~~~~~~~~~~~~~~~~~~~~~~~~~~~~~~~~~~~
     · G  N  F   D  L  L   K  L  A  G   D  V  E   S  N  P   G  P  G  G   K  T  G   I  A  V   M  I  G  L   I  A  C·
1901 AGGGCAATTT TGACCTGTTA AAACTGGCCG GGGACGTCGA AAGCAACCCC GGTCCGGGAG GAAAGACCGG TATTGCAGTC ATGATTGGCC TGATCGCCTG
     TCCCGTTAAA ACTGGACAAT TTTGACCGGC CCCTGCAGCT TTCGTTGGGG CCAGGCCCTC CTTTCTGGCC ATAACGTCAG TACTAACCGG ACTAGCGGAC
      C Anchor
     ~~~~~~~~~~~
                                                          prM
               ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
     ·V  G  A   V  T  L  S   N  F  Q   G  K  V   M  M  T  V   N  A  T   D  V  T   D  V  I  T   I  P
2001 CGTAGGAGCA GTTACCCTCT CTAACTTCCA AGGGAAGGTG ATGATGACGG TAAATGCTAC TGACGTCACA GATGTCATCA CGATTCCA
          GCATCCTCGT CAATGGGAGA GATTGAAGGT TCCCTTCCAC TACTACTGCC ATTTACGATG ACTGCAGTGT CTACAGTAGT GCTAAGGT
```

Appendix 7

1. PIV-WN (ΔprME)-HIV Gag

RV230 9AA-FMD-AM96 Gag
13260 bp

2. Sequence of PIV-WN (ΔprME)-HIV Gag (partial).

```
                                                                                                              C
                                               5' UTR
                                                                                                            M  S ·
  1 AGTAGTTCGC CTGTGTGAGC TGACAAACTT AGTAGTGTTT GTGAGGATTA CAACAATTA ACACAGTGCG AGCTGTTTCT TAGCACGAAG ATCTCCATGT
    TCATCAAGCG GACACACTCG ACTGTTTGAA TCATCACAAA CACTCCTAAT TGTTGTTAAT TGTGTCACGC TCGACAAAGA TCGTGCTTC  TAGAGCTACA
                                                                                      C
     ·  K   K   P   G   G   P   G   K   S   R   A   V   Y   L   L   K   R   G   M   P   R   V   L   S   L   I   G   L   K   R   A   M   L  ·
101 CTAAGAAACC AGGAGGGCCC GGCAAGAGCC GGGCTGTCTA TTTGCTAAAA CGCGGAATGC CCCGCGTGTT GTCCTTGATT GGACTTAAGA GGGCTATGTT
    GATTCTTTGG TCCTCCCGGG CCGTTCTCGG CCCGACAGAT AAACGATTTT GCGCCTTACG GGGCGCACAA CAGGAACTAA CCTGAATTCT CCCGATACAA
                                                            C
     · S   L   I   D   G   K   G   P   I   R   F   V   L   A   L   L   A   F   F   R   F   T   A   I   A  ?   T   R   A   V   L   D   R
201 GAGCCTGATC GACGGCAAGG GGCCAATACG ATTTGTGTTG GCTCTCTTGG CGTTCTTCAG GTTCACAGCA ATTGCTCCGA CCCGAGCAGT GCTGGATCGA
    CTCGGACTAG CTGCCGTTCC CCGGTTATGC TAAACACAAC CGAGAGAACC GCAAGAAGTC CAAGTGTCGT TAACGAGGCT GGGCTCGTCA CGACCCTAGCT
                                                            C
                                                                                                         NS3 Cleavage W   R   G   V   N   K   Q   T   A   M   K   H   L   L   S   F   K   K   E   L   G   T   L   T   S   A   I   N   R   R   S   S   K   Q ·
```

```
301 TGGAGAGGTG TGAACAAACA AACAGCGATG AAACACCTTC TGAGTTTCAA GAAGGAACTA CGGACCTTGA CCAGTGCTAT CAATCGGCGG AGCTCAAAGC
    ACCTCTCCAC ACTTGTTTGT TTGTCGCTAC TTTGTGGAAG ACTCAAAGTT CTTCCTTGAT CCCTGGAACT GGTCACGATA GTTAGCCGCC TCGAGTTTCG
                                  9AA C Signal
         NS3 Cleavage                                               FMDV2A                           ZM96 Gag

· K  K  R   G  G  K   T  G  I  A   V  I  N   F  D  L

```
      TCTAGCACGC CTACATGTCG GGACACAGGT AGGACCTGTA GTTCGTCCCT GGGTTTCTCG GGAAGGCCCT GATGCACCTG GCCAAGAAGT TCTGGGACTC
                                                ZM96 Gag

·A E Q  A T Q  E  V K N  W M T  D T L L  V Q N  A N P  D C K T  I L K  A L G
1401  AGCCGAGCAG GCCACCCAAG AGGTGAAGAA CTGGATGACC GACACCCTGC TGGTGCAGAA CGCCAACCCC GACTGCAAGA CCATCCTGAA GGCCCTGGGA
      TCGGCTCGTC CGGTGGGTTC TCCACTTCTT GACCTACTGG CTGTGGGACG ACCACGTCTT GCGGTTGGGG CTGACGTTCT GGTAGGACTT CCGGGACCCT
                                                ZM96 Gag

P G A T  L E E  M M T  A C Q G  V G G  P S H  K A R V  L A E  A M S  Q T N S·
1501  CCTGGAGCCA CCCTGGAAGA GATGATGACC GCCTGCCAGG GCGTGGGAGG ACCCAGCCAC AAGGCTCGGG TGCTGGCCGA GGCCATGAGC CAGACCAACA
      GGACCTCGGT GGGACCTTCT CTACTACTGG CGGACGGTCC CGCACCCTCC TGGGTCGGTG TTCCGAGCCC ACGACCGGCT CCGGTACTCG GTCTGGTTGT
                                                ZM96 Gag

· V N I  L M Q  K S N F  K G N  K R M  V K C F  N C G  K E G  H I A R  N C R·
1601  GCGTGAACAT CCTGATGCAG AAGTCCAACT TCAAGGGCAA CAAGCGGATG GTGAAGTGCT TCAACTGTGG AAAGGAGGGC CACATTGCCA GAAACTGCAG
      CGCACTTGTA GGACTACGTC TTCAGGTTGA AGTTCCCGTT GTTCGCCTAC CACTTCACGA AGTTGACACC TTTCCTCCCG GTGTAACGGT CTTTGACGTC
                                                ZM96 Gag

·A P R  K K G C  W K C  G K E  G H Q M  K D C  T E R  Q A N F  L G K  I W P
1701  AGCCCCAAGA AAAAAGGGCT GCTGGAAGTG CGGCAAAGAG GGGCACCAGA TGAAGGACTG CACCGAGCGG CAGGCTAACT TCCTGGGCAA GATCTGGCCC
      TCGGGGTTCT TTTTTCCCGA CGACCTTCAC GCCGTTTCTC CCCGTGGTCT ACTTCCTGAC GTGGCTCGCC GTCCGATTGA AGGACCCGTT CTAGACCGGG
                                                ZM96 Gag

S H K G  R P G  N F L  Q N R P  E P T  A P P  A E S F  R F E  E T T  P A P K·
1801  TCCCACAAGG GCAGACCAGG CAACTTCCTG CAGAACAGAC CCGAGCCAAC AGCCCCTCCT GCCGAGAGCT TCAGATTCGA GGAAACCACC CCTGCCCCAA
      AGGGTGTTCC CGTCTGGTCC GTTGAAGGAC GTCTTGTCTG GGCTCGGTTG TCGGGGAGGA CGGCTCTCGA AGTCTAAGCT CCTTTGGTGG GGACGGGGTT
                                  ZM96 Gag

FMDV2A

· Q E S  K D R  E A L T  S L K  S L F  G S D P  L S Q  N F D  L L K L  A G D·
1901  AGCAGGAAAG CAAGGACCGG GAGGCCCTGA CCTCCCTGAA GTCCCTGTTC GGCAGCGACC CCTGAGCCA GAATTTCGAC CTGCTTAAAC TTGCTGGCGA
      TCGTCCTTTC GTTCCTGGCC CTCCGGGACT GGAGGGACTT CAGGGACAAG CCGTCGCTGG GGGACTCGGT CTTAAAGCTG GACGAATTTG AACGACCGCT
                                                           TM Domain WN E (split)

FMDV2A          prE/NS1 Sig

·V E S  N P G P  A R D  R S I  A L T F  L A V  G G V  L L F L  S V N  V H A
2001  CGTTGAGTCA AATCCGGGCC CTGCCCGGGA CAGGTCCATA GCTCTCACGT TTCTCGCAGT TGGAGGAGTT CTGCTCTTCC TCTCCGTGAA CGTGCACGCT
      GCAACTCAGT TTAGGCCCGG GACGGGCCCT GTCCAGGTAT CGAGAGTGCA AAGAGCGTCA ACCTCCTCAA GACGAGAAGG AGAGGCACTT GCACGTGCGA
                                                 NS1

D T G C  A I D  I S R  Q E L R  C G S  G V F  I H N D  V E A  W M D  R Y K Y·
2101  GACACTGGGT GTGCCATAGA CATCAGCCGG CAAGAGCTGA GATGTGGAAG TGGAGTGTTC ATACACAATG ATGTGGAGGC TTGGATGGAC CGGTACAAGT
      CTGTGACCCA CACGGTATCT GTAGTCGGCC GTTCTCGACT CTACACCTTC ACCTCACAAG TATGTGTTAC TACACCTCCG AACCTACCTG GCCATGTTCA
                                                 NS1

· Y P E  T P Q  G L A K  I I Q  K A H  K E G V  C G L  R S V  S R L E  H Q M·
2201  ATTACCCTGA AACGCCACAA GGCCTAGCCA AGATCATTCA GAAAGCTCAT AAGGAAGGAG TGTGCGGTCT ACGATCAGTT TCCAGACTGG AGCATCAAAT
      TAATGGGACT TTGCGGTGTT CCGGATCGGT TCTAGTAAGT CTTTCGAGTA TTCCTTCCTC ACACGCCAGA TGCTAGTCAA AGGTCTGACC TCGTAGTTTA
                                                 NS1

·W E A  V K D E  L N T  L L K
```

```
2301 GTGGGAAGCA GTGAAGGACG AGCTGAACAC TCTTTTGAAG
     CACCCTTCGT CACTTCCTGC TCGACTTGTG AGAAAACTTC
```

1. PIV-WN (ΔprME)-HIV Env Gp140

RV230 ZM96 EnvGP140
13746 bp

2. Sequence of PIV-WN (ΔprME)-HIV Env Gp140 (partial).

```
                                                                                                          C
                                         5' UTR
                                                                                                    M   S ·
  1 AGTAGTTCGC CTGTGTGAGC TGACAAACTT AGTAGTGTTT GTGAGGATTA ACAACAATTA ACACAGTGCG AGCTGTTTCT TAGCACGAAG ATCTCGATGT
    TCATCAAGCG GACACACTCG ACTGTTTGAA TCATCACAAA CACTCCTAAT TGTTGTTAAT TGTGTCACGC TCGACAAAGA ATCGTGCTTC TAGAGCTACA
                                                                      C
    · K   K   P   G   G   P   G   K   S   R   A   V   Y   L   L   K   R   G   M   P   R   V   L   S   L   I   G   L   K   R   A   M   L ·
101 CTAAGAAACC AGGAGGGCCC GGCAAGAGCC GGGCTGTCTA TTTGCTAAAA CGCGGAATGC CCCGCGTGTT GTCCTTGATT GGACTTAAGA GGGCTATGTT
    GATTCTTTGG TCCTCCCGGG CCGTTCTCGG CCCGACAGAT AAACGATTTT GCGCCTTACG GGGCGCACAA CAGGAACTAA CCTGAATTCT CCCGATACAA
                                                  C
    · S   L   I   D   G   K   G   P   I   R   F   V   L   A   L   L   A   F   F   R   F   T   A   I   A   P   T   R   A   V   L   D   R
201 GAGCCTGATC GACGGCAAGG GGCCAATACG ATTTGTGTTG GCTCTCTTGG CGTTCTTCAG GTTCACAGCA ATTGCTCCGA CCCGAGCAGT GCTGGATCGA
    CTCGGACTAG CTGCCGTTCC CCGGTTATGC TAAACACAAC CGAGAGAACC GCAAGAAGTC CAAGTGTCGT TAACGAGGCT GGGCTCGTCA CGACCTAGCT
                                                  C
                                                                                                   NS3 Cleavage
      W   R   G   V   N   K   Q   T   A   M   K   H   L   L   S   F   K   K   E   L   G   T   L   T   S   A   I   N   R   R   S   S   K   Q ·
301 TGGAGAGGTG TGAACAAACA AACAGCGATG AAACACCTTC TGAGTTTCAA GAAGGAACTA GGGACCTTGA CCAGTGCTAT CAATCGGCGG AGCTCAAAGC
    ACCTCTCCAC ACTTGTTTGT TTGTCGCTAC TTTGTGGAAG ACTCAAAGTT CTTCCTTGAT CCCTGGAACT GGTCACGATA GTTAGCCGCC TCGAGTTTCG
```

```
                        Partial C Signal
                     ~~~~~~~~~~~~~~~~~~~~~~~~~
      NS3 Cleavage                                                       gp140
     ~~~~~~~~~~~~                                                 ~~~~~~~~~~~~~~~~~~~~~~~~~~~~~~~~~~~~~~~~~
      · K   K   R    G   G   K    T   G   I    A   V   I    M   G   V    R   E   I    L   R   N    W   Q   R    W   W   T    W   G   I   L   G   F ·
 401  AGAAAAAGCG GGGCGGAAAG ACAGGTATTG CTGTGATCAT GGGAGTGCGG GAGATCCTGC GGAACTGGCA GCGGTGGTGG ACCTGGGCA TCCTGGGCTT
      TCTTTTTCGC CCCGCCTTTC TGTCCATAAC GACACTAGTA CCCTCACGCC CTCTAGGACG CCTTGACCGT CGCCACCACC TGGACCCCGT AGGACCCGAA
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                  gp140
      · W   M   L    M   I   C    N   V   W    G   N   L    W   V   T    V   Y   Y    G   V   P    V   W   K    E   A   K    T   T   L   F   C   A ·
 501  TTGGATGCTG ATGATCTGCA ACGTGTGGGG CAACCTGTGG GTGACCGTGT ACTACGGCGT GCCCGTGTGG AAAGAGGCCA AGACCACCCT GTTCTGCGCC
      AACCTACGAC TACTAGACGT TGCACACCCC GTTGGACACC CACTGGCACA TGATGCCGCA CGGGCACACC TTTCTCCGGT TCTGGTGGGA CAAGACGCGG
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                  gp140
        S   D   A   K    S   Y   E    K   E   V    H   N   V    W   A   T    H   A   C    V   P   T    D   P   N    P   Q   E    I   V   L   G   N   V ·
 601  AGCGACGCCA AGAGCTACGA AGGAAAGTG CACAATGTGT GGGCCACCCA CGCCTGCGTG CCCACCGACC CCAACCCCCA GGAAATCGTC CTGGGCAACG
      TCGCTGCGGT TCTCGATGCT TCCTTTCAC GTGTTACACA CCCGGTGGGT GCGGACGCAC GGGTGGCTGG GGTTGGGGGT CCTTTAGCAG GACCCGTTGC
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                  gp140
      · T   E   N    F   N   M    W   K   N    D   M   V    D   Q   M    H   E   D    I   I   S    L   W   D    Q   S   L    K   P   C   V   K   L ·
 701  TGACCGAGAA CTTCAACATG TGGAAGAACG ACATGGTGGA CCAGATGCAC GAGGACATCA TCAGCCTGTG GGACCAGAGC CTGAAGCCCT GCGTGAAGCT
      ACTGGCTCTT GAAGTTGTAC ACCTTCTTGC TGTACCACCT GGTCTACGTG CTCCTGTAGT AGTCGGACAC CCTGGTCTCG GACTTCGGGA CGCACTTCGA
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                  gp140
      · T   P   L    C   V   T    L   N   C    T   E   V    N   V   T    R   N   V    N   N   S    V   V   N    N   T   T    T   N   V   N   N   S   M ·
 801  GACCCCCCTG TGCGTGACCC TGAACTGCAC CGAAGTGAAC GTGACCCGGA ACGTGAACAA CAGCGTGGTG AACAACACAC CAACGTGAA TAACTCCATG
      CTGGGGGGAC ACGCACTGGG ACTTGACGTG GCTTCACTTG CACTGGGCCT TGCACTTGTT GTCGCACCAC TTGTTGTGTG GGTTGCACTT ATTGAGGTAC
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                  gp140
        N   G   D   M    K   N   C    S   F   N    I   T   T    T   E    L   K   C    K   K   K    N   V   Y    A   L   F    Y   K   L   D    I   V   S   L ·
 901  AACGGCGACA TGAAGAACTG CAGCTTCAAC ATCACCACCG AGCTGAAGGA CAAGAAAAG AACGTGTACG CCCTGTTCTA CAAGCTGGAC ATCGTGTCCC
      TTGCCGCTGT ACTTCTTGAC GTCGAAGTTG TAGTGGTGGC TCGACTTCCT GTTCTTTTC TTGCACATGC GGGACAAGAT GTTCGACCTG TAGCACAGGG
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                  gp140
      · N   E   T    D   D   S    E   T   G    N   S   S    K   Y   Y    R   L   I    N   C   N    T   S   A    L   T   Q    A   C   P   K   V   S ·
1001  TGAACGAGAC AGACGACAGC GAGACAGGCA ACAGCAGCAA GTACTACCGG CTGAACTGCA ACACCAGCGC CCTGACCCAG GCCTGCCCCA AGGTGTC
      ACTTGCTCTG TCTGCTGTCG CTCTGTCCGT TGTCGTCGTT CATGATGGCC GACTTGACGT CGTTGGTCG GGGACTGGG TCCGGACGG GGTTCCACAG
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                  gp140
      · F   D   P    I   P   I   H    Y   C   A    P   A   G    Y   A   I    L   K   C   N    N   K   T    F   N   G   T    G   P   C   H   N   V ·
1101  CTTCGACCCC ATCCCCATCC ACTACTGCGC CCCTGCCGGC TACGCCATCC TGAAGTGCAA CAACAAGACC TTCAACGGCA CCGGCCCCTG CCACAACGTG
      GAAGCTGGGG TAGGGGTAGG TGATGACGCG GGGACGGCCG ATGCGGTAGG ACTTCACGTT GTTGTTCTGG AAGTTGCCGT GGCCGGGGAC GGTGTTGCAC
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                  gp140
        S   T   V   Q    C   T   H    G   I   K    P   V   V   S    T   Q   L    L   L   N    G   S   L    A   E   E    G   I   I   I    R   S   E   N ·
1201  TCCACCGTGC AGTGCACCCA CGGCATCAAG CCCGTGGTGT CCACCCAGCT GCTGCTGAAC GGCAGCCTGG CCGAGGAAGG CATCATCATC AGAAGCGAGA
      AGGTGGCACG TCACGTGGGT GCCGTAGTTC GGGCACCACA GGTGGGTCGA CGACGACTTG CCGTCGGACC GGCTCCTTCC GTAGTAGTAG TCTTCGCTCT
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                  gp140
      · L   T   N    N   V   K    T   I   I   V    H   L   N    R   S   I    E   I   V   C    V   R   P    N   N   N    T   R   Q   S    I   R   I ·
1301  ACCTGACCAA CAACGTGAAA ACCATCATCG TGCACCTGAA CAGATCCATC GAGATCGTGT GCGTGCGGCC CAACAACAAC ACCCGGCAGA GCATCCGGAT
      TGGACTGGTT GTTGCACTTT TGGTAGTAGC ACGTGGACTT GTCTAGGTAG CTCTAGCACA CGCACGCCGG GTTGTTGTTG TGGGCCGTCT CGTAGGCCTA
                                                                  gp140
```

```
              · G  P  G   Q  T  F  Y   A  T  G   D  I  I   G  D  I   R  Q  A  H   C  N  I   S  R  T  N   W  T  K   T  L  R
1401  CGGCCCTGGC CAGACCTTTT ACGCCACCGG CGACATCATC GGCGACATCA GACAGGCCCA CTGCAACATC AGCCGGACCA ACTGACCAA GACCCTGCGG
      GCCGGGACCG GTCTGGAAAA TGCGGTGGCC GCTGTAGTAG CCGCTGTAGT CTGTCCGGGT GACGTTGTAG TCGGCCTGGT TGACCTGGTT CTGGGACGCC
                                                                 gp140
        E  V  R  N   K  L  R   E  H  F   P  N  K  N   I  T  F   P  K  P  S   S  G  G  D   L  E  I   T  T  H   S  F  N  C·
1501  GAAGTGCGGA ACAAGCTGCG GGAGCACTTC CCCAACAAGA ACATCACCTT CAAGCCCAGC TCTGGCGGCG ACCTGGAAAT CACCACCCAC AGCTTCAACT
      CTTCACGCCT TGTTCGACGC CCTCGTGAAG GGGTTGTTCT TGTAGTGGAA GTTCGGGTCG AGACCGCCGC TGGACCTTTA GTGGTGGGTG TCGAAGTTGA
                                                                 gp140
      · R  G  E   F  F  Y   C  N  T  S   G  L  F   S  I  N   Y  T  E  N   N  T  D   G  T  P   I  T  L  P   C  R  I·
1601  GCAGGGGCGA GTTCTTCTAC TGCAATACCT CCGGCCTGTT CAGCATCAAC TACACCGAGA ACAACACCGA CGGCACCCCC ATCACCCTGC CCTGCAGAAT
      CGTCCCCGCT CAAGAAGATG ACGTTATGGA GGCCGGACAA GTCGTAGTTG ATGTGGCTCT TGTTGTGGCT GCCGTGGGGG TAGTGGGACG GGACGTCTTA
                                                                 gp140
      · R  Q  I   I  N  M  W   Q  E  V   G  R  A   M  Y  A  P   P  I  E   G  N  I   A  C  K  S   D  I  T   G  L  L
1701  CCGGCAGATC ATCAATATGT GGCAGGAGGT GGGCAGGGCC ATGTACGCCC CTCCCATCGA GGGCAATATC GCCTGCAAGA GCGACATCAC CGGCCTGCTG
      GGCCGTCTAG TAGTTATACA CCGTCCTCCA CCCGTCCCGG TACATGCGGG GAGGGTAGCT CCCGTTATAG CGGACGTTCT CGCTGTAGTG GCCGGACGAC
                                                                 gp140
        L  V  R  D   G  G  S   T  N  D   S  T  N  N   N  T  E   I  F  R   P  A  G  G   D  M  R   D  N  W   R  S  E  L·
1801  CTGGTGCGGG ACGGCGGCAG CACCAACGAC AGCACCAACA ACAATACCGA GATCTTCCGG CCTGCCGGCG GAGACATGCG GGACAACTGG CGGAGCGAGC
      GACCACGCCC TGCCGCCGTC GTGGTTGCTG TCGTGGTTGT TGTTATGGCT CTAGAAGGCC GGACGGCCGC CTCTGTACGC CCTGTTGACC GCCTCGCTCG
                                                                 gp140
      · Y  K  Y   K  V  V   E  I  K  P   L  G  I   A  P  T   E  A  K  R   R  V  V   E  R  E   K  S  A  V   G  I  G·
1901  TGTACAAGTA CAAGGTGGTG GAGATCAAGC CTCTGGGCAT TGCTCCCACC GAGGCCAAGC GGCGGGTGGT GGAGCGGGAG AAGAGCGCCG TGGGCATCGG
      ACATGTTCAT GTTCCACCAC CTCTAGTTCG GAGACCCGTA ACGAGGGTGG CTCCGGTTCG CCGCCCACCA CCTCGCCCTC TTCTCGCGGC ACCCGTAGCC
                                                                 gp140
      · A  V  F   L  G  F  L   G  A  A   G  S  T   M  G  A  A   S  I  T   L  T  A   Q  A  R  Q   V  L  S   G  I  V
2001  CGCCGTGTTT CTGGGCTTCC TGGGAGCCGC CGGAAGCACA ATGGGAGCCG CCAGCATCAC CCTGACCGCC CAGGCCCGGC AGGTGCTGTC CGGCATCGTG
      GCGGCACAAA GACCCGAAGG ACCCTCGGCG GCCTTCGTGT TACCCTCGGC GGTCGTAGTG GGACTGGCGG GTCCGGGCCG TCCACGACAG GCCGTAGCAC
                                                                 gp140
        C  Q  Q  S   N  L  L   R  A  I   E  A  Q  Q   H  L  L   Q  L  T   V  W  G  I   K  Q  L   Q  T  R   V  L  A  I·
2101  CAGCAGCAGA GCAACCTGCT GAGAGCCATC GAGGCTCAGC AGCACCTGCT GCAGCTGACA GTGTGGGGCA TCAAGCAGCT GCAGACCCGG GTGCTGGCCA
      GTCGTCGTCT CGTTGGACGA CTCTCGGTAG CTCCGAGTCG TCGTGGACGA CGTCGACTGT CACACCCCGT AGTTCGTCGA CGTCTGGGCC CACGACCGGT
                                                                 gp140
      · E  R  Y   L  K  D   Q  Q  L  L   G  L  W   G  C  S   G  K  L  I   C  T  T   A  V  P   W  N  I  S   W  S  N·
2201  TCGAGAGATA CCTGAAGGAT CAGCAGCTCC TGGGCCTGTG GGGCTGCAGC GGCAAGCTGA TCTGCACCAC CGCCGTGCCC TGGAACATCA GCTGGTCCAA
      AGCTCTCTAT GGACTTCCTA GTCGTCGAGG ACCCGGACAC CCCGACGTCG CCGTTCGACT AGACGTGGTG GCGGCACGGG ACCTTGTAGT CGACCAGGTT
                                                                 gp140
      · K  S  K   T  D  I  W   D  N  M   T  W  M   Q  W  D  R   E  I  S   N  Y  T   N  T  I  Y   R  L  L   E  D  S
2301  CAAGAGCAAG ACCGACATCT GGGACAACAT GACCTGGATG CAGTGGGACC GGGAGATCAG CAACTACACC AACACCATCT ACCGGCTGCT GGAAGATAGC
      GTTCTCGTTC TGGCTGTAGA CCCTGTTGTA CTGGACCTAC GTCACCCTGG CCCTCTAGTC GTTGATGTGA TTGTGGTAGA TGGCCGACGA CCTTCTATCG
                                                                 gp140
                                                                                                         FMDV2A
```

```
      Q S Q Q E Q N E K D L L A L D S W N N N F D L L K L A G D V E S N P·
2401  CAGAGCCAGC AGGAACAGAA CGAGAAGGAC CTGCTGGCCC TGGACAGCTG GAACAACAAT TTCGACCTGC TTAAACTTGC TGGCGACGTT GAGTCAAATC
      GTCTCGGTCG TCCTTGTCTT GCTCTTCCTG GACGACCGGG ACCTGTCGAC CTTGTTGTTA AAGCTGGACG AATTTGAACG ACCGCTGCAA CTCAGTTTAG
                                           TM Domain WN E (split)
                            ~~~~~~~~~~~~~~~~~~~~~~~~~~~~~~~~~~~~~~~~~~~~~~~~~~~~~~~~~~~~~~~~~~~
      FMDV2A  prE/NS1 Sig                                                                       NS1
      ~~~~~~~ ~~~~~~~~~~                                                                   ~~~~~~~~~~~~~
      · G P A R D R S I A L T F L A V G G V L L F L S V N V H A D T G C A·
2501  CGGGCCCTGC CCGGGACAGG TCCATAGCTC TCACGTTTCT CGCAGTTGGA GGAGTTCTGC TCTTCCTCTC CGTGAACGTG CACGCTGACA CTGGGTGTGC
      GCCCGGGACG GGCCCTGTCC AGGTATCGAG AGTGCAAAGA GCGTCAACCT CCTCAAGACG AGAAGGAGAG GCACTTGCAC GTGCGACTGT GACCCACACG
                                                   NS1
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      ·I D I S R Q E L R C G S G V F I H N D V E A W M D R Y K Y Y P E T
2601  CATAGACATC AGCCGGCAAG AGCTGAGATG TGGAAGTGGA GTGTTCATAC ACAATGATGT GGAGGCTTGG ATGGACCGGT ACAAGTATTA CCCTGAAACG
      GTATCTGTAG TCGGCCGTTC TCGACTCTAC ACCTTCACCT CACAAGTATG TGTTACTACA CCTCCGAACC TACCTGGCCA TGTTCATAAT GGGACTTTGC
                                                   NS1
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      P Q G L A K I I Q K A H K E G V C G L R S V S R L E H Q M W E A V K·
2701  CCACAAGGCC TAGCCAAGAT CATTCAGAAA GCTCATAAGG AAGGAGTGTG CGGTCTACGA TCAGTTTCCA GACTGGAGCA TCAAATGTGG GAAGCAGTGA
      GGTGTTCCGG ATCGGTTCTA GTAAGTCTTT CGAGTATTCC TTCCTCACAC GCCAGATGCT AGTCAAAGGT CTGACCTCGT AGTTTACACC CTTCGTCACT
                                                   NS1
      ~~~~~~~~~~~~~~~~~~~~~~~~~~~
      · D E L N T L L K
2801  AGGACGAGCT GAACACTCTT TTGAAG
           TCCTGCTCGA CTTGTGAGAA AACTTC
```

Appendix 8

Construct 1
1. PIV-WN (ΔprME)-HA New Caledonia

RV230 HA New Cal Sequence
13419bp

2. Sequence of PIV-WN (ΔprME)-HA New Caledonia (partial).

```
                                                                                                    C
                                                5' UTR
                                                                                                   M  S  ·
  1 AGTAGTTCGC CTGTGTGAGC TGACAAACTT AGTAGTGTTT GTGAGGATTA ACAACAATTA ACACAGTGCG AGCTGTTTCT TAGCACGAAG ATCTCGATGT
    TCATCAAGCG GACACACTCG ACTGTTTGAA TCATCACAAA CACTCCTAAT TGTTGTTAAT TGTGTCACGC TCGACAAAGA ATCGTGCTTC TAGAGCTACA
                                    C
    ·  K   K   P    G   G   P    G   K   S   R    A   V   Y    L   L   K    R   G   M    P   R   V   L    S   L   I    G   L   K   R    A   M   L  ·
101 CTAAGAAACC AGGAGGGCCC GGCAAGAGCC GGGCTGTCTA TTTGCTAAAA CGCGGAATGC CCCGCGTGTT GTCCTTGATT GGACTTAAGA GAGCCATGCT
    GATTCTTTGG TCCTCCCGGG CCGTTCTCGG CCCGACAGAT AAACGATTTT GCGCCTTACG GGGCGCACAA CAGGAACTAA CCTGAATTCT CTCGGTACGA
                                                                                                                  C
    ·  S   L   I    D   G   K    G   P   I    R   F   V   L    A   L   L    A   F   F   R    F   T   A    I   A   P   T    R   A   V    L   D   R
201 TTCGCTCATT GACGGAAAGG GACCCATCCG ATTCGTACTG GCGTTGCTCG CATTCTTCCG GTTTACGGCT ATTGCGCCCA CGAGAGCGGT ACTCGACAGG
    AAGCGAGTAA CTGCCTTTCC CTGGGTAGGC TAAGCATGAC CGCAACGAGC GTAAGAAGGC CAAATGCCGA TAACGCGGGT GCTCTCGCCA TGAGCTGTCC
                                                                                                                  NS3 Cleavage
                           C
       W   R   G   V    N   K   Q    T   A   M    K   H   L   L    S   F   K    K   E   L    G   T   L   T    S   A   I    N   R   R    S   S   K   Q   ·
301 TGGCGCGGAG TAAACAAGCA AACAGCCATG AAACACTTGT TGTCGTTCAA AAAGGAACTC GGGACCTTGA CCTCCGCCAT CAACCGACGG AGCTCAAAAC
```

```
     ACCGCGCCTC ATTTGTTCGT TTGTCGGTAC TTTGTGAACA ACAGCAAGTT TTTCCTTGAG CCCTGGAACT GGAGGCCGTA GTTGGCTGCC TCGAGTTTTG
                              Partial C signal                                                              New Cal HA
                 ~~~~~~~~~~~~~~~~~~~~~~~~~~~~~~~                                                            ~~~~~~~~~~~
          NS3 Cleavage                            HA signal
          ~~~~~~~~~~~~                ~~~~~~~~~~~~~~~~~~~~~~~~~~~~~~~~~~
         · K K R  G G K  T G I A  V I K  A K L  L V L L  C T F  T A T  Y A D T  I C I ·
     401 AGAAGAAGAG GGGAGGAAAG ACGGGAATCG CAGTCATTAA GGCAAAACTG TTGGTGTTGC TCTGTACATT CACTGCGACG TACGCGGATA CAATCTGTAT
         TCTTCTTCTC CCCTCCTTTC TGCCCTTAGC GTCAGTAATT CCGTTTTGAC AACCACAACG AGACATGTAA GTGACGCTGC ATGCGCCTAT GTTAGACATA
                                                          New Cal HA · G Y H  A N N  S  T D T  V D T  V L E K  N V T  V T H  S V N L  L E D  S H N
     501 CGGGTACCAT GCCAACAATT CGACCGACAC CGTGGATACC GTCTTGGAAA AGAATGTCAC AGTGACTCAT TCGGTAAACC TCCTTGAGGA TTCGCATAAC
         GCCCATGGTA CGGTTGTTAA GCTGGCTGTG GCACCTATGG CAGAACCTTT TCTTACAGTG TCACTGAGTA AGCCATTTGG AGGAACTCCT AAGCGTATTG
                                                          New Cal HA G K L  C  L L K  G I A  P L Q L  G N C  S V A  G W I L  G N P  E C E  L L I S ·
     601 GGGAAGTTGT GCCTTCTTAA AGGGATCGCA CCGCTGCAAC TGGGTAACTG TTCGGTCGCC GGCTGGATTC TCGGAAACCC CGAGTGTGAA CTGCTTATCT
         CCCTTCAACA CGGAAGAATT TCCCTAGCGT GGCGACGTTG ACCCATTGAC AAGCCAGCGG CCGACCTAAG AGCCTTTGGG GCTCACACTT GACGAATAGA
                                                          New Cal HA · K E S  W S Y  I V E T  P N P  E N G  T C Y P  G Y F  A D Y  E E L R  E Q L ·
     701 CAAAGGAATC GTGGTCCTAT ATCGTGGAGA CACCGAACCC GGAGAATGCG ACGTGCTACC CTGGTTATTT CGCAGACTAC GAAGAACTTC GAGAACAACT
         GTTTCCTTAG CACCAGGATA TAGCACCTCT GTGGCTTGGG CCTCTTACCC TGCACGATGG GACCAATAAA GCGTCTGATG CTTCTTGAAG CTCTTGTTGA
                                                          New Cal HA · S S V  S S F E  R F E  I F P  K E S S  W P N  H T V  T G V S  A S C  S H N
     801 GTCCTCCGTC AGCTCGTTCG AGCGATTCGA AATCTTTCCG AAAGAGTCAT CGTGGCCGAA TCACACGGTA ACGGGTGTGT CCGGGTCATG TAGCCATAAT
         CAGGAGGCAG TCGAGCAAGC TCGCTAAGCT TTAGAAAGGC TTTCTCAGTA GCACCGGCTT AGTGTGCCAT TGCCCACACA GGCCAGTAC ATCGGTATTA
                                                          New Cal HA G K S S  F Y R  N L L  W L T G  K N G  L Y P  N L S K  S Y V  N N K  E K E V ·
     901 GGGAAGTCCT CGTTCTATCG CAACCTGTTG TGGCTTACTG GGAAAAACGG GTTGTACCCT AATCTCAGCA AGAGCTACGT CAATAACAAA GAAAAAGAGG
         CCCTTCAGGA GCAAGATAGC GTTGGACAAC ACCGAATGAC CCTTTTTGCC CAACATGGGA TTAGAGTCGT TCTCGATGCA GTTATTGTTT CTTTTTCTCC
                                                          New Cal HA · L V L  W G V  H H P P  N I G  N Q R  A L Y H  T E N  A Y V  S V V S  S H Y ·
    1001 TGCTGGTCTT GTGGGTGTG CATCACCCAC CTAACATTGG AATCAGAGG GCACTGTACC ACACTGAGAA TGCATACGTG AGCGTGGTGT CGAGCCACTA
         ACGACCAGAA CACCCCACAC GTAGTGGGTG GATTGTAACC CTTAGTCTCC CGTGACATGG TGTGACTCTT ACGTATGCAC TCGCACCACA GCTCGGTGAT
                                                          New Cal HA S R R  F T P E  I A K  R P K  V R D Q  E G R  I N Y  Y W T L  L E P  G D T
    1101 TAGCCGGAGA TTCACACCGG AGATTCGCGA AGCGGCCCAAA GTCCGCGACC AGGAGGGGCG GATTAACTAC TACTGGACCC TCCTCGAGCC TGGCGATACG
         ATCGGCCTCT AAGTGTGGCC TCTAAGCGCT TCGCCGGGTTT CAGGCGCTGG TCCTCCCCGC CTAATTGATG ATGACCTGGG AGGAGCTCGG ACCGCTATGC
                                                          New Cal HA I I F E  A N G  N L I  A P W Y  A F A  L S R  G F G S  G I I  T S N  A P M D ·
    1201 ATCATCTTTG AAGCGAATGG TAATCTTATC GCCCCGTGGT ATGCTTTTGC GCTTTCAAGA GGATTGGAT CAGGGATCAT CACATCAAAT GCGCCGATGG
         TAGTAGAAAC TTCGCTTACC ATTAGAATAG CGGGGCACCA TACGAAAACG CGAAAGTTCT CCTAAACCTA GTCCCTAGTA GTGTAGTTTA CGCGGCTACC
                                                          New Cal HA · E C D  A K C  Q T P Q  G A I  N S S  L P F Q  N V H  P V T  I G E C  P K Y ·
    1301 ACGAGTGCGA TGCTAACTGT CAGACTCCCC AAGGCGCTAT CAACTCGTCG TTGCCCTTTC AAAACGTGCA CCCCGTAACG ATCGGAGAGT GTCCCAAGTA
```

```
     TGCTCACGCT ACGATTCACA GTCTGAGGGG TTCCGCGATA GTTGAGCAGC AACGGGAAAG TTTTGCACGT GGGGCATTGC TAGCCTCTCA CAGGGTTCAT
                                               New Cal HA

·V R S  A K L R  M V T  G L R  N I P S  I Q S  R G L  F G A I  A G F  I E G
1401 TGTCAGATCG GCGAAACTTA GGATGGTGAC CGGACTCCGC AATATCCCCT CGATCCAGTC ACGGGGATTG TTTGGAGCCA TTGCGGGCTT CATCGAAGGG
     ACAGTCTAGC CGCTTTGAAT CCTACCACTG GCCTGAGGCG TTATAGGGGA GCTAGGTCAG TGCCCCTAAC AAACCTCGGT AACGCCCGAA GTAGCTTCCC
                                               New Cal HA

G W T G  M V D  G W Y  G Y H H  Q N E  Q G S  G Y A A  D Q K  S T Q  N A I N·
1501 GGCTGGACTG GAATGGTCGA TGGGTGGTAC GGTTATCACC ACCAGAATGA GCAGGGTTCC GGGTATGCCG CGGATCAGAA ATCGACACAG AACGCAATCA
     CCGACCTGAC CTTACCAGCT ACCCACCATG CCAATAGTGG TGGTCTTACT CGTCCCAAGG CCCATACGGC GCCTAGTCTT TAGCTGTGTC TTGCGTTAGT
                                               New Cal HA

· G I T  N K V  N S V I  E K M  N T Q  F T A V  G K E  F N K  L E R R  M E N·
1601 ACGGGATTAC GAACAAGGTA AACAGCGTCA TTGAGAAGAT GAATACACAG TTTACAGCCG TGGGGAAAGA ATTCAACAAA CTCGAGCGCC GGATGGAGAA
     TGCCCTAATG CTTGTTCCAT TTGTCGCAGT AACTCTTCTA CTTATGTGTC AAATGTCGGC ACCCCTTTCT TAAGTTGTTT GAGCTCGCGG CCTACCTCTT
                                               New Cal HA

·L N K  K V D D  G F L  D I W  T Y N A  E L L  V L L  E N E R  T L D  F H D
1701 TTTGAATAAG AAAGTGGACG ATGGTTTCCT CGATATCTGG ACGTACAATG CGGAGCTGCT TGTCCTGCTC GAAAATGAGA GGACGCTCGA CTTTCATGAC
     AAACTTATTC TTTCACCTGC TACCAAAGGA GCTATAGACC TGCATGTTAC GCCTCGACGA ACAGGACGAG CTTTTACTCT CCTGCGAGCT GAAAGTACTG
                                               New Cal HA

S N V K  N L Y  E K V  K S Q L  K N N  A K E  I G N G  C F E  F Y H  K C N N·
1801 TCCAATGTGA AGAACCTTTA CGAGAAGGTG AAGTCCCAAT TGAAGAATAA CGCCAAGGAA ATTGGAAACG GCTGCTTCGA ATTCTACCAC AAATGCAACA
     AGGTTACACT TCTTGGAAAT GCTCTTCCAC TTCAGGGTTA ACTTCTTATT GCGGTTCCTT TAACCTTTGC CGACGAAGCT TAAGATGGTG TTTACGTTGT
                                               New Cal HA

· E C M  E S V  K N G T  Y D Y  P K Y  S E E S  K L N  R E K  I D G V  K L E·
1901 ATGAGTGCAT GGAATCGGTC AAAAATGGAA CATATGATTA TCCCAAATAC TCGGAGGAGT CAAAGCTTAA TAGGGAGAAA ATTGATGGGG TAAAACTTGA
     TACTCACGTA CCTTAGCCAG TTTTTACCTT GTATACTAAT AGGGTTTATG AGCCTCCTCA GTTTCGAATT ATCCCTCTTT TAACTACCCC ATTTGAACT
                                               New Cal HA

·S M G  V Y Q I  L A I  Y S T  V A S S  L V L  L V S  L G A I  S F W  M C S
2001 GAGCATGGGT GTATATCAGA TCCTGGCAAT CTACTCAACC GTGGCGTCGT CACTGGTACT CCTCGTGTCC CTGGGCGCCA TTAGCTTTTG GATGTGTTCG
     CTCGTACCCA CATATAGTCT AGGACCGTTA GATGAGTTGG CACCGCAGCA GTGACCATGA GGAGCACAGG GACCCGCGGT AATCGAAAAC CTACACAAGC
                New Cal HA                                                                   prE/NS1 signal FMD2A                                       TM of WN E split
      N G S L  Q C R  I C I  N F D L  L K L  A G D  V E S N  P G P  A R D  R S I A·
2101 AATGGATCGC TCCAGTGCCG CATCTGCATC AACTTTGACC TGCTGAAGCT CGCGGGTGAC GTCGAATCCA ACCCAGGGCC AGCCCGGGAC AGAAGCATTG
     TTACCTAGCG AGGTCACGGC GTAGACGTAG TTGAAACTGG ACGACTTCGA GCGCCCACTG CAGCTTAGGT TGGGTCCCGG TCGGGCCCTG TCTTCGTAAC
                          TM of WN E split NS1
      · L T F  L A V  G G V L  L F L  S V N  V H A D  T G C  A I D  I S R Q  E L R·
2201 CGCTCACTTT TCTCGCGGTA GGAGGTGTGC TGTTGTTCCT GTCAGTGAAC GTCCACGCAG ACACGGGATG CGCGATTGAT ATCTCCAGAC AAGAATTGAG
     GCGAGTGAAA AGAGCGCCAT CCTCCACACG ACAACAAGGA CAGTCACTTG CAGGTGCGTC TGTGCCCTAC GCGCTAACTA TAGAGGTCTG TTCTTAACTC
                                                   NS1

·C G S  G V F I  H N D  V E A  W M D R  Y K Y  Y P E  T P Q G  L A K  I I Q

```
2301  GTGCGGGTCG GGGGTCTTTA TCCATAACGA CGTGGAGGCG TGGATGGACA GGTATAAGTA TTACCCTGAA ACGCCGCAGG GACTTGCGAA AATCATTCAG
      CACGCCCAGC CCCCAGAAAT AGGTATTGCT GCACCTCCGC ACCTACCTGT CCATATTCAT AATGGGACTT TGCGGCGTCC CTGAACGCTT TTAGTAAGTC
                                                                    NS1
      ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
       K A H K   E G V   C G L   R S V S   R L E   H Q M   W E A V   K D E   L N T   L L K
2401  AAAGCCCATA AGGAAGGTGT GTGTGGATTG AGATCAGTCT CACGCCTTGA GCACCAGATG TGGGAGGCTG TCAAGGATGA ATTGAACACA CTTTTGAAGG
      TTTCGGGTAT TCCTTCCACA CACACCTAAC TCTAGTCAGA GTGCGGAACT CGTGGTCTAC ACCCTCCGAC AGTTCCTACT TAACTTGTGT GAAAACTTCC
```

Construct 2

1. PIV-WN (ΔCprME)-HA New Caledonia

DeleteC230 HA New Cal
13209bp

2. Sequence of PIV-WN (ΔCprME)-HA New Caledonia (partial).

```
                                                                                                               C
                                                                                                              ~~~~
                                          5' UTR
      ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                                            M  S  ·
1     AGTAGTTCGC CTGTGTGAGC TGACAAACTT AGTAGTGTTT GTGAGGATTA ACAACAATTA ACACAGTGCG AGCTGTTTCT TAGCACGAAG ATCTCGATGT
      TCATCAAGCG GACACACTCG ACTGTTTGAA TCATCACAAA CACTCCTAAT TGTTGTTAAT TGTGTCACGC TCGACAAAGA ATCGTGCTTC TAGAGCTACA
                                                                                                            NS3 cleavage
                                                                                                           ~~~~~~~~~~~~~
```

```
                                                                C
                      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      · K K P   G G P   G K S R   A V Y L   L L K R   G M P   R V L   S L I   G L K Q   K K R ·
  101   CTAAGAAACC AGGAGGGCCC GGCAAGAGCC GGGCTGTCTA TTTGCTAAAA CGCGGAATGC CCCGCGTGTT GTCCTTGATT GGACTTAAGC AGAAGAAGAG
        GATTCTTTGG TCCTCCCGGG CCGTTCTCGG CCCGACAGAT AAACGATTTT GCGCCTTACG GGGCGCACAA CAGGAACTAA CCTGAATTCG TCTTCTTCTC
              Partial C signal                                                                          New Cal HA
        ~~~~~~~~~~~~~~~~~~~                                                                         ~~~~~~~~~~~~~~~~~~~
        NS3 cleavage                                    HA signal
      ~                                  ~~~~~~~~~~~~~~~~~~~~~~~~~~~~~~~~~~~~~~~~~
      · G G K   T G I A   V I K   A K L   L V L L   C T F   T A T   Y A D T   I C I   G Y H
  201   GGGAGGAAAG ACGGGAATCG CAGTCATTAA GGCAAAACTG TTGCTGTTGC TCTGTACATT CACTGCGACG TACCGGGATA CAATCTGTAT CGGGTACCAT
        CCCTCCTTTC TGCCCTTAGC GTCAGTAATT CCGTTTTGAC AACCACAACG AGACATGTAA GTGACGCTGC ATGGCCCTAT GTTAGACATA GCCCATGGTA
                                                                                    New Cal HA
        A N N S   T D T   V D T   V L E K   N V T   V T H   S V N L   L E D   S H N   G K L C ·
  301   GCCAACAATT CGACCGACAC CGTGGATACC GTCTTGGAAA AGAATGTCAC AGTGACTCAT TCGGTAAACC TCCTTGAGGA TTCGCATAAC GGGAAGTTGT
        CGGTTGTTAA GCTGGCTGTG GCACCTATGG CAGAACCTTT TCTTACAGTG TCACTGAGTA AGCCATTTGG AGGAACTCCT AAGCGTATTG CCCTTCAACA
                                                                                    New Cal HA
      · L L K   G I A   P L Q L   G N C   S V A   G W I L   G N P   E C E   L L I S   K E S ·
  401   GCCTTCTTAA AGGGATCGCA CCCGCTGCAAC TGGGTAACTG TTCGGTCGCC GGCTGGATTC TCGGAAACCC CGAGTGTGAA CTGCTTATCT CAAAGGAATC
        CGGAAGAATT TCCCTAGCGT GGCGACGTTG ACCCATTGAC AAGCCAGCGG CCGACCTAAG AGCCTTTGGG GCTCACACTT GACGAATAGA GTTTCCTTAG
                                                                                    New Cal HA
      · W S Y   I V E T   P N P   E N G   T C Y P   G Y F   A D Y   E E L R   E Q L   S S V
  501   GTGGTCCTAT ATCGTGGAGA CACCGAACCC GGAGAATGGG ACGTGCTACC CTGGTTATTT CGCAGACTAC GAAGAACTTC GAGAACAACT GTCCTCCGTC
        CACCAGGATA TAGCACCTCT GTGGCTTGGG CCTCTTACCC TGCACGATGG GACCAATAAA GCGTCTGATG CTTCTTGAAG CTCTTGTTGA CAGGAGGCAG
                                                                 New Cal HA
      S S F E   R F E   I F P   K E S S   W P N   H T V   T G V S   A S C   S H N   G K S S ·
  601   AGCTCGTTCG AGCGATTCGA ATCTTTCCG AAAGAGTCAT CGTGGCCGAA TCACACGGTA ACGGGTGTGT CCGCGTCATG TAGCCATAAT GGGAAGTCCT
        TCGAGCAAGC TCGCTAAGCT TTAGAAAGGC TTTCTCAGTA GCACCGGCTT AGTGTGCCAT TGCCCACACA GGCGCAGTAC ATCGGTATTA CCCTTCAGGA
                                                                                    New Cal HA
      · F Y R   N L L   W L T G   K N G   L Y P   N L S K   S Y V   N N K   E K E V   L V L ·
  701   CGTTCTATCG CAACCTGTTG TGGCTTACTG GGAAAAACGG GTTGTACCCT AATCTCAGCA AGAGCTACGT CAATAACAAA GAAAAAGAGG TGCTGGTCTT
        GCAAGATAGC GTTGGACAAC ACCGAATGAC CCTTTTTGCC CAACATGGGA TTAGAGTCGT TCTCGATGCA GTTATTGTTT CTTTTTCTCC ACGACCAGAA
                                                                                    New Cal HA
      · W G V   H H P P   N I G   K Q R   A L Y H   T E N   A Y V   S V V S   S E Y   S R R
  801   GTGGGGTGTG CATCACCCAC CTAACATTGG GAATCAGAGG GCACTGTACC ACACTGAGAA TGCATACGTG AGCGTGGTGT CGAGCCACTA TAGCCGGAGA
        CACCCCACAC GTAGTGGGTG GATTGTAACC CTTAGTCTCC CGTGACATGG TGTGACTCTT ACGTATGCAC TCGCACCACA GCTCGGTGAT ATCGGCCTCT
                                                                                    New Cal HA
      F T P E   I A K   R P K   V R D Q   E G R   I N Y   Y W T L   L E P   G D T   I I F E ·
  901   TTCACACCAG AGATTGCGAA GCGGCCCAAA GTCCGCGACC AGGAGGGGCG GATTAACTAC TACTGGACCC TCCTCGAGCC TGGCGATACG ATCATCTTTG
        AAGTGTGGTC TCTAACGCTT CGCCGGGTTT CAGGCGCTGG TCCTCCCCGC CTAATTGATG ATGACCTGGG AGGAGCTCGG ACCGCTATGC TAGTAGAAAC
                                                                                    New Cal HA
      · A N G   N L I   A P W Y   A F A L   S R   G F G S   G I I   T S N   A P M D   E C D ·
 1001   AAGCGAATGG TAATCTTATC GCCCCGTGGT ATGCTTTTGC GCTTTCAAGA GGATTTGGAT CAGGGATCAT CACATCAAAT GCGCCGATGG ACGAGTGCGA
```

```
                TTCGCTTACC ATTAGAATAG CGGGGCACCA TACGAAAACG CGAAAGTTCT CCTAAACCTA GTCCCTAGTA GTGTAGTTTA CGCGGCTACC TGCTCACGCT
                                                                        New Cal HA
                ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                 · A  K  C  Q  T  P  Q  G  A  I  N  S  S    L  P  F  Q  N  V  H   P  V  T    I  G  E  C    P  K  Y  V  R  S
          1101  TGCTAAGTGT CAGACTCCCC AAGGCGCTAT CAACTCGTCG TTGCCCTTTC AAAACGTGCA CCCCGTAACG ATCGGAGAGT GTCCCAAGTA TGTCAGATCG
                ACGATTCACA GTCTGAGGGG TTCCGCGATA GTTGAGCAGC AACGGGAAAG TTTTGCACGT GGGGCATTGC TAGCCTCTCA CAGGGTTCAT ACAGTCTAGC
                                                                        New Cal HA
                ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                  A  K  L  R  M  V  T   G  L  R  N  I  P  S    I  Q  S   R  G  L   F  G  A  I    A  G  F    I  E  G  G  N  T  G ·
          1201  GCGAAACTTA GGATGGTGAC CGGACTCCGC AATATCCCCT CGATCCAGTC ACGGGGATTG TTTGGAGCCA TTGCGGGCTT CATCGAAGGG GGCTGGACTG
                CGCTTTGAAT CCTACCACTG GCCTGAGGCG TTATAGGGGA GCTAGGTCAG TGCCCCTAAC AAACCTCGGT AACGCCCGAA GTAGCTTCCC CCGACCTGAC
                                                                        New Cal HA
                ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                 · M  V  D  G  W  Y     G  Y  H  H    Q  N  E    Q  G  S    G  Y  A  A    D  Q  K    S  T  Q  N  A  I  N   G  I  T ·
          1301  GAATGGTCGA TGGGTGGTAC GGTTATCACC ACCAGAATGA GCAGGGTTCC GGGTATGCCG CGGATCAGAA ATCGACACAG AACGCAATCA ACGGGATTAC
                CTTACCAGCT ACCCACCATG CCAATAGTGG TGGTCTTACT CGTCCCAAGG CCCATACGGC GCCTAGTCTT TAGCTGTGTC TTGCGTTAGT TGCCCTAATG
                                                                        New Cal HA
                ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                 · N  K  V  N  S  V  I   E  K  M   N  T  Q    F  T  A  V    G  K  E    F  N  K    L  E  R  R    M  E  N    L  N  K ·
          1401  GAACAAGGTA AACAGCGTCA TTGAGAAGAT GAATACACAG TTTACAGCCG TGGGGAAAGA ATTCAACAAA CTCGAGCGCC GGATGGAGAA TTTGAATAAG
                CTTGTTCCAT TTGTCGCAGT AACTCTTCTA CTTATGTGTC AAATGTCGGC ACCCCTTTCT TAAGTTGTTT GAGCTCGCGG CCTACCTCTT AAACTTATTC
                                                                        New Cal HA
                ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                  K  V  D  D  G  F  L     D  I  W   T  Y  N  A    E  L  L      V  L  L     E  N  E  R    T  L  D     F  H  D   S  N  V  K ·
          1501  AAAGTGGACG ATGGTTTCCT CGATATCTGG ACGTACAATG CGGAGCTGCT TGTCCTGCTC GAAAATGAGA GGACGCTCGA CTTTCATGAC TCCAATGTGA
                TTTCACCTGC TACCAAAGGA GCTATAGACC TGCATGTTAC GCCTCGACGA ACAGGACGAG CTTTTACTCT CCTGCGAGCT GAAAGTACTG AGGTTACACT
                                                                        New Cal HA
                ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                 · N  L  Y    E  K  V   K  S  Q  L    K  N  N    A  K  E    I  G  N  G    C  F  E    F  Y  H    K  C  N  N    E  C  M ·
          1601  AGAACCTTTA CGAGAAGGTG AAGTCCCAAT TGAAGAATAA CGCCAAGGAA ATTGGCAACG GCTGCTTCGA ATTCTACCAC AAATGCAACA ATGAGTGCAT
                TCTTGGAAAT GCTCTTCCAC TTCAGGGTTA ACTTCTTATT GCGGTTCCTT TAACCTTGTT CGACGAAGCT TAAGATGGTG TTTACGTTGT TACTCACGTA
                                                                        New Cal HA
                ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                 · E  S  V    K  N  G  T    Y  D  Y    P  K  Y    S  E  E  S    K  L  N    R  E  K    I  D  G  V    K  L  E    S  M  G
          1701  GGAATCGGTC AAAAATGGAA CATATGATTA TCCCAAATAC TGGAGGAGT CAAAGCTTAA TAGGGAGAAA ATTGATGGGG TAAAACTTGA GAGCATGGGT
                CCTTAGCCAG TTTTTACCTT GTATACTAAT AGGGTTTATG AGCCTCCTCA GTTTCGAATT ATCCCTCTTT TAACTACCCC ATTTTGAACT CTCGTACCCA
                                                                        New Cal HA
                ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                  V  Y  Q  I    L  A  I    Y  S  T    V  A  S  S    L  V  L    L  V  S    L  G  A  I    S  F  W    M  C  S    N  G  S  L ·
          1801  GTATATCAGA TCCTGGCAAT CTACTCAACC GTGGCGTCGT CACTGGTACT CCTCGTGTCC CTGGGCGCCA TTAGCTTTTG GATGTGTTCG AATGGATCGC
                CATATAGTCT AGGACCGTTA GATGAGTTGG CACCGCAGCA GTGACCATGA GGAGCACAGG GACCCGCGGT AATCGAAAAC CTACACAAGC TTACCTAGCG
                                                                          FMDV2A                                  TM of WN E split
                                                            ~~~~~~~~~~~~~~~~~~~~~~~~~~~~~~~~~~~~~~~~~     ~~~~~~~~~~~~~~~~~~~~~~~~
                         New Cal HA                                                                              prE/NS1 Signal
                ~~~~~~~~~~~~~~~~~~~~~~~~~~~~~~~~~~~~~~~~~~~~~~~~~~~~~~~~~~~~~~~~~~~~~~~~~~                      ~~~~~~~~~~~~~~~~~
                 · Q  C  R    I  C  I   N  F  D  L    L  K  L    A  G  D    V  E  S  N    P  G  P    A  R  D   R  S  I  A    L  T  F ·
          1901  TCCAGTGCCG CATCTGCATC AACTTTGACC TGCTCAAGCT CGCGGGTGAC GTCGAATCCA ACCCAGGGCC AGCCCGGGAC AGAAGCATTG CGCTCACTTT
                AGGTCACGGC GTAGACGTAG TTGAAACTGG ACGAGTTCGA GCGCCCACTG CAGCTTAGGT TGGGTCCCGG TCGGGCCCTG TCTTCGTAAC GCGAGTGAAA
                                                                                                                        NS1
                                                                                                            ~~~~~~~~~~~~~~~~~~~~~~~~
                             TM of WN E split
                ~~~~~~~~~~~~~~~~~~~~~~~~~~~~~~~~~~~~~~~~~~~~~
```

```
       · L  A  V     G  G  V  L     L  F  L     S  V  N     V  H  A  D     T  G  C     A  I  D     I  S  R  Q     E  L  R     C  G  S
2001   TCTCGCGGTA GGAGGTGTGC TGTTGTTCCT GTCAGTGAAC GTCCACGCAG ACACGGGATG CGCGATTGAT ATCTCCAGAC AAGAATTGAG GTGCGGGTCG
       AGAGCGCCAT CCTCCACACG ACAACAAGGA CAGTCACTTG CAGGTGCGTC TGTGCCCTAC GCGCTAACTA TAGAGGTCTG TTCTTAACTC CACGCCCAGC
                                                          NS1
       ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
         G  V  F  I  H  N  D     V  E  A     W  M  D  R     Y  K  Y     Y  P  E     T  P  Q  G     L  A  K     I  I  Q     K  A  H  K ·
2101   GGGGTCTTTA TCCATAACGA CGTGGAGGCG TGGATGGACA GGTATAAGTA TTACCCTGAA ACGCCGCAGG GACTTGCGAA AATCATTCAG AAAGCCCATA
       CCCCAGAAAT AGGTATTGCT GCACCTCCGC ACCTACCTGT CCATATTCAT AATGGGACTT TGCGGCGTCC CTGAACGCTT TTAGTAAGTC TTTCGGGTAT
                                                          NS1
       ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
       ·  E  G  V     C  G  L     R  S  V  S     R  L  E     H  Q  M     W  E  A  V     K  D  E     L  N  T     L  L  K
2201   AGGAAGGTGT GTGTGGATTG AGATCAGTCT CACGCCTTGA GCACCAGATG TGGGAGGCTG TCAAGGATGA ATTGAACACA CTTTTGAAG
       TCCTTCCACA CACACCTAAC TCTAGTCAGA GTGCGGAACT CGTGGTCTAC ACCCTCCGAC AGTTCCTACT TAACTTGTGT GAAAACTTC
```

OTHER EMBODIMENTS

All publications, patent applications, and patents mentioned in this specification are incorporated herein by reference in their entirety as if each individual publication, patent application, or patent were specifically and individually indicated to be incorporated by reference. In particular, U.S. 2011/0135686 is hereby incorporated by reference in its entirety.

Various modifications and variations of the described viruses, vectors, compositions, and methods of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the fields of medicine, pharmacology, or related fields are intended to be within the scope of the invention. Use of singular forms herein, such as "a" and "the," does not exclude indication of the corresponding plural form, unless the context indicates to the contrary. Similarly, use of plural terms does not exclude indication of a corresponding singular form. Other embodiments are within the scope of the following claims.

SEQUENCE LISTING

```
<160> NUMBER OF SEQ ID NOS: 78

<210> SEQ ID NO 1
<211> LENGTH: 12
<212> TYPE: PRT
<213> ORGANISM: Yellow Fever Virus

<400> SEQUENCE: 1

Ser His Asp Val Leu Thr Val Gln Phe Leu Ile Leu
1               5                   10

<210> SEQ ID NO 2
<211> LENGTH: 8
<212> TYPE: PRT
<213> ORGANISM: Tick-borne Encephalitis Virus

<400> SEQUENCE: 2

Gly Met Leu Gly Met Thr Ile Ala
1               5

<210> SEQ ID NO 3
<211> LENGTH: 20
<212> TYPE: PRT
<213> ORGANISM: Artificial Sequence
<220> FEATURE:
<223> OTHER INFORMATION: Synthetic Construct

<400> SEQUENCE: 3

Ser His Asp Val Leu Thr Val Gln Phe Leu Ile Leu Gly Met Leu Gly
1               5                   10                  15

Met Thr Ile Ala
            20

<210> SEQ ID NO 4
<211> LENGTH: 20
<212> TYPE: PRT
<213> ORGANISM: Tick-borne Encephalitis Virus

<400> SEQUENCE: 4

Gly Gly Thr Asp Trp Met Ser Trp Leu Leu Val Ile Gly Met Leu Gly
1               5                   10                  15

Met Thr Ile Ala
            20

<210> SEQ ID NO 5
<211> LENGTH: 9
<212> TYPE: PRT
<213> ORGANISM: Borrelia burgdorferi
```

```
<400> SEQUENCE: 5

Tyr Val Leu Glu Gly Thr Leu Thr Ala
1               5

<210> SEQ ID NO 6
<211> LENGTH: 9
<212> TYPE: PRT
<213> ORGANISM: Borrelia afzelii

<400> SEQUENCE: 6

Phe Thr Leu Glu Gly Lys Val Ala Asn
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Phe Thr Leu Glu Gly Lys Leu Thr Ala
1               5

<210> SEQ ID NO 8
<211> LENGTH: 273
<212> TYPE: PRT
<213> ORGANISM: Borrelia burgdorferi

<400> SEQUENCE: 8

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220
```

```
Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
            245                 250                 255

Gly Ser Ala Val Glu Ile Thr Lys Leu Asp Glu Ile Lys Asn Ala Leu
        260                 265                 270

Lys

<210> SEQ ID NO 9
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: X is Glu or Gly
<220> FEATURE:
<221> NAME/KEY: MISC_FEATURE
<222> LOCATION: (5)..(5)
<223> OTHER INFORMATION: X is Met or Ile
<220> FEATURE:
<221> NAME/KEY: MISC_FEATURE
<222> LOCATION: (6)..(6)
<223> OTHER INFORMATION: X is Lys, Thr or Gly

<400> SEQUENCE: 9

Leu Pro Gly Xaa Xaa Xaa Val Leu
1               5

<210> SEQ ID NO 10
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: X is Asn, Ser, or Asp
<220> FEATURE:
<221> NAME/KEY: MISC_FEATURE
<222> LOCATION: (11)..(11)
<223> OTHER INFORMATION: X is Val, or Thr

<400> SEQUENCE: 10

Gly Thr Ser Asp Lys Xaa Asn Gly Ser Gly Xaa
1               5                   10

<210> SEQ ID NO 11
<211> LENGTH: 31
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Asn, His, or Glu
<220> FEATURE:
<221> NAME/KEY: MISC_FEATURE
<222> LOCATION: (3)..(3)
<223> OTHER INFORMATION: Xaa is Ser, Pro, Leu, Ala, or Ser
<220> FEATURE:
<221> NAME/KEY: MISC_FEATURE
<222> LOCATION: (4)..(4)
<223> OTHER INFORMATION: Xaa is Lys or Asn
<220> FEATURE:
<221> NAME/KEY: MISC_FEATURE
<222> LOCATION: (8)..(8)
```

```
<223> OTHER INFORMATION: Xaa is Val or Ile
<220> FEATURE:
<221> NAME/KEY: MISC_FEATURE
<222> LOCATION: (9)..(9)
<223> OTHER INFORMATION: Xaa is Ser or Thr
<220> FEATURE:
<221> NAME/KEY: MISC_FEATURE
<222> LOCATION: (10)..(10)
<223> OTHER INFORMATION: Xaa is Val or Ala
<220> FEATURE:
<221> NAME/KEY: MISC_FEATURE
<222> LOCATION: (11)..(11)
<223> OTHER INFORMATION: Xaa is Glu or Ala
<220> FEATURE:
<221> NAME/KEY: MISC_FEATURE
<222> LOCATION: (13)..(13)
<223> OTHER INFORMATION: Xaa is Asn or Asp
<220> FEATURE:
<221> NAME/KEY: MISC_FEATURE
<222> LOCATION: (15)..(15)
<223> OTHER INFORMATION: Xaa is Thr or Ser
<220> FEATURE:
<221> NAME/KEY: MISC_FEATURE
<222> LOCATION: (16)..(16)
<223> OTHER INFORMATION: Xaa is Asp or Asn
<220> FEATURE:
<221> NAME/KEY: MISC_FEATURE
<222> LOCATION: (17)..(17)
<223> OTHER INFORMATION: Xaa is Ser or Thr
<220> FEATURE:
<221> NAME/KEY: MISC_FEATURE
<222> LOCATION: (18)..(18)
<223> OTHER INFORMATION: Xaa is Ser or Thr
<220> FEATURE:
<221> NAME/KEY: MISC_FEATURE
<222> LOCATION: (19)..(19)
<223> OTHER INFORMATION: Xaa is Ala, Gln, or Arg
<220> FEATURE:
<221> NAME/KEY: MISC_FEATURE
<222> LOCATION: (25)..(25)
<223> OTHER INFORMATION: Xaa is Ala or Gly
<220> FEATURE:
<221> NAME/KEY: MISC_FEATURE
<222> LOCATION: (26)..(26)
<223> OTHER INFORMATION: Xaa is Ala, Lys, or Thr
<220> FEATURE:
<221> NAME/KEY: MISC_FEATURE
<222> LOCATION: (28)..(28)
<223> OTHER INFORMATION: Xaa is Asn or Asp
<220> FEATURE:
<221> NAME/KEY: MISC_FEATURE
<222> LOCATION: (29)..(29)
<223> OTHER INFORMATION: Xaa is Ser or Ala
<220> FEATURE:
<221> NAME/KEY: MISC_FEATURE
<222> LOCATION: (30)..(30)
<223> OTHER INFORMATION: Xaa is Gly, Asn, or Lys

<400> SEQUENCE: 11

Xaa Ile Xaa Xaa Ser Gly Glu Xaa Xaa Xaa Xaa Leu Xaa Asp Xaa Xaa
1               5                   10                  15

Xaa Xaa Xaa Ala Thr Lys Lys Thr Xaa Xaa Trp Xaa Xaa Xaa Thr
            20                  25                  30

<210> SEQ ID NO 12
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Asn or Ala
<220> FEATURE:
<221> NAME/KEY: MISC_FEATURE
```

```
<222> LOCATION: (5)..(5)
<223> OTHER INFORMATION: Xaa is Lys or Asn
<220> FEATURE:
<221> NAME/KEY: MISC_FEATURE
<222> LOCATION: (9)..(9)
<223> OTHER INFORMATION: Xaa is Ser, Asn, Lys, or Thr
<220> FEATURE:
<221> NAME/KEY: MISC_FEATURE
<222> LOCATION: (14)..(14)
<223> OTHER INFORMATION: Xaa is Thr or Lys
<220> FEATURE:
<221> NAME/KEY: MISC_FEATURE
<222> LOCATION: (15)..(15)
<223> OTHER INFORMATION: Xaa is Thr or Lys
<220> FEATURE:
<221> NAME/KEY: MISC_FEATURE
<222> LOCATION: (17)..(17)
<223> OTHER INFORMATION: Xaa is Asp or Lys
<220> FEATURE:
<221> NAME/KEY: MISC_FEATURE
<222> LOCATION: (19)..(19)
<223> OTHER INFORMATION: Xaa is Ile or Leu

<400> SEQUENCE: 12

Ser Xaa Gly Thr Xaa Leu Glu Gly Xaa Ala Val Glu Ile Xaa Xaa Leu
1               5                   10                  15

Xaa Glu Xaa Lys Asn
            20

<210> SEQ ID NO 13
<211> LENGTH: 154
<212> TYPE: PRT
<213> ORGANISM: Rhipicephalus appendiculatus

<400> SEQUENCE: 13

Met Lys Ala Phe Phe Val Leu Ser Leu Leu Ser Thr Ala Ala Leu Thr
1               5                   10                  15

Asn Ala Ala Arg Ala Gly Arg Leu Gly Ser Asp Leu Asp Thr Phe Gly
                20                  25                  30

Arg Val His Gly Asn Leu Tyr Ala Gly Ile Glu Arg Ala Gly Pro Arg
            35                  40                  45

Gly Tyr Pro Gly Leu Thr Ala Ser Ile Gly Glu Val Gly Ala Arg
        50                  55                  60

Leu Gly Gly Arg Ala Gly Val Gly Val Ser Ser Tyr Gly Tyr Gly Tyr
65              70                  75                  80

Pro Ser Trp Gly Tyr Pro Gly Gly Tyr Gly Gly Tyr Gly Gly Tyr
                85                  90                  95

Gly Gly Tyr Gly Gly Tyr Asp Gln Gly Phe Gly Ser Ala Tyr Gly Gly
            100                 105                 110

Tyr Pro Gly Tyr Tyr Gly Tyr Tyr Pro Ser Gly Tyr Gly Gly
        115                 120                 125

Tyr Gly Gly Ser Tyr Gly Gly Ser Tyr Gly Gly Ser Tyr Thr Tyr Pro
130             135                 140

Asn Val Arg Ala Ser Ala Gly Ala Ala Ala
145                 150

<210> SEQ ID NO 14
<211> LENGTH: 184
<212> TYPE: PRT
<213> ORGANISM: Ixodes scapularis

<400> SEQUENCE: 14

Met Arg Thr Ala Phe Thr Cys Ala Leu Leu Ala Ile Ser Phe Leu Gly
1               5                   10                  15
```

```
Ser Pro Cys Ser Ser Glu Asp Gly Leu Glu Gln Asp Thr Ile Val
        20                  25                  30

Glu Thr Thr Thr Gln Asn Leu Tyr Glu Arg His Tyr Arg Asn His Ser
 35                      40                  45

Gly Leu Cys Gly Ala Gln Tyr Arg Asn Ser Ser His Ala Glu Ala Val
 50                      55                  60

Tyr Asn Cys Thr Leu Asn His Leu Pro Pro Val Val Asn Ala Thr Trp
65                   70                  75                  80

Glu Gly Ile Arg His Arg Ile Asn Lys Thr Ile Pro Gln Phe Val Lys
                85                  90                  95

Leu Ile Cys Asn Phe Thr Val Ala Met Pro Gln Glu Phe Tyr Leu Val
            100                 105                 110

Tyr Met Gly Ser Asp Gly Asn Ser Asp Phe Glu Glu Asp Lys Glu Ser
                115                 120                 125

Thr Gly Thr Asp Glu Asp Ser Asn Thr Gly Ser Ser Ala Ala Ala Lys
    130                 135                 140

Val Thr Glu Ala Leu Ile Ile Glu Ala Glu Asn Cys Thr Ala His
145                 150                 155                 160

Ile Thr Gly Trp Thr Thr Glu Thr Pro Thr Thr Leu Glu Pro Thr Thr
                165                 170                 175

Glu Ser Gln Phe Glu Ala Ile Pro
            180

<210> SEQ ID NO 15
<211> LENGTH: 177
<212> TYPE: PRT
<213> ORGANISM: Ixodes scapularis

<400> SEQUENCE: 15

Met Arg Thr Ala Leu Thr Cys Ala Leu Leu Ala Ile Ser Phe Leu Gly
1               5                   10                  15

Ser Pro Cys Ser Ser Ser Glu Gly Gly Leu Glu Lys Asp Ser Arg Val
            20                  25                  30

Glu Thr Thr Thr Gln Asn Leu Tyr Glu Arg Tyr Tyr Arg Lys His Pro
 35                      40                  45

Gly Leu Cys Gly Ala Gln Tyr Arg Asn Ser Ser His Ala Glu Ala Val
 50                      55                  60

Tyr Asn Cys Thr Leu Ser Leu Pro Leu Ser Val Asn Thr Thr Trp
65                   70                  75                  80

Glu Gly Ile Arg His Arg Ile Asn Lys Thr Ile Pro Glu Phe Val Asn
                85                  90                  95

Leu Ile Cys Asn Phe Thr Val Ala Met Pro Asp Gln Phe Tyr Leu Val
            100                 105                 110

Tyr Met Gly Ser Asn Gly Asn Ser Tyr Ser Glu Glu Asp Glu Asp Gly
                115                 120                 125

Lys Thr Gly Ser Ser Ala Ala Val Gln Val Thr Glu Gln Leu Ile Ile
    130                 135                 140

Gln Ala Glu Glu Asn Cys Thr Ala His Ile Thr Gly Trp Thr Thr Glu
145                 150                 155                 160

Ala Pro Thr Thr Leu Glu Pro Thr Thr Glu Thr Gln Phe Glu Ala Ile
                165                 170                 175

Ser

<210> SEQ ID NO 16
```

```
<211> LENGTH: 19
<212> TYPE: PRT
<213> ORGANISM: Influenza A virus

<400> SEQUENCE: 16

Pro Ala Lys Leu Leu Lys Glu Arg Gly Phe Phe Gly Ala Ile Ala Gly
1               5                   10                  15

Phe Leu Glu

<210> SEQ ID NO 17
<211> LENGTH: 23
<212> TYPE: PRT
<213> ORGANISM: Influenza A virus

<400> SEQUENCE: 17

Pro Ala Lys Leu Leu Lys Glu Arg Gly Phe Phe Gly Ala Ile Ala Gly
1               5                   10                  15

Phe Leu Glu Gly Ser Gly Cys
            20

<210> SEQ ID NO 18
<211> LENGTH: 19
<212> TYPE: PRT
<213> ORGANISM: Influenza B virus

<400> SEQUENCE: 18

Asn Asn Ala Thr Phe Asn Tyr Thr Asn Val Asn Pro Ile Ser His Ile
1               5                   10                  15

Arg Gly Ser

<210> SEQ ID NO 19
<211> LENGTH: 24
<212> TYPE: PRT
<213> ORGANISM: Influenza A virus

<400> SEQUENCE: 19

Met Ser Leu Leu Thr Glu Val Glu Thr Pro Ile Arg Asn Glu Trp Gly
1               5                   10                  15

Cys Arg Cys Asn Asp Ser Ser Asp
            20

<210> SEQ ID NO 20
<211> LENGTH: 24
<212> TYPE: PRT
<213> ORGANISM: Influenza A virus

<400> SEQUENCE: 20

Met Ser Leu Leu Thr Glu Val Glu Thr Pro Thr Arg Asn Glu Trp Glu
1               5                   10                  15

Cys Arg Cys Ser Asp Ser Ser Asp
            20

<210> SEQ ID NO 21
<211> LENGTH: 24
<212> TYPE: PRT
<213> ORGANISM: Influenza A virus

<400> SEQUENCE: 21

Met Ser Leu Leu Thr Glu Val Glu Thr Leu Thr Arg Asn Gly Trp Gly
1               5                   10                  15

Cys Arg Cys Ser Asp Ser Ser Asp
            20
```

<210> SEQ ID NO 22
<211> LENGTH: 8
<212> TYPE: PRT
<213> ORGANISM: Influenza A virus

<400> SEQUENCE: 22

Glu Val Glu Thr Pro Thr Arg Asn
1               5

<210> SEQ ID NO 23
<211> LENGTH: 23
<212> TYPE: PRT
<213> ORGANISM: Influenza A virus

<400> SEQUENCE: 23

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 24
<211> LENGTH: 17
<212> TYPE: PRT
<213> ORGANISM: Influenza A virus

<400> SEQUENCE: 24

Ser Leu Leu Thr Glu Val Glu Thr Pro Ile Arg Asn Glu Trp Gly Cys
1               5                   10                  15

Arg

<210> SEQ ID NO 25
<211> LENGTH: 6
<212> TYPE: PRT
<213> ORGANISM: Influenza B virus

<400> SEQUENCE: 25

Met Leu Glu Pro Phe Gln
1               5

<210> SEQ ID NO 26
<211> LENGTH: 12
<212> TYPE: PRT
<213> ORGANISM: Influenza B virus

<400> SEQUENCE: 26

Leu Glu Pro Phe Gln Ile Leu Ser Ile Ser Gly Cys
1               5                   10

<210> SEQ ID NO 27
<211> LENGTH: 24
<212> TYPE: PRT
<213> ORGANISM: Artificial Sequence
<220> FEATURE:
<223> OTHER INFORMATION: Avian Influenza A virus Subtype H5N1

<400> SEQUENCE: 27

Met Ser Leu Leu Thr Glu Val Glu Thr Leu Thr Arg Asn Gly Trp Gly
1               5                   10                  15

Cys Arg Cys Ser Asp Ser Ser Asp
            20

<210> SEQ ID NO 28

```
<211> LENGTH: 28
<212> TYPE: PRT
<213> ORGANISM: Artificial Sequence
<220> FEATURE:
<223> OTHER INFORMATION: Synthetic Construct

<400> SEQUENCE: 28

Arg Lys Arg Arg Ser His Asp Val Leu Thr Val Gln Phe Leu Ile Leu
1               5                   10                  15

Gly Met Leu Gly Met Thr Ile Ala Ala Thr Val Arg
            20                  25

<210> SEQ ID NO 29
<211> LENGTH: 84
<212> TYPE: DNA
<213> ORGANISM: Artificial Sequence
<220> FEATURE:
<223> OTHER INFORMATION: Synthetic Construct

<400> SEQUENCE: 29
aggaaacgcc gttcccatga tgttctgact gtgcaattcc taattttggg catgctgggc     60
atgacaatcg cagctacggt tcgc                                           84

<210> SEQ ID NO 30
<211> LENGTH: 84
<212> TYPE: DNA
<213> ORGANISM: Artificial Sequence
<220> FEATURE:
<223> OTHER INFORMATION: Synthetic Construct

<400> SEQUENCE: 30
tcctttgcgg caagggtact acaagactga cacgttaagg attaaaaccc gtacgacccg     60
tactgttagc gtcgatgcca agcg                                           84

<210> SEQ ID NO 31
<211> LENGTH: 28
<212> TYPE: PRT
<213> ORGANISM: Artificial Sequence
<220> FEATURE:
<223> OTHER INFORMATION: Synthetic Construct

<400> SEQUENCE: 31

Arg Lys Arg Arg Ser His Asp Val Leu Thr Val Gln Phe Leu Ile Leu
1               5                   10                  15

Gly Met Leu Ala Cys Val Gly Ala Ala Thr Val Arg
            20                  25

<210> SEQ ID NO 32
<211> LENGTH: 84
<212> TYPE: DNA
<213> ORGANISM: Artificial Sequence
<220> FEATURE:
<223> OTHER INFORMATION: Synthetic Construct

<400> SEQUENCE: 32
aggaaacgcc gttcccatga tgttctgact gtgcaattcc taattttggg catgctggct     60
tgtgtcggag cagctaccgt gcga                                           84

<210> SEQ ID NO 33
<211> LENGTH: 84
<212> TYPE: DNA
<213> ORGANISM: Artificial Sequence
<220> FEATURE:
<223> OTHER INFORMATION: Synthetic Construct
```

```
<400> SEQUENCE: 33
tcctttgcgg caagggtact acaagactga cacgttaagg attaaaaccc gtacgaccga    60
acacagcctc gtcgatggca cgct                                          84

<210> SEQ ID NO 34
<211> LENGTH: 28
<212> TYPE: PRT
<213> ORGANISM: Artificial Sequence
<220> FEATURE:
<223> OTHER INFORMATION: Synthetic Construct

<400> SEQUENCE: 34

Gln Lys Lys Arg Gly Gly Thr Asp Trp Met Ser Trp Leu Leu Val Ile
1               5                   10                  15

Gly Met Leu Gly Met Thr Ile Ala Ala Thr Val Arg
            20                  25

<210> SEQ ID NO 35
<211> LENGTH: 84
<212> TYPE: DNA
<213> ORGANISM: Artificial Sequence
<220> FEATURE:
<223> OTHER INFORMATION: Synthetic Construct

<400> SEQUENCE: 35
caaaagaaac gggggggaac agactggatg agctggctgc tcgtaatcgg catgctgggc    60
atgacaatcg cagctacggt tcgc                                          84

<210> SEQ ID NO 36
<211> LENGTH: 84
<212> TYPE: DNA
<213> ORGANISM: Artificial Sequence
<220> FEATURE:
<223> OTHER INFORMATION: Synthetic Construct

<400> SEQUENCE: 36
gttttctttg ccccccttg tctgacctac tcgaccgacg agcattagcc gtacgacccg     60
tactgttagc gtcgatgcca agcg                                          84

<210> SEQ ID NO 37
<211> LENGTH: 26
<212> TYPE: PRT
<213> ORGANISM: Artificial Sequence
<220> FEATURE:
<223> OTHER INFORMATION: Synthetic Construct

<400> SEQUENCE: 37

Gln Lys Lys Arg Gly Gly Lys Thr Gly Ile Ala Val Met Ile Gly Met
1               5                   10                  15

Leu Ala Cys Val Gly Ala Ala Thr Val Arg
            20                  25

<210> SEQ ID NO 38
<211> LENGTH: 78
<212> TYPE: DNA
<213> ORGANISM: Artificial Sequence
<220> FEATURE:
<223> OTHER INFORMATION: Synthetic Construct

<400> SEQUENCE: 38
caaaagaaac gcgggggaaa gacaggcata gctgtgatga taggcatgct ggcttgtgtc    60
```

```
ggagcagcta ccgtgcga                                                   78
```

<210> SEQ ID NO 39
<211> LENGTH: 78
<212> TYPE: DNA
<213> ORGANISM: Artificial Sequence
<220> FEATURE:
<223> OTHER INFORMATION: Synthetic Construct

<400> SEQUENCE: 39

```
gttttctttg cgcccctttt ctgtccgtat cgacactact atccgtacga ccgaacacag    60
cctcgtcgat ggcacgct                                                   78
```

<210> SEQ ID NO 40
<211> LENGTH: 793
<212> TYPE: PRT
<213> ORGANISM: Artificial Sequence
<220> FEATURE:
<223> OTHER INFORMATION: Synthetic Construct

<400> SEQUENCE: 40

```
Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile
        35                  40                  45

Phe Phe Phe Leu Phe Asn Ile Leu Thr Gly Lys Lys Ile Thr Ala His
    50                  55                  60

Leu Lys Arg Leu Trp Lys Met Leu Asp Pro Arg Gln Gly Leu Ala Val
65                  70                  75                  80

Leu Arg Lys Val Lys Arg Val Ser Leu Met Arg Gly Leu Ser Ser
                85                  90                  95

Arg Lys Arg Arg Ser His Asp Val Leu Thr Val Gln Phe Leu Ile Leu
            100                 105                 110

Gly Met Leu Gly Met Thr Ile Ala Ala Thr Val Arg Lys Glu Arg Asp
        115                 120                 125

Gly Ser Thr Val Ile Arg Ala Glu Gly Lys Asp Ala Thr Gln Val
    130                 135                 140

Arg Val Glu Asn Gly Thr Cys Val Ile Leu Ala Thr Asp Met Gly Ser
145                 150                 155                 160

Trp Cys Asp Asp Ser Leu Ser Tyr Glu Cys Val Thr Ile Asp Gln Gly
                165                 170                 175

Glu Glu Pro Val Asp Val Asp Cys Phe Cys Arg Asn Val Asp Gly Val
            180                 185                 190

Tyr Leu Glu Tyr Gly Arg Cys Gly Lys Gln Glu Gly Ser Arg Thr Arg
        195                 200                 205

Arg Ser Val Leu Ile Pro Ser His Ala Gln Gly Glu Leu Thr Gly Arg
    210                 215                 220

Gly His Lys Trp Leu Glu Gly Asp Ser Leu Arg Thr His Leu Thr Arg
225                 230                 235                 240

Val Glu Gly Trp Val Trp Lys Asn Arg Leu Leu Ala Leu Ala Met Val
                245                 250                 255

Thr Val Val Trp Leu Thr Leu Glu Ser Val Val Thr Arg Val Ala Val
            260                 265                 270

Leu Val Val Leu Leu Cys Leu Ala Pro Val Tyr Ala Ser Arg Cys Thr
        275                 280                 285
```

-continued

```
His Leu Glu Asn Arg Asp Phe Val Thr Gly Thr Gln Gly Thr Thr Arg
    290                 295                 300

Val Thr Leu Val Leu Glu Leu Gly Gly Cys Val Thr Ile Thr Ala Glu
305                 310                 315                 320

Gly Lys Pro Ser Met Asp Val Trp Leu Asp Ala Ile Tyr Gln Glu Asn
                325                 330                 335

Pro Ala Gln Thr Arg Glu Tyr Cys Leu His Ala Lys Leu Ser Asp Thr
            340                 345                 350

Lys Val Ala Ala Arg Cys Pro Thr Met Gly Pro Ala Thr Leu Ala Glu
        355                 360                 365

Glu His Gln Gly Gly Thr Val Cys Lys Arg Asp Gln Ser Asp Arg Gly
    370                 375                 380

Trp Gly Asn His Cys Gly Leu Phe Gly Lys Gly Ser Ile Val Ala Cys
385                 390                 395                 400

Val Lys Ala Ala Cys Glu Ala Lys Lys Lys Ala Thr Gly His Val Tyr
                405                 410                 415

Asp Ala Asn Lys Ile Val Tyr Thr Val Lys Val Glu Pro His Thr Gly
            420                 425                 430

Asp Tyr Val Ala Ala Asn Glu Thr His Ser Gly Arg Lys Thr Ala Ser
        435                 440                 445

Phe Thr Val Ser Ser Glu Lys Thr Ile Leu Thr Met Gly Glu Tyr Gly
    450                 455                 460

Asp Val Ser Leu Leu Cys Arg Val Ala Ser Gly Val Asp Leu Ala Gln
465                 470                 475                 480

Thr Val Ile Leu Glu Leu Asp Lys Thr Val Glu His Leu Pro Thr Ala
                485                 490                 495

Trp Gln Val His Arg Asp Trp Phe Asn Asp Leu Ala Leu Pro Trp Lys
            500                 505                 510

His Glu Gly Ala Arg Asn Trp Asn Asn Ala Glu Arg Leu Val Glu Phe
        515                 520                 525

Gly Ala Pro His Ala Val Lys Met Asp Val Tyr Asn Leu Gly Asp Gln
    530                 535                 540

Thr Gly Val Leu Leu Lys Ala Leu Ala Gly Val Pro Val Ala His Ile
545                 550                 555                 560

Glu Gly Thr Lys Tyr His Leu Lys Ser Gly His Val Thr Cys Glu Val
                565                 570                 575

Gly Leu Glu Lys Leu Lys Met Lys Gly Leu Thr Tyr Thr Met Cys Asp
            580                 585                 590

Lys Thr Lys Phe Thr Trp Lys Arg Ala Pro Thr Asp Ser Gly His Asp
        595                 600                 605

Thr Val Val Met Glu Val Thr Phe Ser Gly Thr Lys Pro Cys Arg Ile
    610                 615                 620

Pro Val Arg Ala Val Ala His Gly Ser Pro Asp Val Asn Val Ala Met
625                 630                 635                 640

Leu Ile Thr Pro Asn Pro Thr Ile Glu Asn Asn Gly Gly Gly Phe Ile
                645                 650                 655

Glu Met Gln Leu Pro Pro Gly Asp Asn Ile Ile Tyr Val Gly Glu Leu
            660                 665                 670

Ser Tyr Gln Trp Phe Gln Lys Gly Ser Ser Ile Gly Arg Val Phe Gln
        675                 680                 685

Lys Thr Lys Lys Gly Ile Glu Arg Leu Thr Val Ile Gly Glu His Ala
    690                 695                 700
```

```
Trp Asp Phe Gly Ser Ala Gly Gly Phe Leu Ser Ile Gly Lys Ala
705                 710                 715                 720

Leu His Thr Val Leu Gly Gly Ala Phe Asn Ser Ile Phe Gly Gly Val
                725                 730                 735

Gly Phe Leu Pro Lys Leu Leu Leu Gly Val Ala Leu Ala Trp Leu Gly
            740                 745                 750

Leu Asn Met Arg Asn Pro Thr Met Ser Met Ser Phe Leu Leu Ala Gly
        755                 760                 765

Val Leu Val Leu Ala Met Thr Leu Gly Val Gly Ala Asp Gln Gly Cys
    770                 775                 780

Ala Ile Asn Phe Gly Lys Arg Glu Leu
785                 790

<210> SEQ ID NO 41
<211> LENGTH: 2500
<212> TYPE: DNA
<213> ORGANISM: Artificial Sequence
<220> FEATURE:
<223> OTHER INFORMATION: Synthetic Construct

<400> SEQUENCE: 41
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaaccct gggcgtcaat atggtacgac gaggagttcg     180
ctccttgtca aacaaaataa aacaaaaaac aaaacaaatt ggaaacagac ctggaccttc     240
aagaggtgtt caaggattta tcttttctt tttgttcaac atttttgactg gaaaaaagat     300 cacagcccac ctaaagaggt tgtggaaaat gctggaccca agacaaggct tggctgttct     360
aaggaaagtc aagagagtgg tggccagttt gatgagagga ttgtcctcaa ggaaacgccg     420
ttcccatgat gttctgactg tgcaattcct aattttgggc atgctgggca tgacaatcgc     480
agctacggtt cgcaaggaaa gagacggcag tacggtcata cgcgcggaag gtaaggatgc     540
cgctacccaa gtgagagtgg aaaatggtac ctgcgtcatt ctggccaccg acatgggctc     600
ttggtgtgat gatagccttt cttatgagtg cgtaaccata gatcaaggtg aggaacctgt     660
tgacgttgat tgcttctgcc gaaacgtgga tgggtgtat ctcgaatatg acggtgtgg      720 taaacaagaa ggaagcagaa ccagacgctc agtgcttata ccctcccacg ctcaaggaga     780
gctgaccgga cggggacata atggttgga gggcgactca ctccgaacac atttgacccg     840
cgtcgagggc tgggtctgga aaaatcggct gttggccctc gctatggtga cagtcgtttg     900
gctcacgctg gagtctgtgg ttactcgcgt ggcagtgctg gtggtgctcc tctgtcttgc     960
ccctgtctac gcgtccaggt gtactcattt ggaaaacaga gattttgtca ccggcaccca    1020
ggggacgact cgggtaaccc tggtgcttga actgggtggt tgcgttacta ttaccgctga    1080
gggcaaaccc tctatggatg tgtggctgga tgcaatctat caggagaatc ccgcacaaac    1140
cagggaatat tgccttcacg caaagctgtc cgatacaaag gtcgcggcta ggtgcccaac    1200
aatgggaccg gccaccctgg cggaggaaca tcagggaggt acagtgtgca acgggaccca    1260
gagtgataga ggctggggta atcactgcgg cctgttcggc aaaggaagta ttgtcgcttg    1320
cgtcaaggca gcctgtgagg ccaaaaagaa ggctactggg cacgtctatg acgccaacaa    1380
gatcgtttat acagtgaaag tggaaccaca cacaggggat tacgtggcgg ccaacgagac    1440
tcattccggt cgcaaaacgg ccagcttcac cgtgtcatcc gaaaagacca tcctcactat    1500
gggggagtat ggcgacgttt ctctgctctg ccggggtggct agcggagtcg acctggccca    1560
```

```
gacagtcatc ctggaactgg ataaaacagt tgagcatctg cctaccgctt ggcaggtgca   1620
cagggattgg tttaacgacc ttgccctgcc atgaaacat gaaggagcga gaaactggaa    1680
taatgcagag cgactcgtag aattcggtgc ccctcatgcc gtgaagatgg acgtctacaa   1740
tctgggtgat cagaccggcg ttctccttaa agctctcgct ggcgtaccag ttgcccacat   1800
cgaaggaacg aagtaccacc tgaagtcagg ccatgtaact tgcgaggtgg gcctggagaa   1860
gttgaaaatg aaaggtctta cgtacacaat gtgtgacaag accaagttca catgaaagag   1920
ggcccccaca gatagcggcc acgatactgt ggtgatggag gtgaccttt ctggaacaaa    1980 accctgcaga ataccgtgc gggctgtagc tcacggatct cccgatgtca atgttgctat    2040
gctgattaca cctaacccta ccatcgagaa taacggtggt ggttttattg agatgcagct   2100
tccgccaggc gataacatca tctacgtggg cgaactctct taccagtggt tcagaaagg    2160 gagttcaatt gggcgggtct tccaaaaaac gaagaaggga atcgaacgat tgacggttat   2220
cggcgagcac gcatgggatt ttggttccgc aggggattc ctgtcttcta ttggtaaggc    2280
actgcatacc gtgctggggg gcgcattcaa ttctattttc ggggcgtgg ggttcctgcc    2340 taaactcctg ctgggagtag ccctggcctg gttgggactg aatatgcgga atccgacgat   2400
gtccatgtca ttcctcttgg ccggcgtgct tgtactggcc atgacactgg gcgttggcgc   2460
cgatcaagga tgcgccatca actttggcaa gagagagctc              2500

<210> SEQ ID NO 42
<211> LENGTH: 2496
<212> TYPE: DNA
<213> ORGANISM: Artificial Sequence
<220> FEATURE:
<223> OTHER INFORMATION: Synthetic Construct

<400> SEQUENCE: 42
tcatttagga cacacgatta actccacgta accagacgtt tagctcaacg atccgttatt    60
tgtgtaaacc taattaaaat tagcaagcaa ctcgctaatc gtctcttgac tggtcttgta   120
cagaccagca tttcgagtcc cttttggga cccgcagtta taccatgctg ctcctcaagc    180
gaggaacagt ttgttttatt ttgttttttg ttttgtttaa cctttgtctg gacctggaag   240
ttctccacaa gttcctaaat agaaaaagaa aaacaagttg taaaactgac ctttttttcta  300 gtgtcgggtg gatttctcca acaccttta cgacctgggt tctgttccga accgacaaga   360
ttcctttcag ttctctcacc accggtcaaa ctactctcct aacaggagtt cctttgcggc   420
aagggtacta caagactgac acgttaagga ttaaaacccg tacgaccgt actgttagcg    480 tcgatgccaa gcgttccttt ctctgccgtc atgccagtat gcgcgccttc cattcctacg   540
gcgatgggtt cactctcacc ttttaccatg gacgcagtaa gaccggtggc tgtacccgag   600
aaccacacta ctatcggaaa gaatactcac gcattggtat ctagttccac tccttggaca   660
actgcaacta acgaagacgg cttttgcacct acccccacata gagcttatac ctgccacacc  720
atttgttctt ccttcgtctt ggtctgcgag tcacgaatat gggagggtgc gagttcctct   780
cgactggcct gccctgtat ttaccaacct cccgctgagt gaggcttgtg taaactgggc    840
gcagctcccg acccagacct ttttagccga caacggggag cgataccact gtcagcaaac   900
cgagtgcgac ctcagacacc aatgagcgca ccgtcacgac caccacgagg agacagaacg   960
gggacagatg cgcaggtcca catgagtaaa ccttttgtct ctaaaacagt ggccgtgggt   1020
cccctgctga gcccattggg accacgaact tgacccacca acgcaatgat aatggcgact  1080
```

```
cccgtttggg agatacctac acaccgacct acgttagata gtcctcttag ggcgtgtttg    1140
gtcccttata acggaagtgc gtttcgacag gctatgtttc cagcgccgat ccacgggttg   1200
ttaccctggc cggtgggacc gcctccttgt agtccctcca tgtcacacgt ttgccctggt   1260
ctcactatct ccgaccccat tagtgacgcc ggacaagccg tttccttcat aacagcgaac   1320
gcagttccgt cggacactcc ggttttctt ccgatgaccc gtgcagatac tgcggttgtt    1380
ctagcaaata tgtcactttc accttggtgt gtgtcccta atgcaccgcc ggttgctctg    1440
agtaaggcca gcgttttgcc ggtcgaagtg gcacagtagg ctttctggt aggagtgata    1500
cccctcata ccgctgcaaa gagacgagac ggcccaccga tcgcctcagc tggacccggt    1560
ctgtcagtag gaccttgacc tattttgtca actcgtagac ggatggcgaa ccgtccacgt   1620
gtccctaacc aaattgctgg aacgggacgg tacctttgta cttcctcgct ctttgacctt   1680
attacgtctc gctgagcatc ttaagccacg gggagtacgg cacttctacc tgcagatgtt   1740
agacccacta gtctggccgc aagaggaatt tcgagagcga ccgcatggtc aacgggtgta   1800
gcttccttgc ttcatggtgg acttcagtcc ggtacattga acgctccacc cggacctctt   1860
caactttta tttccagaat gcatgtgtta cacactgttc tggttcaagt gtaccttctc    1920
ccgggggtgt ctatcgccgg tgctatgaca ccactacctc cactggaaaa gaccttgttt   1980
tgggacgtct tatgggcacg cccgacatcg agtgcctaga gggctacagt tacaacgata   2040
cgactaatgt ggattgggat ggtagctctt attgccacca ccaaaataac tctacgtcga   2100
aggcggtccg ctattgtagt agatgcaccc gcttgagaga atggtcacca aagtctttcc   2160
ctcaagttaa cccgcccaga aggttttttg cttcttccct tagcttgcta actgccaata   2220
gccgctcgtg cgtaccctaa aaccaaggcg tcccctaag gacagaagat aaccattccg    2280
tgacgtatgg cacgaccccc cgcgtaagtt aagataaaag cccccgcacc ccaaggacgg   2340
atttgaggac gaccctcatc gggaccggac caaccctgac ttatacgcct taggctgcta   2400
tacagtaagg agaaccggcc gcacgaacat gaccggtact gtgacccgca accgcggcta   2460
gttcctacgc ggtagttgaa accgttctct ctcgag                             2496
```

<210> SEQ ID NO 43
<211> LENGTH: 793
<212> TYPE: PRT
<213> ORGANISM: Artificial Sequence
<220> FEATURE:
<223> OTHER INFORMATION: Synthetic Construct

<400> SEQUENCE: 43

```
Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
                20                  25                  30

Gln Ile Gly Asn Arg Pro Gly Pro Ser Arg Gly Val Gln Gly Phe Ile
            35                  40                  45

Phe Phe Phe Leu Phe Asn Ile Leu Thr Gly Lys Lys Ile Thr Ala His
        50                  55                  60

Leu Lys Arg Leu Trp Lys Met Leu Asp Pro Arg Gln Gly Leu Ala Val
65                  70                  75                  80

Leu Arg Lys Val Lys Arg Val Val Ala Ser Leu Met Arg Gly Leu Ser
                85                  90                  95

Ser Arg Lys Arg Arg Ser His Asp Val Leu Thr Val Gln Phe Leu Ile
                100                 105                 110
```

```
Leu Gly Met Leu Ala Cys Val Gly Ala Ala Thr Val Arg Lys Glu Arg
            115                 120                 125

Asp Gly Ser Thr Val Ile Arg Ala Glu Gly Lys Asp Ala Ala Thr Gln
130                 135                 140

Val Arg Val Glu Asn Gly Thr Cys Val Ile Leu Ala Thr Asp Met Gly
145                 150                 155                 160

Ser Trp Cys Asp Asp Ser Leu Ser Tyr Glu Cys Val Thr Ile Asp Gln
                165                 170                 175

Gly Glu Glu Pro Val Asp Val Asp Cys Phe Cys Arg Asn Val Asp Gly
            180                 185                 190

Val Tyr Leu Glu Tyr Gly Arg Cys Gly Lys Gln Glu Gly Ser Arg Thr
195                 200                 205

Arg Arg Ser Val Leu Ile Pro Ser His Ala Gln Gly Glu Leu Thr Gly
210                 215                 220

Arg Gly His Lys Trp Leu Glu Gly Asp Ser Leu Arg Thr His Leu Thr
225                 230                 235                 240

Arg Val Glu Gly Trp Val Trp Lys Asn Arg Leu Leu Ala Leu Ala Met
                245                 250                 255

Val Thr Val Val Trp Leu Thr Leu Glu Ser Val Val Thr Arg Val Ala
            260                 265                 270

Val Leu Val Leu Leu Cys Leu Ala Pro Val Tyr Ala Ser Arg Cys
275                 280                 285

Thr His Leu Glu Asn Arg Asp Phe Val Thr Gly Thr Gln Gly Thr Thr
            290                 295                 300

Arg Val Thr Leu Val Leu Glu Leu Gly Gly Cys Val Thr Ile Thr Ala
305                 310                 315                 320

Glu Gly Lys Pro Ser Met Asp Val Trp Leu Asp Ala Ile Tyr Gln Glu
                325                 330                 335

Asn Pro Ala Gln Thr Arg Glu Tyr Cys Leu His Ala Lys Leu Ser Asp
            340                 345                 350

Thr Lys Val Ala Ala Arg Cys Pro Thr Met Gly Pro Ala Thr Leu Ala
355                 360                 365

Glu Glu His Gln Gly Gly Thr Val Cys Lys Arg Asp Gln Ser Asp Arg
370                 375                 380

Gly Trp Gly Asn His Cys Gly Leu Phe Gly Lys Gly Ser Ile Val Ala
385                 390                 395                 400

Cys Val Lys Ala Ala Cys Glu Ala Lys Lys Lys Ala Thr Gly His Val
                405                 410                 415

Tyr Asp Ala Asn Lys Ile Val Tyr Thr Val Lys Glu Pro His Thr Gly
            420                 425                 430

Asp Tyr Val Ala Ala Asn Glu Thr His Ser Gly Arg Lys Thr Ala Ser
435                 440                 445

Phe Thr Val Ser Ser Glu Lys Thr Ile Leu Thr Met Gly Glu Tyr Gly
450                 455                 460

Asp Val Ser Leu Leu Cys Arg Val Ala Ser Gly Val Asp Leu Ala Gln
465                 470                 475                 480

Thr Val Ile Leu Glu Leu Asp Lys Thr Val Glu His Leu Pro Thr Ala
                485                 490                 495

Trp Gln Val His Arg Asp Trp Phe Asn Asp Leu Ala Leu Pro Trp Lys
            500                 505                 510

His Glu Gly Ala Arg Asn Trp Asn Asn Ala Glu Arg Leu Val Glu Phe
515                 520                 525

Gly Ala Pro His Ala Val Lys Met Asp Val Tyr Asn Leu Gly Asp Gln
```

```
                530             535             540
Thr Gly Val Leu Leu Lys Ala Leu Ala Gly Val Pro Val Ala His Ile
545                 550             555                 560

Glu Gly Thr Lys Tyr His Leu Lys Ser Gly His Val Thr Cys Glu Val
                565             570                 575

Gly Leu Glu Lys Leu Lys Met Lys Gly Leu Thr Tyr Thr Met Cys Asp
            580             585                 590

Lys Thr Lys Phe Thr Trp Lys Arg Ala Pro Thr Asp Ser Gly His Asp
        595             600             605

Thr Val Val Met Glu Val Thr Phe Ser Gly Thr Lys Pro Cys Arg Ile
    610             615             620

Pro Val Arg Ala Val Ala His Gly Ser Pro Asp Val Asn Val Ala Met
625             630             635             640

Leu Ile Thr Pro Asn Pro Thr Ile Glu Asn Asn Gly Gly Phe Ile
                645             650             655

Glu Met Gln Leu Pro Pro Gly Asp Asn Ile Ile Tyr Val Gly Glu Leu
            660             665             670

Ser Tyr Gln Trp Phe Gln Lys Gly Ser Ser Ile Gly Arg Val Phe Gln
        675             680             685

Lys Thr Lys Lys Gly Ile Glu Arg Leu Thr Val Ile Gly Glu His Ala
        690             695             700

Trp Asp Phe Gly Ser Ala Gly Gly Phe Leu Ser Ser Ile Gly Lys Ala
705             710             715                 720

Leu His Thr Val Leu Gly Gly Ala Phe Asn Ser Ile Phe Gly Val
                725             730             735

Gly Phe Leu Pro Lys Leu Leu Leu Gly Val Ala Leu Ala Trp Leu Gly
            740             745             750

Leu Asn Met Arg Asn Pro Thr Met Ser Met Ser Phe Leu Leu Ala Gly
            755             760             765

Val Leu Val Leu Ala Met Thr Leu Gly Val Gly Ala Asp Gln Gly Cys
        770             775             780

Ala Ile Asn Phe Gly Lys Arg Glu Leu
785                 790
```

<210> SEQ ID NO 44
<211> LENGTH: 2500
<212> TYPE: DNA
<213> ORGANISM: Artificial Sequence
<220> FEATURE:
<223> OTHER INFORMATION: Synthetic Construct

<400> SEQUENCE: 44

```
agtaaatcct gtgtgctaat tgaggtgcat tggtctgcaa atcgagttgc taggcaataa    60
acacatttgg attaatttta atcgttcgtt gagcgattag cagagaactg accagaacat   120
gtctggtcgt aaagctcagg gaaaaaccct gggcgtcaat atggtacgac gaggagttcg   180
ctccttgtca aacaaaataa aacaaaaaac aaaacaaatt ggaaacagac ctggaccttc   240
aagaggtgtt caaggattta tcttttttctt tttgttcaac attttgactg gaaaaaagat   300
cacagcccac ctaagaggt tgtggaaaat gctggaccca agacaaggct ggctgttct     360
aaggaaagtc aagagagtgg tggccagttt gatgagagga ttgtcctcaa ggaaacgccg   420
ttcccatgat gttctgactg tgcaattcct aattttgggc atgctggctt gtgtcggagc   480
agctaccgtg cgaaaagaac gcgacggaag caccgtgata agggctgagg gtaaggatgc   540
ggctacgcag gtgagagtag agaatggcac ttgcgtaata ctcgcgactg atatgggatc   600
```

```
ctggtgtgac gatagcctca gttatgaatg cgtaacaata gaccagggcg aagaacctgt        660
ggacgttgac tgtttctgta gaaatgtgga tggcgtttat ctggagtacg gccgctgtgg        720
aaaacaggag ggctcacgaa ctcgaagatc tgtgctgatt ccaagtcacg cgcaaggaga        780
gttgaccggt agaggccaca agtggcttga aggggactca ttgaggaccc acctgactag        840
ggtggagggt tgggtttgga agaatcggtt gctcgcgctc gctatggtca ccgtcgtgtg        900
gctgacactg gagagtgtcg tgactcgggt tgctgtgttg gttgtcctcc tctgtttggc        960
cccagtgtac gcgtccaggt gtactcattt ggaaaacaga gattttgtca ccggcaccca       1020
ggggacgact cgggtaaccc tggtgcttga actgggtggt tgcgttacta ttaccgctga       1080
gggcaaaccc tctatggatg tgtggctgga tgcaatctat caggagaatc ccgcacaaac       1140
cagggaatat tgccttcacg caaagctgtc cgatacaaag gtcgcggcta ggtgcccaac       1200
aatgggaccg gccaccctgg cggaggaaca tcagggaggt acagtgtgca aacgggacca       1260
gagtgataga ggctggggta atcactgcgg cctgttcggc aaaggaagta ttgtcgcttg       1320
cgtcaaggca gcctgtgagg ccaaaaagaa ggctactggg cacgtctatg acgccaacaa       1380
gatcgtttat acagtgaaag tggaaccaca cacaggggat tacgtggcgg ccaacgagac       1440
tcattccggt cgcaaaacgg ccagcttcac cgtgtcatcc gaaaagacca tcctcactat       1500 ggggagtat ggcgacgttt ctctgctctg ccgggtggct agcggagtcg acctggccca       1560
gacagtcatc ctggaactgg ataaaacagt tgagcatctg cctaccgctt ggcaggtgca       1620
cagggattgg tttaacgacc ttgccctgcc atggaaacat gaaggagcga gaaactggaa       1680
taatgcagag cgactcgtag aattcggtgc ccctcatgcc gtgaagatgg acgtctacaa       1740
tctgggtgat cagaccggcg ttctccttaa agctctcgct ggcgtaccag ttgcccacat       1800
cgaaggaacg aagtaccacc tgaagtcagg ccatgtaact tgcgaggtgg gcctggagaa       1860
gttgaaaatg aaaggtctta cgtacacaat gtgtgacaag accaagttca catggaagag       1920
ggcccccaca gatagcggcc acgatactgt ggtgatggag gtgacctttt ctggaacaaa       1980
accctgcaga ataccgtgc gggctgtagc tcacggatct cccgatgtca atgttgctat       2040
gctgattaca cctaacccta ccatcgagaa taacggtggt ggttttattg agatgcagct       2100
tccgccaggc gataacatca tctacgtggg cgaactctct taccagtggt ttcagaaagg       2160
gagttcaatt gggcgggtct tccaaaaaac gaagaaggga atcgaacgat tgacggttat       2220
cggcgagcac gcatgggatt ttggttccgc aggggggatt ctgtcttcta ttggtaaggc       2280
actgcatacc gtgctggggg gcgcattcaa ttctattttc gggggcgtgg ggttcctgcc       2340
taaactcctg ctgggagtag ccctggcctg gttgggactg aatatgcgga atccgacgat       2400
gtccatgtca ttcctcttgg ccggcgtgct tgtactggcc atgacactgg gcgttggcgc       2460
cgatcaagga tgcgccatca actttggcaa gagagagctc                             2500
```

<210> SEQ ID NO 45
<211> LENGTH: 2500
<212> TYPE: DNA
<213> ORGANISM: Artificial Sequence
<220> FEATURE:
<223> OTHER INFORMATION: Synthetic Construct

<400> SEQUENCE: 45

```
tcatttagga cacacgatta actccacgta accagacgtt tagctcaacg atccgttatt         60
tgtgtaaacc taattaaaat tagcaagcaa ctcgctaatc gtctcttgac tggtcttgta        120
```

```
cagaccagca tttcgagtcc cttttttggga cccgcagtta taccatgctg ctcctcaagc      180
gaggaacagt tgttttatt ttgttttttg ttttgtttaa cctttgtctg gacctggaag        240
ttctccacaa gttcctaaat agaaaagaa aaacaagttg taaaactgac cttttttcta       300
gtgtcgggtg gatttctcca acaccttttta cgacctgggt tctgttccga accgacaaga      360
ttcctttcag ttctctcacc accggtcaaa ctactctcct aacaggagtt cctttgcggc      420
aagggtacta caagactgac acgttaagga ttaaaacccg tacgaccgaa cacagcctcg      480
tcgatggcac gcttttcttg cgctgccttc gtggcactat tcccgactcc cattcctacg     540
ccgatgcgtc cactctcatc tcttaccgtg aacgcattat gagcgctgac tatacccctag    600 gaccacactg ctatcggagt caatacttac gcattgttat ctggtcccgc ttcttggaca     660
cctgcaactg acaaagacat ctttacacct accgcaaata gacctcatgc cggcgacacc     720
ttttgtcctc ccgagtgctt gagcttctag acacgactaa ggttcagtgc gcgttcctct    780
caactggcca tctccggtgt tcaccgaact tcccctgagt aactcctggg tggactgatc    840
ccacctccca acccaaacct tcttagccaa cgagcgcgag cgataccagt ggcagcacac    900
cgactgtgac ctctcacagc actgagccca cgacacaac caacaggagg agacaaaccg    960
gggtcacatg cgcaggtcca catgagtaaa ccttttgtct ctaaaacagt ggccgtgggt   1020 ccctgctga gcccattggg accacgaact tgacccacca acgcaatgat aatggcgact   1080
cccgtttggg agatacctac acaccgacct acgttagata gtcctcttag ggcgtgtttg   1140
gtcccttata acggaagtgc gtttcgacag gctatgtttc cagcgccgat ccacgggttg   1200
ttaccctggc cggtgggacc gcctccttgt agtcccctcca tgtcacacgt ttgccctggt   1260
ctcactatct ccgaccccat tagtgacgcc ggacaagccg tttccttcat aacagcgaac   1320
gcagttccgt cggacactcc ggttttcctt ccgatgaccc gtgcagatac tgcggttgtt   1380
ctagcaaata tgtcactttc accttggtgt gtgtccccta atgcaccgcc ggttgctctg   1440
agtaaggcca gcgttttgcc ggtcgaagtg gcacagtagg ctttctggt aggagtgata   1500 cccctcata ccgctgcaaa gagacgagac ggcccaccga tcgcctcagc tggaccgggt    1560
ctgtcagtag gaccttgacc tattttgtca actcgtagac ggatggcgaa ccgtccacgt   1620
gtccctaacc aaattgctgg aacgggacgg tacctttgta cttcctcgct ctttgacctt   1680
attacgtctc gctgagcatc ttaagccacg gggagtacgg cacttctacc tgcagatgtt   1740
agacccacta gtctggccgc aagaggaatt tcgagagcga ccgcatggtc aacgggtgta   1800
gcttccttgc ttcatggtgg acttcagtcc ggtacattga acgctccacc cggacctctt   1860 caactttta tttccagaat gcatgtgtta cacactgttc tggttcaagt gtaccttctc    1920 ccggggtgt ctatcgccgg tgctatgaca ccactacctc cactggaaaa gaccttgttt    1980
tgggacgtct tatgggcacg cccgacatcg agtgcctaga gggctacagt tacaacgata   2040
cgactaatgt ggattgggat ggtagctctt attgccacca ccaaaataac tctacgtcga   2100
aggcggtccg ctattgtagt agatgcaccc gcttgagaga atggtcacca aagtctttcc   2160
ctcaagttaa cccgcccaga aggttttttg cttcttccct tagcttgcta actgccaata   2220
gccgctcgtg cgtaccctaa aaccaaggcg tcccctaag gacagaagat aaccattccg    2280
tgacgtatgg cacgaccccc cgcgtaagtt aagataaag ccccgcacc ccaaggacgg     2340 atttgaggac gaccctcatc gggaccggac caacccgtgac ttatacgcct taggctgcta   2400
caggtacagt aaggagaacc ggccgcacga acatgaccgg tactgtgacc cgcaaccgcg   2460
gctagttcct acgcggtagt tgaaaccgtt ctctctcgag                         2500
```

<210> SEQ ID NO 46
<211> LENGTH: 794
<212> TYPE: PRT
<213> ORGANISM: Artificial Sequence
<220> FEATURE:
<223> OTHER INFORMATION: Synthetic Construct

<400> SEQUENCE: 46

```
Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile
        35                  40                  45

Phe Phe Phe Leu Phe Asn Ile Leu Thr Gly Lys Lys Ile Thr Ala His
    50                  55                  60

Leu Lys Arg Leu Trp Lys Met Leu Asp Pro Arg Gln Gly Leu Ala Val
65                  70                  75                  80

Leu Arg Lys Val Lys Arg Val Ala Ser Leu Met Arg Gly Leu Ser
                85                  90                  95

Ser Arg Lys Arg Arg Ser His Asp Val Leu Thr Val Gln Phe Leu Ile
            100                 105                 110

Leu Gly Met Leu Gly Met Thr Ile Ala Ala Thr Val Arg Arg Glu Arg
        115                 120                 125

Asp Gly Ser Met Val Ile Arg Ala Glu Gly Arg Asp Ala Ala Thr Gln
    130                 135                 140

Val Arg Val Glu Asn Gly Thr Cys Val Ile Leu Ala Thr Asp Met Gly
145                 150                 155                 160

Ser Trp Cys Asp Asp Ser Leu Ala Tyr Glu Cys Val Thr Ile Asp Gln
                165                 170                 175

Gly Glu Glu Pro Val Asp Val Asp Cys Phe Cys Arg Gly Val Glu Lys
            180                 185                 190

Val Thr Leu Glu Tyr Gly Arg Cys Gly Arg Arg Glu Gly Ser Arg Ser
        195                 200                 205

Arg Arg Ser Val Leu Ile Pro Ser His Ala Gln Arg Asp Leu Thr Gly
    210                 215                 220

Arg Gly His Gln Trp Leu Glu Gly Glu Ala Val Lys Ala His Leu Thr
225                 230                 235                 240

Arg Val Glu Gly Trp Val Trp Lys Asn Lys Leu Phe Thr Leu Ser Leu
                245                 250                 255

Val Met Val Ala Trp Leu Met Val Asp Gly Leu Leu Pro Arg Ile Leu
            260                 265                 270

Ile Val Val Ala Leu Ala Leu Ala Pro Ala Tyr Ala Ser Arg Cys
        275                 280                 285

Thr His Leu Glu Asn Arg Asp Phe Val Thr Gly Val Gln Gly Thr Thr
    290                 295                 300

Arg Leu Thr Leu Val Leu Glu Leu Gly Gly Cys Val Thr Val Thr Ala
305                 310                 315                 320

Asp Gly Lys Pro Ser Leu Asp Val Trp Leu Asp Ser Ile Tyr Gln Glu
                325                 330                 335

Ser Pro Ala Gln Thr Arg Glu Tyr Cys Leu His Ala Lys Leu Thr Gly
            340                 345                 350

Thr Lys Val Ala Ala Arg Cys Pro Thr Met Gly Pro Ala Thr Leu Pro
        355                 360                 365
```

-continued

```
Glu Glu His Gln Ser Gly Thr Val Cys Lys Arg Asp Gln Ser Asp Arg
    370                 375                 380

Gly Trp Gly Asn His Cys Gly Leu Phe Gly Lys Gly Ser Ile Val Thr
385                 390                 395                 400

Cys Val Lys Val Thr Cys Glu Asp Lys Lys Ala Thr Gly His Val
                405                 410                 415

Tyr Asp Val Asn Lys Ile Thr Tyr Thr Ile Lys Val Glu Pro His Thr
                420                 425                 430

Gly Glu Phe Val Ala Ala Asn Glu Thr His Ser Gly Arg Lys Ser Ala
                435                 440                 445

Ser Phe Thr Val Ser Ser Glu Lys Thr Ile Leu Thr Leu Gly Asp Tyr
    450                 455                 460

Gly Asp Val Ser Leu Leu Cys Arg Val Ala Ser Gly Val Asp Leu Ala
465                 470                 475                 480

Gln Thr Val Val Leu Ala Leu Asp Lys Thr His Glu His Leu Pro Thr
                485                 490                 495

Ala Trp Gln Val His Arg Asp Trp Phe Asn Asp Leu Ala Leu Pro Trp
                500                 505                 510

Lys His Asp Gly Ala Glu Ala Trp Asn Glu Ala Gly Arg Leu Val Glu
                515                 520                 525

Phe Gly Thr Pro His Ala Val Lys Met Asp Val Phe Asn Leu Gly Asp
    530                 535                 540

Gln Thr Gly Val Leu Leu Lys Ser Leu Ala Gly Val Pro Val Ala Ser
545                 550                 555                 560

Ile Glu Gly Thr Lys Tyr His Leu Lys Ser Gly His Val Thr Cys Glu
                565                 570                 575

Val Gly Leu Glu Lys Leu Lys Met Lys Gly Leu Thr Tyr Thr Val Cys
                580                 585                 590

Asp Lys Thr Lys Phe Thr Trp Lys Arg Ala Pro Thr Asp Ser Gly His
                595                 600                 605

Asp Thr Val Val Met Glu Val Gly Phe Ser Gly Thr Arg Pro Cys Arg
    610                 615                 620

Ile Pro Val Arg Ala Val Ala His Gly Val Pro Glu Val Asn Val Ala
625                 630                 635                 640

Met Leu Ile Thr Pro Asn Pro Thr Met Glu Asn Asn Gly Gly Gly Phe
                645                 650                 655

Ile Glu Met Gln Leu Pro Pro Gly Asp Asn Ile Ile Tyr Val Gly Asp
                660                 665                 670

Leu Asp His Gln Trp Phe Gln Lys Gly Ser Ser Ile Gly Arg Val Leu
                675                 680                 685

Gln Lys Thr Arg Lys Gly Ile Glu Arg Leu Thr Val Leu Gly Glu His
    690                 695                 700

Ala Trp Asp Phe Gly Ser Val Gly Gly Val Met Thr Ser Ile Gly Arg
705                 710                 715                 720

Ala Met His Thr Val Leu Gly Gly Ala Phe Asn Thr Leu Leu Gly Gly
                725                 730                 735

Val Gly Phe Leu Pro Lys Ile Leu Leu Gly Val Ala Met Ala Trp Leu
                740                 745                 750

Gly Leu Asn Met Arg Asn Pro Thr Leu Ser Met Gly Phe Leu Leu Ser
    755                 760                 765

Gly Gly Leu Val Leu Ala Met Thr Leu Gly Val Gly Ala Asp Gln Gly
770                 775                 780
```

Cys Ala Ile Asn Phe Gly Lys Arg Glu Leu
785                 790

<210> SEQ ID NO 47
<211> LENGTH: 2500
<212> TYPE: DNA
<213> ORGANISM: Artificial Sequence
<220> FEATURE:
<223> OTHER INFORMATION: Synthetic Construct

<400> SEQUENCE: 47

| | | | | | |
|---|---|---|---|---|---|
| agtaaatcct | gtgtgctaat | tgaggtgcat | tggtctgcaa | atcgagttgc | taggcaataa | 60 |
| acacatttgg | attaatttta | atcgttcgtt | gagcgattag | cagagaactg | accagaacat | 120 |
| gtctggtcgt | aaagctcagg | gaaaaaccct | gggcgtcaat | atggtacgac | gaggagttcg | 180 |
| ctccttgtca | aacaaaataa | aacaaaaaac | aaaacaaatt | ggaaacagac | ctggaccttc | 240 |
| aagaggtgtt | caaggattta | tcttttttctt | tttgttcaac | attttgactg | gaaaaaagat | 300 |
| cacagcccac | ctaaagaggt | tgtggaaaat | gctggaccca | agacaaggct | tggctgttct | 360 |
| aaggaaagtc | aagagagtgg | tggccagttt | gatgagagga | ttgtcctcaa | ggaaacgccg | 420 |
| ttcccatgat | gttctgactg | tgcaattcct | aattttgggc | atgctgggga | tgacgatcgc | 480 |
| agctactgtg | cgaagggaga | gagacggctc | tatggtgatc | agagccgaag | gtagggacgc | 540 |
| tgcgacccag | gtgagggtcg | aaaatggcac | tgtgttatt | ctggcgaccg | acatgggctc | 600 |
| ctggtgtgat | gattctctgg | cttatgaatg | tgttactatt | gatcagggtg | aagagcctgt | 660 |
| ggacgtggac | tgtttctgta | gaggcgtcga | gaaagtgacc | ctggaatatg | acgatgtgg | 720 |
| ccggcgagaa | ggctccagga | gtcggagatc | cgtgttgatc | ccttcacatg | cgcagcgcga | 780 |
| tctgacaggg | aggggtcacc | agtggctcga | aggcgaagca | gtcaaggccc | atctgactcg | 840 |
| cgttgaaggc | tgggtgtgga | aaacaaaact | ctttaccctt | agcctggtga | tggtcgcgtg | 900 |
| gctgatggta | gacggactcc | ttccccgcat | tctcattgtt | gtggtggctc | tcgcgctcgc | 960 |
| ccctgcatac | gcgtccaggt | gtacgcacct | cgaaaatcga | gatttcgtca | caggcgtcca | 1020 |
| aggtactacc | cggctcaccc | tcgtgctgga | gctgggaggc | tgtgtcactg | ttacagccga | 1080 |
| cggaaaacct | agtctggatg | tgtggctgga | ctccatctat | caggagagcc | cggcacagac | 1140 |
| cagggagtac | tgcctccacg | ctaagctgac | tgggacaaag | gtagccgcaa | gatgtcccac | 1200 |
| aatgggcct | gccaccttgc | ccgaggaaca | ccaatccggt | acggtatgca | agcgagatca | 1260 |
| gtctgatcgc | ggatgggga | atcattgcgg | cctcttcggt | aaaggcagca | ttgtcacttg | 1320 |
| cgtgaaggtg | acatgcgagg | acaagaagaa | ggccacaggt | catgtatatg | atgtgaacaa | 1380 |
| aatcacatat | accattaagg | tagaaccaca | tacaggggaa | ttcgtggcag | caaacgagac | 1440 |
| tcatagcgga | cgaaagtccg | cctccttcac | cgtctcctcc | gagaaaacaa | tcctgaccct | 1500 |
| cggagactac | ggcgacgtat | ctttgctgtg | cagggtggcc | agcggcgtgg | accttgctca | 1560 |
| gacagtcgtg | ttggccctgg | acaagacaca | tgagcacttg | ccaacagcct | ggcaggtgca | 1620 |
| cagggactgg | tttaacgacc | tggcgctccc | gtggaaacat | gacggcgctg | aagcatggaa | 1680 |
| tgaggcaggg | agactggtgg | aatttggaac | cccacacgcc | gtaaagatgg | acgttttcaa | 1740 |
| tcttggtgac | cagacagggg | tgctcctgaa | atcactggcg | ggcgtgcctg | tagccagcat | 1800 |
| cgagggcaca | aagtatcacc | tgaagtctgg | gcatgtaacc | tgcgaagtgg | gcctggaaaa | 1860 |
| gctgaagatg | aaaggactta | cgtacactgt | ttgtgataag | accaagttta | catgaagcg | 1920 |
| agccccaacg | gattccggcc | atgataccgt | cgtgatggag | gttggtttct | ccggcaccag | 1980 |

```
accatgtaga ataccagtga gagctgtcgc ccacggtgta cccgaggtaa acgtggccat    2040
gctgattaca ccgaatccca ctatggagaa caatggcgga gggttcatcg aaatgcagct    2100
gccgcctgga gacaacatca tttatgtcgg cgacctcgat catcaatggt tccagaaagg    2160
gtcttccatc ggccgcgtcc ttcagaagac acgaaaaggc attgaaagac ttacagtcct    2220
gggcgaacat gcctgggact tcgggtcagt tggcggggta atgacaagca taggcagagc    2280
tatgcacacc gttctcggtg gggcatttaa tactctgttg ggtggcgtgg gtttttcttcc    2340 gaaaatcctg ctcggtgtcg caatggcctg gcttggactg aatatgcgca atcctacact    2400
gagtatgggg tttcttctgt caggaggcct ggtcctggca atgactctgg gagtgggcgc    2460
cgatcaagga tgcgccatca actttggcaa gagagagctc                         2500
```

<210> SEQ ID NO 48
<211> LENGTH: 2500
<212> TYPE: DNA
<213> ORGANISM: Artificial Sequence
<220> FEATURE:
<223> OTHER INFORMATION: Synthetic Construct

<400> SEQUENCE: 48

```
tcatttagga cacacgatta actccacgta accagacgtt tagctcaacg atccgttatt      60
tgtgtaaacc taattaaaat tagcaagcaa ctcgctaatc gtctcttgac tggtcttgta     120
cagaccagca tttcgagtcc ctttttggga cccgcagtta taccatgctg ctcctcaagc     180
gaggaacagt ttgttttatt ttgtttttttg ttttgtttaa cctttgtctg gacctggaag    240
ttctccacaa gttcctaaat agaaaaagaa aaacaagttg taaaactgac cttttttcta     300
gtgtcgggtg gatttctcca acaccttttta cgacctgggt tctgttccga accgacaaga    360
ttcctttcag ttctctcacc accggtcaaa ctactctcct aacaggagtt cctttgcggc     420
aagggtacta caagactgac acgttaagga ttaaaacccg tacgaccect actgctagcg     480 tcgatgacac gcttccctct ctctgccgag ataccactag tctcggcttc catccctgcg     540
acgctgggtc cactcccagc ttttaccgtg gacacaataa gaccgctggc tgtacccgag     600
gaccacacta ctaagagacc gaatacttac acaatgataa ctagtcccac ttctcggaca     660
cctgcacctg acaaagacat ctccgcagct cttcactgg gaccttatac ctgctacacc      720
ggccgctctt ccgaggtcct cagcctctag gcacaactag gaagtgtac gcgtcgcgct      780 agactgtccc tccccagtgg tcaccgagct tccgcttcgt cagttccggg tagactgagc     840
gcaacttccg acccacacct ttttgtttga gaaatgggaa tcggaccact accagcgcac     900
cgactaccat ctgcctgagg aagggggcgta agagtaacaa caccaccgag agcgcgagcg    960
gggacgtatg cgcaggtcca catgcgtgga gctttttagct ctaaagcagt gtccgcaggt   1020
tccatgatgg gccgagtggg agcacgacct cgaccctccg acacagtgac aatgtcggct   1080
gccttttgga tcagacctac acaccgacct gaggtagata gtcctctcgg gccgtgtctg   1140
gtccctcatg acggaggtgc gattcgactg acccctgtttc catcggcgtt ctacagggtg   1200
ttaccccgga cggtggaacg ggctccttgt ggttaggcca tgccatacgt tcgctctagt   1260
cagactagcg cctacccect tagtaacgcc ggagaagcca tttccgtcgt aacagtgaac   1320
gcacttccac tgtacgctcc tgttcttctt ccggtgtcca gtacatatac tacacttgtt   1380
ttagtgtata tggtaattcc atcttggtgt atgtcccctt aagcaccgtc gtttgctctg   1440
agtatcgcct gctttcaggc ggaggaagtg gcagaggagg ctcttttgtt aggactggga   1500
gcctctgatg ccgctgcata gaaacgacac gtcccaccgg tcgccgcacc tggaacgagt   1560
```

```
ctgtcagcac aaccgggacc tgttctgtgt actcgtgaac ggttgtcgga ccgtccacgt    1620
gtccctgacc aaattgctgg accgcgaggg cacctttgta ctgccgcgac ttcgtacctt    1680
actccgtccc tctgaccacc ttaaaccttg gggtgtgcgg catttctacc tgcaaaagtt    1740
agaaccactg gtctgtcccc acgaggactt tagtgaccgc ccgcacggac atcggtcgta    1800
gctcccgtgt ttcatagtgg acttcagacc cgtacattgg acgcttcacc cggacctttt    1860
cgacttctac tttcctgaat gcatgtgaca aacactattc tggttcaaat gtaccttcgc    1920
tcggggttgc ctaaggccgg tactatggca gcactacctc caaccaaaga ggccgtggtc    1980
tggtacatct tatggtcact ctcgacagcg ggtgccacat gggctccatt tgcaccggta    2040
cgactaatgt ggcttagggt gatacctctt gttaccgcct cccaagtagc tttacgtcga    2100
cggcggacct ctgttgtagt aaatacagcc gctggagcta gtagttacca aggtcttttcc   2160
cagaaggtag ccggcgcagg aagtcttctg tgcttttccg taactttctg aatgtcagga    2220
cccgcttgta cggaccctga agcccagtca accgcccat tactgttcgt atccgtctcg     2280
atacgtgtgg caagagccac cccgtaaatt atgagacaac ccaccgcacc caaaagaagg    2340
cttttaggac gagccacagc gttaccggac cgaacctgac ttatacgcgt taggatgtga    2400
ctcatacccc aaagaagaca gtcctccgga ccaggaccgt tactgagacc ctcacccgcg    2460
gctagttcct acgcggtagt tgaaaccgtt ctctctcgag                          2500
```

<210> SEQ ID NO 49
<211> LENGTH: 791
<212> TYPE: PRT
<213> ORGANISM: Artificial Sequence
<220> FEATURE:
<223> OTHER INFORMATION: Synthetic Construct

<400> SEQUENCE: 49

```
Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30

Gln Ile Gly Asn Arg Pro Gly Gly Val Gln Gly Phe Ile Phe Phe
        35                  40                  45

Leu Phe Asn Ile Leu Thr Gly Lys Lys Ile Thr Ala His Leu Lys Arg
    50                  55                  60

Leu Trp Lys Met Leu Asp Pro Arg Gln Gly Leu Ala Val Leu Arg Lys
65                  70                  75                  80

Val Lys Arg Val Val Ala Ser Leu Met Arg Gly Leu Ser Ser Arg Lys
                85                  90                  95

Arg Arg Ser His Asp Val Leu Thr Val Gln Phe Leu Ile Leu Gly Met
            100                 105                 110

Leu Gly Met Thr Ile Ala Ala Thr Val Arg Lys Glu Arg Asp Gly Ser
        115                 120                 125

Thr Val Ile Arg Ala Glu Gly Lys Asp Ala Ala Thr Gln Val Arg Val
    130                 135                 140

Glu Asn Gly Thr Cys Val Ile Leu Ala Thr Asp Met Gly Ser Trp Cys
145                 150                 155                 160

Asp Asp Ser Leu Ser Tyr Glu Cys Val Thr Ile Asp Gln Gly Glu Glu
                165                 170                 175

Pro Val Asp Val Asp Cys Phe Cys Arg Asn Val Asp Gly Val Tyr Leu
            180                 185                 190
```

-continued

```
Glu Tyr Gly Arg Cys Gly Lys Gln Glu Gly Ser Arg Thr Arg Arg Ser
            195                 200                 205

Val Leu Ile Pro Ser His Ala Gln Gly Glu Leu Thr Gly Arg Gly His
        210                 215                 220

Lys Trp Leu Glu Gly Asp Ser Leu Arg Thr His Leu Thr Arg Val Glu
225                 230                 235                 240

Gly Trp Val Trp Lys Asn Arg Leu Leu Ala Leu Ala Met Val Thr Val
                245                 250                 255

Val Trp Leu Thr Leu Glu Ser Val Val Thr Arg Val Ala Val Leu Val
                260                 265                 270

Val Leu Leu Cys Leu Ala Pro Val Tyr Ala Ser Arg Cys Thr His Leu
            275                 280                 285

Glu Asn Arg Asp Phe Val Thr Gly Thr Gln Gly Thr Thr Arg Val Thr
        290                 295                 300

Leu Val Leu Glu Leu Gly Gly Cys Val Thr Ile Thr Ala Glu Gly Lys
305                 310                 315                 320

Pro Ser Met Asp Val Trp Leu Asp Ala Ile Tyr Gln Glu Asn Pro Ala
                325                 330                 335

Gln Thr Arg Glu Tyr Cys Leu His Ala Lys Leu Ser Asp Thr Lys Val
            340                 345                 350

Ala Ala Arg Cys Pro Thr Met Gly Pro Ala Thr Leu Ala Glu Glu His
        355                 360                 365

Gln Gly Gly Thr Val Cys Lys Arg Asp Gln Ser Asp Arg Gly Trp Gly
        370                 375                 380

Asn His Cys Gly Leu Phe Gly Lys Gly Ser Ile Val Ala Cys Val Lys
385                 390                 395                 400

Ala Ala Cys Glu Ala Lys Lys Lys Ala Thr Gly His Val Tyr Asp Ala
                405                 410                 415

Asn Lys Ile Val Tyr Thr Val Lys Val Glu Pro His Thr Gly Asp Tyr
            420                 425                 430

Val Ala Ala Asn Glu Thr His Ser Gly Arg Lys Thr Ala Ser Phe Thr
        435                 440                 445

Val Ser Ser Glu Lys Thr Ile Leu Thr Met Gly Glu Tyr Gly Asp Val
450                 455                 460

Ser Leu Leu Cys Arg Val Ala Ser Gly Val Asp Leu Ala Gln Thr Val
465                 470                 475                 480

Ile Leu Glu Leu Asp Lys Thr Val Glu His Leu Pro Thr Ala Trp Gln
                485                 490                 495

Val His Arg Asp Trp Phe Asn Asp Leu Ala Leu Pro Trp Lys His Glu
            500                 505                 510

Gly Ala Arg Asn Trp Asn Asn Ala Glu Arg Leu Val Glu Phe Gly Ala
        515                 520                 525

Pro His Ala Val Lys Met Asp Val Tyr Asn Leu Gly Asp Gln Thr Gly
        530                 535                 540

Val Leu Leu Lys Ala Leu Ala Gly Val Pro Val Ala His Ile Glu Gly
545                 550                 555                 560

Thr Lys Tyr His Leu Lys Ser Gly His Val Thr Cys Glu Val Gly Leu
                565                 570                 575

Glu Lys Leu Lys Met Lys Gly Leu Thr Tyr Thr Met Cys Asp Lys Thr
            580                 585                 590

Lys Phe Thr Trp Lys Arg Ala Pro Thr Asp Ser Gly His Asp Thr Val
        595                 600                 605

Val Met Glu Val Thr Phe Ser Gly Thr Lys Pro Cys Arg Ile Pro Val
```

```
             610                 615                 620
Arg Ala Val Ala His Gly Ser Pro Asp Val Asn Val Ala Met Leu Ile
625                 630                 635                 640

Thr Pro Asn Pro Thr Ile Glu Asn Asn Gly Gly Phe Ile Glu Met
                645                 650                 655

Gln Leu Pro Pro Gly Asp Asn Ile Ile Tyr Val Gly Glu Leu Ser Tyr
                660                 665                 670

Gln Trp Phe Gln Lys Gly Ser Ser Ile Gly Arg Val Phe Gln Lys Thr
                675                 680                 685

Lys Lys Gly Ile Glu Arg Leu Thr Val Ile Gly Glu His Ala Trp Asp
                690                 695                 700

Phe Gly Ser Ala Gly Gly Phe Leu Ser Ser Ile Gly Lys Ala Leu His
705                 710                 715                 720

Thr Val Leu Gly Gly Ala Phe Asn Ser Ile Phe Gly Gly Val Gly Phe
                725                 730                 735

Leu Pro Lys Leu Leu Leu Gly Val Ala Leu Ala Trp Leu Gly Leu Asn
                740                 745                 750

Met Arg Asn Pro Thr Met Ser Met Ser Phe Leu Leu Ala Gly Val Leu
                755                 760                 765

Val Leu Ala Met Thr Leu Gly Val Gly Ala Asp Gln Gly Cys Ala Ile
                770                 775                 780

Asn Phe Gly Lys Arg Glu Leu
785                 790

<210> SEQ ID NO 50
<211> LENGTH: 2491
<212> TYPE: DNA
<213> ORGANISM: Artificial Sequence
<220> FEATURE:
<223> OTHER INFORMATION: Synthetic Construct

<400> SEQUENCE: 50
agtaaatcct gtgtgctaat tgaggtgcat tggtctgcaa atcgagttgc taggcaataa      60
acacatttgg attaattta atcgttcgtt gagcgattag cagagaactg accagaacat     120
gtctggtcgt aaagctcagg gaaaaaccct gggcgtcaat atggtacgac gaggagttcg     180
ctccttgtca aacaaaataa aacaaaaaac aaaacaaatt ggaaacagac ctggaggtgt     240
tcaaggattt atctttttct ttttgttcaa cattttgact ggaaaaaaga tcacagccca     300
cctaaagagg ttgtggaaaa tgctggaccc aagacaaggc ttggctgttc taaggaaagt     360
caagagagtg gtggccagtt tgatgagagg attgtcctca aggaaacgcc gttcccatga     420
tgttctgact gtgcaattcc taattttggg catgctgggc atgacaatcg cagctacggt     480
tcgcaaggaa agagacggca gtacggtcat acgcgcggaa ggtaaggatg ccgctaccca     540
agtgagagtg aaaatggta cctgcgtcat tctggccacc gacatgggct cttggtgtga     600
tgatagcctt tcttatgagt gcgtaaccat agatcaaggt gaggaacctg ttgacgttga     660
ttgcttctgc cgaaacgtgg atgggtgta tctcgaatat ggacggtgtg gtaaacaaga     720
aggaagcaga accagacgct cagtgcttat accctcccac gctcaaggag agctgaccgg     780
acggggacat aaatggttgg agggcgactc actccgaaca catttgaccc gcgtcgaggg     840
ctgggtctgg aaaaatcggc tgttggccct cgctatggtg acagtcgttt ggctcacgct     900
ggagtctgtg gttactcgcg tggcagtgct ggtggtgctc ctctgtcttg ccctgtctta     960
cgcgtccagg tgtactcatt tggaaaacag agattttgtc accggcaccc aggggacgac    1020
```

```
tcgggtaacc ctggtgcttg aactgggtgg ttgcgttact attaccgctg agggcaaacc      1080
ctctatggat gtgtggctgg atgcaatcta tcaggagaat cccgcacaaa ccagggaata      1140
ttgccttcac gcaaagctgt ccgatacaaa ggtcgcggct aggtgcccaa caatgggacc      1200
ggccaccctg gcggaggaac atcagggagg tacagtgtgc aaacgggacc agagtgatag      1260
aggctggggt aatcactgcg gcctgttcgg caaaggaagt attgtcgctt gcgtcaaggc      1320
agcctgtgag gccaaaaaga aggctactgg gcacgtctat gacgccaaca agatcgttta      1380
tacagtgaaa gtggaaccac acacagggga ttacgtggcg ccaacgaga ctcattccgg       1440 tcgcaaaacg gccagcttca ccgtgtcatc cgaaaagacc atcctcacta tgggggagta     1500
tggcgacgtt tctctgctct gccgggtggc tagcggagtc gacctggccc agacagtcat      1560
cctggaactg gataaaacag ttgagcatct gcctaccgct tggcaggtgc acagggattg     1620
gtttaacgac cttgccctgc catggaaaca tgaaggagcg agaaactgga ataatgcaga     1680
gcgactcgta gaattcggtg cccctcatgc cgtgaagatg gacgtctaca atctgggtga     1740
tcagaccggc gttctcctta aagctctcgc tggcgtacca gttgcccaca tcgaaggaac     1800
gaagtaccac ctgaagtcag gccatgtaac ttgcgaggtg ggcctggaga agttgaaaat     1860
gaaaggtctt acgtacacaa tgtgtgacaa gaccaagttc acatggaaga gggcccccac     1920
agatagcggc cacgtactg tggtgatgga ggtgaccttt tctggaacaa aaccctgcag      1980
aatacccgtg cgggctgtag ctcacggatc tcccgatgtc aatgttgcta tgctgattac     2040
acctaaccct accatcgaga ataacggtgg tggttttatt gagatgcagc ttccgccagg     2100
cgataacatc atctacgtgg gcgaactctc ttaccagtgg tttcagaaag ggagttcaat     2160
tgggcgggtc ttccaaaaaa cgaagaaggg aatcgaacga ttgacggtta tcggcgagca     2220
cgcatgggat tttggttccg caggggggat cctgtcttct attggtaagg cactgcatac     2280
cgtgctgggg ggcgcattca attctatttt cggggggcgtg gggttcctgc ctaaactcct     2340
gctgggagta gccctggcct ggttgggact gaatatgcgg aatccgacga tgtccatgtc     2400
attcctcttg gccggcgtgc ttgtactggc catgacactg ggcgttggcg ccgatcaagg     2460
atgcgccatc aactttggca agagagagct c                                     2491

<210> SEQ ID NO 51
<211> LENGTH: 2491
<212> TYPE: DNA
<213> ORGANISM: Artificial Sequence
<220> FEATURE:
<223> OTHER INFORMATION: Synthetic Construct

<400> SEQUENCE: 51
tcatttagga cacacgatta actccacgta accagacgtt tagctcaacg atccgttatt        60
tgtgtaaacc taattaaaat tagcaagcaa ctcgctaatc gtctcttgac tggtcttgta       120
cagaccagca tttcgagtcc cttttttgga cccgcagtta taccatgctg ctcctcaagc      180
gaggaacagt ttgttttatt ttgttttttg ttttgtttaa cctttgtctg gacctccaca      240
agttcctaaa tagaaaaaga aaacaagtt gtaaaactga ccttttttct agtgtcgggt       300
ggatttctcc aacacctttt acgacctggg ttctgttccg aaccgacaag attcctttca      360
gttctctcac caccggtcaa actactctcc taacaggagt tcctttgcgg caagggtact     420
acaagactga cacgttaagg attaaaaccc gtacgacccg tactgttagc gtcgatgcca     480
agcgttcctt tctctgccgt catgccagta tgcgcgcctt ccattcctac ggcgatgggt     540
tcactctcac cttttaccat ggacgcagta agaccggtgg ctgtacccga gaaccacact    600
```

```
actatcggaa agaatactca cgcattggta tctagttcca ctccttggac aactgcaact      660
aacgaagacg gctttgcacc tacccccacat agagcttata cctgccacac catttgttct    720
tccttcgtct tggtctgcga gtcacgaata tgggagggtg cgagttcctc tcgactggcc     780
tgcccctgta tttaccaacc tcccgctgag tgaggcttgt gtaaactggg cgcagctccc     840
gacccagacc ttttagccg acaaccggga gcgataccac tgtcagcaaa ccgagtgcga       900
cctcagacac caatgagcgc accgtcacga ccaccacgag gagacagaac ggggacagat     960
gcgcaggtcc acatgagtaa accttttgtc tctaaaacag tggccgtggg tccctgctg       1020
agcccattgg gaccacgaac ttgacccacc aacgcaatga taatggcgac tcccgtttgg    1080
gagataccta cacaccgacc tacgttagat agtcctctta gggcgtgttt ggtcccttat    1140
aacggaagtg cgtttcgaca ggctatgttt ccagcgccga tccacgggtt gttaccctgg   1200
ccggtgggac cgcctccttg tagtccctcc atgtcacacg tttgccctgg tctcactatc    1260
tccgaccca ttagtgacgc cggacaagcc gtttccttca taacagcgaa cgcagttccg      1320
tcggacactc cggttttct tccgatgacc cgtgcagata ctgcggttgt tctagcaaat     1380
atgtcacttt caccttggtg tgtgtcccct aatgcaccgc cggttgctct gagtaaggcc     1440
agcgttttgc cggtcgaagt ggcacagtag cttttctgg taggagtgat acccctcat       1500
accgctgcaa agagacgaga cggcccaccg atcgcctcag ctggaccggg tctgtcagta     1560
ggaccttgac ctattttgtc aactcgtaga cggatggcga accgtccacg tgtccctaac     1620
caaattgctg gaacgggacg gtacctttgt acttcctcgc tctttgacct tattacgtct    1680
cgctgagcat cttaagccac ggggagtacg gcacttctac ctgcagatgt tagacccact    1740
agtctggccg caagaggaat ttcgagagcg accgcatggt caacgggtgt agcttccttg    1800
cttcatggtg gacttcagtc cggtacattg aacgctccac ccggacctct tcaacttta     1860
ctttccagaa tgcatgtgtt acacactgtt ctggttcaag tgtaccttct cccgggggtg    1920
tctatcgccg gtgctatgac accactacct ccactggaaa agaccttgtt ttgggacgtc    1980
ttatgggcac gcccgacatc gagtgcctag agggctacag ttacaacgat acgactaatg    2040
tggattggga tggtagctct tattgccacc accaaaataa ctctacgtcg aaggcggtcc    2100
gctattgtag tagatgcacc cgcttgagag aatggtcacc aaagtctttc cctcaagtta    2160
acccgcccag aaggttttt gcttcttccc ttagcttgct aactgccaat agccgctcgt     2220
gcgtaccta aaaccaaggc gtccccctaa ggacagaaga taaccattcc gtgacgtatg     2280
gcacgacccc ccgcgtaagt taagataaaa gcccccgcac cccaaggacg gatttgagga    2340
cgaccctcat cgggaccgga ccaaccctga cttatacgcc ttaggctgct acaggtacag    2400
taaggagaac cggccgcacg aacatgaccg gtactgtgac ccgcaaccgc ggctagttcc    2460
tacgcggtag ttgaaaccgt tctctctcga g                                    2491
```

<210> SEQ ID NO 52
<211> LENGTH: 730
<212> TYPE: PRT
<213> ORGANISM: Artificial Sequence
<220> FEATURE:
<223> OTHER INFORMATION: Synthetic Construct

<400> SEQUENCE: 52

Met Ser Lys Lys Pro Gly Gly Pro Gly Lys Ser Arg Ala Val Tyr Leu
1               5                   10                  15

Leu Lys Arg Gly Met Pro Arg Val Leu Ser Leu Ile Gly Leu Lys Arg

```
            20                  25                  30
Ser Ser Lys Gln Lys Lys Arg Gly Gly Thr Asp Trp Met Ser Trp Leu
         35                  40                  45
Leu Val Ile Gly Met Leu Gly Met Thr Ile Ala Ala Thr Val Arg Lys
         50                  55                  60
Glu Arg Asp Gly Ser Thr Val Ile Arg Ala Glu Gly Lys Asp Ala Ala
 65                  70                  75                  80
Thr Gln Val Arg Val Glu Asn Gly Thr Cys Val Ile Leu Ala Thr Asp
                 85                  90                  95
Met Gly Ser Trp Cys Asp Asp Ser Leu Ser Tyr Glu Cys Val Thr Ile
                100                 105                 110
Asp Gln Gly Glu Glu Pro Val Asp Val Asp Cys Phe Cys Arg Asn Val
                115                 120                 125
Asp Gly Val Tyr Leu Glu Tyr Gly Arg Cys Gly Lys Gln Glu Gly Ser
                130                 135                 140
Arg Thr Arg Arg Ser Val Leu Ile Pro Ser His Ala Gln Gly Glu Leu
145                 150                 155                 160
Thr Gly Arg Gly His Lys Trp Leu Glu Gly Asp Ser Leu Arg Thr His
                165                 170                 175
Leu Thr Arg Val Glu Gly Trp Val Trp Lys Asn Arg Leu Leu Ala Leu
                180                 185                 190
Ala Met Val Thr Val Val Trp Leu Thr Leu Glu Ser Val Val Thr Arg
                195                 200                 205
Val Ala Val Leu Val Val Leu Leu Cys Leu Ala Pro Val Tyr Ala Ser
                210                 215                 220
Arg Cys Thr His Leu Glu Asn Arg Asp Phe Val Thr Gly Thr Gln Gly
225                 230                 235                 240
Thr Thr Arg Val Thr Leu Val Leu Glu Leu Gly Gly Cys Val Thr Ile
                245                 250                 255
Thr Ala Glu Gly Lys Pro Ser Met Asp Val Trp Leu Asp Ala Ile Tyr
                260                 265                 270
Gln Glu Asn Pro Ala Gln Thr Arg Glu Tyr Cys Leu His Ala Lys Leu
                275                 280                 285
Ser Asp Thr Lys Val Ala Ala Arg Cys Pro Thr Met Gly Pro Ala Thr
                290                 295                 300
Leu Ala Glu Glu His Gln Gly Gly Thr Val Cys Lys Arg Asp Gln Ser
305                 310                 315                 320
Asp Arg Gly Trp Gly Asn His Cys Gly Leu Phe Gly Lys Gly Ser Ile
                325                 330                 335
Val Ala Cys Val Lys Ala Ala Cys Glu Ala Lys Lys Lys Ala Thr Gly
                340                 345                 350
His Val Tyr Asp Ala Asn Lys Ile Val Tyr Thr Val Lys Val Glu Pro
                355                 360                 365
His Thr Gly Asp Tyr Val Ala Ala Asn Glu Thr His Ser Gly Arg Lys
                370                 375                 380
Thr Ala Ser Phe Thr Val Ser Ser Glu Lys Thr Ile Leu Thr Met Gly
385                 390                 395                 400
Glu Tyr Gly Asp Val Ser Leu Leu Cys Arg Val Ala Ser Gly Val Asp
                405                 410                 415
Leu Ala Gln Thr Val Ile Leu Glu Leu Asp Lys Thr Val Glu His Leu
                420                 425                 430
Pro Thr Ala Trp Gln Val His Arg Asp Trp Phe Asn Asp Leu Ala Leu
                435                 440                 445
```

```
Pro Trp Lys His Glu Gly Ala Arg Asn Trp Asn Asn Ala Glu Arg Leu
    450                 455                 460
Val Glu Phe Gly Ala Pro His Ala Val Lys Met Asp Val Tyr Asn Leu
465                 470                 475                 480
Gly Asp Gln Thr Gly Val Leu Leu Lys Ala Leu Ala Gly Val Pro Val
                485                 490                 495
Ala His Ile Glu Gly Thr Lys Tyr His Leu Lys Ser Gly His Val Thr
            500                 505                 510
Cys Glu Val Gly Leu Glu Lys Leu Met Lys Gly Leu Thr Tyr Thr
        515                 520                 525
Met Cys Asp Lys Thr Lys Phe Thr Trp Lys Arg Ala Pro Thr Asp Ser
    530                 535                 540
Gly His Asp Thr Val Val Met Glu Val Thr Phe Ser Gly Thr Lys Pro
545                 550                 555                 560
Cys Arg Ile Pro Val Arg Ala Val Ala His Gly Ser Pro Asp Val Asn
                565                 570                 575
Val Ala Met Leu Ile Thr Pro Asn Pro Thr Ile Glu Asn Asn Gly Gly
            580                 585                 590
Gly Phe Ile Glu Met Gln Leu Pro Pro Gly Asp Asn Ile Ile Tyr Val
        595                 600                 605
Gly Glu Leu Ser Tyr Gln Trp Phe Gln Lys Gly Ser Ser Ile Gly Arg
    610                 615                 620
Val Phe Gln Lys Thr Lys Lys Gly Ile Glu Arg Leu Thr Val Ile Gly
625                 630                 635                 640
Glu His Ala Trp Asp Phe Gly Ser Ala Gly Gly Phe Leu Ser Ser Ile
                645                 650                 655
Gly Lys Ala Leu His Thr Val Leu Gly Gly Ala Phe Asn Ser Ile Phe
            660                 665                 670
Gly Gly Val Gly Phe Leu Pro Lys Leu Leu Leu Gly Val Ala Leu Ala
        675                 680                 685
Trp Leu Gly Leu Asn Met Arg Asn Pro Thr Met Ser Met Ser Phe Leu
    690                 695                 700
Leu Ala Gly Val Leu Val Leu Ala Met Thr Leu Gly Val Gly Ala Asp
705                 710                 715                 720
Thr Gly Cys Ala Ile Asp Ile Ser Arg Gln
                725                 730

<210> SEQ ID NO 53
<211> LENGTH: 2286
<212> TYPE: DNA
<213> ORGANISM: Artificial Sequence
<220> FEATURE:
<223> OTHER INFORMATION: Synthetic Construct

<400> SEQUENCE: 53
agtagttcgc ctgtgtgagc tgacaaactt agtagtgttt gtgaggatta acaacaatta    60
acacagtgcg agctgtttct tagcacgaag atctcgatgt ctaagaaacc aggagggccc   120
ggcaagagcc gggctgtcta tttgctaaaa cgcggaatgc cccgcgtgtt gtccttgatt   180
ggacttaagc ggagctccaa acaaaagaaa cgggggggaa cagactggat gagctggctg   240
ctcgtaatcg gcatgctggg catgacaatc gcagctacgg ttcgcaagga agagacggc    300 agtacggtca tacgcgcgga aggtaaggat gccgctaccc aagtgagagt ggaaaatggt   360
acctgcgtca ttctggccac cgacatgggc tcttggtgtg atgatagcct ttcttatgag   420
```

```
tgcgtaacca tagatcaagg tgaggaacct gttgacgttg attgcttctg ccgaaacgtg      480 gatgggtgt atctcgaata tggacggtgt ggtaaacaag aaggaagcag aaccagacgc        540
tcagtgctta taccctccca cgctcaagga gagctgaccg gacggggaca taaatggttg       600
gagggcgact cactccgaac acatttgacc cgcgtcgagg gctgggtctg gaaaaatcgg       660
ctgttggccc tcgctatggt gacagtcgtt tggctcacgc tggagtctgt ggttactcgc      720
gtggcagtgc tggtggtgct cctctgtctt gcccctgtct acgcgtccag gtgtactcat      780
ttggaaaaca gagattttgt caccggcacc caggggacga ctcgggtaac cctggtgctt       840
gaactgggtg gttgcgttac tattaccgct gagggcaaac cctctatgga tgtgtggctg       900
gatgcaatct atcaggagaa tcccgcacaa accagggaat attgccttca cgcaaagctg       960
tccgatacaa aggtcgcggc taggtgccca acaatgggac cggccaccct ggcggaggaa      1020
catcagggag gtacagtgtg caaacgggac cagagtgata gaggctgggg taatcactgc      1080
ggcctgttcg gcaaaggaag tattgtcgct tgcgtcaagg cagcctgtga ggccaaaaag      1140
aaggctactg ggcacgtcta tgacgccaac aagatcgttt atacagtgaa agtggaacca     1200
cacacagggg attacgtggc ggccaacgag actcattccg gtcgcaaaac ggccagcttc      1260
accgtgtcat ccgaaaagac catcctcact atggggagt atggcgacgt ttctctgctc       1320
tgccgggtgg ctagcggagt cgacctggcc cagacagtca tcctggaact ggataaaaca     1380
gttgagcatc tgcctaccgc ttggcaggtg cacagggatt ggtttaacga ccttgccctg     1440
ccatggaaac atgaaggagc gagaaactgg aataatgcag agcgactcgt agaattcggt      1500
gcccctcatg ccgtgaagat ggacgtctac aatctgggtg atcagaccgg cgttctcctt      1560
aaagctctcg ctggcgtacc agttgcccac atcgaaggaa cgaagtacca cctgaagtca     1620
ggccatgtaa cttgcgaggt gggcctggag aagttgaaaa tgaaaggtct tacgtacaca    1680
atgtgtgaca agaccaagtt cacatggaag agggccccca cagatagcgg ccacgatact      1740
gtggtgatgg aggtgacctt ttctggaaca aaaccctgca gaatacccgt gcgggctgta     1800
gctcacggat ctcccgatgt caatgttgct atgctgatta cacctaaccc taccatcgag     1860
aataacggtg gtggtttat tgagatgcag cttccgccag cgataacat catctacgtg     1920 ggcgaactct cttaccagtg gtttcagaaa gggagttcaa ttgggcgggt cttccaaaaa    1980
acgaagaagg gaatcgaacg attgacggtt atcggcgagc acgcatggga ttttggttcc      2040
gcagggggat tcctgtcttc tattggtaag gcactgcata ccgtgctggg gggcgcattc     2100
aattctattt tcggggcgt gggttcctg cctaaactcc tgctgggagt agccctggcc       2160
tggttgggac tgaatatgcg gaatccgacg atgtccatgt cattcctctt ggccggcgtg     2220
cttgtactgg ccatgacact gggcgttggc gccgacactg ggtgtgccat agacatcagc     2280
cggcaa                                                                2286
```

<210> SEQ ID NO 54
<211> LENGTH: 2286
<212> TYPE: DNA
<213> ORGANISM: Artificial Sequence
<220> FEATURE:
<223> OTHER INFORMATION: Synthetic Construct

<400> SEQUENCE: 54

```
tcatcaagcg acacactcg actgtttgaa tcatcacaaa cactcctaat tgttgttaat        60
tgtgtcacgc tcgacaaaga atcgtgcttc tagagctaca gattctttgg tcctcccggg     120
ccgttctcgg cccgacagat aaacgatttt gcgccttacg gggcgcacaa caggaactaa     180
```

```
cctgaattcg cctcgaggtt tgttttcttt gccccccctt gtctgaccta ctcgaccgac    240
gagcattagc cgtacgaccc gtactgttag cgtcgatgcc aagcgttcct ttctctgccg    300
tcatgccagt atgcgcgcct tccattccta cggcgatggg ttcactctca ccttttacca    360
tggacgcagt aagaccggtg gctgtacccg agaaccacac tactatcgga agaatactc     420 acgcattggt atctagttcc actccttgga caactgcaac taacgaagac ggctttgcac    480
ctaccccaca tagagcttat acctgccaca ccatttgttc ttccttcgtc ttggtctgcg    540
agtcacgaat atgggagggt gcgagttcct ctcgactggc ctgcccctgt atttaccaac    600
ctcccgctga gtgaggcttg tgtaaactgg gcgcagctcc cgacccagac cttttttagcc   660 gacaaccggg agcgatacca ctgtcagcaa accgagtgcg acctcagaca ccaatgagcg    720
caccgtcacg accaccacga ggagacagaa cggggacaga tgcgcaggtc cacatgagta    780
aaccttttgt ctctaaaaca gtggccgtgg gtcccctgct gagcccattg ggaccacgaa    840
cttgacccac caacgcaatg ataatggcga ctcccgtttg ggagatacct acacaccgac    900
ctacgttaga tagtcctctt agggcgtgtt tggtccctta taacggaagt gcgtttcgac    960
aggctatgtt tccagcgccg atccacgggt tgttaccctg gccggtggga ccgcctcctt   1020
gtagtccctc catgtcacac gtttgccctg gtctcactat ctccgacccc attagtgacg   1080
ccggacaagc cgtttccttc ataacagcga acgcagttcc gtcggacact ccggtttttc   1140
ttccgatgac ccgtgcagat actgcggttg ttctagcaaa tatgtcactt tcaccttggt   1200
gtgtgtcccc taatgcaccg ccggttgctc tgagtaaggc cagcgttttg ccggtcgaag   1260
tggcacagta ggcttttctg gtaggagtga taccccctca taccgctgca aagagacgag   1320
acggcccacc gatcgcctca gctggaccgg gtctgtcagt aggaccttga cctattttgt   1380
caactcgtag acggatggcg aaccgtccac gtgtccctaa ccaaattgct ggaacgggac   1440
ggtacctttg tacttcctcg ctctttgacc ttattacgtc tcgctgagca tcttaagcca   1500
cggggagtac ggcacttcta cctgcagatg ttagaccccca tagtctggcc gcaagaggaa   1560
tttcgagagc gaccgcatgg tcaacgggtg tagcttcctt gcttcatggt ggacttcagt   1620
ccggtacatt gaacgctcca cccggacctc ttcaactttt actttccaga atgcatgtgt   1680
tacacactgt tctggttcaa gtgtaccttc tcccgggggt gtctatcgcc ggtgctatga   1740
caccactacc tccactggaa aagaccttgt tttgggacgt cttatgggca cgcccgacat   1800
cgagtgccta gagggctaca gttacaacga tacgactaat gtggattggg atggtagctc   1860
ttattgccac caccaaaata actctacgtc gaaggcggtc cgctattgta gtagatgcac   1920
ccgcttgaga gaatggtcac caaagtcttt ccctcaagtt aacccgccca gaaggttttt   1980
tgcttcttcc cttagcttgc taactgccaa tagccgctcg tgcgtaccct aaaaccaagg   2040
cgtcccccta aggacagaag ataaccattc cgtgacgtat ggcacgaccc ccgcgtaag   2100 ttaagataaa agcccccgca ccccaaggac ggatttgagg acgaccctca tcgggaccgg   2160
accaaccctg acttatacgc cttaggctgc tacaggtaca gtaaggagaa ccggccgcac   2220
gaacatgacc ggtactgtga cccgcaaccg cggctgtgac ccacacggta tctgtagtcg   2280
gccgtt                                                              2286
```

<210> SEQ ID NO 55
<211> LENGTH: 727
<212> TYPE: PRT
<213> ORGANISM: Artificial Sequence
<220> FEATURE:

<223> OTHER INFORMATION: Synthetic Construct

<400> SEQUENCE: 55

```
Met Ser Lys Lys Pro Gly Gly Pro Gly Lys Ser Arg Ala Val Tyr Leu
1               5                   10                  15

Leu Lys Arg Gly Met Pro Arg Val Leu Ser Leu Ile Gly Leu Lys Arg
            20                  25                  30

Ser Ser Lys Gln Lys Lys Arg Gly Gly Lys Thr Gly Ile Ala Val Met
        35                  40                  45

Ile Gly Met Leu Ala Cys Val Gly Ala Ala Thr Val Arg Lys Glu Arg
    50                  55                  60

Asp Gly Ser Thr Val Ile Arg Ala Glu Gly Lys Asp Ala Ala Thr Gln
65                  70                  75                  80

Val Arg Val Glu Asn Gly Thr Cys Val Ile Leu Ala Thr Asp Met Gly
                85                  90                  95

Ser Trp Cys Asp Asp Ser Leu Ser Tyr Glu Cys Val Thr Ile Asp Gln
            100                 105                 110

Gly Glu Glu Pro Val Asp Val Asp Cys Phe Cys Arg Asn Val Asp Gly
        115                 120                 125

Val Tyr Leu Glu Tyr Gly Arg Cys Gly Lys Gln Glu Gly Ser Arg Thr
    130                 135                 140

Arg Arg Ser Val Leu Ile Pro Ser His Ala Gln Gly Glu Leu Thr Gly
145                 150                 155                 160

Arg Gly His Lys Trp Leu Glu Gly Asp Ser Leu Arg Thr His Leu Thr
                165                 170                 175

Arg Val Glu Gly Trp Val Trp Lys Asn Arg Leu Leu Ala Leu Ala Met
            180                 185                 190

Val Thr Val Val Trp Leu Thr Leu Glu Ser Val Val Thr Arg Val Ala
    195                 200                 205

Val Leu Val Val Leu Leu Cys Leu Ala Pro Val Tyr Ala Ser Arg Cys
    210                 215                 220

Thr His Leu Glu Asn Arg Asp Phe Val Thr Gly Thr Gln Gly Thr Thr
225                 230                 235                 240

Arg Val Thr Leu Val Leu Glu Leu Gly Gly Cys Val Thr Ile Thr Ala
                245                 250                 255

Glu Gly Lys Pro Ser Met Asp Val Trp Leu Asp Ala Ile Tyr Gln Glu
            260                 265                 270

Asn Pro Ala Gln Thr Arg Glu Tyr Cys Leu His Ala Lys Leu Ser Asp
        275                 280                 285

Thr Lys Val Ala Ala Arg Cys Pro Thr Met Gly Pro Ala Thr Leu Ala
    290                 295                 300

Glu Glu His Gln Gly Gly Thr Val Cys Lys Arg Asp Gln Ser Asp Arg
305                 310                 315                 320

Gly Trp Gly Asn His Cys Gly Leu Phe Gly Lys Gly Ser Ile Val Ala
                325                 330                 335

Cys Val Lys Ala Ala Cys Glu Ala Lys Lys Ala Thr Gly His Val
            340                 345                 350

Tyr Asp Ala Asn Lys Ile Val Tyr Thr Val Lys Val Glu Pro His Thr
        355                 360                 365

Gly Asp Tyr Val Ala Ala Asn Glu Thr His Ser Gly Arg Lys Thr Ala
    370                 375                 380

Ser Phe Thr Val Ser Ser Glu Lys Thr Ile Leu Thr Met Gly Glu Tyr
385                 390                 395                 400
```

```
Gly Asp Val Ser Leu Leu Cys Arg Val Ala Ser Gly Val Asp Leu Ala
                405                 410                 415

Gln Thr Val Ile Leu Glu Leu Asp Lys Thr Val Glu His Leu Pro Thr
            420                 425                 430

Ala Trp Gln Val His Arg Asp Trp Phe Asn Asp Leu Ala Leu Pro Trp
        435                 440                 445

Lys His Glu Gly Ala Arg Asn Trp Asn Asn Ala Glu Arg Leu Val Glu
    450                 455                 460

Phe Gly Ala Pro Ala Val Lys Met Asp Val Tyr Asn Leu Gly Asp Gln
465                 470                 475                 480

Thr Gly Val Leu Leu Lys Ala Leu Ala Gly Val Pro Val Ala His Ile
                485                 490                 495

Glu Gly Thr Lys Tyr His Leu Lys Ser Gly His Val Thr Cys Glu Val
            500                 505                 510

Gly Leu Glu Lys Leu Lys Met Lys Gly Leu Thr Tyr Thr Met Cys Asp
        515                 520                 525

Lys Thr Lys Phe Thr Trp Lys Arg Ala Pro Thr Asp Ser Gly His Asp
    530                 535                 540

Thr Val Val Met Glu Val Thr Phe Ser Gly Thr Lys Pro Cys Arg Ile
545                 550                 555                 560

Pro Val Arg Ala Val Ala His Gly Ser Pro Asp Val Asn Val Ala Met
                565                 570                 575

Leu Ile Thr Pro Asn Pro Thr Ile Glu Asn Asn Gly Gly Gly Phe Ile
            580                 585                 590

Glu Met Gln Leu Pro Pro Gly Asp Asn Ile Ile Tyr Val Gly Glu Leu
        595                 600                 605

Ser Tyr Gln Trp Phe Gln Lys Gly Ser Ser Ile Gly Arg Val Phe Gln
    610                 615                 620

Lys Thr Lys Lys Gly Ile Glu Arg Leu Thr Val Ile Gly Glu His Ala
625                 630                 635                 640

Trp Asp Phe Gly Ser Ala Gly Gly Phe Leu Ser Ser Ile Gly Lys Ala
                645                 650                 655

Leu His Thr Val Leu Gly Gly Ala Phe Asn Ser Ile Phe Gly Gly Val
            660                 665                 670

Gly Phe Leu Pro Lys Leu Leu Leu Gly Val Ala Leu Ala Trp Leu Gly
        675                 680                 685

Leu Asn Met Arg Asn Pro Thr Met Ser Met Ser Phe Leu Leu Ala Gly
    690                 695                 700

Val Leu Val Leu Ala Met Thr Leu Gly Val Gly Ala Asp Thr Gly Cys
705                 710                 715                 720

Ala Ile Asp Ile Ser Arg Gln
                725

<210> SEQ ID NO 56
<211> LENGTH: 2280
<212> TYPE: DNA
<213> ORGANISM: Artificial Sequence
<220> FEATURE:
<223> OTHER INFORMATION: Synthetic Construct

<400> SEQUENCE: 56
agtagttcgc ctgtgtgagc tgacaaactt agtagtgttt gtgaggatta acaacaatta    60
acacagtgcg agctgtttct tagcacgaag atctcgatgt ctaagaaacc aggagggccc   120
ggcaagagcc gggctgtcta tttgctaaaa cgcggaatgc ccgcgtgtgt gtccttgatt   180
```

```
ggacttaagc ggagctccaa gcaaaagaaa cgcggggaa agacaggcat agctgtgatg      240
ataggcatgc tggcttgtgt cggagcagct accgtgcgaa aagaacgcga cggaagcacc      300
gtgataaggg ctgagggtaa ggatgcggct acgcaggtga gagtagagaa tggcacttgc      360
gtaatactcg cgactgatat gggatcctgg tgtgacgata gcctcagtta tgaatgcgta      420
acaatagacc agggcgaaga acctgtggac gttgactgtt tctgtagaaa tgtggatggc      480
gtttatctgg agtacggccg ctgtggaaaa caggagggct cacgaactcg aagatctgtg      540
ctgattccaa gtcacgcgca aggagagttg accggtagag gccacaagtg gcttgaaggg      600
gactcattga ggacccacct gactagggtg gagggttggg tttggaagaa tcggttgctc      660
gcgctcgcta tggtcaccgt cgtgtggctg acactggaga gtgtcgtgac tcggtttgct      720
gtgttggttg tcctcctctg tttggcccca gtgtacgcgt ccaggtgtac tcatttggaa      780
aacagagatt ttgtcaccgg cacccagggg acgactcggg taaccctggt gcttgaactg      840
ggtggttgcg ttactattac cgctgagggc aaaccctcta tggatgtgtg gctggatgca      900
atctatcagg agaatcccgc acaaaccagg gaatattgcc ttcacgcaaa gctgtccgat      960
acaaaggtcg cggctaggtg cccaacaatg ggaccggcca ccctggcgga ggaacatcag     1020
ggaggtacag tgtgcaaacg ggaccagagt gatagaggct ggggtaatca ctgcggcctg     1080
ttcggcaaag gaagtattgt cgcttgcgtc aaggcagcct gtgaggccaa aagaaggct      1140 actgggcacg tctatgacgc caacaagatc gtttatacag tgaaagtgga accacacaca     1200
ggggattacg tggcggccaa cgagactcat tccggtcgca aaacggccag cttcaccgtg     1260
tcatccgaaa agaccatcct cactatgggg gagtatggcg acgtttctct gctctgccgg     1320
gtggctagcg gagtcgacct ggcccagaca gtcatcctgg aactggataa aacagttgag     1380
catctgccta ccgcttggca ggtgcacagg gattggttta cgaccttgc cctgccatgg      1440 aaacatgaag gagcgagaaa ctggaataat gcagagcgac tcgtagaatt cggtgcccct     1500
catgccgtga gatggacgt ctacaatctg ggtgatcaga ccggcgttct ccttaaagct      1560
ctcgctggcg taccagttgc ccacatcgaa ggaacgaagt accacctgaa gtcaggccat     1620
gtaacttgcg aggtgggcct ggagaagttg aaaatgaaag gtcttacgta cacaatgtgt     1680
gacaagacca agttcacatg gaagagggcc cccacagata gcggccacga tactgtggtg     1740
atggaggtga cctttctgg aacaaaaccc tgcagaatac ccgtgcgggc tgtagctcac     1800
ggatctcccg atgtcaatgt tgctatgctg attacaccta accctaccat cgagaataac     1860
ggtggtggtt ttattgagat gcagcttccg ccaggcgata acatcatcta cgtgggcgaa     1920
ctctcttacc agtggtttca gaagggagt tcaattgggc gggtcttcca aaaacgaag      1980 aagggaatcg aacgattgac ggttatcggc gagcacgcat gggattttgg ttccgcaggg     2040
ggattcctgt cttctattgg taaggcactg catacgctgc tgggggcgc attcaattct      2100 attttcgggg gcgtggggtt cctgcctaaa ctcctgctgg gagtagccct ggcctggttg     2160
ggactgaata tgcggaatcc gacgatgtcc atgtcattcc tcttggccgg cgtgcttgta     2220
ctggccatga cactgggcgt tggcgccgac actgggtgtg ccatagacat cagccggcaa     2280
```

<210> SEQ ID NO 57
<211> LENGTH: 2280
<212> TYPE: DNA
<213> ORGANISM: Artificial Sequence
<220> FEATURE:
<223> OTHER INFORMATION: Synthetic Construct

<400> SEQUENCE: 57

```
tcatcaagcg gacacactcg actgtttgaa tcatcacaaa cactcctaat tgttgttaat      60
tgtgtcacgc tcgacaaaga atcgtgcttc tagagctaca gattctttgg tcctcccggg     120
ccgttctcgg cccgacagat aaacgatttt gcgccttacg gggcgcacaa caggaactaa     180
cctgaattcg cctcgaggtt cgttttcttt gcgccccctt tctgtccgta tcgacactac     240
tatccgtacg accgaacaca gcctcgtcga tggcacgctt ttcttgcgct gccttcgtgg     300
cactattccc gactcccatt cctacgccga tgcgtccact ctcatctctt accgtgaacg     360
cattatgagc gctgactata ccctaggacc acactgctat cggagtcaat acttacgcat     420
tgttatctgg tcccgcttct tggacacctg caactgacaa agacatcttt acacctaccg     480
caaatagacc tcatgccggc gacaccttt gtcctcccga gtgcttgagc ttctagacac      540
gactaaggtt cagtgcgcgt tcctctcaac tggccatctc cggtgttcac cgaacttccc     600
ctgagtaact cctgggtgga ctgatcccac ctcccaaccc aaaccttctt agccaacgag     660
cgcgagcgat accagtggca gcacaccgac tgtgacctct cacagcactg agcccaacga     720
cacaaccaac aggaggagac aaaccggggt cacatgcgca ggtccacatg agtaaacctt     780
ttgtctctaa aacagtggcc gtgggtcccc tgctgagccc attgggacca cgaacttgac     840
ccaccaacgc aatgataatg gcgactcccg tttgggagat acctacacac cgacctacgt     900
tagatagtcc tcttagggcg tgtttggtcc cttataacgg aagtgcgttt cgacaggcta     960
tgtttccagc gccgatccac gggttgttac cctggccggt gggaccgcct ccttgtagtc    1020
cctccatgtc acacgtttgc cctggtctca ctatctccga ccccattagt gacgccggac    1080
aagccgtttc cttcataaca gcgaacgcag ttccgtcgga cactccggtt tttcttccga    1140
tgacccgtgc agatactgcg gttgttctag caaatatgtc actttcacct tggtgtgtgt    1200
cccctaatgc accgccggtt gctctgagta aggccagcgt tttgccggtc gaagtggcac    1260
agtaggcttt tctggtagga gtgataccccc ctcataccgc tgcaaagaga cgagacggcc    1320
caccgatcgc ctcagctgga ccgggtctgt cagtaggacc ttgacctatt ttgtcaactc    1380
gtagacggat ggcgaaccgt ccacgtgtcc ctaaccaaat tgctggaacg ggacgggtacc   1440
tttgtacttc ctcgctcttt gaccttatta cgtctcgctg agcatcttaa gccacgggga   1500
gtacggcact tctacctgca gatgttagac ccactagtct ggccgcaaga ggaatttcga    1560
gagcgaccgc atggtcaacg ggtgtagctt ccttgcttca tggtggactt cagtccggta    1620
cattgaacgc tccacccgga cctcttcaac ttttactttc cagaatgcat gtgttacaca    1680
ctgttctggt tcaagtgtac cttctcccgg gggtgtctat cgccggtgct atgacaccac    1740
tacctccact ggaaaagacc ttgttttggg acgtcttatg ggcacgcccg acatcgagtg    1800
cctagagggc tacagttaca acgatacgac taatgtggat tgggatggta gctcttattg    1860
ccaccaccaa aataactcta cgtcgaaggc ggtccgctat tgtagtagat gcacccgctt    1920
gagagaatgg tcaccaaagt ctttccctca agttaacccg cccagaaggt ttttgcttc     1980
ttcccttagc ttgctaactg ccaatagccg ctcgtgcgta ccctaaaacc aaggcgtccc    2040
cctaaggaca gaagataacc attccgtgac gtatggcacg accccccgcg taagttaaga    2100
taaaagcccc cgcaccccaa ggacggattt gaggacgacc ctcatcggga ccggaccaac    2160
cctgacttat acgccttagg ctgctacagg tacagtaagg agaaccggcc gcacgaacat    2220
gaccggtact gtgacccgca accgcggctg tgacccacac ggtatctgta gtcggccgtt    2280
```

<210> SEQ ID NO 58

```
<211> LENGTH: 635
<212> TYPE: PRT
<213> ORGANISM: Artificial Seqeunce
<220> FEATURE:
<223> OTHER INFORMATION: Synthetic Construct

<400> SEQUENCE: 58

Met Ser Lys Lys Pro Gly Gly Pro Gly Lys Ser Arg Ala Val Tyr Leu
1               5                   10                  15

Leu Lys Arg Gly Met Pro Arg Val Leu Ser Leu Ile Gly Leu Lys Gln
            20                  25                  30

Lys Lys Arg Gly Gly Lys Thr Gly Ile Ala Val Ile Val Pro Gln Ala
        35                  40                  45

Leu Leu Phe Val Pro Leu Leu Val Phe Pro Leu Cys Phe Gly Lys Phe
    50                  55                  60

Pro Ile Tyr Thr Ile Pro Asp Lys Leu Gly Pro Trp Ser Pro Ile Asp
65                  70                  75                  80

Ile His His Leu Ser Cys Pro Asn Asn Leu Val Val Glu Asp Glu Gly
                85                  90                  95

Cys Thr Asn Leu Ser Gly Phe Ser Tyr Met Glu Leu Lys Val Gly Tyr
            100                 105                 110

Ile Ser Ala Ile Lys Met Asn Gly Phe Thr Cys Thr Gly Val Val Thr
        115                 120                 125

Glu Ala Glu Thr Tyr Thr Asn Phe Val Gly Tyr Val Thr Thr Thr Phe
    130                 135                 140

Lys Arg Lys His Phe Arg Pro Thr Pro Asp Ala Cys Arg Ala Ala Tyr
145                 150                 155                 160

Asn Trp Lys Met Ala Gly Asp Pro Arg Tyr Glu Glu Ser Leu His Asn
                165                 170                 175

Pro Tyr Pro Asp Tyr His Trp Leu Arg Thr Val Lys Thr Thr Lys Glu
            180                 185                 190

Ser Leu Val Ile Ile Ser Pro Ser Val Ala Asp Leu Asp Pro Tyr Asp
        195                 200                 205

Arg Ser Leu His Ser Arg Val Phe Pro Gly Gly Asn Cys Ser Gly Val
    210                 215                 220

Ala Val Ser Ser Thr Tyr Cys Ser Thr Asn His Asp Tyr Thr Ile Trp
225                 230                 235                 240

Met Pro Glu Asn Pro Arg Leu Gly Met Ser Cys Asp Ile Phe Thr Asn
                245                 250                 255

Ser Arg Gly Lys Arg Ala Ser Lys Gly Ser Glu Thr Cys Gly Phe Val
            260                 265                 270

Asp Glu Arg Gly Leu Tyr Lys Ser Leu Lys Gly Ala Cys Lys Leu Lys
        275                 280                 285

Leu Cys Gly Val Leu Gly Leu Arg Leu Met Asp Gly Thr Trp Val Ala
    290                 295                 300

Met Gln Thr Ser Asn Glu Thr Lys Trp Cys Pro Pro Gly Gln Leu Val
305                 310                 315                 320

Asn Leu His Asp Phe Arg Ser Asp Glu Ile Glu His Leu Val Val Glu
                325                 330                 335

Glu Leu Val Lys Lys Arg Glu Glu Cys Leu Asp Ala Leu Glu Ser Ile
            340                 345                 350

Met Thr Thr Lys Ser Val Ser Phe Arg Arg Leu Ser His Leu Arg Lys
        355                 360                 365

Leu Val Pro Gly Phe Gly Lys Ala Tyr Thr Ile Phe Asn Lys Thr Leu
    370                 375                 380
```

```
Met Glu Ala Asp Ala His Tyr Lys Ser Val Arg Thr Trp Asn Glu Ile
385                 390                 395                 400

Ile Pro Ser Lys Gly Cys Leu Arg Val Gly Arg Cys His Pro His
            405                 410                 415

Val Asn Gly Val Phe Phe Asn Gly Ile Ile Leu Gly Pro Asp Gly Asn
            420                 425                 430

Val Leu Ile Pro Glu Met Gln Ser Ser Leu Leu Gln Gln His Met Glu
            435                 440                 445

Leu Leu Val Ser Ser Val Ile Pro Leu Met His Pro Leu Ala Asp Pro
        450                 455                 460

Ser Thr Val Phe Lys Asn Gly Asp Glu Ala Glu Asp Phe Val Glu Val
465                 470                 475                 480

His Leu Pro Asp Val His Glu Arg Ile Ser Gly Val Asp Leu Gly Leu
                485                 490                 495

Pro Asn Trp Gly Lys Tyr Val Leu Leu Ser Ala Gly Ala Leu Thr Ala
                500                 505                 510

Leu Met Leu Ile Ile Phe Leu Met Thr Cys Trp Arg Val Asn Arg
        515                 520                 525

Ser Glu Pro Thr Gln His Asn Leu Arg Gly Thr Gly Arg Glu Val Ser
            530                 535                 540

Val Thr Pro Gln Ser Gly Lys Ile Ile Ser Ser Trp Glu Ser Tyr Lys
545                 550                 555                 560

Ser Gly Gly Glu Thr Gly Leu Asn Phe Asp Leu Leu Lys Leu Ala Gly
                565                 570                 575

Asp Val Glu Ser Asn Pro Gly Pro Ala Arg Asp Arg Ser Ile Ala Leu
                580                 585                 590

Thr Phe Leu Ala Val Gly Gly Val Leu Leu Phe Leu Ser Val Asn Val
        595                 600                 605

His Ala Asp Thr Gly Cys Ala Ile Asp Ile Ser Arg Gln Glu Leu Arg
            610                 615                 620

Cys Gly Ser Gly Val Phe Ile His Asn Asp Val
625                 630                 635

<210> SEQ ID NO 59
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 59
agtagttcgc ctgtgtgagc tgacaaactt agtagtgttt gtgaggatta acaacaatta      60
acacagtgcg agctgtttct tagcacgaag atctcgatgt ctaagaaacc aggagggccc     120
ggcaagagcc gggctgtcta tttgctaaaa cgcggaatgc cccgcgtgtt gtccttgatt     180
ggacttaagc aaaagaagcg aggggggcaag actggtatag ctgtgatcgt tcctcaggct    240
cttttgtttg taccettgct ggtatttccc ctttgctttg gtaaatttcc tatctatacc     300
atccctgata agctcgggcc ttggagtccc attgatattc accattttgag ctgcccaaac    360 aacctcgtcg ttgaggatga agggtgcact aatctttctg gattttccta catggagttg    420
aaagtgggct atatttcagc cattaagatg aacggcttta cttgtacagg agtcgtgacc    480
gaagccgaga catatacaaa tttcgtggga tacgtcacca ccaccttcaa gagaaaacac    540
ttccgcccaa cgcctgacgc ttgtcgggcc gcttacaact ggaagatggc aggagatcct    600
```

| | |
|---|---|
| cgatatgaag aatctctgca caacccgtat cctgattacc attggctgcg gacagtcaag | 660 |
| actaccaagg agagtctggt cattatatca ccaagcgtgg ccgatcttga tccttatgat | 720 |
| agatccctgc acagtagggt ttttcctggc gggaattgta gcggtgttgc agtatcaagt | 780 |
| acctactgct ccactaacca cgactacact atatggatgc ctgagaaccc tcgactcggt | 840 |
| atgagttgcg acatttttac gaactcacgg ggcaagcggg catctaaggg gtctgaaaca | 900 |
| tgcgggtttg ttgatgagcg ggggttgtat aaatctctta aaggcgcctg taagctgaaa | 960 |
| ctctgtggcg tactggggct gcgcctgatg gacggcacat gggtggctat gcagacaagc | 1020 |
| aatgaaacaa agtggtgtcc ccctggtcag ctggttaatc tgcacgactt taggtctgac | 1080 |
| gaaatcgagc accttgtggt ggaggaactg gtgaagaaac gcgaagagtg cctggacgca | 1140 |
| cttgagagta ttatgaccac caaatccgtt tccttcagaa gactgagcca cctgcgaaag | 1200 |
| ctggtgccag ggttcgggaa ggcttatact attttcaaca agactcttat ggaggcggat | 1260 |
| gcccattata agtcagttag gacttggaat gagataattc cctccaaagg atgtctgaga | 1320 |
| gtcggtggga gatgccaccc ccatgtcaat ggggtgttct ttaacggaat catcctggga | 1380 |
| cctgacggga acgtgctgat tcccgagatg caatcttccc ttctgcagca acacatggaa | 1440 |
| ctcctggtgt cttcagtgat accctgatg cacccactgg ccgaccccag cactgtgttc | 1500 |
| aaaaatggcg atgaggccga agactttgtg gaagttcacc tgcccgatgt acacgaaagg | 1560 |
| atatctggag tagacctggg ccttcctaat tggggtaagt acgtgctcct gagtgcgggt | 1620 |
| gccttgaccg ctttgatgct gatcattttt ctgatgacct gctggcggag ggtgaatcgc | 1680 |
| tccgagccga cacagcacaa tctcagaggg acaggccggg aagtaagtgt gactccgcaa | 1740 |
| tctggcaaga ttattagtag ttgggagagt tacaagtctg gaggagagac tgggttgaat | 1800 |
| tttgatctgc tcaaacttgc aggcgatgta gaatcaaatc ctggacccgc ccgggacagg | 1860 |
| tccatagctc tcacgtttct cgcagttgga ggagttctgc tcttcctctc cgtgaacgtg | 1920 |
| cacgctgaca ctgggtgtgc catagacatc agccggcaag agctgagatg tggaagtgga | 1980 |
| gtgttcatac acaatgatgt | 2000 |

<210> SEQ ID NO 60
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 60

| | |
|---|---|
| tcatcaagcg gacacactcg actgtttgaa tcatcacaaa cactcctaat tgttgttaat | 60 |
| tgtgtcacgc tcgacaaaga atcgtgcttc tagagctaca gattctttgg tcctcccggg | 120 |
| ccgttctcgg cccgacagat aaacgatttt gcgccttacg gggcgcacaa caggaactaa | 180 |
| cctgaattcg ttttcttcgc tcccccgttc tgaccatatc gacactagca aggagtccga | 240 |
| gaaaacaaac atgggaacga ccataaaggg gaaacgaaac catttaaagg atagatatgg | 300 |
| tagggactat tcgagcccgg aacctcaggg taactataag tggtaaactc gacgggtttg | 360 |
| ttggagcagc aactcctact tcccacgtga ttagaaagac ctaaaaggat gtacctcaac | 420 |
| tttcacccga tataaagtcg gtaattctac ttgccgaaat gaacatgtcc tcagcactgg | 480 |
| cttcggctct gtatatgttt aaagcaccct atgcagtggt ggtggaagtt ctcttttgtg | 540 |
| aaggcgggtt gcggactgcg aacagcccgg cgaatgttga ccttctaccg tcctctagga | 600 |
| gctatacttc ttagagacgt gttgggcata ggactaatgg taaccgacgc ctgtcagttc | 660 |

```
tgatggttcc tctcagacca gtaatatagt ggttcgcacc ggctagaact aggaatacta    720
tctagggacg tgtcatccca aaaaggaccg cccttaacat cgccacaacg tcatagttca    780
tggatgacga ggtgattggt gctgatgtga tatacctacg gactcttggg agctgagcca    840
tactcaacgc tgtaaaaatg cttgagtgcc ccgttcgccc gtagattccc cagactttgt    900
acgcccaaac aactactcgc ccccaacata tttagagaat tccgcggac  attcgacttt    960
gagacaccgc atgaccccga cgcggactac ctgccgtgta ccaccgata  cgtctgttcg   1020
ttactttgtt tcaccacagg gggaccagtc gaccaattag acgtgctgaa atccagactg   1080
ctttagctcg tggaacacca cctccttgac cacttctttg cgcttctcac ggacctgcgt   1140
gaactctcat aatactggtg gtttaggcaa aggaagtctt ctgactcggt ggacgctttc   1200
gaccacggtc ccaagccctt ccgaatatga taaaagttgt tctgagaata cctccgccta   1260
cgggtaatat tcagtcaatc ctgaacctta ctctattaag ggaggtttcc tacagactct   1320
cagccaccct ctacggtggg ggtacagtta ccccacaaga aattgcctta gtaggaccct   1380
ggactgccct tgcacgacta agggctctac gttagaaggg aagacgtcgt tgtgtacctt   1440
gaggaccaca gaagtcacta tggggactac gtgggtgacc ggctggggtc gtgacacaag   1500
ttttaccgc  tactccggct tctgaaacac cttcaagtgg acgggctaca tgtgctttcc   1560
tatagacctc atctggaccc ggaaggatta accccattca tgcacgagga ctcacgccca   1620
cggaactggc gaaactacga ctagtaaaaa gactactgga cgaccgcctc ccacttagcg   1680
aggctcggct gtgtcgtgtt agagtctccc tgtccggccc ttcattcaca ctgaggcgtt   1740
agaccgttct aataatcatc aaccctctca atgttcagac ctcctctctg acccaactta   1800
aaactagacg agtttgaacg tccgctacat cttagtttag gacctgggcg ggccctgtcc   1860
aggtatcgag agtgcaaaga gcgtcaacct cctcaagacg agaaggagag gcacttgcac   1920
gtgcgactgt gacccacacg gtatctgtag tcggccgttc tcgactctac accttcacct   1980
cacaagtatg tgttactaca                                               2000
```

<210> SEQ ID NO 61
<211> LENGTH: 1303
<212> TYPE: PRT
<213> ORGANISM: Artificial Sequence
<220> FEATURE:
<223> OTHER INFORMATION: Synthetic Construct

<400> SEQUENCE: 61

Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Gln
            20                  25                  30

Lys Lys Arg Gly Gly Lys Thr Gly Ile Ala Val Ile Val Pro Gln Ala
        35                  40                  45

Leu Leu Phe Val Pro Leu Leu Val Phe Pro Leu Cys Phe Gly Lys Phe
    50                  55                  60

Pro Ile Tyr Thr Ile Pro Asp Lys Leu Gly Pro Trp Ser Pro Ile Asp
65                  70                  75                  80

Ile His His Leu Ser Cys Pro Asn Asn Leu Val Val Glu Asp Glu Gly
                85                  90                  95

Cys Thr Asn Leu Ser Gly Phe Ser Tyr Met Glu Leu Lys Val Gly Tyr
            100                 105                 110

Ile Ser Ala Ile Lys Met Asn Gly Phe Thr Cys Thr Gly Val Val Thr

-continued

```
            115                 120                 125
Glu Ala Glu Thr Tyr Thr Asn Phe Val Gly Tyr Val Thr Thr Thr Phe
            130                 135                 140
Lys Arg Lys His Phe Arg Pro Thr Pro Asp Ala Cys Arg Ala Ala Tyr
145                 150                 155                 160
Asn Trp Lys Met Ala Gly Asp Pro Arg Tyr Glu Glu Ser Leu His Asn
                    165                 170                 175
Pro Tyr Pro Asp Tyr His Trp Leu Arg Thr Val Lys Thr Thr Lys Glu
                180                 185                 190
Ser Leu Val Ile Ile Ser Pro Val Ala Asp Leu Asp Pro Tyr Asp
            195                 200                 205
Arg Ser Leu His Ser Arg Val Phe Pro Gly Gly Asn Cys Ser Gly Val
210                 215                 220
Ala Val Ser Ser Thr Tyr Cys Ser Thr Asn His Asp Tyr Thr Ile Trp
225                 230                 235                 240
Met Pro Glu Asn Pro Arg Leu Gly Met Ser Cys Asp Ile Phe Thr Asn
                245                 250                 255
Ser Arg Gly Lys Arg Ala Ser Lys Gly Ser Glu Thr Cys Gly Phe Val
                260                 265                 270
Asp Glu Arg Gly Leu Tyr Lys Ser Leu Lys Gly Ala Cys Lys Leu Lys
            275                 280                 285
Leu Cys Gly Val Leu Gly Leu Arg Leu Met Asp Gly Thr Trp Val Ala
290                 295                 300
Met Gln Thr Ser Asn Glu Thr Lys Trp Cys Pro Pro Gly Gln Leu Val
305                 310                 315                 320
Asn Leu His Asp Phe Arg Ser Asp Glu Ile Glu His Leu Val Val Glu
                325                 330                 335
Glu Leu Val Lys Lys Arg Glu Glu Cys Leu Asp Ala Leu Glu Ser Ile
                340                 345                 350
Met Thr Thr Lys Ser Val Ser Phe Arg Arg Leu Ser His Leu Arg Lys
            355                 360                 365
Leu Val Pro Gly Phe Gly Lys Ala Tyr Thr Ile Phe Asn Lys Thr Leu
370                 375                 380
Met Glu Ala Asp Ala His Tyr Lys Ser Val Arg Thr Trp Asn Glu Ile
385                 390                 395                 400
Ile Pro Ser Lys Gly Cys Leu Arg Val Gly Gly Arg Cys His Pro His
                405                 410                 415
Val Asn Gly Val Phe Phe Asn Gly Ile Ile Leu Gly Pro Asp Gly Asn
                420                 425                 430
Val Leu Ile Pro Glu Met Gln Ser Ser Leu Leu Gln Gln His Met Glu
            435                 440                 445
Leu Leu Val Ser Ser Val Ile Pro Leu Met His Pro Leu Ala Asp Pro
450                 455                 460
Ser Thr Val Phe Lys Asn Gly Asp Glu Ala Glu Asp Phe Val Glu Val
465                 470                 475                 480
His Leu Pro Asp Val His Glu Arg Ile Ser Gly Val Asp Leu Gly Leu
                485                 490                 495
Pro Asn Trp Gly Lys Tyr Val Leu Ser Ala Gly Ala Leu Thr Ala
                500                 505                 510
Leu Met Leu Ile Ile Phe Leu Met Thr Cys Trp Arg Arg Val Asn Arg
            515                 520                 525
Ser Glu Pro Thr Gln His Asn Leu Arg Gly Thr Gly Arg Glu Val Ser
530                 535                 540
```

```
Val Thr Pro Gln Ser Gly Lys Ile Ile Ser Ser Trp Glu Ser Tyr Lys
545                 550                 555                 560

Ser Gly Gly Glu Thr Gly Leu Asn Phe Asp Leu Leu Lys Leu Ala Gly
                565                 570                 575

Asp Val Glu Ser Asn Pro Gly Pro Gly Gly Lys Thr Gly Ile Ala Val
                580                 585                 590

Met Ile Gly Leu Ile Ala Cys Val Gly Ala Val Thr Leu Ser Asn Phe
                595                 600                 605

Gln Gly Lys Val Met Met Thr Val Asn Ala Thr Asp Val Thr Asp Val
610                 615                 620

Ile Thr Ile Pro Thr Ala Ala Gly Lys Asn Leu Cys Ile Val Arg Ala
625                 630                 635                 640

Met Asp Val Gly Tyr Met Cys Asp Asp Thr Ile Thr Tyr Glu Cys Pro
                645                 650                 655

Val Leu Ser Ala Gly Asn Asp Pro Glu Asp Ile Asp Cys Trp Cys Thr
                660                 665                 670

Lys Ser Ala Val Tyr Val Arg Tyr Gly Arg Cys Thr Lys Thr Arg His
                675                 680                 685

Ser Arg Arg Ser Arg Arg Ser Leu Thr Val Gln Thr His Gly Glu Ser
                690                 695                 700

Thr Leu Ala Asn Lys Lys Gly Ala Trp Met Asp Ser Thr Lys Ala Thr
705                 710                 715                 720

Arg Tyr Leu Val Lys Thr Glu Ser Trp Ile Leu Arg Asn Pro Gly Tyr
                725                 730                 735

Ala Leu Val Ala Ala Val Ile Gly Trp Met Leu Gly Ser Asn Thr Met
                740                 745                 750

Gln Arg Val Val Phe Val Leu Leu Leu Leu Val Ala Pro Ala Tyr
                755                 760                 765

Ser Phe Asn Cys Leu Gly Met Ser Asn Arg Asp Phe Leu Glu Gly Val
                770                 775                 780

Ser Gly Ala Thr Trp Val Asp Leu Val Leu Glu Gly Asp Ser Cys Val
785                 790                 795                 800

Thr Ile Met Ser Lys Asp Lys Pro Thr Ile Asp Val Lys Met Met Asn
                805                 810                 815

Met Glu Ala Ala Asn Leu Ala Glu Val Arg Ser Tyr Cys Tyr Leu Ala
                820                 825                 830

Thr Val Ser Asp Leu Ser Thr Lys Ala Ala Cys Pro Ala Met Gly Glu
                835                 840                 845

Ala His Asn Asp Lys Arg Ala Asp Pro Ala Phe Val Cys Arg Gln Gly
                850                 855                 860

Val Val Asp Arg Gly Trp Gly Asn Gly Cys Gly Leu Phe Gly Lys Gly
865                 870                 875                 880

Ser Ile Asp Thr Cys Ala Lys Phe Ala Cys Ser Thr Lys Ala Ile Gly
                885                 890                 895

Arg Thr Ile Leu Lys Glu Asn Ile Lys Tyr Glu Val Ala Ile Phe Val
                900                 905                 910

His Gly Pro Thr Thr Val Glu Ser His Gly Asn Tyr Ser Thr Gln Val
                915                 920                 925

Gly Ala Thr Gln Ala Gly Arg Phe Ser Ile Thr Pro Ala Ala Pro Ser
                930                 935                 940

Tyr Thr Leu Lys Leu Gly Glu Tyr Gly Glu Val Thr Val Asp Cys Glu
945                 950                 955                 960
```

Pro Arg Ser Gly Ile Asp Thr Asn Ala Tyr Tyr Val Met Thr Val Gly
              965                 970                 975

Thr Lys Thr Phe Leu Val His Arg Glu Trp Phe Met Asp Leu Asn Leu
        980                 985                 990

Pro Trp Ser Ser Ala Gly Ser Thr Val Trp Arg Asn Arg Glu Thr Leu
            995                1000                1005

Met Glu Phe Glu Glu Pro His Ala Thr Lys Gln Ser Val Ile Ala
    1010                1015                1020

Leu Gly Ser Gln Glu Gly Ala Leu His Gln Ala Leu Ala Gly Ala
    1025                1030                1035

Ile Pro Val Glu Phe Ser Ser Asn Thr Val Lys Leu Thr Ser Gly
    1040                1045                1050

His Leu Lys Cys Arg Val Lys Met Glu Lys Leu Gln Leu Lys Gly
    1055                1060                1065

Thr Thr Tyr Gly Val Cys Ser Lys Ala Phe Lys Phe Leu Gly Thr
    1070                1075                1080

Pro Ala Asp Thr Gly His Gly Thr Val Val Leu Glu Leu Gln Tyr
    1085                1090                1095

Thr Gly Thr Asp Gly Pro Cys Lys Val Pro Ile Ser Ser Val Ala
    1100                1105                1110

Ser Leu Asn Asp Leu Thr Pro Val Gly Arg Leu Val Thr Val Asn
    1115                1120                1125

Pro Phe Val Ser Val Ala Thr Ala Asn Ala Lys Val Leu Ile Glu
    1130                1135                1140

Leu Glu Pro Pro Phe Gly Asp Ser Tyr Ile Val Val Gly Arg Gly
    1145                1150                1155

Glu Gln Gln Ile Asn His His Trp His Lys Ser Gly Ser Ser Ile
    1160                1165                1170

Gly Lys Ala Phe Thr Thr Thr Leu Lys Gly Ala Gln Arg Leu Ala
    1175                1180                1185

Ala Leu Gly Asp Thr Ala Trp Asp Phe Gly Ser Val Gly Gly Val
    1190                1195                1200

Phe Thr Ser Val Gly Lys Ala Val His Gln Val Phe Gly Gly Ala
    1205                1210                1215

Phe Arg Ser Leu Phe Gly Gly Met Ser Trp Ile Thr Gln Gly Leu
    1220                1225                1230

Leu Gly Ala Leu Leu Leu Trp Met Gly Ile Asn Ala Arg Asp Arg
    1235                1240                1245

Ser Ile Ala Leu Thr Phe Leu Ala Val Gly Gly Val Leu Leu Phe
    1250                1255                1260

Leu Ser Val Asn Val Glu His Ala Asp Thr Gly Cys Ala Ile Asp
    1265                1270                1275

Ile Ser Arg Gln Glu Leu Arg Cys Gly Ser Gly Val Phe Ile His
    1280                1285                1290

Asn Asp Val Glu Ala Trp Met Asp Arg Tyr
    1295                1300

<210> SEQ ID NO 62
<211> LENGTH: 4000
<212> TYPE: DNA
<213> ORGANISM: Artificial Sequence
<220> FEATURE:
<223> OTHER INFORMATION: Synthetic Construct

<400> SEQUENCE: 62

```
agtagttcgc ctgtgtgagc tgacaaactt agtagtgttt gtgaggatta acaacaatta      60
acacagtgcg agctgtttct tagcacgaag atctcgatgt ctaagaaacc aggagggccc     120
ggcaagagcc gggctgtcaa tatgctaaaa cgcggaatgc cccgcgtgtt gtccttgatt     180
ggacttaagc aaaagaagcg aggggggcaag actggtatag ctgtgatcgt tcctcaggct     240
cttttgtttg taccettget ggtatttccc ctttgetttg gtaaatttcc tatctatacc     300
atccctgata agctcgggcc ttggagtccc attgatattc accatttgag ctgcccaaac     360
aacctcgtcg ttgaggatga agggtgcact aatctttctg gatttttccta catggagttg    420 aaagtgggct atatttcagc cattaagatg aacggcttta cttgtacagg agtcgtgacc     480
gaagccgaga catatacaaa tttcgtggga tacgtcacca ccaccttcaa gagaaaacac    540
ttccgcccaa cgcctgacgc ttgtcggggcc gcttacaact ggaagatggc aggagatcct   600
cgatatgaag aatctctgca caacccgtat cctgattacc attggctgcg acagtcaag     660 actaccaagg agagtctggt cattatatca ccaagcgtgg ccgatcttga tccttatgat    720
agatccctgc acagtagggt ttttcctggc gggaattgta gcggtgttgc agtatcaagt    780
acctactgct ccactaacca cgactacact atatggatgc ctgagaaccc tcgactcggt    840
atgagttgcg acattttac gaactcacgg ggcaagcggg catctaaggg gtctgaaaca    900
tgcgggtttg ttgatgagcg ggggttgtat aaatctctta aaggcgcctg taagctgaaa   960
ctctgtggcg tactggggct cgcctgatg acggcacat gggtggctat gcagacaagc    1020
aatgaaacaa agtggtgtcc ccctggtcag ctggttaatc tgcacgactt taggtctgac  1080
gaaatcgagc accttgtggt ggaggaactg gtgaagaaac gcgaagagtg cctggacgca  1140
cttgagagta ttatgaccac caaatccgtt tccttcagaa gactgagcca cctgcgaaag  1200
ctggtgccag ggttcgggaa ggcttatact attttcaaca agactcttat ggaggcggat  1260
gcccattata agtcagttag acttggaat gagataattc cctccaaagg atgtctgaga   1320
gtcggtggga gatgccaccc ccatgtcaat ggggtgttct ttaacggaat catcctggga   1380
cctgacggga acgtgctgat tcccgagatg caatcttccc ttctgcagca acacatggaa   1440
ctcctggtgt cttcagtgat acccctgatg cacccactgg ccgacccag cactgtgttc   1500 aaaaatggcg atgaggccga agactttgtg gaagttcacc tgcccgatgt acacgaaagg   1560
atatctggag tagacctggg ccttcctaat tggggtaagt acgtgctcct gagtgcgggt   1620
gccttgaccg cttttgatgct gatcattttt ctgatgacct gctggcggag ggtgaatcgc   1680
tccgagccga cacagcacaa tctcagaggg acaggccggg aagtaagtgt gactccgcaa   1740
tctggcaaga ttattagtag ttgggagagt tacaagtctg gaggagagac tgggttgaat   1800
tttgatctgc tcaaacttgc aggcgatgta gaatcaaatc ctggacccgg aggaaagacc   1860
ggtattgcag tcatgattgg cctgatcgcc tgcgtaggag cagttaccct ctctaacttc   1920
caagggaagg tgatgatgac ggtaaatgct actgacgtca cagatgtcat cacgattcca   1980
acagctgctg gaaagaacct atgcattgtc agagcaatgg atgtgggata catgtgcgat   2040
gatactatca cttatgaatg cccagtgctg tcggctggta atgatccaga agacatcgac   2100
tgttggtgca caaagtcagc agtctacgtc aggtatggaa gatgcaccaa gacacgccac   2160
tcaagacgca gtcggaggtc actgacagtg cagacacacg agaaagcac tctagcgaac   2220 aagaaggggg cttggatgga cagcaccaag gccacaaggt atttggtaaa aacagaatca   2280
tggatcttga ggaaccctgg atatgccctg gtggcagccg tcattggttg gatgcttggg   2340
agcaacacca tgcagagagt tgtgtttgtc gtgctattgc ttttggtggc cccagcttac   2400
```

```
agctttaact gccttggaat gagcaacaga gacttcttgg aaggagtgtc tggagcaaca    2460
tgggtggatt tggttctcga aggcgacagc tgcgtgacta tcatgtctaa ggacaagcct    2520
accatcgatg tgaagatgat gaatatggag gcggccaacc tggcagaggt ccgcagttat    2580
tgctatttgg ctaccgtcag cgatctctcc accaaagctg cgtgcccggc catgggagaa    2640
gctcacaatg acaaacgtgc tgacccagct tttgtgtgca gacaaggagt ggtggacagg    2700
ggctggggca acggctgcgg actatttggc aaaggaagca ttgacacatg cgccaaattt    2760
gcctgctcta ccaaggcaat aggaagaacc attttgaaag agaatatcaa gtacgaagtg    2820 gccattttg tccatggacc aactactgtg gagtcgcacg gaaactactc cacacaggtt    2880
ggagccactc aggcagggag attcagcatc actcctgcgg cgccttcata cacactaaag    2940
cttggagaat atggagaggt gacagtggac tgtgaaccac ggtcagggat tgacaccaat    3000
gcatactacg tgatgactgt tggaacaaag acgttcttgg tccatcgtga gtggttcatg    3060
gacctcaacc tcccttggag cagtgctgga agtactgtgt ggaggaacag agagacgtta    3120
atggagtttg aggaaccaca cgccacgaag cagtctgtga tagcattggg ctcacaagag    3180
ggagctctgc atcaagcttt ggctggagcc attcctgtgg aattttcaag caacactgtc    3240
aagttgacgt cgggtcattt gaagtgtaga gtgaagatgg aaaaattgca gttgaaggga    3300
acaacctatg gcgtctgttc aaaggctttc aagtttcttg ggactcccgc agacacaggt    3360
cacggcactg tggtgttgga attgcagtac actggcacgg atggaccttg caaagttcct    3420
atctcgtcag tggcttcatt gaacgaccta acgccagtgg gcagattggt cactgtcaac    3480 cctttgttt cagtggccac ggccaacgct aaggtcctga ttgaattgga accacccttt    3540
ggagactcat acatagtggt gggcagagga gaacaacaga tcaatcacca ctggcacaag    3600
tctggaagca gcattggcaa agcctttaca accaccctca aaggagcgca gagactagcc    3660
gctctaggag acacagcttg ggactttgga tcagttggag gggtgttcac ctcagttggg    3720
aaggctgtcc atcaagtgtt cggaggagca ttccgctcac tgttcggagg catgtcctgg    3780
ataacgcaag gattgctggg ggctctcctg ttgtggatgg gcatcaatgc tcgtgacagg    3840
tccatagctc tcacgtttct cgcagttgga ggagttctgc tcttcctctc cgtgaacgtg    3900
cacgctgaca ctgggtgtgc catagacatc agccggcaag agctgagatg tggaagtgga    3960
gtgttcatac acaatgatgt ggaggcttgg atggaccggt                          4000
```

<210> SEQ ID NO 63
<211> LENGTH: 4000
<212> TYPE: DNA
<213> ORGANISM: Artificial Sequence
<220> FEATURE:
<223> OTHER INFORMATION: Synthetic Construct

<400> SEQUENCE: 63

```
tcatcaagcg acacactcg actgtttgaa tcatcacaaa cactcctaat tgttgttaat      60
tgtgtcacgc tcgacaaaga atcgtgcttc tagagctaca gattctttgg tcctcccggg    120
ccgttctcgg cccgacagtt atacgatttt gcgccttacg gggcgcacaa caggaactaa    180
cctgaattcg ttttcttcgc tccccgttc tgaccatatc gacactagca aggagtccga    240
gaaaacaaac atgggaacga ccataaaggg gaaacgaaac catttaaagg atagatatgg    300
tagggactat tcgagcccgg aacctcaggg taactataag tggtaaactc gacgggtttg    360
ttggagcagc aactcctact tcccacgtga ttagaaagac ctaaaaggat gtacctcaac    420
```

-continued

| | | |
|---|---|---|
| tttcacccga tataaagtcg gtaattctac ttgccgaaat gaacatgtcc tcagcactgg | 480 |
| cttcggctct gtatatgttt aaagcaccct atgcagtggt ggtggaagtt ctcttttgtg | 540 |
| aaggcgggtt gcggactgcg aacagcccgg cgaatgttga ccttctaccg tcctctagga | 600 |
| gctatacttc ttagagacgt gttgggcata ggactaatgg taaccgacgc ctgtcagttc | 660 |
| tgatggttcc tctcagacca gtaatatagt ggttcgcacc ggctagaact aggaatacta | 720 |
| tctagggacg tgtcatccca aaaaggaccg cccttaacat cgccacaacg tcatagttca | 780 |
| tggatgacga ggtgattggt gctgatgtga tatacctacg gactcttggg agctgagcca | 840 |
| tactcaacgc tgtaaaaatg cttgagtgcc ccgttcgccc gtagattccc cagactttgt | 900 |
| acgcccaaac aactactcgc ccccaacata tttagagaat ttccgcggac attcgacttt | 960 |
| gagacaccgc atgaccccga cgcggactac ctgccgtgta cccaccgata cgtctgttcg | 1020 |
| ttactttgtt tcaccacagg gggaccagtc gaccaattag acgtgctgaa atccagactg | 1080 |
| ctttagctcg tggaacacca cctccttgac cacttctttg cgcttctcac ggacctgcgt | 1140 |
| gaactctcat aatactggtg gtttaggcaa aggaagtctt ctgactcggt ggacgctttc | 1200 |
| gaccacggtc ccaagccctt ccgaatatga taaaagttgt tctgagaata cctccgccta | 1260 |
| cgggtaatat tcagtcaatc ctgaaccttu ctctattaag ggaggtttcc tacagactct | 1320 |
| cagccaccct ctacggtggg ggtacagtta ccccacaaga aattgcctta gtaggaccct | 1380 |
| ggactgccct tgcacgacta agggctctac gttagaaggg aagacgtcgt tgtgtacctt | 1440 |
| gaggaccaca gaagtcacta tggggactac gtgggtgacc ggctgggggc gtgacacaag | 1500 |
| tttttaccgc tactccggct tctgaaacac cttcaagtgg acgggctaca tgtgctttcc | 1560 |
| tatagacctc atctggaccc ggaaggatta accccattca tgcacgagga ctcacgccca | 1620 |
| cggaactggc gaaactacga ctagtaaaaa gactactgga cgaccgcctc ccacttagcg | 1680 |
| aggctcggct gtgtcgtgtt agagtctccc tgtccggccc ttcattcaca ctgaggcgtt | 1740 |
| agaccgttct aataatcatc aaccctctca atgttcagac ctcctctctg acccaactta | 1800 |
| aaactagacg agtttgaacg tccgctacat cttagtttag gacctgggcc tcctttctgg | 1860 |
| ccataacgtc agtactaacc ggactagcgg acgcatcctc gtcaatggga gagattgaag | 1920 |
| gttcccttcc actactactg ccatttacga tgactgcagt gtctacagta gtgctaaggt | 1980 |
| tgtcgacgac ctttcttgga tacgtaacag tctcgttacc tacaccctat gtacacgcta | 2040 |
| ctatgatagt gaatacttac gggtcacgac agccgaccat tactaggtct tctgtagctg | 2100 |
| acaaccacgt gtttcagtcg tcagatgcag tccataccttc ctacgtggtt ctgtgcggtg | 2160 |
| agttctgcgt cagcctccag tgactgtcac gtctgtgtgc ctctttcgtg agatcgcttg | 2220 |
| ttcttccccc gaacctacct gtcgtggttc cggtgttcca taaaccatttt ttgtcttagt | 2280 |
| acctagaact ccttgggacc tatacgggac caccgtcggc agtaaccaac ctacgaaccc | 2340 |
| tcgttgtggt acgtctctca acacaaacag cacgataacg aaaaccaccg gggtcgaatg | 2400 |
| tcgaaattga cggaacctta ctcgttgtct ctgaagaacc ttcctcacag acctcgttgt | 2460 |
| acccacctaa accaagagct tccgctgtcg acgcactgat agtacagatt cctgttcgga | 2520 |
| tggtagctac acttctacta cttataccctc cgccggttgg accgtctcca ggcgtcaata | 2580 |
| acgataaacc gatggcagtc gctagagagg tggtttcgac gcacgggccg gtaccctctt | 2640 |
| cgagtgttac tgtttgcacg actgggtcga aacacacgt ctgttcctca ccacctgtcc | 2700 |
| ccgacccccgt tgccgacgcc tgataaaccg tttccttcgt aactgtgtac gcggtttaaa | 2760 |
| cggacgagat ggttccgtta tccttcttgg taaaactttc tcttatagtt catgcttcac | 2820 |

-continued

```
cggtaaaaac aggtacctgg ttgatgacac ctcagcgtgc ctttgatgag gtgtgtccaa    2880
cctcggtgag tccgtccctc taagtcgtag tgaggacgcc gcggaagtat gtgtgatttc    2940
gaacctctta tacctctcca ctgtcacctg acacttggtg ccagtcccta actgtggtta    3000
cgtatgatgc actactgaca accttgtttc tgcaagaacc aggtagcact caccaagtac    3060
ctggagttgg agggaacctc gtcacgacct tcatgacaca cctccttgtc tctctgcaat    3120
tacctcaaac tccttggtgt gcggtgcttc gtcagacact atcgtaaccc gagtgttctc    3180
cctcgagacg tagttcgaaa ccgacctcgg taaggacacc ttaaaagttc gttgtgacag    3240
ttcaactgca gcccagtaaa cttcacatct cacttctacc tttttaacgt caacttccct    3300
tgttggatac cgcagacaag tttccgaaag ttcaagaaac cctgagggcg tctgtgtcca    3360
gtgccgtgac accacaacct taacgtcatg tgaccgtgcc tacctggaac gtttcaagga    3420
tagagcagtc accgaagtaa cttgctggat tgcggtcacc cgtctaacca gtgacagttg    3480
ggaaaacaaa gtcaccggtg ccggttgcga ttccaggact aacttaacct tggtgggaaa    3540
cctctgagta tgtatcacca cccgtctcct cttgttgtct agttagtggt gaccgtgttc    3600
agaccttcgt cgtaaccgtt tcggaaatgt tggtgggagt ttcctcgcgt ctctgatcgg    3660
cgagatcctc tgtgtcgaac cctgaaacct agtcaacctc cccacaagtg gagtcaaccc    3720
ttccgacagg tagttcacaa gcctcctcgt aaggcgagtg acaagcctcc gtacaggacc    3780
tattgcgttc ctaacgaccc ccgagaggac aacacctacc cgtagttacg agcactgtcc    3840
aggtatcgag agtgcaaaga gcgtcaacct cctcaagacg agaaggagag gcacttgcac    3900
gtgcgactgt gacccacacg gtatctgtag tcggccgttc tcgactctac accttcacct    3960
cacaagtatg tgttactaca cctccgaacc tacctggcca                          4000
```

<210> SEQ ID NO 64
<211> LENGTH: 702
<212> TYPE: PRT
<213> ORGANISM: Artificial Sequence
<220> FEATURE:
<223> OTHER INFORMATION: Synthetic Construct

<400> SEQUENCE: 64

```
Met Ser Lys Lys Pro Gly Gly Pro Gly Lys Ser Arg Ala Val Tyr Leu
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Gly Ile Ala
            100                 105                 110

Val Ile Val Pro Gln Ala Leu Leu Phe Val Pro Leu Val Phe Pro
        115                 120                 125

Leu Cys Phe Gly Lys Phe Pro Ile Tyr Thr Ile Pro Asp Lys Leu Gly
    130                 135                 140

Pro Trp Ser Pro Ile Asp Ile His His Leu Ser Cys Pro Asn Asn Leu
```

```
            145                 150                 155                 160
Val Val Glu Asp Glu Gly Cys Thr Asn Leu Ser Gly Phe Ser Tyr Met
                165                 170                 175
Glu Leu Lys Val Gly Tyr Ile Ser Ala Ile Lys Met Asn Gly Phe Thr
                180                 185                 190
Cys Thr Gly Val Val Thr Glu Ala Glu Thr Tyr Thr Asn Phe Val Gly
                195                 200                 205
Tyr Val Thr Thr Thr Phe Lys Arg Lys His Phe Arg Pro Thr Pro Asp
            210                 215                 220
Ala Cys Arg Ala Ala Tyr Asn Trp Lys Met Ala Gly Asp Pro Arg Tyr
225                 230                 235                 240
Glu Glu Ser Leu His Asn Pro Tyr Pro Asp Tyr His Trp Leu Arg Thr
                245                 250                 255
Val Lys Thr Thr Lys Glu Ser Leu Val Ile Ile Ser Pro Ser Val Ala
                260                 265                 270
Asp Leu Asp Pro Tyr Asp Arg Ser Leu His Ser Arg Val Phe Pro Gly
                275                 280                 285
Gly Asn Cys Ser Gly Val Ala Val Ser Ser Thr Tyr Cys Ser Thr Asn
            290                 295                 300
His Asp Tyr Thr Ile Trp Met Pro Glu Asn Pro Arg Leu Gly Met Ser
305                 310                 315                 320
Cys Asp Ile Phe Thr Asn Ser Arg Gly Lys Arg Ala Ser Lys Gly Ser
                325                 330                 335
Glu Thr Cys Gly Phe Val Asp Glu Arg Gly Leu Tyr Lys Ser Leu Lys
                340                 345                 350
Gly Ala Cys Lys Leu Lys Leu Cys Gly Val Leu Gly Leu Arg Leu Met
                355                 360                 365
Asp Gly Thr Trp Val Ala Met Gln Thr Ser Asn Glu Thr Lys Trp Cys
            370                 375                 380
Pro Pro Gly Gln Leu Val Asn Leu His Asp Phe Arg Ser Asp Glu Ile
385                 390                 395                 400
Glu His Leu Val Val Glu Leu Val Lys Lys Arg Glu Glu Cys Leu
                405                 410                 415
Asp Ala Leu Glu Ser Ile Met Thr Thr Lys Ser Val Ser Phe Arg Arg
                420                 425                 430
Leu Ser His Leu Arg Lys Leu Val Pro Gly Phe Gly Lys Ala Tyr Thr
                435                 440                 445
Ile Phe Asn Lys Thr Leu Met Glu Ala Asp Ala His Tyr Lys Ser Val
            450                 455                 460
Arg Thr Trp Asn Glu Ile Ile Pro Ser Lys Gly Cys Leu Arg Val Gly
465                 470                 475                 480
Gly Arg Cys His Pro His Val Asn Gly Val Phe Phe Asn Gly Ile Ile
                485                 490                 495
Leu Gly Pro Asp Gly Asn Val Leu Ile Pro Glu Met Gln Ser Ser Leu
                500                 505                 510
Leu Gln Gln His Met Glu Leu Leu Val Ser Ser Val Ile Pro Leu Met
                515                 520                 525
His Pro Leu Ala Asp Pro Ser Thr Val Phe Lys Asn Gly Asp Glu Ala
                530                 535                 540
Glu Asp Phe Val Glu Val His Leu Pro Asp Val His Glu Arg Ile Ser
545                 550                 555                 560
Gly Val Asp Leu Gly Leu Pro Asn Trp Gly Lys Tyr Val Leu Leu Ser
                565                 570                 575
```

```
Ala Gly Ala Leu Thr Ala Leu Met Leu Ile Ile Phe Leu Met Thr Cys
            580                 585                 590

Trp Arg Arg Val Asn Arg Ser Glu Pro Thr Gln His Asn Leu Arg Gly
        595                 600                 605

Thr Gly Arg Glu Val Ser Val Thr Pro Gln Ser Gly Lys Ile Ile Ser
    610                 615                 620

Ser Trp Glu Ser Tyr Lys Ser Gly Glu Thr Gly Leu Asn Phe Asp
625                 630                 635                 640

Leu Leu Lys Leu Ala Gly Asp Val Glu Ser Asn Pro Gly Pro Ala Arg
                645                 650                 655

Asp Arg Ser Ile Ala Leu Thr Phe Leu Ala Val Gly Gly Val Leu Leu
            660                 665                 670

Phe Leu Ser Val Asn Val His Ala Asp Thr Gly Cys Ala Ile Asp Ile
        675                 680                 685

Ser Arg Gln Glu Leu Arg Cys Gly Ser Gly Val Phe Ile His
    690                 695                 700
```

<210> SEQ ID NO 65
<211> LENGTH: 2200
<212> TYPE: DNA
<213> ORGANISM: Artificial Sequence
<220> FEATURE:
<223> OTHER INFORMATION: Synthetic Construct

<400> SEQUENCE: 65

```
agtagttcgc ctgtgtgagc tgacaaactt agtagtgttt gtgaggatta acaacaatta      60
acacagtgcg agctgtttct tagcacgaag atctcgatgt ctaagaaacc aggagggccc     120
ggcaagagcc gggctgtcta tttgctaaaa cgcggaatgc cccgcgtgtt gtccttgatt     180
ggacttaaga gggctatgtt gagcctgatc gacggcaagg ggccaatacg atttgtgttg     240
gctctcttgg cgttcttcag gttcacagca attgctccga cccgagcagt gctggatcga     300
tggagaggtg tgaacaaaca aacagcgatg aaacaccttc tgagtttcaa gaaggaacta     360
gggaccttga ccagtgctat caatcggcgg agctcaaagc aaaagaagcg agggggcaag     420
actggtatag ctgtgatcgt tcctcaggct cttttgtttg tacccttgct ggtatttccc     480
ctttgctttg gtaaatttcc tatctatacc atccctgata agctcgggcc ttggagtccc     540
attgatattc accatttgag ctgcccaaac aacctcgtcg ttgaggatga agggtgcact     600
aatctttctg gattttccta catggagttg aaagtgggct atatttcagc cattaagatg     660
aacggcttta cttgtacagg agtcgtgacc gaagccgaga catatacaaa tttcgtggga     720
tacgtcacca ccaccttcaa gagaaaacac ttccgcccaa cgcctgacgc ttgtcgggcc     780
gcttacaact ggaagatggc aggagatcct cgatatgaag aatctctgca caacccgtat     840
cctgattacc attggctgcg gacagtcaag actaccaagg agagtctggt cattatatca     900
ccaagcgtgg ccgatcttga tccttatgat agatccctgc acagtagggt ttttcctggc     960
gggaattgta gcggtgttgc agtatcaagt acctactgct ccactaacca cgactacact    1020
atatggatgc ctgagaaccc tcgactcggt atgagttgcg acatttttac gaactcacgg    1080
ggcaagcggg catctaaggg gtctgaaaca tgcgggtttg ttgatgagcg ggggttgtat    1140
aaatctctta aggcgcctg taagctgaaa ctctgtggcg tactggggct cgcctgatg     1200
gacggcacat gggtggctat gcagacaagc aatgaaacaa gtggtgtcc ccctggtcag     1260
ctggttaatc tgcacgactt taggtctgac gaaatcgagc accttgtggt ggaggaactg    1320
```

```
gtgaagaaac gcgaagagtg cctggacgca cttgagagta ttatgaccac caaatccgtt   1380
tccttcagaa gactgagcca cctgcgaaag ctggtgccag ggttcgggaa ggcttatact   1440 atttttcaaca agactcttat ggaggcggat gcccattata agtcagttag gacttggaat   1500
gagataattc cctccaaagg atgtctgaga gtcggtggga gatgccaccc ccatgtcaat   1560
ggggtgttct ttaacggaat catcctggga cctgacggga acgtgctgat tcccgagatg   1620
caatcttccc ttctgcagca acacatgaaa ctcctggtgt cttcagtgat accccctgatg   1680 cacccactgg ccgaccccag cactgtgttc aaaaatggcg atgaggccga agactttgtg   1740
gaagttcacc tgcccgatgt acacgaaagg atatctggag tagacctggg ccttcctaat   1800
tggggtaagt acgtgctcct gagtgcgggt gccttgaccg ctttgatgct gatcattttt   1860
ctgatgacct gctggcggag ggtgaatcgc tccgagccga cacagcacaa tctcagaggg   1920
acaggccggg aagtaagtgt gactccgcaa tctggcaaga ttattagtag ttgggagagt   1980
tacaagtctg gaggagagac tgggttgaat tttgatctgc tcaaacttgc aggcgatgta   2040
gaatcaaatc ctggacccgc ccgggacagg tccatagctc tcacgtttct cgcagttgga   2100
ggagttctgc tcttcctctc cgtgaacgtg cacgctgaca ctgggtgtgc catagacatc   2160
agccggcaag agctgagatg tggaagtgga gtgttcatac                         2200
```

<210> SEQ ID NO 66
<211> LENGTH: 2200
<212> TYPE: DNA
<213> ORGANISM: Artificial Sequence
<220> FEATURE:
<223> OTHER INFORMATION: Synthetic Construct

<400> SEQUENCE: 66

```
tcatcaagcg gacacactcg actgtttgaa tcatcacaaa cactcctaat tgttgttaat     60
tgtgtcacgc tcgacaaaga atcgtgcttc tagagctaca gattctttgg tcctcccggg    120
ccgttctcgg cccgacagat aaacgatttt gcgccttacg gggcgcacaa caggaactaa    180
cctgaattct cccgatacaa ctcggactag ctgccgttcc ccggttatgc taaacacaac    240
cgagagaacc gcaagaagtc caagtgtcgt taacgaggct gggctcgtca cgacctagct    300
acctctccac acttgtttgt ttgtcgctac tttgtggaag actcaaagtt cttccttgat    360
ccctggaact ggtcacgata gttagccgcc tcgagtttcg ttttcttcgc tccccgttc     420 tgaccatatc gacactagca aggagtccga gaaacaaac atgggaacga ccataaaggg     480
gaaacgaaac catttaaagg atagatatgg tagggactat tcgagcccgg aacctcaggg    540
taactataag tggtaaactc gacgggtttg ttggagcagc aactcctact tcccacgtga    600
ttagaaagac ctaaaggat gtacctcaac tttcacccga tataagtcg gtaattctac       660 ttgccgaaat gaacatgtcc tcagcactgg cttcggctct gtatatgttt aaagcaccct    720
atgcagtggt ggtggaagtt ctcttttgtg aaggcgggtt gcggactgcg aacagcccgg    780
cgaatgttga ccttctaccg tcctctagga gctatacttc ttagagacgt gttgggcata    840
ggactaatgg taaccgacgc ctgtcagttc tgatggttcc tctcagacca gtaatatagt    900
ggttcgcacc ggctagaact aggaatacta tctagggacg tgtcatccca aaaggaccg     960 cccttaacat cgccacaacg tcatagttca tggatgacga ggtgattggt gctgatgtga   1020
tatacctacg gactcttggg agctgagcca tactcaacgc tgtaaaaatg cttgagtgcc   1080
ccgttcgccc gtagattccc cagactttgt acgcccaaac aactactcgc ccccaacata   1140
tttagagaat ttccgcggac attcgacttt gagacaccgc atgaccccga cgcggactac   1200
```

```
ctgccgtgta cccaccgata cgtctgttcg ttactttgtt tcaccacagg gggaccagtc    1260
gaccaattag acgtgctgaa atccagactg ctttagctcg tggaacacca cctccttgac    1320
cacttctttg cgcttctcac ggacctgcgt gaactctcat aatactggtg gtttaggcaa    1380
aggaagtctt ctgactcggt ggacgctttc gaccacggtc ccaagccctt ccgaatatga    1440
taaaagttgt tctgagaata cctccgccta cgggtaatat tcagtcaatc ctgaacctta    1500
ctctattaag ggaggtttcc tacagactct cagccaccct ctacggtggg ggtacagtta    1560
ccccacaaga aattgcctta gtaggaccct ggactgccct tgcacgacta agggctctac    1620
gttagaaggg aagacgtcgt tgtgtacctt gaggaccaca gaagtcacta tggggactac    1680
gtgggtgacc ggctggggtc gtgacacaag tttttaccgc tactccggct tctgaaacac    1740
cttcaagtgg acgggctaca tgtgctttcc tatagacctc atctggaccc ggaaggatta    1800
accccattca tgcacgagga ctcacgccca cggaactggc gaaactacga ctagtaaaaa    1860
gactactgga cgaccgcctc ccacttagcg aggctcggct gtgtcgtgtt agagtctccc    1920
tgtccggccc ttcattcaca ctgaggcgtt agaccgttct aataatcatc aaccctctca    1980
atgttcagac ctcctctctg acccaactta aaactagacg agtttgaacg tccgctacat    2040
cttagtttag gacctgggcg ggccctgtcc aggtatcgag agtgcaaaga gcgtcaacct    2100
cctcaagacg agaaggagag gcacttgcac gtgcgactgt gacccacacg gtatctgtag    2160
tcggccgttc tcgactctac accttcacct cacaagtatg                          2200
```

<210> SEQ ID NO 67
<211> LENGTH: 868
<212> TYPE: PRT
<213> ORGANISM: Artificial Sequence
<220> FEATURE:
<223> OTHER INFORMATION: Synthetic Construct

<400> SEQUENCE: 67

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Gly Ile Ala
            100                 105                 110

Val Met Ile Gly Leu Ile Ala Ser Val Gly Ala Val Thr Leu Ser Asn
        115                 120                 125

Phe Gln Gly Lys Val Met Met Thr Val Asn Ala Thr Asp Val Thr Asp
    130                 135                 140

Val Ile Thr Ile Pro Thr Ala Ala Gly Lys Asn Leu Cys Ile Val Arg
145                 150                 155                 160

Ala Met Asp Val Gly Tyr Met Cys Asp Asp Thr Ile Thr Tyr Glu Cys
                165                 170                 175

Pro Val Leu Ser Ala Gly Asn Asp Pro Glu Asp Ile Asp Cys Trp Cys
```

```
            180                 185                 190
Thr Lys Ser Ala Val Tyr Val Arg Tyr Gly Arg Cys Thr Lys Thr Arg
            195                 200                 205
His Ser Arg Arg Ser Arg Ser Leu Thr Val Gln Thr His Gly Glu
            210                 215                 220
Ser Thr Leu Ala Asn Lys Lys Gly Ala Trp Met Asp Ser Thr Lys Ala
225                 230                 235                 240
Thr Arg Tyr Leu Val Lys Thr Glu Ser Trp Ile Leu Arg Asn Pro Gly
                245                 250                 255
Tyr Ala Leu Val Ala Ala Val Ile Gly Trp Met Leu Gly Ser Asn Thr
            260                 265                 270
Met Gln Arg Val Val Phe Val Leu Leu Leu Val Ala Pro Ala
            275                 280                 285
Tyr Ser Phe Asn Cys Leu Gly Met Ser Asn Arg Asp Phe Leu Glu Gly
            290                 295                 300
Val Ser Gly Ala Thr Trp Val Asp Leu Val Leu Glu Gly Asp Ser Cys
305                 310                 315                 320
Val Thr Ile Met Ser Lys Asp Lys Pro Thr Ile Asp Val Lys Met Met
                325                 330                 335
Asn Met Glu Ala Ala Asn Leu Ala Glu Val Arg Ser Tyr Cys Tyr Leu
            340                 345                 350
Ala Thr Val Ser Asp Leu Ser Thr Lys Ala Ala Cys Pro Ala Met Gly
            355                 360                 365
Glu Ala His Asn Asp Lys Arg Ala Asp Pro Ala Phe Val Cys Arg Gln
            370                 375                 380
Gly Val Val Asp Arg Gly Trp Gly Asn Gly Cys Gly Leu Phe Gly Lys
385                 390                 395                 400
Gly Ser Ile Asp Thr Cys Ala Lys Phe Ala Cys Ser Thr Lys Ala Ile
                405                 410                 415
Gly Arg Thr Ile Leu Lys Glu Asn Ile Lys Tyr Glu Val Ala Ile Phe
                420                 425                 430
Val His Gly Pro Thr Thr Val Glu Ser His Gly Asn Tyr Ser Thr Gln
            435                 440                 445
Val Gly Ala Thr Gln Ala Gly Arg Phe Ser Ile Thr Pro Ala Ala Pro
            450                 455                 460
Ser Tyr Thr Leu Lys Leu Gly Glu Tyr Gly Glu Val Thr Val Asp Cys
465                 470                 475                 480
Glu Pro Arg Ser Gly Ile Asp Thr Asn Ala Tyr Tyr Val Met Thr Val
                485                 490                 495
Gly Thr Lys Thr Phe Leu Val His Arg Glu Trp Phe Met Asp Leu Asn
                500                 505                 510
Leu Pro Trp Ser Ser Ala Gly Ser Thr Val Trp Arg Asn Arg Glu Thr
            515                 520                 525
Leu Met Glu Phe Glu Glu Pro His Ala Thr Lys Gln Ser Val Ile Ala
            530                 535                 540
Leu Gly Ser Gln Glu Gly Ala Leu His Gln Ala Leu Ala Gly Ala Ile
545                 550                 555                 560
Pro Val Glu Phe Ser Ser Asn Thr Val Lys Leu Thr Ser Gly His Leu
                565                 570                 575
Lys Cys Arg Val Lys Met Glu Lys Leu Gln Leu Lys Gly Thr Thr Tyr
            580                 585                 590
Gly Val Cys Ser Lys Ala Phe Lys Phe Leu Gly Thr Pro Ala Asp Thr
            595                 600                 605
```

```
Gly His Gly Thr Val Val Leu Glu Leu Gln Tyr Thr Gly Thr Asp Gly
        610                 615                 620

Pro Cys Lys Val Pro Ile Ser Ser Val Ala Ser Leu Asn Asp Leu Thr
625                 630                 635                 640

Pro Val Gly Arg Leu Val Thr Val Asn Pro Phe Val Ser Val Ala Thr
                645                 650                 655

Ala Asn Ala Lys Val Leu Ile Glu Leu Glu Pro Pro Phe Gly Asp Ser
            660                 665                 670

Tyr Ile Val Val Gly Arg Gly Glu Gln Gln Ile Asn His His Trp His
        675                 680                 685

Lys Ser Gly Ser Ser Ile Gly Lys Ala Phe Thr Thr Thr Leu Lys Gly
    690                 695                 700

Ala Gln Arg Leu Ala Ala Leu Gly Asp Thr Ala Trp Asp Phe Gly Ser
705                 710                 715                 720

Val Gly Gly Val Phe Thr Ser Val Gly Lys Ala Val His Gln Val Phe
                725                 730                 735

Gly Gly Ala Phe Arg Ser Leu Phe Gly Gly Met Ser Trp Ile Thr Gln
            740                 745                 750

Gly Leu Leu Gly Ala Leu Leu Leu Trp Met Gly Ile Asn Ala Arg Asp
        755                 760                 765

Arg Ser Ile Ala Leu Thr Phe Leu Ala Val Gly Gly Val Leu Leu Phe
    770                 775                 780

Leu Ser Val Asn Val His Ala Asp Thr Gly Ile His Arg Gly Pro Ala
785                 790                 795                 800

Thr Arg Thr Thr Thr Glu Ser Gly Lys Leu Ile Thr Asp Trp Cys Cys
                805                 810                 815

Arg Ser Cys Thr Leu Pro Pro Leu Arg Tyr Gln Thr Asp Ser Gly Cys
            820                 825                 830

Trp Tyr Gly Met Glu Ile Arg Pro Gln Arg His Asp Glu Lys Thr Leu
        835                 840                 845

Val Gln Ser Gln Val Asn Ala Tyr Asn Ala Asp Met Ile Asp Pro Phe
    850                 855                 860

Gln Leu Gly Leu
865

<210> SEQ ID NO 68
<211> LENGTH: 2700
<212> TYPE: DNA
<213> ORGANISM: Artificial Sequence
<220> FEATURE:
<223> OTHER INFORMATION: Synthetic Construct

<400> SEQUENCE: 68
agtagttcgc ctgtgtgagc tgacaaactt agtagtgttt gtgaggatta acaacaatta      60
acacagtgcg agctgtttct tagcacgaag atctcgatgt ctaagaaacc aggagggccc     120
ggcaagagcc gggctgtcaa tatgctaaaa cgcggaatgc cccgcgtgtt gtccttgatt     180
ggacttaaga gggctatgtt gagcctgatc gacggcaagg ggccaatacg atttgtgttg     240
gctctcttgg cgttcttcag gttcacagca attgctccga cccgagcagt gctggatcga     300
tggagaggtg tgaacaaaca aacagcgatg aaacaccttc tgagtttcaa gaaggaacta     360
gggaccttga ccagtgctat caatcggcgg agctcaaaac aaaagaaaag aggaggaaag     420
accggaattg cagtcatgat tggcctgatc gccagcgtag gagcagttac cctctctaac     480
ttccaaggga aggtgatgat gacggtaaat gctactgacg tcacagatgt catcacgatt     540
```

```
ccaacagctg ctggaaagaa cctatgcatt gtcagagcaa tggatgtggg atacatgtgc    600
gatgatacta tcacttatga atgcccagtg ctgtcggctg gtaatgatcc agaagacatc    660
gactgttggt gcacaaagtc agcagtctac gtcaggtatg aagatgcac caagacacgc     720 cactcaagac gcagtcggag gtcactgaca gtgcagacac acggagaaag cactctagcg    780
aacaagaagg gggcttggat ggacagcacc aaggccacaa ggtatttggt aaaaacagaa    840
tcatggatct tgaggaaccc tggatatgcc ctggtgcag ccgtcattgg ttggatgctt     900
gggagcaaca ccatgcagag agttgtgttt gtcgtgctat tgcttttggt ggccccagct    960 tacagctta actgccttgg aatgagcaac agagacttct tggaaggagt gtctggagca    1020
acatgggtgg atttggttct cgaaggcgac agctgcgtga ctatcatgtc taaggacaag   1080
cctaccatcg atgtgaagat gatgaatatg gaggcggcca acctggcaga ggtccgcagt   1140
tattgctatt tggctaccgt cagcgatctc tccaccaaag ctgcgtgccc ggccatggga   1200
gaagctcaca atgacaaacg tgctgaccca gcttttgtgt gcagacaagg agtggtggac   1260
aggggctggg gcaacggctg cggactattt ggcaaaggaa gcattgacac atgcgccaaa   1320
tttgcctgct ctaccaaggc aataggaaga accattttga agagaatat caagtacgaa    1380 gtggccattt tgtccatgg accaactact gtggagtcgc acggaaacta ctccacacag   1440
gttggagcca ctcaggcagg gagattcagc atcactcctg cggcgccttc atacacacta   1500
aagcttggag aatatggaga ggtgacagtg gactgtgaac cacggtcagg gattgacacc   1560
aatgcatact acgtgatgac tgttggaaca aagacgttct tggtccatcg tgagtggttc   1620
atggacctca acctcccttg gagcagtgct ggaagtactg tgtggaggaa cagagagacg   1680
ttaatggagt tgaggaacc acacgccacg aagcagtctg tgatagcatt gggctcacaa   1740
gagggagctc tgcatcaagc tttggctgga gccattcctg tggaattttc aagcaacact   1800
gtcaagttga cgtcgggtca tttgaagtgt agagtgaaga tggaaaaatt gcagttgaag   1860
ggaacaacct atggcgtctg ttcaaaggct ttcaagtttc ttgggactcc cgcagacaca   1920
ggtcacggca ctgtggtgtt ggaattgcag tacactggca cggatggacc ttgcaaagtt   1980
cctatctcgt cagtggcttc attgaacgac ctaacgccag tggcagatt ggtcactgtc    2040 aacccttttg tttcagtggc cacggccaac gctaaggtcc tgattgaatt ggaaccaccc   2100
tttggagact catacatagt ggtgggcaga ggagaacaac agatcaatca ccactggcac   2160
aagtctggaa gcagcattgg caaagccttt acaaccaccc tcaaaggagc gcagagacta   2220
gccgctctag gagacacagc ttgggactt ggatcagttg gaggggtgtt caccctcagtt   2280 gggaaggctg tccatcaagt gttcggagga gcattccgct cactgttcgg aggcatgtcc   2340
tggataacgc aaggattgct gggggctctc ctgttgtgga tgggcatcaa tgctcgtgac   2400
aggtccatag ctctcacgtt tctcgcagtt ggaggagttc tgctcttcct ctccgtgaac   2460
gtgcacgctg acactgggat ccaccgtgga cctgccactc gcaccaccac agagagcgga   2520
aagttgataa cagattggtg ctgcaggagc tgcaccttac caccactgcg ctaccaaact   2580
gacagcggct gttggtatgg tatggagatc agaccacaga gacatgatga aaagaccctc   2640
gtgcagtcac aagtgaatgc ttataatgct gatatgattg accctttca gttgggcctt   2700
```

<210> SEQ ID NO 69
<211> LENGTH: 2700
<212> TYPE: DNA
<213> ORGANISM: Artificial Sequence
<220> FEATURE:

<223> OTHER INFORMATION: Synthetic Construct

<400> SEQUENCE: 69

```
tcatcaagcg acacactcg actgtttgaa tcatcacaaa cactcctaat tgttgttaat      60
tgtgtcacgc tcgacaaaga atcgtgcttc tagagctaca gattctttgg tcctcccggg    120
ccgttctcgg cccgacagtt atacgatttt gcgccttacg gggcgcacaa caggaactaa    180
cctgaattct cccgatacaa ctcggactag ctgccgttcc ccggttatgc taaacacaac    240
cgagagaacc gcaagaagtc caagtgtcgt taacgaggct gggctcgtca cgacctagct    300
acctctccac acttgtttgt ttgtcgctac tttgtggaag actcaaagtt cttccttgat    360
ccctggaact ggtcacgata gttagccgcc tcgagttttg ttttcttttc tcctcctttc    420
tggccttaac gtcagtacta accggactag cggtcgcatc ctcgtcaatg ggagagattg    480
aaggttccct tccactacta ctgccattta cgatgactgc agtgtctaca gtagtgctaa    540
ggttgtcgac gacctttctt ggatacgtaa cagtctcgtt acctacaccc tatgtacacg    600
ctactatgat agtgaatact tacgggtcac gacagccgac cattactagg tcttctgtag    660
ctgacaacca cgtgtttcag tcgtcagatg cagtccatac cttctacgtg gttctgtgcg    720
gtgagttctg cgtcagcctc cagtgactgt cacgtctgtg tgcctctttc gtgagatcgc    780
ttgttcttcc cccgaaccta cctgtcgtgg ttccggtgtt ccataaacca tttttgtctt    840
agtacctaga actccttggg acctatacga gaccaccgtc ggcagtaacc aacctacgaa    900
ccctcgttgt ggtacgtctc tcaacacaaa cagcacgata acgaaaacca ccggggtcga    960
atgtcgaaat tgacggaacc ttactcgttg tctctgaaga accttcctca cagacctcgt   1020
tgtacccacc taaaccaaga gcttccgctg tcgacgcact gatagtacag attcctgttc   1080
ggatggtagc tacacttcta ctacttatac ctccgccggt tggaccgtct ccaggcgtca   1140
ataacgataa accgatggca gtcgctagag aggtggtttc gacgcacggg ccggtaccct   1200
cttcgagtgt tactgtttgc acgactgggt cgaaaacaca cgtctgttcc tcaccacctg   1260
tccccgaccc cgttgccgac gcctgataaa ccgtttcctt cgtaactgtg tacgcggttt   1320
aaacggacga gatggttccg ttatccttct tggtaaaact ttctcttata gttcatgctt   1380
caccggtaaa aacaggtacc tggttgatga cacctcagcg tgcctttgat gaggtgtgtc   1440
caacctcggt gagtccgtcc ctctaagtcg tagtgaggac gccgcggaag tatgtgtgat   1500
ttcgaacctc ttatacctct ccactgtcac ctgacacttg gtgccagtcc ctaactgtgg   1560
ttacgtatga tgcactactg acaaccttgt ttctgcaaga accaggtagc actcaccaag   1620
tacctggagt tggagggaac ctcgtcacga ccttcatgac acacctcctt gtctctctgc   1680
aattacctca aactccttgg tgtgcggtgc ttcgtcagac actatcgtaa cccgagtgtt   1740
ctccctcgag acgtagttcg aaaccgacct cggtaaggac accttaaaag ttcgttgtga   1800
cagttcaact gcagcccagt aaacttcaca tctcacttct accttttttaa cgtcaacttc   1860
ccttgttgga taccgcagac aagtttccga aagttcaaag aaccctgagg gcgtctgtgt   1920
ccagtgccgt gacaccacaa ccttaacgtc atgtgaccgt gcctacctgg aacgtttcaa   1980
ggatagagca gtcaccgaag taacttgctg gattgcggtc acccgtctaa ccagtgacag   2040
ttgggaaaac aaagtcaccg gtgccggttg cgattccagg actaacttaa ccttggtggg   2100
aaacctctga gtatgtatca ccaccgtct cctcttgttg tctagttagt ggtgaccgtg    2160
ttcagacctt cgtcgtaacc gtttcggaaa tgttggtggg agtttcctcg cgtctctgat   2220
cggcgagatc ctctgtgtcg aaccctgaaa cctagtcaac ctccccacaa gtggagtcaa   2280
```

```
cccttccgac aggtagttca caagcctcct cgtaaggcga gtgacaagcc tccgtacagg    2340
acctattgcg ttcctaacga cccccgagag gacaacacct acccgtagtt acgagcactg    2400
tccaggtatc gagagtgcaa agagcgtcaa cctcctcaag acgagaagga gaggcacttg    2460
cacgtgcgac tgtgacccta ggtggcacct ggacggtgag cgtggtggtg tctctcgcct    2520
ttcaactatt gtctaaccac gacgtcctcg acgtggaatg gtggtgacgc gatggtttga    2580
ctgtcgccga caaccatacc atacctctag tctggtgtct ctgtactact tttctgggag    2640
cacgtcagtg ttcacttacg aatattacga ctatactaac tgggaaaagt caacccggaa    2700
```

<210> SEQ ID NO 70
<211> LENGTH: 734
<212> TYPE: PRT
<213> ORGANISM: Artificial Sequence
<220> FEATURE:
<223> OTHER INFORMATION: Synthetic Construct

<400> SEQUENCE: 70

```
Met Ser Lys Lys Pro Gly Gly Pro Gly Lys Ser Arg Ala Val Tyr Leu
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Glu Leu Leu Ile Leu
            100                 105                 110

Lys Ala Asn Ala Ile Thr Thr Ile Leu Thr Ala Val Thr Phe Cys Phe
        115                 120                 125

Ala Ser Gly Gln Asn Ile Thr Glu Glu Phe Tyr Gln Ser Thr Cys Ser
    130                 135                 140

Ala Val Ser Lys Gly Tyr Leu Ser Ala Leu Arg Thr Gly Trp Tyr Thr
145                 150                 155                 160

Ser Val Ile Thr Ile Glu Leu Ser Asn Ile Lys Glu Asn Lys Cys Asn
                165                 170                 175

Gly Thr Asp Ala Lys Val Lys Leu Ile Lys Gln Glu Leu Asp Lys Tyr
            180                 185                 190

Lys Asn Ala Val Thr Glu Leu Gln Leu Leu Met Gln Ser Thr Pro Pro
        195                 200                 205

Thr Asn Asn Arg Ala Arg Arg Glu Leu Pro Arg Phe Met Asn Tyr Thr
    210                 215                 220

Leu Asn Asn Ala Lys Lys Thr Asn Val Thr Leu Ser Lys Lys Arg Lys
225                 230                 235                 240

Arg Arg Phe Leu Gly Phe Leu Leu Gly Val Gly Ser Ala Ile Ala Ser
                245                 250                 255

Gly Val Ala Val Ser Lys Val Leu His Leu Glu Gly Glu Val Asn Lys
            260                 265                 270

Ile Lys Ser Ala Leu Leu Ser Thr Asn Lys Ala Val Val Ser Leu Ser
        275                 280                 285
```

-continued

```
Asn Gly Val Ser Val Leu Thr Ser Lys Val Leu Asp Leu Lys Asn Tyr
    290                 295                 300
Ile Asp Lys Gln Leu Leu Pro Ile Val Asn Lys Gln Ser Cys Ser Ile
305                 310                 315                 320
Ser Asn Ile Glu Thr Val Ile Glu Phe Gln Gln Lys Asn Asn Arg Leu
                325                 330                 335
Leu Glu Ile Thr Arg Glu Phe Ser Val Asn Ala Gly Val Thr Thr Pro
            340                 345                 350
Val Ser Thr Tyr Met Leu Thr Asn Ser Glu Leu Leu Ser Leu Ile Asn
        355                 360                 365
Asp Met Pro Ile Thr Asn Asp Gln Lys Lys Leu Met Ser Asn Asn Val
370                 375                 380
Gln Ile Val Arg Gln Gln Ser Tyr Ser Ile Met Ser Ile Ile Lys Glu
385                 390                 395                 400
Glu Val Leu Ala Tyr Val Val Gln Leu Pro Leu Tyr Gly Val Ile Asp
                405                 410                 415
Thr Pro Cys Trp Lys Leu His Thr Ser Pro Leu Cys Thr Thr Asn Thr
            420                 425                 430
Lys Glu Gly Ser Asn Ile Cys Leu Thr Arg Thr Asp Arg Gly Trp Tyr
        435                 440                 445
Cys Asp Asn Ala Gly Ser Val Ser Phe Phe Pro Gln Ala Glu Thr Cys
450                 455                 460
Lys Val Gln Ser Asn Arg Val Phe Cys Asp Thr Met Asn Ser Leu Thr
465                 470                 475                 480
Leu Pro Ser Glu Ile Asn Leu Cys Asn Val Asp Ile Phe Asn Pro Lys
                485                 490                 495
Tyr Asp Cys Lys Ile Met Thr Ser Lys Thr Asp Val Ser Ser Ser Val
            500                 505                 510
Ile Thr Ser Leu Gly Ala Ile Val Ser Cys Tyr Gly Lys Thr Lys Cys
        515                 520                 525
Thr Ala Ser Asn Lys Asn Arg Gly Ile Ile Lys Thr Phe Ser Asn Gly
530                 535                 540
Cys Asp Tyr Val Ser Asn Lys Gly Met Asp Thr Val Ser Val Gly Asn
545                 550                 555                 560
Thr Leu Tyr Tyr Val Asn Lys Gln Glu Gly Lys Ser Leu Tyr Val Lys
                565                 570                 575
Gly Glu Pro Ile Ile Asn Phe Tyr Asp Pro Leu Val Phe Pro Ser Asp
            580                 585                 590
Glu Phe Asp Ala Ser Ile Ser Gln Val Asn Glu Lys Ile Asn Gln Ser
        595                 600                 605
Leu Ala Phe Ile Arg Lys Ser Asp Glu Leu Leu His Asn Val Asn Ala
610                 615                 620
Gly Lys Ser Thr Thr Asn Ile Met Ile Thr Thr Ile Ile Ile Val Ile
625                 630                 635                 640
Ile Val Ile Leu Leu Ser Leu Ile Ala Val Gly Leu Leu Leu Tyr Cys
                645                 650                 655
Lys Ala Arg Ser Thr Pro Val Thr Leu Ser Lys Asp Gln Leu Ser Gly
            660                 665                 670
Ile Asn Asn Ile Ala Phe Ser Asn Phe Asp Leu Leu Lys Leu Ala
        675                 680                 685
Gly Asp Val Glu Ser Asn Pro Gly Pro Ala Arg Asp Arg Ser Ile Ala
690                 695                 700
Leu Thr Phe Leu Ala Val Gly Gly Val Leu Leu Phe Leu Ser Val Asn
```

Val His Ala Asp Thr Gly Cys Ala Ile Asp Ile Ser Arg Gln
    705             710             715             720
                725             730

<210> SEQ ID NO 71
<211> LENGTH: 2298
<212> TYPE: DNA
<213> ORGANISM: Artificial Sequence
<220> FEATURE:
<223> OTHER INFORMATION: Synthetic Construct

<400> SEQUENCE: 71

| | | | | | |
|---|---|---|---|---|---|
| agtagttcgc | ctgtgtgagc | tgacaaactt | agtagtgttt | gtgaggatta | acaacaatta | 60 |
| acacagtgcg | agctgtttct | tagcacgaag | atctcgatgt | ctaagaaacc | aggagggccc | 120 |
| ggcaagagcc | gggctgtcta | tttgctaaaa | cgcggaatgc | cccgcgtgtt | gtccttgatt | 180 |
| ggacttaaga | gggctatgtt | gagcctgatc | gacggcaagg | ggccaatacg | atttgtgttg | 240 |
| gctctcttgg | cgttcttcag | gttcacagca | attgctccga | cccgagcagt | gctggatcga | 300 |
| tggagaggtg | tgaacaaaca | aacagcgatg | aaacaccttc | tgagtttcaa | gaaggaacta | 360 |
| gggaccttga | ccagtgctat | caatcggcgg | agctcaaagc | aaaagaagcg | agggggcgag | 420 |
| ttgctaatcc | tcaaagcaaa | tgcaattacc | acaatcctca | ctgcagtcac | attttgtttt | 480 |
| gcttctggtc | aaaacatcac | tgaagaattt | tatcaatcaa | catgcagtgc | agttagcaaa | 540 |
| ggctatctta | gtgctctgag | aactggttgg | tataccagtg | ttataactat | agaattaagt | 600 |
| aatatcaagg | aaaataagtg | taatggaaca | gatgctaagg | taaaattgat | aaaacaagaa | 660 |
| ttagataaat | ataaaaatgc | tgtaacagaa | ttgcagttgc | tcatgcaaag | cacaccacca | 720 |
| acaaacaatc | gagccagaag | agaactacca | aggtttatga | attatacact | caacaatgcc | 780 |
| aaaaaaacca | atgtaacatt | aagcaagaaa | aggaaaagaa | gatttcttgg | ttttttgtta | 840 |
| ggtgttggat | ctgcaatcgc | cagtggcgtt | gctgtatcta | aggtcctgca | cctagaaggg | 900 |
| gaagtgaaca | agatcaaaag | tgctctacta | tccacaaaca | aggctgtagt | cagcttatca | 960 |
| aatggagtta | gtgtcttaac | cagcaaagtg | ttagacctca | aaaactatat | agataaacaa | 1020 |
| ttgttaccta | ttgtgaacaa | gcaaagctgc | agcatatcaa | atatagaaac | tgtgatagag | 1080 |
| ttccaacaaa | agaacaacag | actactagag | attaccaggg | aatttagtgt | taatgcaggt | 1140 |
| gtaactacac | ctgtaagcac | ttacatgtta | actaatagtg | aattattgtc | attaatcaat | 1200 |
| gatatgccta | taacaaatga | tcagaaaaag | ttaatgtcca | acaatgttca | aatagttaga | 1260 |
| cagcaaagtt | actctatcat | gtccataata | aagaggaag | tcttagcata | tgtagtacaa | 1320 |
| ttaccactat | atggtgttat | agatacaccc | tgttggaaac | tacacacatc | ccctctatgt | 1380 |
| acaaccaaca | caaagaagg | gtccaacatc | tgtttaacaa | gaactgacag | aggatggtac | 1440 |
| tgtgacaatg | caggatcagt | atctttcttc | ccacaagctg | aaacatgtaa | agttcaatca | 1500 |
| aatcgagtat | tttgtgacac | aatgaacagt | ttaacattac | caagtgaaat | aaatctctgc | 1560 |
| aatgttgaca | tattcaaccc | caaatatgat | tgtaaaatta | tgacttcaaa | acagatgta | 1620 |
| agcagctccg | ttatcacatc | tctaggagcc | attgtgtcat | gctatggcaa | aactaaatgt | 1680 |
| acagcatcca | ataaaaatcg | tggaatcata | aagacatttt | ctaacgggtg | cgattatgta | 1740 |
| tcaaataaag | ggatggacac | tgtgtctgta | ggtaacacat | tatattatgt | aaataagcaa | 1800 |
| gaaggtaaaa | gtctctatgt | aaaaggtgaa | ccaataataa | atttctatga | cccattagta | 1860 |
| ttccctctg | atgaatttga | tgcatcaata | tctcaagtca | acgagaagat | taaccagagc | 1920 |

```
ctagcattta ttcgtaaatc cgatgaatta ttacataatg taaatgctgg taaatccacc    1980
acaaatatca tgataactac tataattata gtgattatag taatattgtt atcattaatt    2040
gctgttggac tgctcttata ctgtaaggcc agaagcacac cagtcacact aagcaaagat    2100
caactgagtg gtataaataa tattgcattt agtaacaatt ttgatctgct caaacttgca    2160
ggcgatgtag aatcaaatcc tggacccgcc cgggacaggt ccatagctct cacgtttctc    2220
gcagttggag gagttctgct cttcctctcc gtgaacgtgc acgctgacac tgggtgtgcc    2280
atagacatca gccggcaa                                                  2298
```

<210> SEQ ID NO 72
<211> LENGTH: 2298
<212> TYPE: DNA
<213> ORGANISM: Artificial Sequence
<220> FEATURE:
<223> OTHER INFORMATION: Synthetic Construct

<400> SEQUENCE: 72

```
tcatcaagcg gacacactcg actgtttgaa tcatcacaaa cactcctaat tgttgttaat      60
tgtgtcacgc tcgacaaaga atcgtgcttc tagagctaca gattctttgg tcctcccggg     120
ccgttctcgg cccgacagat aaacgatttt gcgccttacg gggcgcacaa caggaactaa     180
cctgaattct cccgatacaa ctcggactag ctgccgttcc ccggttatgc taaacacaac     240
cgagagaacc gcaagaagtc caagtgtcgt taacgaggct gggctcgtca cgacctagct     300
acctctccac acttgtttgt ttgtcgctac tttgtggaag actcaaagtt cttccttgat     360
ccctggaact ggtcacgata gttagccgcc tcgagtttcg ttttcttcgc tcccccgctc     420
aacgattagg agtttcgttt acgttaatgg tgttaggagt gacgtcagtg taaaacaaaa     480
cgaagaccag ttttgtagtg acttcttaaa atagttagtt gtacgtcacg tcaatcgttt     540
ccgatagaat cacgagactc ttgaccaacc atatggtcac aatattgata tcttaattca     600
ttatagttcc ttttattcac attaccttgt ctacgattcc attttaacta tttgttctt      660 aatctattta tattttacg acattgtctt aacgtcaacg agtacgtttc gtgtggtggt      720
tgtttgttag ctcggtcttc tcttgatggt tccaaatact taatatgtga gttgttacgg     780
tttttttggt tacattgtaa ttcgttcttt tccttttctt ctaaagaacc aaaaaacaat     840
ccacaaccta gacgttagcg gtcaccgcaa cgacatagat tccaggacgt ggatcttccc     900
cttcacttgt tctagttttc acgagatgat aggtgtttgt tccgacatca gtcgaatagt     960
ttacctcaat cacagaattg gtcgtttcac aatctggagt ttttgatata tctatttgtt    1020
aacaatggat aacacttgtt cgtttcgacg tcgtatagtt tatatctttg acactatctc    1080
aaggttgttt tcttgttgtc tgatgatctc taatggtccc ttaaatcaca attacgtcca    1140
cattgatgtg gacattcgtg aatgtacaat tgattatcac ttaataacag taattagtta    1200
ctatacggat attgtttact agtctttttc aattacaggt tgttacaagt ttatcaatct    1260
gtcgtttcaa tgagatagta caggtattat tttctccttc agaatcgtat acatcatgtt    1320
aatggtgata taccacaata tctatgtggg acaaccttg atgtgtgtag gggagataca     1380
tgttggttgt gttttcttcc caggttgtag acaaattgtt cttgactgtc tcctaccatg    1440
acactgttac gtcctagtca tagaaagaag ggtgttcgac tttgtacatt tcaagttagt    1500
ttagctcata aaaacactgtg ttacttgtca aattgtaatg gttcacttta tttagagacg    1560
ttacaactgt ataagtttggg gtttatacta acatttaat actgaagttt ttgtctacat    1620
tcgtcgaggc aatagtgtag agatcctcgg taacacagta cgataccgtt tgatttaca    1680
```

```
tgtcgtaggt tattttagc accttagtat ttctgtaaaa gattgcccac gctaatacat    1740
agtttatttc cctacctgtg acacagacat ccattgtgta atataataca tttattcgtt    1800
cttccatttt cagagataca ttttccactt ggttattatt taaagatact gggtaatcat    1860
aaggggagac tacttaaact acgtagttat agagttcagt tgctcttcta attggtctcg    1920
gatcgtaaat aagcatttag gctacttaat aatgtattac atttacgacc atttaggtgg    1980
tgtttatagt actattgatg atattaatat cactaatatc attataacaa tagtaattaa    2040
cgacaacctg acgagaatat gacattccgg tcttcgtgtg gtcagtgtga ttcgtttcta    2100
gttgactcac catatttatt ataacgtaaa tcattgttaa aactagacga gtttgaacgt    2160
ccgctacatc ttagtttagg acctgggcgg gccctgtcca ggtatcgaga gtgcaaagag    2220
cgtcaacctc ctcaagacga gaaggagagg cacttgcacg tgcgactgtg acccacacgg    2280
tatctgtagt cggccgtt                                                  2298
```

<210> SEQ ID NO 73
<211> LENGTH: 667
<212> TYPE: PRT
<213> ORGANISM: Artificial Sequence
<220> FEATURE:
<223> OTHER INFORMATION: Synthetic Construct

<400> SEQUENCE: 73

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Gln
            20                  25                  30

Lys Lys Arg Gly Gly Glu Leu Leu Ile Leu Lys Ala Asn Ala Ile Thr
        35                  40                  45

Thr Ile Leu Thr Ala Val Thr Phe Cys Phe Ala Ser Gly Gln Asn Ile
    50                  55                  60

Thr Glu Glu Phe Tyr Gln Ser Thr Cys Ser Ala Val Ser Lys Gly Tyr
65                  70                  75                  80

Leu Ser Ala Leu Arg Thr Gly Trp Tyr Thr Ser Val Ile Thr Ile Glu
                85                  90                  95

Leu Ser Asn Ile Lys Glu Asn Lys Cys Asn Gly Thr Asp Ala Lys Val
            100                 105                 110

Lys Leu Ile Lys Gln Glu Leu Asp Lys Tyr Lys Asn Ala Val Thr Glu
        115                 120                 125

Leu Gln Leu Leu Met Gln Ser Thr Pro Pro Thr Asn Asn Arg Ala Arg
    130                 135                 140

Arg Glu Leu Pro Arg Phe Met Asn Tyr Thr Leu Asn Asn Ala Lys Lys
145                 150                 155                 160

Thr Asn Val Thr Leu Ser Lys Lys Arg Lys Arg Arg Phe Leu Gly Phe
                165                 170                 175

Leu Leu Gly Val Gly Ser Ala Ile Ala Ser Gly Val Ala Val Ser Lys
            180                 185                 190

Val Leu His Leu Glu Gly Glu Val Asn Lys Ile Lys Ser Ala Leu Leu
        195                 200                 205

Ser Thr Asn Lys Ala Val Val Ser Leu Ser Asn Gly Val Ser Val Leu
    210                 215                 220

Thr Ser Lys Val Leu Asp Leu Lys Asn Tyr Ile Asp Lys Gln Leu Leu
225                 230                 235                 240

Pro Ile Val Asn Lys Gln Ser Cys Ser Ile Ser Asn Ile Glu Thr Val
```

```
                    245                 250                 255
Ile Glu Phe Gln Gln Lys Asn Asn Arg Leu Leu Glu Ile Thr Arg Glu
            260                 265                 270

Phe Ser Val Asn Ala Gly Val Thr Thr Pro Val Ser Thr Tyr Met Leu
        275                 280                 285

Thr Asn Ser Glu Leu Leu Ser Leu Ile Asn Asp Met Pro Ile Thr Asn
    290                 295                 300

Asp Gln Lys Lys Leu Met Ser Asn Asn Val Gln Ile Val Arg Gln Gln
305                 310                 315                 320

Ser Tyr Ser Ile Met Ser Ile Ile Lys Glu Glu Val Leu Ala Tyr Val
                325                 330                 335

Val Gln Leu Pro Leu Tyr Gly Val Ile Asp Thr Pro Cys Trp Lys Leu
            340                 345                 350

His Thr Ser Pro Leu Cys Thr Thr Asn Thr Lys Glu Gly Ser Asn Ile
        355                 360                 365

Cys Leu Thr Arg Thr Asp Arg Gly Trp Tyr Cys Asp Asn Ala Gly Ser
    370                 375                 380

Val Ser Phe Phe Pro Gln Ala Glu Thr Cys Lys Val Gln Ser Asn Arg
385                 390                 395                 400

Val Phe Cys Asp Thr Met Asn Ser Leu Thr Leu Pro Ser Glu Ile Asn
                405                 410                 415

Leu Cys Asn Val Asp Ile Phe Asn Pro Lys Tyr Asp Cys Lys Ile Met
            420                 425                 430

Thr Ser Lys Thr Asp Val Ser Ser Val Ile Thr Ser Leu Gly Ala
        435                 440                 445

Ile Val Ser Cys Tyr Gly Lys Thr Lys Cys Thr Ala Ser Asn Lys Asn
    450                 455                 460

Arg Gly Ile Ile Lys Thr Phe Ser Asn Gly Cys Asp Tyr Val Ser Asn
465                 470                 475                 480

Lys Gly Met Asp Thr Val Ser Val Gly Asn Thr Leu Tyr Tyr Val Asn
                485                 490                 495

Lys Gln Glu Gly Lys Ser Leu Tyr Val Lys Gly Glu Pro Ile Ile Asn
            500                 505                 510

Phe Tyr Asp Pro Leu Val Phe Pro Ser Asp Glu Phe Asp Ala Ser Ile
        515                 520                 525

Ser Gln Val Asn Glu Lys Ile Asn Gln Ser Leu Ala Phe Ile Arg Lys
    530                 535                 540

Ser Asp Glu Leu Leu His Asn Val Asn Ala Gly Lys Ser Thr Thr Asn
545                 550                 555                 560

Ile Met Ile Thr Thr Ile Ile Ile Val Ile Ile Val Ile Leu Leu Ser
                565                 570                 575

Leu Ile Ala Val Gly Leu Leu Leu Tyr Cys Lys Ala Arg Ser Thr Pro
            580                 585                 590

Val Thr Leu Ser Lys Asp Gln Leu Ser Gly Ile Asn Asn Ile Ala Phe
        595                 600                 605

Ser Asn Asn Phe Asp Leu Leu Lys Leu Ala Gly Asp Val Glu Ser Asn
    610                 615                 620

Pro Gly Pro Ala Arg Asp Arg Ser Ile Ala Leu Thr Phe Leu Ala Val
625                 630                 635                 640

Gly Gly Val Leu Leu Phe Leu Ser Val Asn Val His Ala Asp Thr Gly
                645                 650                 655

Cys Ala Ile Asp Ile Ser Arg Gln Glu Leu Arg
            660                 665
```

<210> SEQ ID NO 74
<211> LENGTH: 2097
<212> TYPE: DNA
<213> ORGANISM: Artificial Sequence
<220> FEATURE:
<223> OTHER INFORMATION: Synthetic Construct

<400> SEQUENCE: 74

| | | | | | |
|---|---|---|---|---|---|
| agtagttcgc | ctgtgtgagc | tgacaaactt | agtagtgttt | gtgaggatta | acaacaatta | 60 |
| acacagtgcg | agctgtttct | tagcacgaag | atctcgatgt | ctaagaaacc | aggagggccc | 120 |
| ggcaagagcc | gggctgtcaa | tatgctaaaa | cgcggaatgc | cccgcgtgtt | gtccttgatt | 180 |
| ggacttaagc | aaaagaagcg | aggggggcgag | ttgctaatcc | tcaaagcaaa | tgcaattacc | 240 |
| acaatcctca | ctgcagtcac | attttgtttt | gcttctggtc | aaaacatcac | tgaagaattt | 300 |
| tatcaatcaa | catgcagtgc | agttagcaaa | ggctatctta | gtgctctgag | aactggttgg | 360 |
| tataccagtg | ttataactat | agaattaagt | aatatcaagg | aaaataagtg | taatggaaca | 420 |
| gatgctaagg | taaaattgat | aaaacaagaa | ttagataaat | ataaaaatgc | tgtaacagaa | 480 |
| ttgcagttgc | tcatgcaaag | cacaccacca | acaaacaatc | gagccagaag | agaactacca | 540 |
| aggtttatga | attatacact | caacaatgcc | aaaaaaacca | atgtaacatt | aagcaagaaa | 600 |
| aggaaaagaa | gatttcttgg | ttttttgtta | ggtgttggat | ctgcaatcgc | cagtggcgtt | 660 |
| gctgtatcta | aggtcctgca | cctagaaggg | gaagtgaaca | agatcaaaag | tgctctacta | 720 |
| tccacaaaca | aggctgtagt | cagcttatca | aatggagtta | gtgtcttaac | cagcaaagtg | 780 |
| ttagacctca | aaaactatat | agataaacaa | ttgttaccta | ttgtgaacaa | gcaaagctgc | 840 |
| agcatatcaa | atatagaaac | tgtgatagag | ttccaacaaa | agaacaacag | actactagag | 900 |
| attaccaggg | aatttagtgt | taatgcaggt | gtaactacac | ctgtaagcac | ttacatgtta | 960 |
| actaatagtg | aattattgtc | attaatcaat | gatatgccta | taacaaatga | tcagaaaaag | 1020 |
| ttaatgtcca | acaatgttca | aatagttaga | cagcaaagtt | actctatcat | gtccataata | 1080 |
| aaagaggaag | tcttagcata | tgtagtacaa | ttaccactat | atggtgttat | agatacaccc | 1140 |
| tgttggaaac | tacacacatc | ccctctatgt | acaaccaaca | caaaagaagg | gtccaacatc | 1200 |
| tgtttaacaa | gaactgacag | aggatggtac | tgtgacaatg | caggatcagt | atctttcttc | 1260 |
| ccacaagctg | aaacatgtaa | agttcaatca | aatcgagtat | tttgtgacac | aatgaacagt | 1320 |
| ttaacattac | caagtgaaat | aaatctctgc | aatgttgaca | tattcaaccc | caaatatgat | 1380 |
| tgtaaaatta | tgacttcaaa | aacagatgta | agcagctccg | ttatcacatc | tctaggagcc | 1440 |
| attgtgtcat | gctatggcaa | aactaaatgt | acagcatcca | ataaaaatcg | tggaatcata | 1500 |
| aagacatttt | ctaacgggtg | cgattatgta | tcaataaaag | ggatggacac | tgtgtctgta | 1560 |
| ggtaacacat | tatattatgt | aaataagcaa | gaaggtaaaa | gtctctatgt | aaaaggtgaa | 1620 |
| ccaataataa | atttctatga | cccattagta | ttcccctctg | atgaatttga | tgcatcaata | 1680 |
| tctcaagtca | acgagaagat | taaccagagc | ctagcattta | ttcgtaaatc | cgatgaatta | 1740 |
| ttacataatg | taaatgctgg | taaatccacc | acaaatatca | tgataactac | tataattata | 1800 |
| gtgattatag | taatatttgtt | atcattaatt | gctgttggac | tgctcttata | ctgtaaggcc | 1860 |
| agaagcacac | cagtcacact | aagcaaagat | caactgagtg | gtataaataa | tattgcattt | 1920 |
| agtaacaatt | ttgatctgct | caaacttgca | ggcgatgtag | aatcaaatcc | tggacccgcc | 1980 |
| cgggacaggt | ccatagctct | cacgtttctc | gcagttggag | gagttctgct | cttcctctcc | 2040 | gtgaacgtgc acgctgacac tgggtgtgcc atagacatca gccggcaaga gctgaga    2097

<210> SEQ ID NO 75
<211> LENGTH: 2097
<212> TYPE: DNA
<213> ORGANISM: Artificial Sequence
<220> FEATURE:
<223> OTHER INFORMATION: Synthetic Construct

<400> SEQUENCE: 75
tcatcaagcg gacacactcg actgtttgaa tcatcacaaa cactcctaat tgttgttaat     60
tgtgtcacgc tcgacaaaga tcgtgcttc tagagctaca gattctttgg tcctcccggg    120
ccgttctcgg cccgacagtt atacgatttt gcgccttacg gggcgcacaa caggaactaa    180
cctgaattcg ttttcttcgc tcccccgctc aacgattagg agtttcgttt acgttaatgg    240
tgttaggagt gacgtcagtg taaaacaaaa cgaagaccag ttttgtagtg acttcttaaa    300
atagttagtt gtacgtcacg tcaatcgttt ccgatagaat cacgagactc ttgaccaacc    360
atatggtcac aatattgata tcttaattca ttatagttcc ttttattcac attaccttgt    420
ctacgattcc attttaacta ttttgttctt aatctattta tatttttacg acattgtctt    480
aacgtcaacg agtacgtttc gtgtggtggt tgtttgttag ctcggtcttc tcttgatggt    540
tccaaatact aatatgtga gttgttacgg ttttttggt tacattgtaa ttcgttcttt    600
tcctttctt ctaaagaacc aaaaaacaat ccacaaccta gacgttagcg gtcaccgcaa    660
cgacatagat tccaggacgt ggatcttccc cttcacttgt tctagttttc acgagatgat    720
aggtgtttgt tccgacatca gtcgaatagt ttacctcaat cacagaattg gtcgtttcac    780
aatctggagt ttttgatata tctatttgtt aacaatggat aacacttgtt cgtttcgacg    840
tcgtatagtt tatatctttg acactatctc aaggttgttt tcttgttgtc tgatgatctc    900
taatggtccc ttaaatcaca attacgtcca cattgatgtg gacattcgtg aatgtacaat    960
tgattatcac ttaataacag taattagtta ctatacggat attgtttact agtcttttc   1020
aattacaggt tgttacaagt ttatcaatct gtcgtttcaa tgagatagta caggtattat   1080
tttctcctt agaatcgtat acatcatgtt aatggtgata taccacaata tctatgtggg   1140
acaacctttg atgtgtgtag gggagataca tgttggttgt gttttcttcc caggttgtag   1200
acaaattgtt cttgactgtc tcctaccatg acactgttac gtcctagtca tagaaagaag   1260
ggtgttcgac tttgtacatt tcaagttagt ttagctcata aaacactgtg ttacttgtca   1320
aattgtaatg gttcacttta tttagagacg ttacaactgt ataagttggg gtttatacta   1380
acattttaat actgaagttt ttgtctacat tcgtcgaggc aatagtgtag agatcctcgg   1440
taacacagta cgataccgtt ttgatttaca tgtcgtaggt tatttttagc accttagtat   1500
ttctgtaaaa gattgcccac gctaatacat agtttatttc cctacctgtg acacagacat   1560
ccattgtgta atataataca tttattcgtt cttccatttt cagagataca ttttccactt   1620
ggttattatt taaagatact gggtaatcat aaggggagac tacttaaact acgtagttat   1680
agagttcagt tgctcttcta attggtctcg gatcgtaaat aagcatttag gctacttaat   1740
aatgtattac atttacgacc atttaggtgg tgtttatagt actattgatg atattaatat   1800
cactaatatc attataacaa tagtaattaa cgacaacctg acgagaatat gacattccgg   1860
tcttcgtgtg gtcagtgtga ttcgtttcta gttgactcac catatttatt ataacgtaaa   1920
tcattgttaa aactagacga gtttgaacgt ccgctcatc ttagtttagg acctgggcgg   1980
gccctgtcca ggtatcgaga gtgcaaagag cgtcaacctc ctcaagacga aaggagagg   2040 cacttgcacg tgcgactgtg acccacacgg tatctgtagt cggccgttct cgactct    2097

<210> SEQ ID NO 76
<211> LENGTH: 1327
<212> TYPE: PRT
<213> ORGANISM: Artificial Sequence
<220> FEATURE:
<223> OTHER INFORMATION: Synthetic Construct

<400> SEQUENCE: 76

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Gln
            20                  25                  30

Lys Lys Arg Gly Gly Glu Leu Leu Ile Leu Lys Ala Asn Ala Ile Thr
        35                  40                  45

Thr Ile Leu Thr Ala Val Thr Phe Cys Phe Ala Ser Gly Gln Asn Ile
    50                  55                  60

Thr Glu Glu Phe Tyr Gln Ser Thr Cys Ser Ala Val Ser Lys Gly Tyr
65                  70                  75                  80

Leu Ser Ala Leu Arg Thr Gly Trp Tyr Thr Ser Val Ile Thr Ile Glu
                85                  90                  95

Leu Ser Asn Ile Lys Glu Asn Lys Cys Asn Gly Thr Asp Ala Lys Val
            100                 105                 110

Lys Leu Ile Lys Gln Glu Leu Asp Lys Tyr Lys Asn Ala Val Thr Glu
        115                 120                 125

Leu Gln Leu Leu Met Gln Ser Thr Pro Pro Thr Asn Asn Arg Ala Arg
    130                 135                 140

Arg Glu Leu Pro Arg Phe Met Asn Tyr Thr Leu Asn Asn Ala Lys Lys
145                 150                 155                 160

Thr Asn Val Thr Leu Ser Lys Lys Arg Lys Arg Arg Phe Leu Gly Phe
                165                 170                 175

Leu Leu Gly Val Gly Ser Ala Ile Ala Ser Gly Val Ala Val Ser Lys
            180                 185                 190

Val Leu His Leu Glu Gly Glu Val Asn Lys Ile Lys Ser Ala Leu Leu
        195                 200                 205

Ser Thr Asn Lys Ala Val Val Ser Leu Ser Asn Gly Val Ser Val Leu
    210                 215                 220

Thr Ser Lys Val Leu Asp Leu Lys Asn Tyr Ile Asp Lys Gln Leu Leu
225                 230                 235                 240

Pro Ile Val Asn Lys Gln Ser Cys Ser Ile Ser Asn Ile Glu Thr Val
                245                 250                 255

Ile Glu Phe Gln Gln Lys Asn Asn Arg Leu Leu Glu Ile Thr Arg Glu
            260                 265                 270

Phe Ser Val Asn Ala Gly Val Thr Thr Pro Val Ser Thr Tyr Met Leu
        275                 280                 285

Thr Asn Ser Glu Leu Leu Ser Leu Ile Asn Asp Met Pro Ile Thr Asn
    290                 295                 300

Asp Gln Lys Lys Leu Met Ser Asn Asn Val Gln Ile Val Arg Gln Gln
305                 310                 315                 320

Ser Tyr Ser Ile Met Ser Ile Ile Lys Glu Glu Val Leu Ala Tyr Val
                325                 330                 335

Val Gln Leu Pro Leu Tyr Gly Val Ile Asp Thr Pro Cys Trp Lys Leu
            340                 345                 350
```

His Thr Ser Pro Leu Cys Thr Thr Asn Thr Lys Glu Gly Ser Asn Ile
355                 360                 365

Cys Leu Thr Arg Thr Asp Arg Gly Trp Tyr Cys Asp Asn Ala Gly Ser
370                 375                 380

Val Ser Phe Phe Pro Gln Ala Glu Thr Cys Lys Val Gln Ser Asn Arg
385                 390                 395                 400

Val Phe Cys Asp Thr Met Asn Ser Leu Thr Leu Pro Ser Glu Ile Asn
            405                 410                 415

Leu Cys Asn Val Asp Ile Phe Asn Pro Lys Tyr Asp Cys Lys Ile Met
            420                 425                 430

Thr Ser Lys Thr Asp Val Ser Ser Val Ile Thr Ser Leu Gly Ala
            435                 440                 445

Ile Val Ser Cys Tyr Gly Lys Thr Lys Cys Thr Ala Ser Asn Lys Asn
450                 455                 460

Arg Gly Ile Ile Lys Thr Phe Ser Asn Gly Cys Asp Tyr Val Ser Asn
465                 470                 475                 480

Lys Gly Met Asp Thr Val Ser Val Gly Asn Thr Leu Tyr Tyr Val Asn
            485                 490                 495

Lys Gln Glu Gly Lys Ser Leu Tyr Val Lys Gly Glu Pro Ile Ile Asn
            500                 505                 510

Phe Tyr Asp Pro Leu Val Phe Pro Ser Asp Glu Phe Asp Ala Ser Ile
            515                 520                 525

Ser Gln Val Asn Glu Lys Ile Asn Gln Ser Leu Ala Phe Ile Arg Lys
            530                 535                 540

Ser Asp Glu Leu Leu His Asn Val Asn Ala Gly Lys Ser Thr Thr Asn
545                 550                 555                 560

Ile Met Ile Thr Thr Ile Ile Val Ile Ile Val Ile Leu Leu Ser
            565                 570                 575

Leu Ile Ala Val Gly Leu Leu Leu Tyr Cys Lys Ala Arg Ser Thr Pro
            580                 585                 590

Val Thr Leu Ser Lys Asp Gln Leu Ser Gly Ile Asn Asn Ile Ala Phe
            595                 600                 605

Ser Asn Asn Phe Asp Leu Leu Lys Leu Ala Gly Asp Val Glu Ser Asn
610                 615                 620

Pro Gly Pro Gly Gly Lys Thr Gly Ile Ala Val Met Ile Gly Leu Ile
625                 630                 635                 640

Ala Cys Val Gly Ala Val Thr Leu Ser Asn Phe Gln Gly Lys Val Met
                645                 650                 655

Met Thr Val Asn Ala Thr Asp Val Thr Asp Val Ile Thr Ile Pro Thr
            660                 665                 670

Ala Ala Gly Lys Asn Leu Cys Ile Val Arg Ala Met Asp Val Gly Tyr
            675                 680                 685

Met Cys Asp Asp Thr Ile Thr Tyr Glu Cys Pro Val Leu Ser Ala Gly
690                 695                 700

Asn Asp Pro Glu Asp Ile Asp Cys Trp Cys Thr Lys Ser Ala Val Tyr
705                 710                 715                 720

Val Arg Tyr Gly Arg Cys Thr Lys Thr Arg His Ser Arg Arg Ser Arg
            725                 730                 735

Arg Ser Leu Thr Val Gln Thr His Gly Glu Ser Thr Leu Ala Asn Lys
            740                 745                 750

Lys Gly Ala Trp Met Asp Ser Thr Lys Ala Thr Arg Tyr Leu Val Lys
            755                 760                 765

Thr Glu Ser Trp Ile Leu Arg Asn Pro Gly Tyr Ala Leu Val Ala Ala

-continued

```
            770                 775                 780
Val Ile Gly Trp Met Leu Gly Ser Asn Thr Met Gln Arg Val Val Phe
785                 790                 795                 800

Val Val Leu Leu Leu Leu Val Ala Pro Ala Tyr Ser Phe Asn Cys Leu
                805                 810                 815

Gly Met Ser Asn Arg Asp Phe Leu Glu Gly Val Ser Gly Ala Thr Trp
                820                 825                 830

Val Asp Leu Val Leu Glu Gly Asp Ser Cys Val Thr Ile Met Ser Lys
                835                 840                 845

Asp Lys Pro Thr Ile Asp Val Lys Met Met Asn Met Glu Ala Ala Asn
                850                 855                 860

Leu Ala Glu Val Arg Ser Tyr Cys Tyr Leu Ala Thr Val Ser Asp Leu
865                 870                 875                 880

Ser Thr Lys Ala Ala Cys Pro Ala Met Gly Glu Ala His Asn Asp Lys
                885                 890                 895

Arg Ala Asp Pro Ala Phe Val Cys Arg Gln Gly Val Val Asp Arg Gly
                900                 905                 910

Trp Gly Asn Gly Cys Gly Leu Phe Gly Lys Gly Ser Ile Asp Thr Cys
                915                 920                 925

Ala Lys Phe Ala Cys Ser Thr Lys Ala Ile Gly Arg Thr Ile Leu Lys
                930                 935                 940

Glu Asn Ile Lys Tyr Glu Val Ala Ile Phe Val His Gly Pro Thr Thr
945                 950                 955                 960

Val Glu Ser His Gly Asn Tyr Ser Thr Gln Val Gly Ala Thr Gln Ala
                965                 970                 975

Gly Arg Phe Ser Ile Thr Pro Ala Ala Pro Ser Tyr Thr Leu Lys Leu
                980                 985                 990

Gly Glu Tyr Gly Glu Val Thr Val Asp Cys Glu Pro Arg Ser Gly Ile
                995                 1000                1005

Asp Thr Asn Ala Tyr Tyr Val Met Thr Val Gly Thr Lys Thr Phe
                1010                1015                1020

Leu Val His Arg Glu Trp Phe Met Asp Leu Asn Leu Pro Trp Ser
                1025                1030                1035

Ser Ala Gly Ser Thr Val Trp Arg Asn Arg Glu Thr Leu Met Glu
                1040                1045                1050

Phe Glu Glu Pro His Ala Thr Lys Gln Ser Val Ile Ala Leu Gly
                1055                1060                1065

Ser Gln Glu Gly Ala Leu His Gln Ala Leu Ala Gly Ala Ile Pro
                1070                1075                1080

Val Glu Phe Ser Ser Asn Thr Val Lys Leu Thr Ser Gly His Leu
                1085                1090                1095

Lys Cys Arg Val Lys Met Glu Lys Leu Gln Leu Lys Gly Thr Thr
                1100                1105                1110

Tyr Gly Val Cys Ser Lys Ala Phe Lys Phe Leu Gly Thr Pro Ala
                1115                1120                1125

Asp Thr Gly His Gly Thr Val Val Leu Glu Leu Gln Tyr Thr Gly
                1130                1135                1140

Thr Asp Gly Pro Cys Lys Val Pro Ile Ser Ser Val Ala Ser Leu
                1145                1150                1155

Asn Asp Leu Thr Pro Val Gly Arg Leu Val Thr Val Asn Pro Phe
                1160                1165                1170

Val Ser Val Ala Thr Ala Asn Ala Lys Val Leu Ile Glu Leu Glu
                1175                1180                1185
```

| Pro | Pro | Phe | Gly | Asp | Ser | Tyr | Ile | Val | Val | Gly | Arg | Gly | Glu | Gln |
|---|---|---|---|---|---|---|---|---|---|---|---|---|---|---|
|  | 1190 |  |  |  | 1195 |  |  |  | 1200 |  |  |  |  |  |

| Gln | Ile | Asn | His | His | Trp | His | Lys | Ser | Gly | Ser | Ser | Ile | Gly | Lys |
|---|---|---|---|---|---|---|---|---|---|---|---|---|---|---|
| 1205 |  |  |  |  | 1210 |  |  |  |  | 1215 |  |  |  |  |

| Ala | Phe | Thr | Thr | Thr | Leu | Lys | Gly | Ala | Gln | Arg | Leu | Ala | Ala | Leu |
|---|---|---|---|---|---|---|---|---|---|---|---|---|---|---|
| 1220 |  |  |  |  | 1225 |  |  |  |  | 1230 |  |  |  |  |

| Gly | Asp | Thr | Ala | Trp | Asp | Phe | Gly | Ser | Val | Gly | Val | Phe | Thr |
|---|---|---|---|---|---|---|---|---|---|---|---|---|---|
| 1235 |  |  |  |  | 1240 |  |  |  |  | 1245 |  |  |  |

| Ser | Val | Gly | Lys | Ala | Val | His | Gln | Val | Phe | Gly | Ala | Phe | Arg |
|---|---|---|---|---|---|---|---|---|---|---|---|---|---|
| 1250 |  |  |  |  | 1255 |  |  |  |  | 1260 |  |  |  |

| Ser | Leu | Phe | Gly | Gly | Met | Ser | Trp | Ile | Thr | Gln | Gly | Leu | Leu | Gly |
|---|---|---|---|---|---|---|---|---|---|---|---|---|---|---|
| 1265 |  |  |  |  | 1270 |  |  |  |  | 1275 |  |  |  |  |

| Ala | Leu | Leu | Leu | Trp | Met | Gly | Ile | Asn | Ala | Arg | Asp | Arg | Ser | Ile |
|---|---|---|---|---|---|---|---|---|---|---|---|---|---|---|
| 1280 |  |  |  |  | 1285 |  |  |  |  | 1290 |  |  |  |  |

| Ala | Leu | Thr | Phe | Leu | Ala | Val | Gly | Gly | Val | Leu | Leu | Phe | Leu | Ser |
|---|---|---|---|---|---|---|---|---|---|---|---|---|---|---|
| 1295 |  |  |  |  | 1300 |  |  |  |  | 1305 |  |  |  |  |

| Val | Asn | Val | His | Ala | Asp | Thr | Gly | Cys | Ala | Ile | Asp | Ile | Ser | Arg |
|---|---|---|---|---|---|---|---|---|---|---|---|---|---|---|
| 1310 |  |  |  |  | 1315 |  |  |  |  | 1320 |  |  |  |  |

| Gln | Glu | Leu | Arg |
|---|---|---|---|
| 1325 |  |  |  |

<210> SEQ ID NO 77
<211> LENGTH: 4100
<212> TYPE: DNA
<213> ORGANISM: Artificial Sequence
<220> FEATURE:
<223> OTHER INFORMATION: Synthetic Construct

<400> SEQUENCE: 77

| gatcctaata cgactcacta tagagtagtt cgcctgtgtg agctgacaaa cttagtagtg | 60 |
|---|---|
| tttgtgagga ttaacaacaa ttaacacagt gcgagctgtt tcttagcacg aagatctcga | 120 |
| tgtctaagaa accaggaggg cccggcaaga gccgggctgt caatatgcta aaacgcggaa | 180 |
| tgccccgcgt gttgtccttg attggactta agcaaaagaa gcgaggggc gagttgctaa | 240 |
| tcctcaaagc aaatgcaatt accacaatcc tcactgcagt cacattttgt tttgcttctg | 300 |
| gtcaaaacat cactgaagaa ttttatcaat caacatgcag tgcagttagc aaaggctatc | 360 |
| ttagtgctct gagaactggt tggtatacca gtgttataac tatagaatta gtaatatca | 420 |
| aggaaaataa gtgtaatgga acagatgcta aggtaaaatt gataaaacaa gaattagata | 480 |
| aatataaaaa tgctgtaaca gaattgcagt tgctcatgca agcacacca ccaacaaaca | 540 |
| atcgagccag aagagaacta ccaaggttta tgaattatac actcaacaat gccaaaaaaa | 600 |
| ccaatgtaac attaagcaag aaaaggaaaa gaagatttct ggttttttg ttaggtgttg | 660 |
| gatctgcaat cgccagtggc gttgctgtat ctaaggtcct gcacctagaa ggggaagtga | 720 |
| acaagatcaa aagtgctcta ctatccacaa acaaggctgt agtcagctta tcaaatggag | 780 |
| ttagtgtctt aaccagcaaa gtgttagacc tcaaaaacta tatagataaa caattgttac | 840 |
| ctattgtgaa caagcaaagc tgcagcatat caaatataga aactgtgata gagttccaac | 900 |
| aaaagaacaa cagactacta gagattacca gggaatttag tgttaatgca ggtgtaacta | 960 |
| cacctgtaag cacttacatg ttaactaata gtgaattatt gtcattaatc aatgatatgc | 1020 |
| ctataacaaa tgatcagaaa aagtaatgt ccaacaatgt tcaaatagtt agacagcaaa | 1080 |
| gttactctat catgtccata ataaaagagg aagtcttagc atatgtagta caattaccac | 1140 |

```
tatatggtgt tatagataca ccctgttgga aactacacac atcccctcta tgtacaacca   1200
acacaaaaga agggtccaac atctgtttaa caagaactga cagaggatgg tactgtgaca   1260
atgcaggatc agtatctttc ttcccacaag ctgaaacatg taaagttcaa tcaaatcgag   1320
tattttgtga cacaatgaac agtttaacat taccaagtga aataaatctc tgcaatgttg   1380
acatattcaa ccccaaatat gattgtaaaa ttatgacttc aaaaacagat gtaagcagct   1440
ccgttatcac atctctagga gccattgtgt catgctatgg caaaactaaa tgtacagcat   1500
ccaataaaaa tcgtggaatc ataaagacat tttctaacgg gtgcgattat gtatcaaata   1560
aagggatgga cactgtgtct gtaggtaaca cattatatta tgtaaataag caagaaggta   1620
aaagtctcta tgtaaaaggt gaaccaataa taaatttcta tgacccatta gtattcccct   1680
ctgatgaatt tgatgcatca atatctcaag tcaacgagaa gattaaccag agcctagcat   1740
ttattcgtaa atccgatgaa ttattacata atgtaaatgc tggtaaatcc accacaaata   1800
tcatgataac tactataatt atagtgatta tagtaatatt gttatcatta attgctgttg   1860
gactgctctt atactgtaag gccagaagca caccagtcac actaagcaaa gatcaactga   1920
gtggtataaa taatattgca tttagtaaca attttgatct gctcaaactt gcaggcgatg   1980
tagaatcaaa tcctggaccc ggaggaaaga ccggtattgc agtcatgatt ggcctgatcg   2040
cctgcgtagg agcagttacc ctctctaact tccagggaaa ggtgatgatg acggtaaatg   2100
ctactgacgt cacagatgtc atcacgattc aacagctgc tggaaagaac ctatgcattg    2160
tcagagcaat ggatgtggga tacatgtgcg atgatactat cacttatgaa tgcccagtgc   2220
tgtcggctgg taatgatcca gaagacatcg actgttggtg cacaaagtca gcagtctacg   2280
tcaggtatgg aagatgcacc aagacacgcc actcaagacg cagtcggagg tcactgacag   2340
tgcagacaca cggagaaagc actctagcga acaagaaggg ggcttggatg acagcacca   2400 aggccacaag gtatttggta aaaacagaat catggatctt gaggaaccct ggatatgccc   2460
tggtggcagc cgtcattggt tggatgcttg ggagcaacac catgcagaga gttgtgtttg   2520
tcgtgctatt gcttttggtg gccccagctt acagctttaa ctgccttgga atgagcaaca   2580
gagacttctt ggaaggagtg tctggagcaa catgggtgga tttggttctc gaaggcgaca   2640
gctgcgtgac tatcatgtct aaggacaagc ctaccatcga tgtgaagatg atgaatatgg   2700
aggcggccaa cctggcagag gtccgcagtt attgctattt ggctaccgtc agcgatctct   2760
ccaccaaagc tgcgtgcccg gccatgggag aagctcacaa tgacaaacgt gctgacccag   2820
cttttgtgtg cagacaagga gtggtggaca ggggctgggg caacggctgc ggactatttg   2880
gcaaaggaag cattgacaca tgcgccaaat ttgcctgctc taccaaggca ataggaagaa   2940
ccatttttga agagaatatc aagtacgaag tggccatttt tgtccatgga ccaactactg   3000
tggagtcgca cggaaactac tccacacagg ttggagccac tcaggcaggg agattcagca   3060
tcactcctgc ggcgccttca tacacactaa agcttggaga atatggagag gtgacagtgg   3120
actgtgaacc acggtcaggg attgacacca atgcatacta cgtgatgact gttggaacaa   3180
agacgttctt ggtccatcgt gagtggttca tggacctcaa cctcccttgg agcagtgctg   3240
gaagtactgt gtggaggaac agagagacgt taatggagtt tgaggaacca cacgccacga   3300
agcagtctgt gatagcattg ggctcacaag agggagctct gcatcaagct ttggctggag   3360
ccattcctgt ggaattttca agcaacactg tcaagttgac gtcgggtcat ttgaagtgta   3420
gagtgaagat ggaaaaattg cagttgaagg gaacaaccta tggcgtctgt tcaaaggctt   3480
tcaagtttct tgggactccc gcagacacag gtcacggcac tgtggtgttg gaattgcagt   3540
```

```
acactggcac ggatggacct tgcaaagttc ctatctcgtc agtggcttca ttgaacgacc    3600
taacgccagt gggcagattg gtcactgtca acccttttgt ttcagtggcc acggccaacg    3660
ctaaggtcct gattgaattg gaaccaccct ttggagactc atacatagtg gtgggcagag    3720
gagaacaaca gatcaatcac cactggcaca agtctggaag cagcattggc aaagccttta    3780
caaccaccct caaaggagcg cagagactag ccgctctagg agacacagct gggactttg     3840 gatcagttgg aggggtgttc acctcagttg ggaaggctgt ccatcaagtg ttcggaggag    3900
cattccgctc actgttcgga ggcatgtcct ggataacgca aggattgctg ggggctctcc    3960
tgttgtggat gggcatcaat gctcgtgaca ggtccatagc tctcacgttt ctcgcagttg    4020
gaggagttct gctcttcctc tccgtgaacg tgcacgctga cactgggtgt gccatagaca    4080
tcagccggca agagctgaga                                                4100

<210> SEQ ID NO 78
<211> LENGTH: 4100
<212> TYPE: DNA
<213> ORGANISM: Artificial Sequence
<220> FEATURE:
<223> OTHER INFORMATION: Synthetic Construct

<400> SEQUENCE: 78
ctaggattat gctgagtgat atctcatcaa gcggacacac tcgactgttt gaatcatcac      60
aaacactcct aattgttgtt aattgtgtca cgctcgacaa agaatcgtgc ttctagagct     120
acagattctt tggtcctccc gggccgttct cggcccgaca gttatacgat tttgcgcctt     180
acggggcgca caacaggaac taacctgaat tcgttttctt cgctcccccg ctcaacgatt     240
aggagtttcg tttacgttaa tggtgttagg agtgacgtca gtgtaaaaca aaacgaagac     300
cagttttgta gtgacttctt aaaatagtta gttgtacgtc acgtcaatcg tttccgatag     360
aatcacgaga ctcttgacca accatatggt cacaatattg atatcttaat tcattatagt     420 tcctttatt cacattacct tgtctacgat tccattttaa ctattttgtt cttaatctat      480 ttatatttt acgacattgt cttaacgtca acgagtacgt ttcgtgtggt ggttgtttgt      540
tagctcggtc ttctcttgat ggttccaaat acttaatatg tgagttgtta cggttttttt     600
ggttacattg taattcgttc ttttccttt cttctaaaga accaaaaaac aatccacaac      660
ctagacgtta gcggtcaccg caacgacata gattccagga cgtggatctt cccttcact     720 tgttctagtt ttcacgagat gataggtgtt tgttccgaca tcagtcgaat agtttacctc     780
aatcacagaa ttggtcgttt cacaatctgg agttttgat atatctattt gttaacaatg     840
gataacactt gttcgtttcg acgtcgtata gtttatatct ttgacactat ctcaaggttg     900
ttttcttgtt gtctgatgat ctctaatggt cccttaaatc acaattacgt ccacattgat     960
gtggacattc gtgaatgtac aattgattat cacttaataa cagtaattag ttactatacg    1020
gatattgttt actagtcttt ttcaattaca ggttgttaca agtttatcaa tctgtcgttt    1080
caatgagata gtacaggtat tatttctcc ttcagaatcg tatacatcat gttaatggtg    1140 ataccaca atatctatgt gggacaacct tgatgtgtg taggggagat acatgttggt       1200
tgtgttttct tcccaggttg tagacaaatt gttcttgact gtctcctacc atgacactgt    1260
tacgtcctag tcatagaaag aagggtgttc gactttgtac atttcaagtt agtttagctc    1320
ataaaacact gtgttacttg tcaaattgta atggttcact ttatttagag acgttacaac    1380
tgtataagtt gggggtttata ctaacatttt aatactgaag ttttgtcta cattcgtcga    1440
```

```
ggcaatagtg tagagatcct cggtaacaca gtacgatacc gttttgattt acatgtcgta    1500
ggttatttt agcaccttag tatttctgta aaagattgcc cacgctaata catagtttat    1560
ttccctacct gtgacacaga catccattgt gtaatataat acatttattc gttcttccat    1620
tttcagagat acattttcca cttggttatt atttaaagat actgggtaat cataagggga    1680
gactacttaa actacgtagt tatagagttc agttgctctt ctaattggtc tcggatcgta    1740
aataagcatt taggctactt aataatgtat tacatttacg accatttagg tggtgtttat    1800
agtactattg atgatattaa tatcactaat atcattataa caatagtaat taacgacaac    1860
ctgacgagaa tatgacattc cggtcttcgt gtggtcagtg tgattcgttt ctagttgact    1920
caccatattt attataacgt aaatcattgt taaaactaga cgagtttgaa cgtccgctac    1980
atcttagttt aggacctggg cctcctttct ggccataacg tcagtactaa ccggactagc    2040
ggacgcatcc tcgtcaatgg gagagattga aggttcccctt ccactactac tgccatttac    2100
gatgactgca gtgtctacag tagtgctaag gttgtcgacg accttcttg gatacgtaac    2160
agtctcgtta cctacaccct atgtacacgc tactatgata gtgaatactt acgggtcacg    2220
acagccgacc attactaggt cttctgtagc tgacaaccac gtgtttcagt cgtcagatgc    2280
agtccatacc ttctacgtgg ttctgtgcgg tgagttctgc gtcagcctcc agtgactgtc    2340
acgtctgtgt gcctctttcg tgagatcgct tgttcttccc ccgaacctac ctgtcgtggt    2400
tccggtgttc cataaaccat ttttgtctta gtacctagaa ctccttggga cctatacggg    2460
accaccgtcg gcagtaacca acctacgaac cctcgttgtg gtacgtctct caacacaaac    2520
agcacgataa cgaaaccac cgggqtcgaa tgtcgaaatt gacggaacct tactcgttgt    2580
ctctgaagaa ccttcctcac agacctcgtt gtacccacct aaaccaagag cttccgctgt    2640
cgacgcactg atagtacaga ttcctgttcg gatggtagct acacttctac tacttatacc    2700
tccgccggtt ggaccgtctc caggcgtcaa taacgataaa ccgatggcag tcgctagaga    2760
ggtggtttcg acgcacgggc cggtaccctc ttcgagtgtt actgtttgca cgactgggtc    2820
gaaaacacac gtctgttcct caccacctgt ccccgacccc gttgccgacg cctgataaac    2880
cgtttccttc gtaactgtgt acgcggttta aacggacgag atggttccgt tatccttctt    2940
ggtaaaactt tctcttatag ttcatgcttc accggtaaaa acaggtacct ggttgatgac    3000
acctcagcgt gcctttgatg aggtgtgtcc aacctcggtg agtccgtccc tctaagtcgt    3060
agtgaggacg ccgcggaagt atgtgtgatt tcgaacctct tatcctctc cactgtcacc    3120
tgacacttgg tgccagtccc taactgtggt tacgtatgat gcactactga caaccttgtt    3180
tctgcaagaa ccaggtagca ctcaccaagt acctggagtt ggagggaacc tcgtcacgac    3240
cttcatgaca cacctccttg tctctctgca attacctcaa actccttggt gtgcggtgct    3300
tcgtcagaca ctatcgtaac ccgagtgttc tccctcgaga cgtagttcga aaccgacctc    3360
ggtaaggaca ccttaaaagt tcgttgtgac agttcaactg cagcccagta aacttcacat    3420
ctcacttcta ccttttaac gtcaacttcc cttgttggat accgcagaca gtttccgaa    3480
agttcaaaga accctgaggg cgtctgtgtc cagtgccgtg acaccacaac cttaacgtca    3540
tgtgaccgtg cctacctgga acgtttcaag gatagagcag tcaccgaagt aacttgctgg    3600
attgcggtca cccgtctaac cagtgacagt tgggaaaaca aagtcaccgg tgccggttgc    3660
gattccagga ctaacttaac cttggtggga aacctctgag tatgtatcac cacccgtctc    3720
ctcttgttgt ctagttagtg gtgaccgtgt tcagaccttc gtcgtaaccg tttcggaaat    3780
gttggtggga gtttcctcgc gtctctgatc ggcgagatcc tctgtgtcga accctgaaac    3840
```

```
ctagtcaacc tcccacaag tggagtcaac ccttccgaca ggtagttcac aagcctcctc    3900
gtaaggcgag tgacaagcct ccgtacagga cctattgcgt tcctaacgac ccccgag

UNITED STATES PATENT AND TRADEMARK OFFICE
CERTIFICATE OF CORRECTION

PATENT NO.       : 9,217,158 B2
APPLICATION NO.  : 13/633436
DATED            : December 22, 2015
INVENTOR(S)      : Pugachev et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 181 days.

Signed and Sealed this
Twelfth Day of July, 2016

Michelle K. Lee
*Director of the United States Patent and Trademark Office*